United States Patent
Yang et al.

(10) Patent No.: US 9,951,071 B2
(45) Date of Patent: Apr. 24, 2018

(54) DIHYDROPYRIDONE P1 AS FACTOR XIA INHIBITORS

(71) Applicant: BRISTOL-MYERS SQUIBB COMPANY, Princeton, NJ (US)

(72) Inventors: Wu Yang, Princeton Junction, NJ (US); James R. Corte, Lawrenceville, NJ (US); Paul J. Gilligan, Wilmington, DE (US); Donald J. P. Pinto, Churchville, PA (US); William R. Ewing, Yardley, PA (US); Andrew K. Dilger, Ewing, NJ (US); Yufeng Wang, North Brunswick, NJ (US); Tianan Fang, Levittown, PA (US); Kumar B. Pabbisetty, Piscataway, NJ (US); Leon M. Smith, II, Somerset, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/205,059

(22) Filed: Jul. 8, 2016

(65) Prior Publication Data

US 2016/0340360 A1 Nov. 24, 2016

Related U.S. Application Data

(62) Division of application No. 14/419,002, filed as application No. PCT/US2013/053416 on Aug. 2, 2013, now Pat. No. 9,409,908.

(60) Provisional application No. 61/679,197, filed on Aug. 3, 2012, provisional application No. 61/787,081, filed on Mar. 15, 2013.

(51) Int. Cl.
| | | |
|---|---|---|
| *C07D 471/04* | (2006.01) | |
| *C07D 471/08* | (2006.01) | |
| *C07D 471/18* | (2006.01) | |
| *C07D 487/08* | (2006.01) | |
| *C07D 401/04* | (2006.01) | |
| *C07D 487/18* | (2006.01) | |
| *C07H 17/02* | (2006.01) | |
| *C07C 53/18* | (2006.01) | |

(52) U.S. Cl.
CPC ............ *C07D 471/08* (2013.01); *C07C 53/18* (2013.01); *C07D 401/04* (2013.01); *C07D 471/18* (2013.01); *C07D 487/08* (2013.01); *C07D 487/18* (2013.01); *C07H 17/02* (2013.01)

(58) Field of Classification Search
CPC .. C07D 471/04; C07D 471/08; C07D 471/18; C07D 487/08
See application file for complete search history.

(56) References Cited

FOREIGN PATENT DOCUMENTS

| | | |
|---|---|---|
| WO | WO 2004/080971 | 9/2004 |
| WO | WO 2004/094372 | 11/2004 |
| WO | WO 2005/099709 | 10/2005 |
| WO | WO 2005/123050 | 12/2005 |
| WO | WO 2005/123680 | 12/2005 |
| WO | WO 2006/076575 | 7/2006 |
| WO | WO 2006/089005 | 8/2006 |
| WO | WO 2007/070816 | 6/2007 |
| WO | WO 2007/070818 | 6/2007 |
| WO | WO 2007/070826 | 6/2007 |
| WO | WO 2008/076805 | 6/2008 |
| WO | WO 2008/079836 | 7/2008 |
| WO | WO 2008/157162 | 12/2008 |
| WO | WO 2009/114677 | 9/2009 |
| WO | WO 2011/100401 | 8/2011 |
| WO | WO 2011/100402 | 8/2011 |
| WO | WO 2013/022814 | 2/2013 |
| WO | WO 2013/022818 | 2/2013 |
| WO | WO 2013/055984 | 4/2013 |
| WO | WO 2013/056034 | 4/2013 |
| WO | WO 2013/056060 | 4/2013 |
| WO | WO 2013/093484 | 6/2013 |
| WO | WO 2013/118805 | 8/2013 |
| WO | WO 2013/174937 | 11/2013 |

*Primary Examiner* — Bruck Kifle
(74) *Attorney, Agent, or Firm* — Hong Liu

(57) ABSTRACT

The present invention provides compounds of Formula (V):

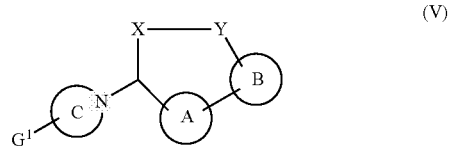

(V)

or stereoisomers, tautomers, or pharmaceutically acceptable salts thereof, wherein all the variables are as defined herein. These compounds are selective factor XIa inhibitors or dual inhibitors of FXIa and plasma kallikrein. This invention also relates to pharmaceutical compositions comprising these compounds and methods of treating thromboembolic and/or inflammatory disorders using the same.

7 Claims, No Drawings

DIHYDROPYRIDONE P1 AS FACTOR XIA INHIBITORS

CROSS REFERENCES TO RELATED APPLICATIONS

This application is a divisional of U.S. Ser. No. 14/419,002, filed Feb. 2, 2015, now allowed, which is a 371 of International Application No. PCT/US2013/053416, filed on Aug. 2, 2013, which claims the benefit of U.S. Provisional Application Ser. No. 61/679,197 filed on Aug. 3, 2012 and U.S. Provisional Application Ser. No. 61/787,081 filed on Mar. 15, 2013 which are incorporated herein by reference.

FIELD OF THE INVENTION

The present invention relates generally to novel macrocyclic compounds, and their analogues thereof, which are inhibitors of factor XIa and/or plasma kallikrein, compositions containing them, and methods of using them, for example, for the treatment or prophylaxis of thromboembolic disorders, or for the treatment of retinal vascular permeability associated with diabetic retinopathy and diabetic macular edema.

BACKGROUND OF THE INVENTION

Thromboembolic diseases remain the leading cause of death in developed countries despite the availability of anticoagulants such as warfarin (COUMADIN®), heparin, low molecular weight heparins (LMWH), and synthetic pentasaccharides and antiplatelet agents such as aspirin and clopidogrel (PLAVIX®). The oral anticoagulant warfarin, inhibits the post-translational maturation of coagulation factors VII, IX, X and prothrombin, and has proven effective in both venous and arterial thrombosis. However, its usage is limited due to its narrow therapeutic index, slow onset of therapeutic effect, numerous dietary and drug interactions, and a need for monitoring and dose adjustment. Thus discovering and developing safe and efficacious oral anticoagulants for the prevention and treatment of a wide range of thromboembolic disorders has become increasingly important.

One approach is to inhibit thrombin generation by targeting the inhibition of coagulation factor XIa (FXIa). Factor XIa is a plasma serine protease involved in the regulation of blood coagulation, which is initiated in vivo by the binding of tissue factor (TF) to factor VII (FVII) to generate factor VIIa (FVIIa). The resulting TF:FVIIa complex activates factor IX (FIX) and factor X (FX) that leads to the production of factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Gailani, D. et al., *Arterioscler. Thromb. Vasc. Biol.*, 27:2507-2513 (2007).) The resulting burst of thrombin converts fibrinogen to fibrin that polymerizes to form the structural framework of a blood clot, and activates platelets, which are a key cellular component of coagulation (Hoffman, M., *Blood Reviews*, 17:S1-S5 (2003)). Therefore, factor XIa plays a key role in propagating this amplification loop and is thus an attractive target for anti-thrombotic therapy.

Plasma prekallikrein is a zymogen of a trypsin-like serine protease and is present in plasma at 35 to 50 µg/mL. The gene structure is similar to that of factor XI. Overall, the amino acid sequence of plasma kallikrein has 58% homology to factor XI. Plasma kallikrein is thought to play a role in a number of inflammatory disorders. The major inhibitor of plasma kallikrein is the serpin C1 esterase inhibitor. Patients who present with a genetic deficiency in C1 esterase inhibitor suffer from hereditary angioedema (HAE) which results in intermittent swelling of face, hands, throat, gastrointestinal tract and genitals. Blisters formed during acute episodes contain high levels of plasma kallikrein which cleaves high molecular weight kininogen liberating bradykinin leading to increased vascular permeability. Treatment with a large protein plasma kallikrein inhibitor has been shown to effectively treat HAE by preventing the release of bradykinin which causes increased vascular permeability (A. Lehmann "Ecallantide (DX-88), a plasma kallikrein inhibitor for the treatment of hereditary angioedema and the prevention of blood loss in on-pump cardiothoracic surgery" Expert Opin. Biol. Ther. 8, p 1187-99).

The plasma kallikrein-kinin system is abnormally abundant in patients with advanced diabetic macular edema. It has been recently published that plasma kallikrein contributes to retinal vascular dysfunctions in diabetic rats (A. Clermont et al. "Plasma kallikrein mediates retinal vascular dysfunction and induces retinal thickening in diabetic rats" Diabetes, 2011, 60, p 1590-98). Furthermore, administration of the plasma kallikrein inhibitor ASP-440 ameliorated both retinal vascular permeability and retinal blood flow abnormalities in diabetic rats. Therefore, a plasma kallikrein inhibitor should have utility as a treatment to reduce retinal vascular permeability associated with diabetic retinopathy and diabetic macular edema. Other complications of diabetes such as cerebral hemorrhage, nephropathy, cardiomyopathy and neuropathy, all of which have associations with plasma kallikrein may also be considered as targets for a plasma kallikrein inhibitor.

To date, no small molecule synthetic plasma kallikrein inhibitor has been approved for medical use. The large protein plasma kallikrein inhibitors present risks of anaphylactic reactions, as has been reported for Ecallantide. Thus there remains a need for compounds that inhibit plasma kallikrein, that do not induce anaphylaxis and that are orally available. Furthermore, the molecules in the known art feature a highly polar and ionizable guanidine or amidine functionality. It is well known that such functionalities may be limiting to gut permeability and therefore to oral availability.

SUMMARY OF THE INVENTION

The present invention provides novel macrocyclic compounds, their analogues, including stereoisomers, tautomers, pharmaceutically acceptable salts, or solvates thereof, which are useful as selective inhibitors of serine protease enzymes, especially factor XIa and/or plasma kallikrein.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of thromboembolic disorders.

The compounds of the invention may be used in the treatment of retinal vascular permeability associated with diabetic retinopathy and diabetic macular edema.

The compounds of the present invention may be used in therapy.

The compounds of the present invention may be used for the manufacture of a medicament for the treatment and/or prophylaxis of a thromboembolic disorder.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (X):

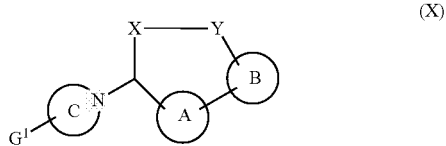

or stereoisomers, tautomers, pharmaceutically acceptable salts, solvates, or prodrugs thereof, wherein:

ring A is independently selected from a 6-membered aryl and a 5- to 6-membered heterocycle, wherein said aryl and heterocycle are optionally substituted with, where valence allows, one or more $R^4$;

ring B is independently selected from a 6-membered aryl and a 5- to 10-membered heterocycle, wherein said aryl and heterocycle are optionally substituted with, where valence allows, one or more $R^3$;

ring C is independently selected from

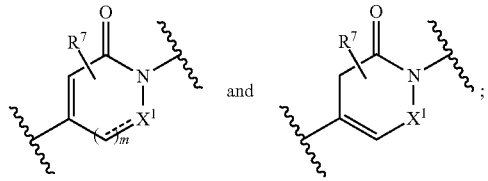

- - - is an optional bond;

$G^1$ is independently selected from a $C_{3-10}$ carbocycle and a 5- to 10-membered heterocycle wherein said carbocycle and heterocycle are optionally substituted with, where valence allows, one or more $R^8$;

X is independently selected from $C_{4-8}$ alkylene and $C_{4-8}$ alkenylene, wherein said alkylene and alkenylene are substituted with $R^1$ and $R^2$; alternatively one or more of the carbon atoms of said alkylene and alkenylene may be replaced by O, C=O, S(O)$_p$, S(O)$_p$NH, NH, and N($C_{1-4}$ alkyl);

$X^1$ is independently selected from $CR_7$ and N;

Y is independently selected from —NH—C(O)— and —C(O)—NH—;

$R^1$ and $R^2$ are independently selected from H, halogen, haloalkyl, $C_{1-6}$ alkyl (optionally substituted with $R^6$), hydroxyl, and alkoxy (optionally substituted with $R^6$), and $C_{3-6}$ cycloalkyl optionally substituted with $R^6$; optionally, when $R^1$ and $R^2$ are attached to the same carbon atom, together they form an oxo group or $C_{3-6}$ cycloalkyl; optionally, when $R^1$ and $R^2$ are attached to carbon atoms adjacent to each other, together they form a bond or a carbocycle;

$R^3$ is independently selected from H, NO$_2$, =O, halogen, haloalkyl, $C_{1-4}$alkyl (optionally substituted with $R^6$), $C_{2-4}$alkenyl (optionally substituted with $R^6$), $C_{2-4}$alkynyl (optionally substituted with $R^6$), CN, —(CH$_2$)$_n$—OR$^5$, —(CH$_2$)$_n$NR$^5$R$^5$, —(CH$_2$)$_n$—C(O)OR$^5$, —(CH$_2$)$_n$—NR$^9$C(O)OR$^5$, —(CH$_2$)$_n$—NR$^9$C(O)R$^5$, —(CH$_2$)$_n$—NR$^9$C(N=CN)NHR$^5$, —(CH$_2$)$_n$—NR$^9$C(NH)NHR$^5$, —(CH$_2$)$_n$—N=CR$^9$NR$^5$R$^5$, —(CH$_2$)$_n$—NR$^9$C(O)NR$^5$R$^5$, —(CH$_2$)$_n$—C(O)NR$^5$R$^5$, —(CH$_2$)$_n$—NR$^9$C(S)NR$^9$C(O)R$^5$, —(CH$_2$)$_n$—S(O)$_p$R$^{12}$, —(CH$_2$)$_n$—S(O)$_p$NR$^5$R$^5$, —(CH$_2$)$_n$—NR$^9$S(O)$_p$NR$^5$R$^5$, —(CH$_2$)$_n$—NR$^9$S(O)$_p$R$^{12}$, —(CH$_2$)$_n$—C$_{3-10}$ carbocycle and —(CH$_2$)$_n$-4- to 10-membered heterocycle, wherein said carbocycle and heterocycle are optionally substituted with $R^6$; optionally, two adjacent $R^3$ groups on the carbocycle and heterocycle may form a ring optionally substituted with $R^6$;

$R^4$ is independently selected from H, OH, NH$_2$, halogen, CN, $C_{1-4}$ alkyl, $C_{1-4}$ haloalkyl, $C_{1-4}$ alkoxy, —CH$_2$OH, —CO$_2$H, —CH$_2$CO$_2$H, —CO$_2$($C_{1-4}$ alkyl), —C(O)NH$_2$, —C(O)NH($C_{1-4}$ alkyl), —C(O)N($C_{1-4}$ alkyl)$_2$, S(O)$_2$NH$_2$, $C_{3-6}$ cycloalkyl, aryl, and a 5- to 6-membered heterocycle, where said cycloalkyl, aryl and hterecycle are optionally substituted with $R^6$;

$R^5$ is independently selected from H, $C_{1-4}$ alkyl (optionally substituted with halogen, hydroxyl, alkoxy, carboxy, alkoxycarbonyl, amino, substituted amino), —(CH$_2$)$_n$—C$_{3-10}$ carbocycle and —(CH$_2$)$_n$-4- to 10-membered heterocycle, wherein said carbocycle and heterocycle are optionally substituted with $R^6$; alternatively, $R^5$ and $R^5$ together with the nitrogen atom to which they are both attached form a heterocyclic ring optionally substituted with $R^6$;

$R^6$ is independently selected from —(CH$_2$)$_n$—OH, =O, —(CH$_2$)$_n$NH$_2$, —(CH$_2$)$_n$CN, halogen, $C_{1-6}$ alkyl, —(CH$_2$)$_n$—C(=O)OH, —(CH$_2$)$_n$—C(=O)OC$_{1-4}$ alkyl, —(CH$_2$)$_n$—OC$_{1-4}$ alkyl, —(CH$_2$)$_n$—C$_{3-10}$ carbocycle, —(CH$_2$)$_n$-4- to 10-membered heterocycle, and —O-4- to 10-membered heterocycle, wherein said carbocycle and heterocycle are optionally substituted with $R^{10}$;

$R^7$ is independently selected from H, hydroxyl, alkoxy, halogen, $C_{1-3}$ alkyl;

$R^8$ is independently selected from H, halogen, CN, NH$_2$, $C_{1-6}$ alkyl, haloalkyl, haloalkylcarbonylamine, alkylcarbonyl, alkoxy, haloalkoxy, —(CH$_2$)$_n$-aryl, —(CH$_2$)$_n$—C$_{3-6}$ cycloalkyl, and —(CH$_2$)$_n$-4-6 membered heterocycle; optionally, two adjacent $R^8$ groups on the carbocycle and heterocycle may form a ring optionally substituted with $R^{10}$;

$R^9$ is H or $C_{1-6}$ alkyl;

$R^{10}$ is independently selected from $C_{1-6}$ alkyl (optionally substituted) with $R^{11}$, $C_{2-6}$ alkenyl, $C_{2-6}$ alkynyl, —(CH$_2$)$_n$—C$_{3-6}$ cycloalkyl (optionally substituted with $R^{11}$), —O-4- to 10-membered heterocycle (optionally substituted with $R^{11}$), F, Cl, Br, CN, NO$_2$, =O, CO$_2$H, —(CH$_2$)$_n$—OC$_{1-5}$ alkyl, —(CH$_2$)$_n$—OR$^{11}$, and —(CH$_2$)$_n$—NR$^{11}$R$^{11}$;

$R^{11}$, at each occurrence, is independently selected from H, $C_{1-5}$ alkyl, —(CH$_2$)$_n$—OH, $C_{3-6}$ cycloalkyl, and phenyl, or $R^{11}$ and $R^{11}$ together with the nitrogen atom to which they are both attached form a heterocyclic ring optionally substituted with $C_{1-4}$alkyl;

$R^{12}$ is $C_{1-6}$ alkyl optionally substituted with $R^{11}$;

m is an integer independently selected from 0 and 1;

n, at each occurrence, is an integer independently selected from 0, 1, 2, 3, and 4;

p, at each occurrence, is an integer independently selected from 0, 1, and 2; provided the following compounds are excluded:

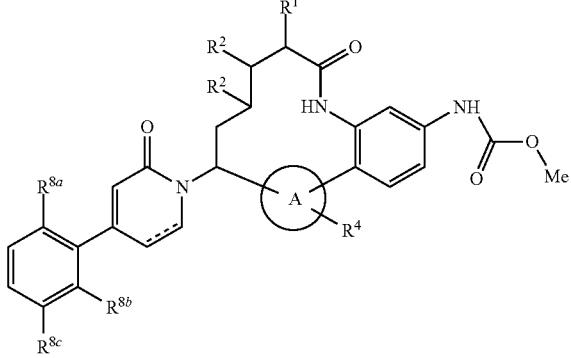

(VIII)

wherein ring A is independently selected from

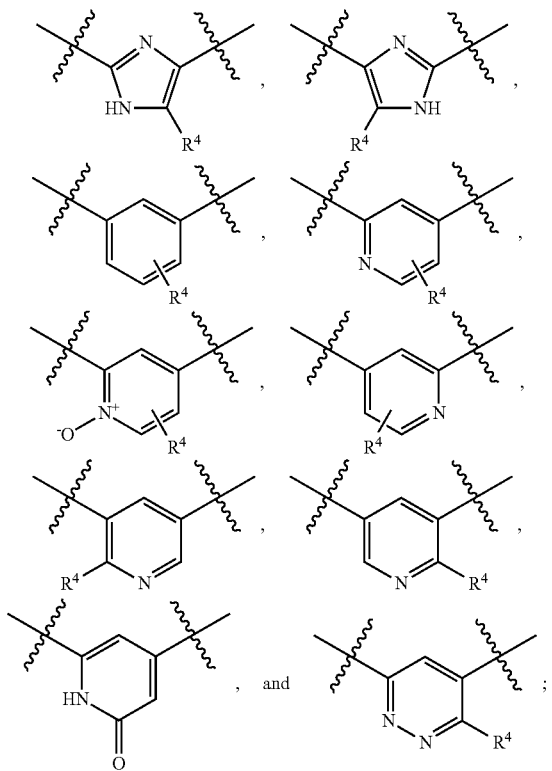

- - - is an optional bond;
$R^1$ is independently selected from H, hydroxyl, and $C_{1-4}$alkyl;
$R^2$, at each occurrence, is independently selected from H and hydroxyl;
$R^4$ is independently selected from H, OH, F, $OC_{1-4}$ alkyl, and CN;
$R^{8a}$ is independently selected from H, F, Cl, and Br;
$R^{8b}$ is independently selected from H and F; and
$R^{8c}$ is independently selected from H, F, and Cl.

In another aspect, the present invention provides compounds of Formula (XI):

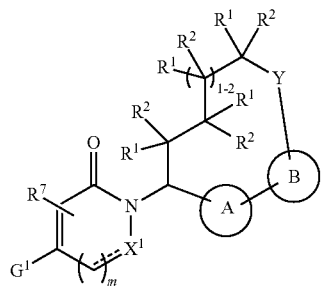

(XI)

or stereoisomers, tautomers, pharmaceutically acceptable salts, solvates, or prodrugs thereof, wherein:

ring A is independently selected from a 6-membered aryl and a 5- to 6-membered heterocycle, wherein said aryl and heterocycle are substituted with 1-4 $R^4$;

ring B is independently selected from a 6-membered aryl and a 5- to 10-membered heterocycle, wherein said aryl and heterocycle are substituted with 1-4 $R^3$;

$G^1$ is independently selected from a $C_{3-10}$ carbocycle and a 5- to 10-membered heterocycle wherein said carbocycle and heterocycle are substituted with 1-4 $R^8$;

$X^1$ is independently selected from $CR_7$ and N;

- - - is an optional bond;

Y is independently selected from —NH—C(O)— and —C(O)—NH—;

$R^1$ and $R^2$ are independently selected from H, halogen, haloalkyl, $C_{1-4}$ alkyl (optionally substituted with $R^6$), hydroxyl, and alkoxy (optionally substituted with $R^6$), and $C_{3-5}$ cycloalkyl optionally substituted with $R^6$;

$R^3$ is independently selected from H, =O, halogen, haloalkyl, $C_{1-4}$alkyl (optionally substituted with $R^6$), $C_{2-4}$alkenyl (optionally substituted with $R^6$), $C_{2-4}$alkynyl (optionally substituted with $R^6$), CN, $NO_2$, —$(CH_2)_n$—$OR^5$, —$(CH_2)_n$—$NR^5R^5$, —$(CH_2)_n$—$C(O)OR^5$, —$(CH_2)_n$—$NR^9C(O)OR^5$, —$(CH_2)_n$—$NR^9C(O)R^5$, —$(CH_2)_n$—$NR^9C(N—CN)NHR^5$, —$(CH_2)_n$—$NR^9C(NH)NHR^5$, —$(CH_2)_n$—$N=CR^9NR^5R^5$, —$(CH_2)_n$—$NR^9C(O)NR^5R^5$, —$(CH_2)_n$—$C(O)NR^5R^5$, —$(CH_2)_n$—$NR^9C(S)NR^9C(O)R^5$, —$(CH_2)_n$—$S(O)_pR^{12}$, —$(CH_2)_n$—$S(O)_pNR^5R^5$, —$(CH_2)_n$—$NR^9S(O)_pNR^5R^5$, —$(CH_2)_n$—$NR^9S(O)_pR^{12}$, —$(CH_2)_n$—$C_{3-10}$ carbocycle and —$(CH_2)_n$-4- to 10-membered heterocycle, wherein said carbocycle and heterocycle are optionally substituted with $R^6$; optionally, two adjacent $R^3$ groups on the carbocycle and heterocycle may form a ring optionally substituted with $R^6$.

$R^4$ is independently selected from H, OH, halogen, CN, $C_{1-4}$ alkyl, $C_{1-4}$ haloalkyl, $C_{1-4}$ alkoxy, —$C(O)NH_2$, —$C(O)NH(C_{1-4}$ alkyl), —$C(O)N(C_{1-4}$ alkyl$)_2$, and $C_{3-6}$ cycloalkyl, $C_{3-6}$ cycloalkyl, aryl, and a 5- to 6-membered heterocycle, where said cycloalkyl, aryl and hterecycle are optionally substituted with $R^6$;

$R^5$ is independently selected from H, $C_{1-4}$ alkyl (optionally substituted with halogen, hydroxyl, alkoxy, carboxy, alkoxycarbonyl, amino, substituted amino), $C_{3-10}$ carbocycle and 4- to 10-membered heterocycle, wherein said carbocycle and heterocycle are optionally substituted with $R^6$; alternatively, $R^5$ and $R^5$ together with the nitrogen atom to which they are both attached form a heterocyclic ring optionally substituted with $R^6$;

$R^6$ is independently selected from OH, =O, —$(CH_2)_nNH_2$, —$(CH_2)_nCN$, halogen, $C_{1-6}$ alkyl, —$(CH_2)_n$—$C(=O)OH$, —$(CH_2)_n$—$C(=O)OC_{1-4}$ alkyl, —$(CH_2)_n$—$OC_{1-4}$ alkyl, —$(CH_2)_n$—$C_{3-10}$ carbocycle, —(CH$_2$)$_n$-4- to 10-membered heterocycle, and —(CH$_2$)$_n$-4- to 10-membered heterocycle, wherein said carbocycle and heterocycle are optionally substituted with R$^{10}$;

R$^7$ is independently selected from H, hydroxyl, alkoxy, halogen, methyl, ethyl, and isopropyl;

R$^8$ is independently selected from H, halogen, CN, NH$_2$, C$_{1-6}$ alkyl, haloalkyl, alkylcarbonyl, alkoxy, haloalkoxy, —(CH$_2$)$_n$-aryl, —(CH$_2$)$_n$—C$_{3-6}$ cycloalkyl, and —(CH$_2$)$_n$-4-6 membered heterocycle; optionally, two adjacent R$^8$ groups on the carbocycle and heterocycle may form a ring optionally substituted with R$^{10}$;

R$^9$ is H or C$_{1-6}$ alkyl;

R$^{10}$ is independently selected from C$_{1-6}$ alkyl (optionally substituted with R$^{11}$), C$_{2-6}$ alkenyl, C$_{2-6}$ alkynyl, —(CH$_2$)$_n$—C$_{3-6}$ cycloalkyl, —O-4- to 10-membered heterocycle (optionally substituted with R$^{11}$), F, Cl, Br, CN, NO$_2$, =O, CO$_2$H, —(CH$_2$)$_n$—OC$_{1-5}$ alkyl, —(CH$_2$)$_n$—OR$^1$, and —(CH$_2$)$_n$—NR$^{11}$R$^{11}$;

R$^{11}$, at each occurrence, is independently selected from H, C$_{1-5}$ alkyl, —(CH$_2$)$_n$—OH, C$_{3-6}$ cycloalkyl, and phenyl, or R$^{11}$ and R$^{11}$ together with the nitrogen atom to which they are both attached form a heterocyclic ring optionally substituted with C$_{1-4}$alkyl;

R$^{12}$ is C$_{1-6}$ alkyl optionally substituted with R$^{11}$;

m is an integer independently selected from 0 and 1;

n, at each occurrence, is an integer independently selected from 0, 1, 2, 3, and 4;

p, at each occurrence, is an integer independently selected from 0, 1, and 2;

other variables are as defined in Formula (X) above.

In another aspect, the present invention provides compounds of Formula (XII):

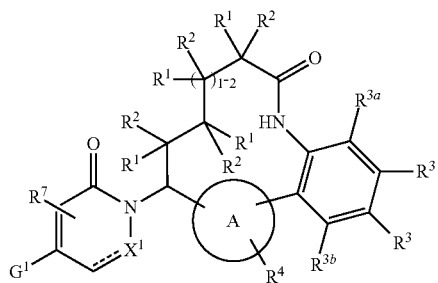

(XII)

or stereoisomers, tautomers, pharmaceutically acceptable salts, solvates, or prodrugs thereof, wherein:

ring A is independently selected from phenyl and a 5- to 6-membered heterocycle;

G$^1$ is independently selected from aryl, C$_{3-6}$cycloalkyl and a 5- to 6-membered heterocycle wherein said aryl, cycloalkyl and heterocycle are substituted with 1-4 R$^8$;

R$^1$ and R$^2$ are independently selected from H, halogen, CF$_3$, C$_{1-6}$ alkyl, and hydroxyl;

R$^3$ is independently selected from H, halogen, haloalkyl, C$_{1-4}$alkyl (optionally substituted with R$^6$), C$_{2-4}$alkenyl (optionally substituted with R$^6$), CN, NO$_2$, —(CH$_2$)$_n$—OR$^5$, —(CH$_2$)$_n$—NR$^5$R$^5$, —(CH$_2$)$_n$—C(O)OR$^5$, —(CH$_2$)$_n$—NHC(O)OR$^5$, —(CH$_2$)$_n$—NHC(O)R$^5$, —(CH$_2$)$_n$—NHC(N—CN)NHR$^5$, —(CH$_2$)$_n$—NHC(NH)NHR$^5$, —(CH$_2$)$_n$—N=CHNR$^5$R$^5$, —(CH$_2$)$_n$—NHC(O)NR$^5$R$^5$, —(CH$_2$)$_n$—C(O)NR$^5$R$^5$, —(CH$_2$)$_n$—NHC(S)NR$^9$C(O)R, —(CH$_2$)$_n$—S(O)$_p$R$^{12}$, —(CH$_2$)$_n$—S(O)$_p$NR$^5$R$^5$, —(CH$_2$)$_n$—NHS(O)$_p$NR$^5$R$^5$, —(CH$_2$)$_n$—NHS(O)$_p$R$^{12}$, —(CH$_2$)$_n$—C$_{3-10}$ carbocycle and —(CH$_2$)$_n$-4- to 10-membered heterocycle, wherein said carbocycle and heterocycle are optionally substituted with R$^6$; optionally, two adjacent R$^3$ groups on the carbocycle and heterocycle may form a ring optionally substituted with R$^6$;

R$^{3a}$ is independently selected from H and halogen;

R$^{3b}$ is independently selected from H, halogen, and CN;

R$^4$ is independently selected from H, OH, F, Cl, Br, C$_{1-4}$ alkyl, C$_{1-4}$ alkoxy, CF$_3$CN, C$_{3-6}$ cycloalkyl, aryl, and a 5- to 6-membered heterocycle, where said cycloalkyl, aryl and hterecycle are optionally substituted with R$^6$;

R$^5$ is independently selected from H, C$_{1-4}$ alkyl (optionally substituted with halogen, hydroxyl, alkoxy, carboxy, alkoxycarbonyl, amino, substituted amino), —(CH$_2$)$_n$—C$_{3-10}$ carbocycle and —(CH$_2$)$_n$-4- to 10-membered heterocycle, wherein said carbocycle and heterocycle are optionally substituted with R$^6$;

R$^6$ is independently selected from —(CH$_2$)$_n$—OH, =O, NH$_2$, —(CH$_2$)$_n$—CN, halogen, C$_{1-6}$ alkyl, —(CH$_2$)$_n$—C(O)OH, —(CH$_2$)$_n$—C(O)OC$_{1-4}$ alkyl, —(CH$_2$)$_n$—OC$_{1-4}$ alkyl, —(CH$_2$)$_n$—C$_{3-6}$ cycloalkyl, —(CH$_2$)$_n$-4- to 10-membered heterocycle, and —O—(CH$_2$)$_n$-4- to 10-membered heterocycle, wherein said cycloalkyl and heterocycle are optionally substituted with R$^{10}$;

R$^7$ is independently selected from H, F, methyl, and ethyl;

R$^8$ is independently selected from H, halogen, CN, NH$_2$, C$_{1-6}$ alkyl, haloalkyl, alkylcarbonyl, alkoxy, haloalkoxy, aryl, C$_{3-6}$ cycloalkyl, and 4-6 membered heterocycle;

Optionally, two adjacent R$^8$ groups are taken together to form a carbocycle or heterocycle comprising carbon atoms and 1-4 heteroatoms selected from N, NH, N(C$_{1-4}$ alkyl), O, and S(O)$_p$, wherein said carbocycle and heterocycle are optionally substituted with OH, NH$_2$, halogen, and C$_{1-6}$ alkyl;

m is an integer independently selected from 0 and 1;

n, at each occurrence, is an integer independently selected from 0, 1, and 2; and p, at each occurrence, is an integer independently selected from 0, 1, and 2;

other variables are as defined in Formula (XI) above.

In another aspect, the present invention provides compounds of Formula (XIII):

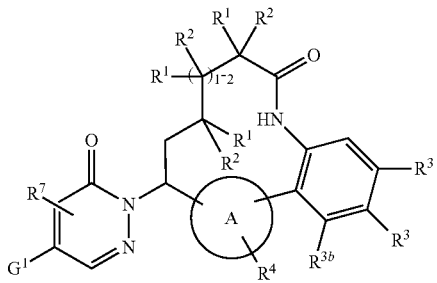

(XIII)

or stereoisomers, tautomers, pharmaceutically acceptable salts, solvates, or prodrugs thereof, within the scope of the second aspect, wherein:

ring A is independently selected from phenyl and a 5- to 6-membered heterocycle;

G$^1$ is independently selected from aryl, C$_{3-6}$cycloalkyl and a 5- to 6-membered heterocycle wherein said aryl, cycloalkyl and heterocycle are substituted with 1-4 R$^8$;

R$^1$ and R$^2$ are independently selected from H, halogen, CF$_3$, C$_{1-6}$ alkyl, and hydroxyl;

R³ is independently selected from H, halogen, haloalkyl, $C_{1-4}$alkyl (optionally substituted with $R^6$), $C_{2-4}$alkenyl (optionally substituted with $R^6$), CN, $NO_2$, —$(CH_2)_n$—$OR^5$, —$(CH_2)_n$—$NR^5R^5$, —$(CH_2)_n$—$C(O)OR^5$, —$(CH_2)_n$—$NHC(O)OR^5$, —$(CH_2)_n$—$NHC(O)R^5$, —$(CH_2)_n$—NHC(N—CN)$NHR^5$, —$(CH_2)_n$—$NHC(NH)NHR^5$, —$(CH_2)_n$—N=$CHNR^5R^5$, —$(CH_2)_n$—$NHC(O)NR^5R^5$, —$(CH_2)_n$—$NHC(O)NR^5R^5$—, —$(CH_2)_n$—$C(O)NR^5R^5$, —$(CH_2)_n$—$NR^9C(S)NR^9C(O)R^5$, —$(CH_2)_n$—$S(O)_pR^{12}$, —$(CH_2)_n$—$S(O)_pNR^5R^5$, —$(CH_2)_n$—$NHS(O)_pNR^5R^5$, —$(CH_2)_n$—$NHS(O)_pR^{12}$, —$(CH_2)_n$—$C_{3-10}$ carbocycle and —$(CH_2)_n$-4- to 10-membered heterocycle, wherein said carbocycle and heterocycle are optionally substituted with $R^6$;

$R^{3b}$ is independently selected from H, F, Cl, CN, C(O)OH, and C(O)O$C_{1-4}$alkyl;

$R^4$ is independently selected from H, OH, F, Cl, Br, $C_{1-6}$ alkyl, $C_{1-6}$ alkoxy, $CF_3$, CN, $C_{3-6}$ cycloalkyl, aryl, and a 5- to 6-membered heterocycle, where said cycloalkyl, aryl and hterecycle are optionally substituted with $R^6$;

$R^5$ is independently selected from H, $C_{1-4}$ alkyl (optionally substituted with halogen, hydroxyl, alkoxy, carboxy, alkoxycarbonyl), —$(CH_2)_n$—$C_{3-10}$ carbocycle and —$(CH_2)_n$-4- to 10-membered heterocycle, wherein said carbocycle and heterocycle are optionally substituted with $R^6$; alternatively, two adjacent $R^5$ groups are taken together to form a carbocycle or heterocycle optionally substituted with $R^6$;

$R^7$ is independently selected from H, F, methyl, and ethyl;

$R^6$ is independently selected from OH, $NH_2$, halogen, $C_{1-6}$ alkyl, —$(CH_2)_n$—C(=O)OH, —$(CH_2)_n$—C(=O)O$C_{1-4}$ alkyl, —$(CH_2)_n$—O$C_{1-4}$ alkyl, =O, —$(CH_2)_n$—$C_{3-6}$ cycloalkyl and —$(CH_2)_n$-4- to 10-membered heterocycle, wherein said cycloalkyl and heterocycle are optionally substituted with $R^{10}$;

$R^8$ is independently selected from H, halogen, CN, $NH_2$, $C_{1-6}$ alkyl, alkylcarbonyl, haloalkyl, alkoxy, haloalkoxy, aryl, $C_{3-6}$ cycloalkyl, and 4-6 membered heterocycle;

Optionally, two adjacent $R^8$ groups are taken together to form a carbocycle or heterocycle comprising carbon atoms and 1-4 heteroatoms selected from N, NH, N($C_{1-4}$ alkyl), O, and S(O)$_p$, wherein said carbocycle and heterocycle are optionally substituted with OH, $NH_2$, halogen, and $C_{1-6}$ alkyl;

n, at each occurrence, is an integer independently selected from 0, 1, and 2; and p, at each occurrence, is an integer independently selected from 0, 1, and 2;

other variables are as defined in Formula (XII) above.

In another aspect, the present invention provides compounds of Formula (XIV):

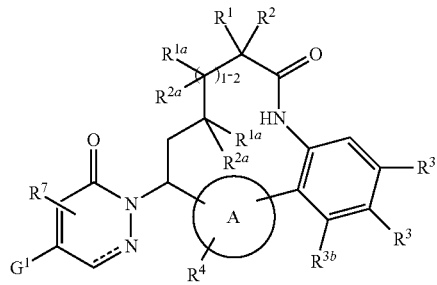

(XIV)

or stereoisomers, tautomers, pharmaceutically acceptable salts, solvates, or prodrugs thereof, wherein:

ring A is selected from phenyl, imidazole, pyridine, pyridazine, pyrimidine, pyridone, and pyridazinone;

$G^1$ is independently selected from phenyl, cyclopropyl, cyclobutyl, cyclopentyl, cyclohexyl, pyrazinyl, pyrimidinyl, pyridazinyl, triazinyl, furyl, thienyl, imidazolyl, thiazolyl, pyrrolyl, oxazolyl, isoxazolyl, pyrazolyl, triazolyl, tetrazolyl, pyridinyl, piperazinyl, piperidinyl, morpholinyl, and oxadiazolyl, each substituted with 1-4 $R^8$;

$R^1$ and $R^2$ are independently selected from H, F, $C_{1-4}$ alkyl, alkoxy, and hydroxyl;

$R^{1a}$ and $R^{2a}$ are independently selected from H, F, and hydroxyl;

$R^3$ is independently selected from H, halogen, haloalkyl, $C_{1-4}$alkyl (optionally substituted with $R^6$), $C_{2-4}$alkenyl (optionally substituted with $R^6$), $C_{2-4}$alkynyl (optionally substituted with $R^6$), CN, $NO_2$, —$(CH_2)_n$—$OR^5$, $NR^5R^5$, —$(CH_2)_n$—$C(O)OR^5$, —$NHC(O)OR^5$, —$NHC(O)R^5$, —$NHC(O)NR^5R^5$, —$NHC(O)NR^5R^5$—, —$C(O)NR^5R^5$, —$(CH_2)_n$—$NHC(N)NHR^5$, —$(CH_2)_n$—NHC(S)NHC(O)$R^5$, —$NHS(O)_2C_{1-4}$alkyl, —$(CH_2)_n$—$C_{3-10}$ carbocycle and —$(CH_2)_n$-4- to 10-membered heterocycle, wherein said carbocycle and heterocycle are optionally substituted with $R^6$; optionally, two adjacent $R^3$ groups form a heterocycle optionally substituted with $R^6$;

$R^{3b}$ is independently selected from H, F, CN, C(O)OH, and C(O)O$C_{1-4}$alkyl;

$R^4$ is independently selected from H, OH, F, Cl, Br, $C_{1-6}$ alkyl, $C_{1-6}$ alkoxy, $CF_3$, CN, $C_{3-6}$ cycloalkyl, aryl, and a 5- to 6-membered heterocycle, where said cycloalkyl, aryl and hterecycle are optionally substituted with $R^6$;

$R^5$ is independently selected from H, $C_{1-4}$ alkyl (optionally substituted with halogen, hydroxyl, alkoxy, carboxy, alkoxycarbonyl), —$(CH_2)_n$—$C_{3-10}$ carbocycle and —$(CH_2)_n$-4- to 10-membered heterocycle, wherein said carbocycle and heterocycle are optionally substituted with $R^6$;

$R^6$ is independently selected from OH, $NH_2$, halogen, $C_{1-6}$ alkyl, —$(CH_2)_n$—C(=O)OH, —$(CH_2)_n$—C(=O)O$C_{1-4}$ alkyl, —$(CH_2)_n$—O$C_{1-4}$ alkyl, =O, $C_{3-6}$ cycloalkyl and 4- to 10-membered heterocycle, wherein said cycloalkyl and heterocycle are optionally substituted with $R^{10}$;

$R^7$ is independently selected from H and methyl;

$R^8$ is independently selected from H, halogen, CN, $NH_2$, $C_{1-6}$ alkyl, alkylcarbonyl, haloalkyl, alkoxy, haloalkoxy, aryl, $C_{3-6}$ cycloalkyl, and 4-6 membered heterocycle;

other variables are as defined in Formula (XII) above.

In another aspect, the present invention provides compounds of Formula (XIV), or stereoisomers, tautomers, pharmaceutically acceptable salts, solvates, or prodrugs thereof, wherein:

ring A is independently selected from

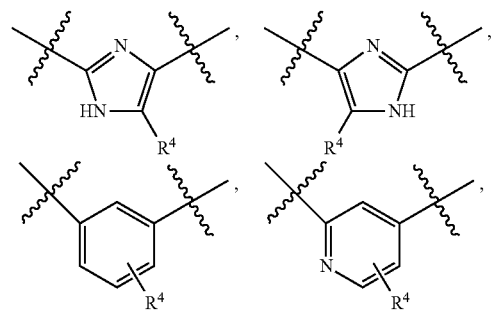

-continued

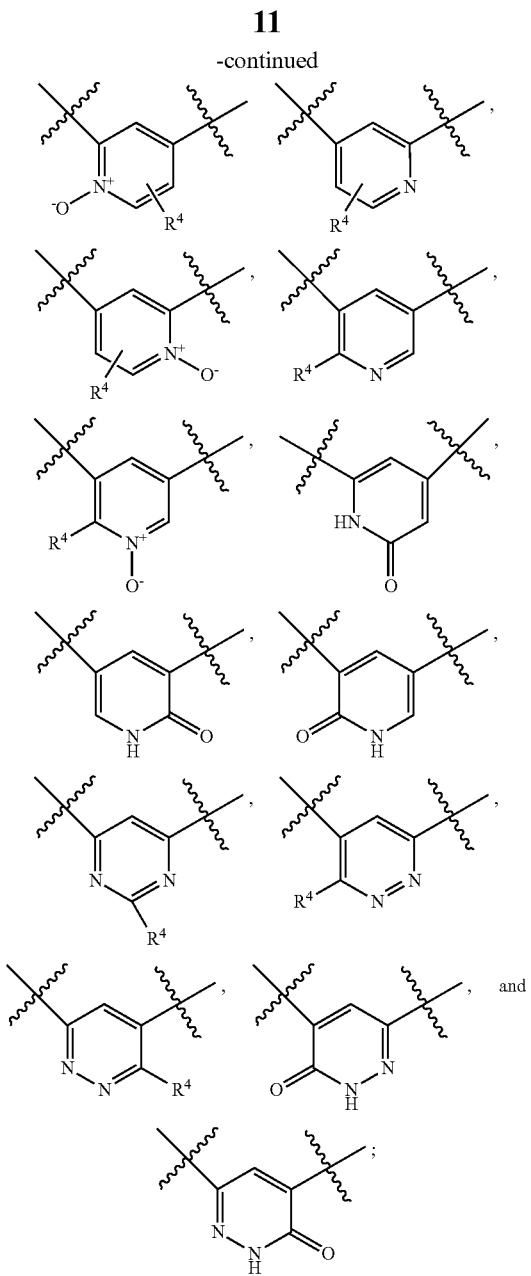

$G^1$ is independently selected from

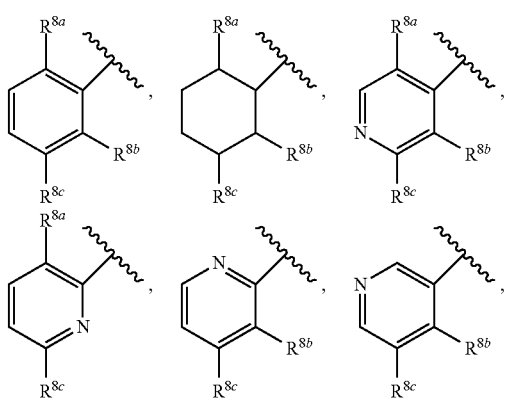

-continued

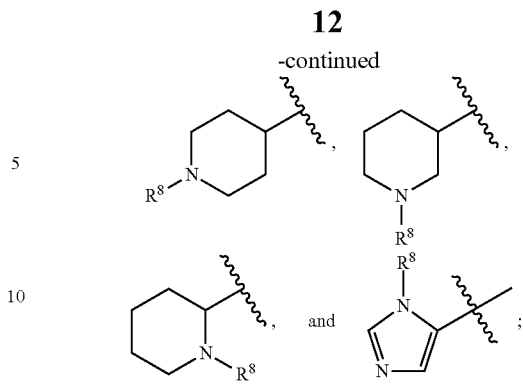

$R^1$ and $R^2$ are independently selected from H, F, methyl, ethyl, isopropyl, and hydroxyl;

$R^{1a}$ and $R^{2a}$ are independently selected from H, F, and OH;

$R^3$ is independently selected from H, F, Cl, Br, I, haloalkyl, $C_{1-4}$alkyl (optionally substituted with $R^6$), $C_{2-4}$alkenyl (optionally substituted with $R^6$), CN, $-(CH_2)_n-OR^5$, $NR^5R^5$, $-(CH_2)_n-C(O)OR^5$, $-NHC(O)OR^5$, $-NHC(O)R^5$, $-NHC(O)NR^5R^5$, $-NHC(O)NR^5R^5-$, $-C(O)NR^5R^5$, $-(CH_2)_n-NHC(S)NHC(O)R^5$, $-NHS(O)_2C_{1-4}$alkyl, $-(CH_2)_n-C_{3-10}$ carbocycle and $-(CH_2)_n$-4- to 10-membered heterocycle, wherein said carbocycle and heterocycle are optionally substituted with $R^6$; optionally, two adjacent $R^3$ groups form a heterocycle optionally substituted with $R^6$;

$R^{3b}$ is independently selected from H, F, CN, C(O)OH, and C(O)OC$_{1-4}$alkyl;

$R^4$ is independently selected from H, OH, F, Cl, Br, $C_{1-6}$ alkyl, $C_{1-6}$ alkoxy, $CF_3$, CN, $C_{3-6}$ cycloalkyl, aryl, and a 5- to 6-membered heterocycle, where said cycloalkyl, aryl and hterecycle are optionally substituted with $R^6$;

$R^5$ is independently selected from H, $C_{1-4}$ alkyl (optionally substituted with halogen, hydroxyl, alkoxy, carboxy, alkoxycarbonyl), $-(CH_2)_n-C_{3-10}$ carbocycle and $-(CH_2)_n$-4- to 10-membered heterocycle, wherein said carbocycle and heterocycle are optionally substituted with $R^6$;

$R^6$ is independently selected from OH, NH$_2$, halogen, $C_{1-6}$ alkyl, $-(CH_2)_n-C(=O)OH$, $-(CH_2)_n-C(=O)OC_{1-4}$ alkyl, $-(CH_2)_n-OC_{1-4}$ alkyl, $=O$, $C_{3-6}$ cycloalkyl and 4- to 10-membered heterocycle, wherein said cycloalkyl and heterocycle are optionally substituted with $R^{10}$;

$R^7$ is independently selected from H and methyl;

$R^8$ is independently selected from H, $C_{1-6}$ alkyl, alkylcarbonyl, haloalkyl, aryl, $C_{3-6}$ cycloalkyl, and 4-6 membered heterocycle.

$R^{8a}$ is independently selected from H, halogen, CN, $C_{1-3}$ alkyl, $C(O)C_{1-4}$ alkyl, $OC_{1-3}$alkyl, $CF_3$, $OCHF_2$, $NHC(O)$ $C_{1-4}$ alkyl, aryl, $C_{3-6}$ cycloalkyl, and 4-6 membered heterocycle;

$R^{8b}$ is independently selected from H and halogen; and $R^{8c}$ is independently selected from H, halogen, CN, $C_{1-4}$ alkyl, alkoxy, NH$_2$ and haloalkoxy;

other variables are as defined in Formula (XIV) above.

In another aspect, the present invention provides compounds of Formula (XIV), or stereoisomers, tautomers, pharmaceutically acceptable salts, solvates, or prodrugs thereof, wherein:

$R^3$ is independently selected from H, F, Cl, Br, I, $C_{2-4}$alkenyl (optionally substituted with $R^6$), CN, $-(CH_2)_n-OR^5$, $NR^5R^5$, $-(CH_2)_n-C(O)OR^5$, $-NHC(O)OR^5$, $-NHC(O)R^5$, $-NHC(O)NR^5R^5$, $-C(O)NR^5R^5$, $-NHC(S)NHC(O)R^5$, $-NHS(O)_2C_{1-4}$alkyl, $-(CH_2)_n-C_{3-10}$ carbocycle and —(CH$_2$)$_n$-4-6 membered heterocycle comprising carbon atoms and 1-4 heteroatoms selected from N, O, and S(O)$_p$, wherein said carbocycle and heterocycle are optionally substituted with R$^6$;

R$^{3b}$ is independently selected from H, F, CN, C(O)OH, and C(O)OC$_{1-4}$alkyl;

R$^5$ is independently selected from H, C$_{1-4}$ alkyl (optionally substituted with halogen, hydroxyl, alkoxy, carboxy, alkoxycarbonyl), —(CH$_2$)$_n$—C$_{3-10}$ carbocycle and —(CH$_2$)$_n$-4-6 membered heterocycle comprising carbon atoms and 1-4 heteroatoms selected from N, O, and S(O)$_p$, wherein said carbocycle and heterocycle are optionally substituted with R$^6$; and R$^6$ is independently selected from OH, NH$_2$, halogen, C$_{1-6}$ alkyl, —(CH$_2$)$_n$—C(=O)OH, —(CH$_2$)$_n$—C(=O)OC$_{1-4}$ alkyl, —(CH$_2$)$_n$—OC$_{1-4}$ alkyl, =O, C$_{3-6}$ cycloalkyl, 4- to 10-membered heterocycle, —O-4- to 10-membered heterocycle, wherein said cycloalkyl and heterocycle are optionally substituted with R$^{10}$;

other variables are as defined in Formula (XIV) above.

In another aspect, the present invention provides compounds of Formula (XIV), or stereoisomers, tautomers, pharmaceutically acceptable salts, solvates, or prodrugs thereof, wherein:

R$^3$ is independently selected from H, F, Cl, Br, I, C$_{2-4}$alkenyl (optionally substituted C(O)OH), CN, —(CH$_2$)$_n$—OR$^5$, NR$^5$R$^5$, —(CH$_2$)$_n$—C(O)OR$^5$, —NHC(O)OR$^5$, —NHC(O)R$^5$, —NHC(O)NR$^5$R$^5$, —C(O)NR$^5$R$^5$, —NHC(S)NHC(O)R$^5$, —NHS(O)$_2$C$_{1-4}$alkyl, and —(CH$_2$)$_n$-4-6 membered heterocycle selected from triazolyl and tetrazolyl, each optionally substituted with R$^6$;

R$^{3b}$ is independently selected from H, F, CN, C(O)OH, and C(O)OC$_{1-4}$alkyl;

R$^5$ is independently selected from H, C$_{1-4}$ alkyl (optionally substituted with halogen, hydroxyl, alkoxy, carboxy, alkoxycarbonyl), —(CH$_2$)$_n$—C$_{3-10}$ carbocycle and —(CH$_2$)$_n$-4-6 membered heterocycle selected from pyrazinyl, pyrimidinyl, pyrazinyl, pyridazinyl, triazinyl, furyl, thienyl, imidazolyl, thiazolyl, pyrrolyl, oxazolyl, isoxazolyl, pyrazolyl, triazolyl, tetrazolyl, pyridinyl, piperazinyl, piperidinyl, morpholinyl, oxanyl, and oxadiazolyl, each optionally substituted with R$^6$; and R$^6$ is independently selected from OH, —(CH$_2$)$_n$—OH, NH$_2$, halogen, C$_{1-6}$ alkyl, —(CH$_2$)$_n$—C(=O)OH, —(CH$_2$)$_n$—C(=O)OC$_{1-4}$ alkyl, —(CH$_2$)$_n$—OC$_{1-4}$ alkyl, =O, C$_{3-6}$ cycloalkyl and 4- to 10-membered heterocycle, wherein said cycloalkyl and heterocycle are optionally substituted with R$^{10}$;

other variables are as defined in Formula (XIV) above.

In another aspect, the present invention provides compounds of Formula (XIV), or stereoisomers, tautomers, pharmaceutically acceptable salts, or prodrugs thereof, wherein:

R$^3$ is independently selected from H, F, Cl, Br, I, C$_{2-4}$alkenyl (optionally substituted C(O)OH), CN, —(CH$_2$)$_n$—OR$^5$, NHR$^5$, —(CH$_2$)$_n$—C(O)OR$^5$, —NHC(O)OR, —NHC(O)R$^5$, —NHC(O)NR$^5$R$^5$, —C(O)NR$^5$R$^5$, —NHC(S)NHC(O)R$^5$, —NHS(O)$_2$C$_{1-4}$alkyl, and —(CH$_2$)$_n$-4-6 membered heterocycle selected from triazolyl and tetrazolyl, each optionally substituted with R$^6$;

R$^5$ is independently selected from H, C$_{1-4}$ alkyl, —(CH$_2$)$_{1-3}$—OH, —(CH$_2$)$_{1-3}$—OC$_{1-4}$ alkyl, —(CH$_2$)$_{1-3}$—C(O)OH, —(CH$_2$)$_{1-3}$—C(O)OC$_{1-4}$ alkyl, —(CH$_2$)$_{1-3}$—NH$_2$, —(CH$_2$)$_{1-3}$—NHC$_{1-4}$ alkyl, —(CH$_2$)$_{1-3}$—N(C$_{1-4}$ alkyl)$_2$, —(CH$_2$)$_n$—C$_{3-10}$ carbocycle and —(CH$_2$)$_n$-4-6 membered heterocycle selected from

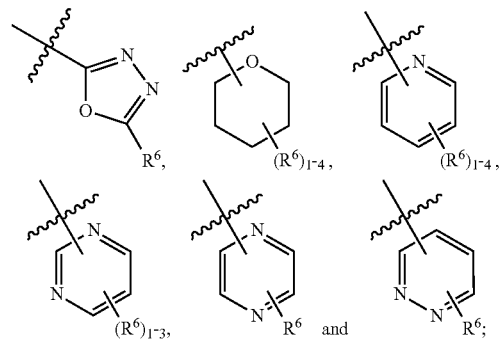

R$^6$ is independently selected from H, —(CH$_2$)$_n$—OH, NH$_2$, halogen, C$_{1-6}$ alkyl, —(CH$_2$)$_n$—CN, —(CH$_2$)$_n$—C(=O)OH, —(CH$_2$)$_n$—C(=O)OC$_{1-4}$ alkyl, —(CH$_2$)$_n$—OC$_{1-4}$ alkyl, =O, C$_{3-6}$ cycloalkyl, 4- to 10-membered heterocycle, —O-4- to 10-membered heterocycle wherein said cycloalkyl and heterocycle are optionally substituted with R$^{10}$;

other variables are as defined in Formula (XIV) above.

In another aspect, the present invention provides compounds of Formula (XV):

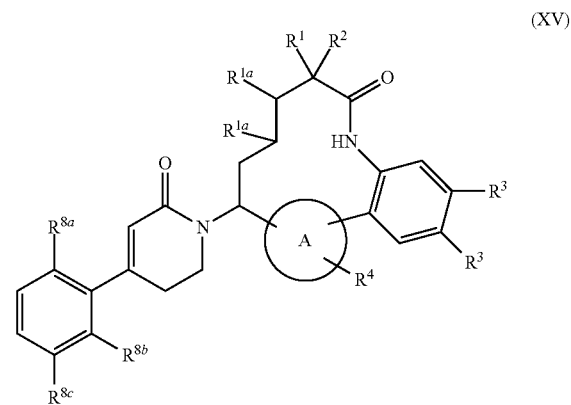

or stereoisomers, tautomers, pharmaceutically acceptable salts, solvates, or prodrugs thereof, within the scope of the second aspect, wherein:

ring A is independently selected from

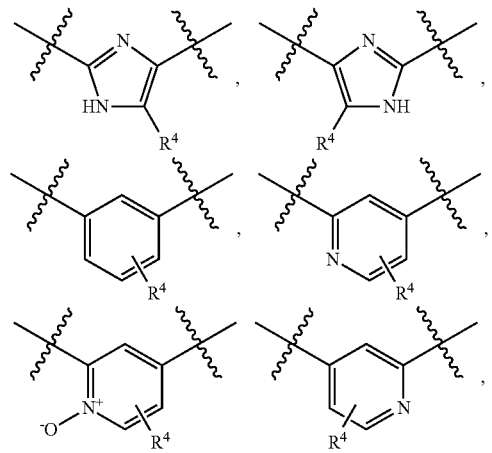

-continued

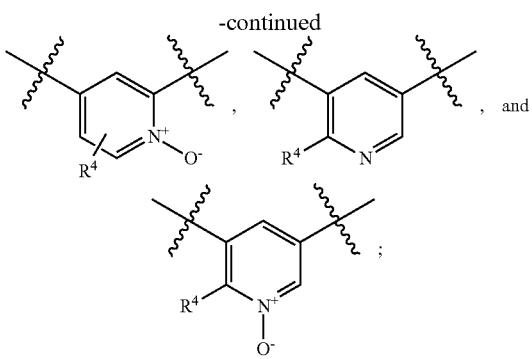

, and ;

R[1] and R[2] are independently selected from H, F, $C_{1-4}$ alkyl, alkoxy, and hydroxyl;

R[1a], at each occurrence, is independently selected from H, F, and hydroxyl;

R[3] is independently selected from H, F, Cl, Br, I, $C_{2-4}$alkenyl (optionally substituted C(O)OH), CN, —(CH$_2$)$_n$—OR[5], NHR[5], —(CH$_2$)$_n$—C(O)OR[5], —NHC(O)OR[5], —NHC(O)R[5], —NHC(O)NR[5]R[5], —C(O)NR[5]R[5], —NHC(S)NHC(O)R[5], —NHS(O)$_2$C$_{1-4}$alkyl, and —(CH$_2$)$_n$-4-6 membered heterocycle selected from triazolyl and tetrazolyl, each optionally substituted with R[6];

R[4] is independently selected from H, OH, F, OC$_{1-4}$ alkyl, $C_{1-4}$ alkyl, CN, $C_{3-6}$ cycloalkyl, aryl, and a 5- to 6-membered heterocycle, where said cycloalkyl, aryl and hterecycle are optionally substituted with R[6];

R[5] is independently selected from H, $C_{1-4}$ alkyl (optionally substituted with halogen, hydroxyl, alkoxy, carboxy, alkoxycarbonyl), —(CH$_2$)$_n$—$C_{3-10}$ carbocycle and —(CH$_2$)$_n$-4- to 10-membered heterocycle, wherein said carbocycle and heterocycle are optionally substituted with R[6];

R[6] is independently selected from OH, NH$_2$, halogen, $C_{1-6}$ alkyl, $C_{3-6}$ cycloalkyl, —(CH$_2$)$_n$—C(=O)OH, —(CH$_2$)$_n$—C(=O)OC$_{1-4}$ alkyl, —(CH$_2$)$_n$—OC$_{1-4}$ alkyl, =O, $C_{3-6}$ cycloalkyl, 4- to 10-membered heterocycle, and —O-4- to 10-membered heterocycle wherein said cycloalkyl and heterocycle are optionally substituted with R[10];

R[8a] is independently selected from H, F, Cl, Br, CN, OCH$_3$, CH$_3$, C(O)CH$_3$, CF$_3$, OCHF$_2$, NHC(O)C$_{1-4}$ alkyl, aryl, $C_{3-6}$ cycloalkyl, and 4-6 membered heterocycle;

R[8b] is independently selected from H and F;

R[8c] is independently selected from H, F, Cl, and OCH$_3$; and n, at each occurrence, is an integer independently selected from 0, 1, and 2;

other variables are as defined in Formula (XIV) above.

In another aspect, the present invention provides compounds of Formula (XV), or stereoisomers, tautomers, pharmaceutically acceptable salts, solvates, or prodrugs thereof, wherein:

R[8a] is independently selected from H, F, Cl, Br, CN, OCH3, CH3, C(O)CH$_3$, CF3, OCHF$_2$, NHC(O)C$_{1-4}$ alkyl, phenyl, $C_{3-6}$ cycloalkyl, and 4-6 membered heterocycle selected from pyrazole, triazole, tetrazole, pyridine, each optionally substituted with R[10];

R[8b] is independently selected from H and F;

R[8c] is independently selected from H, F, Cl, and OCH$_3$;

other variables are as defined in Formula (XIV) above.

In another aspect, the present invention provides compounds of Formula (XI), or stereoisomers, tautomers, pharmaceutically acceptable salts, solvates, or prodrugs thereof, wherein:

ring A is independently selected from

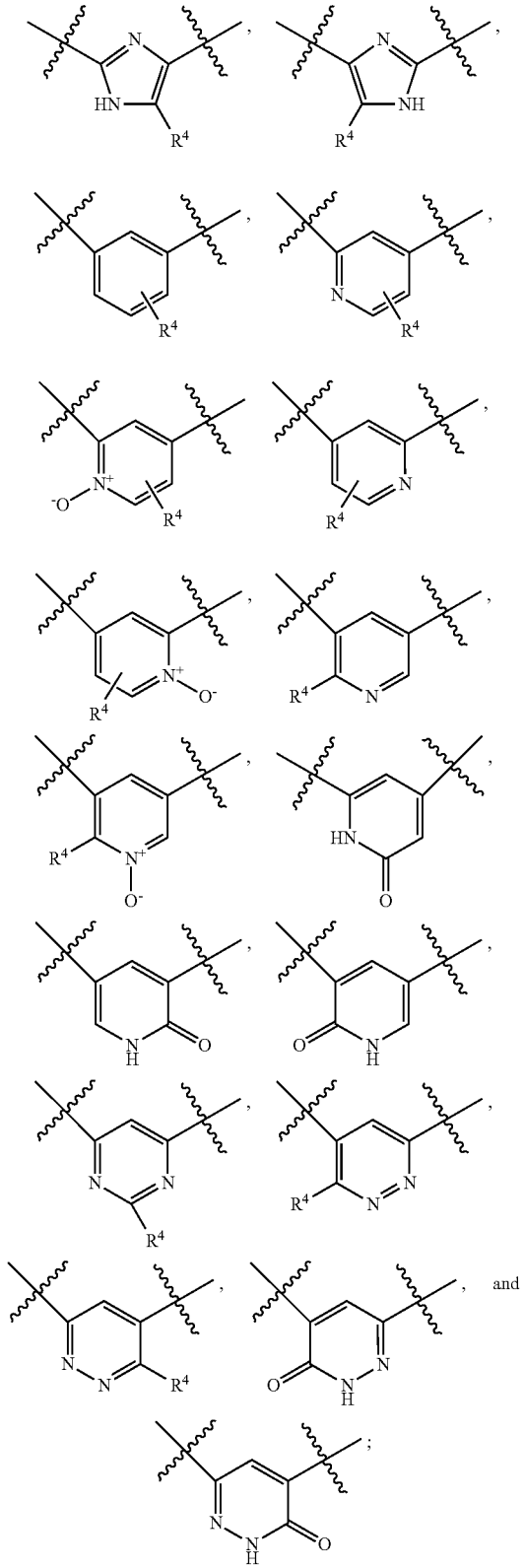

ring B is a 5- to 10-membered heterocycle substituted with 1-4 R[3];

G¹ is independently selected from

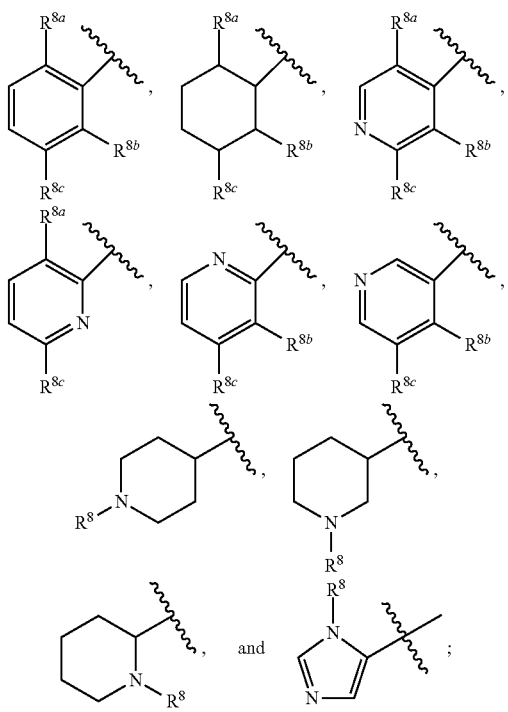

R¹ and R² are independently selected from H, F, methyl, ethyl, isopropyl, and hydroxyl;

R³ is independently selected from H, =O, halogen, haloalkyl, $C_{1-4}$alkyl optionally substituted with $R^6$, $C_{2-4}$alkenyl optionally substituted with $R^6$, $C_{2-4}$alkynyl optionally substituted with $R^6$, CN, $NO_2$, —$(CH_2)_n$—$OR^5$, —$(CH_2)_n$—$NR^5R^5$, —$(CH_2)_n$—$C(O)OR^5$, —$(CH_2)_n$—$NR^9C(O)OR^5$, —$(CH_2)_n$—$NR^9C(O)R^5$, —$(CH_2)_n$—$NR^9C(N$—$CN)NHR^5$, —$(CH_2)_n$—$NR^9C(NH)NHR^5$, —$(CH_2)_nN$=$CR^9NR^5R^5$, —$(CH_2)_n$—$NR^9C(O)NR^5R^5$, —$(CH_2)_n$—$C(O)NR^5R^5$, —$(CH_2)_n$—$NR^9C(S)NR^9C(O)R^5$, —$(CH_2)_n$—$S(O)_pR^{12}$, —$(CH_2)_n$—$S(O)_pNR^5R^5$, —$(CH_2)_n$—$NR^9S(O)_pNR^5R^5$, —$(CH_2)_n$—$NR^9S(O)_pR^{12}$, —$(CH_2)_n$—$C_{3-10}$ carbocycle and —$(CH_2)_n$-4- to 10-membered heterocycle, wherein said carbocycle and heterocycle are optionally substituted with $R^6$; optionally, two adjacent $R^3$ groups on the carbocycle and heterocycle may form a ring optionally substituted with $R^6$.

R⁴ is independently selected from H, OH, halogen, CN, $C_{1-4}$ alkyl, $C_{1-4}$ haloalkyl, $C_{1-4}$ alkoxy, —$C(O)NH_2$, —$C(O)NH(C_{1-4}$ alkyl), —$C(O)N(C_{1-4}$ alkyl)$_2$, and $C_{3-6}$ cycloalkyl, aryl, and a 5- to 6-membered heterocycle, where said cycloalkyl, aryl and hterecycle are optionally substituted with $R^6$;

R⁵ is independently selected from H, $C_{1-4}$ alkyl (optionally substituted with halogen, hydroxyl, alkoxy, carboxy, alkoxycarbonyl, amino, substituted amino), $C_{3-10}$ carbocycle and 4- to 10-membered heterocycle, wherein said carbocycle and heterocycle are optionally substituted with $R^6$; alternatively, $R^5$ and $R^5$ together with the nitrogen atom to which they are both attached form a heterocyclic ring optionally substituted with $R^6$;

R⁶ is independently selected from OH, =O, —$(CH_2)_nNH_2$, —$(CH_2)_nCN$, halogen, $C_{1-6}$ alkyl, —$(CH_2)_n$—$C(=O)OH$, —$(CH_2)_n$—$C(=O)OC_{1-4}$ alkyl, —$(CH_2)_n$—$OC_{1-4}$ alkyl, —$(CH_2)_n$—$C_{3-10}$ carbocycle, —$(CH_2)_n$-4- to 10-membered heterocycle, and —O-4- to 10-membered heterocycle (optionally substituted with $R^1$), wherein said carbocycle and heterocycle are optionally substituted with $R^{10}$;

R⁷ is independently selected from H, F, methyl, and ethyl;

R⁸ is independently selected from H, $C_{1-6}$ alkyl, alkylcarbonyl, haloalkyl, aryl, $C_{3-6}$ cycloalkyl, and 4-6 membered heterocycle.

$R^{8a}$ is independently selected from H, halogen, CN, $C_{1-3}$ alkyl, $C(O)C_{1-4}$ alkyl, $C_{1-3}$alkyl, $CF_3$, $OCHF_2$, $NHC(O)C_{1-4}$ alkyl, aryl, $C_{3-6}$ cycloalkyl, and 4-6 membered heterocycle;

$R^{8b}$ is independently selected from H and halogen; and $R^{8c}$ is independently selected from H, halogen, CN, $C_{1-4}$ alkyl, alkoxy, $NH_2$ and haloalkoxy;

$R^{10}$ is independently selected from $C_{1-6}$ alkyl optionally substituted with $R^{11}$, $C_{2-6}$ alkenyl, $C_{2-6}$ alkynyl, —$(CH_2)_n$—$C_{3-6}$ cycloalkyl, F, Cl, Br, CN, $NO_2$, =O, $CO_2H$, —$(CH_2)_n$—$OC_{1-5}$ alkyl, —$(CH_2)_nOR^{11}$, and —$(CH_2)_n$—$NR^{11}R^{11}$;

$R^{11}$, at each occurrence, is independently selected from H, $C_{1-5}$ alkyl, $C_{3-6}$ cycloalkyl, and phenyl, or $R^{11}$ and $R^{11}$ together with the nitrogen atom to which they are both attached form a heterocyclic ring optionally substituted with $C_{1-4}$alkyl;

$R^{12}$ is $C_{1-6}$ alkyl optionally substituted with $R^{11}$;

m is an integer independently selected from 0 and 1;

n, at each occurrence, is an integer independently selected from 0, 1, 2, 3, and 4;

p, at each occurrence, is an integer independently selected from 0, 1, and 2;

other variables are as defined in Formula (XI) above.

In another aspect, the present invention provides compounds of Formula (XI), or stereoisomers, tautomers, pharmaceutically acceptable salts, solvates, or prodrugs thereof, wherein:

ring B is selected from

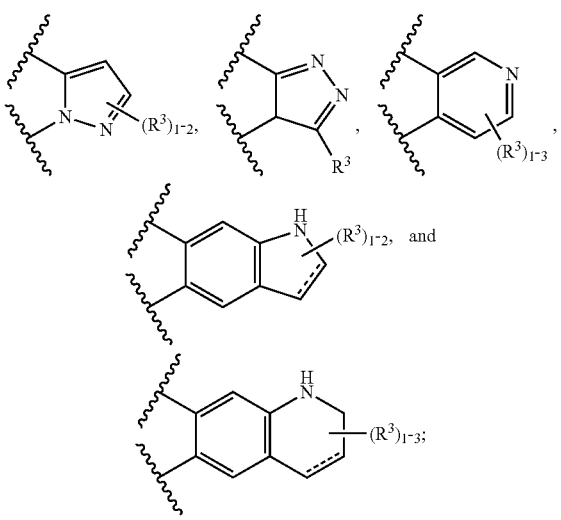

- - - is an optional bond;

R³ is independently selected from H, =O, halogen, $C_{1-4}$alkyl optionally substituted with $R^6$, —$OR^5$, —$NR^5R^5$, —$C(O)OR^5$, —$NR^9C(O)OR^5$, —$(CH_2)_n$—$NR^9C(O)R^5$, —$(CH_2)_n$—$C(O)NR^5R^5$, —$S(O)_pNR^5R^5$, and $C_{3-10}$ carbocycle; and R⁵ is independently selected from H and $C_{1-4}$ alkyl;

other variables are as defined in Formula (XI) above.

In one embodiment, G¹ is independently selected from the group consisting of

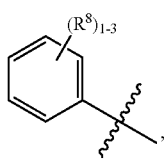

wherein $R^8$ is, independently at each occurrence, selected from the group consisting of H, halogen, CN, $C_{1-6}$ alkyl, haloalkyl, alkoxy, haloalkoxy, and 4-6 membered heterocycle.

In another embodiment, $G^1$ is

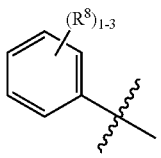

wherein $R^8$ is, independently at each occurrence, selected from the group consisting of H, halogen, CN, methyl, ethyl, $CF_3CHF_2$, OMe, OEt, $OCF_3$, $OCHF_2$, aryl, $C_{3-6}$ cycloalkyl, and 4-6 membered heterocycle.

In another embodiment, $G^1$ is

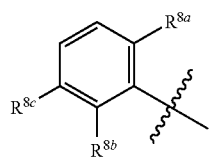

and selected from the group consisting of

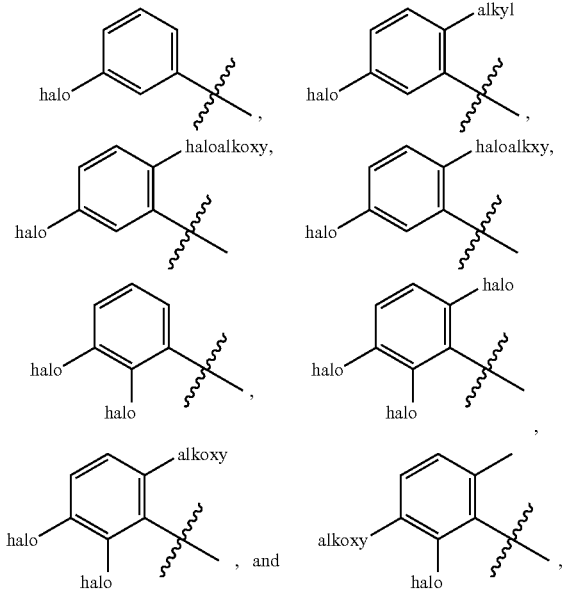

In another embodiment, $G^1$ is

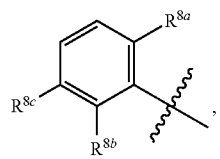

wherein $R^{8a}$, $R^{8b}$, and $R^{8c}$ are independently selected from the group consisting of H, F, Cl, $OCH_3$, $CF_3$ and $OCHF_2$.

In another embodiment, $R^{8a}$ is independently selected from the group consisting of H, F, $OCH_3$, $OCHF_2$, and 4-6 membered heterocycle.

In another embodiment, $R^{8b}$ is independently selected from the group consisting of H, F and Cl.

In another embodiment, $R^{8b}$ is independently selected from the group consisting of H and F.

In another embodiment, $R^{8c}$ is Cl.

In another embodiment, $G^1$

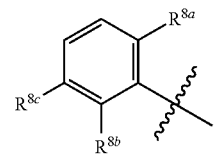

and selected from the group consisting of

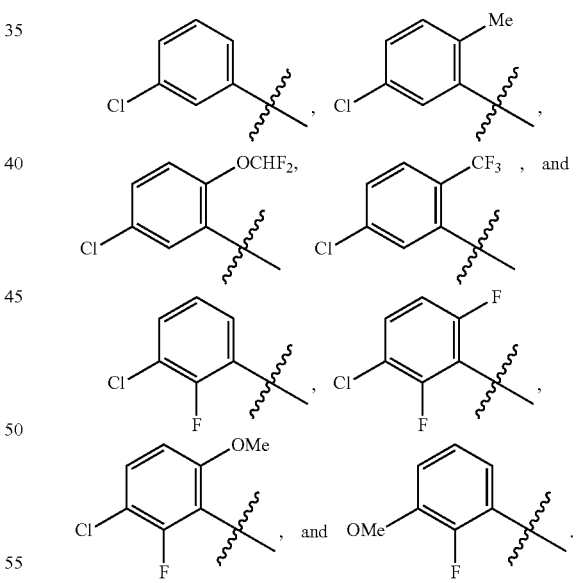

In another embodiment, $G^1$ is

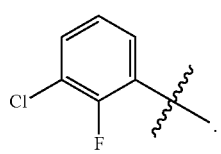 [SMILES: *c1cccc(Cl)c1F]

In one embodiment, the present invention provides compounds of Formulae (X), (XI), (XII), (XIIa), (XIII), (XIV), and (XV) or stereoisomers, tautomers, pharmaceutically acceptable salts, solvates, or prodrugs thereof, wherein ring A is independently selected from the group consisting of imidazole, oxadiazole, pyridine, pyridinone, pyridazine, pyridazinone, and phenyl.

In another embodiment,

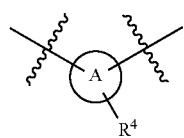

is independently selected from the group consisting of

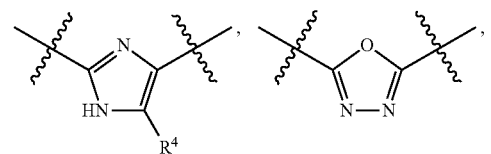

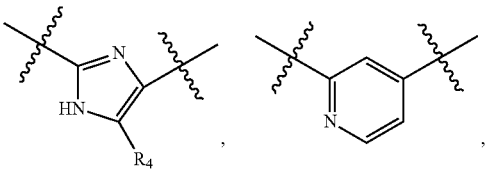

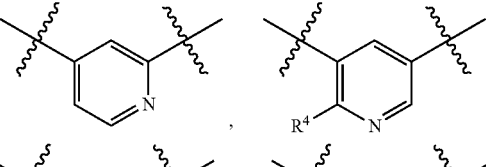

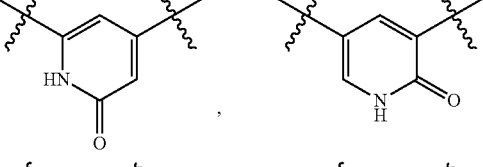

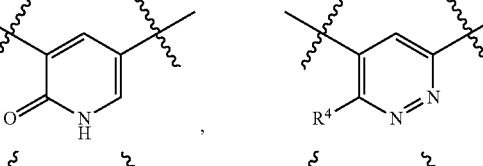

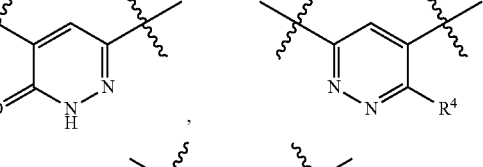

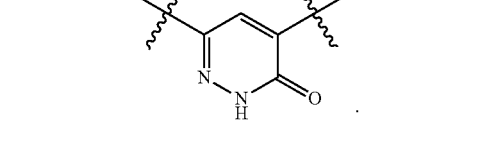

, and

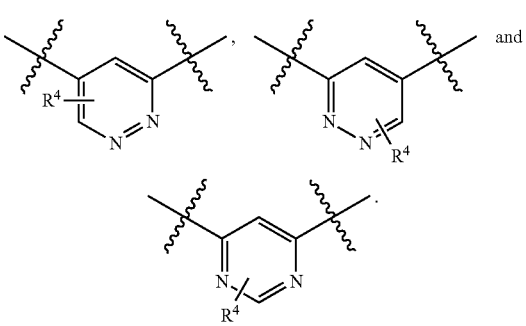

In another embodiment,

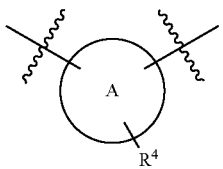

is independently selected from the group consisting of

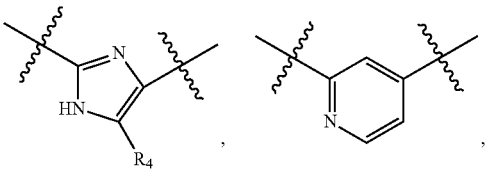

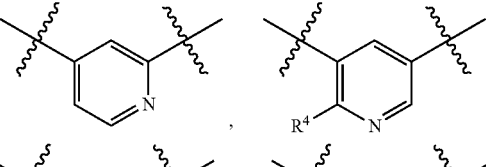

, and

-continued

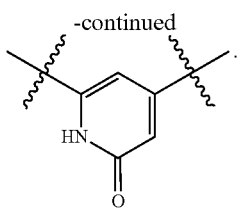

In still another embodiment,

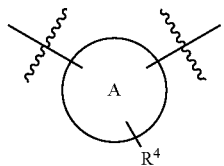

is independently selected from the group consisting

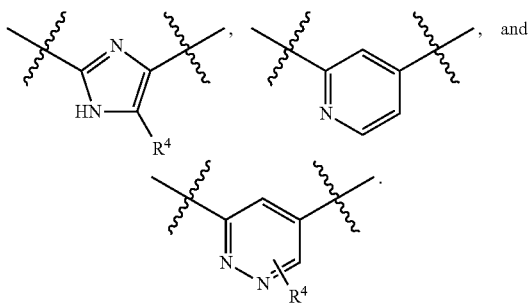
and

In another embodiment,

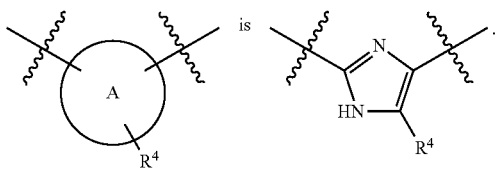

In another embodiment,

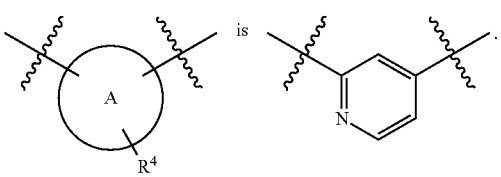

In another embodiment,

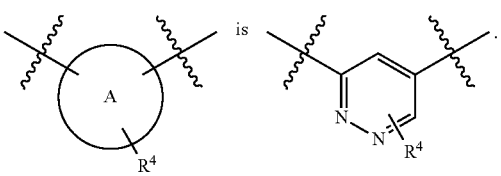

In another embodiment,

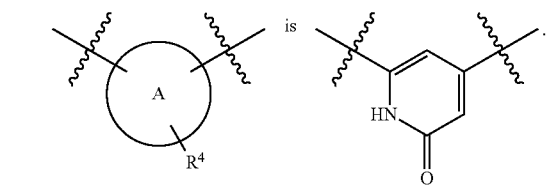

In another embodiment,

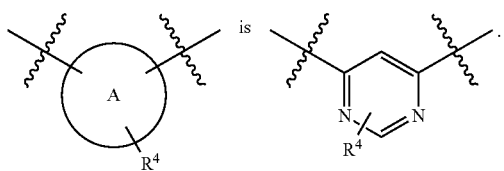

In another embodiment, $R^1$ is independently selected from the group consisting of H, OH, and $C_{1-4}$ alkyl.

In another embodiment, $R^1$ is independently selected from the group consisting of H and methyl, ethyl, and isopropyl.

In one embodiment, $R^2$ is, independently at each occurrence, selected from the group consisting of H and $C_{1-4}$ alkyl.

In another embodiment, $R^2$ is, independently at each occurrence, selected from the group consisting of H and methyl.

In another embodiment, one of $R^1$ and $R^2$ is H and the other is methyl;

In another embodiment, $R^1$ and $R^2$ together are =O;

In one embodiment, $R^3$ is independently selected from H, NO, $NO_2$, =O, halogen, haloalkyl, $C_{1-4}$alkyl (optionally substituted with $R^6$), $C_{2-4}$alkenyl (optionally substituted with $R^6$), $C_{2-4}$alkynyl (optionally substituted with $R^6$), CN, $NO_2$, —$(CH_2)_n$—$OR^5$, —$(CH_2)_n$—$NR^5R^5$, —$(CH_2)_n$—C(O)$OR^5$, —$(CH_2)_n$—$NR^9C(O)OR^5$, —$(CH_2)_n$—$NR^9C(O)R^5$, —$(CH_2)_n$—$NR^9C(O)C(O)R^5$, —$(CH_2)_n$—$NR^9C(N-CN)NHR^5$, —$(CH_2)_n$—$NR^9C(NH)NHR^5$, —$(CH_2)_n$—N=$CR^9NR^5R^5$, —$(CH_2)_n$—$NR^9C(O)NR^5R^5$, —$(CH_2)_n$—$NR^9C(O)NR^5R^5$—, —$(CH_2)_n$—C(O)$NR^5R^5$, —$(CH_2)_n$—$NR^9(S)NR^9C(O)R$, —$(CH_2)_n$—$S(O)_pR^{12}$, —$(CH_2)_n$—$S(O)_pNR^5R^5$, —$(CH_2)_n$—$NR^9S(O)_pNR^5R^5$, —$(CH_2)_n$—$NR^9S(O)_pR^{12}$, —$(CH_2)_n$—$C_{3-10}$ carbocycle and —$(CH_2)_n$-4-10 membered heterocycle, wherein said carbocycle and heterocycle are optionally substituted with $R^6$; optionally, two adjacent $R^3$ groups on the carbocycle and heterocycle may form a ring optionally substituted with $R^6$; $R^5$ is independently selected from H, $C_{1-4}$ alkyl (optionally substituted with halogen, hydroxyl, alkoxy, carboxy, alkoxycarbonyl), —$(CH_2)_n$—$C_{3-10}$ carbocycle and —$(CH_2)_n$-4-10 membered heterocycle, wherein said carbocycle and heterocycle are optionally substituted with $R^6$; alternatively, $R^5$ and $R^5$ together with the nitrogen atom to which they are both attached form a heterocyclic ring optionally substituted with $R^6$.

In another embodiment, $R^3$ is $NHR^5$; $R^5$ is independently selected from H, $C_{1-4}$ alkyl (optionally substituted with halogen, hydroxyl, alkoxy, carboxy, alkoxycarbonyl), —$(CH_2)_n$—$C_{3-10}$ carbocycle and —$(CH_2)_n$-4-10 membered heterocycle, wherein said carbocycle and heterocycle are optionally substituted with $R^6$.

In another embodiment, $R^3$ is $NHR^5$; $R^5$ is $C_{1-4}$ alkyl substituted with halogen, hydroxyl, alkoxy, carboxy, alkoxycarbonyl.

In another embodiment $R^3$ is independently selected from the group consisting of H, halogen, NHC(O)O—$C_{1-4}$ alkyl, CN, OH, O—$C_{1-4}$ alkyl; $CF_3$, $CO_2H$, $CO_2$—$C_{1-4}$ alkyl, —$CH_2CO_2H$, —$(CH_2)_2CO_2H$, —$CH_2CO_2(C_{1-4}$ alkyl), —$(CH_2)_2CO_2(C_{1-4}$ alkyl), $NH_2$, —$CH_2NH_2$, —$NHCO(C_{1-4}$ alkyl), —$NHCO_2(CH_2)_2O(C_{1-4}$ alkyl), —$NHCO_2(CH_2)_{1-3}O$ ($C_{1-4}$ alkyl), $NHCO_2CH_2CH(C_{1-4}$ alkyl)$O(C_{1-4}$ alkyl), —$NHCO_2(CH_2)_{1-2}OH$, —$NHCO_2CH_2CO_2H$, —$CH_2NHCO_2(C_{1-4}$ alkyl), —$NHC(O)NH(C_{1-4}$ alkyl), —$NHC(O)N(C_{1-4}$ alkyl)$_2$, $NHC(O)NH(C_{1-4}$ alkyl)N[5- to 6-membered heterocycle)], —$NHSO_2(C_{1-4}$ alkyl), —$CONH_2$, —$CONH(C_{1-4}$ alkyl), —$CON(C_{1-4}$ alkyl)$_2$, and —$CH_2CONH_2$.

In another embodiment, $R^3$ is independently selected from the group consisting of H, halogen, NHC(O)O—$C_{1-4}$ alkyl, $CONH_2$, $CO_2$—$C_{1-4}$ alkyl, COOH, CN, OH, and O—$C_{1-4}$ alkyl.

In another embodiment, $R^3$ is $NHC(O)OR^5$, $R^5$ is $C_{1-4}$ alkyl substituted with halogen, hydroxyl, alkoxy, carboxy, alkoxycarbonyl, amine and substituted amine.

In another embodiment, the present invention provides compounds of Formula (XII):

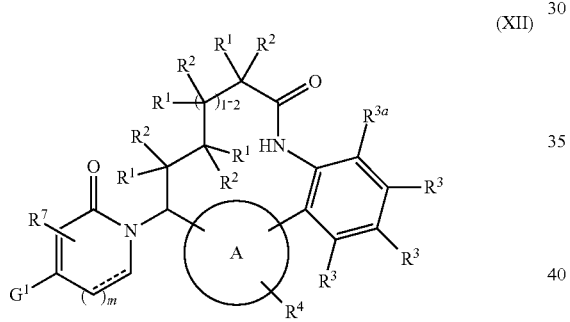

(XII)

or stereoisomers, tautomers, pharmaceutically acceptable salts, solvates, or prodrugs thereof, wherein:

ring A is independently selected from

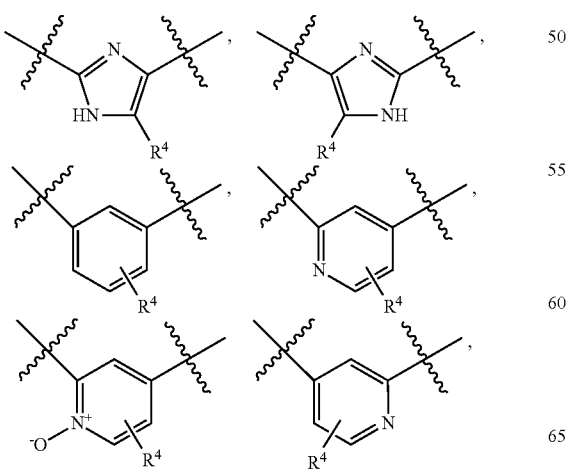

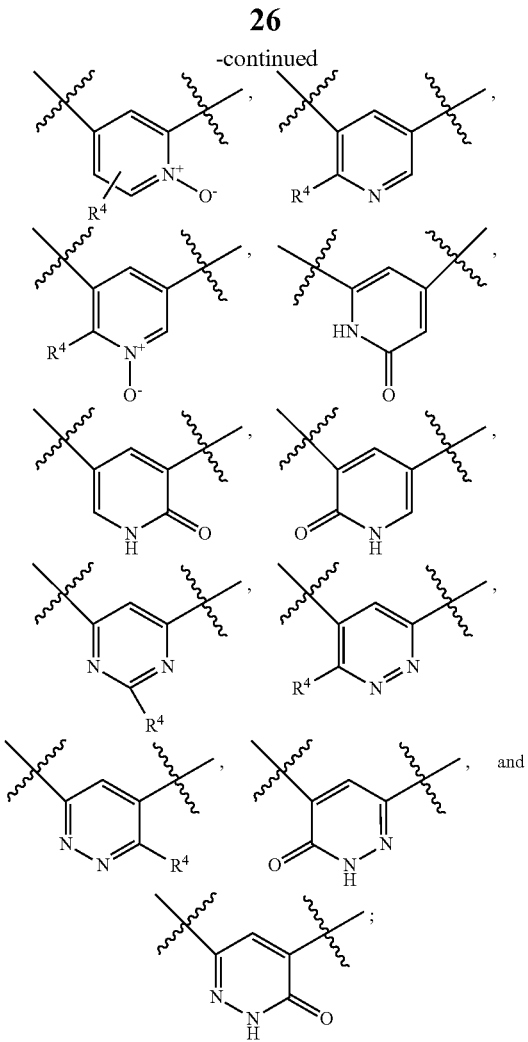

ring B is independently selected from a 6-membered aryl and a 5- to 10-membered heterocycle, wherein said aryl and heterocycle are substituted with 1-4 $R^3$;

$G^1$ is

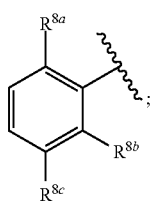

$R^1$ and $R^2$ are independently selected from H, F, methyl, ethyl, isopropyl, and hydroxyl;

$R^3$ is independently selected from H, =O, halogen, haloalkyl, $C_{1-4}$alkyl optionally substituted with $R^6$, $C_{2-4}$alkenyl optionally substituted with $R^6$, $C_{2-4}$alkynyl optionally substituted with $R^6$, CN, $NO_2$, —$(CH_2)_n$—$OR^5$, —$(CH_2)_n$—$NR^5R^5$, —$(CH_2)_n$—$C(O)OR^5$, —$(CH_2)_n$—$NR^9C(O)OR^5$, —$(CH_2)_n$—$NR^9C(O)R^5$, —$(CH_2)_n$—$NR^9C(N$—$CN)NHR^5$, —$(CH_2)_n$—$NR^9C(NH)NHR^5$, —$(CH_2)_nN$=$CR^9NR^5R^5$, —$(CH_2)_n$—$NR^9C(O)NR^5R^5$, —$(CH_2)_n$—$C(O)NR^5R^5$, —$(CH_2)_n$—$NR^9C(S)NR^9C(O)R^5$, —$(CH_2)_n$—$S(O)_pR^{12}$, —$(CH_2)_n$—$S(O)_pNR^5R^5$, —$(CH_2)_n$—$NR^9S(O)_pNR^5R^5$, —$(CH_2)_n$—$NR^9S(O)_pR^{12}$, —(CH$_2$)$_n$—C$_{3-10}$ carbocycle and —(CH$_2$)$_n$-4- to 10-membered heterocycle, wherein said carbocycle and heterocycle are optionally substituted with R$^6$; optionally, two adjacent R$^3$ groups on the carbocycle and heterocycle may form a ring optionally substituted with R$^6$.

R$^4$ is independently selected from H, OH, halogen, CN, C$_{1-4}$ alkyl, C$_{1-4}$ haloalkyl, C$_{1-4}$ alkoxy, —C(O)NH$_2$, —C(O)NH(C$_{1-4}$ alkyl), —C(O)N(C$_{1-4}$ alkyl)$_2$, C$_{3-6}$ cycloalkyl, aryl, and a 5- to 6-membered heterocycle, where said cycloalkyl, aryl and hterecycle are optionally substituted with R$^6$;

R$^5$ is independently selected from H, C$_{1-4}$ alkyl (optionally substituted with halogen, hydroxyl, alkoxy, carboxy, alkoxycarbonyl, amino, substituted amino), C$_{3-10}$ carbocycle and 4- to 10-membered heterocycle, wherein said carbocycle and heterocycle are optionally substituted with R$^6$; alternatively, R$^5$ and R$^5$ together with the nitrogen atom to which they are both attached form a heterocyclic ring optionally substituted with R$^6$.

R$^6$ is independently selected from OH, =O, —(CH$_2$)$_n$NH$_2$, —(CH$_2$)$_n$CN, halogen, C$_{1-6}$ alkyl, —(CH$_2$)$_n$—C(=O)OH, —(CH$_2$)$_n$—C(=O)OC$_{1-4}$ alkyl, —(CH$_2$)$_n$—OC$_{1-4}$ alkyl, —(CH$_2$)$_n$—C$_{3-10}$ carbocycle, —(CH$_2$)$_n$-4- to 10-membered heterocycle, and —O-4- to 10-membered heterocycle, wherein said carbocycle and heterocycle are optionally substituted with R$^{10}$;

R$^7$ is independently selected from H, F, methyl, and ethyl;

R$^{8a}$ is independently selected from H, halogen, CN, C$_{1-3}$ alkyl, C(O)C$_{1-4}$ alkyl, OC$_{1-3}$alkyl, CF$_3$, OCHF$_2$, NHC(O)C$_{1-4}$ alkyl, aryl, C$_{3-6}$ cycloalkyl, and 4-6 membered heterocycle;

R$^{8b}$ is independently selected from H and halogen; and

R$^{8c}$ is independently selected from H, halogen, CN, C$_{1-4}$ alkyl, alkoxy, NH$_2$ and haloalkoxy;

R$^{10}$ is independently selected from C$_{1-6}$ alkyl optionally substituted with R$^{11}$, C$_{2-6}$ alkenyl, C$_{2-6}$ alkynyl, —(CH$_2$)$_n$—C$_{3-6}$ cycloalkyl, F, Cl, Br, CN, NO$_2$, =O, CO$_2$H, —(CH$_2$)$_n$—OC$_{1-5}$ alkyl, —(CH$_2$)$_n$OR$^{11}$, and —(CH$_2$)$_n$—NR$^{11}$R$^{11}$;

R$^{11}$, at each occurrence, is independently selected from H, C$_{1-5}$ alkyl, C$_{3-6}$ cycloalkyl, and phenyl, or R$^{11}$ and R$^{11}$ together with the nitrogen atom to which they are both attached form a heterocyclic ring optionally substituted with C$_{1-4}$alkyl;

R$^{12}$ is C$_{1-6}$ alkyl optionally substituted with R$^{11}$;

m is an integer of 1;

n, at each occurrence, is an integer independently selected from 0, 1, 2, 3, and 4;

p, at each occurrence, is an integer independently selected from 0, 1, and 2.

In another embodiment, the present invention provides compounds of Formula (XII):

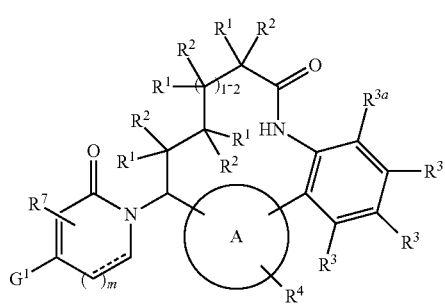

(XII)

or stereoisomers, tautomers, pharmaceutically acceptable salts, solvates, or prodrugs thereof, wherein:

ring A is independently selected from

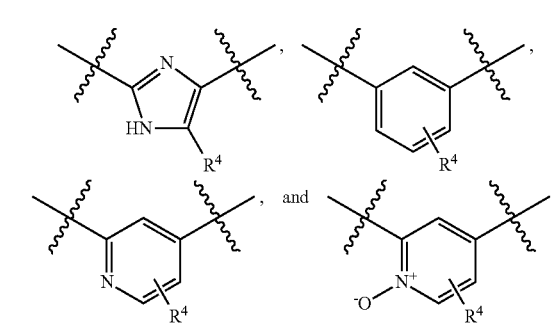

ring B is independently selected from a 6-membered aryl and a 5- to 10-membered heterocycle, wherein said aryl and heterocycle are substituted with 1-4 R$^3$;

G$^1$ is

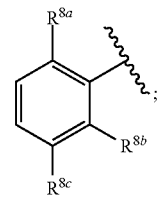

R$^1$ and R$^2$ are independently selected from H, F, methyl, ethyl, isopropyl, and hydroxyl;

R$^3$ is independently selected from H, =O, halogen, haloalkyl, C$_{1-4}$alkyl optionally substituted with R$^6$, C$_{2-4}$alkenyl optionally substituted with R$^6$, C$_{2-4}$alkynyl optionally substituted with R$^6$, CN, NO$_2$, —(CH$_2$)$_n$—OR$^5$, —(CH$_2$)$_n$—NR$^5$R$^5$, —(CH$_2$)$_n$—C(O)OR$^5$, —(CH$_2$)$_n$—NR$^9$C(O)OR$^5$, —(CH$_2$)$_n$—NR$^9$C(O)R$^5$, —(CH$_2$)$_n$—NR$^9$C(O)NR$^5$R$^5$, —(CH$_2$)$_n$—C(O)NR$^5$R$^5$, —(CH$_2$)$_n$—NR$^9$C(S)NR$^9$C(O)R$^5$, —(CH$_2$)$_n$—S(O)$_p$R$^{12}$, —(CH$_2$)$_n$—S(O)$_p$NR$^5$R$^5$, —(CH$_2$)$_n$—NR$^9$S(O)$_p$NR$^5$R$^5$, —(CH$_2$)$_n$—NR$^9$S(O)$_p$R$^{12}$, —(CH$_2$)$_n$—C$_{3-10}$ carbocycle and —(CH$_2$)$_n$-4- to 10-membered heterocycle, wherein said carbocycle and heterocycle are optionally substituted with R$^6$; optionally, two adjacent R$^3$ groups on the carbocycle and heterocycle may form a ring optionally substituted with R$^6$.

R$^4$ is independently selected from H, OH, halogen, CN, C$_{1-4}$ alkyl, C$_{1-4}$ haloalkyl, C$_{1-4}$ alkoxy, —C(O)NH$_2$, —C(O)NH(C$_{1-4}$ alkyl), —C(O)N(C$_{1-4}$ alkyl)$_2$, C$_{3-6}$ cycloalkyl, aryl, and a 5- to 6-membered heterocycle, where said cycloalkyl, aryl and hterecycle are optionally substituted with R$^6$;

R$^5$ is independently selected from H, C$_{1-4}$ alkyl (optionally substituted with halogen, hydroxyl, alkoxy, carboxy, alkoxycarbonyl, amino, substituted amino), C$_{3-10}$ carbocycle and 4- to 10-membered heterocycle, wherein said carbocycle and heterocycle are optionally substituted with R$^6$; alternatively, R$^5$ and R$^5$ together with the nitrogen atom to which they are both attached form a heterocyclic ring optionally substituted with R$^6$;

R$^6$ is independently selected from OH, =O, —(CH$_2$)$_n$NH$_2$, —(CH$_2$)$_n$CN, halogen, C$_{1-6}$ alkyl, —(CH$_2$)$_n$—C(=O)OH, —(CH$_2$)$_n$—C(=O)OC$_{1-4}$ alkyl, —(CH$_2$)$_n$—OC$_{1-4}$ alkyl, —(CH$_2$)$_n$—C$_{3-10}$ carbocycle, —(CH$_2$)$_n$-4- to 10-membered heterocycle, and —O-4- to 10-membered heterocycle, wherein said carbocycle and heterocycle are optionally substituted with $R^{10}$;

$R^7$ is independently selected from H, F, methyl, and ethyl;

$R^{8a}$ is independently selected from H, halogen, CN, $C_{1-3}$ alkyl, $C(O)C_{1-4}$ alkyl, $OC_{1-3}$alkyl, $CF_3$, $OCHF_2$, $NHC(O)C_{1-4}$ alkyl, aryl, $C_{3-6}$ cycloalkyl, and 4-6 membered heterocycle;

$R^{8b}$ is independently selected from H and halogen; and $R^{8c}$ is independently selected from H, halogen, CN, $C_{1-4}$ alkyl, alkoxy, $NH_2$ and haloalkoxy;

$R^{10}$ is independently selected from $C_{1-6}$ alkyl optionally substituted with $R^{11}$, $C_{2-6}$ alkenyl, $C_{2-6}$ alkynyl, $-(CH_2)_n-C_{3-6}$ cycloalkyl, F, Cl, Br, CN, $NO_2$, $=O$, $CO_2H$, $-(CH_2)_n-OC_{1-5}$ alkyl, $-(CH_2)_n OR^{11}$, and $-(CH_2)_n NR^{11}R^{11}$;

$R^{11}$, at each occurrence, is independently selected from H, $C_{1-5}$ alkyl, $C_{3-6}$ cycloalkyl, and phenyl, or $R^{11}$ and $R^{11}$ together with the nitrogen atom to which they are both attached form a heterocyclic ring optionally substituted with $C_{1-4}$alkyl;

$R^{12}$ is $C_{1-6}$ alkyl optionally substituted with $R^{11}$;

m is an integer of 1;

n, at each occurrence, is an integer independently selected from 0, 1, 2, 3, and 4;

p, at each occurrence, is an integer independently selected from 0, 1, and 2.

In another embodiment, the present invention provides compounds of Formula (XII):

(XII)

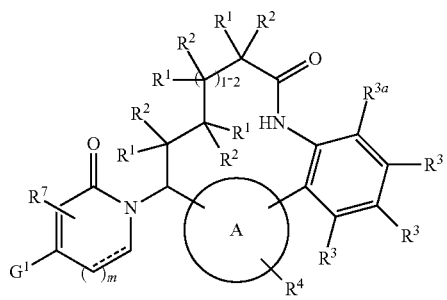

or stereoisomers, tautomers, pharmaceutically acceptable salts, solvates, or prodrugs thereof, wherein:

ring A is independently selected from

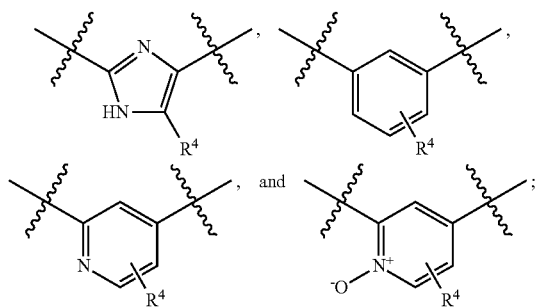

ring B is independently selected from a 6-membered aryl and a 5- to 10-membered heterocycle, wherein said aryl and heterocycle are substituted with 1-4 $R^3$;

$G^1$ is independently selected from

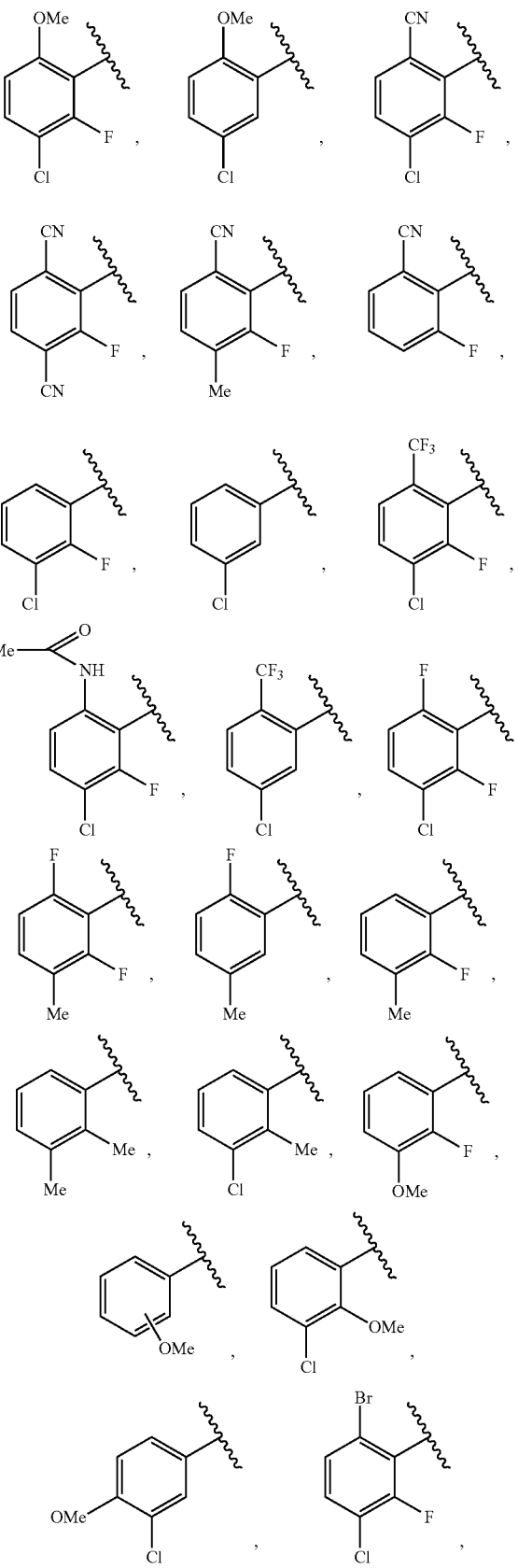

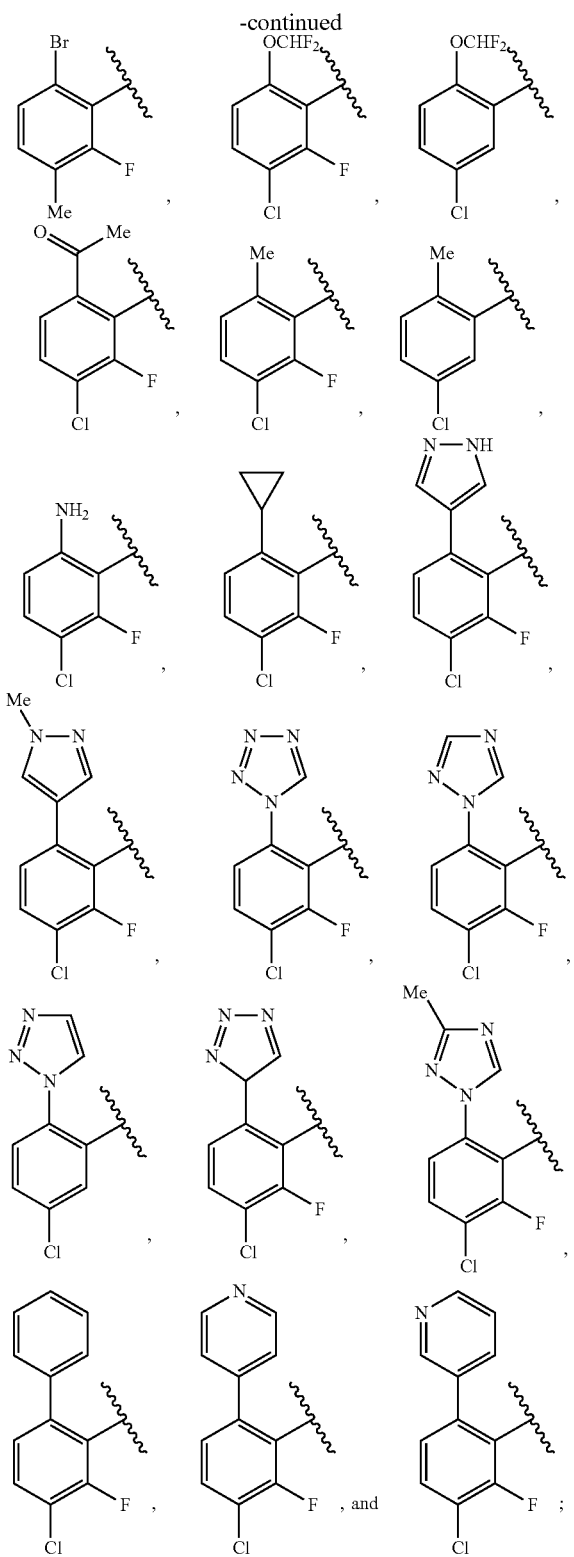

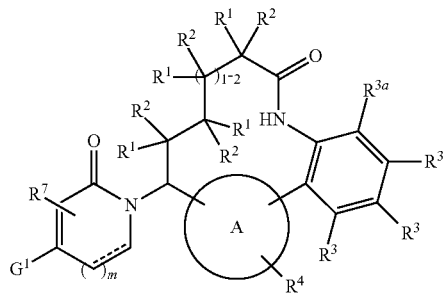

$R^1$ and $R^2$ are independently selected from H, F, methyl, ethyl, isopropyl, and hydroxyl;

$R^3$ is independently selected from H, =O, halogen, haloalkyl, $C_{1-4}$alkyl optionally substituted with $R^6$, $C_{2-4}$alkenyl optionally substituted with $R^6$, $C_{2-4}$alkynyl optionally substituted with $R^6$, CN, $NO_2$, —$(CH_2)_n$—$OR^5$, —$(CH_2)_n$—$NR^5R^5$, —$(CH_2)_n$—C(O)$OR^5$, —$(CH_2)_n$—$NR^9C(O)OR^5$, —$(CH_2)_n$—$NR^9C(O)R^5$, —$(CH_2)_n$—$NR^9C(O)NR^5R^5$, —$(CH_2)_n$—$C(O)NR^5R^5$, —$(CH_2)_n$—$NR^9C(S)NR^9C(O)R^5$, —$(CH_2)_n$—$S(O)_pR^{12}$, —$(CH_2)_n$—$S(O)_pNR^5R^5$, —$(CH_2)_n$—$NR^9S(O)_pNR^5R^5$, —$(CH_2)_n$—$NR^9S(O)_pR^{12}$, —$(CH_2)_n$—$C_{3-10}$ carbocycle and —$(CH_2)_n$-4- to 10-membered heterocycle, wherein said carbocycle and heterocycle are optionally substituted with $R^6$; optionally, two adjacent $R^3$ groups on the carbocycle and heterocycle may form a ring optionally substituted with $R^6$.

$R^4$ is independently selected from H, OH, halogen, CN, $C_{1-4}$ alkyl, $C_{1-4}$ haloalkyl, $C_{1-4}$ alkoxy, —$C(O)NH_2$, —$C(O)NH(C_{1-4}$ alkyl), —$C(O)N(C_{1-4}$ alkyl)$_2$, $C_{3-6}$ cycloalkyl, aryl, and a 5- to 6-membered heterocycle, where said cycloalkyl, aryl and hterecycle are optionally substituted with $R^6$;

$R^5$ is independently selected from H, $C_{1-4}$ alkyl (optionally substituted with halogen, hydroxyl, alkoxy, carboxy, alkoxycarbonyl, amino, substituted amino), $C_{3-10}$ carbocycle and 4- to 10-membered heterocycle, wherein said carbocycle and heterocycle are optionally substituted with $R^6$; alternatively, $R^5$ and $R^5$ together with the nitrogen atom to which they are both attached form a heterocyclic ring optionally substituted with $R^6$;

$R^6$ is independently selected from OH, =O, —$(CH_2)_nNH_2$, —$(CH_2)_nCN$, halogen, $C_{1-6}$ alkyl, —$(CH_2)_n$—C(=O)OH, —$(CH_2)_n$—C(=O)$OC_{1-4}$ alkyl, —$(CH_2)_n$—$OC_{1-4}$ alkyl, —$(CH_2)_n$—$C_{3-10}$ carbocycle, —$(CH_2)_n$-4- to 10-membered heterocycle, and —O-4- to 10-membered heterocycle, wherein said carbocycle and heterocycle are optionally substituted with $R^{10}$;

$R^7$ is independently selected from H, F, methyl, and ethyl;

$R^{8a}$ is independently selected from H, halogen, CN, $C_{1-3}$ alkyl, $C(O)C_{1-4}$ alkyl, $OC_{1-3}$alkyl, $CF_3$, $OCHF_2$, NHC(O)$C_{1-4}$ alkyl, aryl, $C_{3-6}$ cycloalkyl, and 4-6 membered heterocycle;

$R^{8b}$ is independently selected from H and halogen; and $R^{8c}$ is independently selected from H, halogen, CN, $C_{1-4}$ alkyl, alkoxy, $NH_2$ and haloalkoxy;

$R^{10}$ is independently selected from $C_{1-6}$ alkyl optionally substituted with $R^{11}$, $C_{2-6}$ alkenyl, $C_{2-6}$ alkynyl, —$(CH_2)_n$—$C_{3-6}$ cycloalkyl, F, Cl, Br, CN, $NO_2$, =O, $CO_2H$, —$(CH_2)_n$—$OC_{1-5}$ alkyl, —$(CH_2)_nOR^{11}$, and —$(CH_2)_nNR^{11}R^{11}$;

$R^{11}$, at each occurrence, is independently selected from H, $C_{1-5}$ alkyl, $C_{3-6}$ cycloalkyl, and phenyl, or $R^{11}$ and $R^{11}$ together with the nitrogen atom to which they are both attached form a heterocyclic ring optionally substituted with $C_{1-4}$alkyl;

$R^{12}$ is $C_{1-6}$ alkyl optionally substituted with $R^{11}$;

m is an integer of 1;

n, at each occurrence, is an integer independently selected from 0, 1, 2, 3, and 4;

p, at each occurrence, is an integer independently selected from 0, 1, and 2.

In another embodiment, the present invention provides compounds of Formula (XII):

or stereoisomers, tautomers, pharmaceutically acceptable salts, solvates, or prodrugs thereof, wherein:
ring A is
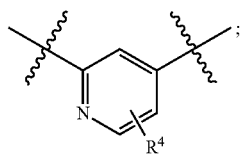
ring B is independently selected from
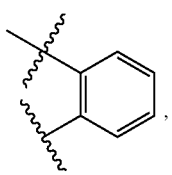 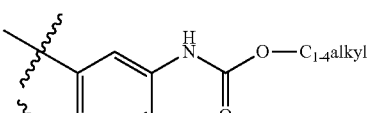
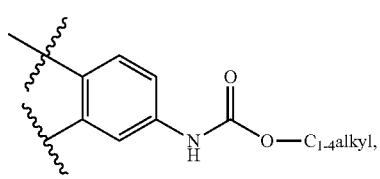
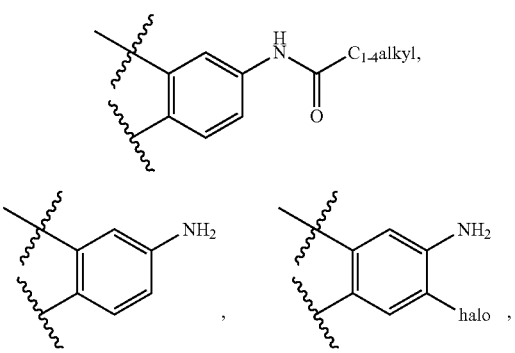
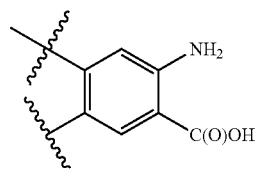
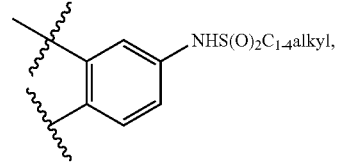
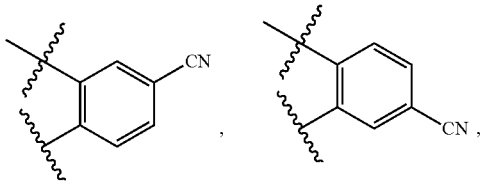
-continued
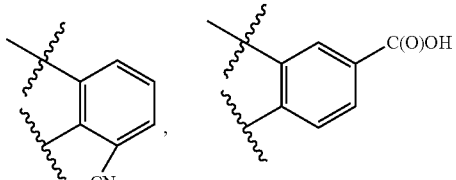
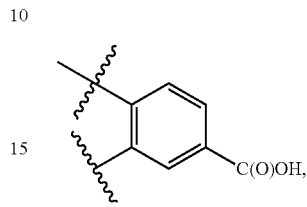 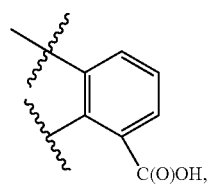
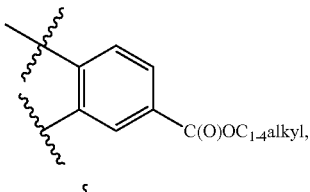
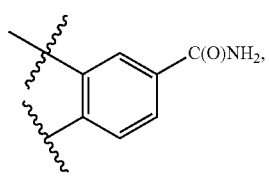
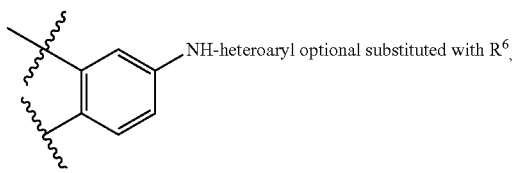 NH-heteroaryl optional substituted with $R^6$,
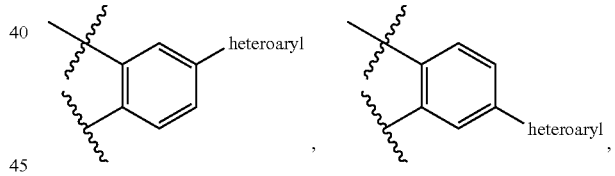
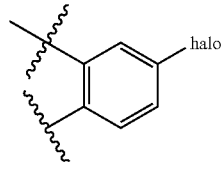 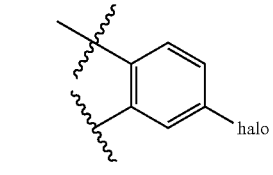
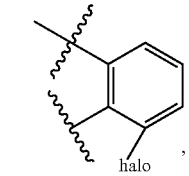 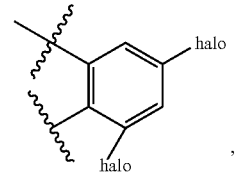
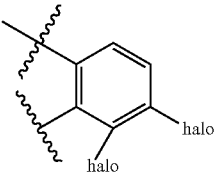 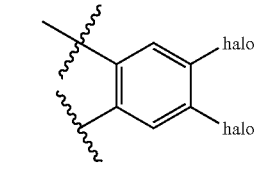

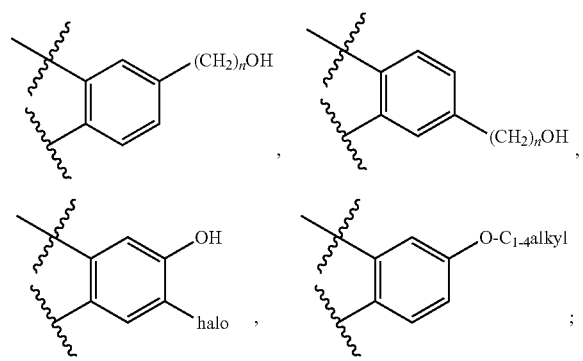
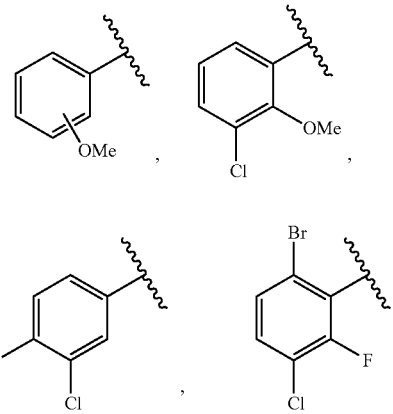
$G^1$ is independently selected from
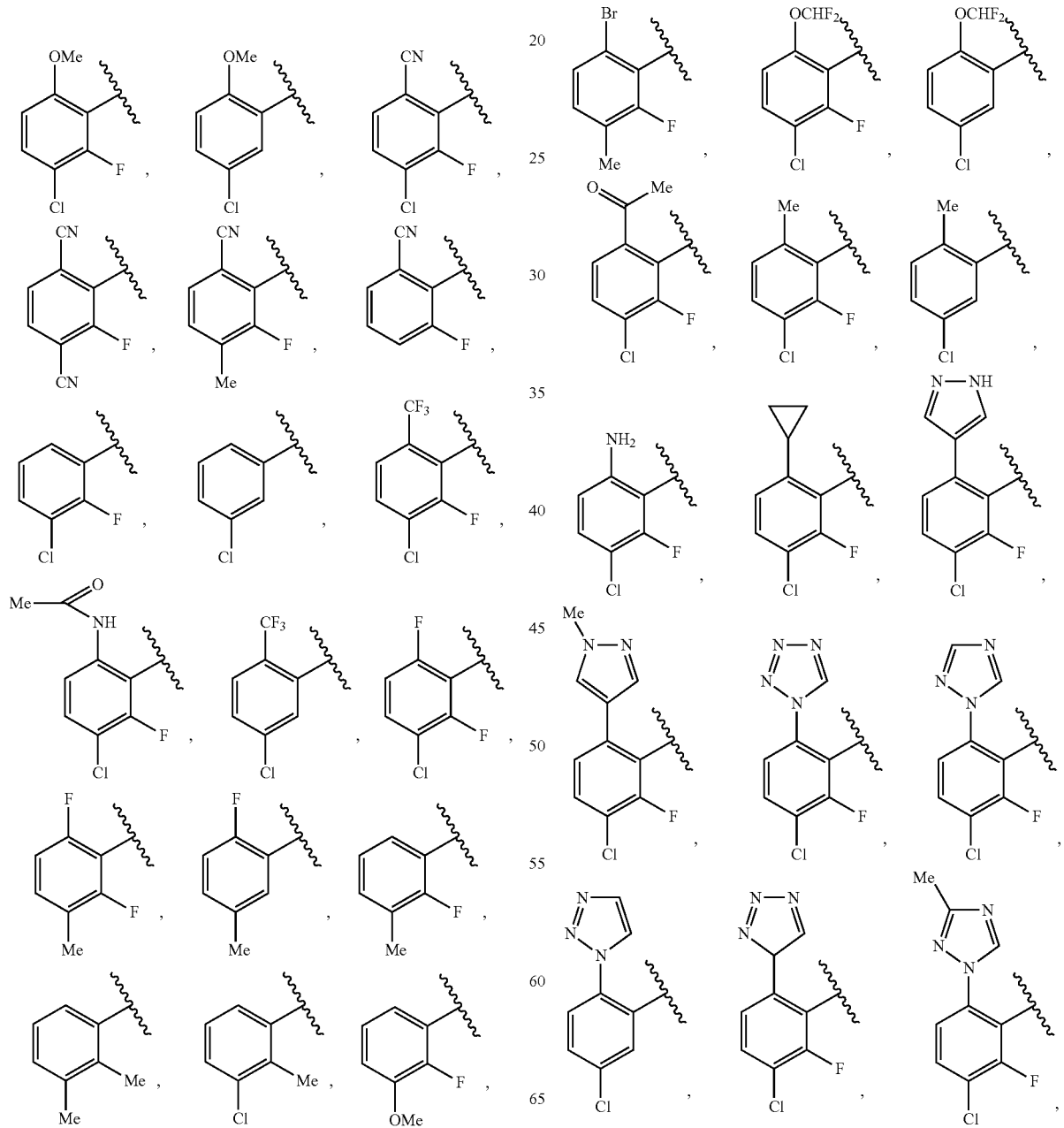

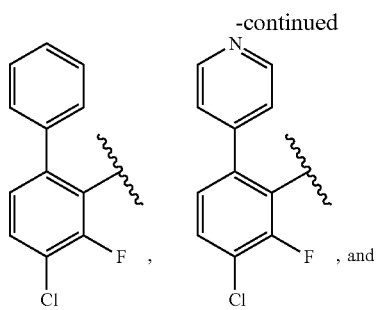

$R^1$ and $R^2$ are independently selected from H, F, methyl, ethyl, isopropyl, and hydroxyl;

$R^3$ is independently selected from H, =O, halogen, haloalkyl, $C_{1-4}$alkyl optionally substituted with $R^6$, $C_{2-4}$alkenyl optionally substituted with $R^6$, $C_{2-4}$alkynyl optionally substituted with $R^6$, CN, $NO_2$, —$(CH_2)_n$—$OR^5$, —$(CH_2)_n$—$NR^5R^5$, —$(CH_2)_n$—$C(O)OR^5$, —$(CH_2)_n$—$NR^9C(O)OR^5$, —$(CH_2)_n$—$NR^9C(O)R^5$, —$(CH_2)_n$—$NR^9C(O)NR^5R^5$, —$(CH_2)_n$—$C(O)NR^5R^5$, —$(CH_2)_n$—$NR^9C(S)NR^9C(O)R^5$, —$(CH_2)_n$—$S(O)_pR^{12}$, —$(CH_2)_n$—$S(O)_pNR^5R^5$, —$(CH_2)_n$—$NR^9S(O)_pNR^5R^5$, —$(CH_2)_n$—$NR^9S(O)_pR^{12}$, —$(CH_2)_n$—$C_{3-10}$ carbocycle and —$(CH_2)_n$-4- to 10-membered heterocycle, wherein said carbocycle and heterocycle are optionally substituted with $R^6$; optionally, two adjacent $R^3$ groups on the carbocycle and heterocycle may form a ring optionally substituted with $R^6$.

$R^4$ is independently selected from H, OH, halogen, CN, $C_{1-4}$ alkyl, $C_{1-4}$ haloalkyl, $C_{1-4}$ alkoxy, —$C(O)NH_2$, —$C(O)NH(C_{1-4}$ alkyl), —$C(O)N(C_{1-4}$ alkyl)$_2$, $C_{3-6}$ cycloalkyl, aryl, and a 5- to 6-membered heterocycle, where said cycloalkyl, aryl and hterecycle are optionally substituted with $R^6$;

$R^5$ is independently selected from H, $C_{1-4}$ alkyl (optionally substituted with halogen, hydroxyl, alkoxy, carboxy, alkoxycarbonyl, amino, substituted amino), $C_{3-10}$ carbocycle and 4- to 10-membered heterocycle, wherein said carbocycle and heterocycle are optionally substituted with $R^6$; alternatively, $R^5$ and $R^5$ together with the nitrogen atom to which they are both attached form a heterocyclic ring optionally substituted with $R^6$;

$R^6$ is independently selected from OH, =O, —$(CH_2)_nNH_2$, —$(CH_2)_nCN$, halogen, $C_{1-6}$ alkyl, —$(CH_2)_n$—$C(=O)OH$, —$(CH_2)_n$—$C(=O)OC_{1-4}$ alkyl, —$(CH_2)_n$—$OC_{1-4}$ alkyl, —$(CH_2)_n$—$C_{3-10}$ carbocycle, —$(CH_2)_n$-4- to 10-membered heterocycle, and —O-4- to 10-membered heterocycle, wherein said carbocycle and heterocycle are optionally substituted with $R^{10}$;

$R^7$ is independently selected from H, F, methyl, and ethyl;

$R^{10}$ is independently selected from $C_{1-6}$ alkyl optionally substituted with $R^{11}$, $C_{2-6}$ alkenyl, $C_{2-6}$ alkynyl, —$(CH_2)_n$—$C_{3-6}$ cycloalkyl, F, Cl, Br, CN, $NO_2$, =O, $CO_2H$, —$(CH_2)_n$—$OC_{1-5}$ alkyl, —$(CH_2)_nOR^{11}$, and —$(CH_2)_n$—$NR^{11}R^{11}$;

$R^{11}$, at each occurrence, is independently selected from H, $C_{1-5}$ alkyl, $C_{3-6}$ cycloalkyl, and phenyl, or $R^{11}$ and $R^{11}$ together with the nitrogen atom to which they are both attached form a heterocyclic ring optionally substituted with $C_{1-4}$alkyl;

$R^{12}$ is $C_{1-6}$ alkyl optionally substituted with $R^{11}$;

m is an integer of 1;

n, at each occurrence, is an integer independently selected from 0, 1, 2, 3, and 4;

p, at each occurrence, is an integer independently selected from 0, 1, and 2.

In another embodiment, the present invention provides compounds of Formula (XIIa):

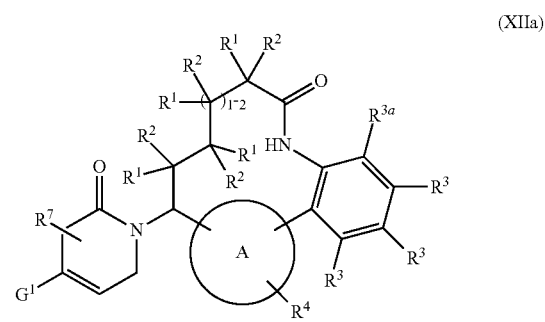

(XIIa)

or stereoisomers, tautomers, pharmaceutically acceptable salts, solvates, or prodrugs thereof, wherein:

ring A is

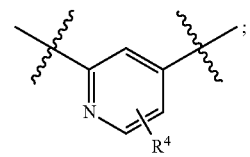

ring B is independently selected from

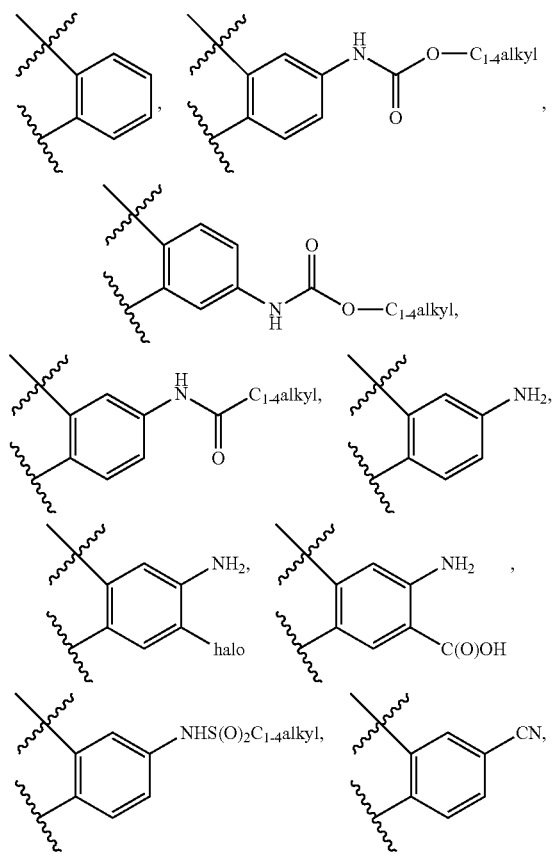

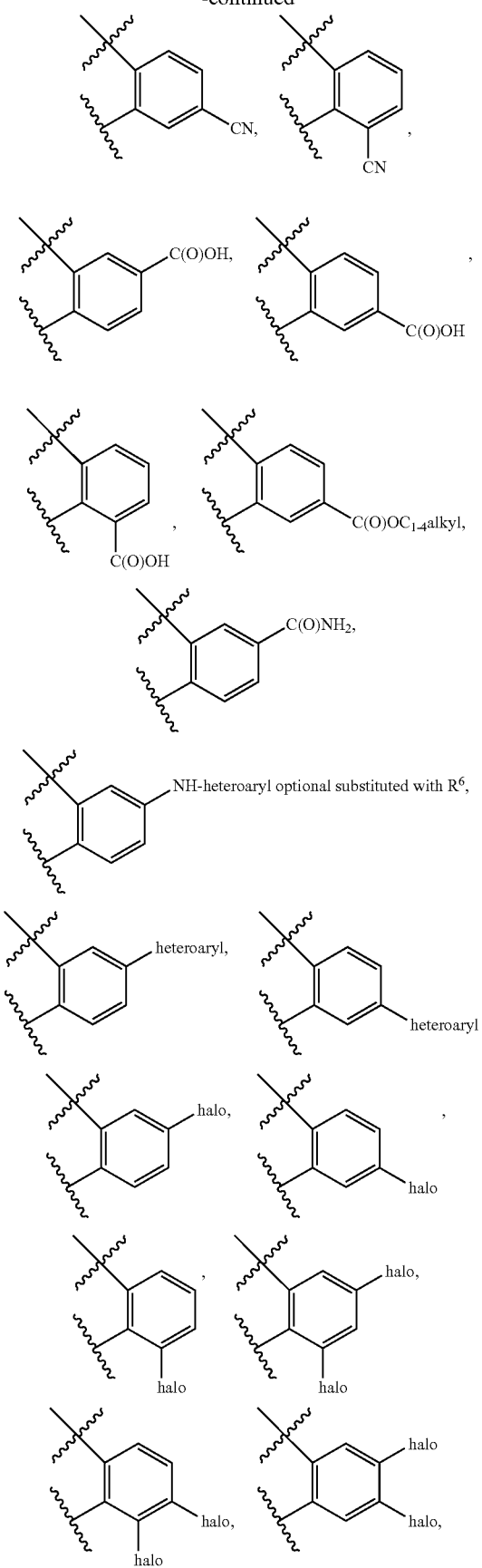
$G^1$ is independently selected from

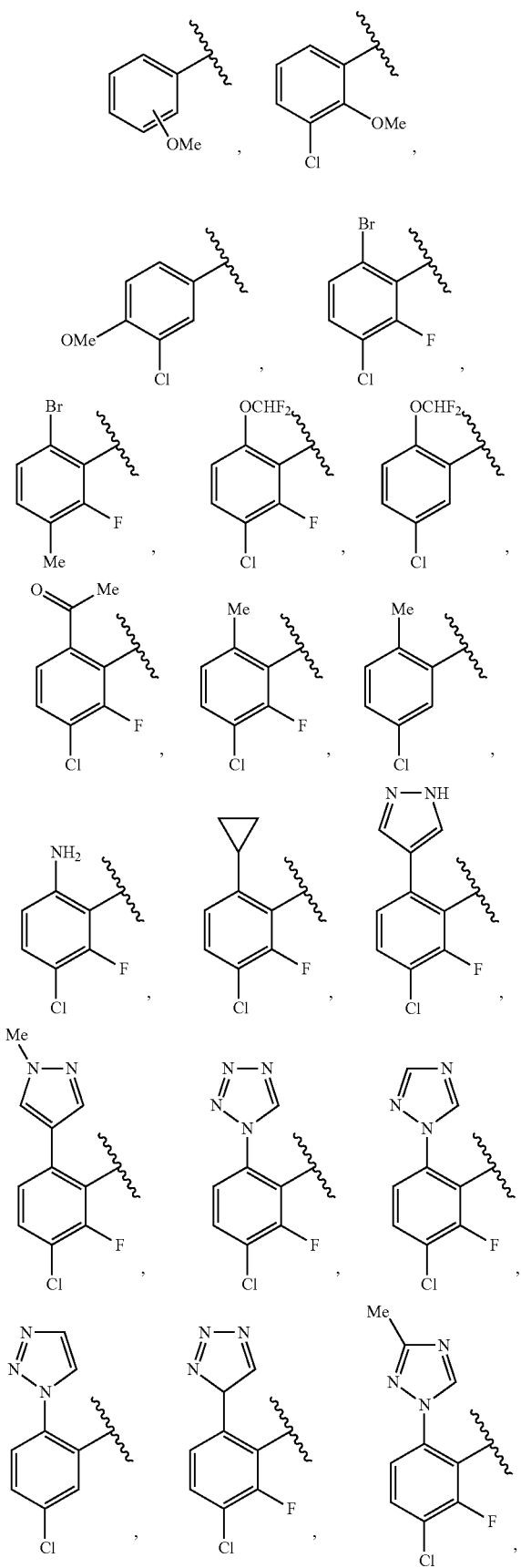

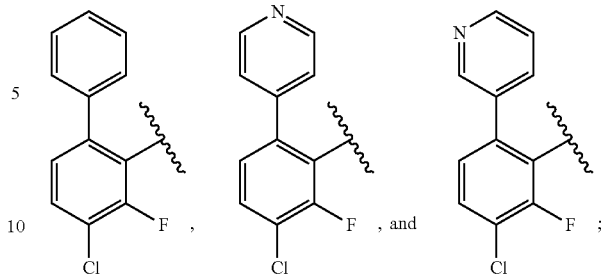

R[1] and R[2] are independently selected from H, F, methyl, ethyl, isopropyl, and hydroxyl;

R[3] is independently selected from H, =O, halogen, haloalkyl, $C_{1-4}$alkyl optionally substituted with R[6], $C_{2-4}$alkenyl optionally substituted with R[6], $C_{2-4}$alkynyl optionally substituted with R[6], CN, $NO_2$, —$(CH_2)_n$—$OR^5$, —$(CH_2)_n$—$NR^5R^5$, —$(CH_2)_n$—$C(O)OR^5$, —$(CH_2)_n$—$NR^9C(O)OR^5$, —$(CH_2)_n$—$NR^9C(O)R^5$, —$(CH_2)_n$—$NR^9C(O)NR^5R^5$, —$(CH_2)_n$—$C(O)NR^5R^5$, —$(CH_2)_n$—$NR^9C(S)NR^9C(O)R^5$, —$(CH_2)_n$—$S(O)_pR^{12}$, —$(CH_2)_n$—$S(O)_pNR^5R^5$, —$(CH_2)_n$—$NR^9S(O)_pNR^5R^5$, —$(CH_2)_n$—$NR^9S(O)_pR^{12}$, —$(CH_2)_n$—$C_{3-10}$ carbocycle and —$(CH_2)_n$—4- to 10-membered heterocycle, wherein said carbocycle and heterocycle are optionally substituted with R[6]; optionally, two adjacent R[3] groups on the carbocycle and heterocycle may form a ring optionally substituted with R[6].

R[4] is independently selected from H, OH, halogen, CN, $C_{1-4}$ alkyl, $C_{1-4}$ haloalkyl, $C_{1-4}$ alkoxy, —$C(O)NH_2$, —$C(O)NH(C_{1-4}$ alkyl), —$C(O)N(C_{1-4}$ alkyl$)_2$, $C_{3-6}$ cycloalkyl, aryl, and a 5- to 6-membered heterocycle, where said cycloalkyl, aryl and hterecycle are optionally substituted with R[6];

R[5] is independently selected from H, $C_{1-4}$ alkyl (optionally substituted with halogen, hydroxyl, alkoxy, carboxy, alkoxycarbonyl, amino, substituted amino), $C_{3-10}$ carbocycle and 4- to 10-membered heterocycle, wherein said carbocycle and heterocycle are optionally substituted with R[6]; alternatively, R[5] and R[5] together with the nitrogen atom to which they are both attached form a heterocyclic ring optionally substituted with R[6];

R[6] is independently selected from OH, =O, —$(CH_2)_nNH_2$, —$(CH_2)_nCN$, halogen, $C_{1-6}$ alkyl, —$(CH_2)_n$—$C(=O)OH$, —$(CH_2)_n$—$C(=O)OC_{1-4}$ alkyl, —$(CH_2)_n$—$OC_{1-4}$ alkyl, —$(CH_2)_n$—$C_{3-10}$ carbocycle, —$(CH_2)_n$-4- to 10-membered heterocycle, and —O-4- to 10-membered heterocycle, wherein said carbocycle and heterocycle are optionally substituted with R[10];

R[7] is independently selected from H, F, methyl, and ethyl;

R[10] is independently selected from $C_{1-6}$ alkyl optionally substituted with R[11], $C_{2-6}$ alkenyl, $C_{2-6}$ alkynyl, —$(CH_2)_n$—$C_{3-6}$ cycloalkyl, F, Cl, Br, CN, $NO_2$, =O, $CO_2H$, —$(CH_2)_n$—$OC_{1-5}$ alkyl, —$(CH_2)_n$—$OR^{11}$, and —$(CH_2)_n$—$NR^{11}R^{11}$;

R[11], at each occurrence, is independently selected from H, $C_{1-5}$ alkyl, $C_{3-6}$ cycloalkyl, and phenyl, or R[11] and R[11] together with the nitrogen atom to which they are both attached form a heterocyclic ring optionally substituted with $C_{1-4}$alkyl;

R[12] is $C_{1-6}$ alkyl optionally substituted with R[11];

m is an integer of 1;

n, at each occurrence, is an integer independently selected from 0, 1, 2, 3, and 4;

p, at each occurrence, is an integer independently selected from 0, 1, and 2.

In another embodiment, the present invention provides compounds of Formula (XI):
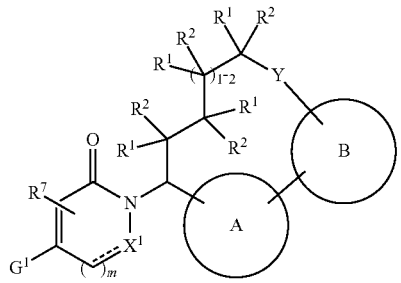
or stereoisomers, tautomers, pharmaceutically acceptable salts, solvates, or prodrugs thereof, wherein:
ring A is
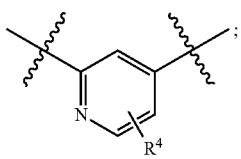
ring B is selected from
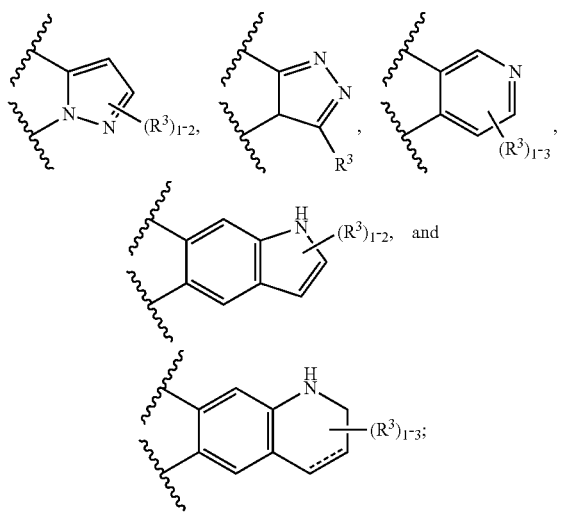
- - - is an optional bond;
$G^1$ is independently selected from
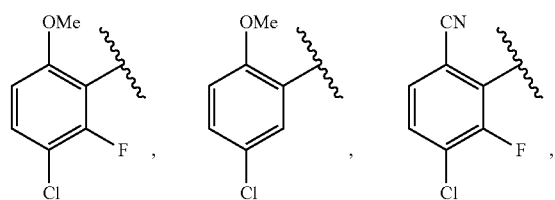
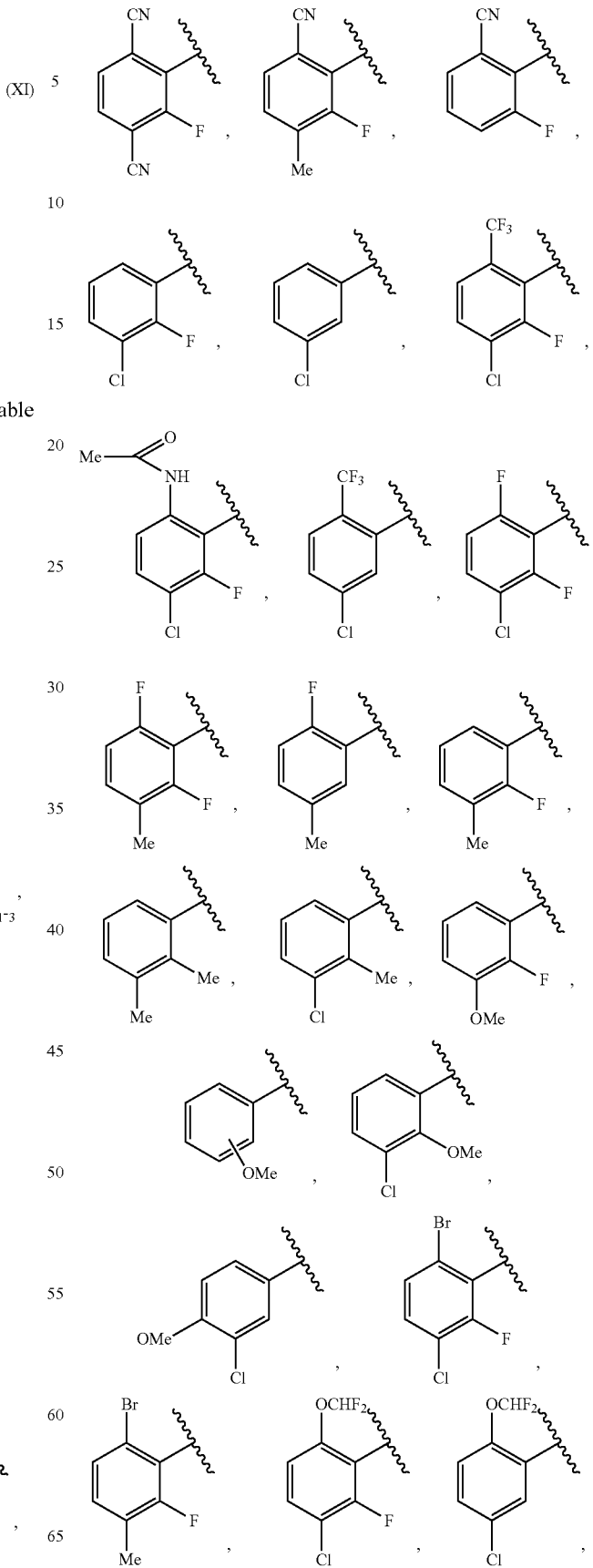

-continued

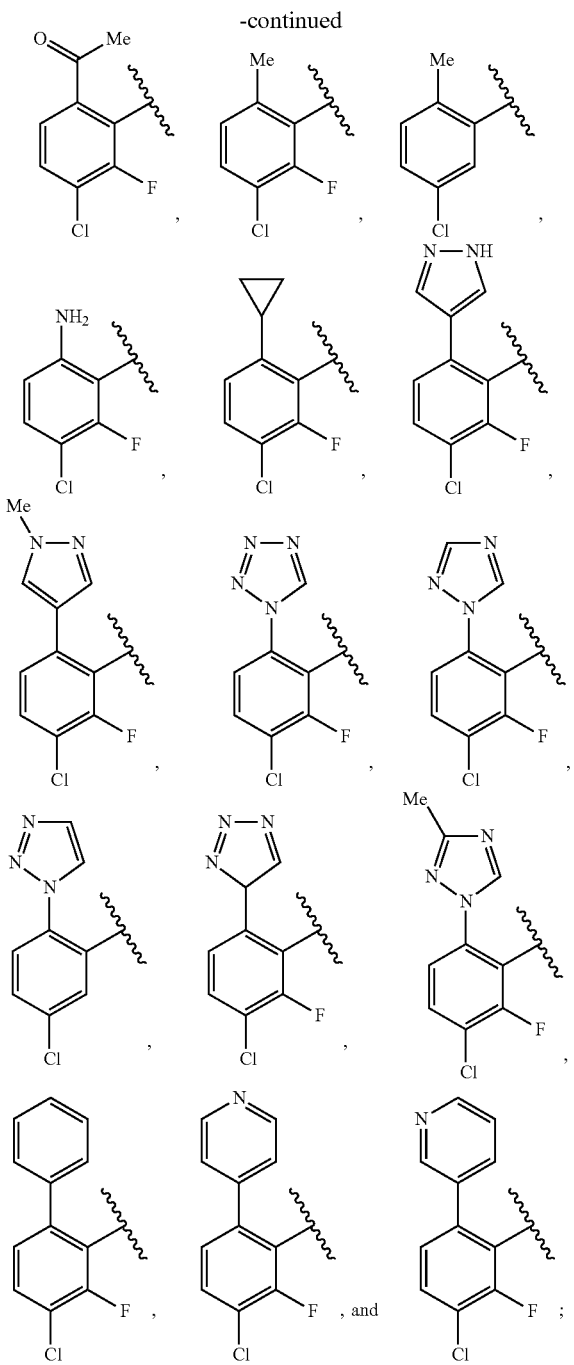

Y is independently selected from —NH—C(O)— and —C(O)—NH—;

$R^1$ and $R^2$ are independently selected from H, F, methyl, ethyl, isopropyl, and hydroxyl;

$R^3$ is independently selected from H, =O, halogen, haloalkyl, $C_{1-4}$alkyl optionally substituted with $R^6$, $C_{2-4}$alkenyl optionally substituted with $R^6$, $C_{2-4}$alkynyl optionally substituted with $R^6$, CN, $NO_2$, —$(CH_2)_n$—$OR^5$, —$(CH_2)_n$—$NR^5R^5$, —$(CH_2)_n$—$C(O)OR^5$, —$(CH_2)_n$—$NR^9C(O)OR^5$, —$(CH_2)_n$—$NR^9C(O)R^5$, —$(CH_2)_n$—$NR^9C(O)NR^5R^5$, —$(CH_2)_n$—$C(O)NR^5R^5$, —$(CH_2)_n$—$NR^9C(S)NR^9C(O)R^5$, —$(CH_2)_n$—$S(O)_pR^{12}$, —$(CH_2)_n$—$S(O)_pNR^5R^5$, —$(CH_2)_n$—$NR^9S(O)_pNR^5R^5$, —$(CH_2)_n$—$NR^9S(O)_pR^{12}$, —$(CH_2)_n$—$C_{3-10}$ carbocycle and —$(CH_2)_n$- 4- to 10-membered heterocycle, wherein said carbocycle and heterocycle are optionally substituted with $R^6$; optionally, two adjacent $R^3$ groups on the carbocycle and heterocycle may form a ring optionally substituted with $R^6$.

$R^4$ is independently selected from H, OH, halogen, CN, $C_{1-4}$ alkyl, $C_{1-4}$ haloalkyl, $C_{1-4}$ alkoxy, —$C(O)NH_2$, —$C(O)NH(C_{1-4}$ alkyl), —$C(O)N(C_{1-4}$ alkyl)$_2$, $C_{3-6}$ cycloalkyl, aryl, and a 5- to 6-membered heterocycle, where said cycloalkyl, aryl and htereycle are optionally substituted with $R^6$;

$R^5$ is independently selected from H, $C_{1-4}$ alkyl (optionally substituted with halogen, hydroxyl, alkoxy, carboxy, alkoxycarbonyl, amino, substituted amino), $C_{3-10}$ carbocycle and 4- to 10-membered heterocycle, wherein said carbocycle and heterocycle are optionally substituted with $R^6$; alternatively, $R^5$ and $R^5$ together with the nitrogen atom to which they are both attached form a heterocyclic ring optionally substituted with $R^6$;

$R^6$ is independently selected from OH, =O, —$(CH_2)_nNH_2$, —$(CH_2)_nCN$, halogen, $C_{1-6}$ alkyl, —$(CH_2)_n$—$C(=O)OH$, —$(CH_2)_n$—$C(=O)OC_{1-4}$ alkyl, —$(CH_2)_n$—$OC_{1-4}$ alkyl, —$(CH_2)_n$—$C_{3-10}$ carbocycle, —$(CH_2)_n$-4- to 10-membered heterocycle, and —O-4- to 10-membered heterocycle, wherein said carbocycle and heterocycle are optionally substituted with $R^{10}$;

$R^7$ is independently selected from H, F, methyl, and ethyl;

$R^{10}$ is independently selected from $C_{1-6}$ alkyl optionally substituted with $R^{11}$, $C_{2-6}$ alkenyl, $C_{2-6}$ alkynyl, —$(CH_2)_n$—$C_{3-6}$ cycloalkyl, F, Cl, Br, CN, $NO_2$, =O, $CO_2H$, —$(CH_2)_n$—$OC_{1-5}$ alkyl, —$(CH_2)_nOR^{11}$, and —$(CH_2)_n$—$NR^{11}R^{11}$;

$R^{11}$, at each occurrence, is independently selected from H, $C_{1-5}$ alkyl, $C_{3-6}$ cycloalkyl, and phenyl, or $R^{11}$ and $R^{11}$ together with the nitrogen atom to which they are both attached form a heterocyclic ring optionally substituted with $C_{1-4}$alkyl;

$R^{12}$ is $C_{1-6}$ alkyl optionally substituted with $R^{11}$;

m is an integer of 1;

n, at each occurrence, is an integer independently selected from 0, 1, 2, 3, and 4;

p, at each occurrence, is an integer independently selected from 0, 1, and 2.

In another aspect, the present invention provides a compound selected from any subset list of compounds exemplified in the present application.

In another embodiment, the compounds of the present invention have Factor XIa or plasma kallikrein Ki values ≤10 μM.

In another embodiment, the compounds of the present invention have Factor XIa or plasma kallikrein Ki values ≤1 μM.

In another embodiment, the compounds of the present invention have Factor XIa or plasma kallikrein Ki values ≤0.5 μM.

In another embodiment, the compounds of the present invention have Factor XIa or plasma kallikrein Ki values ≤0.1 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s). In a preferred embodiment, the present invention provides pharmaceutical composition, wherein the additional therapeutic agent(s) are an anti-platelet agent or a combination thereof. Preferably, the anti-platelet agent(s) are clopidogrel and/or aspirin, or a combination thereof.

In another embodiment, the present invention provides a method for the treatment and/or prophylaxis of a thromboembolic disorder comprising administering to a patient in need of such treatment and/or prophylaxis a therapeutically effective amount of at least one of the compounds of the present invention or a stereoisomer, a tautomer, a pharmaceutically acceptable salt, or a solvate thereof.

In another embodiment, the present invention provides a compound of the present invention or a stereoisomer, a tautomer, a pharmaceutically acceptable salt, or a solvate thereof, for use in therapy.

In another embodiment, the present invention provides a compound of the present invention or a stereoisomer, a tautomer, a pharmaceutically acceptable salt, or a solvate thereof, for use in therapy for the treatment and/or prophylaxis of a thromboembolic disorder.

In another embodiment, the present invention also provides the use of a compound of the present invention or a stereoisomer, a tautomer, a pharmaceutically acceptable salt, or a solvate thereof, for the manufacture of a medicament for the treatment and/or prophylaxis of a thromboembolic disorder.

In another embodiment, the present invention provides a method for treatment and/or prophylaxis of a thromboembolic disorder, comprising: administering to a patient in need thereof a therapeutically effective amount of a first and second therapeutic agent, wherein the first therapeutic agent is a compound of the present invention or a stereoisomer, a tautomer, a pharmaceutically acceptable salt, or a solvate thereof, and the second therapeutic agent is at least one agent selected from a factor Xa inhibitor such as apixaban, rivaroxaban, betrixaban, edoxaban, an anti-coagulant agent, an anti-platelet agent, a thrombin inhibiting agent such as dabigatran, a thrombolytic agent, and a fibrinolytic agent. Preferably, the second therapeutic agent is at least one agent selected from warfarin, unfractionated heparin, low molecular weight heparin, synthetic pentasaccharide, hirudin, argatroban, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, desulfatohirudin, tissue plasminogen activator, modified tissue plasminogen activator, anistreplase, urokinase, and streptokinase. Preferably, the second therapeutic agent is at least one anti-platelet agent. Preferably, the anti-platelet agent(s) are clopidogrel and/or aspirin, or a combination thereof.

The thromboembolic disorder includes arterial cardiovascular thromboembolic disorders, venous cardiovascular thromboembolic disorders, arterial cerebrovascular thromboembolic disorders, and venous cerebrovascular thromboembolic disorders. Examples of the thromboembolic disorder include, but are not limited to, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a method for the treatment and/or prophylaxis of an inflammatory disorder comprising: administering to a patient in need of such treatment and/or prophylaxis a therapeutically effective amount of at least one of the compounds of the present invention or a stereoisomer, a tautomer, a pharmaceutically acceptable salt, or a solvate thereof. Examples of the inflammatory disorder include, but are not limited to, sepsis, acute respiratory distress syndrome, and systemic inflammatory response syndrome.

In another embodiment, the present invention provides a method for the prophylaxis of a disease or condition in which plasma kallikrein activity is implicated comprising administering to a patient in need of such treatment and/or prophylaxis a therapeutically effective amount of at least one of the compounds of the present invention or a stereoisomer, a tautomer, a pharmaceutically acceptable salt, or a solvate thereof.

The disease or condition in which plasma kallikrein activity is implicated includes, but not limited to, impaired visual acuity, diabetic retinopathy, diabetic macular edema, hereditary angioedema, diabetes, pancreatitis, nephropathy, cardio myopathy, neuropathy, inflammatory bowel disease, arthritis, inflammation, septic shock, hypotension, cancer, adult respiratory distress syndrome, disseminated intravascular coagulation, and cardiopulmonary bypass surgery.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment and/or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "alkoxyalkyl," as used herein, refers to an alkyl group substituted with one, two, or three alkoxy groups.

The term "amino," as used herein, refers to —NH$_2$.

The term "substituted amino," as used herein, refers to the defined terms below having the suffix "amino" such as "arylamino," "alkylamino," "arylamino," etc.

The term "alkoxyalkylamino," as used herein, refers to —NHR wherein R is an alkoxyalkyl group.

The term "alkoxycarbonyl," as used herein, refers to an alkoxy group attached to the parent molecular moiety through a carbonyl group.

The term "alkoxycarbonylamino," as used herein, refers to an —NHR wherein R is an alkoxycarbonyl group.

The term "alkylamino," as used herein refers to —NHR, wherein R is an alkyl group.

The term "alkylcarbonyl," as used herein, refers to an alkyl group attached to the parent molecular moiety through a carbonyl group.

The term "alkylcarbonylamino," as used herein, refers to —NHR wherein R is an alkylcarbonyl group.

The term "aminosulfonyl," as used herein, refers to —SO$_2$NH$_2$.

The term "arylalkyl," as used herein, refers to an alkyl group substituted with one, two, or three aryl groups.

The term "arylamino," as used herein, refers to —NHR wherein R is an aryl group.

The term "arylcarbonyl," as used herein, refers to an aryl group attached to the parent molecular moiety through a carbonyl group.

The term "arylcarbonylamino," as used herein refers to —NHR wherein R is an arylcarbonyl group.

The term "carbonyl," as used herein, refers to —C(O)—.

The term "cyano," as used herein, refers to —CN.

The term "cycloalkylamino," as used herein, refers to —NHR wherein R is a cycloalkyl group.

The term "cycloalkylcarbonyl," as used herein, refers to a cycloalkyl group attached to the parent molecular moiety through a carbonyl group.

The term "cycloalkylcarbonylamino," as used herein, refers to —NHR wherein R is a cycloalkylcarbonyl group.

The term "cycloalkyloxy," as used herein, refers to a cycloalkyl group attached to the parent molecular moiety through an oxygen atom.

The term "dialkylamino," as used herein, refers to $NR_2$, wherein each R is an alkyl group. The two alkyl groups are the same or different.

The term "haloalkoxy," as used herein, refers to a haloalkyl group attached to the parent molecular moiety through an oxygen atom.

The term "haloalkyl," as used herein, refers to an alkyl group substituted by one, two, three, or four halogen atoms.

The term "haloalkylamino," as used herein, refers to —NHR wherein R is a haloalkyl group.

The term "carbonyl" refers to C(=O).

The term "carboxy" refers to C(=O)OH.

The term "haloalkylcarbonyl," as used herein, refers to a haloalkyl group attached to the parent molecular moiety through a carbonyl group.

The term "haloalkylcarbonylamino," as used herein, refers to —NHR wherein R is a haloalkylcarbonyl group.

The terms "alkylcarbonyl" refer to an alkyl or substituted alkyl bonded to a carbonyl.

The term "alkoxycarbonyl," as used herein, refers to an alkoxy group attached to the parent molecular moiety through a carbonyl group.

The term "hydroxy" or "hydroxyl" refers to OH.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in *Hawley's Condensed Chemical Dictionary* (13th Ed.), Lewis, R. J., ed., J. Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, C(=O)$CH_3$, $SCH_3$, S(=O)$CH_3$, S(=O)$_2CH_3$, $CH_3$, $CH_2CH_3$, $CO_2H$, and $CO_2CH_3$.

The term "benzyl," as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, C(=O)$CH_3$, $SCH_3$, S(=O)$CH_3$, S(=O)$_2CH_3$, $CH_3$, $CH_2CH_3$, $CO_2H$, and $CO_2CH_3$.

As used herein, the term "heterocycle" or "heterocyclic ring" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benztriazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H, 6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydroquinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention.

Various forms of prodrugs are well known in the art. For examples of such prodrug derivatives, see:
a) Bundgaard, H., ed., *Design of Prodrugs,* Elsevier (1985), and Widder, K. et al., eds., *Methods in Enzymology,* 112:309-396, Academic Press (1985);
b) Bundgaard, H., Chapter 5, "Design and Application of Prodrugs," *A Textbook of Drug Design and Development,* pp. 113-191, Krosgaard-Larsen, P. et al., eds., Harwood Academic Publishers (1991);
c) Bundgaard, H., *Adv. Drug Deliv. Rev.,* 8:1-38 (1992);
d) Bundgaard, H. et al., *J. Pharm. Sci.,* 77:285 (1988); and
e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes.

Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice,* The Royal Society of Chemistry, Cambridge, UK (1994); Testa, B. et al., *Hydrolysis in Drug and Prodrug Metabolism. Chemistry, Biochemistry and Enzymology,* VCHA and Wiley-VCH, Zurich, Switzerland (2003); Wermuth, C. G., ed., *The Practice of Medicinal Chemistry,* Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "RBF" for round bottom flask, "atm" for atmosphere, "psi" for pounds per square inch, "conc." for concentrate, "RCM" for ring-closing metathesis, "sat" or "sat'd" for saturated, "SFC" for supercritical fluid chromatography "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc tert-butyloxycarbonyl
Boc$_2$O di-tert-butyl dicarbonate
AcOH HOAc or acetic acid
AlCl$_3$ aluminum chloride
AIBN Azobisisobutyronitrile
BBr$_3$ boron tribromide
BCl$_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonylmethanimidate
CBz carbobenzyloxy
CH$_2$Cl$_2$ dichloromethane
CH$_3$CN or ACN acetonitrile
CDCl$_3$ deutero-chloroform
CHCl$_3$ chloroform
mCPBA or m-CPBA meta-chloroperbenzoic acid
Cs$_2$CO$_3$ cesium carbonate
Cu(OAc)$_2$ copper (II) acetate
Cy$_2$NMe N-cyclohexyl-N-methylcyclohexanamine
DBU 1,8-diazabicyclo[5.4.0]undec-7-ene
DCE 1,2 dichloroethane
DCM dichloromethane
DEA diethylamine
Dess-Martin 1,1,1-tris(acetyloxy)-1,1-dihydro-1,2-beniziodoxol-3-(1H)-one
DIC or DIPCDI diisopropylcarbodiimide
DIEA, DIPEA or Hunig's base diisopropylethylamine
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylphospholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
Et$_3$N or TEA triethylamine
EtOAc ethyl acetate
Et$_2$O diethyl ether
EtOH ethanol
GMF glass microfiber filter
Grubbs II (1,3-bis(2,4,6-trimethylphenyl)-2-imidazolidinylidene)dichloro (phenylmethyl ene)(triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex hexane
HOBt or HOBT 1-hydroxybenzotriazole
IBX 2-iodoxybenzoic acid
H$_2$SO$_4$ sulfuric acid
Jones reagent CrO$_3$ in aqueous H$_2$SO$_4$, 2 M
K$_2$CO$_3$ potassium carbonate
K$_2$HPO$_4$ potassium phosphate dibasic
KOAc potassium acetate
K$_3$PO$_4$ potassium phosphate
LAH lithium aluminum hydride
LG leaving group
LiOH lithium hydroxide
MeOH methanol
MgSO$_4$ magnesium sulfate
MsOH or MSA methylsulfonic acid
NaCl sodium chloride
NaH sodium hydride
NaHCO$_3$ sodium bicarbonate
Na$_2$CO$_3$ sodium carbonate
NaOH sodium hydroxide
Na$_2$SO$_3$ sodium sulfite
Na$_2$SO$_4$ sodium sulfate
NBS N-bromosuccinimide
NCS N-chlorosuccinimide
NH$_3$ ammonia
NH$_4$Cl ammonium chloride
NH$_4$OH ammonium hydroxide
NH$_4$COOH ammonium formate
OTf triflate or trifluoromethanesulfonate
Pd$_2$(dba)$_3$ tris(dibenzylideneacetone)dipalladium(0)

Pd(OAc)$_2$ palladium(II) acetate
Pd/C palladium on carbon
Pd(dppf)Cl$_2$ [1,1'-bis(diphenylphosphino)-ferrocene]dichloropalladium(II)
Ph$_3$PCl$_2$ triphenylphosphine dichloride
PG protecting group
POCl$_3$ phosphorus oxychloride
i-PrOH or IPA isopropanol
PS Polystyrene
SEM-Cl$_2$-(trimethysilyl)ethoxymethyl chloride
SiO$_2$ silica oxide
SnCl$_2$ tin(II) chloride
TBAI tetra-n-butylammonium iodide
TEA triethylamine
TFA trifluoroacetic acid
THF tetrahydrofuran
TMSCHN$_2$ trimethylsilyldiazomethane
T3P propane phosphonic acid anhydride
TRIS tris (hydroxymethyl) aminomethane
pTsOH p-toluenesulfonic acid The compounds of the present invention can be prepared in a number of ways known to one skilled in the art of organic synthesis.

IV. Biology

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thromboembolic disorders and include acute coronary syndrome, unstable angina, myocardial infarction, thrombosis in the cavity of the heart, ischemic stroke, deep vein thrombosis, peripheral occlusive arterial disease, transient ischemic attack, and pulmonary embolism. In addition, thrombosis occurs on artificial surfaces in contact with blood, including catheters, stents, artificial heart valves, and hemodialysis membranes.

Some conditions contribute to the risk of developing thrombosis. For example, alterations of the vessel wall, changes in the flow of blood, and alterations in the composition of the vascular compartment. These risk factors are collectively known as Virchow's triad. (Colman, R. W. et al., eds., *Hemostasis and Thrombosis, Basic Principles and Clinical Practice*, 5th Edition, p. 853, Lippincott Williams & Wilkins (2006)).

Antithrombotic agents are frequently given to patients at risk of developing thromboembolic disease because of the presence of one or more predisposing risk factors from Virchow's triad to prevent formation of an occlusive thrombus (primary prevention). For example, in an orthopedic surgery setting (e.g., hip and knee replacement), an antithrombotic agent is frequently administered prior to a surgical procedure. The antithrombotic agent counterbalances the prothrombotic stimulus exerted by vascular flow alterations (stasis), potential surgical vessel wall injury, as well as changes in the composition of the blood due to the acute phase response related to surgery. Another example of the use of an antithrombotic agent for primary prevention is dosing with aspirin, a platelet activation inhibitor, in patients at risk for developing thrombotic cardiovascular disease. Well recognized risk factors in this setting include age, male gender, hypertension, diabetes mellitus, lipid alterations, and obesity.

Antithrombotic agents are also indicated for secondary prevention, following an initial thrombotic episode. For example, patients with mutations in factor V (also known as factor V Leiden) and additional risk factors (e.g., pregnancy), are dosed with anticoagulants to prevent the reoccurrence of venous thrombosis. Another example entails secondary prevention of cardiovascular events in patients with a history of acute myocardial infarction or acute coronary syndrome. In a clinical setting, a combination of aspirin and clopidogrel (or other thienopyridines) may be used to prevent a second thrombotic event.

Antithrombotic agents are also given to treat the disease state (i.e., by arresting its development) after it has already started. For example, patients presenting with deep vein thrombosis are treated with anticoagulants (i.e., heparin, warfarin, or LMWH) to prevent further growth of the venous occlusion. Over time, these agents also cause a regression of the disease state because the balance between prothrombotic factors and anticoagulant/profibrinolytic pathways is changed in favor of the latter. Examples on the arterial vascular bed include the treatment of patients with acute myocardial infarction or acute coronary syndrome with aspirin and clopidogrel to prevent further growth of vascular occlusions and eventually leading to a regression of thrombotic occlusions.

Thus, antithrombotic agents are used widely for primary and secondary prevention (i.e., prophylaxis or risk reduction) of thromboembolic disorders, as well as treatment of an already existing thrombotic process. Drugs that inhibit blood coagulation, or anticoagulants, are "pivotal agents for prevention and treatment of thromboembolic disorders" (Hirsh, J. et al., *Blood*, 105:453-463 (2005)).

An alternative way of initiation of coagulation is operative when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., *Blood*, 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact Activation Pathway", *Hemostasis and Thrombosis*, pp. 103-122, Lippincott Williams & Wilkins (2001); Schmaier, A. H., "Contact Activation", *Thrombosis and Hemorrhage*, pp. 105-128 (1998)). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., *J. Exp.*

*Med.*, 202:271-281 (2005); Kleinschmitz et al., *J. Exp. Med.*, 203:513-518 (2006)). The fact that factor XI is down-stream from factor XIIa, combined with the identical phenotype of the XII and XI deficient mice suggest that the contact activation system could play a major role in factor XI activation in vivo.

Factor XI is a zymogen of a trypsin-like serine protease and is present in plasma at a relatively low concentration. Proteolytic activation at an internal R369-I370 bond yields a heavy chain (369 amino acids) and a light chain (238 amino acids). The latter contains a typical trypsin-like catalytic triad (H413, D464, and S557). Activation of factor XI by thrombin is believed to occur on negatively charged surfaces, most likely on the surface of activated platelets. Platelets contain high affinity (0.8 nM) specific sites (130-500/platelet) for activated factor XI. After activation, factor XIa remains surface bound and recognizes factor IX as its normal macromolecular substrate. (Galiani, D., *Trends Cardiovasc. Med.*, 10:198-204 (2000)).

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al., *Thromb. Res.*, 101:329-354 (2001).) Thus, inhibitors of factor XIa are expected to be anticoagulant and profibrinolytic.

Further evidence for the anti-thromboembolic effects of targeting factor XI is derived from mice deficient in factor XI. It has been demonstrated that complete fXI deficiency protected mice from ferric chloride ($FeCl_3$)-induced carotid artery thrombosis (Rosen et al., *Thromb. Haemost.*, 87:774-777 (2002); Wang et al., *J. Thromb. Haemost.*, 3:695-702 (2005)). Also, factor XI deficiency rescues the perinatal lethal phenotype of complete protein C deficiency (Chan et al., *Amer. J. Pathology*, 158:469-479 (2001)). Furthermore, baboon cross-reactive, function blocking antibodies to human factor XI protect against baboon arterial-venous shunt thrombosis (Gruber et al., *Blood*, 102:953-955 (2003)). Evidence for an antithrombotic effect of small molecule inhibitors of factor XIa is also disclosed in published U.S. Patent Publication No. 2004/0180855 A1. Taken together, these studies suggest that targeting factor XI will reduce the propensity for thrombotic and thromboembolic diseases.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or post-traumatic, but rarely spontaneous hemorrhage. Postoperative bleeding occurs mostly in tissue with high concentrations of endogenous fibrinolytic activity (e.g., oral cavity, and urogenital system). The majority of the cases are fortuitously identified by preoperative prolongation of aPTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The aPTT (intrinsic system) is prolonged in a gene dose-dependent fashion. Interestingly, even after severe stimulation of the coagulation system (tail transection), the bleeding time is not significantly prolonged compared to wild-type and heterozygous litter mates. (Gailani, D., *Frontiers in Bioscience*, 6:201-207 (2001); Gailani, D. et al., *Blood Coagulation and Fibrinolysis*, 8:134-144 (1997).) Taken together, these observations suggest that high levels of inhibition of factor XIa should be well tolerated. This is in contrast to gene targeting experiments with other coagulation factors, excluding factor XII.

In vivo activation of factor XI can be determined by complex formation with either C1 inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, factor XI activation contributes to thrombin formation (Minnema, M. C. et al., *Arterioscler. Thromb. Vasc. Biol.*, 20:2489-2493 (2000)). A second study establishes a positive correlation between the extent of coronary arteriosclerosis and factor XIa in complex with alpha 1 antitrypsin (Murakami, T. et al., *Arterioscler. Thromb. Vasc. Biol.*, 15:1107-1113 (1995)). In another study, Factor XI levels above the 90th percentile in patients were associated with a 2.2-fold increased risk for venous thrombosis (Meijers, J. C. M. et al., *N. Engl. J. Med.*, 342:696-701 (2000)).

Also, it is preferred to find new compounds with improved activity in in vitro clotting assays, compared with known serine protease inhibitors, such as the activated partial thromboplastin time (aPTT) or prothrombin time (PT) assay. (for a description of the aPTT and PT assays see, Goodnight, S. H. et al., "Screening Tests of Hemostasis", *Disorders of Thrombosis and Hemostasis: A Clinical Guide*, 2nd Edition, pp. 41-51, McGraw-Hill, New York (2001)).

It is also desirable and preferable to find compounds with advantageous and improved characteristics compared with known serine protease inhibitors, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) factors that improve manufacturing costs or feasibility.

Pre-clinical studies demonstrated significant antithrombotic effects of small molecule factor XIa inhibitors in rabbit and rat model of arterial thrombosis, at doses that preserved hemostasis. (Wong P. C. et al., *American Heart Association Scientific Sessions*, Abstract No. 6118, Nov. 12-15, 2006; Schumacher, W. et al., *Journal of Thrombosis and Haemostasis*, 3(Suppl. 1):P1228 (2005); Schumacher, W. A. et al., *European Journal of Pharmacology*, 167-174 (2007)). Furthermore, it was observed that in vitro prolongation of the aPTT by specific XIa inhibitors is a good predictor of efficacy in our thrombosis models. Thus, the in vitro aPTT test can be used as a surrogate for efficacy in vivo.

As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit factor XIa and/or plasma kallikrein and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi); clotting within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to are family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Risk factors for congenital thrombophilia include gain of function mutations in coagulation factors or loss of function mutations in the anticoagulant- or fibrinolytic pathways.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population (Levitan, N. et al., *Medicine* (Baltimore), 78(5):285-291 (1999); Levine M. et al., *N. Engl. J. Med.*, 334(11):677-681 (1996); Blom, J. W. et al., *JAMA*, 293(6):715-722 (2005)). Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and anti-angiogenic drugs. Thus, it is common clinical practice to dose patients having advanced tumors with heparin or low molecular heparin to prevent thromboembolic disorders. A number of low molecular heparin preparations have been approved by the FDA for these indications.

There are three main clinical situations when considering the prevention of VTE in a medical cancer patient: (i) the patient is bedridden for prolonged periods of time; (ii) the ambulatory patient is receiving chemotherapy or radiation; and (iii) the patient is with indwelling central vein catheters. Unfractionated heparin (UFH) and low molecular weight heparin (LMWH) are effective antithrombotic agents in cancer patients undergoing surgery. (Mismetti, P. et al., *British Journal of Surgery*, 88:913-930 (2001).)

A. In Vitro Assays

The effectiveness of compounds of the present invention as inhibitors of the coagulation Factors XIa, VIIa, IXa, Xa, XIIa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin), which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 25-200 pM (Haematologic Technologies) and the synthetic substrate S-2366 (pyroGlu-Pro-Arg-pNA; CHROMOGENIX® or AnaSpec) at a concentration of 0.0002-0.001 M.

Factor VIIa determinations were made in 0.005 M calcium chloride, 0.15 M sodium chloride, 0.05 M HEPES buffer containing 0.1% PEG 8000 at a pH of 7.5. Determinations were made using purified human Factor VIIa (Haematologic Technologies) or recombinant human Factor VIIa (Novo Nordisk) at a final assay concentration of 0.5-10 nM, recombinant soluble tissue factor at a concentration of 10-40 nM and the synthetic substrate H-D-Ile-Pro-Arg-pNA (S-2288; CHROMOGENIX® or BMPM-2; AnaSpec) at a concentration of 0.001-0.0075 M.

Factor IXa determinations were made in 0.005 M calcium chloride, 0.1 M sodium chloride, 0.0000001 M Refludan (Berlex), 0.05 M TRIS base and 0.5% PEG 8000 at a pH of 7.4. Refludan was added to inhibit small amounts of thrombin in the commercial preparations of human Factor IXa. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Ph'Gly-Arg-AMC; CenterChem) at a concentration of 0.0004-0.0005 M.

Factor Xa determinations were made in 0.1 M sodium phosphate buffer at a pH of 7.5 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; CHROMOGENIX®) at a concentration of 0.0002-0.00035 M.

Factor XIIa determinations were made in 0.05 M HEPES buffer at pH 7.4 containing 0.145 M NaCl, 0.05 M KCl, and 0.1% PEG 8000. Determinations were made using purified human Factor XIIa at a final concentration of 4 nM (American Diagnostica) and the synthetic substrate SPECTROZYME® #312 (H-D-CHT-Gly-L-Arg-pNA.2AcOH; American Diagnostica) at a concentration of 0.00015 M.

Plasma kallikrein determinations were made in 0.1 M sodium phosphate buffer at a pH of 7.5 containing 0.1-0.2 M sodium chloride and 0.5% PEG 8000. Determinations were made using purified human plasma kallikrein (Enzyme Research Laboratories) at a final assay concentration of 200 pM and the synthetic substrate S-2302 (H-(D)-Pro-Phe-Arg-pNA; CHROMOGENIX®) at a concentration of 0.00008-0.0004 M.

Thrombin determinations were made in 0.1 M sodium phosphate buffer at a pH of 7.5 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; CHROMOGENIX® or AnaSpec) at a concentration of 0.0002-0.0004 M.

The Michaelis constant, $K_m$, for substrate hydrolysis by each protease, was determined at 25° C. or 37° C. in the absence of inhibitor. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time) were measured.

The following relationships were used to calculate $K_i$ values:

$$(V_{max}*S)/(K_m+S)$$

$$(v_o-v_s)/v_s=I/(K_i(1+S/K_m)) \text{ for a competitive inhibitor with one binding site; or}$$

$$v_s/v_o=A+((B-A)/1+((IC_{50}/(I)_n))); \text{ and}$$

$$K_i=IC_{50}/(1+S/K_m) \text{ for a competitive inhibitor}$$

where:
  $v_o$ is the velocity of the control in the absence of inhibitor;
  $v_s$ is the velocity in the presence of inhibitor;
  $V_{max}$ is the maximum reaction velocity;
  I is the concentration of inhibitor;
  A is the minimum activity remaining (usually locked at zero);
  B is the maximum activity remaining (usually locked at 1.0);
  n is the Hill coefficient, a measure of the number and cooperativity of potential inhibitor binding sites;
  $IC_{50}$ is the concentration of inhibitor that produces 50% inhibition under the assay conditions;
  $K_i$ is the dissociation constant of the enzyme: inhibitor complex;
  S is the concentration of substrate; and
  $K_m$ is the Michaelis constant for the substrate.

The selectivity of a compound may be evaluated by taking the ratio of the $K_i$ value for a given protease with the $K_i$ value for the protease of interest (i.e., selectivity for FXIa versus protease P=$K_i$ for protease P/$K_i$ for FXIa). Compounds with selectivity ratios >20 are considered selective.

The effectiveness of compounds of the present invention as inhibitors of coagulation can be determined using a standard or modified clotting assay. An increase in the plasma clotting time in the presence of inhibitor is indicative of anticoagulation. Relative clotting time is the clotting time in the presence of an inhibitor divided by the clotting time in the absence of an inhibitor. The results of this assay may be expressed as IC1.5× or IC2×, the inhibitor concentration required to increase the clotting time by 50 or 100 percent, respectively. The IC1.5× or IC2× is found by linear interpolation from relative clotting time versus inhibitor concentration plots using inhibitor concentration that spans the IC1.5× or IC2×.

Clotting times are determined using citrated normal human plasma as well as plasma obtained from a number of laboratory animal species (e.g., rat, or rabbit). A compound is diluted into plasma beginning with a 10 mM DMSO stock solution. The final concentration of DMSO is less than 2%. Plasma clotting assays are performed in an automated coagulation analyzer (Sysmex, Dade-Behring, Illinois). Similarly, clotting times can be determined from laboratory animal species or humans dosed with compounds of the invention.

Activated Partial Thromboplastin Time (aPTT) is determined using ALEXIN® (Trinity Biotech, Ireland) or ACTIN® (Dade-Behring, Illinois) following the directions in the package insert. Plasma (0.05 mL) is warmed to 37° C. for 1 minute. ALEXIN® or ACTIN® (0.05 mL) is added to the plasma and incubated for an additional 2 to 5 minutes. Calcium chloride (25 mM, 0.05 mL) is added to the reaction to initiate coagulation. The clotting time is the time in seconds from the moment calcium chloride is added until a clot is detected.

Prothrombin Time (PT) is determined using thromboplastin (Thromboplastin C Plus or Innovin®, Dade-Behring, Illinois) following the directions in the package insert. Plasma (0.05 mL) is warmed to 37° C. for 1 minute. Thromboplastin (0.1 mL) is added to the plasma to initiate coagulation. The clotting time is the time in seconds from the moment thromboplastin is added until a clot is detected.

The exemplified Examples disclosed below were tested in the Factor XIa assay described above and found having Factor XIa inhibitory activity. A range of Factor XIa inhibitory activity (Ki values) of ≤10 μM (10000 nM) was observed. Table 1 below lists Factor XIa Ki values measured at 37° C. for the following examples.

TABLE 1

| Example No. | Factor XIa Ki (nM) |
| --- | --- |
| 1 | 0.87 |
| 2 | 0.23 |
| 3 | 0.03 |
| 4 | 2.64 |
| 5 | 2.00 |
| 6 | 158.40 |
| 7 | 5.42 |
| 8 | >457.4 |
| 9 | 33.22 |
| 10 | 0.92 |
| 11 | 6.77 |
| 12 | 1.50 |
| 13 | 13.68 |
| 14 | 34.82 |
| 15 | 76.12 |
| 16 | 1.15 |
| 17 | 45.33 |
| 18 | 1.25 |
| 19 | 15.53 |
| 20 | — |
| 21 | 0.46 |
| 22 | >437.5 |
| 23 | 93.25 |
| 24 | 270.50 |
| 25 | 0.10 |
| 26 | 0.09 |
| 27 | 43.61 |
| 28 | >443.3 |
| 29 | 2.88 |
| 30 | 0.21 |
| 31 | 0.04 |
| 32 | 0.06 |
| 33 | 2.02 |
| 34 | 4.17 |
| 35 | 104.30 |
| 36 | 0.09 |
| 37 | 0.87 |
| 38 | 2.77 |
| 39 | 0.67 |
| 40 | 1.17 |
| 41 | 0.69 |
| 42 | 0.45 |
| 43 | 0.38 |
| 44 | 0.13 |
| 45 | 2.08 |
| 46 | 324.90 |
| 47 | 86.27 |
| 48 | 4.77 |
| 49 | 1.06 |

TABLE 1-continued

| Example No. | Factor XIa Ki (nM) |
|---|---|
| 50 | 101.70 |
| 51 | 17.18 |
| 52 | 45.61 |
| 53 | 0.08 |
| 54 | 0.08 |
| 55 | 2.73 |
| 56 | 16.49 |
| 57 | 35.56 |
| 58 | 15.13 |
| 59 | 3.31 |
| 60 | >409.3 |
| 61 | 24.62 |
| 62 | 195.90 |
| 63 | 7.86 |
| 64 | 16.55 |
| 65 | 47.61 |
| 66 | 66.60 |
| 67 | 2.98 |
| 68 | 0.05 |
| 69 | 79.18 |
| 70 | 8.02 |
| 71 | 1.68 |
| 72 | 8.67 |
| 73 | 0.88 |
| 74 | 40.15 |
| 75 | 3.54 |
| 76 | 7.89 |
| 77 | 29.14 |
| 78 | 0.98 |
| 79 | 0.55 |
| 80 | 13.55 |
| 81 | 0.31 |
| 82 | 9.57 |
| 83 | 0.06 |
| 84 | 2.68 |
| 85 | 9.17 |
| 86 | 0.72 |
| 87 | 17.31 |
| 88 | 1.04 |
| 89 | 2.43 |
| 90 | 1.81 |
| 91 | 0.56 |
| 92 | 0.56 |
| 93 | 1.40 |
| 94 | >407.6 |
| 95 | 46.53 |
| 96 | >421.7 |
| 97 | >407.6 |
| 98 | 30.05 |
| 99 | 125.90 |
| 100 | 0.09 |
| 101 | >434.2 |
| 102 | 0.15 |
| 103 | 6.13 |
| 104 | 0.09 |
| 105 | >342 |
| 106 | >342 |
| 107 | 17.42 |
| 108 | 8.13 |
| 109 | 27.87 |
| 110 | 0.62 |
| 111 | 1.42 |
| 112 | 5.85 |
| 113 | 7.24 |
| 114 | 107.90 |
| 115 | 128.60 |
| 116 | 266.70 |
| 117 | >398.20 |
| 118 | >404.30 |
| 119 | >424.20 |
| 120 | 146.50 |
| 121 | 2.56 |
| 122 | 320.80 |
| 123 | 20.11 |
| 124 | 345.60 |
| 125 | 15.17 |
| 126 | 16.08 |
| 127 | 3.61 |
| 128 | 10.26 |
| 129 | 8.29 |
| 130 | 8.51 |
| 131 | 7.22 |
| 132 | 2.56 |
| 133 | 4.77 |
| 134 | 33.56 |
| 135 | 0.05 |
| 136 | 45.26 |
| 137 | 69.57 |
| 138 | 36.17 |
| 139 | >408.00 |
| 140 | 1.34 |
| 141 | 98.92 |
| 142 | 1.66 |
| 143 | 1.31 |
| 144 | 185.70 |
| 145 | 18.63 |
| 146 | 2.45 |
| 147 | 3.59 |
| 148 | 90.09 |
| 149 | 17.51 |
| 150 | 0.99 |
| 151 | 0.84 |
| 152 | 25.62 |
| 153 | 20.03 |
| 154 | 23.55 |
| 155 | 4.88 |
| 156 | >446.40 |
| 157 | 74.94 |
| 158 | >404.30 |
| 159 | 63.22 |
| 160 | 0.20 |
| 161 | 0.59 |
| 162 | 76.48 |
| 163 | >398.20 |
| 164 | >398.20 |
| 165 | >398.20 |
| 166 | 6.38 |
| 167 | 0.81 |
| 168 | >416.70 |
| 169 | >416.70 |
| 170 | 46.60 |
| 171 | 0.17 |
| 172 | 139.80 |
| 173 | 0.42 |
| 174 | >624.80 |
| 175 | >624.80 |
| 176 | >624.80 |
| 177 | 0.80 |
| 178 | 0.92 |
| 179 | 7.38 |
| 180 | 0.18 |
| 181 | 0.10 |
| 182 | 0.11 |
| 183 | 75.09 |
| 184 | <0.05 |
| 185 | 22.82 |
| 186 | 57.93 |
| 187 | 0.44 |
| 188 | 1.60 |
| 189 | 2.28 |
| 190 | 0.27 |
| 191 | 0.23 |
| 192 | 90.97 |
| 193 | 1.02 |
| 194 | >421.50 |
| 195 | 0.47 |
| 196 | 0.80 |
| 197 | 4.54 |
| 198 | <0.05 |
| 199 | <0.05 |
| 200 | 18.06 |
| 201 | 50.04 |
| 202 | 8.56 |
| 203 | 19.36 |

TABLE 1-continued

| Example No. | Factor XIa Ki (nM) |
|---|---|
| 204 | 4.46 |
| 205 | 69.25 |
| 206 | 11.78 |
| 207 | 2.75 |
| 208 | 1.00 |
| 209 | 120.30 |
| 210 | 476.60 |
| 211 | 3.26 |
| 212 | 111.10 |
| 213 | >413.10 |
| 214 | >422.60 |
| 215 | 0.07 |
| 216 | 264.10 |
| 217 | 98.59 |
| 218 | 38.24 |
| 219 | 6.61 |
| 220 | 21.72 |
| 221 | >416.70 |
| 222 | 88.40 |
| 223 | 301.90 |
| 224 | 297.70 |
| 225 | 26.11 |
| 226 | 24.64 |
| 227 | — |

The exemplified Examples disclosed below were tested in the Plasma Kallikrein assay described above and found having Plasma Kallikrein inhibitory activity. A range of Plasma Kallikrein inhibitory activity (Ki values) of ≤10 μM (10000 nM) was observed. Table 2 below lists Plasma Kallikrein Ki values measured at 37° C. or 25° C. for the following examples.

TABLE 2

| Example No. | Plasma Kallikrein Ki (nM) |
|---|---|
| 1 | $10^a$ |
| 2 | $5^a$ |
| 3 | $1^a$ |
| 4 | $1^a$ |
| 5 | $3^a$ |
| 6 | $303^a$ |
| 7 | $10^a$ |
| 8 | $173^a$ |
| 9 | $46^a$ |
| 10 | $1^a$ |
| 11 | $14^a$ |
| 12 | $1^a$ |
| 13 | $8^a$ |
| 14 | $25^a$ |
| 15 | $77^a$ |
| 16 | $1^a$ |
| 17 | $114^a$ |
| 18 | $4^a$ |
| 19 | $52^a$ |
| 20 | $973^a$ |
| 21 | $1^a$ |
| 22 | $352^a$ |
| 24 | $214^a$ |
| 25 | $12^a$ |
| 26 | $1^a$ |
| 27 | $15^a$ |
| 28 | $196^a$ |
| 29 | $3^a$ |
| 30 | $3^a$ |
| 31 | $3^a$ |
| 32 | $6^a$ |
| 33 | $3^a$ |
| 34 | $15^a$ |
| 35 | $26^a$ |
| 36 | $8^a$ |
| 37 | $1^a$ |

TABLE 2-continued

| Example No. | Plasma Kallikrein Ki (nM) |
|---|---|
| 38 | $6^a$ |
| 39 | $2^a$ |
| 40 | $4^a$ |
| 41 | $2^a$ |
| 42 | $2^a$ |
| 45 | $7^b$ |
| 46 | $669^b$ |
| 47 | $66^b$ |
| 48 | $49^b$ |
| 49 | $3^b$ |
| 50 | $130^b$ |
| 51 | $38^b$ |
| 52 | $193^b$ |
| 53 | $2^b$ |
| 54 | $1^b$ |
| 55 | $19^b$ |
| 56 | $137^b$ |
| 57 | $351^b$ |
| 58 | $179^b$ |
| 59 | $68^b$ |
| 60 | $1090^b$ |
| 61 | $7^b$ |
| 62 | $1095^b$ |
| 63 | $48^b$ |
| 64 | $171^b$ |
| 65 | $53^b$ |
| 66 | $45^b$ |
| 67 | $19^b$ |
| 68 | $3^b$ |
| 69 | $338^b$ |
| 70 | $18^b$ |
| 71 | $60^b$ |
| 72 | $19^b$ |
| 73 | $6^b$ |
| 74 | $238^b$ |
| 75 | $4^b$ |
| 76 | $15^b$ |
| 77 | $67^a$ |
| 78 | $5^a$ |
| 79 | $3^a$ |
| 80 | $38^b$ |
| 81 | $1^b$ |
| 82 | $22^b$ |
| 83 | $7^b$ |
| 84 | $16^b$ |
| 85 | $47^b$ |
| 86 | $1^b$ |
| 87 | $63^b$ |
| 88 | $5^b$ |
| 89 | $5^b$ |
| 90 | $4^a$ |
| 91 | $3^b$ |
| 92 | $3^b$ |
| 93 | $3^a$ |
| 94 | $1027^b$ |
| 95 | $107^b$ |
| 96 | $1968^b$ |
| 98 | $36^b$ |
| 99 | $2402^b$ |
| 100 | $4^b$ |
| 103 | $13^b$ |
| 105 | $3920^b$ |
| 106 | $890^b$ |
| 107 | $88^b$ |
| 108 | $29^b$ |
| 109 | $40^b$ |
| 110 | $3.91^b$ |
| 111 | $3.25^b$ |
| 112 | $6.44^b$ |
| 113 | $15.62^b$ |
| 114 | $143.20^b$ |
| 115 | $362.20^b$ |
| 116 | $738.80^b$ |
| 117 | $>13020.00^b$ |
| 118 | $2027.00^b$ |
| 119 | $534.50^b$ |
| 120 | $187.40^b$ |

TABLE 2-continued

| Example No. | Plasma Kallikrein Ki (nM) |
|---|---|
| 121 | 39.29[b] |
| 122 | 9318.00[b] |
| 123 | 26.10[b] |
| 124 | 483.40[b] |
| 125 | 11.60[b] |
| 126 | 37.58[b] |
| 127 | 9.97[b] |
| 128 | 25.46[b] |
| 129 | 21.67[b] |
| 130 | 26.49[b] |
| 131 | 20.82[b] |
| 132 | 17.32[b] |
| 133 | 12.61[b] |
| 134 | 192.40[b] |
| 135 | 0.56[b] |
| 136 | 117.90[b] |
| 137 | 91.28[b] |
| 138 | 31.70[b] |
| 139 | 6046.00[b] |
| 140 | 28.71[b] |
| 141 | 123.10[b] |
| 142 | 7.76[b] |
| 143 | 3.38[b] |
| 144 | 107.90[b] |
| 145 | 28.01[b] |
| 146 | 56.46[b] |
| 147 | 7.51[b] |
| 148 | 118.10[b] |
| 149 | 22.55[b] |
| 150 | 2.27[b] |
| 151 | 23.82[b] |
| 152 | 24.3[b] |
| 153 | 21.16[b] |
| 154 | 117.50[b] |
| 155 | 198.90[b] |
| 156 | 3249.00[b] |
| 157 | 108.00[b] |
| 158 | 10900.00[b] |
| 159 | 58.90[b] |
| 160 | 2.00[b] |
| 161 | 21.57[b] |
| 162 | 124.90[b] |
| 163 | 223.80[b] |
| 164 | 442.20[b] |
| 165 | 9471.00[b] |
| 166 | 112.60[b] |
| 167 | 20.08[b] |
| 168 | 1916.00[b] |
| 169 | 768.40[b] |
| 170 | 7.73[b] |
| 171 | 8.87[b] |
| 172 | — |
| 173 | — |
| 174 | 1398.00[b] |
| 175 | 3809.00[b] |
| 176 | 522.60[b] |
| 177 | 4.02[b] |
| 178 | 5.68[b] |
| 179 | 50.11[b] |
| 180 | 2.42[b] |
| 181 | 3.29[b] |
| 182 | 14.31[b] |
| 183 | 297.00[b] |
| 184 | 2.51[b] |
| 185 | 47.40[b] |
| 186 | 60.46[b] |
| 187 | 17.38[b] |
| 188 | 23.16[b] |
| 189 | 40.42[b] |
| 190 | 1.11[b] |
| 191 | 19.25[b] |
| 192 | 181.60[b] |
| 193 | 3.91[b] |
| 194 | 310[a] |
| 195 | 2.96[b] |
| 196 | 1.52[b] |
| 197 | 4.83[b] |
| 198 | 1.00[b] |
| 199 | 1.79[b] |
| 200 | 28.71[b] |
| 201 | 105.00[b] |
| 202 | 30.11[b] |
| 203 | 44.05[b] |
| 204 | 15.98[b] |
| 205 | 88.36[b] |
| 206 | 27.46[b] |
| 207 | 5.80[b] |
| 208 | 3.10[b] |
| 209 | 457.30[b] |
| 210 | 1200.00[b] |
| 211 | 6.46[b] |
| 212 | 286.20[b] |
| 213 | 3370.00[b] |
| 214 | >13020.00[b] |
| 215 | 3.61[b] |
| 216 | 212.3[b] |
| 217 | 154.50[b] |
| 218 | 377.60[b] |
| 219 | 6.85[b] |
| 220 | 50.16[b] |
| 221 | 1317.00[b] |
| 222 | 501.20[b] |
| 223 | 146.40[b] |
| 224 | 270.80[b] |
| 225 | 95.55[b] |
| 226 | 164.80[b] |
| 227 | 3.90[b] |

[a]tested at 25° C.
[b]tested at 37° C.

B. In Vivo Assays

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

a. In Vivo Electrically-Induced Carotid Artery Thrombosis (ECAT) Model

The rabbit ECAT model, described by Wong et al. (*J. Pharmacol. Exp. Ther.*, 295:212-218 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to or after the initiation of thrombosis. Drug treatment prior to initiation of thrombosis is used to model the ability of test agents to prevent and reduce the risk of thrombus formation, whereas dosing after initiation is used to model the ability to treat existing thrombotic disease. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by the trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

b. In Vivo Rabbit Arterio-Venous (AV) Shunt Thrombosis Model

The rabbit AV shunt model, described by Wong et al. (Wong, P. C. et al., *J. Pharmacol. Exp. Ther.* 292:351-357 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm). The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose that produces 50% inhibition of thrombus formation) are estimated by a nonlinear least square regression program using the Hill sigmoid $E_{max}$ equation (DeltaGraph; SPSS Inc., Chicago, Ill.).

The anti-inflammatory effect of these compounds can be demonstrated in an Evans Blue dye extravasation assay using C1-esterase inhibitor deficient mice. In this model, mice are dosed with a compound of the present invention, Evans Blue dye is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient. In one embodiment, the pharmaceutical composition is a solid formulation, e.g., a spray-dried composition, which may be used as is, or whereto the physician or the patient adds solvents, and/or diluents prior to use.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels. Solid dispersions are also called solid-state dispersions. In some embodiments, any compound described herein is formulated as a spray dried dispersion (SDD). An SDD is a single phase amorphous molecular dispersion of a drug in a polymer matrix. It is a solid solution prepared by dissolving the drug and a polymer in a solvent (e.g., acetone, methanol or the like) and spray drying the solution. The solvent rapidly evaporates from droplets which rapidly solidifies the polymer and drug mixture trapping the drug in amorphous form as an amorphous molecular dispersion.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to about 100 milligrams of the compound of the present invention and about 0.1 to about 100 milligrams per kilogram of patient body weight. For a tablet dosage form, the compounds of this invention generally may be present in an amount of about 5 to about 300 milligrams per dosage unit, and the second anti-coagulant in an amount of about 1 to about 500 milligrams per dosage unit.

Where the compounds of the present invention are administered in combination with an anti-platelet agent, by way of general guidance, typically a daily dosage may be about 0.01 to about 300 milligrams of the compound of the present invention and about 50 to about 150 milligrams of the anti-platelet agent, preferably about 0.1 to about 4 milligrams of the compound of the present invention and about 1 to about 3 milligrams of antiplatelet agents, per kilogram of patient body weight.

Where the compounds of the present invention are administered in combination with thrombolytic agent, typically a daily dosage may be about 0.1 to about 100 milligrams of the compound of the present invention, per kilogram of patient body weight and, in the case of the thrombolytic agents, the usual dosage of the thrombolyic agent when administered alone may be reduced by about 50-80% when administered with a compound of the present invention.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In another embodiment, the present invention provides a pharmaceutical composition further comprising additional therapeutic agent(s) selected from potassium channel openers, potassium channel blockers, calcium channel blockers, sodium hydrogen exchanger inhibitors, antiarrhythmic agents, antiatherosclerotic agents, anticoagulants, anti-thrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In another embodiment, the present invention provides a pharmaceutical composition wherein the additional therapeutic agent is an antihypertensive agent selected from ACE inhibitors, AT-1 receptor antagonists, beta-adrenergic receptor antagonists, ETA receptor antagonists, dual ETA/AT-1 receptor antagonists, renin inhibitors (alliskerin) and vasopepsidase inhibitors, an antiarrythmic agent selected from IKur inhibitors, an anticoagulant selected from thrombin inhibitors, antithrombin-III activators, heparin co-factor II activators, other factor XIa inhibitors, other kallikrein inhibitors, plasminogen activator inhibitor (PAI-1) antagonists, thrombin activatable fibrinolysis inhibitor (TAFI) inhibitors, factor VIIa inhibitors, factor IXa inhibitors, and factor Xa inhibitors, or an antiplatelet agent selected from GPIIb/IIIa blockers, GP Ib/IX blockers, protease activated receptor 1 (PAR-1) antagonists, protease activated receptor 4 (PAR-4) antagonists, prostaglandin E2 receptor EP3 antagonists, collagen receptor antagonists, phosphodiesterase-III inhibitors, $P2Y_1$ receptor antagonists, $P2Y_{12}$ antagonists, thromboxane receptor antagonists, cyclooxygense-1 inhibitors, and aspirin, or a combination thereof.

In another embodiment, the present invention provides pharmaceutical composition, wherein the additional therapeutic agent(s) are an anti-platelet agent or a combination thereof.

In another embodiment, the present invention provides a pharmaceutical composition, wherein the additional therapeutic agent is the anti-platelet agent clopidogrel.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

Compounds that can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVENOX®), synthetic pentasaccharide, direct acting thrombin inhibitors including hirudin and argatroban, as well as other factor VIIa inhibitors, factor IXa inhibitors, factor Xa inhibitors (e.g., ARIXTRA®, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granule-content secretion of platelets. Such agents include, but are not limited to, the various known non-steroidal anti-inflammatory drugs (NSAIDs) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDs, aspirin (acetylsalicylic acid or ASA) and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil), protease-activated receptor 1 (PAR-1) antagonists (e.g., E-5555, SCH-530348, SCH-203099, SCH-529153 and SCH-205831), and pharmaceutically acceptable salts or prodrugs thereof.

Other examples of suitable anti-platelet agents for use in combination with the compounds of the present invention, with or without aspirin, are ADP (adenosine diphosphate) receptor antagonists, preferably antagonists of the purinergic receptors $P2Y_1$ and $P2Y_{12}$, with $P2Y_{12}$ being even more preferred. Preferred $P2Y_{12}$ receptor antagonists include clopidogrel, ticlopidine, prasugrel, ticagrelor, and cangrelor, and pharmaceutically acceptable salts or prodrugs thereof. Ticlopidine and clopidogrel are also preferred compounds since they are known to be more gentle than aspirin on the gastro-intestinal tract in use. Clopidogrel is an even more preferred agent.

A preferred example is a triple combination of a compound of the present invention, aspirin, and another anti-platelet agent. Preferably, the anti-platelet agent is clopidogrel or prasugrel, more preferably clopidogrel.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable cholesterol/lipid lowering agents and lipid profile therapies for use in combination with the compounds of the present invention include HMG-CoA reductase inhibitors (e.g., pravastatin, lovastatin, simvastatin, fluvastatin, atorvastatin, rosuvastatin, and other statins), low-density lipoprotein (LDL) receptor activity modulators (e.g., HOE-402, PCSK9 inhibitors), bile acid sequestrants (e.g., cholestyramine and colestipol), nicotinic acid or derivatives thereof (e.g., NIASPAN®), GPR109B (nicotinic acid receptor) modulators, fenofibric acid derivatives (e.g., gemfibrozil, clofibrate, fenofibrate and benzafibrate) and other peroxisome proliferator-activated receptors (PPAR) alpha modulators, PPARdelta modulators (e.g., GW-501516), PPARgamma modulators (e.g., rosiglitazone), compounds that have multiple functionality for modulating the activities of various combinations of PPARalpha, PPARgamma and PPARdelta, probucol or derivatives thereof (e.g., AGI-1067), cholesterol absorption inhibitors and/or Niemann-Pick C1-like transporter inhibitors (e.g., ezetimibe), cholesterol ester transfer protein inhibitors (e.g., CP-529414), squalene synthase inhibitors and/or squalene epoxidase inhibitors or mixtures thereof, acyl coenzyme A: cholesteryl acyltransferase (ACAT) 1 inhibitors, ACAT2 inhibitors, dual ACAT1/2 inhibitors, ileal bile acid transport inhibitors (or apical sodium co-dependent bile acid transport inhibitors), microsomal triglyceride transfer protein inhibitors, liver-X-receptor (LXR) alpha modulators, LXRbeta modulators, LXR dual alpha/beta modulators, FXR modulators, omega 3 fatty acids (e.g., 3-PUFA), plant stanols and/or fatty acid esters of plant stanols (e.g., sitostanol ester used in BENECOL® margarine), endothelial lipase inhibitors, and HDL functional mimetics which activate reverse cholesterol transport (e.g., apoAI derivatives or apoAI peptide mimetics).

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 μM against the target protease and greater than or equal to 0.1 μM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by many methods available to those skilled in the art of organic chemistry (Maffrand, J. P. et al., *Heterocycles*, 16(1):35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, 4th Edition, Wiley-Interscience (2006)).

Representative compounds of this invention where ring A is a six-membered heterocycle (example—pyridine) can be derived from intermediates 11, the synthesis of which is described in Scheme 1. Condensation of aldehyde 1a (X=N) prepared according to a modified procedure described by Negi (*Synthesis*, 991 (1996)), with (S)-2-methylpropane-2-sulfinamide in the presence of anhydrous copper sulfate or cesium carbonate in a solvent such as DCM gives the sulfinimine 1b (Ellman, J., *J. Org. Chem.*, 64:1278 (1999)). Using a modified procedure described by Kuduk (*Tetrahedron Letters*, 45:6641 (2004)), suitably substituted Grignard reagents, for example allylmagnesium bromide, can be added to sulfinimine 1b to give a sulfinamide 1c, as a mixture of diastereomers which can be separated at various stages of the sequence. The diastereoselectivity for the addition of allylmagnesium bromide to sulfinimine 1b can be improved by employing indium(III) chloride according to a modified procedure of Xu (Xu, M-H, *Organic Letters*, 2008, 10 (6), 1259). Suzuki-Miyaura coupling between 4-chloropyridine 1c and an appropriately substituted aryl or heteroaryl boronic acid or ester 1e in the presence of a base such as potassium phosphate, in a solvent mixture, such as DMSO and H$_2$O, or DMF, using a precatalyst such as Pd(dppf)Cl$_2$.CH$_2$Cl$_2$ complex provides 1g. Alternatively, the Suzuki-Miyaura coupling between boronic acid 1d and an appropriately substituted aryl or heteroaryl halide 1f can be used to prepared 1g. Protecting group interconversion can be accomplished in two steps to give 1h. Alternatively, the protecting group interconversion can take place initially on 1c followed by the Suzuki-Miyaura coupling. The aniline 1h can then be coupled with an appropriately substituted carboxylic acid 1i using T3P and a base, such as pyridine, to give the amide 1j. Using a modified procedure described by Lovely (*Tetrahedron Letters*, 44:1379 (2003)), 1j, following pretreatment with p-toluenesulfonic acid to form the pyridinium ion, can be cyclized via ring-closing metathesis using a catalyst, such as Grubbs (II), in a suitable solvent, such as DCM, DCE, or toluene at elevated temperature, to give the pyridine-containing macrocycle 1k. The alkene can be reduced with hydrogen over either palladium on carbon or platinum oxide, and subsequent deprotection with TFA in DCM or 4M HCl in dioxane provides amine 1l. Compounds of the formulae 11 can be converted to compounds in this invention according to Schemes 3-5.

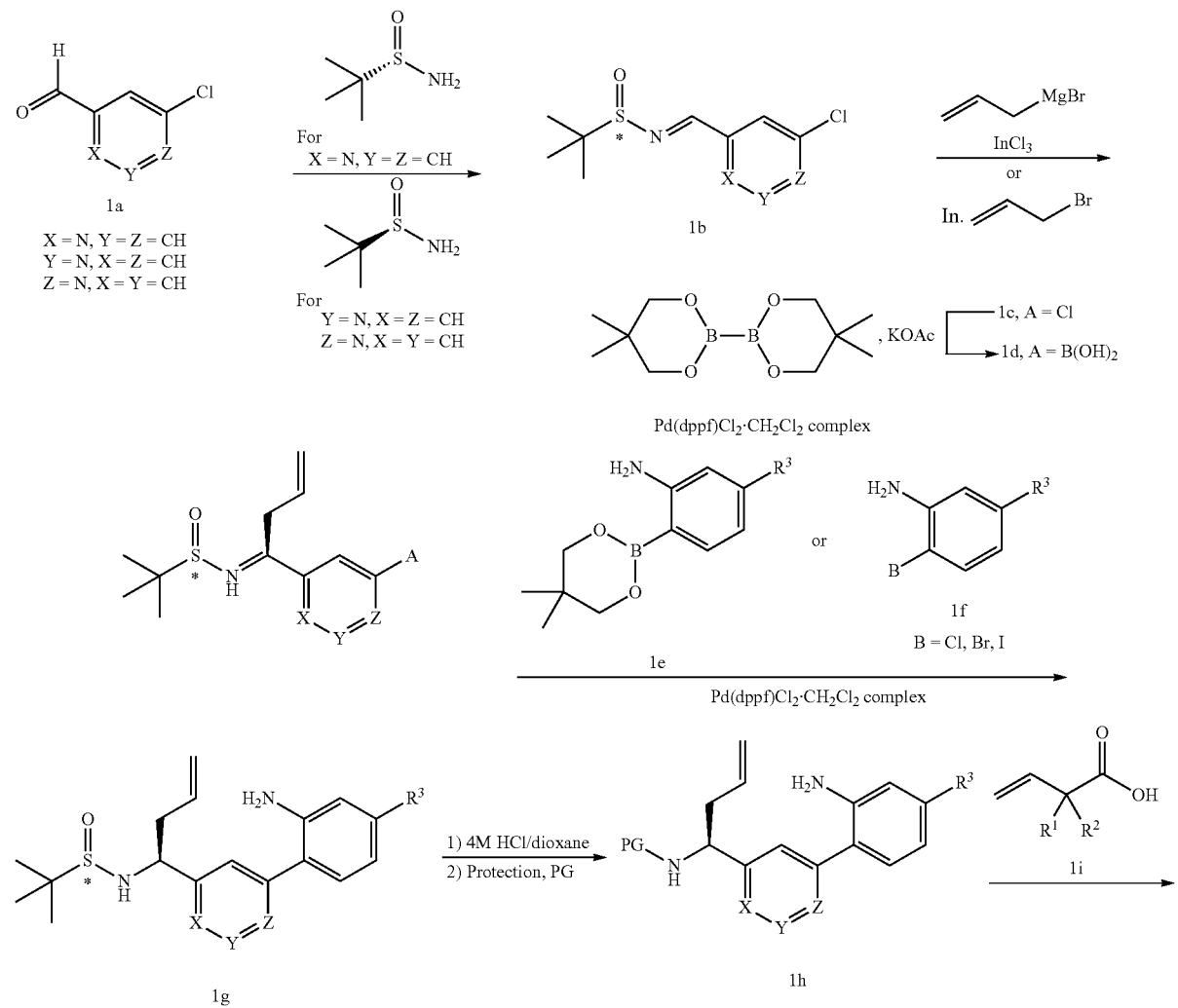

Scheme 1

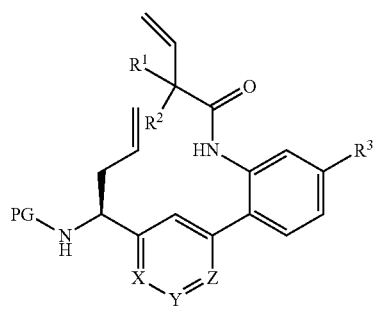

1j

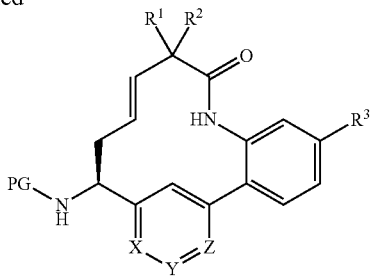

1k

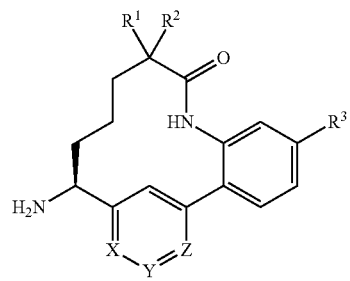

1l

Additional pyridine containing macrocycles useful for the synthesis of compounds of this invention can also be prepared according to Scheme 1. In cases where the pyridine core is a 4-pyridine (Z=N) rather than the 2-pyridine (X=N), conversion of 1h to 1j can be easily accomplished by using an acid chloride of 1i. Intermediates of formulae 1g where $R^3$=$NO_2$ may be modified further to give intermediates where $R^3$=NH $CO_2$—$C_{1-4}$ alkyl either before coupling with acid 1i or after coupling with acid. Reduction of the nitro group to an amino group may be accomplished with a reducing agent (e.g., Zn—$NH_4Cl$) in an inert solvent (e.g., MeOH) to give an intermediate of formula 1h where $R^3$=$NH_2$. These anilino derivatives may be coupled with chloroalkanoates of the formula $ClCO_2$—$C_{1-4}$ alkyl in the presence of a base (e.g., DIEA) in an inert solvent (e.g., DCM) to give intermediates where $R^3$=NH $CO_2$—$C_{1-4}$ alkyl.

Representative synthesis of compounds in this invention where ring A is methoxy-pyridine and $R^3$ is —NHCOOMe is outlined in Scheme 2. Acetal protection of methyl 4-formyl-3-nitrobenzoate 2a, followed by hydrolysis of the ester and acyl azide formation gave intermediate 2c. Subsequent Curtius rearrangement in the presence of MeOH. Upon treatment with aqueous TFA, the acetal group was converted into benzaldehyde 2e which was used in a Horner-Wadsworth-Emmons reaction with (S)-tert-butyl (1-(dimethoxyphosphoryl)-2-oxohex-5-en-3-yl)carbamate (synthesis previously described) to afford 2f. Then, enone 2f was converted into key intermediate 2g by treatment with $NH_4OAc$ and the pyridinium ester followed by nitro group reduction. Chiral separation of 2g necessary due to partial racemization during pyridone ring formation. Methylation of chiral separation product 2g2 gave 2-methyoxy pyridine 2h. Zn mediated reduction of nitro group afforded aniline 2l. Coupling of aniline 2l with the 2-methylbut-3-enoic acid resulted in formation of 2j. The following ring closing metathesis formed two isomers 2k1 and 2k2. Hydrogenation and deprotection of 2k1 and 2k2 gave the crucial intermediate 2l1 and 2l2 which can be coupled with various acids to afford compounds of this invention as shown in Scheme 3.

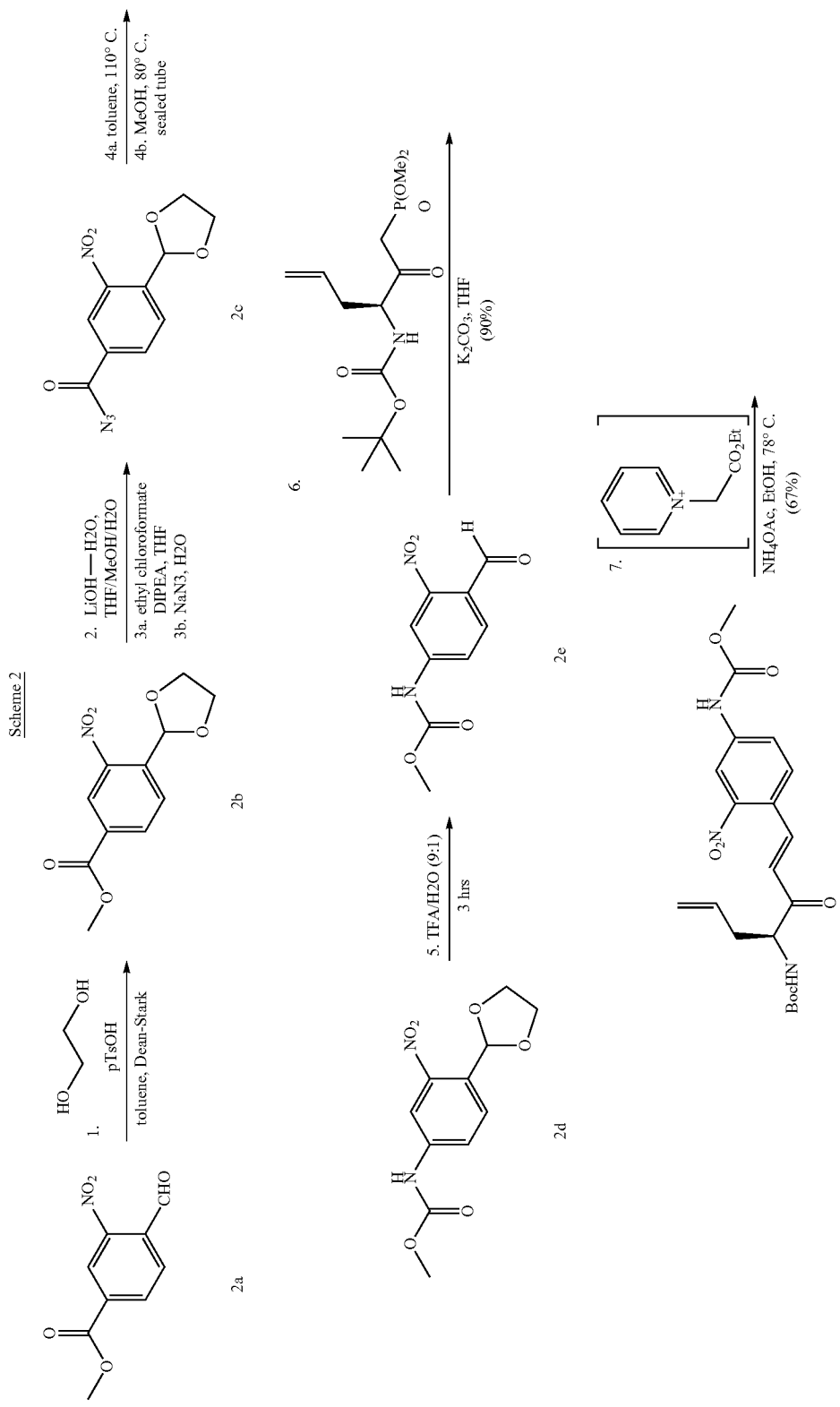

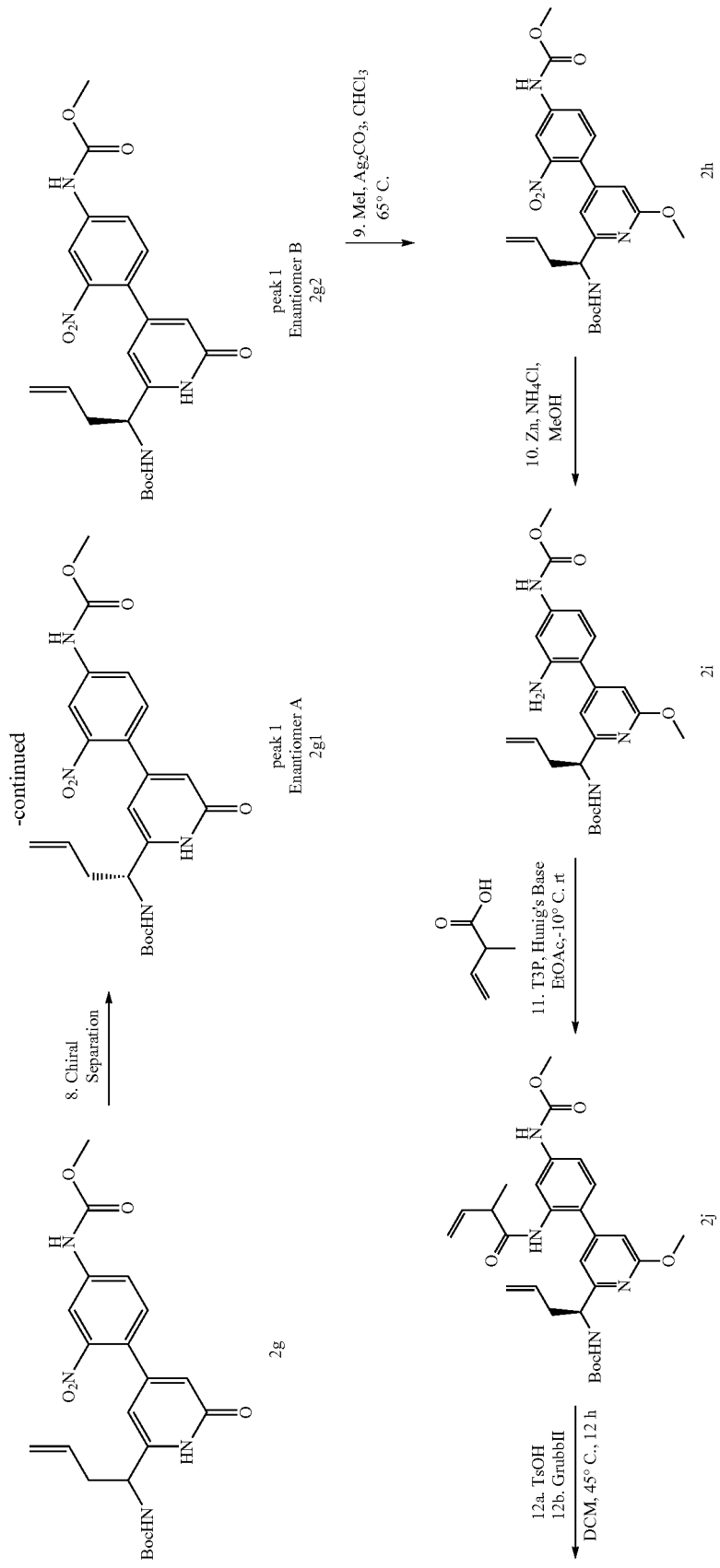

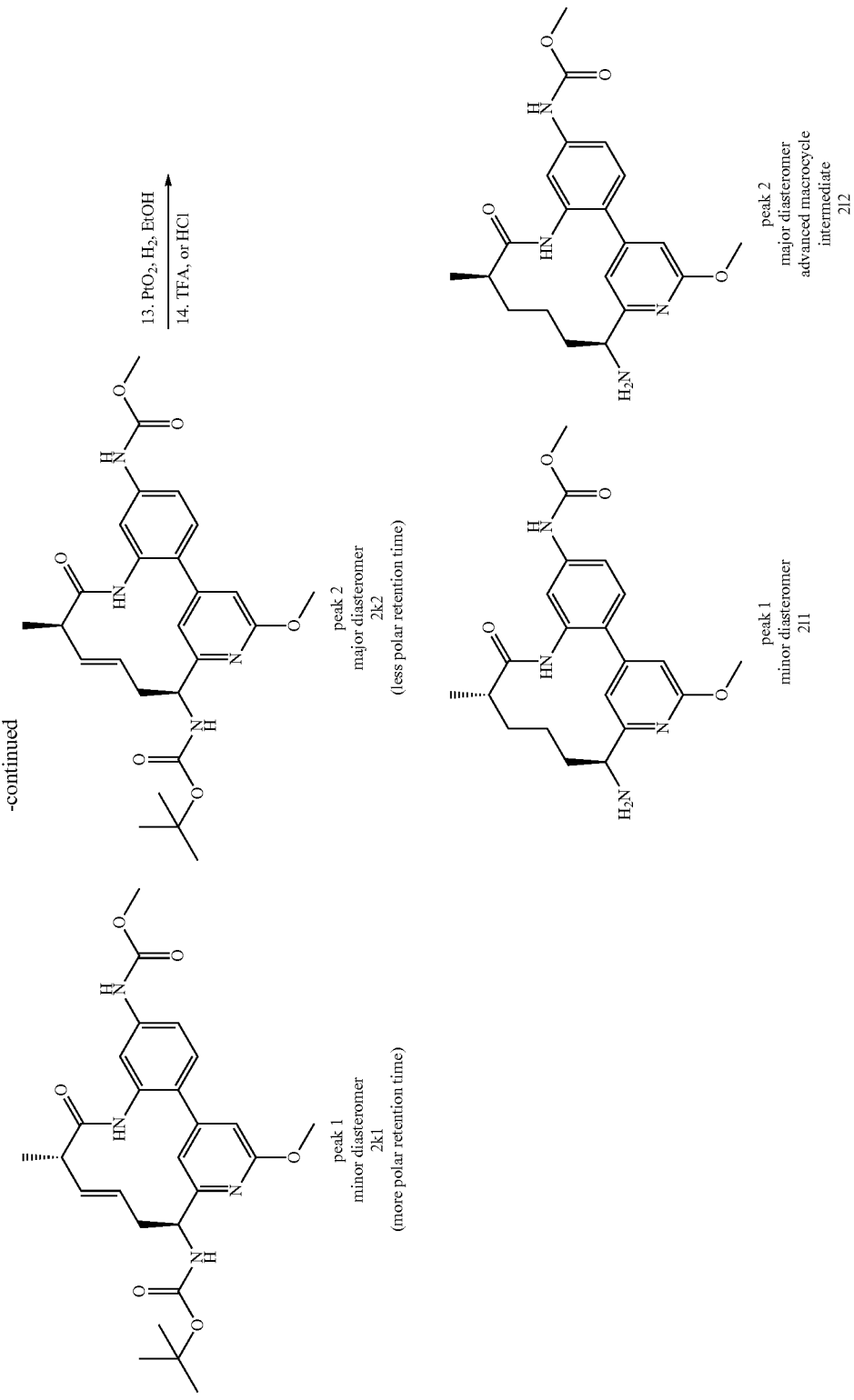

Methods for synthesis of a large variety of substituted pyridine compounds useful as starting materials for the preparation of compounds of the present invention are well known in the art and have been extensively reviewed. (For examples of methods useful for the preparation of pyridine starting materials see: Kroehnke, F., *Synthesis*, 1 (1976); Abramovitch, R. A., ed., "Pyridine and Its Derivatives", *The Chemistry of Heterocyclic Compounds*, 14(Suppl. 1-4), John Wiley & Sons, New York (1974); Boulton, A. J. et al., eds., *Comprehensive Heterocyclic Chemistry*, 2:165-524, Pergamon Press, New York (1984); McKillop, A., ed., *Comprehensive Heterocyclic Chemistry*, 5:1-300, Pergamon Press, New York (1996)).

In cases where suitably substituted boronic acids are not commercially available, a modification to this approach may be adopted wherein an aryl halide is subjected to a palladium mediated coupling with a diboron species such as bis(pinacolato) diboron or bis(neopentyl glycolato)diboron to provide the corresponding 4,4,5,5-tetramethyl-[1,3,2]dioxaborolane or the 5,5-dimethyl-[1,3,2]dioxaborolane intermediates using the method of Ishiyama, T. et al. (*J. Org. Chem.*, 60(23):7508-7510 (1995)). Alternately, this same intermediate can be prepared by reaction of the intermediate halide with the corresponding dialkoxyhydroborane as described by Murata et al. (*J. Org. Chem.*, 62(19):6458-6459 (1997)).

The boron pinacolate intermediates can be used in place of boronic acids for coupling to the aryl/heteroaryl halides or triflates or the boron pinacolate intermediate can be converted to the boronic acids. Alternately, the corresponding boronic acids can be prepared by metal-halogen exchange of the aryl/heteroaryl halide, quenching with a trialkoxyborate reagent, and aqueous workup to provide the boronic acids (Miyaura, N. et al., *Chem. Rev.*, 95:2457 (1995)).

It is also realized that the scope of intermediate synthesis can be further extended outside the use of Suzuki-Miyaura coupling methodology since the precursor aryl halides or triflates described above are also precursors for Stille, Negishi, Hiyama, and Kumada-type cross coupling methodologies (Tsuji, J., *Transition Metal Reagents and Catalysts: Innovations in Organic Synthesis*, John Wiley & Sons (2000); Tsuji, J., *Palladium Reagents and Catalysts: Innovations in Organic Synthesis*, John Wiley & Sons (1996)).

Representative compounds of this invention can be prepared as shown in scheme 3. Starting from aldehyde 3a, vinyl Grignard addition followed by oxidation gives the vinyl ketone 3c. Alternatively, the vinyl Grignard can be reacted with the Weinreb amide 3g to give the vinyl ketone 3c. Michael addition of the amines from schemes 1, 2, and 6 followed by acylation with 3d affords compounds 3e, which upon cyclization with base provides the dihydropyridone 3f.

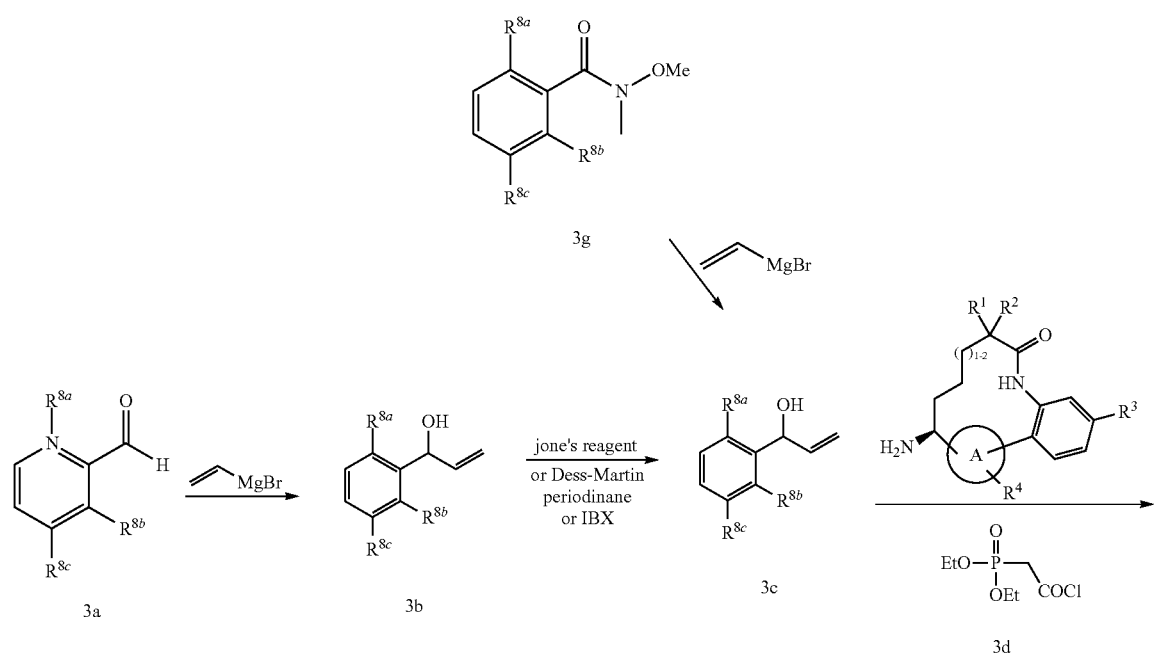

Scheme 3

-continued

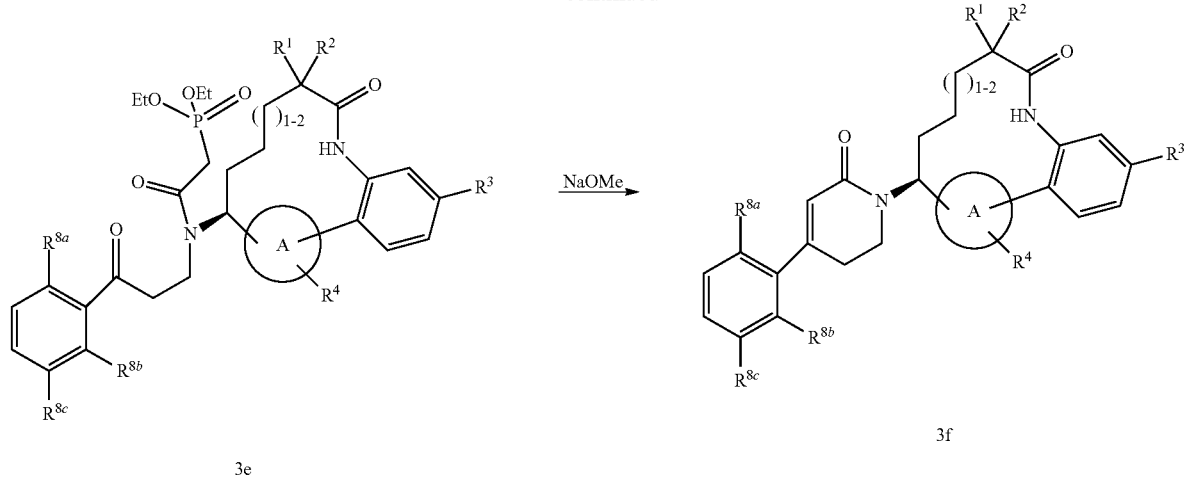

3e → NaOMe → 3f

Alternatively, the compounds in this invention may also be prepared as shown in scheme 4. Ally Grignard addition to compounds 4a followed by TBS protection gives compounds 4b. OsO$_4$ oxidation provides aldehydes 4c. Reductive amination of the amines prepared in schemes 1, 2, and 6 and aldehydes 4c followed by acylation with 3d affords compounds 4e. Deprotection of compounds 4e followed by oxidation and cyclization provides the compounds 4g.

Scheme 4

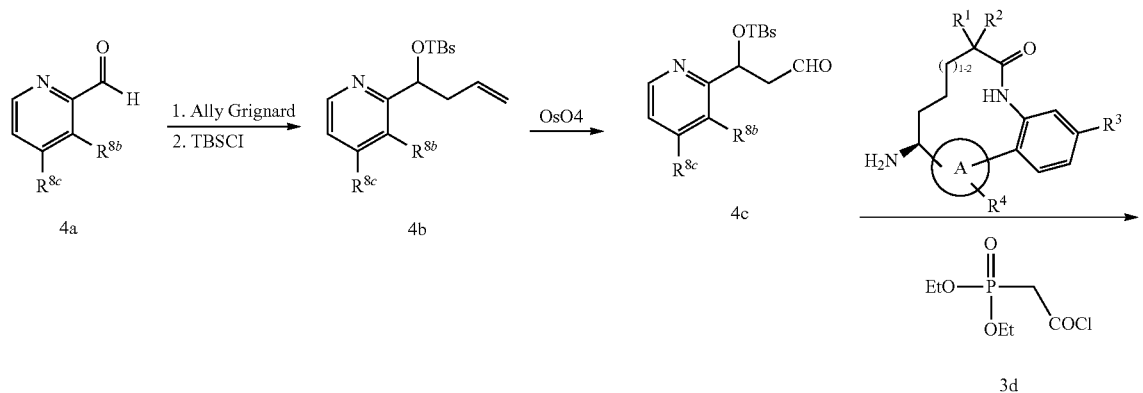

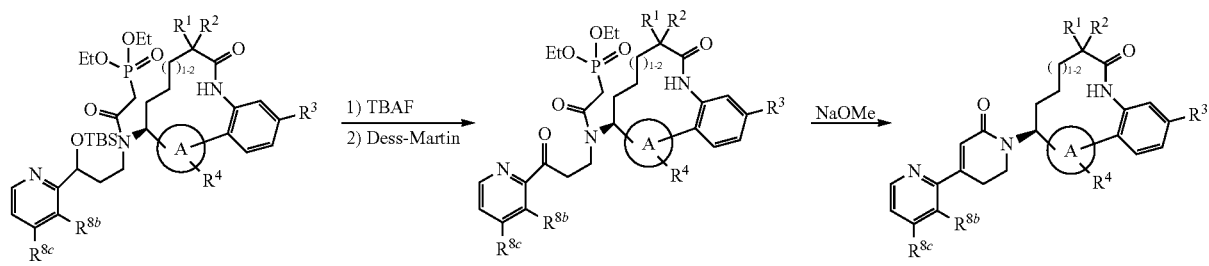

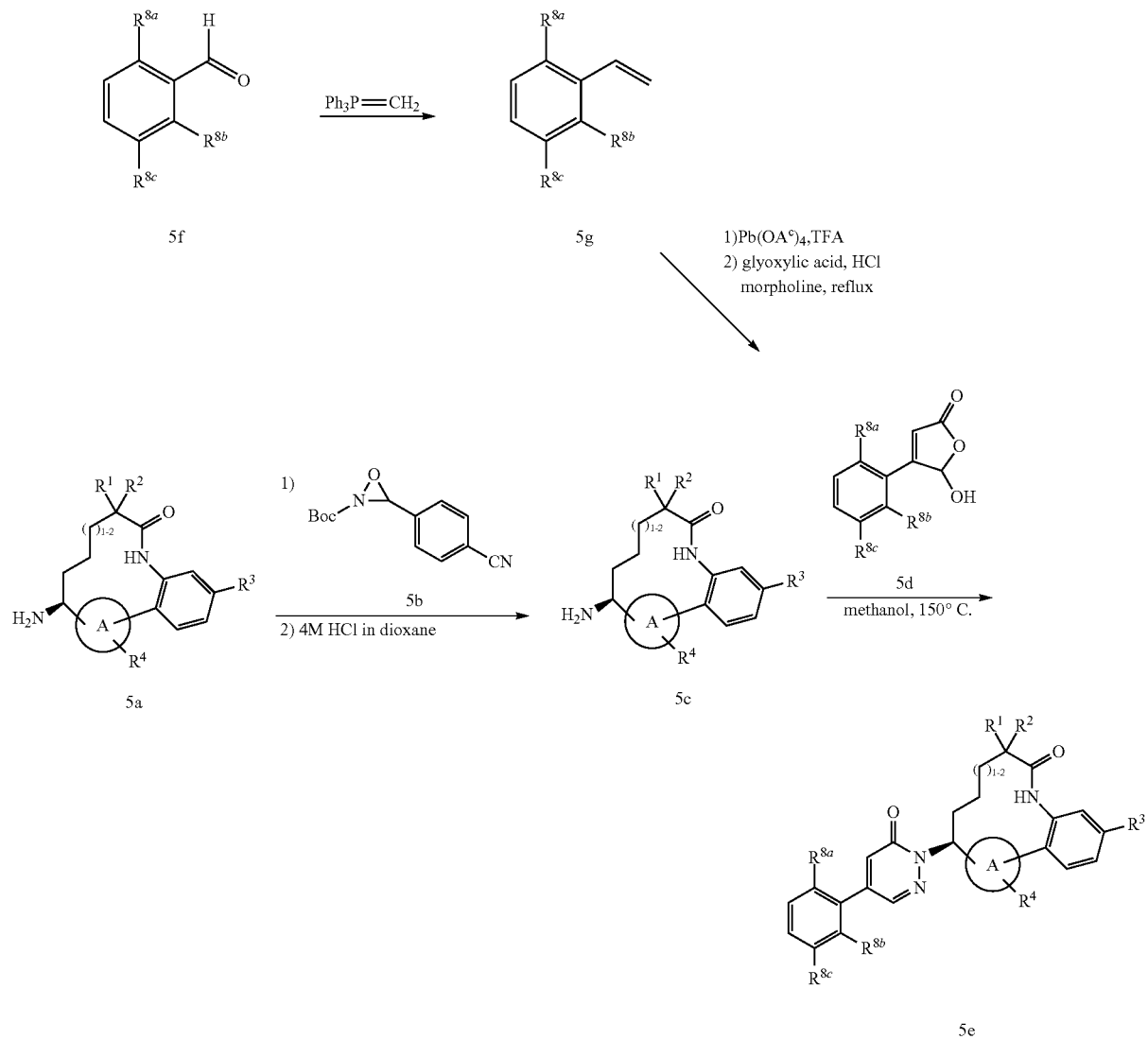

Representative pyridazinone compounds of this invention can be prepared as shown in Scheme 5. Using a modified procedure described by Vidal (*Chem. Eur. J.*, 1997, 3(10), 1691), amine 5a can be reacted with oxaziridine 5b to give the Boc-protected hydrazine derivative. Deprotection with either TFA in dichloromethane or 4M HCl in dioxane affords hydrazine 5c. Condensation of hydrazine 5c and a suitably substituted hydroxy furanone 5d in methanol at elevated temperatures provides the pyridazinone 5e. Suitably substituted hydroxy furanone derivatives 5d can be prepared in two steps from styrene 5g according to a modified procedure described by van Niel (*J. Med. Chem.*, 2005, 48, 6004). Styrene 5g can be oxidized with lead tetraacetate in TFA to give the corresponding acetaldehyde derivative followed by condensation with glyoxylic acid in the presence of morpholine and hydrochloric acid at elevated temperatures will provide 5d.

Intermediates for preparation of compounds of this invention wherein ring A is an imidazole ring, can be prepared from an appropriately N-protected allylglycine 6a according to the general method outlined in Scheme 6 (Contour-Galcera et al., *Bioorg. Med. Chem. Lett.*, 11(5):741-745 (2001)). Condensation of 6a with a suitably substituted bromoacetophenone 6b in the presence of a suitable base such as potassium bicarbonate, $K_2CO_3$ or $Cs_2CO_3$ in a suitable solvent such as DMF provides a keto ester intermediate which can be cyclized to afford an imidazole 6c by heating in the presence of excess ammonium acetate in a solvent such as toluene or xylene. This latter transformation can be conveniently carried out on small scale at 160° C. in a microwave reactor or on larger scale by refluxing the mixture while removing water via a Dean-Stark trap. The resulting imidazole intermediate 6c is then protected by treatment with SEM-Cl in the presence of a base such as sodium hydride or dicyclohexylmethylamine in a solvent such as THF or DCM. The nitro intermediate 6d is then converted to the corresponding aniline 6e by using Zn mediated reduction. Acylation of 6e with the appropriate alkenoic acid and a coupling agent such as T3P or BOP reagent, or alternately, by treatment with an alkenoic acid chloride in the presence of a base such as TEA of DIEA provides diene 6f, which undergoes ring closing metathesis by heating in dilute solution in the presence of p-toluene sulfonic acid and Grubbs II catalyst in a suitable solvent such as DCM or DCE to provide the corresponding macrocycle 6g (*Tetrahedron Letters*, 44:1379 (2003)). The alkene 6g can be reduced with hydrogen over either palladium on carbon or platinum oxide and subsequent deprotection with TFA in DCM provides amine 6k (R=H). When R=alkyl group, imidazole 6h can be brominated by NBS to give bromide 6i. Pd-catalyzed Suzuki coupling with boronic acid provides imidazole 6j and subsequent deprotection with TFA in DCM provides amine 6k. Compounds of the formula 6k can be converted to compounds in this invention according to Scheme 3.

Scheme 6

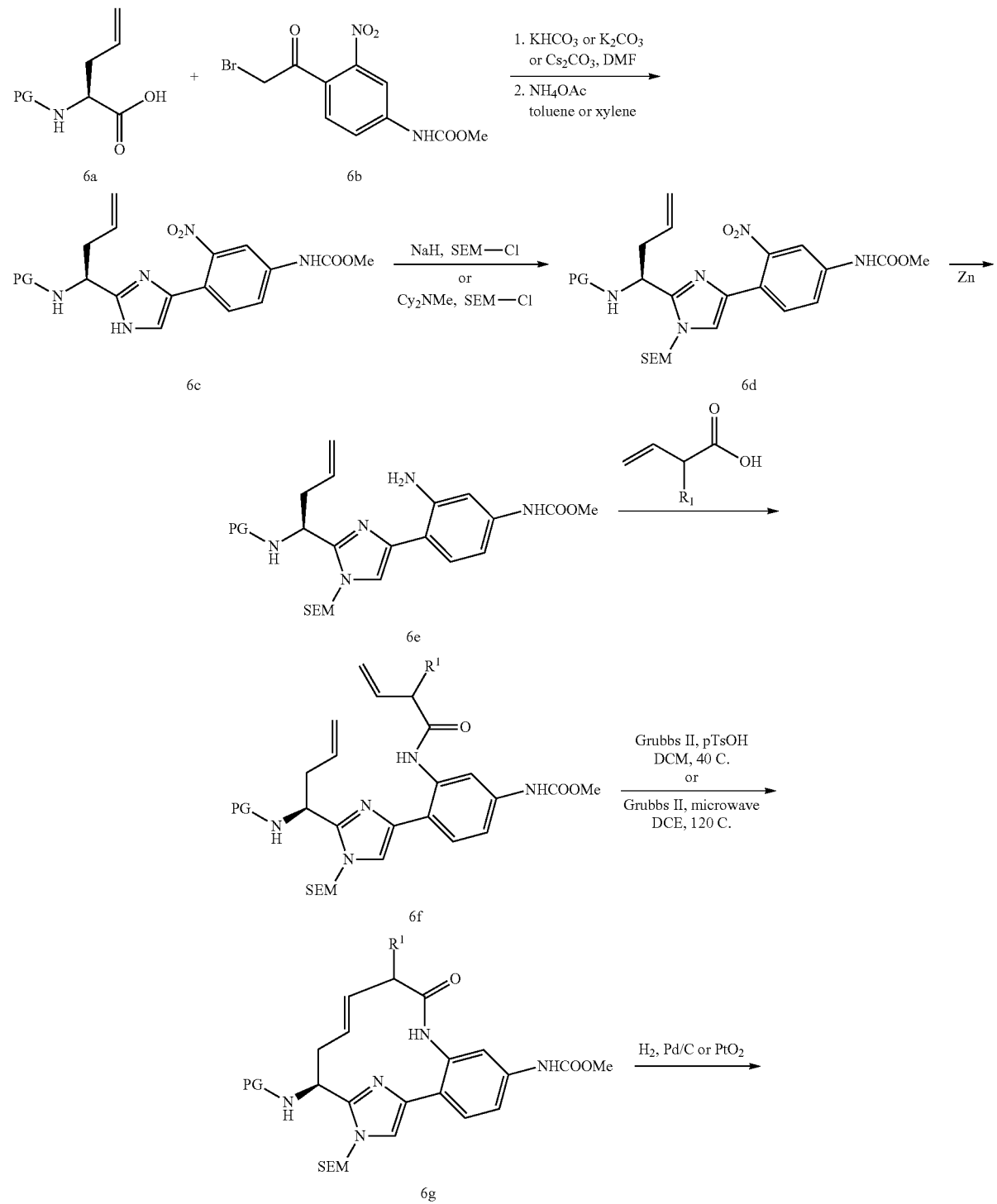

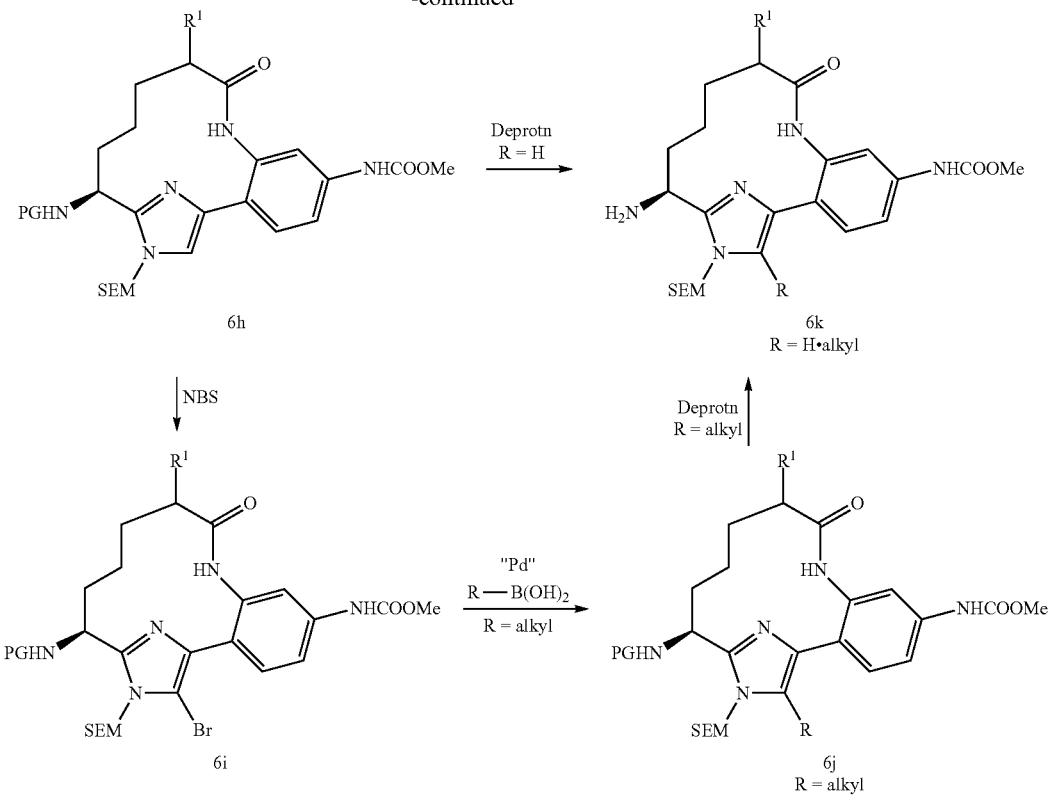

PG = Boc, Cbz

Intermediates for preparation of compounds of this invention wherein ring B is a pyrazole ring, can be prepared from an appropriately chloride 1c according to the general method outlined in Scheme 7. Protecting group interconversion can be accomplished in two steps to give 7a. Suzuki-Miyaura coupling between 4-chloropyridine 7a and boronic ester in the presence of a base such as potassium phosphate, in a solvent mixture, such as DMSO and $H_2O$, or DMF, using a precatalyst such as $Pd(dppf)Cl_2 \cdot CH_2Cl_2$ complex provides 7b. Suzuki coupling of bronic acid 7b and bromide 7c gives pyrazole 7d. Compounds of the formula 7d can be converted to compounds in this invention according to Scheme 1 and Scheme 3.

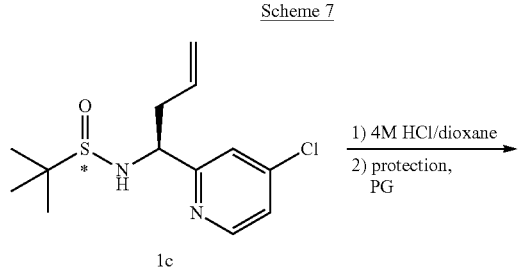

Scheme 7

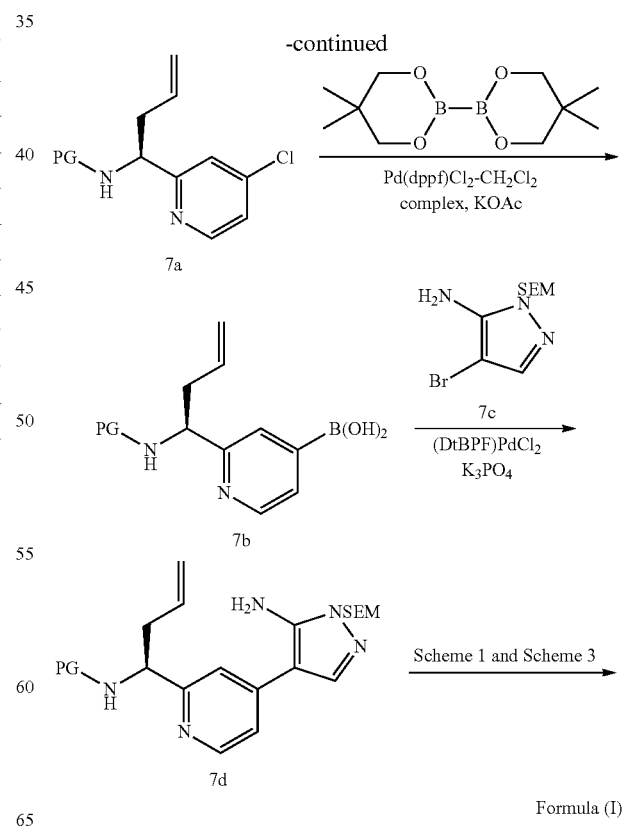

Formula (I)

Representative regioisomeric pyrazole containing amide macrocycle intermediates useful for the synthesis of compounds of this invention are described in Scheme 8. Hydrazine 8a can be obtained by heating pyridine chloride 7a with $NH_2NH_2$ hydrate. Subsequent condensation of hydrazine 8a with cyano ketone 8b provides amino pyrazole 8c. Compounds of the formula 8c can be converted to compounds in this invention according to Scheme 1 and Scheme 3.

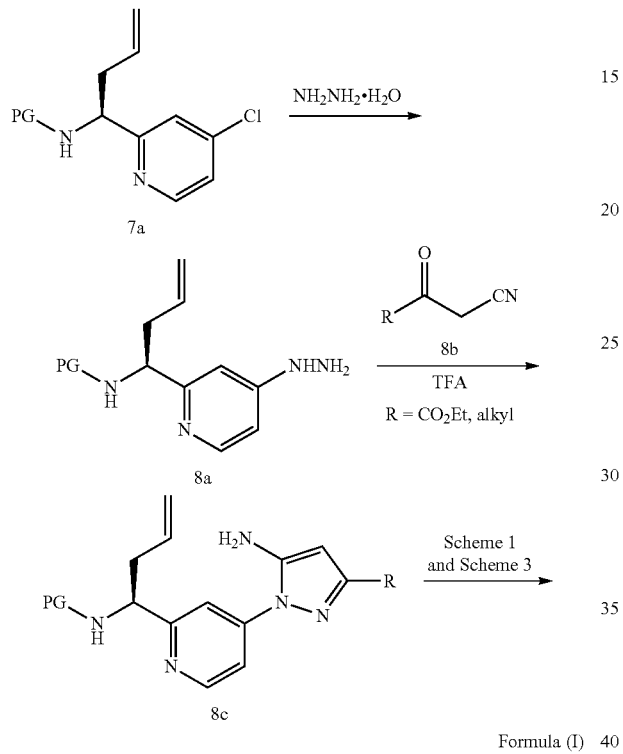

Purification of intermediates and final products was carried out via either normal or reverse phase chromatography. Normal phase chromatography was carried out using prepacked $SiO_2$ cartridges eluting with either gradients of hexanes and ethyl acetate or DCM and MeOH unless otherwise indicated. Reverse phase preparative HPLC was carried out using C18 columns eluting with gradients of Solvent A (90% water, 10% MeOH, 0.1% TFA) and Solvent B (10% water, 90% MeOH, 0.1% TFA, UV 220 nm) or with gradients of Solvent A (90% water, 10% ACN, 0.1% TFA) and Solvent B (10% water, 90% ACN, 0.1% TFA, UV 220 nm) or with gradients of Solvent A (98% water, 2% ACN, 0.05% TFA) and Solvent B (98% ACN, 2% water, 0.05% TFA, UV 220 nm) (or) Sunfire Prep C18 OBD 5 u 30×100 mm, 25 min gradient from 0-100% B. A=$H_2O$/ACN/TFA 90:10:0.1. B=ACN/$H_2O$/TFA 90:10:0.1

Unless otherwise stated, analysis of final products was carried out by reverse phase analytical HPLC.

Method A: A majority of analytical HPLC runs were: SunFire (4.6×150 mm) (15 min gradient—95:5 $H_2O$/ACN— to 95:5ACN/$H_2O$-0.05% TFA).

Method B: A minority of analytical HPLC runs were: Zorbax (4.6×75 mm) (8 min gradient–10:90 MeOH/$H_2O$ to 90:10 MeOH/$H_2O$, 0.2% $H_3PO_4$).

Method C: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Method D: Waters Acquity UPLC BEH C18, 2.1×50 mm, 1.7-μm particles; Mobile Phase A: 5:95 acetonitrile:water with 0.1% TFA; Mobile Phase B: 95:5 acetonitrile:water with 0.1% TFA; Temperature: 50° C.; Gradient: 0-100% B over 3 minutes, then a 0.75-minute hold at 100% B; Flow: 1.11 mL/min A majority of mass spectra runs were: LCMS (ESI) m/z: $[M+H]^+$ Phenomenex Luna C18 (2×30 mm) (2 min gradient 90% $H_2O$/10% MeOH/0.1% TFA to 90% MeOH/10% $H_2O$/0.1% TFA) (or) BEH C18 2.1×50 mm—2 min gradient from 0-100% B. (A: 90/10/0.1$H_2O$/ACN/TFA; B: 90/10/0.1 ACN/$H_2O$/TFA).

Intermediate 1

1-(3-Chloro-2,6-difluorophenyl)prop-2-en-1-one

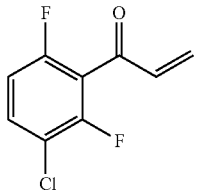

Intermediate 1A.
1-(3-Chloro-2,6-difluorophenyl)prop-2-en-1-ol

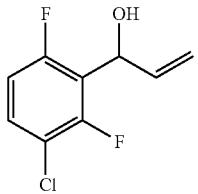

To a 100 mL dry round bottom flask containing vinylmagnesium bromide (1 M in THF) (24 mL, 24.00 mmol) under Ar at 0° C. was added 3-chloro-2,6-difluorobenzaldehyde (3.2 g, 18.13 mmol) in THF (10 mL) dropwise. The reaction was stirred for 1 h and quenched with 1 N HCl to pH 2. The mixture was extracted with $Et_2O$ (3×). The combined organic layer was washed with brine, dried over $MgSO_4$, filtered, and concentrated to yield the desired product (3.71 g, 100%) as pale yellow oil. $^1H$ NMR (500 MHz, $CDCl_3$) δ 7.34 (ddd, J=8.9, 8.1, 5.8 Hz, 1H), 6.90 (td, J=9.2, 1.7 Hz, 1H), 6.23 (dddt, J=17.2, 10.4, 5.8, 1.2 Hz, 1H), 5.60 (dd, J=7.6, 6.7 Hz, 1H), 5.40-5.31 (m, 1H), 5.28 (dt, J=10.2, 1.2 Hz, 1H), 2.38 (dt, J=8.3, 1.9 Hz, 1H).

Intermediate 1

To a solution of 1-(3-chloro-2,6-difluorophenyl)prop-2-en-1-ol (3.7 g, 18.08 mmol) in acetone (90 mL) at 0° C. was added Jones' reagent (8.77 ml, 23.51 mmol) dropwise. Upon finishing addition of Jones' reagent, the reaction was quenched with isopropanol. The mixture was concentrated. The residue was suspended in water and extracted with DCM (3×). The combined organic layer was washed with brine, dried over MgSO$_4$, filtered, and concentrated. The residue was purified by silica gel chromatography to yield the desired product as a yellow oil (3.45 g, 94%) which solidified in freezer. $^1$H NMR (500 MHz, CDCl$_3$) δ 7.48 (ddd, J=9.0, 8.0, 5.5 Hz, 1H), 7.05-6.91 (m, 1H), 6.70 (ddt, J=17.5, 10.5, 1.1 Hz, 1H), 6.29-6.11 (m, 2H).

Intermediate 2

1-(6-Bromo-3-chloro-2-fluorophenyl)prop-2-en-1-one

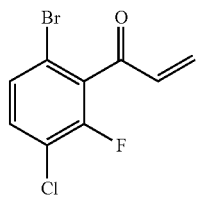

1-(6-Bromo-3-chloro-2-fluorophenyl)prop-2-en-1-one was prepared using a procedure analogous to intermediate 1 except that 3-chloro-2,6-difluorobenzaldehyde was replaced with 6-bromo-3-chloro-2-fluorobenzaldehyde. $^1$H NMR (500 MHz, CDCl$_3$) δ 7.33-7.41 (m, 2H), 6.64 (dd, J=17.6, 10.2 Hz, 1H), 6.25 (d, J=10.7 Hz, 1H), 6.07 (d, J=17.6 Hz, 1H).

Intermediate 3

1-(3-Chloro-2-fluoro-6-methoxyphenyl)prop-2-en-1-one

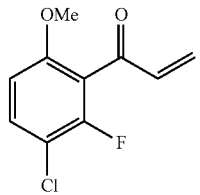

1-(3-Chloro-2-fluoro-6-methoxyphenyl)prop-2-en-1-one was prepared using a procedure analogous to intermediate 1 except that 3-chloro-2,6-difluorobenzaldehyde was replaced with 3-chloro-2-fluoro-6-methoxybenzaldehyde. $^1$H NMR (400 MHz, CHLOROFORM-d) δ 7.43-7.36 (m, 1H), 6.75-6.56 (m, 2H), 6.13-6.03 (m, 2H), 3.80 (s, 3H).

Intermediate 4

1-Cyclohexylprop-2-en-1-one

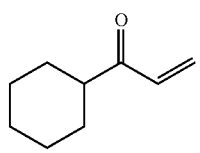

Intermediate 4A. 1-Cyclohexylprop-2-en-1-ol

This compound was prepared according to the procedure described in Intermediate 1A, by replacing 3-chloro-2,6-difluorobenzaldehyde with cyclohexanecarbaldehyde. $^1$H NMR (400 MHz, CHLOROFORM-d) δ 5.86 (ddd, J=17.1, 10.4, 6.6 Hz, 1H), 5.29-5.04 (m, 2H), 3.85 (s, 1H), 1.92-0.79 (m, 11H)

Intermediate 4 was synthesized following a modified procedure by Zhong (*Chemistry—A European Journal,* 2012, 18(32), 9802-9806). IBX (630 mg, 2.250 mmol) was added portionwise to a solution of 1-cyclohexylprop-2-en-1-ol (210 mg, 1.5 mmol) in DMSO (1.5 ml) at rt. The reaction was stirred for 1h, then water (0.9 ml) and DCM (0.9 ml) were added. The solid was removed by filtration. The filtrate was extracted with DCM. The organic layers were combined and concentrated. Purification by normal phase chromatography gave Intermediate 4 (120 mg, 58% yield) as a clear oil. $^1$H NMR (400 MHz, CHLOROFORM-d) δ 6.52-6.38 (m, 1H), 6.33-6.18 (m, 1H), 5.74 (dd, J=10.6, 1.5 Hz, 1H), 2.71-2.53 (m, 1H), 1.89-1.64 (m, 6H), 1.47-1.13 (m, 6H)

Intermediate 5

1-(5-Chloropyridin-3-yl)prop-2-en-1-one

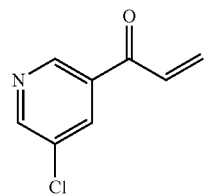

Intermediate 5 was prepared in two steps. The allylic alcohol was prepared according to the procedure described in Intermediate 1A, by replacing 3-chloro-2,6-difluorobenzaldehyde with 5-chloronicotinaldehyde and running the reaction at −78° C. The allylic alcohol was oxidized to the enone according to the procedure described in Intermediate 4. MS (ESI) m/z: 168.1 (M+H)$^+$. $^1$H NMR (400 MHz, CHLOROFORM-d) δ 9.01 (s, 1H), 8.76 (br. s., 1H), 8.20 (t, J=2.1 Hz, 1H), 7.10 (dd, J=17.1, 10.7 Hz, 1H), 6.51 (dd, J=17.2, 1.3 Hz, 1H), 6.07 (dd, J=10.6, 1.1 Hz, 1H).

Intermediate 6

1-(1-Methyl-1H-imidazol-5-yl)prop-2-en-1-one, TFA

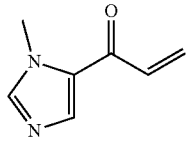

Intermediate 6A. 1-(1-methyl-1H-imidazol-5-yl)prop-2-en-1-ol

This compound was prepared according to the procedure described in Intermediate 1A, by replacing 3-chloro-2,6- difluorobenzaldehyde with 1-methyl-1H-imidazole-5-carbaldehyde. $^1$H NMR (400 MHz, CHLOROFORM-d) δ 7.42-7.27 (m, 1H), 6.89-6.72 (m, 1H), 6.22-6.06 (m, 1H), 5.42 (d, J=17.2 Hz, 1H), 5.34-5.17 (m, 2H), 3.68 (s, 3H).

Intermediate 6

To a cooled solution (0° C.) of Intermediate 6A (32 mg, 0.232 mmol) in DCM (1.544 ml) was added Dess-Martin periodinane (29.5 mg, 0.069 mmol). The ice bath was removed and the mixture was stirred at ambient temperature for 1.5h. Additional Dess-Martin periodinane (29.5 mg, 0.069 mmol) was added and the mixture was stirred for 30 min. then the reaction was quenched with 10% NaHCO$_3$ (15 mL). The mixture was extracted with EtOAc (3×). The combined organic layers were washed with brine and concentrated. The residue was purified by reverse phase chromatography to give Intermediate 6 (14 mg, 24%). MS (ESI) m/z: 137.1 (M+H)$^+$. $^1$H NMR (400 MHz, METHANOL-d$_4$) δ 8.96 (s, 1H), 8.49 (d, J=1.3 Hz, 1H), 7.13 (dd, J=17.1, 10.5 Hz, 1H), 6.54 (dd, J=16.9, 1.3 Hz, 1H), 6.02 (dd, J=10.5, 1.4 Hz, 1H), 4.13 (d, J=0.4 Hz, 3H).

Intermediate 7

1-(1-Benzyl-1H-imidazol-5-yl)prop-2-en-1-one

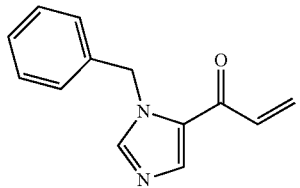 [SMILES: C=CC(=O)c1cncn1Cc1ccccc1]

Intermediate 7 was prepared according to the procedure described in Intermediate 1A, by replacing 3-chloro-2,6-difluorobenzaldehyde with 1-benzyl-1H-imidazole-5-carboxaldehyde, followed by oxidation according to the procedure described in Intermediate 4. MS (ESI) m/z: 213.2 (M+H)$^+$. $^1$H NMR (400 MHz, CHLOROFORM-d) δ 8.00-7.84 (m, 1H), 7.69 (s, 1H), 7.40-7.26 (m, 3H), 7.23-7.12 (m, 2H), 6.96 (dd, J=16.9, 10.3 Hz, 1H), 6.42 (dd, J=16.9, 1.5 Hz, 1H), 5.82 (dd, J=10.5, 1.7 Hz, 1H), 5.60 (s, 2H).

Intermediate 8

Diethyl (2-chloro-2-oxoethyl)phosphonate

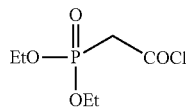

To a solution of 2-(diethoxyphosphoryl)acetic acid (0.1 mL, 0.622 mmol) in CH$_2$Cl$_2$ (1 mL) was added oxalyl dichloride (2 M in DCM) (0.622 mL, 1.244 mmol), followed by a drop of DMF. The reaction was stirred at rt for 2.5 h and concentrated in vacuo to yield the desired product as yellow oil. $^1$H NMR (500 MHz, CHLOROFORM-d) δ 4.24 (dq, J=8.4, 7.1 Hz, 4H), 3.55-3.47 (d, J=21.46 Hz, 2H), 1.42-1.38 (t, J=7.4 Hz, 6H).

Intermediate 9

(R)-3-((tert-Butyldimethylsilyl)oxy)-3-(4-chloro-3-fluoropyridin-2-yl)propanal

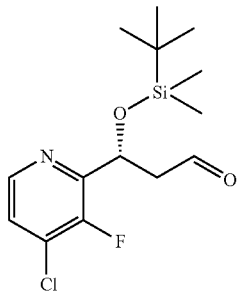 [SMILES: CC(C)(C)[Si](C)(C)O[C@H](CC=O)c1nccc(Cl)c1F]

Intermediate 9A. (R)-1-(4-Chloro-3-fluoropyridin-2-yl)but-3-en-1-ol

A solution of 1 M allylbis((1S,2R,3S,5S)-2,6,6-trimethylbicyclo[3.1.1]heptan-3-yl)borane in pentane in anhydrous THF (10 mL) was cooled to −78° C. To the solution was added 4-chloro-3-fluoropicolinaldehyde (0.5 g, 3.13 mmol) in 10 mL of THF dropwise for 20 min. The resulting solution was stirred for additional 1 h. To the mixture was added MeOH (1 mL), followed addition of lithium hydroxide (0.300 g, 12.54 mmol), hydrogen peroxide (0.384 mL, 12.54 mmol) and 10 mL of 1 N NaOH. The reaction mixture was allowed to warm up to rt and stirred for 1 h. The reaction mixture was diluted with EtOAc, washed with brine (2×20 mL), dried over Na$_2$SO$_4$, concentrated and purified by silica gel chromatography to provide intermediate 9A (0.54 g, 85%). MS (ESI) m/z: 202.1 (M+H)$^+$.

Intermediate 9B. (R)-2-(1-((tert-Butyldimethylsilyl)oxy)but-3-en-1-yl)-4-chloro-3-fluoropyridine A solution of Intermediate 9A (0.52 g, 2.58 mmol), TBS-Cl (0.466 g, 3.09 mmol), imidazole (0.211 g, 3.09 mmol) and DMAP (0.378 g, 3.09 mmol) was stirred for 12 h at rt. The reaction was diluted in EtOAc (30 mL) was washed with aq. NaHCO$_3$ and brine. The organic solution was concentrated in vacuo, yielding an oily residue, which was purified by silica gel chromatography to provide intermediate 9B (0.42 g, 52%). $^1$H NMR (400 MHz, CHLOROFORM-d) δ 8.30 (d, J=5.3 Hz, 1H), 7.38-7.19 (m, 1H), 5.77 (ddt, J=17.2, 10.1, 7.2 Hz, 1H), 5.16-4.95 (m, 3H), 2.83-2.45 (m, 2H), 0.94-0.78 (m, 9H), 0.10-0.03 (m, 3H), −0.02--0.15 (m, 3H).

Intermediate 9. (R)-3-((tert-Butyldimethyl silyl)oxy)-3-(4-chloro-3-fluoropyridin-2-yl)propanal To a solution of intermediate 9B (1.0 g, 3.17 mmol) in MeOH (20 mL) and water (10 mL) in ice bath was added osmic acid (4 wt %) in water (1.739 mL, 0.222 mmol) dropwise followed by sodium periodate (1.693 g, 7.91 mmol). Following the addition, the reaction mixture was stirred at rt for 2 h. To the reaction mixture was added water and the resulting solution was extracted with EtOAc (2×). The combined organic layers were dried over MgSO$_4$ and then concentrated to give the crude product which was purified using silica gel chromatography. The desired fractions were pooled together and combined to give intermediate 9 (0.93 g, 92%). MS (ESI) m/z: 318.1 (M+H)+. 1H NMR (400 MHz, CDCl3) δ 9.79 (s, 1H), 8.27-8.13 (m, 1H), 7.28-7.20 (m, 1H), 5.57-5.45 (m, 1H), 3.04-2.79 (m, 2H), 0.75 (s, 9H), 0.00 (s, 3H), −0.14 (s, 3H).

Intermediate 10

(R)-2-Methylbut-3-enoic acid

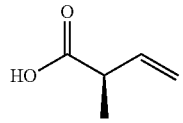

Intermediate 10A. (R)-4-Benzyl-3-((R)-2-methyl-but-3-enoyl)oxazolidin-2-one

To the solution of 2-methylbut-3-enoic acid (5.59 g, 55.9 mmol) and N-methylmorpholine (6.14 ml, 55.9 mmol) in THF (62 mL) at 0° C. was added pivaloyl chloride (6.87 ml, 55.9 mmol) dropwise. The reaction mixture was cooled down to −78° C., and stirred for ~2 h. In a separate flask: To the solution of (R)-4-benzyloxazolidin-2-one (8.25 g, 46.6 mmol) in THF (126 mL) at −78° C. was added N-butyllithium (2.5 M in hexane) (20.49 mL, 51.2 mmol) dropwise. After 35 min, this reaction was transferred via cannula to the first reaction. The reaction mixture was stirred at −78° C. for 2 h, then the cold bath was removed, and the reaction was quenched with sat. NH4Cl. The reaction was diluted with water and extracted with EtOAc (3×). The combined organic layers were washed with brine, dried over Na2SO4, filtered, and concentrated to give a yellow oil (15 g). Purification by silica gel chromatography afforded the desired product (6.59 g, 55%) as a colorless oil. MS (ESI) m/z: 282.1 (M+Na)+. 1H NMR (500 MHz, CDCl3) δ 7.36-7.19 (m, 5H), 6.03-5.93 (m, 1H), 5.23-5.10 (m, 2H), 4.69-4.63 (m, 1H), 4.51-4.43 (m, 1H), 4.23-4.15 (m, 2H), 3.29 (dd, J=13.5, 3.3 Hz, 1H), 2.79 (dd, J=13.5, 9.6 Hz, 1H), 1.35 (d, J=6.9 Hz, 3H) ppm. The other diastereomer (R)-4-benzyl-3-((S)-2-methylbut-3-enoyl)oxazolidin-2-one (4.6 g, 38%) also obtained as a white solid. MS (ESI) m/z: 260.1 (M+H)+.

Intermediate 10. (R)-2-Methylbut-3-enoic acid

To a clear colorless solution of Intermediate 10A (6.05 g, 23.33 mmol) in THF (146 mL) at 0° C. was added dropwise hydrogen peroxide (9.53 mL, 93 mmol) (30% aqueous) followed by 2 N lithium hydroxide (23.33 mL, 46.7 mmol). After 30 min, the reaction was quenched with 25 mL of sat'd Na2SO3 and 25 mL of sat'd NaHCO3. The reaction was then concentrated to remove the THF. The residue was diluted with water and extracted with CHCl3 (3×). The aqueous layer was acidified with conc. HCl to pH~3 and then it was extracted with EtOAc (3×). The EtOAc layers were combined, washed with brine, dried over MgSO4, filtered and concentrated to afford the desired product (2.15 g, 92%) as a colorless oil. 1H NMR (500 MHz, CDCl3) δ 10.84 (br. s., 1H), 5.94 (ddd, J=17.4, 10.1, 7.4 Hz, 1H), 5.22-5.13 (m, 2H), 3.23-3.15 (m, 1H), 1.31 (d, J=7.2 Hz, 3H).

Intermediate 11

4-(3-Chloro-2,6-difluorophenyl)-5-hydroxy-2,5-dihydrofuran-2-one

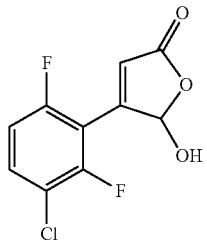 [SMILES: O=C1C=C(c2c(F)ccc(Cl)c2F)C(O)O1]

Intermediate 11A.
1-Chloro-3-ethenyl-2,4-difluorobenzene

To a cooled (−20° C.) suspension of methyltriphenylphosphonium bromide (6.68 g, 18.69 mmol) in diethyl ether (48.6 ml) was added dropwise nBuLi (6.80 ml, 16.99 mmol). The resulting yellow suspension was allowed to warm to 0° C. and stir for 2 h. In a separate flask, a solution of 3-chloro-2,6-difluorobenzaldehyde (3.0 g, 16.99 mmol) in diethyl ether (20 mL) was prepared and cooled to 0° C. Next, the solution of the ylide was added via cannula to give a thick suspension. The suspension was stirred at 0° C. for 30 min and then the reaction was allowed to warmed to rt. After 22 h, the reaction was cooled to 0° C. and then water was added. The reaction was warmed to rt and the layers were separated. The aqueous layer was extracted with diethyl ether. The organic layers were combined and washed with brine, dried over sodium sulfate, filtered and concentrated to give an orange-brown solid weighing 3.20 g. Purification by normal phase chromatography provided the desired product (0.510 g, 13%) as a clear, colorless liquid. 1H NMR (500 MHz, CHCl3) δ 7.22 (td, J=8.5, 5.5 Hz, 1H), 6.84 (td, J=9.4, 1.8 Hz, 1H), 6.69 (dd, J=18.0, 12.0 Hz, 1H), 6.07 (d, J=17.9 Hz, 1H), 5.65 (dd, J=12.1, 1.1 Hz, 1H).

Intermediate 11

A modified procedure described by van Niel (J. Med. Chem., 2005, 48, 6004) was used. To a cooled (−5° C.) clear, colorless solution of lead tetraacetate (1.270 g, 2.86 mmol) in TFA (2.86 ml) was added dropwise a clear, colorless solution of Intermediate 11A (0.500 g, 2.86 mmol) in DCM (2.8 mL). During the addition, the reaction temperature did not go above 2° C. Following the addition, the resulting clear, pale yellow solution was allowed to warm to rt. After 2h, water (10 mL) was added dropwise to give a red-brown suspension. The suspension was filtered through Celite, eluting with DCM. The filtrate was separated and the aqueous layer was extracted with DCM (1×). The organic layers were combined and washed with water, brine, dried over sodium sulfate, filtered and concentrated to give 2-(3-chloro-2,6-difluorophenyl)acetaldehyde (0.639 g) as a clear, pale yellow oil. This material was used in the next step without further purification.

To a solution of morpholine (0.262 ml, 3.01 mmol) in dioxane (1.8 mL) was added 6M HCl (0.487 ml, 2.92 mmol) followed by glyoxylic acid monohydrate (0.250 g, 2.72 mmol). Next, a solution of 2-(3-chloro-2,6-difluorophenyl)

acetaldehyde (0.546 g, 2.87 mmol) in dioxane (2.0 mL) was added. The resulting biphasic reaction mixture was warmed to reflux. After 2 h, the reaction was stopped and cooled to rt. Water was added and the layers were separated. The aqueous layer was extracted with EtOAc (1×). The organic layers were combined and washed with brine, dried over sodium sulfate, filtered and concentrated to give a green oil which solidified under high vacuum to give a green solid weighing 0.657 g. Next, a 1:1 hexane/diethyl ether (2 mL) was added and sonication gave a suspension. The solid was collected by filtration rinsing with 1:1 hexane/diethyl ether, air-drying, and drying under vacuum to give Intermediate 11 (0.240 g, 34%) as an off-white solid. MS (ESI) m/z: 246.9 (M+H)$^+$. $^1$H NMR (500 MHz, DMSO-d$_6$) δ 8.16 (br. s., 1H), 7.86 (td, J=8.7, 5.6 Hz, 1H), 7.44-7.35 (m, 1H), 6.73 (s, 1H), 6.63 (br. s., 1H).

Intermediate 12

(R)-2-Methylbut-3-enoyl chloride

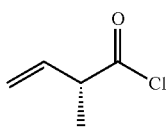

Intermediate 12

To a cooled (0° C.) solution of (R)-2-methylbut-3-enoic acid (0.450 g, 4.49 mmol) in DCM was added dropwise oxalyl chloride (0.393 ml, 4.49 mmol). The reaction mixture was stirred at 0° C. for 30 min and then it was allowed to stir at rt for 1.3 h. The resulting solution of (R)-2-methylbut-3-enoyl chloride was used directly.

Intermediate 13

2-Isopropylbut-3-enoic acid

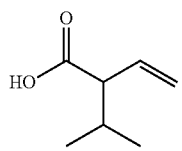

To a solution of diisopropylamine (3.64 ml, 25.6 mmol) in THF (58.1 ml) at −78° C. was added n-butyllithium (15.97 ml, 25.6 mmol) dropwise. The solution was stirred at −78° C. for 30 min then but-3-enoic acid (0.990 ml, 11.62 mmol) was added dropwise. After 30 min, isopropyl iodide (1.739 ml, 17.42 mmol) was added and the reaction was slowly warmed to rt overnight. The resulting white suspension was quenched with the dropwise addition of a sat. NH$_4$Cl solution. Then 1N HCl was added until the mixture was acidic. The mixture was extracted with EtOAc (3×). The combined organic layers were washed with brine and then concentrated. Purification by normal phase chromatography (visualized by KMnO$_4$ stain) gave Intermediate 13 (1.09g, 73%) as a clear oil. $^1$H NMR (400 MHz, CHLOROFORM-d) δ 5.98-5.65 (m, 1H), 5.33-5.05 (m, 2H), 2.73 (t, J=8.8 Hz, 1H), 2.08-1.95 (m, 1H), 1.09-0.74 (m, 6H).

Intermediate 14

2-(5,5-Dimethyl-1,3,2-dioxaborinan-2-yl)-5-nitrophenylamine

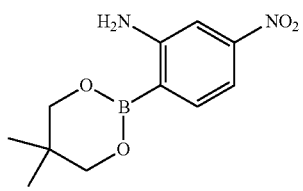 [SMILES: CC1(C)COB(c2ccc([N+](=O)[O-])cc2N)OC1]

To a flame-dried flask, equipped with a reflux condenser, containing 2-bromo-5-nitroaniline (10.0 g, 46.1 mmol), bis(neopentyl glycolato)diboron (13.01 g, 57.6 mmol), potassium acetate (13.57 g, 138 mmol), and PdCl$_2$(dppf)-CH$_2$Cl$_2$ adduct (0.941 g, 1.152 mmol) was added DMSO (132 mL). The resulting dark red-brown suspension was degassed with argon for 30 min and then the reaction was warmed to 80° C. After 4 h, the reaction was stopped and cooled to rt. The reaction was poured slowly into vigorously stirred ice-cold water (300 mL) to give a brown suspension. After stirring for 10 min, the suspension was filtered to collect the solid. The solid was rinsed with water (3×125 mL), air-dried, and then dried under a vacuum to give a brown solid. Purification by normal phase chromatography gave 4.36 g of Intermediate 14 as an orange solid. MS (ESI) m/z: 183.1 (M−C$_5$H$_8$+H)$^+$.

Intermediate 15

4-(6-Bromo-3-chloro-2-fluorophenyl)-5-hydroxyfuran-2(5H)-one

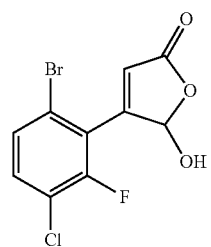 [SMILES: O=C1C=C(c2c(Br)ccc(Cl)c2F)C(O)O1]

Intermediate 15 was prepared according to the procedures described in Intermediate 11, by replacing 3-chloro-2,6-difluorobenzaldehyde with 6-bromo-3-chloro-2-fluorobenzaldehyde. MS (ESI) m/z: 330.9 (M+2+Na)$^+$. $^1$H NMR (500 MHz, CDCl$_3$) δ 7.46 (dd, J=8.8, 1.7 Hz, 1H), 7.40-7.35 (m, 1H), 6.63 (s, 1H), 6.45 (d, J=0.8 Hz, 1H), 4.03 (br. s., 1H).

Intermediate 16

2-(benzyloxy)but-3-enoic acid

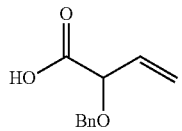

Intermediate 16A. Methyl 2-(benzyloxy)but-3-enoate

In a vial, methyl 2-hydroxybut-3-enoate (1 g, 8.61 mmol) and CHCl$_3$ (10 ml) were combined, then (bromomethyl)benzene (1.536 ml, 12.92 mmol) was added. Silver(I) oxide (5.99 g, 25.8 mmol) was added portion-wise to the vial under a stream of Ar. The reaction mixture was stirred at rt over the weekend. The reaction mixture was filtered through Celite and rinsed with EtOAc, then concentrated. Purification by silica gel chromatography (visualized by KMnO$_4$ stain) gave Intermediate 16A (0.9 g, 50.7% yield) as a colorless oil. MS (ESI) m/z: 229.1 (M+Na)$^+$.

Intermediate 16

A solution of intermediate 16A (0.9 g, 4.36 mmol) in THF (10 ml) and water (5.00 ml) was cooled to 0° C. and treated with lithium hydroxide (2.400 ml, 4.80 mmol), then stirred at 0° C. for 1 hr. LCMS showed that all the starting material had been consumed. While the reaction was still at 0° C., the mixture was acidified with 1 N HCl (5 mL), then concentrated. The residue was purified by silica gel chromatography to yield Intermediate 16 (615 mg, 73.3% yield) as a colorless oil. MS (ESI) m/z: 215.1 (M+Na)$^+$.

Intermediate 17

Methyl 4-(2-bromoacetyl)-3-nitrophenylcarbamate

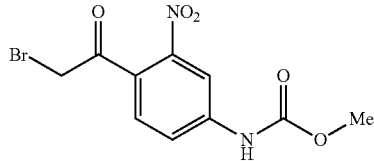 [SMILES: COC(=O)Nc1ccc(C(=O)CBr)c([N+](=O)[O-])c1]

Intermediate 17A. Methyl 4-iodo-3-nitrophenylcarbamate

To a cooled (0° C.), yellow suspension of 4-iodo-3-nitroaniline (8.46 g, 32.0 mmol) in DCM (320 mL) and pyridine (2.85 mL, 35.2 mmol) was added methyl chloroformate (2.61 mL, 33.6 mmol) dropwise. The reaction mixture turned to light yellow solution and stirring was continued for 1.5 h. After 1.5 h, the reaction mixture was diluted with DCM, washed with saturated NaHCO$_3$ solution followed by brine. The organic layers were dried over MgSO$_4$, filtered and concentrated to obtain a residue. The residue was then dissolved in DCM (~100 mL), then hexane (600 mL) was added to give a yellow suspension. The above suspension was filtered and the filtered solid was rinsed with hexane and air-dried to obtain the desired product as yellow solid (10.3 g, 100%). MS (ESI) m/z: 321.3 (M−H)$^+$.

Intermediate 17B. Methyl 4-(1-ethoxyvinyl)-3-nitrophenylcarbamate

A solution of Intermediate 17A (1 g, 3.11 mmol), tributyl(1-ethoxyvinyl)stannane (1.574 mL, 4.66 mmol), and bis(triphenylphosphine)palladium(II) chloride (0.109 g, 0.155 mmol) in toluene (6.21 mL) was heated at 110° C. for 2 h. After 2 h, the reaction was cooled to rt, filtered through a 0.45μ GMF filter and rinsed with EtOAc. The filtrate concentrated to dryness and purified by silica gel chromatography to obtain 17B as brown solid (0.56 g, 68%). MS (ESI) m/z: 267.3 (M+H)$^+$.

Intermediate 17. Methyl 4-(2-bromoacetyl)-3-nitrophenylcarbamate (Reference: *J. Med. Chem.*, 45:2127-2130 (2002)) To a solution of alternative Intermediate 17B (0.56 g, 2.103 mmol) in THF (3.12 mL) and water (1.091 mL) was added NBS (0.374 g, 2.103 mmol). After stirring at rt for 20 min, the reaction mixture was partitioned between EtOAc and brine. The organic layer was washed with brine, dried over Na$_2$SO$_4$, filtered, and concentrated to yield the desired product as yellow oil (0.667 g, 100%). MS (ESI) m/z: 317.2 (M+H)$^+$, 319.2 (M+2H)$^+$.

Intermediate 18

1-(3-Chlorophenyl)prop-2-en-1-one

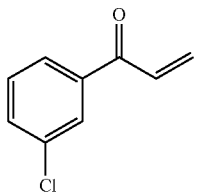

To a solution of 3-chloro-N-methoxy-N-methylbenzamide (100 mg, 0.501 mmol) in tetrahydrofuran (2 mL) at 0° C. was added a solution of vinylmagnesium bromide 1M in THF (0.601 mL, 0.601 mmol) dropwise. After 1 h, additional Grignard reagent (0.2 mL) was added. The clear solution was quenched with sat NH$_4$Cl and then the reaction was extracted with EtOAc (2×). The aqueous layer was acidified with 1N HCl and extracted with EtOAc (2×). The organic layers were combined and concentrated. Purification by silica gel chromatography gave Intermediate 18 (23 mg, 27.6% yield) as clear oil which was used immediately due to product instability. $^1$H NMR (400 MHz, CHLOROFORM-d) δ 7.91 (t, J=1.8 Hz, 1H), 7.84-7.77 (m, 1H), 7.58-7.51 (m, 1H), 7.43 (s, 1H), 7.07 (s, 1H), 6.45 (dd, J=17.2, 1.5 Hz, 1H), 5.98 (dd, J=10.6, 1.5 Hz, 1H)

Intermediate 19

Tert-butyl (4-acryloylpyridin-2-yl)carbamate

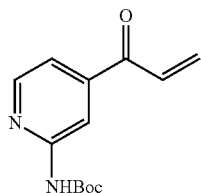 [SMILES: C=CC(=O)c1ccnc(NC(=O)OC(C)(C)C)c1]

Intermediate 19A: tert-butyl (4-(methoxy(methyl) carbamoyl)pyridin-2-yl)carbamate To a suspension of 2-(tert-butoxycarbonylamino)isonicotinic acid (0.20 g, 0.839 mmol), HOBT (0.039 g, 0.252 mmol), EDC (0.193 g, 1.007 mmol) and N,O-dimethylhydroxylamine hydrochloride (0.082 g, 0.839 mmol) in acetonitrile (8 mL) was added Et$_3$N (0.351 mL, 2.52 mmol). After 14 hr, additional EDC (0.130 g, 0.839 mmol) and Et$_3$N (0.351 mL, 2.52 mmol) were added. The reaction was stirred at rt o.n. then quenched with water and sat NH$_4$Cl. The reaction was extracted with EtOAc (2×). The organic layers were combined and concentrated. Purification by silica gel chromatography gave Intermediate 19A (0.079 g, 33.5% yield) as white crystals. MS (ESI) m/z: 282.2 (M+H)$^+$. $^1$H NMR (400 MHz, CHLOROFORM-d) δ 8.91 (s, 1H), 8.38 (dd, J=5.1, 0.7 Hz, 1H), 8.20 (s, 1H), 7.12 (dd, J=5.2, 1.4 Hz, 1H), 3.61 (s, 3H), 3.34 (s, 3H), 1.54 (s, 9H).

Intermediate 19 was prepared using a procedure analogous to Intermediate 18, by replacing 3-chloro-N-methoxy-N-methylbenzamide with Intermediate 19A. MS (ESI) m/z: 249.2 (M+H)$^+$. $^1$H NMR (400 MHz, CHLOROFORM-d) δ 8.46-8.34 (m, 2H), 8.21-8.03 (m, 1H), 7.37 (dd, J=5.2, 1.4 Hz, 1H), 7.10 (dd, J=17.3, 10.7 Hz, 1H), 6.48 (dd, J=17.2, 1.5 Hz, 1H), 6.03 (dd, J=10.6, 1.3 Hz, 1H), 1.61-1.47 (m, 9H).

Intermediate 20 tert-butyl 4-acryloylpiperidine-1-carboxylate

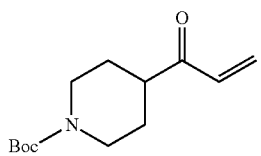 [SMILES: C=CC(=O)C1CCN(C(=O)OC(C)(C)C)CC1]

Intermediate 20 was prepared according to the procedure described in Intermediate 4, by replacing 3-chloro-2,6-difluorobenzaldehyde with tert-butyl 4-formylpiperidine-1-carboxylate. Crude product was used without further purification.

Intermediate 21

1-(2-chloropyridin-4-yl)prop-2-en-1-one

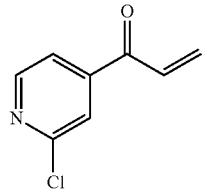

Intermediate 21. 1-(2-chloropyridin-4-yl)prop-2-en-1-one

This compound was prepared according to the procedure described in Intermediate 4, by replacing 3-chloro-2,6-difluorobenzaldehyde with 2-chloroisonicotinaldehyde. MS (ESI) m/z: 167.9 (M+H)$^+$. $^1$H NMR (400 MHz, CHLOROFORM-d) δ 8.58 (dd, J=5.1, 0.7 Hz, 1H), 7.73 (dd, J=1.4, 0.8 Hz, 1H), 7.62 (dd, J=5.1, 1.5 Hz, 1H), 7.08-6.95 (m, 1H), 6.55-6.40 (m, 1H), 6.10 (dd, J=10.6, 1.3 Hz, 1H)

Intermediate 22

1-(6-chloropyridin-2-yl)prop-2-en-1-one

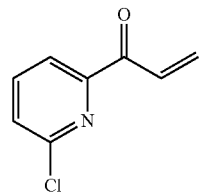

Intermediate 22. 1-(6-chloropyridin-2-yl)prop-2-en-1-one

This compound was prepared according to the procedure described in Intermediate 4, by replacing 3-chloro-2,6-difluorobenzaldehyde with 6-chloropyridine-2-carbaldehyde. MS (ESI) m/z: 168.0 (M+H)$^+$. $^1$H NMR (400 MHz, CHLOROFORM-d) δ 8.06 (dd, J=7.6, 0.8 Hz, 1H), 7.89-7.74 (m, 2H), 7.52 (dd, J=7.9, 0.7 Hz, 1H), 6.63 (dd, J=17.4, 2.0 Hz, 1H), 5.96 (dd, J=10.6, 2.0 Hz, 1H)

Intermediate 23 tert-butyl 2-acryloylpiperidine-1-carboxylate

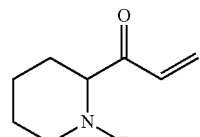

Intermediate 23. tert-butyl 2-acryloylpiperidine-1-carboxylate

This compound was prepared according to the procedure described in Intermediate 4, by replacing 3-chloro-2,6-difluorobenzaldehyde with 1-boc-2-piperidinecarbaldehyde MS (ESI) m/z: 140.1 (M+H-boc)$^+$. $^1$H NMR (400 MHz, CHLOROFORM-d) δ 6.56 (dd, J=17.3, 10.5 Hz, 1H), 6.35 (dd, J=17.3, 1.7 Hz, 1H), 5.73 (dd, J=10.6, 1.3 Hz, 1H), 5.05-4.61 (m, 1H), 3.97 (br. s., 1H), 2.91 (t, J=12.0 Hz, 1H), 2.17 (d, J=12.8 Hz, 1H), 1.74-1.55 (m, 3H), 1.54-1.20 (m, 10H)

Intermediate 24

1-(3-methylcyclohexyl)prop-2-en-1-one

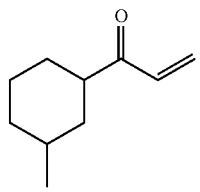

Intermediate 24A. 3-methylcyclohexanecarbonyl chloride

To a solution of 3-methylcyclohexanecarboxylic acid (1 g, 7.03 mmol) in CH$_2$Cl$_2$ (10 mL) at 0° C. was added oxalyl chloride (4.22 mL, 8.44 mmol) followed by 1 drop of DMF. After 30 min, the mixture was warmed up to RT and continued stirring at RT for 1.5h. The reaction was concentrated to dryness to afford the crude methylcyclohexanecarbonyl chloride (1.13 g, 100% yield) as a yellow liquid.

Intermediate 24B. N-methoxy-N,3-dimethylcyclohexanecarboxamide

To a solution of 3-methylcyclohexanecarbonyl chloride (1.13 g, 7.03 mmol) and N,O-dimethylhydroxylamine hydrochloride (0.755 g, 7.74 mmol) in CHCl$_3$ (70 mL) at 0° C. was added pyridine (1.252 mL, 15.48 mmol) dropwise. The ice bath was removed and the mixture was warmed to RT. After 1 h, the reaction was evaporated to dryness, diluted with 1:1 mixture of ether and CH$_2$Cl$_2$ (40 ml) and then washed with brine. The aqueous layer was washed once more with 1:1 mixture of ether and CH$_2$Cl$_2$. The organic layers were combined, dried with MgSO$_4$, filtered, and concentrated to afford the crude N-methoxy-N,3-dimethyl-cyclohexanecarboxamide (1.1g, 84% yield) as clear yellowish oil which was used without further purification. MS (ESI) m/z: 186.1 (M+H)$^+$. $^1$H NMR (400 MHz, CHLOROFORM-d) δ 3.74-3.65 (m, 3H), 3.20-3.14 (m, 3H), 2.71 (m., 1H), 1.85-1.12 (m, 10H), 0.94-0.88 (m, 3H)

Intermediate 24 was prepared using a procedure analogous to Intermediate 18, by replacing 3-chloro-N-methoxy-N-methylbenzamide with Intermediate 24B. Purification by silica gel chromatography gave Intermediate 24 (363 mg, 73.6% yield) as a clear oil and as a mixture of cis/trans isomers. MS (ESI) m/z: 153.1 (M+H)$^+$.

Intermediate 25

1-(5-chloro-2-(1H-1,2,4-triazol-1-yl)phenyl)prop-2-en-1-one

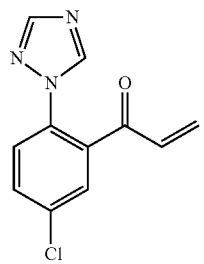 [SMILES: C=CC(=O)c1cc(Cl)ccc1-n1cncn1]

Intermediate 25A. 5-chloro-2-(1H-1,2,4-triazol-1-yl)benzaldehyde 5-chloro-2-fluorobenzaldehyde (1.29 g, 7.89 mmol), 4H-1,2,4-triazole (0.574 g, 7.89 mmol), Cs$_2$CO$_3$ (2.83 g, 8.68 mmol) in DMSO (15.78 ml) was capped and heated at 45° C. for 4 hrs before cooling down to rt and stirred at rt over weekend. The reaction mixture was diluted with EtOAc, washed with water and brine, dried over MgSO$_4$, filtered, concentrated. Purification by silica gel chromatography gave Intermediate 25A (674 mg, 41% yield) as a white solid. MS (ESI) m/z: 208.0 (M+H)$^+$. $^1$H NMR (500 MHz, DMSO-d$_6$) δ 9.90 (s, 1H), 9.17 (s, 1H), 8.33 (s, 1H), 7.99-7.91 (m, 2H), 7.84 (d, J=8.5 Hz, 1H).

Intermediate 25

Intermediate 25 was prepared using a procedure analogous to intermediate 1 except that 3-chloro-2,6-difluorobenzaldehyde was replaced with 5-chloro-2-(1H-1,2,4-triazol-1-yl)benzaldehyde. $^1$H NMR (400 MHz, CHLOROFORM-d) d 8.32-8.27 (m, 1H), 8.05 (s, 1H), 7.66-7.57 (m, 2H), 7.51 (d, J=8.4 Hz, 1H), 6.34-6.26 (m, 1H), 5.97-5.82 (m, 2H).

Intermediate 26

1-(5-chloro-2-(1H-1,2,3-triazol-1-yl)phenyl)prop-2-en-1-one

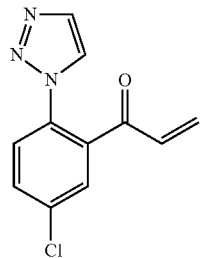 [SMILES: C=CC(=O)c1cc(Cl)ccc1-n1ccnn1]

Intermediate 26A. 5-chloro-2-(1H-1,2,3-triazol-1-yl)benzaldehyde 5-chloro-2-fluorobenzaldehyde (503 mg, 3.08 mmol), 1H-1,2,3-triazole (213 mg, 3.08 mmol), Cs$_2$CO$_3$ (2005 mg, 6.15 mmol) in DMF was stirred at rt over night. Solid was filtered off, rinsed with EtOAc, filtrate was washed with water, and 1st aqueous phase was neutralized with 1N HCl to pH 5, and back extracted with EtOAc, combined EtOAc phases washed with copious amount of water, and brine, dried over MgSO$_4$, filtered, concentrated. Purification by silica gel chromatography gave Intermediate 26A (124 mg, 19% yield) as a white solid. MS (ESI) m/z: 208.1 (M+H)$^+$.

Intermediate 26

Intermediate 26 was prepared using a procedure analogous to intermediate 1 except that 3-chloro-2,6-difluorobenzaldehyde was replaced with 5-chloro-2-(1H-1,2,3-triazol-1-yl)benzaldehyde. $^1$H NMR (400 MHz, METHANOL-d$_4$) δ 9.79 (s, 1H), 8.55 (d, J=1.3 Hz, 1H), 8.09 (d, J=2.4 Hz, 1H), 8.01 (d, J=1.3 Hz, 1H), 7.93 (dd, J=8.6, 2.4 Hz, 1H), 7.74 (d, J=8.6 Hz, 1H).

Intermediate 27

1-(3-chloro-2-fluoro-6-(1H-tetrazol-1-ylphenyl)prop-2-en-1-one

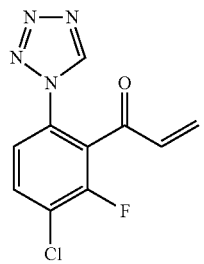 [SMILES: C=CC(=O)c1c(-n2cnnn2)ccc(Cl)c1F]

Intermediate 27 was prepared using a procedure analogous to intermediate 1 except that 3-chloro-2,6-difluorobenzaldehyde was replaced with 3-chloro-2-fluoro-6-(1H-tetrazol-1-yl)benzaldehyde. $^1$H NMR (500 MHz, CHLOROFORM-d) δ 8.88 (s, 1H), 7.74 (dd, J=8.5, 7.4 Hz, 1H), 7.40 (dd, J=8.7, 1.5 Hz, 1H), 6.54 (ddd, J=17.5, 10.5, 1.1 Hz, 1H), 6.16 (d, J=10.7 Hz, 1H), 6.09 (dd, J=17.6, 0.8 Hz, 1H).

Example 1

Methyl N-[(10R,14S)-14-[4-(3-chloro-2-fluoro-6-methoxyphenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate, TFA Salt

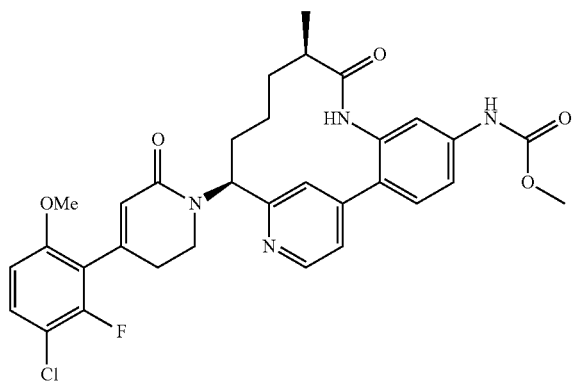 [SMILES: COC(=O)Nc1ccc2c(c1)NC(=O)[C@H](C)CCC[C@H](N1CCC(c3c(OC)ccc(Cl)c3F)=CC1=O)c1cc-2ccn1]

1A. (S,E)-N-((4-Chloropyridin-2-yl)methylene)-2-methylpropane-2-sulfinamide

Liu, G. et al., J. Org. Chem., 64:1278 (1999). To a solution of S-(-)-t-butyl-sulfinamide (0.856 g, 7.06 mmol) in dichloromethane (14.13 mL) was added sequentially copper(II) sulfate (2.481 g, 15.54 mmol) and 4-chloropicolinaldehyde [1.0 g, 7.06 mmol, prepared according to a modified described by Negi (Synthesis, 991 (1996))]. The white suspension was stirred at rt. After 3 h, the brown suspension was filtered through CELITE®, eluting with DCM, to give a clear brown filtrate. Concentration gave a brown oil weighing 1.85 g. Purification by normal phase chromatography gave 1.31 g of 1A as a clear, yellow oil. MS (ESI) m/z: 245.0 (M+H)$^+$.

1B. (S)—N—((S)-1-(4-Chloropyridin-2-yl)but-3-enyl)-2-methylpropane-2-sulfinamide To a cooled (0-5° C.) mixture of indium(III) chloride (13.56 g, 61.3 mmol) in tetrahydrofuran (170 mL) was added dropwise over 30 min. allylmagnesium bromide (1M in diethylether) (62 mL, 61.3 mmol). The reaction was allowed to warm to rt. After 1 h at rt, a solution of 1A (10 g, 40.9 mmol) in ethanol (170 mL) was added. After 2-3 h, the reaction was concentrated under vacuum at 50-55° C. The crude material was partitioned between ethyl acetate (200 ml) and water (1×50 ml) and the layers were separated. The aqueous layer was extracted with ethyl acetate (2×50 ml). The organic layers were combined and washed with brine (1×100 ml), dried over sodium sulfate, filtered and concentrated to give 1B (13.5 g, 106%) as a yellow oil. MS (ESI) m/z: 287.2 (M+H)+. This material was used in the next step without further purification.

1C. (S)-tert-butyl 1-(4-chloropyridin-2-yl)but-3-enylcarbamate 1B (75 g, 261 mmol) was dissolved in methanol (1500 mL). Hydrochloric acid (6N) (750 ml, 4.5 mol) was added. The reaction was stirred at rt for 2-3 hrs and then was concentrated. The residue was diluted with water (2 L), washed with ethyl acetate (500 ml). The aqueous layer was basified with saturated sodium carbonate solution, extracted into ethyl acetate (3×1 L). The combined organic layers were washed with water (1×1 L) and brine (1×1 L), dried over sodium sulfate, filtered and conc. under vacuum at 50-55° C. to give crude product (43g, 90%). MS (ESI) m/z: 183.2 (M+H)+. The crude product (42g, 230 mmol) was dissolved in dichloromethane (420 mL), Et$_3$N (32.1 mL, 230 mmol) was added followed by dropwise addition of BOC$_2$O (53.4 mL, 230 mmol). The reaction was stirred at rt for 2-3 hrs. The reaction was diluted with excess DCM (1 L), washed with water (1×500 ml) and brine (1×500 ml). The organic layer was dried over sodium sulfate, filtered, and concentrated. The crude product was then purified using silica gel chromatography to give 1C (61 g, 86%) as a pale yellow solid. MS (ESI) m/z: 283.2 (M+H)$^+$.

1D. (S)-tert-Butyl 1-(4-(2-amino-4-nitrophenyl)pyridin-2-yl)but-3-enylcarbamate

To a RBF was added 1C (3.33 g, 11.78 mmol), intermediate 14 (5.89 g, 23.55 mmol), PdCl$_2$(dppf)-CH$_2$Cl$_2$ Adduct (0.962 g, 1.178 mmol), and potassium phosphate, tribasic (5.00 g, 23.55 mmol). The RBF was equipped with a reflux condensor then the apparatus was purged with argon for several minutes. Next, degassed DMSO (Volume: 58.9 ml) was added followed by degassed water (1.061 ml, 58.9 mmol). The bright orange suspension was warmed to 90° C. for 6 hrs and then it was cooled to rt and stirred overnight. The reaction was filtered via Buchner funnel, rinsing with EtOAc to remove the solid. The filtrate was then partitioned between EtOAc and water which gave an emulsion. Brine was added to break up the emulsion and the layers were separated. The aqueous layer was extracted with EtOAc (1×). The combined organic layers were washed with brine, dried over $Na_2SO_4$, filtered and concentrated to give a thick black oil weighing 10.2 g. Purification by column chromatography gave 1D as an orange foam (2.90 g, 64%). MS (ESI) 385.1 (M+H)+.

1E. (S)-tert-Butyl 1-(4-(2,4-diaminophenyl)pyridin-2-yl)but-3-enylcarbamate

To a clear, orange solution of 1D (2.9 g, 7.54 mmol) in methanol (75 mL) was added sequentially zinc dust (4.93 g, 75 mmol) and ammonium chloride (4.04 g, 75 mmol). The resulting suspension was stirred vigorously for 4 h. The reaction was yellow filtrate. Concentration of the filtrate gave a yellow-black residue. The residue was partitioned between EtOAc and 0.25 M HCl (50 mL) and the layers were separated. The organic layer was extracted with 0.25 M HCl (1×50 mL). The combined aqueous layers were basified with 1.5M $K_2HPO_4$ and then extracted with EtOAc (3×). The combined organic layers were washed with brine, dried over $Na_2SO_4$, filtered and concentrated to give 1E (2.63 g, 98%) as a brown foam. MS (ESI) m/z: 355.2 (M+H)+.

1F. {3-Amino-4-[2-((S)-1-tert-butoxycarbonylamino-but-3-enyl)-pyridin-4-yl]-phenyl}-carbamic acid methyl ester To a cooled (−78° C.) clear, brown solution of 1E (2.63 g, 7.42 mmol) and pyridine (0.600 ml, 7.42 mmol) in dichloromethane (74.2 ml) was added dropwise over 30 min methyl chloroformate (0.516 ml, 6.68 mmol). The reaction was stirred at −78° C. After 1.5 h, the reaction was quenched with sat. $NH_4Cl$ and the reaction was allowed to warm to rt. The reaction was diluted with DCM and water and the layers were separated. The aqueous layer was extracted with DCM (1×). The combined organic layers were washed with sat. $NaHCO_3$, brine, dried over $Na_2SO_4$, filtered and concentrated. The residue dissolved in DCM (~10 mL) and then hexane (~300 mL) was added to give a brown suspension with brown gummy sticky substance at the bottom. The mixture was sonicated to give a mostly clear solution with the brown substance at the bottom. The solution decanted and the bottom substance rinsed with hexane, dried to give 1F (2.7 g, 88%) as a slightly brown foam. MS (ESI) m/z: 413.2 (M+H)+.

1G. Methyl N-(4-{2-[(1S)-1-{[(tert-butoxy)carbonyl]amino}but-3-en-1-yl]pyridin-4-yl}-3-[(2R)-2-methylbut-3-enamido]phenyl)carbamate Intermediate 10 (1.201 g, 12.00 mmol), 1F (3.3 g, 8.00 mmol), pyridine (1.937 ml, 24.00 mmol) in EtOAc (40.0 ml) was cooled down to −10° C. under Ar, T3P (50% wt in EtOAc) (9.52 ml, 16.00 mmol) was added dropwise and stirred at −10° C., then gradually warmed up to rt over night. The reaction mixture was washed with sat.aq. $NaHCO_3$ twice, combined aqueous layer was back extracted with EtOAc. The combined EtOAc phases washed with brine, dried over $MgSO_4$, filtered, concentrated. The crude product was then purified using silica gel chromatography to give 1G (4.06 g, 97%) as a white solid. $^1$H NMR (500 MHz, METHANOL-$d_4$) δ 8.46 (d, J=5.0 Hz, 1H), 7.64 (s, 1H), 7.47 (dd, J=8.4, 2.1 Hz, 1H), 7.35 (s, 1H), 7.29 (d, J=8.3 Hz, 1H), 7.25 (m, 1H), 5.87-5.73 (m, 2H), 5.16-5.02 (m, 4H), 4.79-4.71 (m, 1H), 3.75 (s, 3H), 3.14-3.05 (m, 1H), 2.64-2.55 (m, 1H), 2.52-2.43 (m, 1H), 1.42 (s, 9H), 1.16 (d, J=6.9 Hz, 3H). MS (ESI) m/z: 495.1 (M+H)+.

1H. Methyl N-[(10R,11E,14S)-14-{[(tert-butoxy)carbonyl]amino}-10-methyl-9-oxo-8,16-diazatricyclo[13.3.1.0$^{2,7}$]nonadeca-1(19),2(7),3,5,11,15,17-heptaen-5-yl]carbamate To a RBF was added 1G (0.5 g, 1.011 mmol), pTsOH monohydrate (0.212 g, 1.112 mmol), and dichloromethane (84 ml). The flask was equipped with a reflux condenser and the clear yellow solution was degassed with argon for 30 min. The reaction was then warmed to reflux for 1 h. Then a solution of Grubbs II (0.172 g, 0.202 mmol) in DCM (2 mL) was added dropwise to the reaction mixture. After 4 h at reflux, the reaction was cooled to rt, washed with sat. $Na_2CO_3$, brine, dried over $MgSO_4$, filtered, and concentrated to give a brown solid. The crude product was then purified using silica gel chromatography to give 1H (0.336 g, 71.2% yield) as a yellow solid. $^1$H NMR (500 MHz, METHANOL-$d_4$) δ 8.52 (d, J=5.2 Hz, 1H), 7.54 (d, J=1.4 Hz, 1H), 7.48-7.43 (m, 1H), 7.38 (d, J=8.3 Hz, 1H), 7.24 (dd, J=5.1, 1.5 Hz, 1H), 6.89 (s, 1H), 5.75-5.65 (m, 1H), 4.60 (dd, J=11.3, 3.6 Hz, 1H), 4.39 (dd, J=15.1, 9.6 Hz, 1H), 3.75 (s, 3H), 3.14-3.06 (m, 1H), 2.75-2.68 (m, 1H), 2.04-1.94 (m, 1H), 1.44 (s, 9H), 1.30 (br. s., 1H), 1.04 (d, J=6.6 Hz, 3H). MS (ESI) m/z: 467.2 (M+H)+.

1I. Methyl N-[(10R,14S)-14-{[(tert-butoxy)carbonyl]amino}-10-methyl-9-oxo-8,16-diazatricyclo[13.3.1.0$^{2,7}$]nonadeca-1(19),2(7),3,5,15,17-hexaen-5-yl]carbamate 1H was dissolved in 200 ml MeOH, vacuumed and refilled with Ar, Pd/C (10% wt) (0.684 g, 0.643 mmol) was added, vacuumed and refilled with Ar, then vacuumed and refilled with $H_2$ 3 times, stirred at rt under 55 psi $H_2$ for 16 hrs. Reaction mixture was filtered off solid through a pad of celite under $N_2$, washed with copious of MeOH, the resulting dark filtrate was further filtered through 6× whatman autovials and 6× target2 nylon 0.2 μM syringe filters under $N_2$ to yield a colorless clear solution, which was concentrated under vacuum to afford 1I (3 g, 6.4 mmol, 100% yield) as a white solid. $^1$H NMR (500 MHz, DMSO-$d_6$) δ 9.87 (s, 1H), 9.65 (s, 1H), 8.54 (d, J=5.0 Hz, 1H), 7.50-7.43 (m, 2H), 7.40 (s, 1H), 7.33 (s, 1H), 7.23 (dd, J=5.0, 1.7 Hz, 1H), 7.03 (d, J=7.4 Hz, 1H), 4.65-4.55 (m, 1H), 3.69 (s, 3H), 2.60 (br. s., 1H), 1.84-1.55 (m, 3H), 1.34 (s, 9H), 1.21-1.06 (m, 2H), 0.79 (d, J=7.2 Hz, 3H), 0.11 (d, J=12.1 Hz, 1H). MS (ESI) m/z: 469.0 (M+H)+.

1J. Methyl N-[(10R,14S)-14-amino-10-methyl-9-oxo-8,16-diazatricyclo[13.3.1.0$^{2,7}$]nonadeca-1(19),2(7),3,5,15,17-hexaen-5-yl]carbamate, TFA Salt 1I (3 g, 6.40 mmol) in $CH_2Cl_2$ (100 mL) was added TFA (14.80 mL, 192 mmol). After 4 hrs, reaction mixture was concentrated under vacuum to afford 1J as a yellow solid (3.8 g, 6.4 mmol). MS (ESI) m/z: 369.0 (M+H)+.

1J. (Alternative, 2HCl): Methyl N-[(10R,14S)-14-amino-10-methyl-9-oxo-8,16-diazatricyclo[13.3.1.0$^{2,7}$]nonadeca-1(19),2(7),3,5,15,17-hexaen-5-yl]carbamate, 2HCl Salt To a flask containing 1I (0.880 g, 1.878 mmol) was added 4.0 M HCl in dioxane (21.13 ml, 85 mmol). The resulting suspension was sonicated to give a clear, yellow solution. After 5 to 10 min, a precipitate formed. After 1h, the reaction was stopped and the precipitate was collected by filtration. The solid was rinsed with dioxane and air-dried to give a hygroscopic, yellow solid. The solid was dissolved in methanol, concentrated, and lyophilized to give 1J (Alternative, 2HCl) (0.7171 g, 87%) as a yellow solid. MS (ESI) m/z: 369.3 (M+H)$^+$.

1K. Methyl N-[(10R,14S)-14-{N-[3-(3-chloro-2,6-difluorophenyl)-3-oxopropyl]-2-(diethoxyphosphoryl)acetamido}-10-methyl-9-oxo-8,16-diazatricyclo[13.3.1.0$^{2,7}$]nonadeca-1(18),2,4,6,15(19),16-hexaen-5-yl]carbamate 1J (75 mg, 0.12 mmol) in CH$_2$Cl$_2$ (1.5 ml) was added DIEA (0.12 ml, 0.69 mmol), sonicated thoroughly. The reaction was stirred at rt for a further 30 mins, intermediate 3 (24 mg, 0.12 mmol) was added, stirred at rt. After 3 hrs, reaction mixture was cooled down to 0° C. under N$_2$, Intermediate 8 (62 mg, 0.29 mmol) was added. After 15 mins, conc. NH$_4$Cl aq was added to quench reaction. DCM phase was separated and washed with 100 ml×10 aq NaHCO$_3$, followed by brine, dried over MgSO$_4$, filtered, concentrated under vacuum to yield a pale yellow solid crude product. The residue was purified by silica gel chromatography to yield 1K as an off white solid (65 mg, 0.085 mmol, 74%). MS (ESI) m/z: 761.3 (M+H)$^+$.

Example 1. Methyl N-[(10R,14S)-14-[4-(3-chloro-2-fluoro-6-methoxyphenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate, TFA Salt 1K (65 mg, 0.085 mmol) in MeOH (1.7 ml) was cooled down to 0° C. under N$_2$. Sodium methoxide (25% wt in MeOH) (55 mg, 0.26 mmol) was added dropwise. After 10 mins, reaction mixture was quenched with HCl (1N in aq) (0.27 ml, 0.34 mmol) at 0° C., then concentrated under vacuum to remove MeOH to yield a white slurry solution, which was added DCM. The mixture was partitioned. DCM phase was further washed with sat. aq. NaHCO$_3$, then with brine; DCM phase was separated. Concentrated under vacuum to a small volume, filtered and the white solid was purified by prep. HPLC, afforded example 1 (24 mg, 46%) as beige solid product. $^1$H NMR (500 MHz, CD$_3$OD) δ 9.68 (s, 1H), 8.77 (d, J=6.1 Hz, 1H), 8.13 (s, 1H), 7.92 (d, J=5.8 Hz, 1H), 7.67 (d, J=8.5 Hz, 1H), 7.54-7.61 (m, 2H), 7.43 (t, J=8.7 Hz, 1H), 6.90 (d, J=10.5 Hz, 1H), 5.96 (s, 1H), 5.37 (dd, J=12.5, 4.8 Hz, 1H), 3.84 (s, 3H), 3.78 (s, 3H), 3.67-3.75 (m, 2H), 2.73-2.84 (m, 1H), 2.59-2.73 (m, 2H), 2.26-2.38 (m, 1H), 2.04-2.14 (m, 1H), 1.87-1.97 (m, 1H), 1.63 (m, J=6.1 Hz, 1H), 1.26-1.40 (m, 1H), 1.06 (d, J=6.9 Hz, 3H), 0.88-1.02 (m, 1H). MS (ESI) m/z: 607.2 (M+H)$^+$.

Example 2

Methyl N-[(10R,14S)-14-[4-(3-chloro-2-fluoro-6-methylphenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate, TFA Salt

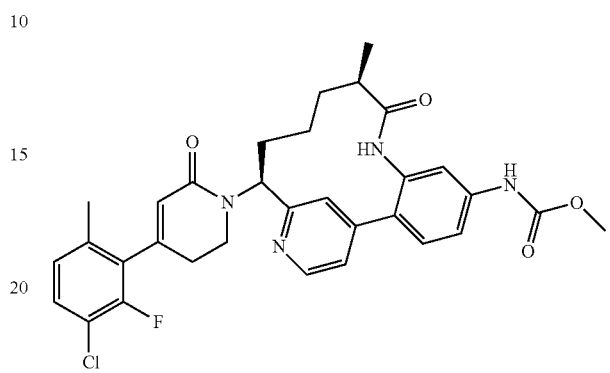

2A: Methyl N-[(10R,14S)-14-[4-(6-bromo-3-chloro-2-fluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate 2A was prepared using a procedure analogous to example 1 except that intermediate 1 was replaced with intermediate 2. $^1$H NMR (500 MHz, MeOD) δ 8.56-8.68 (m, 1H), 7.34-7.67 (m, 8H), 5.92 (br. s., 1H), 5.57-5.71 (m, 1H), 3.89-4.01 (m, 1H), 3.71-3.84 (m, 4H), 2.51-2.68 (m, 3H), 2.10-2.29 (m, 1H), 1.80-2.01 (m, 2H), 1.48-1.63 (m, 1H), 1.04 (d, J=6.3 Hz, 3H), 0.86-0.94 (m, 2H). MS (ESI) m/z: 657.0 (M+H)$^+$. Analytical HPLC (method A): RT=8.1 min.

Example 2

To a microwave tube was added 2A (10 mg, 0.015 mmol), potassium trifluoromethylborate (1.859 mg, 0.015 mmol) and cesium carbonate (14.90 mg, 0.046 mmol) in THF (290 μl) and water (14.52 μl). The reaction mixture was bubbled through Ar for several minutes and PdCl$_2$(dppf)-CH$_2$Cl$_2$Adduct (1.245 mg, 1.525 μmol) was added. Sealed and heated at 90° C. for 5 hrs, then at rt over the weekend. To drive the reaction to completion, more THF, potassium trifluoromethylborate and Pd catalyst were added, degassed and sealed and heated at 90° C. overnight. Diluted with DCM, washed with H$_2$O, brine, dried over MgSO$_4$, filtered and concentrated. Redissolved in MeOH, a drop of TFA was added as well as DMF to ensure product all dissolved. Purification by reverse phase HPLC afforded the example 2 as an off-white solid (7.4 mg, 68%). $^1$H NMR (500 MHz, MeOD) δ 8.76 (d, J=6.1 Hz, 1H), 8.11 (s, 1H), 7.89 (d, J=6.1 Hz, 1H), 7.62-7.70 (m, 1H), 7.52-7.61 (m, 2H), 7.35 (t, J=8.0 Hz, 1H), 7.09 (d, J=8.3 Hz, 1H), 5.88 (s, 1H), 5.40 (dd, J=12.5, 4.7 Hz, 1H), 3.71-3.83 (m, 5H), 2.69-2.81 (m, 1H), 2.56-2.68 (m, 2H), 2.22-2.37 (m, 4H), 2.04-2.15 (m, 1H), 1.86-1.98 (m, 1H), 1.57-1.69 (m, 1H), 1.25-1.40 (m, 1H), 1.06 (d, J=6.8 Hz, 3H), 0.91-1.02 (m, 1H). MS (ESI) m/z: 591.2 (M+H)$^+$. Analytical HPLC (method A): RT=7.6 min, purity=99%.

Example 3

Methyl N-[(10R,14S)-14-[4-(3-chloro-6-cyano-2-fluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate, TFA Salt

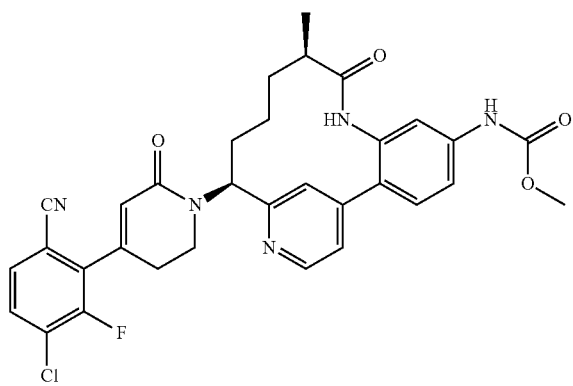 [SMILES: COC(=O)Nc1ccc2c(c1)NC(=O)[C@H](C)CCC[C@H](N1CCC(c3c(C#N)ccc(Cl)c3F)=CC1=O)c1cc-2ccn1]

To a microwave tube containing example 2A (10 mg, 0.015 mmol) was added dicyanozinc (3.58 mg, 0.030 mmol), zinc (0.299 mg, 4.57 µmol), and DMF (1 mL). The mixture was bubbled with Ar for several minutes and bis(tri-t-butylphosphine)palladium(0) (0.779 mg, 1.525 µmol) was added. The reaction was sealed and heated at 80° C. in an oil bath overnight. The reaction was cooled to rt and diluted with EtOAc. The mixture was washed with sat'd NaHCO$_3$, H$_2$O, brine, dried over MgSO$_4$, filtered, and concentrated. Purification by reverse phase HPLC afforded example 3 as a white solid (4 mg, 31%). $^1$H NMR (500 MHz, CDCl$_3$) δ 8.77 (d, J=6.1 Hz, 1H), 8.12 (d, J=1.7 Hz, 1H), 7.86-7.92 (m, 1H), 7.64-7.75 (m, 3H), 7.54-7.60 (m, 2H), 6.19 (s, 1H), 5.42 (dd, J=12.4, 4.7 Hz, 1H), 3.72-3.88 (m, 5H), 2.85-2.95 (m, 1H), 2.75-2.83 (m, 1H), 2.61-2.68 (m, 1H), 2.25-2.34 (m, 1H), 2.05-2.15 (m, 1H), 1.86-1.96 (m, 1H), 1.57-1.69 (m, 1H), 1.28-1.37 (m, 1H), 1.06 (d, J=6.9 Hz, 3H), 0.94-1.02 (m, 1H). MS (ESI) m/z: 602.2 (M+H)$^+$. Analytical HPLC (method A): RT=6.9 min, purity=88%.

Example 4

Methyl N-[(10R,14S)-14-[4-(2-cyano-6-fluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate, TFA Salt

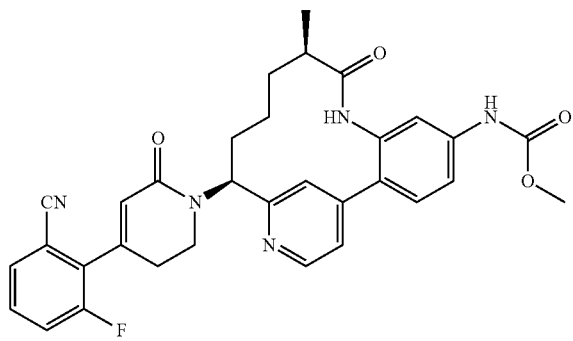 [SMILES: COC(=O)Nc1ccc2c(c1)NC(=O)[C@H](C)CCC[C@H](N1CCC(c3c(F)cccc3C#N)=CC1=O)c1cc-2ccn1]

Example 4 was obtained as a by-product while converting example 2A to example 3. $^1$H NMR (500 MHz, CDCl$_3$) δ 9.64 (s, 1H), 8.74 (d, J=5.8 Hz, 1H), 8.02 (s, 1H), 7.80 (dd, J=5.8, 1.7 Hz, 1H), 7.50-7.70 (m, 5H), 6.15 (s, 1H), 5.47 (dd, J=12.5, 4.5 Hz, 1H), 3.73-3.90 (m, 5H), 2.82-2.92 (m, 1H), 2.72-2.82 (m, 1H), 2.58-2.68 (m, 1H), 2.23-2.33 (m, 1H), 2.01-2.11 (m, 1H), 1.88-1.98 (m, 1H), 1.54-1.68 (m, 1H), 1.28-1.38 (m, 2H), 1.06 (d, J=6.9 Hz, 3H), 0.91-1.03 (m, 1H). MS (ESI) m/z: 568.3 (M+H)$^+$. Analytical HPLC (method A): RT=6.3 min.

Example 5

Methyl N-[(10R,14S)-14-[4-(4-chloro-3-fluoropyridin-2-yl)-6-oxo-1,2,3,6-tetrahydropyridin-1-yl]-17-methoxy-10-methyl-9-oxo-8,16-diazatricyclo[13.3.1.0$^{2,7}$]nonadeca-1(18),2,4,6,15(19),16-hexaen-5-yl]carbamate, TFA Salt

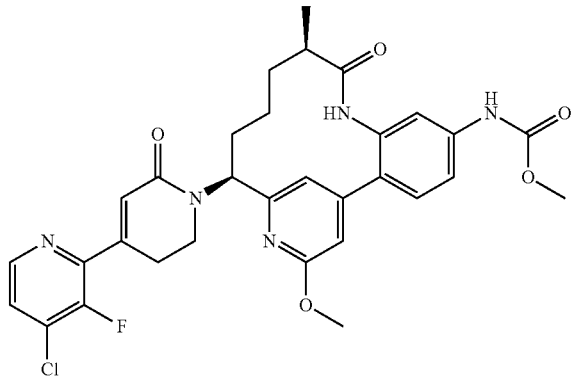 [SMILES: COC(=O)Nc1ccc2c(c1)NC(=O)[C@H](C)CCC[C@H](N1CCC(c3nccc(Cl)c3F)=CC1=O)c1cc-2cc(OC)n1]

5A. Methyl 4-(1,3-dioxolan-2-yl)-3-nitrobenzoate

To a solution of methyl 4-formyl-3-nitrobenzoate (9.0 g, 43.0 mmol) in toluene (150 mL) was added ethylene glycol (7.20 mL, 129 mmol) followed by p-TsOH (0.409 g, 2.152 mmol) and the reaction mixture was heated at reflux temperature with azeotropic removal of H$_2$O using a Dean-Stark trap for 4 h. The reaction mixture was then cooled and diluted with DCM. The DCM layer was then washed with sat. aq. NaHCO$_3$. The organic layer was dried over MgSO$_4$, filtered, and concentrated to yield a residue. The residue was dissolved in minimal quantity of DCM and purified by silica gel chromatography to yield 5A (8.53 g, 78%) as a white solid. $^1$H NMR (400 MHz, DMSO-d$_6$) δ 8.39 (s, 1H), 8.27 (d, J=8.2 Hz, 1H), 7.90 (d, J=8.2 Hz, 1H), 6.38 (s, 1H), 4.00 (dt, J=3.8, 1.9 Hz, 2H), 3.94 (dt, J=3.8, 1.9 Hz, 2H), 3.91 (s, 3H) ppm.

5B. 4-(1,3-Dioxolan-2-yl)-3-nitrobenzoic acid

Lithium hydroxide monohydrate (5.67 g, 135 mmol) was added to a solution of 5A (11.4 g, 45.0 mmol) in THF (120 mL), MeOH (120 mL) and H$_2$O (40.0 mL). The above mixture was then heated to 50° C. for 1 h. After 1 h, the heating was reduced to rt and stirring was continued for overnight. To the reaction mixture was then added H$_2$O (50 mL) and the organics were concentrated. The remaining aqueous layer was made acidic with 1.0 N HCl solution to precipitate out the solids. The solids were collected by filtration, washed with H₂O and dried under vacuum overnight to give 5B. ¹H NMR (400 MHz, DMSO-d₆) δ 13.68 (br. s., 1H), 8.36 (d, J=1.5 Hz, 1H), 8.25 (dd, J=8.1, 1.3 Hz, 1H), 7.88 (d, J=8.1 Hz, 1H), 6.38 (s, 1H), 4.05-3.89 (m, 4H) ppm.

5C. Methyl (4-(1,3-dioxolan-2-yl)-3-nitrophenyl)carbamate

To a solution of 5B (6.77 g, 28.3 mmol) in THF (100 mL) at −5° C. was added TEA (7.89 mL, 56.6 mmol) in THF (25 mL) dropwise. The temperature was maintained at −5° C., and a solution of ethyl chloroformate (3.25 mL, 34.0 mmol) in THF (30 mL) was added dropwise over 10 minutes. After stirring for an additional 30 minutes, a cold solution of sodium azide (3.68 g, 56.6 mmol) in H₂O (12.5 mL) was added dropwise. After stirring for additional 1 hour, the reaction mixture was concentrated in vacuo (without heating). The oily residue was dissolved in the Et₂O (100 mL), washed with H₂O, brine, and dried over sodium sulfate, filtered, and concentrated (without heating) to give the acyl azide. This material was dissolved in toluene (100 mL) and heated to 110° C. After 1 h, the temperature was lowered to 80° C., MeOH (60 mL) was added, and heating was continued for overnight. The reaction mixture was concentrated and purified by silica gel chromatography to yield 7C (5.01 g, 66%) as an amber solid. ¹H NMR (400 MHz, DMSO-d₆) δ 10.21 (s, 1H), 8.10 (d, J=1.6 Hz, 1H), 7.74-7.62 (m, 2H), 6.22 (s, 1H), 3.95-3.90 (m, 4H), 3.69 (s, 3H).

5D. Methyl (4-formyl-3-nitrophenyl)carbamate 5C (5.00 g, 18.64 mmol) was added to a solution of TFA (27 mL) and H₂O (3 mL) and stirred at rt for 3 h. After 3 h, the reaction mixture was concentrated and the residue was partitioned between H₂O and EtOAc. The organic layer was then washed with saturated sodium bicarbonate solution followed by brine. The organic layer was then dried over sodium sulfate, filtered, and concentrated to give a light yellow solid as 5D (3.83 g, 92%). ¹H NMR (400 MHz, DMSO-d₆) δ 10.59 (s, 1H), 10.09 (s, 1H), 8.23 (d, J=1.6 Hz, 1H), 7.92 (d, J=8.2 Hz, 1H), 7.86-7.81 (m, 1H), 3.74 (s, 3H) ppm.

5E. (S)-tert-Butyl 1-(dimethoxyphosphoryl)-2-oxo-hex-5-en-3-ylcarbamate

To a solution of dimethyl methylphosphonate (13.98 mL, 131 mmol) in THF (87 mL) at −78° C. was added n-BuLi (82 mL, 131 mmol) slowly. After completion of addition, the reaction was stirred for 40 min and then a solution of (S)-methyl 2-(tert-butoxycarbonylamino)pent-4-enoate (6.0 g, 26.2 mmol) in THF (30 mL) was added slowly. Stirring was continued for another 40 min at −78° C. The reaction mixture was then quenched by adding H₂O (2.357 mL, 131 mmol). The reaction mixture was diluted with EtOAc (100 mL) and the layers were separated. The organic layer was washed with 1M HCl, saturated NaHCO₃ solution followed by brine. The organic phase was then dried over MgSO₄, filtered and concentrated to give a clear oil. The crude product was purified using silica gel chromatography to give 5E (7.46 g, 89%) as colorless oil. MS (ESI) m/z: 343.9 (M+Na)⁺. ¹H NMR (500 MHz, CDCl₃) δ 5.63-5.76 (1H, m), 5.08-5.17 (2H, m), 4.33-4.43 (1H, m), 3.80 (3H, d, J=2.20 Hz), 3.77 (3H, d, J=2.20 Hz), 3.28-3.37 (1H, m), 3.05-3.16 (1H, m), 2.58-2.69 (1H, m), 2.42 (1H, dt, J=14.58, 7.29 Hz), 1.43 (9H, s).

5F. Methyl (4-((1E,4S)-4-((tert-butoxycarbonyl)amino)-3-oxohepta-1,6-dien-1-yl)-3-nitrophenyl)carbamate To a vigorously stirred solution of 5E (4.47 g, 13.92 mmol) and 5D (2.6 g, 11.60 mmol) in THF (anhydrous) (115 mL) and EtOH (absolute) (1.148 mL) under nitrogen was added portion wise K₂CO₃ (anhydrous) (2.56 g, 18.56 mmol) at 0° C. The reaction mixture was allowed to raise to rt and then the mixture was heated at 55° C. The reaction mixture was then filtered with the aid of EtOAc and the filtrate evaporated to a residue which was dissolved in a small amount of methylene chloride and purified by normal phase chromatography to give 5F (4.38 g, 90%) as yellow solid. MS (ESI) m/z: 420.2 (M+H)⁺. ¹H NMR (400 MHz, DMSO-d₆) δ 10.36 (s, 1H), 8.22 (d, J=2.2 Hz, 1H), 7.89 (d, J=8.8 Hz, 1H), 7.83-7.73 (m, 2H), 7.21 (d, J=7.7 Hz, 1H), 7.02 (d, J=15.9 Hz, 1H), 5.77 (ddt, J=17.0, 10.2, 6.7 Hz, 1H), 5.16-5.01 (m, 2H), 4.32 (td, J=8.5, 4.9 Hz, 1H), 3.71 (s, 3H), 2.34-2.23 (m, 1H), 1.36 (s, 9H) ppm.

5G. Methyl (4-(6-(1-((tert-butoxycarbonyl)amino)but-3-en-1-yl)-2-oxo-1,2-dihydropyridin-4-yl)-3-nitrophenyl)carbamate To a solution of 5F (3.0 g, 7.15 mmol) and 1-(2-ethoxy-2-oxoethyl)pyridinium bromide (1.189 g, 7.15 mmol) in EtOH (130 mL), was added ammonium acetate (11.03 g, 143 mmol) portion wise. After 15 min, the mixture was stirred at 75° C. The reaction mixture was then concentrated and dissolved in EtOAc. The organic layer was then washed with 1.0 N HCl, H₂O, saturated sodium bicarbonate solution and finally by brine. The organic phase was dried over sodium sulfate, filtered and concentrated to yield a residue which was purified by normal phase chromatography to isolate 5G (2.2 g, 67%) as a brown solid. MS (ESI) m/z: 459.3 (M+H)⁺. The racemate was subjected to chiral separation using chiral AD-H 21×250 mm, eluting with a mixture of 35% (50/50 EtOH, i-PrOH and 0.1% DEA) and 65% CO2 with a flow rate of 70 mL/min and 150 bar at 40° C. to give enantiomer 5G1 (peak 1) and enantiomer 5G2 (peak 2).

5H. Methyl N-(4-{2-[(1S)-1-{[(tert-butoxy)carbonyl]amino}but-3-en-1-yl]-6-methoxypyridin-4-yl}-3-nitrophenyl)carbamate To a stirred solution of 5G2 (3.0 g, 6.54 mmol) in chloroform (131 mL) under an argon atmosphere was added silver (I) carbonate (50% on Celite®) (3.61 g, 6.54 mmol) and iodomethane (1.22 mL, 19.63 mmol), respectively. The reaction mixture was heated at 65° C. After stirring for 14 hours, the reaction was filtered, concentrated, and purified by normal phase chromatography to give 5H (2.69 g, 87%) as a tan solid. MS (ESI) m/z: 473 (M+H)⁺.

5I. Methyl N-(3-amino-4-{2-[(1S)-1-{[(tert-butoxy)carbonyl]amino}but-3-en-1-yl]-6-methoxy-pyridin-4-yl}phenyl)carbamate 5H (2.69 g, 5.69 mmol) in MeOH (60 ml) was treated with zinc powder (3.86 g, 59.0 mmol) and ammonium chloride (0.632 g, 11.81 mmol) and heated at 65° C. overnight. The suspension was filtered hot through a plug of Celite® and concentrated. This residue was re-dissolved in EtOAc (with 10% MeOH), washed with saturated sodium bicarbonate solution, brine, dried over sodium sulfate, filtered, and concentrated to give 5I. MS (ESI) m/z: 443 (M+H)+.

5J. Methyl N-(4-{2-[(1S)-1-{[(tert-butoxy)carbonyl]amino}but-3-en-1-yl]-6-methoxypyridin-4-yl}-3-(2-methylbut-3-enamido)phenyl)carbamate DIPEA (3.02 mL, 17.29 mmol) was added to a solution of 2-methylbut-3-enoic acid (0.865 g, 8.64 mmol) and 7I (2.55 g, 5.76 mmol) in EtOAc (57.6 ml) at −10° C. under argon. Next, 1-propanephosphonic acid cyclic anhydride (6.79 ml, 11.53 mmol; 50% solution in EtOAc) was added dropwise and the reaction stirred for 1 h under set conditions and then allowed to come to rt. After 48 hours, the reaction was diluted with EtOAc, washed with sat. aq. NaHCO$_3$, brine, dried over Na$_2$SO$_4$, filtered, and concentrated. Purification by normal phase chromatography gave 5J (2.52 g, 83%) as a white solid. MS (ESI) m/z: 525.1 (M+H)+.

5K2. tert-butyl N-[(10R,11Z,14S)-17-methoxy-5-[(methoxycarbonyl)amino]-10-methyl-9-oxo-8,16-diazatricyclo[13.3.1.0$^{2,7}$]nonadeca-1(19),2,4,6,11,15,17-heptaen-14-yl]carbamate and tert-butyl N-[(10R,11E,14S)-17-methoxy-5-[(methoxycarbonyl)amino]-10-methyl-9-oxo-8,16-diazatricyclo[13.3.1.0$^{2,7}$]nonadeca-1(19),2,4,6,11,15,17-heptaen-14-yl]carbamate as a Mixture A solution of 5J (0.500 g, 0.953 mmol) and Ts-OH (0.199 g, 1.048 mmol) in DCM (112 ml) was heated for 0.5h. The solution was cooled down to room temperature and bubbled with argon for 0.5h. To the solution was added tricyclohexylphosphine[1,3-bis(2,4,6-trimethylphenyl)-4,5-dihydroimidazol-2-ylidene][benzylidine]ruthenium(IV)dichloride (0.243 g, 0.286 mmol) and the resulting solution bubbled with argon for an additional 0.5h before heating at 45° C. for 12 hours. The reaction mixture was cooled to ambient temperature, washed with aqueous saturated NaHCO$_3$ solution, and the aqueous layer was further extracted with DCM (30 mL×2). The combined organic extracts were dried over Na$_2$SO$_4$, concentrated, and purified purified by reverse phase HPLC to give diastereomeric mixtures peak 1 (minor, early eluting) and peak 2 (major, later eluting). Peak 2 was suspended in aqueous sodium bicarbonate and extracted several times with EtOAc, the combined organic layers were washed with brine, dried over sodium sulfate, filtered, and concentrated to give 5K2 (68 mg, 29%). MS (ESI) m/z: 497.1 (M+H)+.

5 L. tert-Butyl N-[(10R,14S)-17-methoxy-5-[(methoxycarbonyl)amino]-10-methyl-9-oxo-8,16-diazatricyclo-[13.3.1.0$^{2,7}$]nonadeca-1(19),2,4,6,15,17-hexaen-14-yl]carbamate Platinum(IV) oxide (3.11 mg, 0.014 mmol) was added to a degassed solution of 5K2 (0.068 g, 0.137 mmol) in EtOH (10 mL) and subjected to a hydrogen atmosphere (55 psi). After 16 hours, the suspension was filtered through a plug of Celite and concentrated. This intermediate was carried forward to the next reaction without further purification. MS (ESI) m/z: 499.1 (M+H)+.

5M 5M was prepared in a similar way as example 1J by replacing 1I with 5L.

5N. Methyl N-[(10R,14S)-14-{[(3R)-3-[(tert-butyldimethylsilyl)oxy]-3-(4-chloro-3-fluoropyridin-2-yl)propyl]amino}-17-methoxy-1-methyl-9-oxo-8,16-diazatricyclo[13.3.1.0$^{2,7}$]nonadeca-1(18),2,4,6,15 (19), 16-hexaen-5-yl]carbamate To a mixture of intermediate 9 (32.5 mg, 0.102 mmol) and 5M (52.4 mg, 0.102 mmol) in anhydrous DCE (4 mL) under nitrogen was added NaBH(OAc)$_3$ (43.3 mg, 0.204 mmol) and the mixture was stirred overnight at ambient temperature. The reaction mixture was diluted with sat'd NaHCO$_3$ and extracted with EtOAc (3×). The combined organic layer was washed with brine, dried (Na$_2$SO$_4$), filtered, and evaporated to give 5N (68 mg, 95%) as a brown solid. MS (ESI) m/z: 700.0 (M+H)+.

5O. Methyl N-[(10R,14S)-14-{N-[(3R)-3-[(tert-butyldimethylsilyl)oxy]-3-(4-chloro-3-fluoropyridin-2-yl)propyl]-2-(diethoxyphosphoryl)acetamido}-17-methoxy-10-methyl-9-oxo-8,16-diazatricyclo[13.3.1.0$^{2,7}$]nonadeca-1(18),2,4,6,15(19), 16-hexaen-5-yl]carbamate To 5N (34.2 mg, 0.049 mmol) and DIPEA (0.017 mL, 0.098 mmol) in anhydrous DCM (2 mL) under nitrogen at 0° C. was added a solution of diethyl (2-chloro-2-oxoethyl) phosphonate (15.72 mg, 0.073 mmol) in anhydrous DCM (0.5 mL). The mixture stirred at 0° C. for 30 min then at ambient temperature overnight. The reaction was quenched with MeOH (1 mL) and concentrated. The residue was purified by silica gel chromatography to give 5O (29 mg, 67%) as a solid. MS (ESI) m/z: 878.1 (M+H)+.

5P. Methyl N-[(10R,14S)-14-{N-[(3R)-3-(4-chloro-3-fluoropyridin-2-yl)-3-hydroxypropyl]-2-(diethoxyphosphoryl)acetamido}-17-methoxy-10-methyl-9-oxo-8,16-diazatricyclo[13.3.1.0$^{2,7}$]nonadeca-1(18),2,4,6,15(19), 16-hexaen-5-yl]carbamate To a mixture of 5O (29 mg, 0.033 mmol) in anhydrous THF (2 mL) under nitrogen was added TBAF (1 M in THF) (0.042 mL, 0.042 mmol). The reaction stirred for 1 h at ambient temperature. The reaction mixture was diluted with water and extracted with EtOAc (3×). The combined organic layer was washed with brine, dried over Na$_2$SO$_4$, filtered, and evaporated to give 5P (16 mg, 62%). MS (ESI) m/z: 764.0 (M+H)+.

5Q. Methyl N-[(10R,14S)-14-{N-[3-(4-chloro-3-fluoropyridin-2-yl)-3-oxopropyl]-2-(diethoxyphosphoryl)acetamido}-17-methoxy-10-methyl-9-oxo-8,16-diazatricyclo[13.3.1.0$^{2,7}$]nonadeca-1(18),2,4,6,15 (19), 16-hexaen-5-yl]carbamate To a solution of 5P (15.5 mg, 0.020 mmol) in anhydrous DCM (4 mL) was added Dess-Martin periodinane (11.18 mg, 0.026 mmol). The mixture was stirred at ambient temperature for 1 h. The reaction mixture was diluted with water and extracted with DCM (3×). The combined organic layer was washed with brine, dried (Na$_2$SO$_4$), filtered, and evaporated to give 5Q (15 mg, 99%). MS (ESI) m/z: 762.0 (M+H)+.

Example 5

Example 5 was prepared using a procedure analogous to example 1 except that 1K was replaced 5Q. $^1$H NMR (500

MHz, CDCl₃) δ 8.42 (d, J=5.2 Hz, 1H), 7.60 (t, J=5.2 Hz, 1H), 7.50-7.44 (m, 3H), 7.16 (d, J=1.1 Hz, 1H), 6.79 (d, J=1.1 Hz, 1H), 6.67 (d, J=0.8 Hz, 1H), 5.68 (dd, J=12.4, 5.0 Hz, 1H), 4.36 (br. s., 1H), 3.98 (s, 3H), 3.91-3.84 (m, 1H), 3.78 (s, 3H), 3.09-2.94 (m, 2H), 2.69 (dd, J=6.1, 3.3 Hz, 1H), 2.27-2.17 (m, 1H), 2.05-1.97 (m, 1H), 1.82-1.72 (m, 1H), 1.59-1.39 (m, 2H), 1.01 (d, J=7.2 Hz, 3H). MS (ESI) m/z: 607.9 (M+H)⁺. Analytical HPLC (method A): RT=9.5 min, purity=92%.

5M 5M was prepared in a similar way as example 1J by replacing 1I with 5 L.

5N. Methyl N-[(10R,14S)-14-{[(3R)-3-[(tert-butyldimethylsilyl)oxy]-3-(4-chloro-3-fluoropyridin-2-yl)propyl]amino}-17-methoxy-10-methyl-9-oxo-8,16-diazatricyclo[13.3.1.0²,⁷]nonadeca-1(18),2,4,6,15(19), 16-hexaen-5-yl]carbamate To a mixture of intermediate 9 (32.5 mg, 0.102 mmol) and 5M (52.4 mg, 0.102 mmol) in anhydrous DCE (4 mL) under nitrogen was added NaBH(OAc)₃ (43.3 mg, 0.204 mmol) and the mixture was stirred overnight at ambient temperature. The reaction mixture was diluted with sat'd NaHCO₃ and extracted with EtOAc (3×). The combined organic layer was washed with brine, dried (Na₂SO₄), filtered, and evaporated to give 5N (68 mg, 95%) as a brown solid. MS (ESI) m/z: 700.0 (M+H)⁺.

5O. Methyl N-[(10R,14S)-14-{N-[(3R)-3-[(tert-butyldimethylsilyl)oxy]-3-(4-chloro-3-fluoropyridin-2-yl)propyl]-2-(diethoxyphosphoryl)acetamido}-17-methoxy-10-methyl-9-oxo-8,16-diazatricyclo[13.3.1.0²,⁷]nonadeca-1(18),2,4,6,15(19), 16-hexaen-5-yl]carbamate To 5N (34.2 mg, 0.049 mmol) and DIPEA (0.017 mL, 0.098 mmol) in anhydrous DCM (2 mL) under nitrogen at 0° C. was added a solution of diethyl (2-chloro-2-oxoethyl)phosphonate (15.72 mg, 0.073 mmol) in anhydrous DCM (0.5 mL). The mixture stirred at 0° C. for 30 min then at ambient temperature overnight. The reaction was quenched with MeOH (1 mL) and concentrated. The residue was purified by silica gel chromatography to give 5O (29 mg, 67%) as a solid. MS (ESI) m/z: 878.1 (M+H)⁺.

5P. Methyl N-[(10R,14S)-14-{N-[(3R)-3-(4-chloro-3-fluoropyridin-2-yl)-3-hydroxypropyl]-2-(diethoxyphosphoryl)acetamido}-17-methoxy-10-methyl-9-oxo-8,16-diazatricyclo[13.3.1.0²,⁷]nonadeca-1(18),2,4,6,15(19), 16-hexaen-5-yl]carbamate To a mixture of 5O (29 mg, 0.033 mmol) in anhydrous THF (2 mL) under nitrogen was added TBAF (1 M in THF) (0.042 mL, 0.042 mmol). The reaction stirred for 1 h at ambient temperature. The reaction mixture was diluted with water and extracted with EtOAc (3×). The combined organic layer was washed with brine, dried over Na₂SO₄, filtered, and evaporated to give 5P (16 mg, 62%). MS (ESI) m/z: 764.0 (M+H)⁺.

5Q. Methyl N-[(10R,14S)-14-{N-[3-(4-chloro-3-fluoropyridin-2-yl)-3-oxopropyl]-2-(diethoxyphosphoryl)acetamido}-17-methoxy-10-methyl-9-oxo-8,16-diazatricyclo[13.3.1.0²,⁷]nonadeca-1(18),2,4,6,15(19), 16-hexaen-5-yl]carbamate To a solution of 5P (15.5 mg, 0.020 mmol) in anhydrous DCM (4 mL) was added Dess-Martin periodinane (11.18 mg, 0.026 mmol). The mixture was stirred at ambient temperature for 1 h. The reaction mixture was diluted with water and extracted with DCM (3×). The combined organic layer was washed with brine, dried (Na₂SO₄), filtered, and evaporated to give 5Q (15 mg, 99%). MS (ESI) m/z: 762.0 (M+H)⁺.

Example 5

Example 5 was prepared using a procedure analogous to example 1 except that 1K was replaced 5Q. ¹H NMR (500 MHz, CDCl₃) δ 8.42 (d, J=5.2 Hz, 1H), 7.60 (t, J=5.2 Hz, 1H), 7.50-7.44 (m, 3H), 7.16 (d, J=1.1 Hz, 1H), 6.79 (d, J=1.1 Hz, 1H), 6.67 (d, J=0.8 Hz, 1H), 5.68 (dd, J=12.4, 5.0 Hz, 1H), 4.36 (br. s., 1H), 3.98 (s, 3H), 3.91-3.84 (m, 1H), 3.78 (s, 3H), 3.09-2.94 (m, 2H), 2.69 (dd, J=6.1, 3.3 Hz, 1H), 2.27-2.17 (m, 1H), 2.05-1.97 (m, 1H), 1.82-1.72 (m, 1H), 1.59-1.39 (m, 2H), 1.01 (d, J=7.2 Hz, 3H). MS (ESI) m/z: 607.9 (M+H)⁺. Analytical HPLC (method A): RT=9.5 min, purity=92%.

Example 6

Methyl N-[(10R,14S)-14-[4-(4-chloro-3-methoxypyridin-2-yl)-6-oxo-1,2,3,6-tetrahydropyridin-1-yl]-17-methoxy-10-methyl-9-oxo-8,16-diazatricyclo[13.3.1.0²,⁷]nonadeca-1(18),2,4,6,15(19), 16-hexaen-5-yl]carbamate, TFA Salt

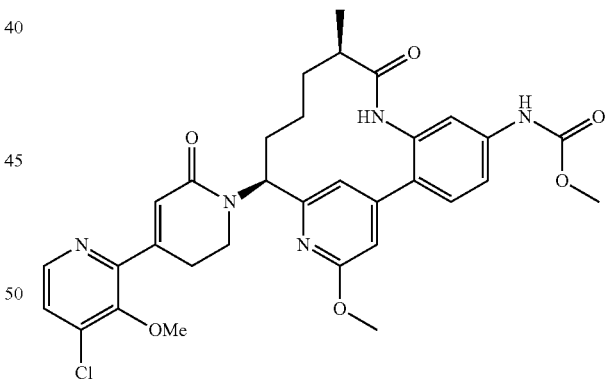

Example 6 was obtained as a by-product while converting 5Q to example 5. ¹H NMR (500 MHz, CDCl₃) δ 8.32 (d, J=5.0 Hz, 1H), 7.52 (d, J=5.2 Hz, 1H), 7.50-7.44 (m, 3H), 7.14 (d, J=1.1 Hz, 1H), 6.75 (d, J=1.1 Hz, 1H), 6.72 (s, 1H), 5.72 (dd, J=12.4, 5.0 Hz, 1H), 4.40 (br. s., 1H), 3.96 (s, 3H), 3.87 (s, 3H), 3.78 (s, 3H), 3.01-2.94 (m, 2H), 2.73-2.65 (m, 1H), 2.26-2.18 (m, 1H), 2.06-1.98 (m, 1H), 1.80-1.71 (m, 1H), 1.58-1.25 (m, 3H), 1.01 (d, J=7.2 Hz, 3H). MS (ESI) m/z: 620.0 (M+H)⁺. Analytical HPLC (method A): RT=9.1 min, purity=95%.

Example 7

Methyl N-[(10R,14S)-14-[4-(3,6-dicyano-2-fluoro-phenyl)-6-oxo-1,2,3,6-tetrahydropyridin-1-yl]-17-methoxy-10-methyl-9-oxo-8,16-diazatricyclo[13.3.1.0²,⁷]nonadeca-1(18),2,4,6,15(19),16-hexaen-5-yl]carbamate

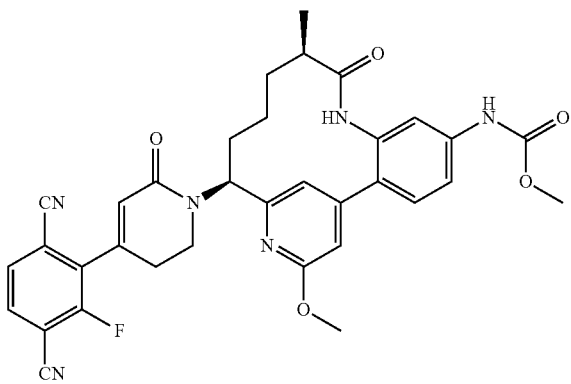 [SMILES: COC(=O)Nc1ccc2c(c1)NC(=O)[C@H](C)CCC[C@H](N1CCC(c3c(C#N)ccc(C#N)c3F)=CC1=O)c1cc-2cc(OC)n1]

7A. Methyl N-[(10R,14S)-14-[4-(6-bromo-3-chloro-2-fluorophenyl)-6-oxo-1,2,3,6-tetrahydropyridin-1-yl]-17-methoxy-10-methyl-9-oxo-8,16-diazatricyclo[13.3.1.0²,⁷]nonadeca-1(18),2,4,6,15(19), 16-hexaen-5-yl]carbamate: 7A was prepared using a procedure analogous to example 1 except that in step 1K intermediate 1 was replaced with intermediate 2 and 1J was replaced with 5M. MS (ESI) m/z: 685.0 (M+H)⁺.

Example 7 was isolated as a side product using a procedure analogous to example 3 except that 2A compound was replaced with 7A. ¹H NMR (400 MHz, METHANOL-d₄) δ 9.33 (s, 1H), 7.88-7.83 (m, 1H), 7.73 (d, J=8.1 Hz, 1H), 7.39-7.32 (m, 3H), 7.02 (s, 1H), 6.63 (s, 1H), 6.13 (s, 1H), 5.60 (dd, J=12.8, 5.2 Hz, 1H), 4.32 (br. s., 1H), 3.83 (s, 3H), 3.66 (s, 3H), 2.80-2.51 (m, 3H), 2.08 (br. s., 1H), 1.95-1.83 (m, 1H), 1.66 (br. s., 1H), 1.39 (d, J=13.1 Hz, 1H), 1.31 (d, J=12.6 Hz, 3H), 0.89 (d, J=6.8 Hz, 3H), 0.63 (br. s., 1H). MS (ESI) m/z: 623.1 (M+H)⁺. Analytical HPLC (method A): RT=8.9 min, purity >95%.

Example 8

Methyl N-[(10R,14S)-14-[4-(3-amino-6-cyano-1H-indazol-7-yl)-6-oxo-1,2,3,6-tetrahydropyridin-1-yl]-17-methoxy-10-methyl-9-oxo-8,16-diazatricyclo[13.3.1.0²,⁷]nonadeca-1(18),2,4,6,15(19),16-hexaen-5-yl]carbamate, TFA Salt

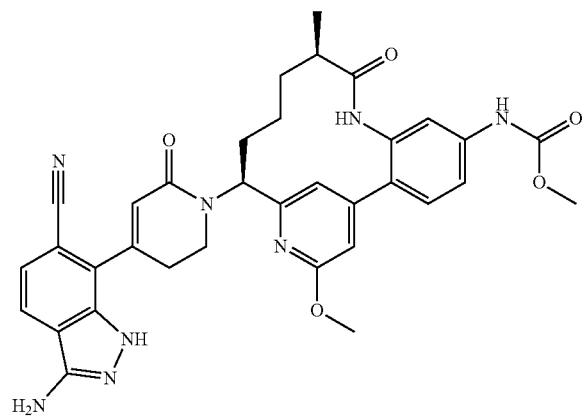 [SMILES: COC(=O)Nc1ccc2c(c1)NC(=O)[C@H](C)CCC[C@H](N1CCC(c3c(C#N)ccc4c(N)n[nH]c34)=CC1=O)c1cc-2cc(OC)n1]

To a microwave vial was charged example 7 (2.4 mg, 3.85 μmol), n-BuOH (1 mL), and lastly hydrazine monohydrate (100 μL, 2.056 mmol). The vial was sealed with a septa and heated to 115° C. for 4 h. The reaction mixture was purified by reverse phase HPLC to give example 8 (0.99 mg, 31.6% yield) as a light yellow solid. ¹H NMR (500 MHz, METHANOL-d₄) δ 9.47 (s, 1H), 7.87 (d, J=8.3 Hz, 1H), 7.50-7.44 (m, 4H), 7.35-7.33 (m, 1H), 7.14 (d, J=1.1 Hz, 1H), 6.76 (d, J=1.4 Hz, 1H), 6.25 (s, 1H), 5.77 (dd, J=12.7, 5.0 Hz, 1H), 4.53 (br. s., 1H), 4.05-3.98 (m, 1H), 3.97 (s, 3H), 3.78 (s, 3H), 3.08-2.99 (m, 1H), 2.92-2.85 (m, 1H), 2.69 (d, J=3.9 Hz, 1H), 2.28-2.20 (m, 1H), 2.07-1.98 (m, 1H), 1.79 (t, J=12.2 Hz, 1H), 1.58-1.43 (m, 2H), 1.01 (d, J=7.2 Hz, 3H). MS (ESI) m/z: 635.1 (M+H)⁺. Analytical HPLC (method A): RT=7.4 min, purity=92%.

Example 9

Methyl N-[(10R,14S)-14-[4-(3-amino-6-cyano-1,2-benzoxazol-7-yl)-6-oxo-1,2,3,6-tetrahydropyridin-1-yl]-17-methoxy-10-methyl-9-oxo-8,16-diazatricyclo[13.3.1.0²,⁷]nonadeca-1(18),2,4,6,15(19),16-hexaen-5-yl]carbamate, TFA Salt

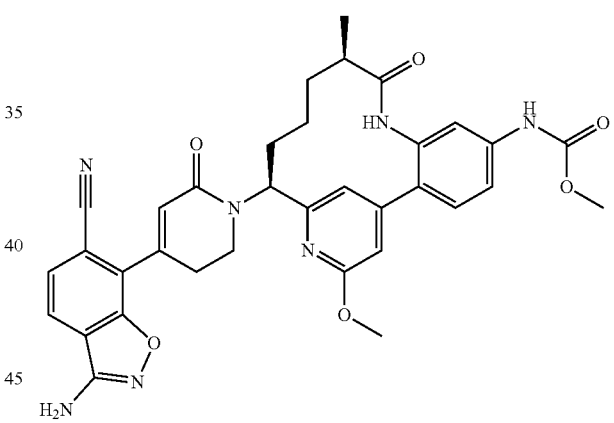

To a solution of N-hydroxyacetamide (4.85 mg, 0.065 mmol) in DMF (1 mL) was added water (0.2 mL), K₂CO₃ (17.85 mg, 0.129 mmol) and the reaction was stirred for 15 min at rt. This solution was added to solid example 7 (13.4 mg, 0.022 mmol) and the reaction mixture was stirred at rt overnight. The reaction mixture was purified by reverse phase HPLC to give example 9 (1.97 mg, 12.21% yield) as a colorless solid. ¹H NMR (500 MHz, METHANOL-d₄) δ 7.95 (d, J=8.3 Hz, 1H), 7.70-7.67 (m, 1H), 7.51-7.43 (m, 3H), 7.16 (d, J=1.1 Hz, 1H), 6.77 (d, J=1.4 Hz, 1H), 6.42-6.39 (m, 1H), 5.73 (dd, J=12.4, 5.0 Hz, 1H), 4.46 (br. s, 1H), 4.01-3.93 (m, 5H), 3.78 (s, 3H), 3.11-3.00 (m, 1H), 2.96 (dt, J=17.2, 5.8 Hz, 1H), 2.69 (br. s, 1H), 2.27-2.18 (m, 1H), 2.07-1.98 (m, 1H), 1.84-1.75 (m, 1H), 1.59-1.45 (m, 2H), 1.01 (d, J=6.9 Hz, 3H). MS (ESI) m/z: 636.0 (M+H)⁺. Analytical HPLC (method A): RT=7.8 min.

Example 10

Methyl N-[(10R,14S)-14-[4-(4-chloro-3-fluoropyridin-2-yl)-6-oxo-1,2,3,6-tetrahydropyridin-1-yl]-10-methyl-9-oxo-8,16-diazatricyclo[13.3.1.0²,⁷]nonadeca-1(18),2,4,6,15(19), 16-hexaen-5-yl]carbamate, TFA Salt

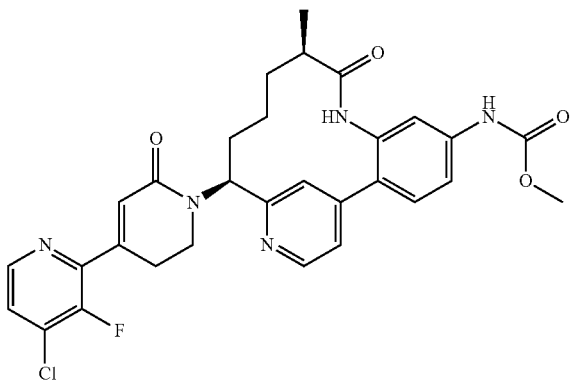 [SMILES: COC(=O)Nc1ccc2c(c1)NC(=O)[C@H](C)CCC[C@H](N1CCC(c3nccc(Cl)c3F)=CC1=O)c1cc-2ccn1]

Example 10 was prepared using a procedure analogous to example 5 except that 5M was replaced with 1J. ¹H NMR (500 MHz, CDCl₃) δ 8.76 (d, J=6.1 Hz, 1H), 8.40 (d, J=5.2 Hz, 1H), 8.13 (d, J=1.4 Hz, 1H), 7.90 (dd, J=6.1, 1.9 Hz, 1H), 7.66 (d, J=8.5 Hz, 1H), 7.62-7.53 (m, 3H), 6.63 (d, J=0.8 Hz, 1H), 5.38 (dd, J=12.5, 4.8 Hz, 1H), 3.82-3.75 (m, 1H), 3.77 (s, 1H), 3.75-3.67 (m, 1H), 3.11-2.96 (m, 2H), 2.65 (td, J=7.2, 2.2 Hz, 1H), 2.38-2.27 (m, 1H), 2.14-2.03 (m, 1H), 1.92 (qd, J=8.9, 5.5 Hz, 1H), 1.69-1.57 (m, 1H), 1.41-1.28 (m, 1H), 1.10-1.02 (m, 3H), 0.98 (d, J=7.4 Hz, 1H). MS (ESI) m/z: 577.9 (M+H)⁺. Analytical HPLC (method A): RT=4.0 min, purity=99%.

Example 11

Methyl N-[(10R,14S)-14-[4-(3-chloro-2,6-difluorophenyl)-6-oxo-1,6-dihydropyridazin-1-yl]-10-methyl-9-oxo-8,16-diazatricyclo[13.3.1.0²,⁷]nonadeca-1(19),2(7),3,5,15,17-hexaen-5-yl]carbamate, TFA Salt

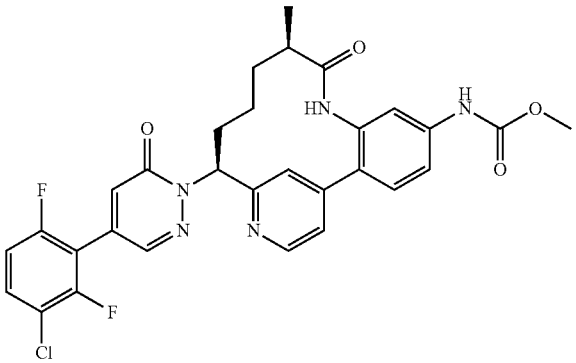 [SMILES: COC(=O)Nc1ccc2c(c1)NC(=O)[C@H](C)CCC[C@H](n1ncc(-c3c(F)ccc(Cl)c3F)cc1=O)c1cc-2ccn1]

11A. Methyl N-[(10R,14S)-14-amino-10-methyl-9-oxo-8,16-diazatricyclo[13.3.1.0²,⁷]nonadeca-1(19),2(7),3,5,15,17-hexaen-5-yl]carbamate: Compound 1J (Alternative, 2HCl) (0.100 g, 0.227 mmol) was dissolved in methanol (1 mL) to give a clear, pale green solution. The solution was added to a pre-rinsed Agilent StratoSpheres SPE PL-HCO₃ MP Resin cartridge. Gravity filtration, eluting with methanol, gave a clear, slightly pink filtrate. Concentration provided 11A (0.080 g, 84%) as a pink solid.

11B. Methyl N-[(10R,14S)-14-({[(tert-butoxy)carbonyl]amino}amino)-10-methyl-9-oxo-8,16-diazatricyclo[13.3.1.0²,⁷]nonadeca-1(19),2(7),3,5,15,17-hexaen-5-yl]carbamate: A modified procedure described by Vidal (Chem. Eur. J., 1997, 3(10), 1691) was used. To a cooled (0° C.) pink suspension of 11A (0.060 g, 0.163 mmol) in dichloromethane (1.30 mL) was added dropwise a clear, colorless solution of tert-butyl 3-(4-cyanophenyl)-1,2-oxaziridine-2-carboxylate (0.050 g, 0.204 mmol) in dichloromethane (0.651 ml). The resulting suspension was allowed to warm to rt and stir overnight. After 24 h, the majority of the solid went into solution and the solution had become a yellow color. The reaction was concentrated. Purification by normal phase chromatography gave 11B (0.033 g, 42%) as a pale yellow solid. MS (ESI) m/z: 484.2 (M+H)⁺. ¹H NMR (500 MHz, CD₃OD) δ 8.58 (d, J=5.0 Hz, 1H), 7.57 (s, 1H), 7.51-7.46 (m, 3H), 7.35 (dd, J=5.0, 1.7 Hz, 1H), 4.29 (dd, J=8.5, 5.2 Hz, 1H), 3.78 (s, 3H), 2.57-2.48 (m, 1H), 1.92-1.80 (m, 1H), 1.73-1.59 (m, 3H), 1.41 (s, 9H), 1.23-1.11 (m, 1H), 1.02 (d, J=6.9 Hz, 3H), 0.79-0.65 (m, 1H).

11C. Methyl N-[(10R,14S)-14-hydrazinyl-10-methyl-9-oxo-8,16-diazatricyclo[13.3.1.0²,⁷]nonadeca-1(19),2(7),3,5,15,17-hexaen-5-yl]carbamate, 2HCl: A clear, yellow solution of 11B (0.033 g, 0.068 mmol) in 4 M HCl in dioxane (2.0 mL, 8.00 mmol) was stirred at rt. Overtime a precipitate formed. After 1h, the reaction was concentrated to give a yellow solid. The solid was dissolved in methanol and concentrated. This was repeated twice to give 11C (0.031 g, 84%) as a yellow solid. This was carried onto the next step without further purification. MS (ESI) m/z: 384.2 (M+H)⁺.

Example 11. A clear yellow solution of 11C (0.031 g, 0.068 mmol) and Intermediate 1I (0.017 g, 0.068 mmol) in MeOH (0.679 ml) was microwaved at 150° C. for 30 min. The resulting reaction mixture was brown with a precipitate. The reaction mixture was diluted with DMF (0.7 mL) and a two drops of TFA were added to give a solution. Purification by reverse phase chromatography gave example 11 (0.0059 g, 12%) as a yellow, granular solid. ¹H NMR (500 MHz, CD₃OD) δ 9.63 (s, 1H), 8.68 (d, J=5.8 Hz, 1H), 8.18-8.12 (m, 2H), 7.79 (dd, J=5.8, 1.7 Hz, 1H), 7.71-7.65 (m, 1H), 7.61 (d, J=8.5 Hz, 1H), 7.57 (d, J=1.9 Hz, 1H), 7.54-7.50 (m, 1H), 7.25-7.17 (m, 2H), 6.22 (dd, J=12.0, 5.1 Hz, 1H), 3.77 (s, 3H), 2.75-2.67 (m, 1H), 2.59-2.49 (m, 1H), 2.25-2.15 (m, 1H), 2.01-1.92 (m, 1H), 1.70-1.61 (m, 1H), 1.55-1.46 (m, 1H), 1.02 (d, J=6.9 Hz, 3H), 0.86-0.75 (m, 1H). MS (ESI) m/z: 594.2 (M+H)⁺. Analytical HPLC (method A): RT=5.6 min, purity=98%.

Example 12

(10R,14S)-5-Amino-14-[4-(3-chloro-2,6-difluorophenyl)-6-oxo-1,2,3,6-tetrahydropyridin-1-yl]-10-methyl-8,16-diazatricyclo[13.3.1.0$^{2,7}$]nonadeca-1(19),2,4,6,15,17-hexaen-9-one

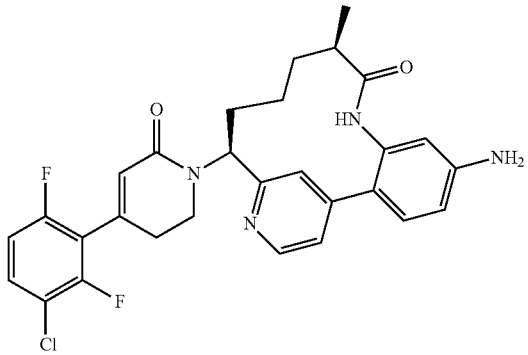 [SMILES: C[C@@H]1CCC[C@H](N2CCC(c3c(F)ccc(Cl)c3F)=CC2=O)c2cc(ccn2)-c2ccc(N)cc2NC1=O]

12A: Methyl N-[(10R,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate, TFA Salt 12A was prepared using a procedure analogous to example 1 except that intermediate 3 was replaced with intermediate 1. $^1$H NMR (500 MHz, DMSO-d$_6$) δ 9.89 (s, 1H), 9.70 (s, 1H), 8.61 (d, J=5.0 Hz, 1H), 7.68 (m, 1H), 7.54-7.45 (m, 3H), 7.37 (s, 1H), 7.33-7.22 (m, 2H), 6.05 (s, 1H), 5.60 (dd, J=12.5, 4.5 Hz, 1H), 3.97 (br. s., 1H), 3.75-3.64 (m, 4H), 2.67-2.54 (m, 3H), 2.11-2.00 (m, 1H), 1.92 (br. s., 1H), 1.73-1.61 (m, 1H), 1.50-1.38 (m, 1H), 1.31-1.16 (m, 1H), 0.88 (d, J=6.9 Hz, 3H), 0.54 (br. s., 1H). MS (ESI) m/z: 595.0 (M+H)$^+$. Analytical HPLC (method A): RT=7.3 min.

Example 12

To a solution of 12A (270 mg, 0.454 mmol) in CH$_2$Cl$_2$ (15 mL) was added iodotrimethylsilane (908 mg, 4.54 mmol). The reaction was sealed and heated at 50° C. over night before cooling down to room temperature. The reaction mixture was diluted with 30 ml DCM, washed with 10% sodium thiosulfate aq solution 3 times, conc. NaHCO$_3$ aq. DCM phase was further washed with brine, dried over MgSO$_4$, concentrated under vacuum to yield crude solid product, which was purified by flash chromatography to give example 12 (215 mg, 88%) as white solid. $^1$H NMR (500 MHz, CHLOROFORM-d) δ 8.62 (d, J=5.0 Hz, 1H), 7.46 (s, 1H), 7.36-7.29 (m, 1H), 7.18 (dd, J=5.0, 1.7 Hz, 1H), 7.07-7.01 (m, 1H), 6.89 (m, 1H), 6.66 (dd, J=8.3, 2.5 Hz, 1H), 6.60 (d, J=2.5 Hz, 1H), 6.17 (s, 1H), 5.78 (dd, J=12.8, 4.3 Hz, 1H), 4.07-3.97 (m, 1H), 3.84 (br. s., 2H), 3.69 (m, 1H), 2.75-2.64 (m, 1H), 2.62-2.52 (m, 1H), 2.48-2.38 (m, 1H), 2.15-2.06 (m, 1H), 1.94-1.78 (m, 2H), 1.46 (m, 1H), 1.37-1.21 (m, 3H), 1.06 (d, J=6.9 Hz, 3H), 1.01 (br. s., 1H). MS (ESI) m/z: 537.2 (M+H)$^+$. Analytical HPLC (method A): RT=5.9 min, purity=99%.

Example 13

(10R,14S)-14-[4-(3-Chloro-2,6-difluorophenyl)-6-oxo-1,2,3,6-tetrahydropyridin-1-yl]-10-methyl-8,16-diazatricyclo[13.3.1.0$^{2,7}$]nonadeca-1(19),2,4,6,15,17-hexaen-9-one

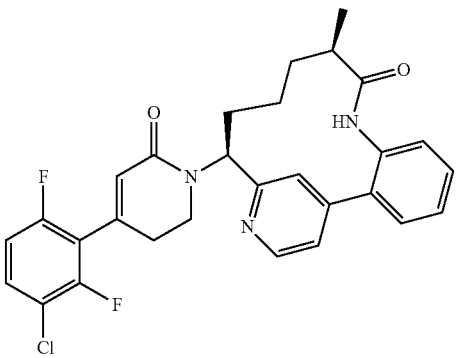 [SMILES: C[C@@H]1CCC[C@H](N2CCC(c3c(F)ccc(Cl)c3F)=CC2=O)c2cc(ccn2)-c2ccccc2NC1=O]

To example 12 (17.6 mg, 0.033 mmol) in a 2-dram vial was added H$_3$PO$_4$ (85%) (460 μl). Heated and sonicated to dissolve. The reaction was cooled to 0° C., sodium nitrite (13.57 mg, 0.197 mmol) in water (23.00 μl) was added dropwise. An ice cold solution of H$_3$PO$_2$ (50% aq.) (172 μl) was added and the vial was taken to ambient temperature and stirred overnight. Ice water was added and poured into a separatory funnel with DCM, sat. NaHCO$_3$ was added carefully to basify the mixture. The resulting solution was extracted 4× with DCM and the combined DCM layers were washed with brine, dried over MgSO$_4$, filtered and concentrated. Purification by reverse phase HPLC afforded example 13 as an off-white solid (13 mg, 63%). $^1$H NMR (500 MHz, CD$_3$OD) δ 8.81 (d, J=5.9 Hz, 1H), 8.12 (d, J=1.5 Hz, 1H), 7.90 (dd, J=5.9, 1.8 Hz, 1H), 7.72 (dd, J=7.7, 1.5 Hz, 1H), 7.64-7.58 (m, 1H), 7.57-7.51 (m, 2H), 7.35 (dd, J=7.9, 1.1 Hz, 1H), 7.09 (td, J=9.3, 1.9 Hz, 1H), 6.10 (s, 1H), 5.40 (dd, J=12.3, 4.8 Hz, 1H), 3.84-3.68 (m, 2H), 2.92-2.80 (m, 1H), 2.79-2.69 (m, 1H), 2.68-2.58 (m, 1H), 2.31 (tdd, J=12.8, 6.3, 3.6 Hz, 1H), 2.14-2.00 (m, 1H), 1.96-1.84 (m, 1H), 1.68-1.51 (m, 1H), 1.39-1.26 (m, 1H), 1.05 (d, J=7.0 Hz, 3H). MS (ESI) m/z: 522.3 (M+H)$^+$. Analytical HPLC (method A): RT=7.2 min, purity=99%.

Example 14

(1R,14S)-14-[4-(3-Chloro-2,6-difluorophenyl)-6-oxo-1,2,3,6-tetrahydropyridin-1-yl]-5-fluoro-10-methyl-8,16-diazatricyclo[13.3.1.0$^{2,7}$]nonadeca-1(19),2,4,6,15,17-hexaen-9-one, TFA Salt

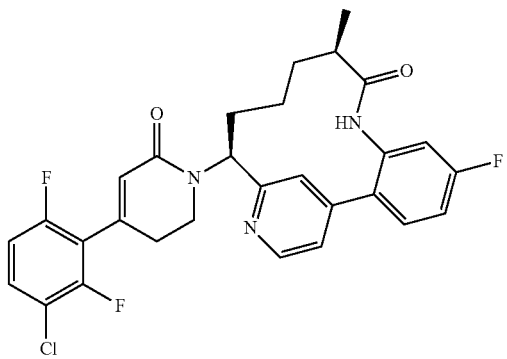 [SMILES: C[C@@H]1CCC[C@H](N2CCC(c3c(F)ccc(Cl)c3F)=CC2=O)c2cc(ccn2)-c2ccc(F)cc2NC1=O]

Example 12 (25 mg, 0.047 mmol) in a 2 dram vial was added nitrosonium tetrafluoroborate (5.98 mg, 0.051 mmol) in 1 ml DCM. After 5 min, more nitrosonium tetrafluoroborate (5.98 mg, 0.051 mmol) was added. The reaction was transferred into a microwavable tube, sealed and microwaved at 120° C. for 30 mins before cooling down to rt. The reaction mixture was concentrated under vacuum. The resulting residue was dissolved in MeOH and purified by reverse phase HPLC. Early eluting fraction yielded example 14 as a pale yellow solid (4.32 mg, 14%). $^1$H NMR (500 MHz, METHANOL-$d_4$) δ 8.79 (d, J=5.8 Hz, 1H), 8.00 (s, 1H), 7.81 (d, J=5.5 Hz, 1H), 7.76 (dd, J=8.8, 6.1 Hz, 1H), 7.56 (m, 1H), 7.30 (m, 1H), 7.18-7.08 (m, 2H), 6.12 (s, 1H), 5.46 (dd, J=12.5, 4.8 Hz, 1H), 3.88 (m, 1H), 3.77 (m, 1H), 2.90-2.81 (m, 1H), 2.79-2.71 (m, 1H), 2.64 (m, 1H), 2.34-2.24 (m, 1H), 2.11-2.00 (m, 1H), 1.97-1.87 (m, 1H), 1.61 (m, 1H), 1.42-1.31 (m, 1H), 1.05 (d, J=6.9 Hz, 2H), 0.98-0.84 (m, 1H). MS (ESI) m/z: 540.2 (M+H)$^+$. Analytical HPLC (method A): RT=7.6 min, purity=98%.

Example 15

(10R,14S)-5-Chloro-14-[4-(3-chloro-2,6-difluorophenyl)-6-oxo-1,2,3,6-tetrahydropyridin-1-yl]-10-methyl-8,16-diazatricyclo[13.3.1.0$^{2,7}$]nonadeca-1(19),2,4,6,15,17-hexaen-9-one, TFA Salt

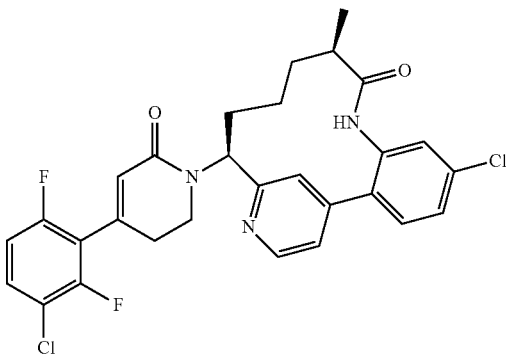 [SMILES: C[C@@H]1CCC[C@H](N2CCC(c3c(F)ccc(Cl)c3F)=CC2=O)c2cc(ccn2)-c2ccc(Cl)cc2NC1=O]

Late eluting fraction from example 14 yielded example 15 as a pale yellow solid (14.8 mg, 46%). $^1$H NMR (500 MHz, METHANOL-$d_4$) δ 8.80 (d, J=5.8 Hz, 1H), 8.03 (d, J=1.4 Hz, 1H), 7.83 (dd, J=5.8, 1.7 Hz, 1H), 7.70 (d, J=8.3 Hz, 1H), 7.58-7.50 (m, 2H), 7.39 (d, J=1.9 Hz, 1H), 7.10 (m, 1H), 6.10 (s, 1H), 5.43 (dd, J=12.4, 5.0 Hz, 1H), 3.92-3.82 (m, 1H), 3.75 (m, 1H), 2.91-2.81 (m, 1H), 2.78-2.69 (m, 1H), 2.63 (m, 1H), 2.29 (m, 1H), 2.11-2.00 (m, 1H), 1.95-1.85 (m, 1H), 1.65-1.54 (m, 1H), 1.41-1.27 (m, 1H), 1.03 (d, J=6.9 Hz, 3H), 0.90 (m, 1H). MS (ESI) m/z: 556.3 (M+H)$^+$. Analytical HPLC (method A): RT=8.3 min, purity=96%.

Example 16

(10R,14S)-14-[4-(3-Chloro-2,6-difluorophenyl)-6-oxo-1,2,3,6-tetrahydropyridin-1-yl]-10-methyl-5-[(pyrimidin-2-yl)amino]-8,16-diazatricyclo[13.3.1.0$^{2,7}$]nonadeca-1(19),2(7),3,5,15,17-hexaen-9-one, 2 TFA Salt

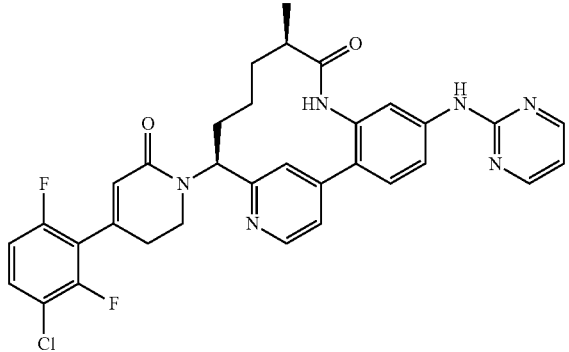

A solution of example 12 (0.016 g, 0.030 mmol), 2-chloropyrimidine (10.24 mg, 0.089 mmol), and TFA (4.59 µl, 0.060 mmol) in EtOH (1 mL) was microwaved at 150° C. for 30 min. Additional 2-chloropyrimidine (10.24 mg, 0.089 mmol) was added and the reaction was microwaved at 150° C. for 1 h, and then cooled to rt. Purification by reverse phase HPLC afforded Example 16 (0.013 g, 49.2% yield) as a yellow solid. $^1$H NMR (500 MHz, CD$_3$OD) δ 8.75 (d, J=6.1 Hz, 1H), 8.51 (d, J=4.7 Hz, 2H), 8.18 (d, J=1.4 Hz, 1H), 7.95-7.91 (m, 2H), 7.86 (dd, J=8.5, 2.2 Hz, 1H), 7.67 (d, J=8.5 Hz, 1H), 7.57-7.50 (m, 1H), 7.10 (td, J=9.2, 1.7 Hz, 1H), 6.90 (t, J=4.8 Hz, 1H), 6.11 (s, 1H), 5.36 (dd, J=12.4, 5.0 Hz, 1H), 3.82-3.69 (m, 2H), 2.94-2.84 (m, 1H), 2.79-2.64 (m, 2H), 2.37-2.28 (m, 1H), 2.15-2.05 (m, 1H), 1.99-1.90 (m, 1H), 1.69-1.60 (m, 1H), 1.42-1.32 (m, 1H), 1.07 (d, J=6.9 Hz, 3H), 1.03-0.91 (m, 1H) ppm. MS (ESI) m/z: 615.3 (M+H)$^+$. Analytical HPLC (method A): RT=6.8 min, purity=95%.

Example 17

(10R,14S)-14-[4-(3-chloro-2,6-difluorophenyl)-6-oxo-1,2,3,6-tetrahydropyridin-1-yl]-5-methoxy-10-methyl-8,16-diazatricyclo[13.3.1.0$^{2,7}$]nonadeca-1(19),2,4,6,15,17-hexaen-9-one, TFA Salt

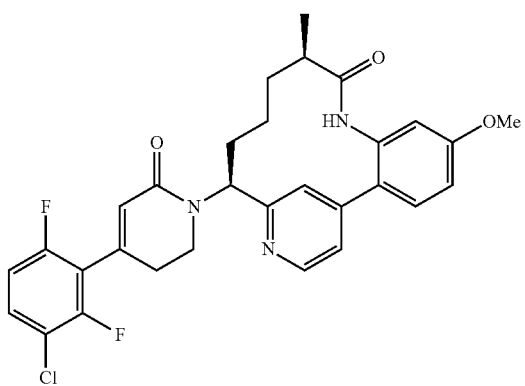 [SMILES: COc1ccc2c(c1)NC(=O)[C@H](C)CCC[C@H](N1CCC(c3c(F)ccc(Cl)c3F)=CC1=O)c1cc-2ccn1]

Example 17 was prepared using a procedure analogous to example 1 except that intermediate 14 was replaced with 5-methoxy-2-(4,4,5,5-tetramethyl-1,3,2-dioxaborolan-2-yl) aniline. $^1$H NMR (500 MHz, METHANOL-$d_4$) δ 8.74 (d, J=5.8 Hz, 1H), 8.07 (s, 1H), 7.85 (d, J=6.1 Hz, 1H), 7.67 (d, J=8.5 Hz, 1H), 7.54 (td, J=8.5, 5.9 Hz, 1H), 7.17-6.99 (m, 2H), 6.89 (d, J=1.9 Hz, 1H), 6.15-6.01 (m, 1H), 5.40 (dd, J=12.4, 4.7 Hz, 1H), 3.90 (s, 4H), 3.82-3.65 (m, 2H), 2.94-2.69 (m, 3H), 2.65 (d, J=1.1 Hz, 3H), 2.30 (br. s., 1H), 2.17-2.01 (m, 1H), 1.92 (dd, J=8.8, 5.5 Hz, 1H), 1.72-1.55 (m, 1H), 1.32 (d, J=6.9 Hz, 1H), 1.06 (d, J=6.9 Hz, 3H), 1.02-0.88 (m, 1H).

MS (ESI) m/z: 552.2 (M+H)$^+$. Analytical HPLC (method A): RT=6.0 min, purity >95%.

Example 18

(10R,14S)-14-[4-(3-Chloro-2,6-difluorophenyl)-6-oxo-1,2,3,6-tetrahydropyridin-1-yl]-5-hydroxy-10-methyl-8,16-diazatricyclo[13.3.1.0$^{2,7}$]nonadeca-1 (19),2,4,6,15,17-hexaen-9-one, TFA Salt

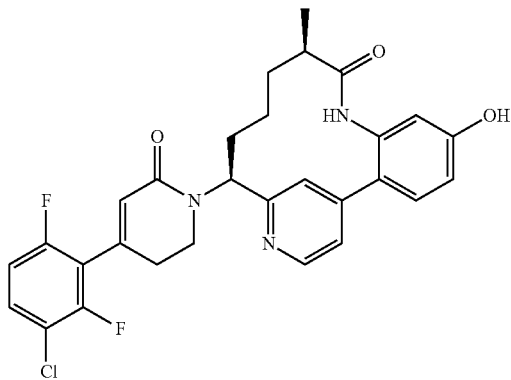 [SMILES: C[C@@H]1CCC[C@H](N2CCC(c3c(F)ccc(Cl)c3F)=CC2=O)c2cc(ccn2)-c2ccc(O)cc2NC1=O]

To a solution of example 17 (12 mg, 0.022 mmol) in DCM (1 mL) was added BBr$_3$ (0.022 mL, 0.022 mmol) in a portion at 0° C. and the resulting solution was stirred for 12h at ambient temperature. The reaction was quenched by adding MeOH (3 mL). The resulting solution was concentrated in vacuo, yielding an oil, which was purified by reverse phase HPLC to provide example 18 (7.8 mg, 0.011 mmol, 52.3% yield). $^1$H NMR (500 MHz, METHANOL-$d_4$) δ 8.72 (d, J=6.1 Hz, 1H), 8.08 (s, 1H), 7.93-7.82 (m, 1H), 7.58 (d, J=8.5 Hz, 1H), 7.54 (d, J=5.5 Hz, 1H), 7.10 (t, J=8.7 Hz, 1H), 6.94 (dd, J=8.5, 2.2 Hz, 1H), 6.76 (d, J=2.2 Hz, 1H), 6.11 (s, 1H), 5.39 (dd, J=12.2, 4.8 Hz, 1H), 3.80-3.68 (m, 2H), 2.91-2.69 (m, 2H), 2.69-2.56 (m, 3H), 2.35-2.21 (m, 1H), 2.08 (dd, J=11.3, 4.7 Hz, 1H), 1.92 (dd, J=8.7, 5.6 Hz, 1H), 1.63 (dd, J=14.2, 6.2 Hz, 1H), 1.31 (br. s., 1H), 1.06 (d, J=6.9 Hz, 3H), 1.03 (m, 1H). MS (ESI) m/z: 538.1 (M+H)$^+$. Analytical HPLC (method A): RT=5.3 min, purity >95%.

Example 19

(10R,14S)-4-Chloro-14-[4-(3-chloro-2,6-difluorophenyl)-6-oxo-1,2,3,6-tetrahydropyridin-1-yl]-5-hydroxy-10-methyl-8,16-diazatricyclo[13.3.1.0$^{2,7}$] nonadeca-1(19),2,4,6,15,17-hexaen-9-one, TFA Salt

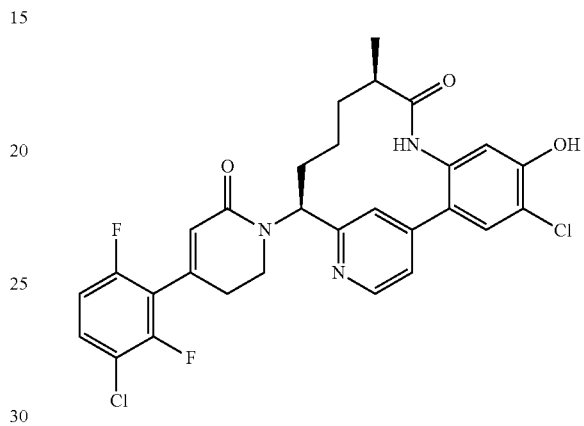

19A

To a solution of example 17 (6.5 mg, 8.33 µmol) in acetonitrile (1 mL) was added sulfuryl chloride (0.675 µl, 8.33 µmol) in a portion and the resulting solution was stirred for 1h at rt. The reaction was quenched by adding MeOH (1 mL). The resulting solution was purified by reverse phase HPLC to provide 19A (3.9 mg, 5.57 µmol, 66.8% yield). MS (ESI) m/z: 586.2 (M+H)$^+$.

Example 19

To a solution of 19A (4 mg, 6.82 µmol) in DCM (1 mL) was added BBr$_3$ (6.82 µl, 6.82 µmol) in a portion at 0° C. and the resulting solution was stirred for 12h at ambient temperature. The reaction was quenched by adding MeOH (3 mL). The resulting solution was concentrated in vacuo, yielding an oil, which was purified by reverse phase HPLC to provide example 19 (1.26 mg, 1.799 µmol, 26.4% yield). $^1$H NMR (400 MHz, METHANOL-$d_4$) δ 8.72 (d, J=5.9 Hz, 1H), 7.99-7.88 (m, 1H), 7.78-7.65 (m, 2H), 7.54 (td, J=8.7, 5.5 Hz, 1H), 7.16-7.04 (m, 1H), 6.88 (s, 1H), 7.02 (s, 1H), 6.11 (s, 1H), 5.39 (dd, J=12.2, 4.8 Hz, 1H), 3.80-3.68 (m, 2H), 2.91-2.69 (m, 2H), 2.69-2.56 (m, 3H), 2.35-2.21 (m, 1H), 2.08 (dd, J=11.3, 4.7 Hz, 1H), 1.92 (dd, J=8.7, 5.6 Hz, 1H), 1.63 (dd, J=14.2, 6.2 Hz, 1H), 1.31 (br. s., 1H), 1.06 (d, J=6.9 Hz, 3H), 1.03 (m, 1H). MS (ESI) m/z: 572.1 (M+H)$^+$. Analytical HPLC (method A): RT=6.0 min, purity=98%.

Example 20

(10R,14S)-4,6-Dichloro-14-[4-(3-chloro-2,6-difluorophenyl)-6-oxo-1,2,3,6-tetrahydropyridin-1-yl]-5-hydroxy-10-methyl-8,16-diazatricyclo[13.3.1.0²,⁷]nonadeca-1(19),2,4,6,15,17-hexaen-9-one, TFA Salt

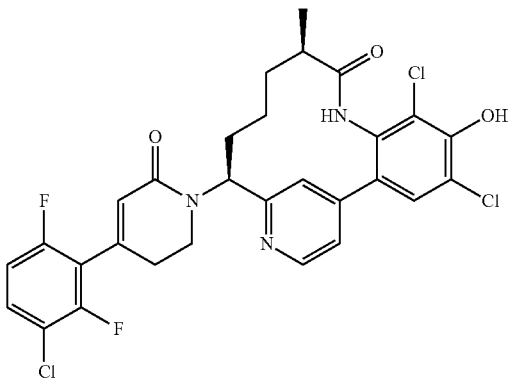 [SMILES: C[C@@H]1CCC[C@H](N2CCC(c3c(F)ccc(Cl)c3F)=CC2=O)c2cc(ccn2)-c2cc(Cl)c(O)c(Cl)c2NC1=O]

To a solution example 18 (8 mg, 0.012 mmol) in acetonitrile (1 mL) was added sulfuryl chloride (3.31 mg, 0.025 mmol) in a portion and the resulting solution was stirred for 1h at rt. The reaction was quenched by adding MeOH (1 mL). The resulting solution was purified by reverse phase HPLC to provide example 20 (2.22 mg, 3.02 μmol, 24.6% yield). $^1$H NMR (400 MHz, METHANOL-$d_4$) δ 8.71 (d, J=5.5 Hz, 1H), 7.86 (s, 1H), 7.71-7.61 (m, 2H), 7.53 (td, J=8.7, 5.5 Hz, 1H), 7.08 (td, J=9.2, 1.8 Hz, 1H), 6.11 (s, 1H), 5.53 (dd, J=12.5, 4.0 Hz, 1H), 3.78-3.58 (m, 2H), 2.76-2.52 (m, 4H), 2.22 (br. s., 1H), 2.08-1.81 (m, 2H), 1.60 (dd, J=14.9, 8.9 Hz, 1H), 1.12 (d, J=6.8 Hz, 4H). MS (ESI) m/z: 606.1 (M+H)⁺. Analytical HPLC (method A): RT=6.5 min, purity >98%.

Example 21

(10R,14S)-14-[4-(3-Chloro-2,6-difluorophenyl)-6-oxo-1,2,3,6-tetrahydropyridin-1-yl]-10-methyl-5-[(5-methyl-1,3,4-oxadiazol-2-yl)amino]-8,16-diazatricyclo[13.3.1.0²,⁷]nonadeca-1(19),2(7),3,5,15,17-hexaen-9-one, TFA Salt

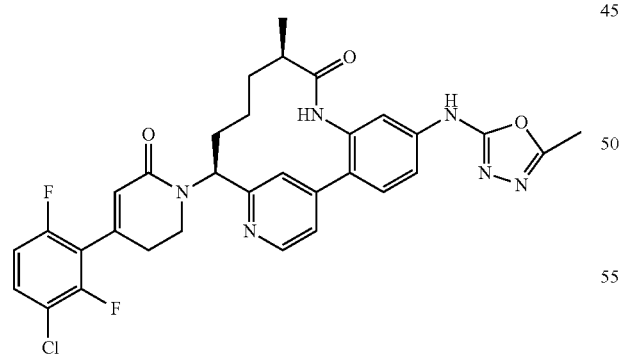

21A. (10R,14S)-14-[4-(3-Chloro-2,6-difluorophenyl)-6-oxo-1,2,3,6-tetrahydropyridin-1-yl]-5-isothiocyanato-10-methyl-8,16-diazatricyclo[13.3.1.0²,⁷]nonadeca-1(19),2,4,6,15,17-hexaen-9-one A solution of the example 12 (14 mg, 0.026 mmol) in DCM (1 mL) was stirred at 0° C. Then a solution of 1,1'-thiocarbonylbis(pyridin-2(1H)-one) (1.644 mg, 7.08 μmol) in dichloromethane (0.1 mL) was added dropwise. The reaction mixture was slowly allowed to rise to room temperature and stirring was continued for 1 h. The crude product mixture was absorbed on 0.5 g silica gel. Then solvent was removed in vacuo. The silica gel powder was loaded into a column equipped with a microfilter. Ethyl acetate was run through silica gel plug by gravity. Collected filtrate for 10 mL. Then solvent was removed in vacuo from filtrate to give a light yellow oily solid 21A (15 mg). MS (ESI) m/z: 579 (M+H)⁺.

21B. N-({[(10R,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0²,⁷]nonadeca-1(19),2(7),3,5,15,17-hexaen-5-yl]carbamothioyl}amino)acetamide A mixture of 25A (7 mg, 0.012 mmol) and acetohydrazide (0.896 mg, 0.012 mmol) in tetrahydrofuran (0.2 mL) was stirred at rt for 14 h under an argon atmosphere.

Solvent was removed in vacuo to give an oil (8 mg). MS (ESI) m/z: 653 (M+H)⁺.

Example 21

A mixture of 21B (8 mg, 0.012 mmol), EDC (9.39 mg, 0.049 mmol) and triethyl amine (10.24 μl, 0.073 mmol) in DMF (0.2 mL) was stirred at rt for 5 h under an argon atmosphere. The reaction was monitored by LCMS until completion. The crude reaction mixture was purified by reverse phase HPLC to give a pale yellow solid (3.2 mg). $^1$H NMR (500 MHz, ACETONITRILE-$d_3$) δ 8.57 (d, J=5.50 Hz, 1H), 8.44 (br. s., 1H), 8.20 (s, 1H), 7.69 (s, 1H), 7.52 (d, J=1.65 Hz, 1H), 7.37-7.49 (m, 4H), 6.97 (t, J=9.22 Hz, 1H), 5.98 (s, 1H), 5.27-5.36 (m, 1H), 3.87-3.95 (m, 1H), 3.61-3.69 (m, 1H), 2.46-2.70 (m, 6H), 1.90-2.00 (m, 2H), 1.69-1.80 (m, 3H), 1.38-1.48 (m, 1H), 1.24-1.32 (m, 1H), 0.84 (d, J=6.88 Hz, 3H), 0.47 (br. s., 1H). MS (ESI) m/z: 619.0 (M+H)⁺. Analytical HPLC (method A): RT=6.3 min, purity=99%.

Example 22

Methyl N-[(10R,14S)-14-[4-(3-chloro-2,6-difluorophenyl)-6-oxo-1,2,3,6-tetrahydropyridin-1-yl]-10-methyl-9,12-dioxo-8,16-diazatricyclo[13.3.1.0²,⁷]nonadeca-1(19),2,4,6,15,17-hexaen-5-yl]carbamate, TFA Salt

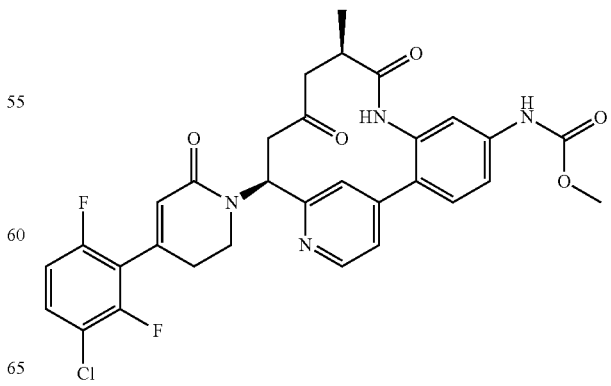

22A. tert-Butyl N-[(10R,14S)-11-hydroxy-5-[(methoxycarbonyl)amino]-10-methyl-9-oxo-8,16-diazatricyclo[13.3.1.0²,⁷]nonadeca-1(18),2,4,6,15(19),16-hexaen-14-yl]carbamate and 22B tert-Butyl N-[(10R,14S)-12-hydroxy-5-[(methoxycarbonyl)amino]-10-methyl-9-oxo-8,16-diazatricyclo[13.3.1.0²,⁷]nonadeca-1(18),2,4,6,15(19),16-hexaen-14-yl]carbamate (Mixture)

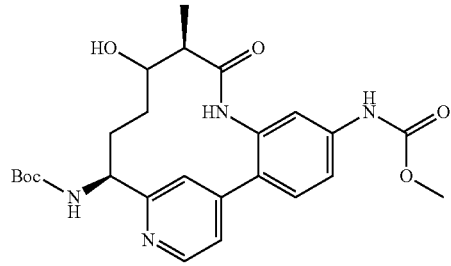

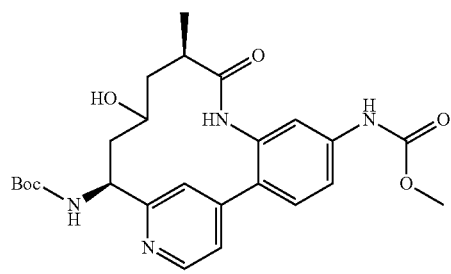

To a solution of tert-butyl N-[(10R,11E,14S)-5-[(methoxycarbonyl)amino]-10-methyl-9-oxo-8,16-diazatricyclo[13.3.1.0²,⁷]nonadeca-1(18),2,4,6,11,15(19), 16-heptaen-14-yl]carbamate (634 mg, 1.36 mmol) 1H in THF (13.6 mL) at 0° C. was added borane tetrahydrofuran complex (4.08 mL, 4.08 mmol) dropwise. The reaction was allowed to warm up to rt and stirred for 2.5 h. The reaction mixture was cooled to 0° C. and added sodium acetate (9.06 ml, 27.2 mmol), followed by hydrogen peroxide (4.16 mL, 40.8 mmol) dropwise. The reaction was warmed up to rt and stirred at for 8 h. The mixture was diluted with H₂O and extracted with EtOAc (2×). The combined organic layer was washed with brine, dried over MgSO₄, filtered, and concentrated. The residue was purified by silica gel chromatography (0-10% MeOH/DCM) to yield a mixture of two products 22A and 22B (323 mg, 49%) as a light grey solid. MS (ESI) m/z: 485.1 (M+H)⁺.

22C. tert-Butyl N-[(10R,14S)-5-[(methoxycarbonyl)amino]-10-methyl-9,11-dioxo-8,16-diazatricyclo[13.3.1.0²,⁷]nonadeca-1(18),2,4,6,15(19),16-hexaen-14-yl]carbamate and 22D tert-Butyl N-[(10R,14S)-5-[(methoxycarbonyl)amino]-10-methyl-9,12-dioxo-8,16-diazatricyclo[13.3.1.0²,⁷]nonadeca-1(18),2,4,6,15(19), 16-hexaen-14-yl]carbamate

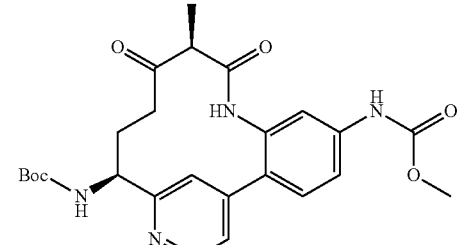

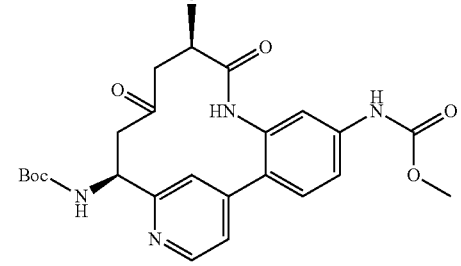

The mixture of 22A and 22B (116 mg, 0.239 mmol) in DCM (2.4 mL) was added Martin's reagent (132 mg, 0.311 mmol) at rt. The reaction was stirred at rt for 1.5 h. The mixture was diluted with DCM, washed with H₂O, brine, dried over MgSO₄, filtered, and concentrated. The residue was purified by silica gel chromatography (0-100% EtOAc/hexanes) to yield a 1:1 mixture of 22C and 22D (78 mg, 68%) as a white solid. MS (ESI) m/z: 483.1 (M+H)⁺.

22E. Methyl N-[(10R,14S)-14-amino-10-methyl-9,11-dioxo-8,16-diazatricyclo[13.3.1.0²,⁷]nonadeca-1(18),2,4,6,15(19), 16-hexaen-5-yl]carbamate and 22F Methyl N-[(10R,14S)-14-amino-10-methyl-9,12-dioxo-8,16-diazatricyclo[13.3.1.0²,⁷]nonadeca-1(18),2,4,6,15(19), 16-hexaen-5-yl]carbamate (Mixture)

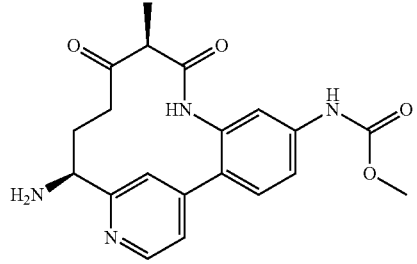

-continued

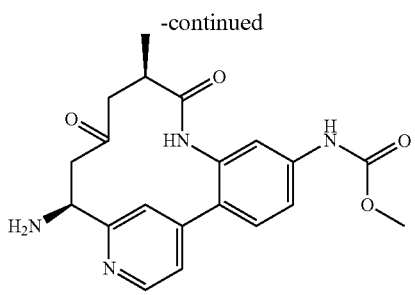

The mixture of 22C and 22D (78 mg, 0.162 mmol) was suspended in DCM (3 mL) and added TFA (0.623 mL, 8.08 mmol). The reaction became a clear light brownish solution and was stirred at rt for 1 h. The reaction was concentrated to yield a mixture of two regioisomers 22E and 22F (105 mg, 100%) as a yellow solid. MS (ESI) m/z: 383.1 (M+H)+.

22G. Methyl N-[(10R,14S)-14-{N-[3-(3-chloro-2,6-difluorophenyl)-3-oxopropyl]-2-(diethoxyphosphoryl)acetamido}-10-methyl-9,12-dioxo-8,16-diazatricyclo[13.3.1.0$^{2,7}$]nonadeca-1(18),2,4,6,15(19),16-hexaen-5-yl]carbamate and 22H. Methyl N-[(10R,14S)-14-{N-[3-(3-chloro-2,6-difluorophenyl)-3-oxopropyl]-2-(diethoxyphosphoryl)acetamido}-10-methyl-9,11-dioxo-8,16-diazatricyclo[13.3.1.0$^{2,7}$]nonadeca-1(18),2,4,6,15(19),16-hexaen-5-yl]carbamate

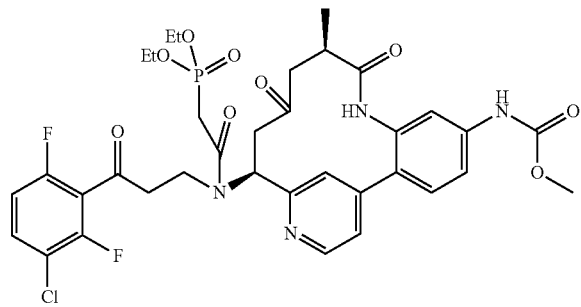

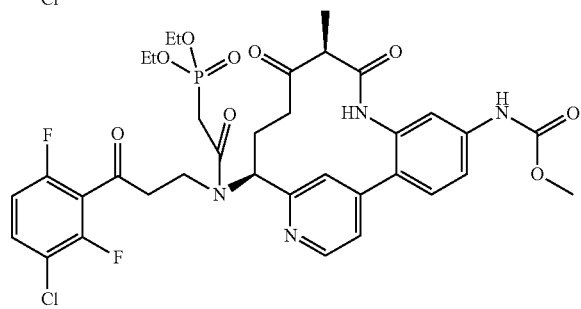

22G and 22H were prepared using a procedure analogous to 1K except that 1J was replaced with a 1:1 mixture of 22E and 22F. 22G was separated as a slower moving regioisomer on preparative HPLC. 22H was separated as a faster moving regioisomer on preparative HPLC MS (ESI) m/z: 763.0 (M+H)+.

Example 22

Example 22 was prepared using a procedure analogous to example 1 except that 1K was replaced with 22G. $^1$H NMR (500 MHz, CDCl$_3$) δ 8.78 (d, J=5.8 Hz, 1H), 7.82 (d, J=5.8 Hz, 1H), 7.62-7.69 (m, 3H), 7.53-7.61 (m, 2H), 7.13 (t, J=9.2 Hz, 1H), 6.14 (s, 1H), 6.09 (dd, J=12.1, 3.5 Hz, 1H), 3.90 (dd, J=18.1, 12.3 Hz, 1H), 3.80 (s, 3H), 3.64-3.73 (m, 1H), 3.42-3.51 (m, 1H), 2.99-3.29 (m, 3H), 2.71-2.81 (m, 2H), 2.36-2.45 (m, 1H), 1.32 (d, J=6.6 Hz, 3H). MS (ESI) m/z: 609.1 (M+H)+. Analytical HPLC (method B): RT=8.6 min, purity=98%.

Example 23

(14R)-14-[4-(3-Chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(18),2,4,6,15(19), 16-hexaene-5-carbonitrile, TFA Salt

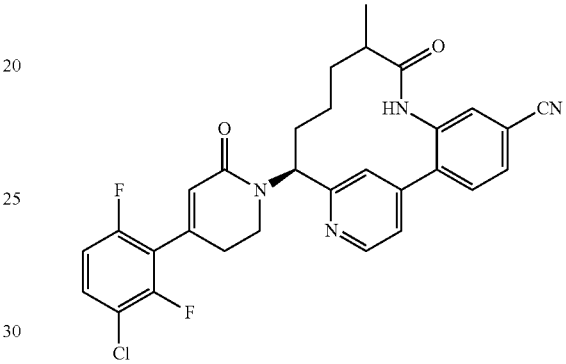

Example 23 was prepared by following the procedures described in Example 1. $^1$H NMR (500 MHz, METHANOL-d$_4$) δ 8.75 (d, J=5.2 Hz, 1H), 7.88-7.80 (m, 2H), 7.74-7.68 (m, 2H), 7.53 (dd, J=5.2, 1.7 Hz, 1H), 7.48 (td, J=8.7, 5.5 Hz, 1H), 7.05 (td, J=9.1, 1.9 Hz, 1H), 6.08 (br. s., 1H), 5.67 (dd, J=12.5, 4.3 Hz, 1H), 4.57 (d, J=16.0 Hz, 1H), 4.44-4.37 (m, 1H), 3.51-3.45 (m, 1H), 2.63 (br. s., 1H), 2.33-2.21 (m, 1H), 2.01-1.88 (m, 2H), 1.66-1.49 (m, 1H), 1.31 (br. s., 2H), 1.07-1.02 (m, 3H), 0.93 (br. s., 1H). MS (ESI) m/z: 547.1 (M+H)+. Analytical HPLC (method A): RT=8.3 min, purity=95%.

Example 24

Methyl N-[(14S)-14-[4-(3-chloro-2,6-difluorophenyl)-6-oxo-1,2,3,6-tetrahydropyridin-1-yl]-8-oxo-9,16-diazatricyclo[13.3.1.0$^{2,7}$]nonadeca-1(19),2(7),3,5,15,17-hexaen-5-yl]carbamate, TFA Salt

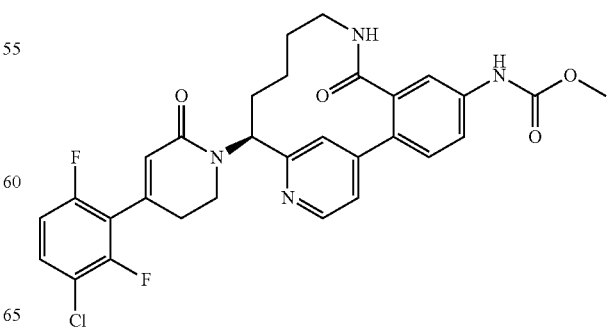

24A. (S)-(2-(1-((tert-Butoxycarbonyl)amino)but-3-en-1-yl)pyridin-4-yl)boronic acid, TFA salt To a solution of 5,5,5',5'-tetramethyl-2,2'-bi(1,3,2-dioxaborinane) (1.198 g, 5.30 mmol) and (S)-tert-butyl (1-(4-chloropyridin-2-yl)but-3-en-1-yl)carbamate (1.0 g, 3.54 mmol) in DMSO (10 mL) was added potassium acetate (1.041 g, 10.61 mmol) and $PdCl_2(dppf)$-$CH_2Cl_2$ adduct (0.289 g, 0.354 mmol). The reaction was purged with argon for 10 min. The reaction mixture was then sealed and stirred for 12 h at 85° C. The reaction mixture was cooled to rt and then it was diluted with EtOAc and washed with water. The aqueous layer was extracted with EtOAc. The organic layers were combined and was washed with brine, dried over sodium sulfate, filtered, and concentrated. Purification by reverse phase chromatography afforded the 24A (1.1 g, 77%) as a white solid. MS (ESI) m/z: 293.2 (M+H)$^+$. $^1$H NMR (500 MHz, MeOD) δ 8.54 (d, J=5.8 Hz, 1H), 8.11 (s, 1H), 8.02 (dd, J=5.8, 0.6 Hz, 1H), 5.79 (ddt, J=17.1, 10.2, 7.1 Hz, 1H), 5.11-5.03 (m, 2H), 4.86 (t, J=7.0 Hz, 1H), 2.69-2.55 (m, 2H), 1.40 (br. s., 9H) ppm.

24B. (S)-Methyl 2-(2-(1-((tert-butoxycarbonyl)amino)but-3-en-1-yl)pyridin-4-yl)-5-nitrobenzoate A solution of 24A (0.2 g, 0.492 mmol), methyl 2-bromo-5-nitrobenzoate (0.141 g, 0.542 mmol), $Cs_2CO_3$ (0.802 g, 2.462 mmol) in DME (8 mL) and water (1.600 mL) was purged under argon for 5 min, then tetrakis(triphenylphosphine)palladium(0) (0.057 g, 0.049 mmol) was added, and the reaction mixture was heated at 90° C. After 4 h, the reaction was cooled to rt. The reaction mixture was partitioned between water/brine and EtOAc and the layers were separated. The organic layer was washed with brine, dried over $Na_2SO_4$, filtered, and concentrated. Purification by normal phase chromatography afforded 24B (0.176 g, 84%) as a white solid. MS (ESI) m/z: 428.2 (M+H)$^+$.

24C. (S)-Methyl 2-(2-(1-((tert-butoxycarbonyl)amino)but-3-en-1-yl)pyridin-4-yl)-5-((methoxycarbonyl)amino)benzoate To the solution of 24B (0.33 g, 0.772 mmol) in MeOH (7.72 ml) was added ammonium chloride (0.413 g, 7.72 mmol) and zinc (0.505 g, 7.72 mmol). The reaction was stirred at 55° C. for 5 h. The reaction was cooled to rt, filtered, and the filtrate was concentrated. The residue was partitioned between EtOAc and sat. $NaHCO_3$ and the layers were separated. The organic layer was washed with water, brine, dried over $Na_2SO_4$, filtered, and concentrated to afford the aniline (0.317 g, 103%) as a yellow solid. MS (ESI) m/z: 398.2 (M+H)$^+$. To a cooled (−78° C.) clear solution of the aniline (0.317 g, 0.798 mmol) and pyridine (0.097 ml, 1.196 mmol) in DCM (7.98 ml) was added dropwise methyl chlorocarbonate (0.074 ml, 0.957 mmol). The reaction was stirred at −78° C. for 1 h, the reaction was quenched with sat. $NH_4Cl$ and the reaction was allowed to warm to RT. The reaction was diluted with DCM and water and the layers were separated. The aqueous layer was extracted with DCM (1×). The combined organic layers were washed with sat. $NaHCO_3$, brine, dried over $Na_2SO_4$, filtered and concentrated to give a brown foam. Purification by normal phase chromatography provided 24C (0.304 g, 84%) as a white solid. MS (ESI) m/z: 456.2 (M+H)$^+$.

24D. (S)-2-(2-(1-((tert-Butoxycarbonyl)amino)but-3-en-1-yl)pyridin-4-yl)-5-((methoxycarbonyl)amino)benzoic acid To the solution of 24C (0.304 g, 0.667 mmol) in MeOH (6.67 ml) was added 1N NaOH (2.67 ml, 2.67 mmol). The reaction was stirred at rt. After 48 h, the reaction was neutralized with 1N HCl and then it was concentrated to remove the MeOH. The residue was extracted with EtOAc (2×). The organic layers were combined and washed with brine, dried over $Na_2SO_4$, filtered, and concentrated to afford 24D (0.291 g, 99%) as a yellow solid. MS (ESI) m/z: 442.2 (M+H)$^+$.

24E. Methyl N-(4-{2-[(1S)-1-{[(tert-butoxy)carbonyl]amino}but-3-en-1-yl]pyridin-4-yl}-3-[(prop-2-en-1-yl)carbamoyl]phenyl)carbamate To a solution of 24D (0.06 g, 0.136 mmol), prop-2-en-1-amine (9.31 mg, 0.163 mmol), EDC (0.052 g, 0.272 mmol) and HOBT (0.042 g, 0.272 mmol) in DMF (1 mL) was added TEA (0.057 mL, 0.408 mmol). The reaction was stirred at rt for 18 h. The reaction was diluted with EtOAc, washed with water, brine, dried over $Na_2SO_4$, filtered, and concentrated. Purification by normal phase chromatography provided 24E (0.056 g, 86%) as a white solid. MS (ESI) m/z: 481.3 (M+H)$^+$.

24F. Methyl N-[(11E,14S)-14-{[(tert-butoxy)carbonyl]amino}-8-oxo-9,16-diazatricyclo[13.3.1.0$^{2,7}$]nonadeca-1(19),2(7),3,5,11,15,17-heptaen-5-yl]carbamate, TFA Salt To a RBF was added 24E (0.056 g, 0.117 mmol), pTsOH monohydrate (0.024 g, 0.128 mmol), and dichloromethane (9.71 ml). The flask was equipped with a reflux condensor and the clear yellow solution was degassed with argon for 30 min. The reaction was then warmed to reflux for 1 h. Then a solution of Grubbs II (0.020 g, 0.023 mmol) in DCM (1 mL) was added dropwise to the reaction mixture. After 3 h at reflux, the reaction was cooled to rt, washed with sat. $Na_2CO_3$, brine, dried over $MgSO_4$, filtered, and concentrated to give a brown solid. Purification by reverse phase chromatography gave 24F (0.026 g, 39.4%) as a white solid. MS (ESI) m/z: 453.2 (M+H)$^+$.

24G. Methyl N-[(14S)-14-{[(tert-butoxy)carbonyl]amino}-8-oxo-9,16-diazatricyclo[13.3.1.0$^{2,7}$]nonadeca-1(19),2(7),3,5,15,17-hexaen-5-yl]carbamate, TFA Salt Hydrogen was bubbled through the mixture of 24F (0.026 g, 0.046 mmol) and 10% palladium on carbon (4.88 mg, 4.59 μmol) in MeOH (2 mL) for 2 minutes, and then the reaction was stirred under a hydrogen atmosphere (balloon). After 48 h, the reaction was filtered through a pad of Celite, rinsing with MeOH. The filtrate was concentrated to afford 24G (0.027 g, 103%) as a white solid. MS (ESI) m/z: 455.2 (M+H)$^+$.

Example 24

Example 24 was prepared according to the procedures described in Example 1, by replacing 1I in step 1J with 24G and by replacing Intermediate 3 in step 1K with Intermediate 1. MS (ESI) m/z: 581.3 (M+H)$^+$. $^1$H NMR (500 MHz, CD$_3$OD) δ 8.73 (d, J=5.5 Hz, 1H), 7.90-7.84 (m, 2H), 7.77-7.70 (m, 3H), 7.54 (td, J=8.6, 5.6 Hz, 1H), 7.10 (t, J=9.2 Hz, 1H), 6.10 (s, 1H), 5.44 (dd, J=12.1, 4.1 Hz, 1H), 3.92 (dt, J=12.1, 6.1 Hz, 1H), 3.82-3.66 (m, 5H), 2.97-2.71 (m, 3H), 2.27-2.18 (m, 1H), 2.08-1.93 (m, 2H), 1.50-1.39

(m, 2H), 1.09-0.97 (m, 1H) ppm. Analytical HPLC (method A) RT=6.7 min, purity=100%.

Example 25

Methyl N-[(10R,14S)-14-{4-[3-chloro-2-fluoro-6-(trifluoromethyl)phenyl]-6-oxo-1,2,3,6-tetrahydropyridin-1-yl}-10-methyl-9-oxo-8,16-diazatricyclo[13.3.1.0$^{2,7}$]nonadeca-1(19),2,4,6,15,17-hexaen-5-yl]carbamate, TFA Salt

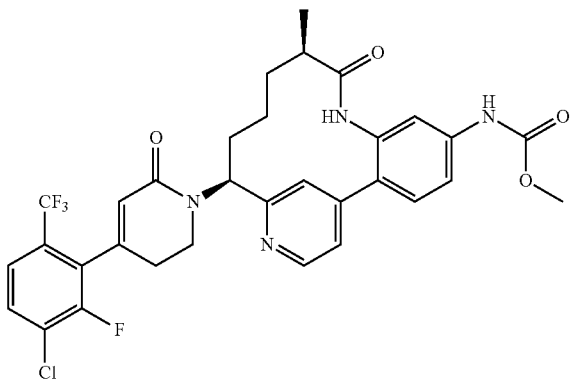 [SMILES: COC(=O)Nc1ccc2c(c1)NC(=O)[C@H](C)CCC[C@H](N1CCC(c3c(C(F)(F)F)ccc(Cl)c3F)=CC1=O)c1cc-2ccn1]

Example 25 was prepared by following the procedures described in Example 1. $^1$H NMR (500 MHz, CD$_3$OD) δ 8.63 (d, J=5.0 Hz, 1H), 7.68-7.77 (m, 1H), 7.59-7.64 (m, 2H), 7.46-7.58 (m, 3H), 7.36-7.42 (m, 1H), 5.93 (s, 1H), 5.66 (dd, J=12.4, 4.1 Hz, 1H), 3.83-3.96 (m, 1H), 3.69-3.81 (m, 4H), 2.51-2.69 (m, 3H), 2.12-2.22 (m, 1H), 1.83-1.99 (m, 2H), 1.50-1.60 (m, 1H), 1.24-1.34 (m, 2H), 1.05 (d, J=6.9 Hz, 3H). MS (ESI) m/z: 645.2 (M+H)$^+$. Analytical HPLC (method A): RT=7.2 min, purity=97%.

Example 26

Methyl N-[(10R,14S)-14-[4-(3-chloro-6-cyano-2-fluorophenyl)-6-oxo-1,2,3,6-tetrahydropyridin-1-yl]-17-methoxy-10-methyl-9-oxo-8,16-diazatricyclo[13.3.1.0$^{2,7}$]nonadeca-1(18),2,4,6,15(19),16-hexaen-5-yl]carbamate

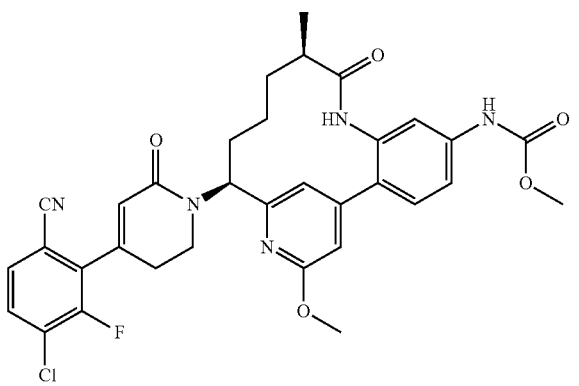 [SMILES: COC(=O)Nc1ccc2c(c1)NC(=O)[C@H](C)CCC[C@H](N1CCC(c3c(C#N)ccc(Cl)c3F)=CC1=O)c1cc-2cc(OC)n1]

Example 26 was prepared by following the procedures described in Example 3 by replacing 2A with 7A. $^1$H NMR (500 MHz, METHANOL-d$_4$) δ 7.75-7.66 (m, 2H), 7.51-7.44 (m, 3H), 7.16 (d, J=1.1 Hz, 1H), 6.78 (d, J=1.4 Hz, 1H), 6.20 (s, 1H), 5.70 (dd, J=12.7, 5.0 Hz, 1H), 4.47-4.37 (m, 1H), 3.96 (s, 3H), 3.95-3.90 (m, 1H), 3.78 (s, 3H), 2.91-2.82 (m, 1H), 2.81-2.73 (m, 1H), 2.72-2.65 (m, 1H), 2.25-2.15 (m, 1H), 2.05-1.97 (m, 1H), 1.83-1.74 (m, 1H), 1.58-1.41 (m, 2H), 1.01 (d, J=6.9 Hz, 3H), 0.74 (br. s., 1H). MS (ESI) m/z: 632.1 (M+H)$^+$. Analytical HPLC (method A): RT=9.9 min, purity=99%.

Example 27 tert-Butyl N-[(10R,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(18),2,4,6,15(19),16-hexaen-5-yl]carbamate, TFA Salt

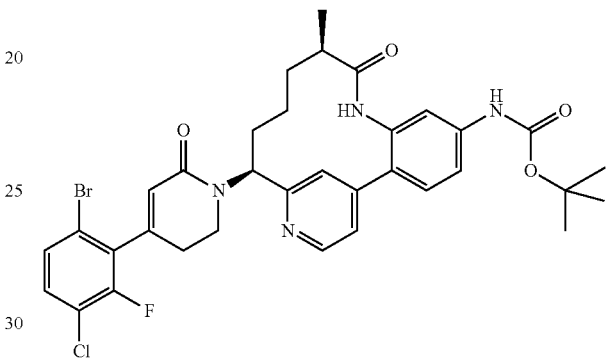

Example 27 was prepared by following the procedures described in Example 1. $^1$H NMR (500 MHz, METHANOL-d$_4$) δ 9.89-9.17 (m, 1H), 8.73-8.60 (m, 1H), 7.79-7.63 (m, 1H), 7.59-7.47 (m, 3H), 7.46-7.41 (m, 1H), 7.17-7.04 (m, 1H), 6.12 (s, 1H), 5.65 (dd, J=12.8, 4.3 Hz, 1H), 3.93-3.80 (m, 1H), 3.77-3.65 (m, 1H), 2.76-2.50 (m, 3H), 2.27-2.13 (m, 1H), 1.99-1.81 (m, 2H), 1.63-1.49 (m, 9H), 1.31-1.19 (m, 2H), 1.14-0.99 (m, 3H), 0.94-0.81 (m, 1H). MS (ESI) m/z: 602.3 (M+H)$^+$. Analytical HPLC (method A): RT=7.9 min, purity=97%

Example 28

(14S)-14-[4-(6-Bromo-3-chloro-2-fluorophenyl)-6-oxo-1,2,3,6-tetrahydropyridin-1-yl]-10-methyl-9-oxo-8,16-diazatricyclo[13.3.1.0$^{2,7}$]nonadeca-1(19),2(7),3,5,15,17-hexaene-5-carboxylic acid, TFA Salt

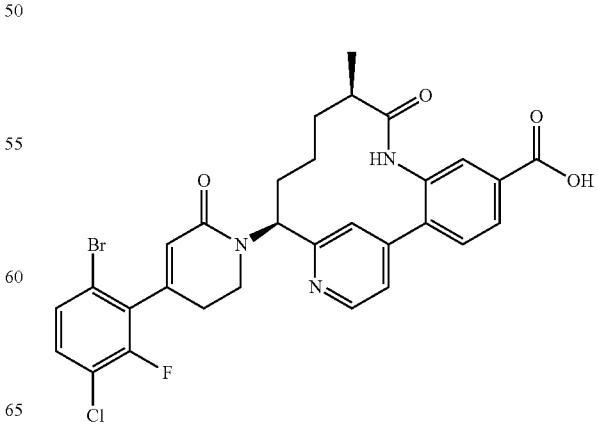

Example 28 was prepared by following the procedures described in Example 1. ¹H NMR (500 MHz, CD₃OD) δ 8.70 (d, J=5.1 Hz, 1H), 8.09 (dd, J=8.1, 1.8 Hz, H), 7.90 (d, J=1.5 Hz, 1H), 7.73 (d, J=8.1 Hz, 1H), 7.64 (s, 1H), 7.39-7.54 (m, 3H), 5.92 (s, 1H), 5.69 (dd, J=12.6, 4.5 Hz, 1H), 3.98-4.12 (m, 1H), 3.78-3.89 (m, 1H), 2.56-2.66 (m, 3H), 2.13-2.25 (m, 1H), 1.79-1.97 (m, 2H), 1.47-1.59 (m, 1H), 1.24-1.38 (m, 1H), 1.04 (d, J=6.8 Hz, 3H), 0.86-0.99 (m, 1H). MS (ESI) m/z: 628.2 (M+H)⁺. Analytical HPLC (method A): RT=7.6 min, purity=96%.

Example 29

(14S)-14-[4-(6-Bromo-3-chloro-2-fluorophenyl)-6-oxo-1,2,3,6-tetrahydropyridin-1-yl]-10-methyl-9-oxo-8,16-diazatricyclo[13.3.1.0²,⁷]nonadeca-1(19),2(7),3,5,15,17-hexaene-5-carboxamide, TFA Salt

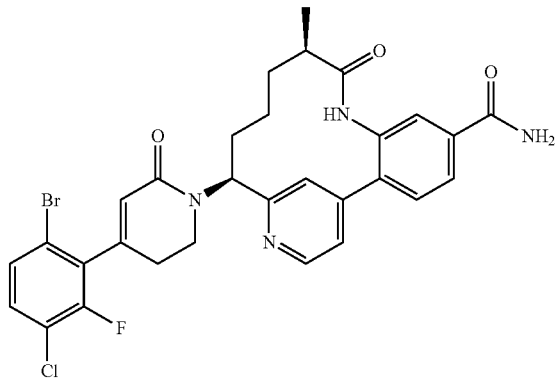 [SMILES: C[C@@H]1CCC[C@H](N2CCC(c3c(Br)ccc(Cl)c3F)=CC2=O)c2cc(ccn2)-c2ccc(C(N)=O)cc2NC1=O]

Example 29 was prepared by following the procedures described in Example 1. ¹H NMR (500 MHz, CD₃OD) δ 8.76 (d, J=5.2 Hz, 1H), 7.98 (dd, J=8.1, 1.8 Hz, 1H), 7.85 (s, 1H), 7.82 (d, J=1.7 Hz, 1H), 7.77 (d, J=8.3 Hz, 1H), 7.66 (dd, J=5.5, 1.7 Hz, 1H), 7.49-7.53 (m, 1H), 7.41-7.46 (m, 1H), 5.93 (s, 1H), 5.58 (dd, J=12.7, 4.7 Hz, 1H), 3.90-3.99 (m, 1H), 3.82 (ddd, J=12.4, 9.2, 5.6 Hz, 1H), 2.58-2.75 (m, 3H), 2.20-2.29 (m, 1H), 1.88-2.03 (m, 2H), 1.53-1.62 (m, 1H), 1.24-1.35 (m, 1H), 1.06 (d, J=6.9 Hz, 3H), 0.97 (br. s., 1H). MS (ESI) m/z: 627.2 (M+H)⁺. Analytical HPLC (method A): RT=6.9 min, purity=99%.

Example 30

Methyl N-[(10R,14S)-14-[4-(3-chloro-6-cyano-2-fluorophenyl)-6-oxo-1,2,3,6-tetrahydropyridin-1-yl]-10-methyl-9,17-dioxo-8,16-diazatricyclo[13.3.1.0²,⁷]nonadeca-1(18),2,4,6,15(19)-pentaen-5-yl]carbamate, TFA Salt

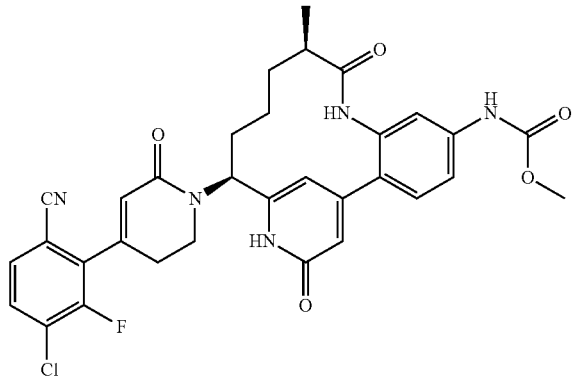 [SMILES: COC(=O)Nc1ccc2c(c1)NC(=O)[C@H](C)CCC[C@H](N1CCC(c3c(C#N)ccc(Cl)c3F)=CC1=O)c1cc-2cc(=O)[nH]1]

Example 30 was prepared by following the procedures described in Example 1. ¹H NMR (500 MHz, METHANOL-d₄) δ 9.53 (s, 1H), 7.75-7.66 (m, 2H), 7.56-7.48 (m, 3H), 6.67 (d, J=1.4 Hz, 1H), 6.55 (d, J=1.4 Hz, 1H), 6.23 (t, J=1.4 Hz, 1H), 5.24-5.17 (m, 1H), 3.78 (s, 3H), 3.62 (dt, J=12.5, 7.4 Hz, 1H), 3.52-3.44 (m, 1H), 2.74 (t, J=6.6 Hz, 2H), 2.57-2.47 (m, 1H), 2.20-2.11 (m, 1H), 1.99-1.90 (m, 1H), 1.89-1.79 (m, 1H), 1.70 (br. s., 1H), 1.62 (ddd, J=14.1, 9.7, 4.5 Hz, 1H), 1.23 (br. s., 1H), 1.19 (d, J=6.9 Hz, 3H). MS (ESI) m/z: 618.0 (M+H)⁺. Analytical HPLC (method A): RT=7.4 min, purity=95%.

Example 31

Methyl N-[(10R,14S)-14-{4-[3-chloro-6-(difluoromethoxy)-2-fluorophenyl]-6-oxo-1,2,3,6-tetrahydropyridin-1-yl})-10-methyl-9-oxo-8,18-diazatricyclo[13.3.1.0²,⁷]nonadeca-1(19),2,4,6,15,17-hexaen-5-yl]carbamate, TFA Salt

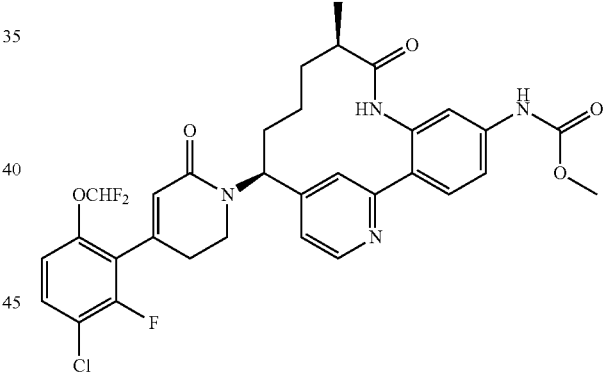

Example 31 was prepared by following the procedures described in Example 1. ¹H NMR (500 MHz, CD3CN) δ 8.71 (d, J=6.1 Hz, 1H), 8.40 (s, 1H), 8.16 (s, 1H), 8.07 (d, J=1.4 Hz, 1H), 7.75 (dd, J=6.3, 1.7 Hz, 1H), 7.66 (d, J=8.5 Hz, 1H), 7.58 (d, J=1.9 Hz, 1H), 7.47-7.54 (m, 2H), 7.06 (dd, J=8.3, 0.8 Hz, 1H), 5.95 (s, 1H), 5.45 (dd, J=11.8, 5.2 Hz, 1H), 3.74 (s, 3H), 3.60-3.72 (m, 2H), 2.58-2.77 (m, 2H), 2.45-2.53 (m, 1H), 1.97-2.12 (m, 2H), 1.74-1.84 (m, 1H), 1.42-1.53 (m, 1H), 1.22-1.33 (m, 1H), 1.00-1.11 (m, 1H), 0.97 (d, J=6.9 Hz, 3H). MS (ESI) m/z: 643.0 (M+H)⁺. Analytical HPLC (method A): RT=6.7 min, purity=100%.

Example 32

Methyl N-[(10R,14S)-14-{4-[3-chloro-6-(difluoromethoxy)-2-fluorophenyl]-6-oxo-1,2,3,6-tetrahydropyridin-1-yl}-10-methyl-9-oxo-8,16-diazatricyclo[13.3.1.0$^{2,7}$]nonadeca-1(19),2,4,6,15,17-hexaen-5-yl]carbamate, TFA Salt

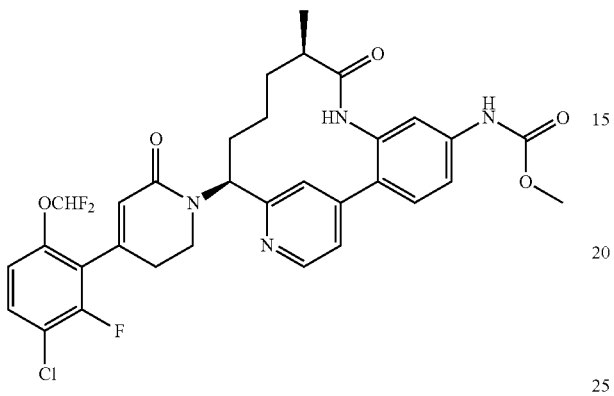

Example 32 was prepared by following the procedures described in Example 1. $^1$H NMR (500 MHz, CD3CN) δ 8.71 (d, J=6.1 Hz, 1H), 8.40 (s, 1H), 8.16 (s, 1H), 8.07 (d, J=1.4 Hz, 1H), 7.75 (dd, J=6.3, 1.7 Hz, 1H), 7.66 (d, J=8.5 Hz, 1H), 7.58 (d, J=1.9 Hz, 1H), 7.47-7.54 (m, 2H), 7.06 (dd, J=8.3, 0.8 Hz, 1H), 5.95 (s, 1H), 5.45 (dd, J=11.8, 5.2 Hz, 1H), 3.74 (s, 3H), 3.60-3.72 (m, 2H), 2.58-2.77 (m, 2H), 2.45-2.53 (m, 1H), 1.97-2.12 (m, 2H), 1.74-1.84 (m, 1H), 1.42-1.53 (m, 1H), 1.22-1.33 (m, 1H), 1.00-1.11 (m, 1H), 0.97 (d, J=6.9 Hz, 3H). MS (ESI) m/z: 643.0 (M+H)$^+$. Analytical HPLC (method A): RT=7.2 min, purity=100%.

Example 33

(10R,14S)-14-[4-(3-Chloro-6-cyano-2-fluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaene-5-carboxamide, TFA Salt

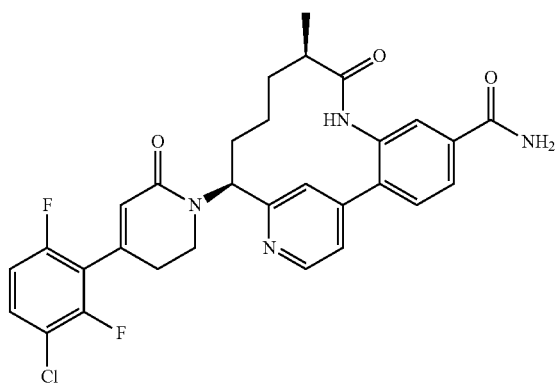 [SMILES: C[C@@H]1CCC[C@H](N2CCC(c3c(F)ccc(Cl)c3F)=CC2=O)c2cc(ccn2)-c2ccc(C(N)=O)cc2NC1=O]

Example 33 was prepared by following the procedures described in Example 3 by repaling 2A with Example 29. $^1$H NMR (500 MHz, CD$_3$OD) δ 8.81 (d, J=5.2 Hz, 1H), 7.97-8.02 (m, 2H), 7.77-7.84 (m, 3H), 7.69-7.74 (m, 1H), 7.64-7.68 (m, 1H), 6.18 (s, 1H), 5.51 (dd, J=12.1, 3.9 Hz, 1H), 3.87-3.95 (m, 1H), 3.80 (ddd, J=12.4, 9.6, 5.2 Hz, 1H), 2.82-2.91 (m, 1H), 2.72-2.81 (m, 1H), 2.59-2.68 (m, 1H), 2.22-2.32 (m, 1H), 2.00-2.10 (m, 1H), 1.87-1.96 (m, 1H), 1.54-1.64 (m, 1H), 1.27-1.38 (m, 1H), 1.06 (d, J=6.9 Hz, 3H), 0.90-1.02 (m, 1H). MS (ESI) m/z: 572.3 (M+H)$^+$. Analytical HPLC (method A): RT=6.0 min, purity=94%.

Example 34

(14S)-14-[4-(6-Acetyl-3-chloro-2-fluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaene-5-carboxamide, TFA Salt

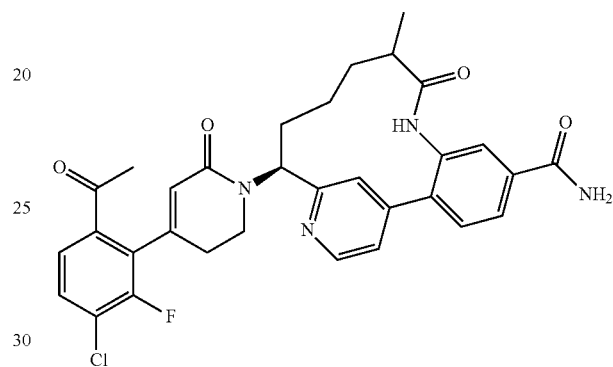

Example 34 was prepared by following the procedures described in Example 48 by replacing 45 with example 29. $^1$H NMR (500 MHz, CD$_3$OD) δ 8.83 (d, J=5.5 Hz, 1H), 8.07-7.97 (m, 2H), 7.91-7.78 (m, 4H), 7.67 (dd, J=8.5, 7.2 Hz, 1H), 5.74 (s, 1H), 5.52 (dd, J=12.5, 4.3 Hz, 1H), 3.97-3.77 (m, 2H), 2.78-2.61 (m, 3H), 2.59 (s, 3H), 2.31 (d, J=6.1 Hz, 1H), 2.13-2.01 (m, 1H), 1.94 (dd, J=8.5, 5.5 Hz, 1H), 1.73-1.58 (m, 1H), 1.47-1.29 (m, 1H), 1.08 (d, J=6.9 Hz, 3H), 1.02-0.96 (m, 1H). MS (ESI) m/z: 589.0 (M+H)$^+$. Analytical HPLC (method A): RT=5.9 min, purity=95%.

Example 35

(14S)-14-[4-(3-Chloro-2-fluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaene-5-carboxamide, TFA Salt

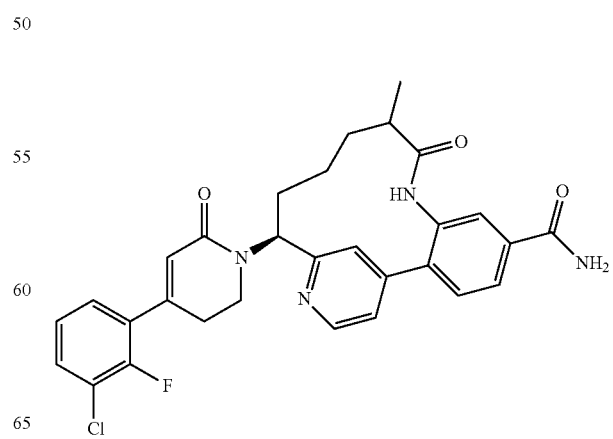

Example 35 was prepared by following the procedures described in Example 1. ¹H NMR (500 MHz, CD₃OD) δ 8.83 (d, J=5.5 Hz, 1H), 8.15-7.98 (m, 2H), 7.89-7.74 (m, 3H), 7.54 (td, J=7.5, 1.5 Hz, 1H), 7.43 (td, J=7.4, 1.5 Hz, 1H), 7.25 (td, J=8.0, 0.8 Hz, 1H), 6.23 (s, 1H), 5.48 (dd, J=12.4, 4.7 Hz, 1H), 3.92-3.79 (m, 1H), 3.75 (ddd, J=12.4, 9.5, 5.4 Hz, 1H), 2.94-2.77 (m, 2H), 2.71-2.61 (m, 1H), 2.31 (br. s., 1H), 2.06 (br. s., 1H), 1.99-1.84 (m, 1H), 1.61 (dd, J=14.4, 6.2 Hz, 1H), 1.35 (br. s., 1H), 1.08 (d, J=6.9 Hz, 3H), 0.96 (d, J=6.3 Hz, 1H). MS (ESI) m/z: 547.0 (M+H)⁺. Analytical HPLC (method A): RT=6.4 min, purity=95%.

Example 36

Methyl N-[(10R,14S)-14-{4-[5-chloro-2-(trifluoromethyl)phenyl]-6-oxo-1,2,3,6-tetrahydropyridin-1-yl})-10-methyl-9-oxo-8,16-diazatricyclo[13.3.1.0²,⁷]nonadeca-1(19),2,4,6,15,17-hexaen-5-yl]carbamate, TFA Salt

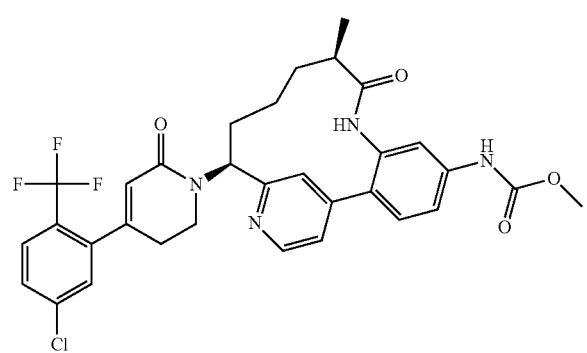 [SMILES: COC(=O)Nc1ccc2c(c1)NC(=O)[C@H](C)CCC[C@H](N1CCC(c3cc(Cl)ccc3C(F)(F)F)=CC1=O)c1cc-2ccn1]

Example 36 was prepared by following the procedures described in Example 1. ¹H NMR (500 MHz, CD₃OD) δ 8.64 (d, J=5.0 Hz, 1H), 7.76 (d, J=8.8 Hz, 1H), 7.63 (d, J=0.8 Hz, 1H), 7.61-7.48 (m, 5H), 7.40 (dd, J=5.0, 1.7 Hz, 1H), 5.88 (s, 1H), 5.67 (dd, J=12.7, 4.4 Hz, 1H), 3.91 (d, J=18.7 Hz, 1H), 3.81-3.71 (m, 4H), 2.69-2.57 (m, 3H), 2.19 (ddt, J=16.2, 12.8, 3.3 Hz, 1H), 2.00-1.82 (m, 2H), 1.63-1.51 (m, 1H), 1.37-1.22 (m, 2H), 1.07 (d, J=6.9 Hz, 3H). MS (ESI) m/z: 627.0 (M+H)⁺. Analytical HPLC (method A): RT=7.33 min, purity=95%.

Example 37

(10R,14S)-14-[4-(3-Chloro-2,6-difluorophenyl)-6-oxo-1,2,3,6-tetrahydropyridin-1-yl]-10-methyl-5-[(5-methyl-1,3,4-oxadiazol-2-yl)amino]-8,18-diazatricyclo[13.3.1.0²,⁷]nonadeca-1(19),2(7),3,5,15,17-hexaen-9-one, TFA Salt

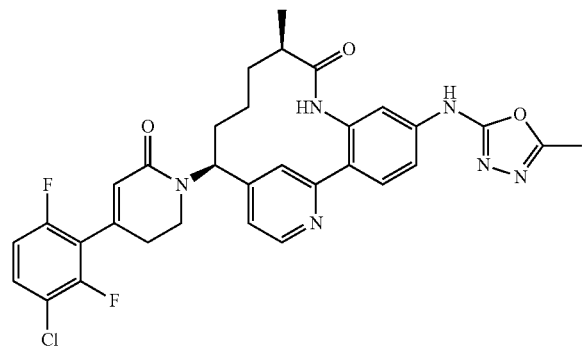 [SMILES: Cc1nnc(Nc2ccc3c(c2)NC(=O)[C@H](C)CCC[C@H](N2CCC(c4c(F)ccc(Cl)c4F)=CC2=O)c2ccnc-3c2)o1]

Example 37 was prepared by following the procedures described in Example 21. ¹H NMR (500 MHz, ACETONITRILE-d3) δ 8.63 (d, J=5.50 Hz, 1H), 8.46 (br. s., 1H), 8.20 (s, 1H), 7.79 (s, 1H), 7.68 (d, J=8.53 Hz, 1H), 7.55 (d, J=2.20 Hz, 1H), 7.47 (dd, J=2.20, 8.53 Hz, 1H), 7.34-7.43 (m, 2H), 6.96 (dt, J=1.51, 9.28 Hz, 1H), 5.96 (s, 1H), 5.42 (dd, J=4.13, 12.38 Hz, 1H), 3.45-3.57 (m, 2H), 3.35 (td, J=6.29, 12.45 Hz, 2H), 2.80 (m, 2H), 2.55 (d, J=4.95 Hz, 3H), 2.34-2.38 (m, 1H), 1.96-2.04 (m, 2H), 1.69-1.76 (m, 1H), 1.37-1.47 (m, 1H), 1.11-1.22 (m, 2H), 0.96 (d, J=6.60 Hz, 3H). MS (ESI) m/z: 619.0 (M+H)⁺. Analytical HPLC (method A): RT=6.1 min, purity=99%

Example 38

(14S)-14-[4-(6-Bromo-3-chloro-2-fluorophenyl)-6-oxo-1,2,3,6-tetrahydropyridin-1-yl]-10-methyl-5-(4H-1,2,4-triazol-3-yl)-8,16-diazatricyclo[13.3.1.0²,⁷]nonadeca-1(19),2(7),3,5,15,17-hexaen-9-one, TFA Salt

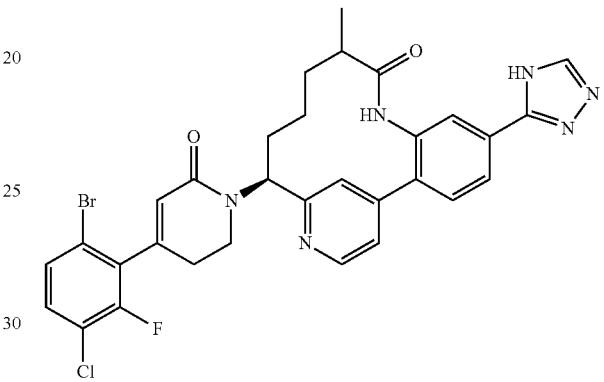

Example 38 was prepared by following the procedures described in Example 1. ¹H NMR (500 MHz, CD₃OD) δ 8.87 (d, J=5.8 Hz, 1H), 8.59 (s, 1H), 8.22 (dd, J=8.0, 1.7 Hz, 1H), 8.18 (s, 1H), 8.05 (d, J=1.7 Hz, 1H), 7.99 (dd, J=6.1, 1.7 Hz, 1H), 7.88 (d, J=8.3 Hz, 1H), 7.58-7.51 (m, 1H), 7.50-7.41 (m, 1H), 5.97 (s, 1H), 5.47 (dd, J=12.2, 4.5 Hz, 1H), 4.00 (s, 1H), 3.92-3.79 (m, 2H), 2.86-2.76 (m, 1H), 2.70 (td, J=11.6, 5.6 Hz, 2H), 2.41-2.30 (m, 1H), 2.18-2.06 (m, 1H), 1.95 (dd, J=8.5, 5.5 Hz, 1H), 1.71-1.60 (m, 1H), 1.35 (br. s., 1H), 1.10 (d, J=6.9 Hz, 3H). MS (ESI) m/z: 651.1 (M+H)⁺. Analytical HPLC (method A): RT=6.8 min, purity=95%.

Example 39

(10R,14S)-14-[4-(3-Chloro-2,6-difluorophenyl)-6-oxo-1,2,3,6-tetrahydropyridin-1-yl]-5-[(5-cyclopropyl-1,3,4-oxadiazol-2-yl)amino]-10-methyl-8,16-diazatricyclo[13.3.1.0²,⁷]nonadeca-1(19),2(7),3,5,15,17-hexaen-9-one, TFA Salt

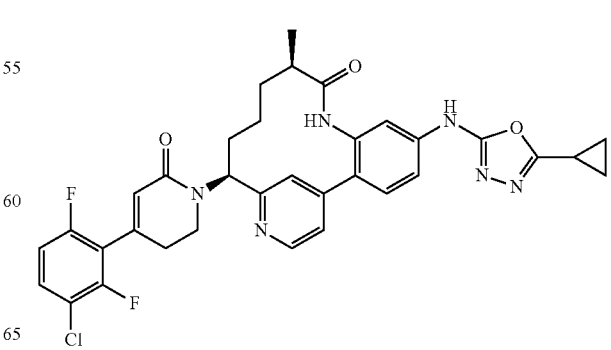

Example 39 was prepared by following the procedures described in Example 21. ¹H NMR (500 MHz, ACETONITRILE-d3) δ 8.56 (d, J=5.50 Hz, 1H), 8.45 (br. s., 1H), 8.23 (s, 1H), 7.70 (s, 1H), 7.36-7.49 (m, 6H), 6.93-7.00 (m, 1H), 5.98 (s, 1H), 5.29 (dd, J=4.40, 12.10 Hz, 1H), 3.86-3.94 (m, 1H), 3.61-3.69 (m, 1H), 2.18 (t, J=12.65 Hz, 2H), 1.94 (dt, J=4.26, 8.73 Hz, 2H), 1.70-1.81 (m, 4H), 1.37-1.47 (m, 1H), 1.28 (td, J=4.75, 9.77 Hz, 1H), 0.98 (dd, J=2.34, 8.39 Hz, 2H), 0.90 (dd, J=1.93, 4.95 Hz, 2H), 0.84 (d, J=6.88 Hz, 3H), 0.50 (br. s., 1H). MS (ESI) m/z: 645.0 (M+H)⁺. Analytical HPLC (method A): RT=6.7 min, purity=99%.

Example 40

2-(5-{[(10R,14S)-14-[4-(3-Chloro-2,6-difluorophenyl)-6-oxo-1,2,3,6-tetrahydropyridin-1-yl]-10-methyl-9-oxo-8,16-diazatricyclo[13.3.1.0²,⁷]nonadeca-1(19),2,4,6,15,17-hexaen-5-yl]amino}-1,3,4-oxadiazol-2-yl)acetonitrile, TFA Salt

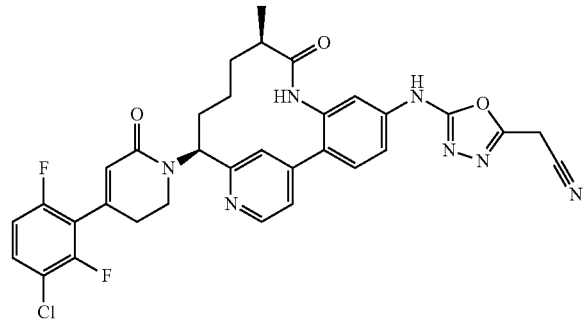 [SMILES: C[C@@H]1CCC[C@H](N2CCC(c3c(F)ccc(Cl)c3F)=CC2=O)c2cc(ccn2)-c2ccc(Nc3nnc(CC#N)o3)cc2NC1=O]

Example 40 was prepared by following the procedures described in Example 21. ¹H NMR (500 MHz, CD3OD) δ 8.75 (d, J=5.8 Hz, 1H), 7.98 (s, 1H), 7.81-7.63 (m, 4H), 7.62-7.51 (m, 1H), 7.13 (t, J=8.7 Hz, 1H), 6.15 (s, 1H), 5.53 (d, J=7.4 Hz, 1H), 4.35 (s, 1H), 3.94-3.74 (m, 2H), 3.32 (m, 2H), 2.88-2.61 (m, 4H), 2.30 (br. s., 1H), 2.12-1.93 (m, 2H), 1.65 (br. s., 1H), 1.37 (br. s., 1H), 1.10 (d, J=6.6 Hz, 3H), 1.00 (br. s., 1H). MS (ESI) m/z: 645.0 (M+H)⁺. Analytical HPLC (method A): RT=6.7 min, purity >95%.

Example 41

(10R,14S)-14-[4-(3-Chloro-2,6-difluorophenyl)-6-oxo-1,2,3,6-tetrahydropyridin-1-yl]-5-{[5-(methoxymethyl)-1,3,4-oxadiazol-2-yl]amino}-10-methyl-8,16-diazatricyclo[13.3.1.0²,⁷]nonadeca-1(19),2,4,6,15,17-hexaen-9-one, TFA Salt

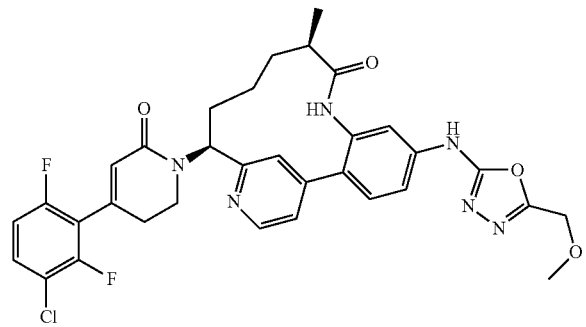 [SMILES: COCc1nnc(Nc2ccc3c(c2)NC(=O)[C@H](C)CCC[C@H](N2CCC(c4c(F)ccc(Cl)c4F)=CC2=O)c2cc-3ccn2)o1]

Example 41 was prepared by following the procedures described in Example 21. ¹H NMR (500 MHz, CD3OD) δ 8.80-8.76 (m, 1H), 8.12-8.06 (m, 1H), 7.87 (d, J=5.8 Hz, 1H), 7.80-7.72 (m, 1H), 7.71-7.64 (m, 2H), 7.57 (td, J=8.6, 5.6 Hz, 1H), 7.13 (t, J=9.2 Hz, 1H), 6.14 (s, 1H), 5.46 (dd, J=12.4, 4.7 Hz, 1H), 4.61 (s, 2H), 3.91-3.70 (m, 2H), 3.48 (s, 3H), 3.32 (m, 2H), 2.96-2.82 (m, 1H), 2.81-2.65 (m, 2H), 2.40-2.24 (m, 1H), 2.19-2.03 (m, 1H), 1.97 (dd, J=8.5, 5.8 Hz, 1H), 1.75-1.58 (m, 1H), 1.37 (br. s., 1H), 1.09 (d, J=6.9 Hz, 3H), 0.99 (br. s., 1H) ppm. MS (ESI) m/z: 649.0 (M+H)⁺. Analytical HPLC (method A): RT=6.5 min, purity >95%.

Example 42

Ethyl 2-(5-{[(10R,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0²,⁷]nonadeca-1(19),2,4,6,15,17-hexaen-5-yl]amino}-1,3,4-oxadiazol-2-yl)acetate, TFA Salt

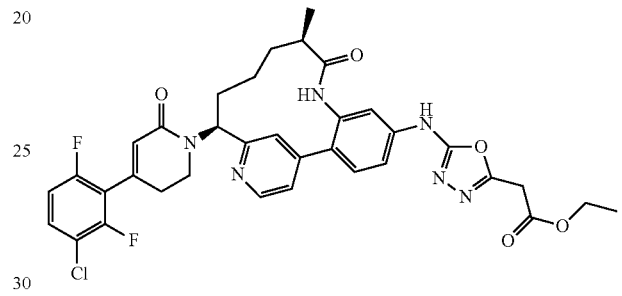

Example 42 was prepared by following the procedures described in Example 21. ¹H NMR (500 MHz, CD3OD) δ 8.77 (d, J=5.8 Hz, 1H), 8.04 (s, 1H), 7.82 (d, J=5.5 Hz, 1H), 7.73 (d, J=8.3 Hz, 1H), 7.70-7.63 (m, 2H), 7.62-7.52 (m, 1H), 7.13 (t, J=9.1 Hz, 1H), 6.15 (s, 1H), 5.49 (dd, J=12.4, 4.7 Hz, 1H), 4.27 (q, J=7.2 Hz, 2H), 4.04-3.99 (m, 1H), 3.91-3.72 (m, 2H), 3.32 (m, 3H), 2.92-2.81 (m, 1H), 2.81-2.63 (m, 2H), 2.31 (br. s., 1H), 2.07 (d, J=6.3 Hz, 1H), 1.97 (br. s., 1H), 1.74-1.57 (m, 1H), 1.33 (t, J=7.2 Hz, 4H), 1.09 (d, J=6.9 Hz, 3H), 1.00 (br. s., 1H). MS (ESI) m/z: 691.0 (M+H)⁺. Analytical HPLC (method A): RT=7.0 min, purity >95%.

Example 43

Methyl N-[(10R,14S)-14-[4-(6-bromo-2-fluoro-3-methylphenyl)-6-oxo-1,2,3,6-tetrahydropyridin-1-yl]-10-methyl-9-oxo-8,16-diazatricyclo[13.3.1.0²,⁷]nonadeca-1(19),2,4,6,15,17-hexaen-5-yl]carbamate, TFA Salt

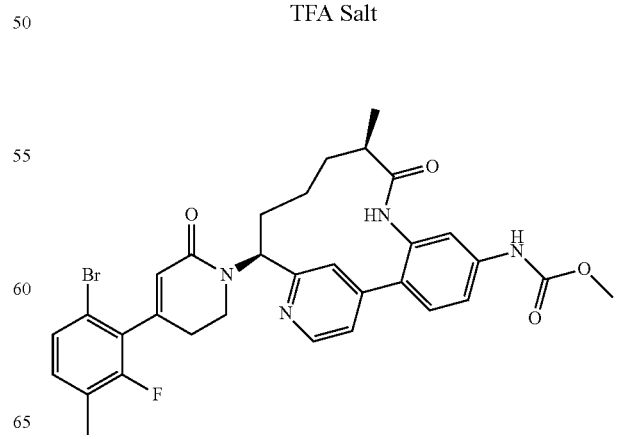

Example 43 was prepared by following the procedures described in Example 1. $^1$H NMR (500 MHz, CD$_3$OD) δ 8.64 (d, J=5.0 Hz, 1H), 7.64 (s, 1H), 7.59-7.50 (m, 3H), 7.45-7.37 (m, 2H), 7.19 (t, J=7.8 Hz, 1H), 5.89 (s, 1H), 5.68 (dd, J=12.7, 4.4 Hz, 1H), 3.93 (br. s., 1H), 3.82-3.76 (m, 5H), 2.69-2.55 (m, 2H), 2.28-2.18 (m, 2H), 1.98-1.82 (m, 2H), 1.58 (d, J=8.3 Hz, 1H), 1.51-1.41 (m, 1H), 1.37-1.25 (m, 1H), 1.07 (d, J=6.9 Hz, 3H). MS (ESI) m/z: 636.9 (M+H)$^+$. Analytical HPLC (method A): RT=7.14 min, purity=97%.

Example 44

Methyl N-[(10R,14S)-14-{4-[5-chloro-2-(difluoromethoxy)phenyl]-6-oxo-1,2,3,6-tetrahydropyridin-1-yl}-10-methyl-9-oxo-8,16-diazatricyclo[13.3.1.0$^{2,7}$]nonadeca-1(19),2,4,6,15,17-hexaen-5-yl]carbamate, TFA Salt

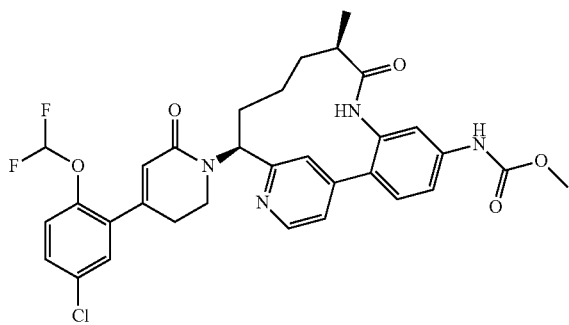 [SMILES: COC(=O)Nc1ccc2c(c1)NC(=O)[C@H](C)CCC[C@H](N1CCC(c3cc(Cl)ccc3OC(F)F)=CC1=O)c1cc-2ccn1]

Example 44 was prepared by following the procedures described in Example 1. $^1$H NMR (500 MHz, CD3OD) δ 8.78 (d, J=6.1 Hz, 1H), 8.13 (d, J=1.1 Hz, 1H), 7.91 (dd, J=6.1, 1.7 Hz, 1H), 7.69 (d, J=8.3 Hz, 1H), 7.64-7.55 (m, 2H), 7.51-7.42 (m, 2H), 7.26 (d, J=9.1 Hz, 1H), 7.09-6.71 (m, 1H), 6.11 (s, 1H), 5.40 (dd, J=12.4, 4.7 Hz, 1H), 3.82-3.65 (m, 5H), 3.32 (m, 1H), 2.96-2.76 (m, 2H), 2.72-2.63 (m, 1H), 2.40-2.27 (m, 1H), 2.16-2.03 (m, 1H), 1.99-1.86 (m, 1H), 1.71-1.56 (m, 1H), 1.37 (t, J=7.0 Hz, 2H), 1.08 (d, J=6.9 Hz, 3H), 0.99 (br. s., 1H). MS (ESI) m/z: 625.0 (M+H)$^+$. Analytical HPLC (method A): RT=7.1 min, purity >95%.

Example 45

(10R,14S)-14-[4-(6-Bromo-3-chloro-2-fluorophenyl)-6-oxo-1,2,3,6-tetrahydropyridin-1-yl]-10-methyl-8,16-diazatricyclo[13.3.1.0$^{2,7}$]nonadeca-1(19),2,4,6,15,17-hexaen-9-one, TFA Salt

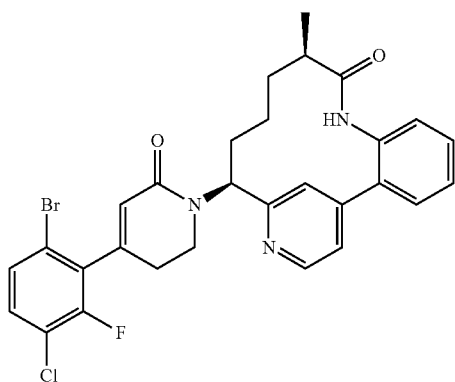 [SMILES: C[C@@H]1CCC[C@H](N2CCC(c3c(Br)ccc(Cl)c3F)=CC2=O)c2cc(ccn2)-c2ccccc2NC1=O]

45A. (S,E)-N-((4-Chloropyridin-2-yl)methylene)-2-methylpropane-2-sulfinamide

Liu, G. et al., J. Org. Chem., 64:1278 (1999). To a solution of S-(−)-t-butyl-sulfinamide (0.856 g, 7.06 mmol) in dichloromethane (14.13 mL) was added sequentially copper(II) sulfate (2.481 g, 15.54 mmol) and 4-chloropicolinaldehyde [1.0 g, 7.06 mmol, prepared according to a modified described by Negi etc, Synthesis, 991 (1996)]. The white suspension was stirred at rt. After 3 h, the brown suspension was filtered through CELITE®, eluting with DCM, to give a clear brown filtrate. Concentration gave a brown oil weighing 1.85 g. Purification by normal phase chromatography gave 1.31 g of 45A as a clear, yellow oil. MS (ESI) m/z: 245.0 (M+H)$^+$.

45B. (S)—N—((S)-1-(4-Chloropyridin-2-yl)but-3-enyl)-2-methylpropane-2-sulfinamide To a cooled (0-5° C.) mixture of indium(III) chloride (13.56 g, 61.3 mmol) in THF (170 mL) was added allylmagnesium bromide (1M in diethylether) (62 mL, 61.3 mmol) dropwise over 30 min. The reaction was allowed to warm to rt. After 1 h at rt, a solution of 45A (10 g, 40.9 mmol) in ethanol (170 mL) was added. After 2-3 h, the reaction was concentrated under vacuum at 50-55° C. The crude material was partitioned between ethyl acetate (200 ml) and water (1×50 ml) and the layers were separated. The aqueous layer was extracted with ethyl acetate (2×50 ml). The organic layers were combined and washed with brine (1×100 ml), dried over sodium sulfate, filtered and concentrated to give 45B (13.5 g, 106%) as a yellow oil. MS (ESI) m/z: 287.2 (M+H)+. This material was used in the next step without further purification.

45C. (S)-tert-Butyl 1-(4-chloropyridin-2-yl)but-3-enylcarbamate 45B (75 g, 261 mmol) was dissolved in methanol (1500 mL). Hydrochloric acid (6N, 750 ml, 4.5 mol) was added. The reaction was stirred at rt for 2-3 hrs and then was concentrated. The residue was diluted with water (2 L), washed with ethyl acetate (500 ml). The aqueous layer was basified with saturated sodium carbonate solution, extracted into ethyl acetate (3×1 L). The combined organic layers were washed with water (1×1 L) and brine (1×1 L), dried over sodium sulfate, filtered and concentrated under vacuum at 50-55° C. to give crude product (43g, 90%). MS (ESI) m/z: 183.2 (M+H)+. The crude product (42g, 230 mmol) was dissolved in dichloromethane (420 mL), Et$_3$N (32.1 mL, 230 mmol) was added followed by portionwise addition of Boc$_2$O (53.4 mL, 230 mmol). The reaction was stirred at rt for 2-3 hrs. The reaction was diluted with excess DCM (1 L), washed with water (1×500 ml) and brine (1×500 ml). The organic layer was dried over sodium sulfate, filtered, and concentrated. The crude product was then purified using silica gel chromatography to give 45C (61 g, 86%) as a pale yellow solid. MS (ESI) m/z: 283.2 (M+H)$^+$.

45D. tert-Butyl N-[(1S)-1-[4-(2-aminophenyl)pyridin-2-yl]but-3-en-1-yl]carbamate 45C (2 g, 7.07 mmol) and (2-aminophenyl)boronic acid (1.065 g, 7.78 mmol) in DMSO (35.4 ml) and H$_2$O (0.637 ml, 35.4 mmol) was de-gassed for 30 min. Then, Phosphoric acid, potassium salt (3.00 g, 14.15 mmol) and 1,1'-bis(diphenylphosphino)ferrocenedichloro palladium(ii) dichloromethane complex (0.518 g, 0.707 mmol) were added. The dark red reaction mixture was sealed and heated at 90° C. overnight. The reaction mixture was diluted with EtOAc/Ether and washed with water and brine. The organic layer was dried over MgSO$_4$. Filtered and concentrated to give the crude product as a black oil. The residue was purified by silica gel chromatography to give the desired product (2.0 g, 83%) as a light brownish foam. $^1$H NMR (400 MHz, CHLOROFORM-d) δ 8.61 (d, J=4.8 Hz, 1H), 7.37-7.28 (m, 2H), 7.27-7.16 (m, 2H), 7.12 (d, J=7.7 Hz, 1H), 6.85 (t, J=7.5 Hz, 1H), 6.77 (d, J=7.9 Hz, 1H), 5.79-5.58 (m, 2H), 5.12-4.97 (m, 2H), 4.90-4.80 (m, 1H), 3.80 (br. s., 2H), 2.62 (t, J=6.6 Hz, 2H), 1.44 (s, 9H). MS (ESI) m/z: 340.1 (M+H)$^+$.

45E. tert-Butyl N-[(1S)-1-(4-{2-[(2R)-2-methylbut-3-enamido]phenyl}pyridin-2-yl)but-3-en-1-yl]carbamate To a solution of 45D (1.4 g, 4.12 mmol), (R)-2-methylbut-3-enoic acid (0.58 g, 5.79 mmol) in EtOAc (41.2 ml) was added pryridine (1.001 ml, 12.37 mmol). The reaction was cooled down to 0° C. under Ar and propane phosphonic acid anhydride (4.91 ml, 8.25 mmol) was added dropwise. The reaction was then gradually warmed up to rt over night. The reaction mixture was diluted and washed with sat. aq. NaHCO$_3$, aqueous layer back-extracted with EtOAc, combined EtOAc phase washed with brine, dried over MgSO4, filtered, concentrated. The residue was purified by silica gel chromatography to give the desired product (1.47 g, 85%) as an offwhite foam. $^1$H NMR (500 MHz, CHLOROFORM-d) δ 8.65-8.60 (m, 1H), 8.19 (d, J=8.3 Hz, 1H), 7.47-7.36 (m, 2H), 7.24-7.18 (m, 3H), 7.16 (dd, J=5.0, 1.4 Hz, 1H), 5.82-5.62 (m, 3H), 5.10-5.01 (m, 4H), 4.86 (d, J=7.2 Hz, 1H), 3.03 (quin, J=7.2 Hz, 1H), 2.62 (tq, J=14.1, 6.9 Hz, 2H), 1.49-1.36 (m, 9H), 1.25 (d, J=7.2 Hz, 3H). MS (ESI) m/z: 422.1 (M+H)$^+$.

45F. tert-Butyl N-[(10R,11E,14S)-10-methyl-9-oxo-8,16-diazatricyclo[13.3.1.0$^{2,7}$]nonadeca-1(19),2(7),3,5,11,15,17-heptaen-14-yl]carbamate To a round bottom flask was added 45E (1.34 g, 3.18 mmol), pTsOH (0.665 g, 3.50 mmol), and dichloromethane (265 ml). The clear yellow solution was degassed with argon for 30 min. The reaction was then warmed to 40° C. for 1 h. Then a solution of GrubbsII (0.486 g, 0.572 mmol) in DCM (4 mL) was added dropwise to the reaction mixture. After 4.5 h, the reaction was cooled to rt, washed with sat. NaHCO$_3$, brine, dried over MgSO$_4$, filtered, and concentrated to give brown solid. The residue was purified by silica gel chromatography to give the desired product (0.97 g, 78%) as light brownish foam. $^1$H NMR (500 MHz, METHANOL-d$_4$) δ 8.57-8.52 (m, 1H), 7.51-7.41 (m, 3H), 7.34-7.30 (m, 1H), 7.28 (dd, J=5.2, 1.7 Hz, 1H), 6.92 (s, 1H), 5.71 (ddd, J=15.3, 10.5, 4.7 Hz, 1H), 4.61 (dd, J=11.4, 3.4 Hz, 1H), 4.39 (dd, J=15.1, 9.4 Hz, 1H), 3.14-3.07 (m, 1H), 2.72 (ddd, J=8.6, 7.2, 3.7 Hz, 1H), 2.05-1.95 (m, 1H), 1.44 (s, 9H), 1.04 (d, J=6.9 Hz, 3H). MS (ESI) m/z: 394.1 (M+H)$^+$.

45G. tert-Butyl N-[(10R,14S)-10-methyl-9-oxo-8,16-diazatricyclo[13.3.1.0$^{2,7}$]nonadeca-1(19),2(7),3,5,15,17-hexaen-14-yl]carbamate 45F (974 mg, 2.475 mmol) in EtOAc (49.500 mL) was added platinum(IV) oxide (56.2 mg, 0.248 mmol). The reaction mixture was charged with H$_2$ balloon and vacuum/H$_2$ several times. The reaction was stirred at rt under H$_2$ overnight. The reaction was filtered and concentrated to give the desired product (0.95 g, 97%) as a brownish solid. $^1$H NMR (500 MHz, CHLOROFORM-d) δ 8.68 (d, J=5.0 Hz, 1H), 7.47-7.30 (m, 5H), 7.26-7.22 (m, 1H), 6.79 (br. s., 1H), 5.85 (d, J=7.7 Hz, 1H), 4.74 (br. s., 1H), 2.52-2.42 (m, 1H), 2.18-2.07 (m, 1H), 1.66-1.57 (m, 1H), 1.51-1.46 (m, 1H), 1.43 (s, 9H), 1.40-1.33 (m, 1H), 1.07 (br. s., 1H), 1.00 (d, J=6.9 Hz, 3H), 0.83 (d, J=9.9 Hz, 1H). MS (ESI) m/z: 396.2 (M+H)$^+$.

45H. (10R,14S)-14-Amino-10-methyl-8,16-diazatricyclo[13.3.1.0$^{2,7}$]nonadeca-1(19),2(7),3,5,15,17-hexaen-9-one To a suspension of 45G (950 mg, 2.402 mmol) in DCM (20.300 ml) was added TFA (5.55 ml, 72.1 mmol) dropwise over 10 min. The dark brownish solution was stirred at rt for 1 hour. The reaction mixture was concentrated to give example 45H compound as a dark brownish gum. Used in next step without purification. MS (ESI) m/z: 296.2 (M+H)$^+$.

45I. Diethyl ({[3-(6-bromo-3-chloro-2-fluorophenyl)-3-oxopropyl][(10R,14S)-10-methyl-9-oxo-8,16-diazatricyclo[13.3.1.0$^{2,7}$]nonadeca-1(19),2,4,6,15,17-hexaen-14-yl]carbamoyl}methyl)phosphonate To a solution of 45H (0.52 g, 0.874 mmol) in DCM (17.48 ml) was added DIEA (0.916 ml, 5.25 mmol). The reaction was stirred for 45 min to free base the salt. Intermediate 2 (0.230 g, 0.874 mmol) in DCM (1 ml) was added dropwise. The reaction was continued for 1 hr before it was cooled down in a salt bath. diethyl (2-chloro-2-oxoethyl)phosphonate (0.413 g, 1.923 mmol) in DCM (1.0 mL) was added dropwise. After 5 min, the reaction was quenched by addition of NH$_4$Cl, extracted with DCM. DCM layer washed twice with sat. NH$_4$Cl, brine, dried over MgSO$_4$, filtered and concentrated. The residue was purified by silica gel chromatography to give the desired product (0.55 g, 85%) as a white foam. $^1$H NMR (500 MHz, METHANOL-d$_4$) (3:2 mixture of rotamers) δ 8.69 (d, J=5.0 Hz, 0.6H), 8.60 (d, J=5.0 Hz, 0.4H), 7.69 (s, 0.6H), 7.68 (s, 0.4H), 7.65-7.58 (m, 1H), 7.56-7.42 (m, 5H), 7.42-7.28 (m, 1H), 5.49-5.43 (m, 0.4H), 5.08 (dd, J=12.4, 3.9 Hz, 0.6H), 4.84-4.82 (m, 2H), 4.25-4.11 (m, 5H), 3.92-3.72 (m, 2H), 3.31-3.17 (m, 2H), 2.57-2.45 (m, 1H), 2.30-2.07 (m, 2H), 1.96-1.82 (m, 1H), 1.58 (qd, J=15.0, 5.5 Hz, 1H), 1.38-1.30 (m, 7H), 1.13 (d, J=6.9 Hz, 2H), 1.07 (d, J=6.6 Hz, 1H). MS (ESI) m/z: 739.9 (M+H)$^+$.

Example 45. (10R,14S)-14-[4-(6-Bromo-3-chloro-2-fluorophenyl)-6-oxo-1,2,3,6-tetrahydropyridin-1-yl]-10-methyl-8,16-diazatricyclo[13.3.1.0$^{2,7}$]nonadeca-1(19),2,4,6,15,17-hexaen-9-one, TFA Salt To a clear solution of 45I (550 mg, 0.746 mmol) in MeOH (14.9 ml) was added NaOMe (25% in MeOH) (484 mg, 2.239 mmol). The reaction was stirred at rt for 10 min and added NaOMe (25% in MeOH) (968 mg, 4.5 mmol). Then, 0.3 mL of 1.25 N HCl in MeOH and 2 ml of 1N HCl was added and MeOH was removed in vacuo to give a white solid suspension. The mixture was diluted with DCM, washed with NaHCO$_3$. The aqueous layer was extracted twice with DCM, and the combined organic layers was washed with brine, dried over MgSO$_4$, filtered and concentrated. The residue was purified by silica gel chromatography to give the desired product (0.396 g, 89%) as white foam. $^1$H NMR (500 MHz, METHANOL-$d_4$) δ 8.69-8.62 (m, 1H), 7.69-7.58 (m, 2H), 7.52-7.39 (m, 5H), 7.31-7.25 (m, 1H), 5.92 (t, J=1.4 Hz, 1H), 5.66 (dd, J=12.7, 4.4 Hz, 1H), 3.94 (d, J=5.5 Hz, 1H), 3.80 (ddd, J=12.6, 8.5, 6.2 Hz, 1H), 2.66-2.53 (m, 3H), 2.18 (tdd, J=12.9, 6.9, 3.4 Hz, 1H), 1.96-1.83 (m, 2H), 1.59-1.47 (m, 1H), 1.34-1.21 (m, 1H), 1.07-1.01 (m, 3H). MS (ESI) m/z: 582.0 (M+H)$^+$. Analytical HPLC (method A): RT=7.4 min, purity=99%.

Example 46

(10R,14S)-14-[4-(3,6-Dicyano-2-fluorophenyl)-6-oxo-1,2,3,6-tetrahydropyridin-1-yl]-10-methyl-8,16-diazatricyclo[13.3.1.0$^{2,7}$]nonadeca-1(19),2,4,6,15,17-hexaen-9-one, TFA Salt

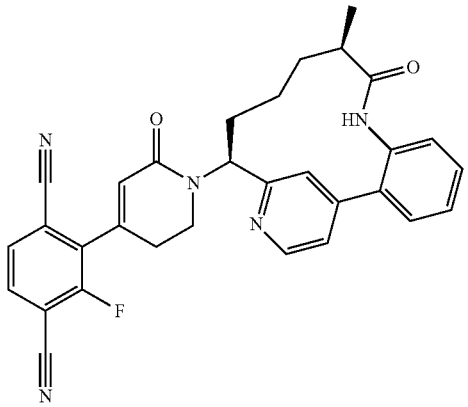 [SMILES: C[C@@H]1CCC[C@H](N2CCC(c3c(C#N)ccc(C#N)c3F)=CC2=O)c2cc(ccn2)-c2ccccc2NC1=O]

Example 46 was prepared as a side product in example 49. $^1$H NMR (500 MHz, DMSO-$d_6$) δ 9.72 (s, 1H), 8.69 (d, J=5.2 Hz, 1H), 8.19 (dd, J=8.0, 6.3 Hz, 1H), 8.04 (d, J=8.3 Hz, 1H), 7.63-7.57 (m, 2H), 7.52-7.40 (m, 3H), 7.24 (d, J=7.7 Hz, 1H), 6.21 (s, 1H), 5.60 (dd, J=12.4, 4.1 Hz, 1H), 4.00 (br. s., 1H), 3.81-3.71 (m, 1H), 2.72-2.63 (m, 1H), 2.62-2.54 (m, 1H), 2.14-2.04 (m, 1H), 1.91 (br. s., 1H), 1.78-1.68 (m, 1H), 1.49-1.39 (m, 1H), 0.89 (d, J=6.9 Hz, 3H), 0.58 (br. s., 1H). MS (ESI) m/z: 520.3 (M+H)$^+$. Analytical HPLC (method D): RT=1.1 min, purity=96%.

Example 47

(10R,14S)-14-[4-(3-Chloro-2-fluorophenyl)-6-oxo-1,2,3,6-tetrahydropyridin-1-yl]-10-methyl-8,16-diazatricyclo[13.3.1.0$^{2,7}$]nonadeca-1(19),2,4,6,15,17-hexaen-9-one, TFA Salt

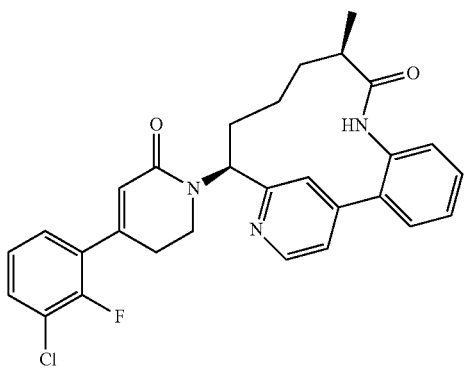 [SMILES: C[C@@H]1CCC[C@H](N2CCC(c3cccc(Cl)c3F)=CC2=O)c2cc(ccn2)-c2ccccc2NC1=O]

Example 47 was prepared as a side product in example 49. $^1$H NMR (500 MHz, DMSO-$d_6$) δ 9.71 (s, 1H), 8.67 (d, J=5.2 Hz, 1H), 7.66-7.56 (m, 3H), 7.52-7.38 (m, 4H), 7.32-7.21 (m, 2H), 6.13 (s, 1H), 5.59 (dd, J=12.5, 4.3 Hz, 1H), 4.00-3.88 (m, 1H), 3.74-3.65 (m, 1H), 2.79-2.67 (m, 2H), 2.62-2.54 (m, 1H), 2.14-2.02 (m, 1H), 1.91 (d, J=9.9 Hz, 1H), 1.75-1.63 (m, 1H), 1.49-1.37 (m, 1H), 1.29-1.16 (m, 1H), 0.89 (d, J=6.9 Hz, 3H), 0.60 (br. s., 1H). MS (ESI) m/z: 504.3 (M+H)$^+$. Analytical HPLC (method C): RT=1.7 min, purity=100%.

Example 48

(10R,14S)-14-[4-(6-Acetyl-3-chloro-2-fluorophenyl)-6-oxo-1,2,3,6-tetrahydropyridin-1-yl]-10-methyl-8,16-diazatricyclo[13.3.1.0$^{2,7}$]nonadeca-1(19),2,4,6,15,17-hexaen-9-one, TFA Salt

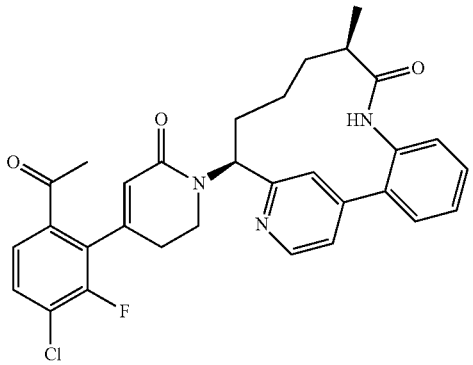 [SMILES: CC(=O)c1ccc(Cl)c(F)c1C1=CC(=O)N([C@H]2CCC[C@@H](C)C(=O)Nc3ccccc3-c3ccnc2c3)CC1]

A mixture of example 45 (27 mg, 0.046 mmol), tributyl (1-ethoxyvinyl)stannane (0.031 ml, 0.093 mmol) and Pd(PPh$_3$)$_2$Cl$_2$ (3.25 mg, 4.63 μmol) in toluene (1.029 ml) was degassed and heated at 110° C. for 24 h. The reaction mixture was concentrated to remove the solvent, then diluted with 2 ml of a 1:1 mixture of 1N HCl and THF. The mixture was stirred at rt for 0.5 h. The solvents were removed. The residue was purified by preparative HPLC to yield the desired product (22.2 mg, 71%). $^1$H NMR (500 MHz, DMSO-$d_6$) δ 9.72 (s, 1H), 8.74-8.66 (m, 1H), 7.84-7.74 (m, 2H), 7.66-7.57 (m, 2H), 7.53-7.40 (m, 3H), 7.24 (d, J=7.4 Hz, 1H), 5.70 (s, 1H), 5.59 (dd, J=12.7, 4.1 Hz, 1H), 3.99 (br. s., 1H), 3.80-3.71 (m, 1H), 2.56 (m, 4H), 2.09 (t, J=12.7 Hz, 1H), 1.91 (br. s., 1H), 1.77-1.65 (m, 1H), 1.50-1.38 (m, 1H), 1.23 (br. s., 1H), 0.89 (d, J=6.9 Hz, 3H), 0.58 (br. s., 1H). MS (ESI) m/z: 546.2 (M+H)$^+$. Analytical HPLC (method C): RT=1.6 min, purity=95%.

Example 49

4-Chloro-3-fluoro-2-{1-[(10R,14S)-10-methyl-9-oxo-8,16-diazatricyclo[13.3.1.0²,⁷]nonadeca-1(19),2,4,6,15,17-hexaen-14-yl]-6-oxo-1,2,3,6-tetrahydropyridin-4-yl}benzonitrile, TFA Salt

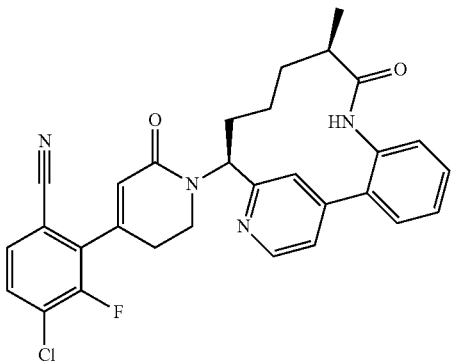 [SMILES: C[C@@H]1CCC[C@H](N2CCC(c3c(C#N)ccc(Cl)c3F)=CC2=O)c2cc(ccn2)-c2ccccc2NC1=O]

Example 49 was prepared by following the procedures described in example 3 by replacing 2A with example 45. ¹H NMR (500 MHz, METHANOL-d₄) δ 8.76 (d, J=5.5 Hz, 1H), 7.96 (s, 1H), 7.77-7.63 (m, 4H), 7.60-7.48 (m, 2H), 7.33 (dd, J=7.7, 1.1 Hz, 1H), 6.17 (s, 1H), 5.52 (dd, J=12.4, 4.7 Hz, 1H), 3.93-3.74 (m, 2H), 2.89-2.71 (m, 2H), 2.61 (dd, J=7.0, 5.1 Hz, 1H), 2.32-2.20 (m, 1H), 2.09-1.97 (m, 1H), 1.95-1.85 (m, 1H), 1.64-1.53 (m, 1H), 1.35-1.23 (m, 1H), 1.05 (d, J=6.9 Hz, 3H), 1.02-0.92 (m, 1H). MS (ESI) m/z: 529.2 (M+H)⁺. Analytical HPLC (method A): RT=6.5 min, purity=99%.

Example 50

3-Fluoro-2-{1-[(10R,14S)-10-methyl-9-oxo-8,16-diazatricyclo[13.3.1.0²,⁷]nonadeca-1(19),2,4,6,15,17-hexaen-14-yl]-6-oxo-1,2,3,6-tetrahydropyridin-4-yl}benzonitrile, TFA Salt

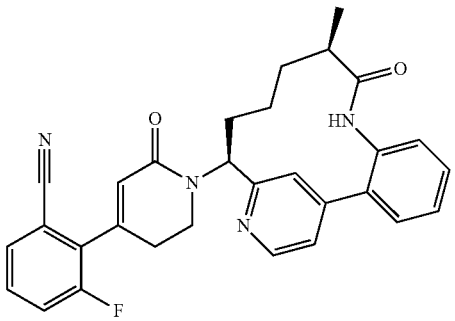 [SMILES: C[C@@H]1CCC[C@H](N2CCC(c3c(F)cccc3C#N)=CC2=O)c2cc(ccn2)-c2ccccc2NC1=O]

Example 50 was prepared as a side product in example 49. ¹H NMR (500 MHz, METHANOL-d₄) δ 8.82 (d, J=5.8 Hz, 1H), 8.09 (d, J=1.4 Hz, 1H), 7.88 (dd, J=5.8, 1.7 Hz, 1H), 7.76-7.68 (m, 2H), 7.65-7.53 (m, 4H), 7.37 (dd, J=7.8, 1.2 Hz, 1H), 6.17 (s, 1H), 5.49 (dd, J=12.5, 4.8 Hz, 1H), 3.91-3.75 (m, 2H), 2.95-2.76 (m, 2H), 2.68-2.60 (m, 1H), 2.37-2.28 (m, 1H), 2.15-2.05 (m, 1H), 1.98-1.88 (m, 1H), 1.68-1.57 (m, 1H), 1.38-1.28 (m, 1H), 1.07 (d, J=7.2 Hz, 3H), 1.05-0.93 (m, 1H). MS (ESI) m/z: 495.2 (M+H)⁺. Analytical HPLC (method A): RT=6.5 min, purity=98%.

Example 51

(10R,14S)-14-[4-(3-Chloro-2-fluoro-6-methylphenyl)-6-oxo-1,2,3,6-tetrahydropyridin-1-yl]-10-methyl-8,16-diazatricyclo[13.3.1.0²,⁷]nonadeca-1(19),2,4,6,15,17-hexaen-9-one, TFA Salt

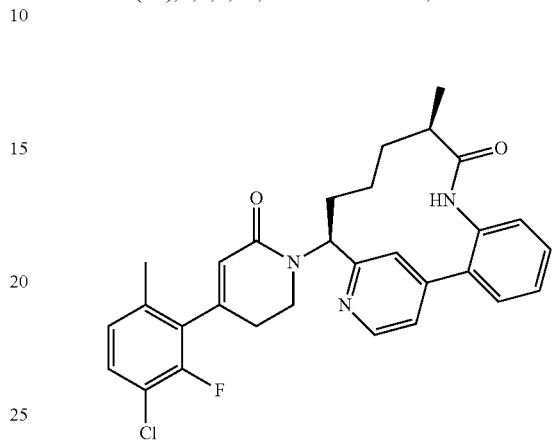

Example 51 was prepared by following the procedures described in example 2 by replacing 2A with example 45. ¹H NMR (500 MHz, DMSO-d₆) δ 9.70 (s, 1H), 8.67 (d, J=5.0 Hz, 1H), 7.62-7.55 (m, 2H), 7.51-7.36 (m, 4H), 7.27-7.14 (m, 2H), 5.84 (s, 1H), 5.63 (dd, J=12.7, 4.1 Hz, 1H), 3.99 (br. s., 1H), 3.79-3.70 (m, 1H), 2.63-2.54 (m, 2H), 2.25 (s, 3H), 2.08 (t, J=12.8 Hz, 1H), 1.92 (br. s., 1H), 1.77-1.63 (m, 1H), 1.44 (d, J=7.7 Hz, 1H), 1.25 (br. s., 1H), 0.94-0.82 (m, 4H), 0.57 (br. s., 1H). MS (ESI) m/z: 546.2 (M+H)⁺. Analytical HPLC (method C): RT=1.8 min, purity=95%.

Example 52

(10R,14S)-14-[4-(3-Chloro-6-cyclopropyl-2-fluorophenyl)-6-oxo-1,2,3,6-tetrahydropyridin-1-yl]-10-methyl-8,16-diazatricyclo[13.3.1.0²,⁷]nonadeca-1(19),2,4,6,15,17-hexaen-9-one, TFA Salt

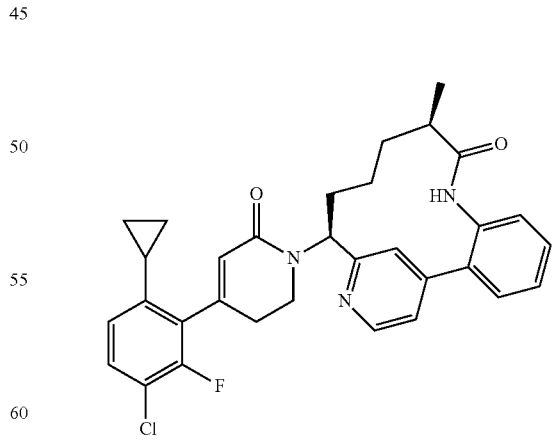

Example 52 was prepared by following the procedures described in example 55. ¹H NMR (500 MHz, METHANOL-d₄) δ 8.78 (d, J=5.8 Hz, 1H), 8.01-7.98 (m, 1H), 7.81-7.77 (m, 1H), 7.70 (dd, J=7.6, 1.5 Hz, 1H), 7.61-7.55 (m, 1H), 7.55-7.50 (m, 1H), 7.37-7.31 (m, 2H), 6.79 (dd, J=8.5, 0.8 Hz, 1H), 5.96 (t, J=1.4 Hz, 1H), 5.48 (dd, J=12.5, 4.5 Hz, 1H), 3.88-3.74 (m, 2H), 2.81-2.56 (m, 3H), 2.29 (tdd, J=12.8, 6.7, 3.4 Hz, 1H), 2.10-1.99 (m, 1H), 1.94-1.84 (m, 2H), 1.65-1.54 (m, 1H), 1.29 (d, J=2.5 Hz, 1H), 1.08-1.02 (m, 3H), 1.01-0.94 (m, 2H), 0.74-0.70 (m, 1H). MS (ESI) m/z: 543.9 (M+H)+. Analytical HPLC (method A): RT=8.0 min, purity=96%.

Example 53

2-(tert-Butoxy)ethyl N-[(10R,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate, TFA Salt

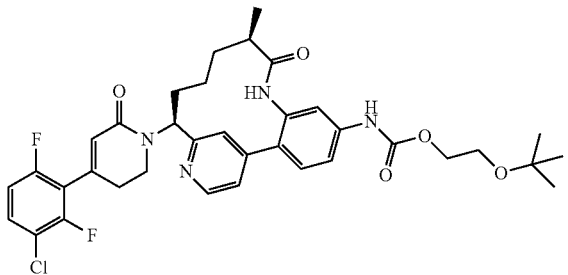 [SMILES: C[C@@H]1CCC[C@H](N2CCC(c3c(F)ccc(Cl)c3F)=CC2=O)c2cc(ccn2)-c2ccc(NC(=O)OCCOC(C)(C)C)cc2NC1=O]

To a clear light yellow solution of example 12 (60 mg, 0.112 mmol) in DCM (3 ml)/MeCN (3 ml) at 0° C. was added NaHCO$_3$ (28.2 mg, 0.335 mmol) followed by phosgene solution (20% in toluene) (0.176 ml, 0.335 mmol). After 30 min, the reaction was concentrated in vacuo for 30 min to remove the solvent and extra phosgene. The residue was dissolved in MeCN (1 mL)/DCM (1 mL) and to this solution at 0° C. under argon was added 2-hydroxyacetic acid (6.18 mg, 0.081 mmol) and Et$_3$N (7.55 µl, 0.054 mmol). The resulted cloudy mixture was stirred at 0° C. for 30 min, then at rt for 3 days. The reaction was concentrated and the residue was purified by preparative HPLC to yield the desired product as a pale yellow solid (17.4 mg, 19%). $^1$H NMR (500 MHz, METHANOL-d$_4$) δ 9.74 (s, 1H), 8.79 (d, J=6.1 Hz, 1H), 8.16 (d, J=1.4 Hz, 1H), 7.94 (dd, J=5.9, 1.8 Hz, 1H), 7.69 (d, J=8.3 Hz, 1H), 7.63-7.52 (m, 3H), 7.12 (td, J=9.3, 1.8 Hz, 1H), 6.14 (s, 1H), 5.39 (dd, J=12.4, 4.7 Hz, 1H), 4.30-4.25 (m, 2H), 3.84-3.71 (m, 2H), 3.70-3.65 (m, 2H), 2.95-2.85 (m, 1H), 2.81-2.73 (m, 1H), 2.71-2.62 (m, 1H), 2.39-2.28 (m, 1H), 2.16-2.07 (m, 1H), 1.99-1.89 (m, 1H), 1.71-1.60 (m, 1H), 1.42-1.31 (m, 1H), 1.23 (s, 9H), 1.08 (d, J=6.9 Hz, 3H), 1.04-0.89 (m, 1H). MS (ESI) m/z: 681.2 (M+H)+. Analytical HPLC (method A): RT=7.7 min, purity=99%.

Example 54

2-Hydroxyethyl N-[(10R,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate, TFA Salt

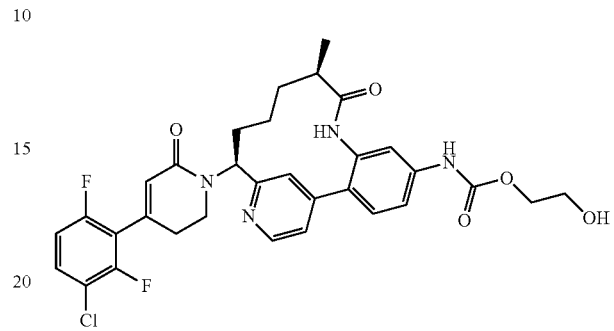

To a solution of example 53 (15.8 mg, 0.020 mmol) in DCM (0.7 mL) was added TFA (0.153 mL, 1.987 mmol). The clear solution was stirred at rt for 5 hr. The reaction mixture was concentrated and the residue was purified by preparative HPLC to yield the desired product as a pale yellow solid (10 mg, 67%). $^1$H NMR (500 MHz, METHANOL-d$_4$) δ 9.66 (s, 1H), 8.74 (d, J=6.1 Hz, 1H), 8.06 (s, 1H), 7.84 (dd, J=6.1, 1.7 Hz, 1H), 7.66-7.63 (m, 1H), 7.59-7.50 (m, 3H), 7.10 (td, J=9.3, 1.8 Hz, 1H), 6.11 (s, 1H), 5.41 (dd, J=12.7, 4.7 Hz, 1H), 4.27-4.22 (m, 2H), 3.82-3.68 (m, 4H), 2.90-2.59 (m, 3H), 2.29 (ddt, J=16.0, 13.0, 3.3 Hz, 1H), 2.12-2.01 (m, 1H), 1.97-1.86 (m, 1H), 1.67-1.55 (m, 1H), 1.32 (br. s., 1H), 1.05 (d, J=6.9 Hz, 3H), 1.02-0.88 (m, 1H). MS (ESI) m/z: 625.2 (M+H)+. Analytical HPLC (method A): RT=5.8 min, purity=99%.

Example 55

(10R,14S)-14-{4-[3-Chloro-2-fluoro-6-(1H-pyrazol-4-yl)phenyl]-6-oxo-1,2,3,6-tetrahydropyridin-1-yl}-10-methyl-8,16-diazatricyclo[13.3.1.0$^{2,7}$]nonadeca-1(19),2,4,6,15,17-hexaen-9-one, TFA Salt

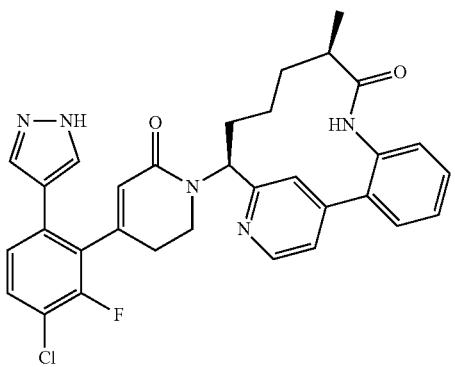 [SMILES: C[C@@H]1CCC[C@H](N2CCC(c3c(-c4cn[nH]c4)ccc(Cl)c3F)=CC2=O)c2cc(ccn2)-c2ccccc2NC1=O]

To a microwave tube was added example 45 (19 mg, 0.033 mmol), tert-butyl 4-(4,4,5,5-tetramethyl-1,3,2-dioxaborolan-2-yl)-1H-pyrazole-1-carboxylate (10.55 mg, 0.036 mmol), potassium phosphate (32.6 µl, 0.098 mmol) and THF (326 μl). The reaction mixture was bubbled through Ar for several minutes and (DtBPF)PdCl$_2$ (1.062 mg, 1.630 μmol) was added. The reaction vessel was sealed and heated at 65° C. overnight. Then, the reaction mixture was cooled down to rt. 0.05 ml of MeOH and NaOH was added, stirred at rt overnight. A few drops of MeOH and 1N NaOH were added, heated at 50° C. for 1 hrs. The solvent was removed and the residue was purified by preparative HPLC to yield the desired product (10 mg, 38%) as a white solid. $^1$H NMR (500 MHz, METHANOL-d$_4$) δ 8.81 (d, J=6.1 Hz, 1H), 8.11 (d, J=1.4 Hz, 1H), 7.92 (dd, J=5.9, 1.8 Hz, 1H), 7.77 (s, 2H), 7.72 (dd, J=7.7, 1.4 Hz, 1H), 7.64-7.58 (m, 1H), 7.56-7.51 (m, 1H), 7.49 (dd, J=8.3, 7.7 Hz, 1H), 7.34 (dd, J=8.0, 1.1 Hz, 1H), 7.28 (dd, J=8.4, 1.2 Hz, 1H), 5.96 (s, 1H), 5.37 (dd, J=12.5, 4.8 Hz, 1H), 3.70-3.56 (m, 2H), 2.66-2.52 (m, 2H), 2.49-2.41 (m, 1H), 2.32-2.22 (m, 1H), 2.09-2.00 (m, 1H), 1.93-1.82 (m, 1H), 1.64-1.54 (m, 1H), 1.29 (br. s., 1H), 1.04 (d, J=6.9 Hz, 3H), 0.96 (br. s., 1H). MS (ESI) m/z: 570.1 (M+H)$^+$. Analytical HPLC (method A): RT=6.3 min, purity=99%.

Example 56

(10R,14S)-14-{4-[3-Chloro-2-fluoro-6-(pyridin-4-yl)phenyl]-6-oxo-1,2,3,6-tetrahydropyridin-1-yl}-10-methyl-8,16-diazatricyclo[13.3.1.0$^{2,7}$]nonadeca-1(19),2,4,6,15,17-hexaen-9-one, TFA Salt

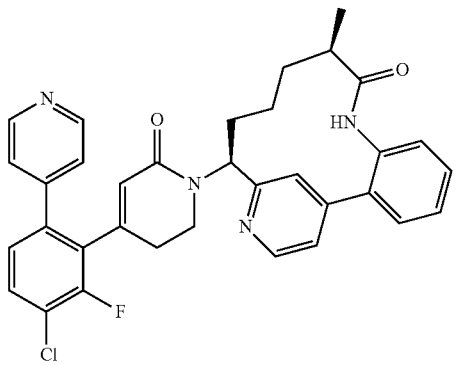 [SMILES: C[C@@H]1CCC[C@H](N2CCC(c3c(-c4ccncc4)ccc(Cl)c3F)=CC2=O)c2cc(ccn2)-c2ccccc2NC1=O]

Example 56 was prepared by following the procedures described in example 55. $^1$H NMR (400 MHz, METHANOL-d$_4$) δ 8.79 (d, J=6.6 Hz, 2H), 8.71 (d, J=5.3 Hz, 1H), 7.92 (d, J=6.6 Hz, 2H), 7.81 (s, 1H), 7.71 (dd, J=8.4, 7.3 Hz, 1H), 7.66-7.62 (m, 2H), 7.58-7.46 (m, 2H), 7.40-7.28 (m, 2H), 5.73 (s, 1H), 5.43 (dd, J=12.8, 4.4 Hz, 1H), 3.75-3.54 (m, 2H), 2.68-2.50 (m, 3H), 2.25-2.10 (m, 1H), 1.97-1.78 (m, 2H), 1.60-1.46 (m, 1H), 1.34-1.16 (m, 1H), 1.04 (d, J=6.9 Hz, 3H), 1.01-0.93 (m, 1H). MS (ESI) m/z: 581.1 (M+H)$^+$. Analytical HPLC (method A): RT=5.0 min, purity=98%.

Example 57

(10R,14S)-14-[4-(3-Chloro-2-fluoro-6-phenylphenyl)-6-oxo-1,2,3,6-tetrahydropyridin-1-yl]-10-methyl-8,16-diazatricyclo[13.3.1.0$^{2,7}$]nonadeca-1(19),2,4,6,15,17-hexaen-9-one, TFA Salt

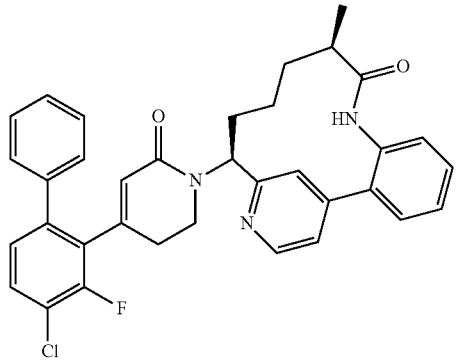 [SMILES: C[C@@H]1CCC[C@H](N2CCC(c3c(-c4ccccc4)ccc(Cl)c3F)=CC2=O)c2cc(ccn2)-c2ccccc2NC1=O]

Example 57 was prepared by following the procedures described in example 55. $^1$H NMR (400 MHz, METHANOL-d$_4$) δ 8.78 (d, J=5.7 Hz, 1H), 8.04 (d, J=1.5 Hz, 1H), 7.89 (dd, J=5.9, 1.8 Hz, 1H), 7.71 (dd, J=7.7, 1.5 Hz, 1H), 7.63-7.49 (m, 3H), 7.43-7.31 (m, 6H), 7.21 (dd, J=8.4, 1.3 Hz, 1H), 5.85 (s, 1H), 5.29 (dd, J=12.3, 4.8 Hz, 1H), 3.55-3.36 (m, 2H), 2.60 (td, J=7.3, 2.6 Hz, 1H), 2.52-2.40 (m, 1H), 2.36-2.15 (m, 2H), 2.01-1.79 (m, 2H), 1.62-1.50 (m, 1H), 1.31-1.19 (m, 1H), 1.02 (d, J=7.0 Hz, 3H), 0.98-0.81 (m, 1H). MS (ESI) m/z: 580.3 (M+H)$^+$. Analytical HPLC (method A): RT=8.6 min, purity=99%.

Example 58

(10R,14S)-14-{4-[3-Chloro-2-fluoro-6-(pyridin-3-yl)phenyl]-6-oxo-1,2,3,6-tetrahydropyridin-1-yl}-10-methyl-8,16-diazatricyclo[13.3.1.0$^{2,7}$]nonadeca-1(19),2,4,6,15,17-hexaen-9-one, TFA Salt

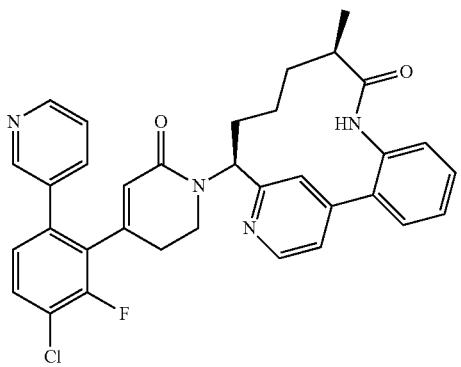 [SMILES: C[C@@H]1CCC[C@H](N2CCC(c3c(-c4cccnc4)ccc(Cl)c3F)=CC2=O)c2cc(ccn2)-c2ccccc2NC1=O]

Example 58 was prepared by following the procedures described in example 55. $^1$H NMR (500 MHz, DMSO-d$_6$) δ 9.69 (s, 1H), 8.64 (d, J=8.8 Hz, 3H), 8.00-7.88 (m, 2H), 7.75 (t, J=7.8 Hz, 1H), 7.62-7.51 (m, 3H), 7.50-7.33 (m, 4H), 7.23 (d, J=7.4 Hz, 1H), 5.76 (s, 1H), 5.50 (d, J=11.0 Hz, 1H), 3.50-3.41 (m, 2H), 2.56 (br. s., 1H), 2.35 (br. s., 2H), 1.99 (t, J=12.5 Hz, 1H), 1.87 (br. s., 1H), 1.61 (br. s., 1H), 1.40

(d, J=6.1 Hz, 1H), 1.19 (br. s., 1H), 0.87 (d, J=6.6 Hz, 3H), 0.51 (br. s., 1H). MS (ESI) m/z: 581.2 (M+H)⁺. Analytical HPLC (method C): RT=1.8 min, purity=100%.

Example 59

(10R,14S)-14-{4-[3-Chloro-2-fluoro-6-(1-methyl-1H-pyrazol-4-yl)phenyl]-6-oxo-1,2,3,6-tetrahydro-pyridin-1-yl}-10-methyl-8,16-diazatricyclo[13.3.1.0$^{2,7}$]nonadeca-1(19),2,4,6,15,17-hexaen-9-one, TFA Salt

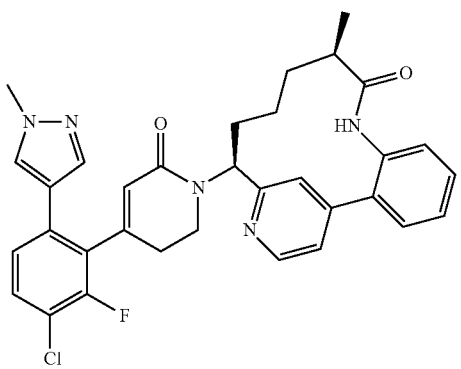 [SMILES: C[C@@H]1CCC[C@H](N2CCC(c3c(-c4cnn(C)c4)ccc(Cl)c3F)=CC2=O)c2cc(ccn2)-c2ccccc2NC1=O]

Example 59 was prepared by following the procedures described in example 55. ¹H NMR (500 MHz, DMSO-d$_6$) δ 9.70 (br. s., 1H), 8.66 (br. s., 1H), 7.95 (br. s., 2H), 7.58 (br. s., 4H), 7.50-7.38 (m, 3H), 7.29 (d, J=8.5 Hz, 1H), 7.22 (d, J=7.2 Hz, 1H), 5.87 (br. s., 1H), 5.57 (d, J=12.4 Hz, 1H), 3.84 (br. s., 3H), 3.62 (br. s., 2H), 2.56 (br. s., 1H), 2.35 (br. s., 2H), 2.09-1.98 (m, 1H), 1.89 (br. s., 1H), 1.69 (br. s., 1H), 1.42 (br. s., 1H), 1.21 (br. s., 1H), 0.87 (br. s., 3H), 0.55 (br. s., 1H). MS (ESI) m/z: 581.2 (M+H)⁺. Analytical HPLC (method C): RT=1.9 min, purity=96%.

Example 60

(10R,14S)-14-{4-[3-Chloro-6-(1,3-dimethyl-1H-pyrazol-4-yl)-2-fluorophenyl]-6-oxo-1,2,3,6-tetrahydropyridin-1-yl}-10-methyl-8,16-diazatricyclo[13.3.1.0$^{2,7}$]nonadeca-1(19),2,4,6,15,17-hexaen-9-one, TFA Salt

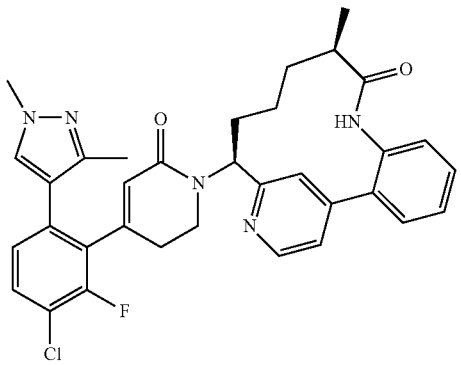 [SMILES: Cc1nn(C)cc1-c1ccc(Cl)c(F)c1C1=CC(=O)N([C@H]2CCC[C@@H](C)C(=O)Nc3ccccc3-c3ccnc2c3)CC1]

Example 60 was prepared by following the procedures described in example 55. ¹H NMR (500 MHz, DMSO-d$_6$) δ 9.70 (s, 1H), 8.62 (d, J=5.0 Hz, 1H), 7.95 (s, 1H), 7.65 (s, 1H), 7.62-7.54 (m, 2H), 7.51-7.38 (m, 3H), 7.37-7.32 (m, 1H), 7.23-7.19 (m, 1H), 7.15 (d, J=8.3 Hz, 1H), 5.82 (s, 1H), 5.56 (dd, J=12.7, 4.4 Hz, 1H), 3.73 (s, 4H), 3.50-3.40 (m, 1H), 2.61-2.52 (m, 1H), 2.26-2.14 (m, 2H), 2.05 (s, 3H), 2.02-1.94 (m, 1H), 1.89 (br. s., 1H), 1.67-1.55 (m, 1H), 1.46-1.34 (m, 1H), 1.27-1.11 (m, 1H), 0.85 (d, J=6.9 Hz, 3H), 0.48 (br. s., 1H). MS (ESI) m/z: 598.2 (M+H)⁺. Analytical HPLC (method D): RT=1.7 min, purity=96%.

Example 61

(10R,14S)-5-Amino-14-[4-(3-chloro-2,6-difluorophenyl)-6-oxo-1,2,3,6-tetrahydropyridin-1-yl]-4-iodo-10-methyl-8,16-diazatricyclo[13.3.1.0$^{2,7}$]nonadeca-1(19),2,4,6,15,17-hexaen-9-one, TFA Salt

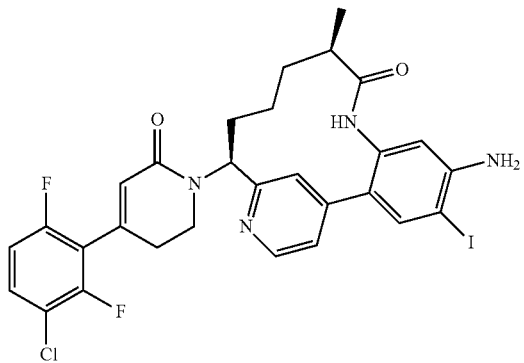 [SMILES: C[C@@H]1CCC[C@H](N2CCC(c3c(F)ccc(Cl)c3F)=CC2=O)c2cc(ccn2)-c2cc(I)c(N)cc2NC1=O]

To cooled (0° C.) solution of Example 12 (25 mg, 0.047 mmol) in MeOH (4 mL) was added dropwise a solution of iodine monochloride (11.34 mg, 0.070 mmol) in CH$_2$Cl$_2$ (0.2 mL). After 5 min., the reaction mixture was concentrated to yield a yellow solid. The solid was partitioned between EtOAc and sat. aq. NaHCO$_3$ and the layers were separated. The organic layer was washed with brine, dried over MgSO$_4$, filtered, and concentrated. Purification by silica gel chromatography gave the title compound as a white solid (19 mg, 58%). ¹H NMR (500 MHz, METHANOL-d$_4$) δ 8.57 (d, J=4.4 Hz, 1H), 7.83 (s, 1H), 7.59-7.47 (m, 2H), 7.31 (d, J=3.6 Hz, 1H), 7.08 (t, J=8.9 Hz, 1H), 6.67 (s, 1H), 6.10 (br. s., 1H), 5.62 (d, J=11.8 Hz, 1H), 3.81 (br. s., 1H), 3.73-3.62 (m, 1H), 2.65 (br. s., 2H), 2.54 (br. s., 1H), 2.21-2.09 (m, 1H), 1.98-1.79 (m, 2H), 1.55 (d, J=7.4 Hz, 1H), 1.38-1.14 (m, 1H), 1.04 (d, J=6.3 Hz, 3H), 0.90 (br. s., 1H). MS (ESI) m/z: 663.0 (M+H)⁺. Analytical HPLC (method A): RT=6.9 min, purity=94%.

Example 62

Methyl N-[(10R,14S)-14-[4-(3-chloro-2,6-difluoro-phenyl)-6-oxo-1,2,3,6-tetrahydropyridin-1-yl]-4-iodo-10-methyl-9-oxo-8,16-diazatricyclo[13.3.1.0$^{2,7}$]nonadeca-1(19),2,4,6,15,17-hexaen-5-yl]carbamate, TFA Salt

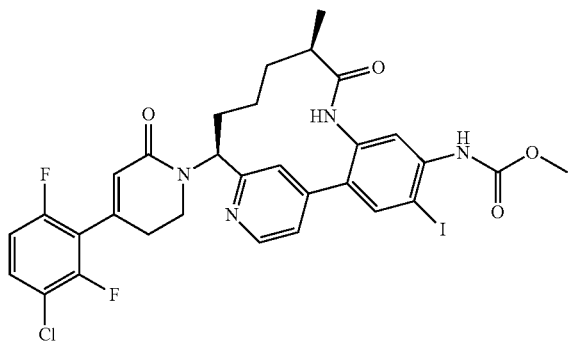 [SMILES: COC(=O)Nc1cc2c(cc1I)-c1ccnc(c1)[C@@H](N1CCC(c3c(F)ccc(Cl)c3F)=CC1=O)CCC[C@@H](C)C(=O)N2]

To a solution of example 61(18 mg, 0.027 mmol) and pyridine (4.30 mg, 0.054 mmol) in CH$_2$Cl$_2$ (2 mL) was added methyl carbonochloridate (3.08 mg, 0.033 mmol) at 0° C. The reaction mixture was warmed up to rt and stirred at rt. Excess methyl carbonochloridate (5.13 mg, 0.054 mmol) and pyridine (4.39 μl, 0.054 mmol) was added to. After 2.5 hrs, reaction mixture was concentrated in vacuo. The residue was purified by prep HPLC to yield example 62 as a pale yellow solid (16.54 mg, 71%). $^1$H NMR (500 MHz, METHANOL-d$_4$) δ 9.30 (s, 1H), 8.87 (d, J=5.5 Hz, 1H), 8.10 (s, 1H), 7.98 (s, 1H), 7.83 (s, 1H), 7.73 (dd, J=5.5, 1.4 Hz, 1H), 7.68 (s, 1H), 7.59 (td, J=8.7, 5.5 Hz, 1H), 7.17 (td, J=9.2, 1.7 Hz, 1H), 6.11 (s, 1H), 5.53 (dd, J=12.5, 5.1 Hz, 1H), 4.22 (dt, J=12.1, 6.1 Hz, 1H), 3.85 (ddd, J=12.3, 10.0, 5.0 Hz, 1H), 3.78 (s, 3H), 3.00-2.89 (m, 1H), 2.81-2.68 (m, 2H), 2.37 (m, 1H), 2.05-2.00 (m, 1H), 1.97-1.90 (m, 1H), 1.65-1.53 (m, 1H), 1.49-1.37 (m, 1H), 0.93 (d, J=6.9 Hz, 3H), 0.65-0.50 (m, 1H). MS (ESI) m/z: 721.1 (M+H)$^+$. Analytical HPLC (method A): RT=8.2 min, purity=97%.

Example 63

3-Acetyl-1-[(10R,14S)-14-[4-(3-chloro-2,6-difluoro-phenyl)-6-oxo-1,2,3,6-tetrahydropyridin-1-yl]-10-methyl-9-oxo-8,16-diazatricyclo[13.3.1.0$^{2,7}$]non-adeca-1(19),2,4,6,15,17-hexaen-5-yl]thiourea

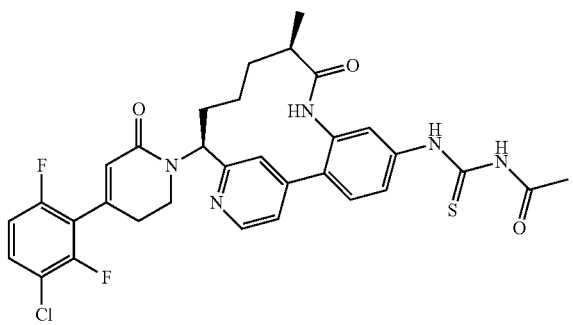 [SMILES: CC(=O)NC(=S)Nc1ccc2c(c1)NC(=O)[C@H](C)CCC[C@H](N1CCC(c3c(F)ccc(Cl)c3F)=CC1=O)c1cc-2ccn1]

To example 12 (8 mg, 0.015 mmol) in acetone (0.5 mL) was added acetyl isothiocyanate (2.260 mg, 0.022 mmol). The reaction mixture was stirred at rt and monitored by LCMS. The reaction mixture was concentrated in vacuo and purified by prep HPLC. The desired fraction was neutralized by passing through a NaHCO$_3$ resin cartridge, then concentrated to yield pale yellow solid (0.88 mg, 9%). $^1$H NMR (500 MHz, METHANOL-d$_4$) δ 8.66 (d, J=5.0 Hz, 1H), 8.01-7.95 (m, 1H), 7.81 (dq, J=4.5, 2.2 Hz, 2H), 7.66-7.60 (m, 2H), 7.55-7.46 (m, 1H), 7.44-7.35 (m, 1H), 7.08 (td, J=9.2, 1.9 Hz, 1H), 6.10 (s, 1H), 5.67 (dd, J=12.7, 4.4 Hz, 1H), 3.95 (br. s., 1H), 3.82-3.70 (m, 1H), 2.74-2.54 (m, 3H), 2.23-2.12 (m, 4H), 2.00-1.81 (m, 2H), 1.61-1.49 (m, 1H), 1.29 (m, 1H), 1.03 (d, J=6.9 Hz, 3H), 0.99-0.77 (m, 1H). MS (ESI) m/z: 638.2 (M+H)$^+$. Analytical HPLC (method B): RT=6.2 min, purity=92%.

Example 64

Methyl N-[(10R,14S)-14-[4-(3-chloro-2,6-difluoro-phenyl)-5-methyl-6-oxo-1,2,3,6-tetrahydropyridin-1-yl]-10-methyl-9-oxo-8,16-diazatricyclo[13.3.1.0$^{\{2,7\}}$]nonadeca-1(19),2,4,6,15,17-hexaen-5-yl]carbamate, TFA Salt

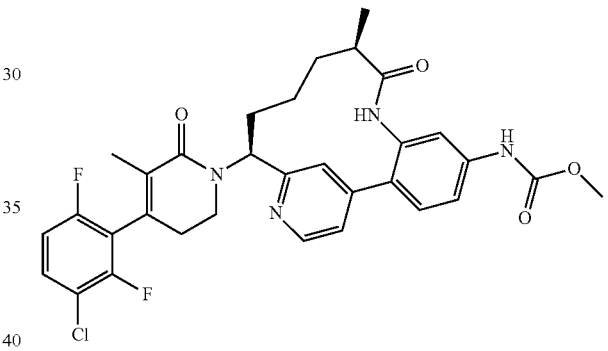

64A Ethyl (1-chloro-1-oxopropan-2-yl)phosphonate

To a solution of 2-(diethoxyphosphoryl)propanoic acid (242 mg, 1.151 mmol, prepared according to Luke, G. P. et al., *J. Org. Chem.*, 73:6397 (2008)) in CH$_2$Cl$_2$ (0.8 mL) was added oxalyl dichloride (2M in DCM) (0.8 mL, 1.600 mmol) and followed by a drop DMF and stirred at rt. The reaction mixture was concentrated in vacuo to yield 64A as yellow oil (263 mg, 100%). $^1$H NMR (500 MHz, CHLOROFORM-d) δ 4.27-4.17 (m, 4H), 3.51 (dq, J=23.4, 7.2 Hz, 1H), 1.57 (dd, J=17.1, 7.2 Hz, 3H), 1.38 (m, 6H). $^{31}$P NMR (500 MHz, CHLOROFORM-d) δ ppm: 18.82.

64B methyl N-[(10R,14S)-14-[4-(3-chloro-2,6-difluoro-phenyl)-5-methyl-6-oxo-1,2,3,6-tetrahydropyridin-1-yl]-10-methyl-9-oxo-8,16-diazatricyclo[13.3.1.0$^{2,7}$]nonadeca-1 (19),2,4,6,15,17-hexaen-5-yl]carbamate was prepared according the procedure 1K by change intermediate 8 to 64A.

Example 64

To a solution of 64B (35 mg, 0.046 mmol) in THF (3 mL) was added DBU (57.5 mg, 0.229 mmol) and lithium chloride (19.44 mg, 0.459 mmol). The reaction mixture was stirred at rt. After 16 hrs, the reaction mixture was concentrated and purified by prep HPLC to yield the desired product as pale yellow solid (1.22 mg, 3%). ¹H NMR (500 MHz, METHANOL-d₄) δ 9.63 (s, 1H), 8.73 (dd, J=5.5, 2.5 Hz, 1H), 7.93 (s, 2H), 7.73-7.53 (m, 4H), 7.17-7.09 (m, 1H), 5.54 (dd, J=12.9, 3.9 Hz, 1H), 3.86-3.68 (m, 5H), 2.72-2.53 (m, 2H), 2.34-2.20 (m, 1H), 2.11-1.91 (m, 2H), 1.86-1.57 (m, 5H), 1.42-1.27 (m, 1H), 1.09 (d, J=6.9 Hz, 3H), 1.05-0.85 (m, 1H). MS (ESI) m/z: 609.1 (M+H)⁺. Analytical HPLC (method B): RT=4.1 min, purity=90%.

Example 65

(10R,14S)-14-[4-(3-Chloro-2-fluorophenyl)-2-oxo-1,2-dihydropyridin-1-yl]-10-methyl-8,16-diazatricyclo[13.3.1.0²,⁷]nonadeca-1(19),2,4,6,15,17-hexaen-9-one, TFA Salt

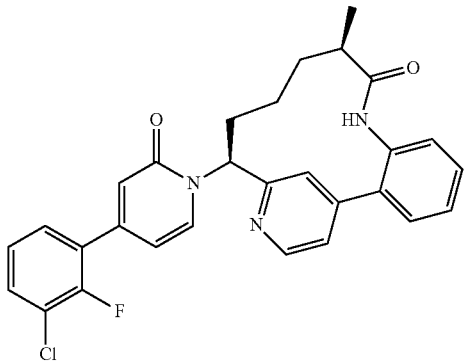 [SMILES: C[C@@H]1CCC[C@H](n2ccc(-c3cccc(Cl)c3F)cc2=O)c2cc(ccn2)-c2ccccc2NC1=O]

To a solution of example 45 (31 mg, 0.053 mmol), NH₄OH (9.62 μl, 0.069 mmol), CuI (2.026 mg, 10.64 μmol), L-proline (2.449 mg, 0.021 mmol), K₂CO₃ (22.05 mg, 0.160 mmol) in DMSO (500 μl) was bubbled with Ar. The reaction mixture was sealed and heated at 95C for 16 hrs. The reaction mixture was filtered and purified by prep HPLC to yield the desired product as white solid (7.3 mg, 22%). ¹H NMR (500 MHz, METHANOL-d₄) δ 8.74 (br. s., 1H), 8.26 (d, J=7.2 Hz, 1H), 8.00 (br. s., 1H), 7.72-7.64 (m, 2H), 7.63-7.45 (m, 4H), 7.36-7.26 (m, 2H), 6.75 (s, 1H), 6.72-6.66 (m, 1H), 6.15-6.03 (m, 1H), 2.77-2.67 (m, 1H), 2.47-2.36 (m, 1H), 2.18-2.08 (m, 1H), 2.07-1.96 (m, 1H), 1.66-1.46 (m, 2H), 1.02 (d, J=6.9 Hz, 3H), 0.82 (br. s., 1H). MS (ESI) m/z: 502.0 (M+H)⁺. Analytical HPLC (method B): RT=8.5 min, purity=99%.

Example 66

(10R,14S)-14-[4-(6-Amino-3-chloro-2-fluorophenyl)-6-oxo-1,2,3,6-tetrahydropyridin-1-yl]-10-methyl-8,16-diazatricyclo[13.3.1.0²,⁷]nonadeca-1(19),2,4,6,15,17-hexaen-9-one, TFA Salt

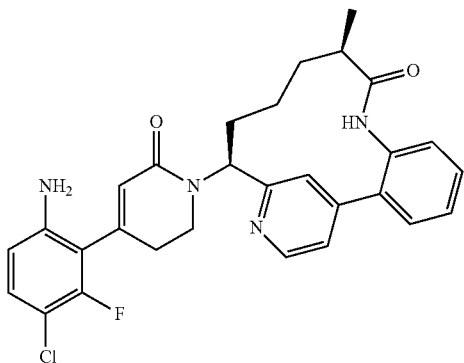 [SMILES: C[C@@H]1CCC[C@H](N2CCC(c3c(N)ccc(Cl)c3F)=CC2=O)c2cc(ccn2)-c2ccccc2NC1=O]

To a solution of example 45 (31 mg, 0.053 mmol), NH₄OH (9.62 μl, 0.069 mmol), CuI (2.026 mg, 10.64 μmol), L-proline (2.449 mg, 0.021 mmol), K₂CO₃ (22.05 mg, 0.160 mmol) in DMSO (500 μl) was bubbled with Ar. The reaction mixture was sealed and heated at 95C for 16 hrs. The reaction mixture was filtered and purified by prep HPLC to yield the desired product as pale yellow solid (1.4 mg, 3.5%). ¹H NMR (500 MHz, METHANOL-d₄) δ 88.73 (d, J=5.2 Hz, 1H), 7.81 (s, 1H), 7.67 (dd, J=7.4, 1.7 Hz, 1H), 7.62-7.48 (m, 3H), 7.33 (dd, J=7.7, 1.4 Hz, 1H), 7.11 (t, J=8.7 Hz, 1H), 6.56 (dd, J=8.8, 1.4 Hz, 1H), 6.05-5.98 (m, 1H), 5.60 (dd, J=12.5, 4.3 Hz, 1H), 3.89-3.71 (m, 2H), 2.72-2.55 (m, 3H), 2.30-2.19 (m, 1H), 2.11-1.86 (m, 2H), 1.69-1.53 (m, 1H), 1.43-1.23 (m, 2H), 1.08 (d, J=6.9 Hz, 3H). MS (ESI) m/z: 519.1 (M+H)⁺. Analytical HPLC (method B): RT=6.6 min, purity=99%.

Example 67

(10R,14S)-14-{4-[3-Chloro-2-fluoro-6-(trifluoromethyl)phenyl]-6-oxo-1,2,3,6-tetrahydropyridin-1-yl}-10-methyl-8,16-diazatricyclo[13.3.1.0²,⁷]nonadeca-1(19),2(7),3,5,15,17-hexaen-9-one, TFA Salt

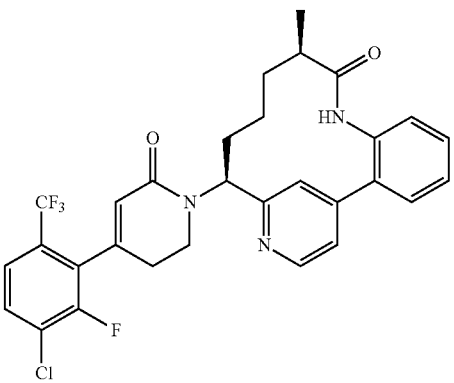

Example 67 was prepared by following the procedures described in example 45. ¹H NMR (500 MHz, 1:1 MeOD:CDCl₃) δ 8.64 (d, J=5.4 Hz, 1H), 7.62-7.56 (m, 3H), 7.55-7.48 (m, 2H), 7.47-7.39 (m, 2H), 7.37-7.32 (m, 1H), 7.27-7.21 (m, 1H), 5.92 (s, 1H), 5.67 (dd, J=12.9, 4.5 Hz, 1H), 3.97 (br. s., 1H), 3.83-3.64 (m, 1H), 2.61-2.51 (m, 2H), 2.22-2.09 (m, 1H), 1.96-1.77 (m, 2H), 1.58-1.46 (m, 1H), 1.32-1.20 (m, 1H), 1.01 (d, J=6.9 Hz, 3H), 0.88 (br. s., 1H). MS (ESI) m/z: 571.9 (M+H)⁺. Analytical HPLC (method C): RT=2.0 min, purity=100%.

Example 68

(10R,14S)-14-{4-[3-Chloro-2-fluoro-6-(1H-1,2,3,4-tetrazol-1-yl)phenyl]-6-oxo-1,2,3,6-tetrahydropyridin-1-yl}-10-methyl-8,16-diazatricyclo[13.3.1.0²,⁷]nonadeca-1(19),2(7),3,5,15,17-hexaen-9-one, TFA Salt

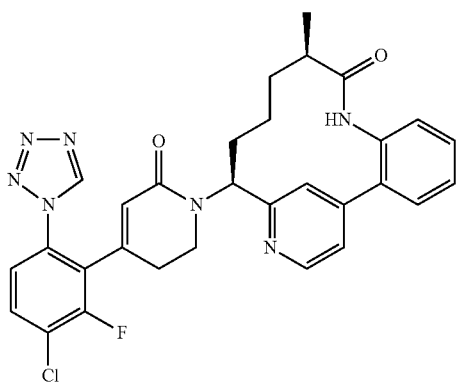 [SMILES: C[C@@H]1CCC[C@H](N2CCC(c3c(-n4cnnn4)ccc(Cl)c3F)=CC2=O)c2cc(ccn2)-c2ccccc2NC1=O]

Example 68 was prepared by following the procedures described in example 45. ¹H NMR (500 MHz, CDCl₃) 8.95 (s, 1H), 8.82 (br. s., 1H), 8.71 (d, J=5.8 Hz, 1H), 8.24 (s, 1H), 7.72 (dd, J=5.9, 1.5 Hz, 1H), 7.64 (dd, J=8.5, 7.7 Hz, 1H), 7.55-7.49 (m, 2H), 7.49-7.44 (m, 1H), 7.32-7.23 (m, 2H), 5.66 (s, 1H), 5.15 (dd, J=12.4, 5.0 Hz, 1H), 3.83 (d, J=5.2 Hz, 1H), 3.63 (ddd, J=12.4, 8.9, 5.4 Hz, 1H), 2.80-2.60 (m, 2H), 2.57-2.35 (m, 2H), 1.98-1.80 (m, 2H), 1.62-1.49 (m, 1H), 1.37 (br. s., 1H), 0.98 (d, J=6.9 Hz, 3H), 0.62 (br. s., 1H). MS (ESI) m/z: 571.8 (M+H)⁺. Analytical HPLC (method A): RT=6.4 min, purity >95%.

Example 69

(10R,14S)-5-Bromo-14-[4-(3-chloro-2,6-difluorophenyl)-6-oxo-1,2,3,6-tetrahydropyridin-1-yl]-10-methyl-8,16-diazatricyclo[13.3.1.0²,⁷]nonadeca-1(19),2,4,6,15,17-hexaen-9-one, TFA Salt

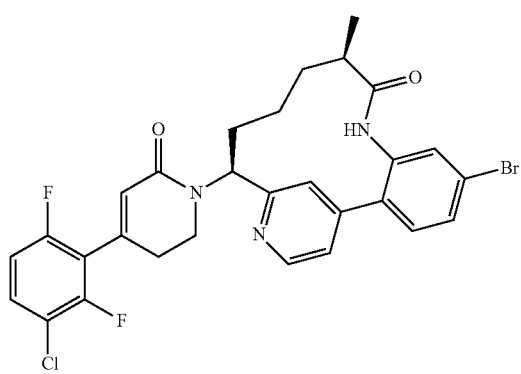 [SMILES: C[C@@H]1CCC[C@H](N2CCC(c3c(F)ccc(Cl)c3F)=CC2=O)c2cc(ccn2)-c2ccc(Br)cc2NC1=O]

To a solution of tert-butyl nitrite (0.029 mL, 0.218 mmol) in MeCN (0.5 mL) was added CuBr₂ (48.7 mg, 0.218 mmol) and the mixture was stirred at rt for 10 mins. Then, it was added to a solution of Example 12 (78 mg, 0.145 mmol) in 3 ml MeCN. The mixture was stirred at rt for 24 hrs. Then, the reaction mixture was diluted with EtOAc, washed with diluted 1N HCl in water and brine, dried over MgSO₄, filtered off solid, concentrated and purified by ISCO to yield the desired product as off-white solid (63 mg, 69%). ¹H NMR (500 MHz, METHANOL-d₄) 8.65 (d, J=5.1 Hz, 1H), 7.63-7.55 (m, 2H), 7.55-7.47 (m, 2H), 7.44 (d, J=2.0 Hz, 1H), 7.37 (dd, J=5.2, 1.7 Hz, 1H), 7.07 (td, J=9.2, 1.8 Hz, 1H), 6.10 (s, 1H), 5.66 (dd, J=12.7, 4.5 Hz, 1H), 4.05-3.93 (m, 1H), 3.82-3.71 (m, 1H), 2.77-2.52 (m, 3H), 2.22-2.10 (m, 1H), 1.97-1.78 (m, 2H), 1.58-1.45 (m, 1H), 1.38-1.22 (m, 1H), 1.01 (d, J=7.0 Hz, 1H), 0.93-0.78 (m, 1H). MS (ESI) m/z: 600.0 (M+H)⁺. Analytical HPLC (method A): RT=8.6 min, purity >95%.

Example 70

(10R,14S)-5-Amino-14-[4-(3-chloro-2,6-difluorophenyl)-6-oxo-1,2,3,6-tetrahydropyridin-1-yl]-10-methyl-9-oxo-8,16-diazatricyclo[13.3.1.0²,⁷]nonadeca-1(19),2,4,6,15,17-hexaen-16-ium-16-olate, TFA Salt

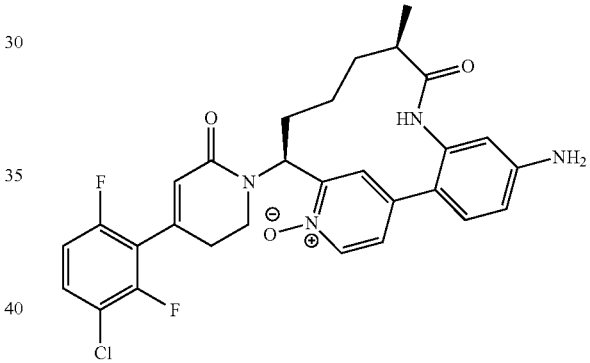

To a solution of example 12 (20 mg, 0.033 mmol) in CH₂Cl₂ (1 mL) was added iodotrimethylsilane (65.5 mg, 0.327 mmol). The reaction mixture was sealed and heated at 50° C. for 3 hrs. Then, the reaction mixture was quenched with 10% sodium thiosulfate aqueous solution. The organic phase was washed with brine, dried over MgSO₄, filtered and concentrated. The residue was purified by prep HPLC to yield the desired product as a solid (2.24 mg, 12%). ¹H NMR (500 MHz, DMSO-d₆) δ 9.49 (br. s., 1H), 8.24 (d, J=6.6 Hz, 1H), 7.66 (d, J=7.2 Hz, 1H), 7.53 (br. s., 1H), 7.35 (d, J=6.3 Hz, 1H), 7.30-7.20 (m, 2H), 6.61 (d, J=8.3 Hz, 1H), 6.44 (br. s., 1H), 5.97 (br. s., 1H), 5.50 (br. s., 2H), 5.27 (d, J=12.7 Hz, 1H), 3.41 (br. s., 1H), 3.23-3.12 (m, 1H), 2.66-2.54 (m, 2H), 2.40-2.29 (m, 1H), 2.18-2.04 (m, 1H), 1.95-1.82 (m, 1H), 1.74-1.64 (m, 1H), 1.56 (br. s., 1H), 1.48-1.35 (m, 1H), 1.03 (d, J=5.2 Hz, 3H), 0.99-0.85 (m, 1H). MS (ESI) m/z: 553.3 (M+H)⁺. Analytical HPLC (method C): RT=1.5 min, purity=98%.

Example 71

(10R,14S)-14-{4-[5-Chloro-2-(1H-1,2,4-triazol-1-yl)phenyl]-6-oxo-1,2,3,6-tetrahydropyridin-1-yl}-10-methyl-8,16-diazatricyclo[13.3.1.0$^{2,7}$]nonadeca-1(19),2(7),3,5,15,17-hexaen-9-one, TFA Salt

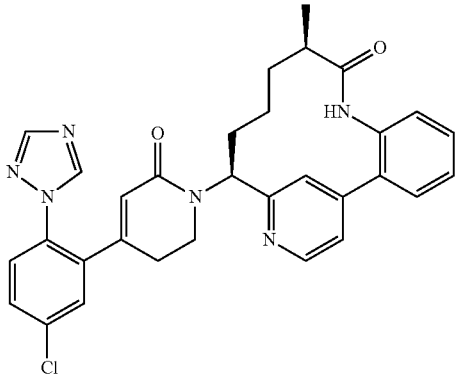 [SMILES: C[C@@H]1CCC[C@H](N2CCC(c3cc(Cl)ccc3-n3cncn3)=CC2=O)c2cc(ccn2)-c2ccccc2NC1=O]

71A 5-Chloro-2-(1H-1,2,4-triazol-1-yl)benzaldehyde

To a reaction vessel was added 5-chloro-2-fluorobenzaldehyde (1.29 g, 7.89 mmol), 4H-1,2,4-triazole (0.574 g, 7.89 mmol), $Cs_2CO_3$ (2.83 g, 8.68 mmol) and DMSO (15.78 ml). The mixture was capped and heated at 45° C. for 4 hrs before cooling down to rt and stirred at rt over weekend. The reaction mixture was diluted with EtOAc, washed with water and brine, dried over $MgSO_4$, filtered, concentrated and purified by flash chromatography to yield 71A as white solid product (674 mg, 41%). $^1$H NMR (500 MHz, DMSO-d$_6$) δ 9.90 (s, 1H), 9.17 (s, 1H), 8.33 (s, 1H), 7.99-7.91 (m, 2H), 7.84 (d, J=8.5 Hz, 1H).

Example 71 was prepared by following the procedures described in example 45 by using 71A as intermediate. $^1$H NMR (500 MHz, METHANOL-d$_4$) δ 8.81 (d, J=5.8 Hz, 1H), 8.78 (s, 1H), 8.17 (s, 1H), 8.10 (d, J=1.7 Hz, 1H), 7.93 (dd, J=5.9, 1.8 Hz, 1H), 7.72 (dd, J=7.6, 1.5 Hz, 1H), 7.64-7.51 (m, 5H), 7.34 (dd, J=8.0, 1.1 Hz, 1H), 5.82 (s, 1H), 5.31 (dd, J=12.4, 4.7 Hz, 1H), 3.65-3.50 (m, 2H), 2.66-2.57 (m, 1H), 2.44-2.35 (m, 1H), 2.32-2.21 (m, 2H), 2.06-1.96 (m, 1H), 1.91-1.82 (m, 1H), 1.63-1.53 (m, 1H), 1.33-1.22 (m, 1H), 1.04 (d, J=6.9 Hz, 3H), 0.99-0.86 (m, 1H). MS (ESI) m/z: 553.2 (M+H)$^+$. Analytical HPLC (method A): RT=5.5 min, purity=100%.

Example 72

(10R,14S)-14-[4-(3-Chloro-2,6-difluorophenyl)-6-oxo-1,2,3,6-tetrahydropyridin-1-yl]-10-methyl-5,8,16-triazatricyclo[13.3.1.0$^{2,7}$]nonadeca-1(19),2(7),3,5,15,17-hexaen-9-one, TFA Salt

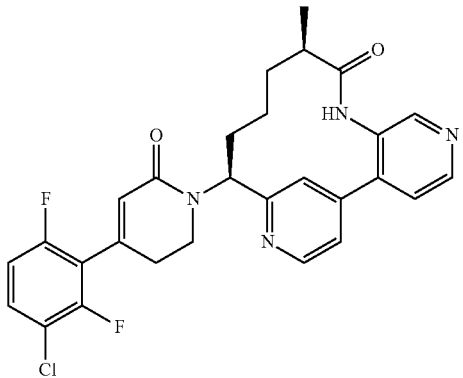

72A. tert-Butyl N-(4-{2-[(1S)-1-{[(tert-butoxy)carbonyl]amino}but-3-en-1-yl]pyridin-4-yl}pyridin-3-yl)carbamate To 1C (1.080 g, 3.82 mmol) and (3-((tert-butoxycarbonyl)amino)pyridin-4-yl)boronic acid (1 g, 4.20 mmol) in a sealable flask was added THF (19.09 ml), potassium phosphate tribasic (5.09 ml, 15.28 mmol) and degassed with Ar. (DtBPF)PdCl$_2$ (0.249 g, 0.382 mmol) was added, degassed further. The reaction mixture was heated at 75° C. for overnight. Then, the mixture was washed with water and extracted with EtOAc. The combined organic layers were dried over $MgSO_4$, filtered, concentrated and purified by ISCO to yield 72A as brown solid (670 mg, 40%). $^1$H NMR (500 MHz, METHANOL-d$_4$) δ 8.65 (br. s., 1H), 8.62-8.57 (m, 1H), 8.46 (d, J=5.0 Hz, 1H), 7.46 (s, 1H), 7.41 (d, J=5.2 Hz, 1H), 7.39 (m, 1H), 5.86-5.75 (m, 1H), 5.15-5.03 (m, 2H), 4.81-4.75 (m, 1H), 2.68-2.57 (m, 1H), 2.55-2.46 (m, 1H), 1.46-1.27 (m, 18H).

72B 4-{2-[(1S)-1-Aminobut-3-en-1-yl]pyridin-4-yl}pyridin-3-amine, TFA Salt

To a solution of 72A (670 mg, 1.521 mmol) in $CH_2Cl_2$ (5 mL) was added TFA (3.52 mL, 45.6 mmol) and stirred at rt. After 30 mins, the reaction mixture was concentrated to yield 72B as a yellow brown semi-solid (900 mg, 100%). $^1$H NMR (500 MHz, METHANOL-d$_4$) δ 8.87 (dd, J=5.1, 0.7 Hz, 1H), 8.26 (d, J=0.5 Hz, 1H), 8.11 (dd, J=5.8, 0.8 Hz, 1H), 7.74-7.57 (m, 3H), 5.92-5.73 (m, 1H), 5.25 (m, 2H), 4.66 (t, J=6.9 Hz, 1H), 4.00 (s, 2H), 2.94-2.64 (m, 2H).

72C. tert-Butyl N-[(1S)-1-[4-(3-aminopyridin-4-yl)pyridin-2-yl]but-3-en-1-yl]carbamate To a solution of 72B (360 mg, 1.5 mmol) in MeOH (10 mL) was added triethylamine (1 ml, 7.17 mmol). The mixture was cooled down to 0° C. and di-tert-butyl dicarbonate (327 mg, 1.500 mmol) was added. After 1 hr, the reaction mixture was concentrated, diluted with DCM and washed with brine. The organic phase was dried over $MgSO_4$, filtered, concentrated and purified by ISCO to yield 72C as pale yellow solid (425 mg, 83%). $^1$H NMR (500 MHz, CHLOROFORM-d) δ $^1$H NMR (500 MHz, METHANOL-d$_4$) δ 8.56 (d, J=5.0 Hz, 1H), 8.10 (s, 1H), 7.84 (d, J=5.0 Hz, 1H), 7.50 (s, 1H), 7.36 (d, J=3.9 Hz, 1H), 7.04 (m, 2H), 5.83-5.73 (m, 1H), 5.09-4.98 (m, 2H), 4.79 (m, 1H), 2.67-2.58 (m, 1H), 2.54-2.44 (m, 1H), 1.38 (br. s., 9H).

72D. tert-Butyl N-[(1S)-1-(4-{3-[(2R)-2-methylbut-3-enamido]pyridin-4-yl}pyridin-2-yl)but-3-en-1-yl]carbamate To a solution of 72C (425 mg, 1.248 mmol) in $CH_2Cl_2$(3 mL) was added pyridine (1 mL, 12.36 mmol), intermediate 12 (356 mg, 3 mmol) dropwise and stirred at rt. After 5 mins, the reaction mixture washed with sat. NaHCO$_3$ aq, brine, dried over $MgSO_4$, filtered, concentrated and purified by flash chromatography to yield the desired product as off white solid (325 mg, 62%). $^1$H NMR (500 MHz, CHLOROFORM-d) δ 9.45 (s, 1H), 8.70 (dd, J=5.0, 0.6 Hz, 1H), 8.49 (d, J=5.0 Hz, 1H), 7.25-7.10 (m, 4H), 5.88-5.62 (m, 2H), 5.50 (m, 1H), 5.17-5.03 (m, 4H), 4.87 (m, 1H), 3.08 (m, 1H), 2.73-2.55 (m, 2H), 1.44 (s, 9H), 1.29 (d, J=7.2 Hz, 3H).

72E tert-Butyl N-[(10R,11E,14S)-10-methyl-9-oxo-5,8,16-triazatricyclo[13.3.1.0$^{2,7}$]nonadeca-1(19),2(7),3,5,11,15,17-heptaen-14-yl]carbamate To a solution of 72D (220 mg, 0.521 mmol), pTsOH (194 mg, 1.020 mmol) in CH$_2$Cl$_2$ (100 mL) was degassed by bubbling Ar through for 10 mins and heated at 40° C. for 10 mins. Then, Grubbs II (190 mg, 0.224 mmol) in 3 ml Ar degassed DCM was added dropwise via a syring pump under Ar, heated at 40° C. for a total of 24 hrs. The reaction mixture was neutralized with sat. aq. NaHCO$_3$ and the organic phase separated and washed with brine, dried over MgSO$_4$, filtered, and concentrated. The residue was purified by prep HPLC and the desired fractions neutralized with conc. NaHCO$_3$, concentrated to small volume, extracted with EtOAc, dried over MgSO$_4$, filtered and concentrated to yield the desired product as a white solid (15 mg, 7.3%). $^1$H NMR (400 MHz, METHANOL-d$_4$) δ 8.65 (dd, J=11.4, 5.1 Hz, 2H), 8.54 (s, 1H), 7.60 (d, J=5.1 Hz, 1H), 7.37 (dd, J=5.1, 1.5 Hz, 1H), 6.99 (s, 1H), 5.76 (ddd, J=15.3, 10.6, 4.7 Hz, 1H), 4.68 (dd, J=11.2, 3.5 Hz, 1H), 4.41 (dd, J=15.2, 9.5 Hz, 1H), 3.18 (dq, J=9.3, 6.7 Hz, 1H), 2.78 (ddd, J=8.4, 7.3, 3.9 Hz, 1H), 2.04 (q, J=11.4 Hz, 1H), 1.47 (s, 9H), 1.10 (d, J=6.8 Hz, 3H).

Example 72 was prepared by following the procedures described in Example 1 by using 72E as intermediate. $^1$H NMR (400 MHz, METHANOL-d$_4$) δ 8.84 (d, J=5.3 Hz, 1H), 8.76 (d, J=5.5 Hz, 1H), 8.66 (s, 1H), 7.98 (d, J=5.5 Hz, 1H), 7.82 (d, J=0.9 Hz, 1H), 7.66 (dd, J=5.3, 1.8 Hz, 1H), 7.58-7.48 (m, 1H), 7.09 (td, J=9.2, 1.8 Hz, 1H), 6.09 (s, 1H), 5.62 (dd, J=12.5, 5.1 Hz, 1H), 4.17-4.06 (m, J=12.5, 6.3, 6.3 Hz, 1H), 3.89-3.77 (m, 1H), 2.87-2.66 (m, 3H), 2.30-2.17 (m, 1H), 2.02-1.87 (m, 2H), 1.66-1.51 (m, 1H), 1.47-1.31 (m, 1H), 1.01 (d, J=6.8 Hz, 3H), 0.69 (br. s., 1H). MS (ESI) m/z: 523.1 (M+H)$^+$. Analytical HPLC (method A): RT=6.6 min, purity=96%.

Example 73

Methyl N-[(10R,14S)-14-[4-(3-chloro-2,6-difluorophenyl)-3-methyl-6-oxo-1,2,3,6-tetrahydropyridin-1-yl]-10-methyl-9-oxo-8,16-diazatricyclo[13.3.1.0$^{2,7}$]nonadeca-1(19),2(7),3,5,15,17-hexaen-5-yl]carbamate, TFA Salt

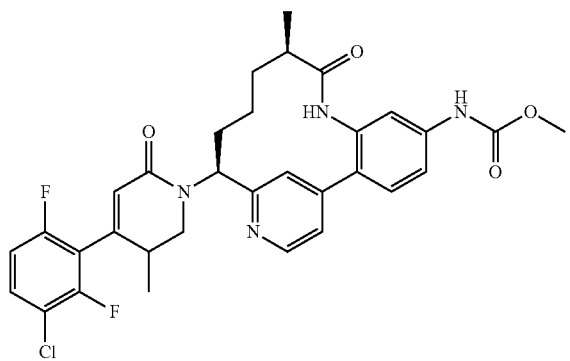 [SMILES: COC(=O)Nc1ccc2c(c1)NC(=O)[C@H](C)CCC[C@H](N1CC(C)C(c3c(F)ccc(Cl)c3F)=CC1=O)c1cc-2ccn1]

73A. 1-(3-Chloro-2,6-difluorophenyl)-2-methyl-prop-2-en-1-ol

To a solution of prop-1-en-2-ylmagnesium bromide (0.5M in THF) (2 mL, 1.000 mmol) was added 3-chloro-2,6-difluorobenzaldehyde (136 mg, 0.769 mmol) in THF (1 mL) dropwise at 0° C. under Ar and stirred at 0° C. for 15 mins. The reaction mixture was quenched with sat. aq NH$_4$Cl and extracted with ether. The organic phase was washed with sat. aq. NH$_4$Cl and brine, dried over MgSO$_4$, filtered, and concentrated. Purification by flash chromatography to yield 73A as colorless oil (87 mg, 52%). $^1$H NMR (400 MHz, CHLOROFORM-d) δ 7.36-7.28 (m, 1H), 6.91-6.83 (m, 1H), 5.48 (d, J=9.2 Hz, 1H), 5.12-5.06 (m, 1H), 5.04-4.99 (m, 1H), 2.56 (dt, J=9.2, 2.2 Hz, 1H), 1.75 (s, 3H).

73B 1-(3-Chloro-2,6-difluorophenyl)-2-methylprop-2-en-1-one

A (87 mg, 0.398 mmol) in CH$_2$Cl$_2$ (2 mL) was added Dess-MartinPeriodinane (253 mg, 0.597 mmol), stirred at rt. white turbid solution after 30 mins, reaction mixture was diluted with EtOAc, washed with conc. NaHCO$_3$ and 10% Na$_2$S$_2$O$_3$ solution, followed by brine, dried over MgSO$_4$, filtered, concentrated and purified by flash chromatography to yield 73B as colorless oil (79 mg, 92%). $^1$H NMR (500 MHz, CHLOROFORM-d) δ 7.50-7.38 (m, 1H), 6.98-6.87 (m, 1H), 6.18-6.06 (m, 1H), 5.75 (d, J=0.8 Hz, 1H), 2.11-1.98 (m, 3H).

73C. methyl N-[(10R,14S)-14-{[3-(3-chloro-2,6-difluorophenyl)-2-methyl-3-oxopropyl]amino}-10-methyl-9-oxo-8,16-diazatricyclo[13.3.1.0$^{2,7}$]nonadeca-1(19),2(7),3,5,15,17-hexaen-5-yl]carbamate To a solution of 73B (44 mg, 0.203 mmol) in CH$_2$Cl$_2$ (3 mL) and MeOH (1 ml) was added 1J (74.8 mg, 0.203 mmol) and DIEA (0.142 mL, 0.813 mmol) and stirred at rt for 3 days. The reaction mixture was concentrated and purified by prep HPLC to yield 73C as yellow solid (54.7 mg, 33%). MS (ESI) m/z: 585.2 (M+H)$^+$.

Example 73

To a solution of 73C (24 mg, 0.031 mmol) in MeOH (1 mL) was added sodium methoxide (25 wt % in MeOH) (27.2 mg, 0.126 mmol) diluted in MeOH (0.3 mL) dropwise at 0° C. under Ar and stirred at 0° C. After 45 mins, the reaction mixture was quenched with 0.1 ml 1N aq HCl and purified by prep HPLC to yield the desired product as pale yellow crystalline solid (12.5 mg, 54%), TFA salt, as a pair of diastereomers, with ratio about 1:1. $^1$H NMR (500 MHz, METHANOL-d$_4$) δ 9.66 (s, 1H), 8.81-8.73 (m, 1H), 8.11-8.00 (m, 1H), 7.87 (m, 1H), 7.69-7.63 (m, 1H), 7.62-7.50 (m, 3H), 7.15-7.04 (m, 1H), 5.99 (s, 1H), 5.53-5.40 (m, 1H), 3.91-3.71 (m, 4H), 3.54-3.43 (m, 1H), 3.08-2.86 (m, 1H), 2.68-2.54 (m, 1H), 2.43-2.24 (m, 1H), 2.11-2.00 (m, 1H), 1.98-1.84 (m, 1H), 1.71-1.56 (m, 1H), 1.40-1.14 (m, 1H), 1.12-0.85 (m, 6H). MS (ESI) m/z: 609.2 (M+H)$^+$. Analytical HPLC (method A): RT=7.1 min, purity=99%.

Example 74

(10R,14S)-14-{4-[5-Chloro-2-(3-methyl-1H-1,2,4-triazol-1-yl)phenyl]-6-oxo-1,2,3,6-tetrahydropyridin-1-yl}-10-methyl-8,16-diazatricyclo[13.3.1.0$^{2,7}$]nonadeca-1(19),2(7),3,5,15,17-hexaen-9-one, TFA Salt

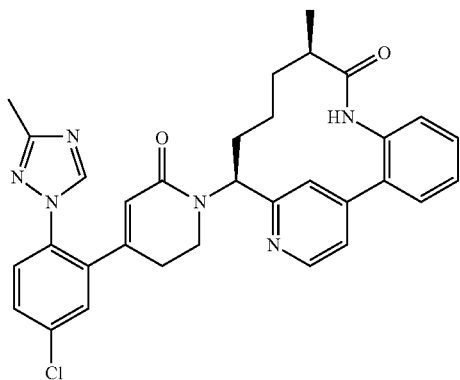 [SMILES: Cc1ncn(-c2ccc(Cl)cc2C2=CC(=O)N([C@H]3CCC[C@@H](C)C(=O)Nc4ccccc4-c4ccnc3c4)CC2)n1]

74A 5-Chloro-2-(3-methyl-1H-1,2,4-triazol-1-yl)benzaldehyde

In a 25 ml RBF, a mixture of 5-chloro-2-fluorobenzaldehyde (505 mg, 3.09 mmol), 3-methyl-1H-1,2,4-triazole (270 mg, 3.09 mmol), Cs$_2$CO$_3$ (1007 mg, 3.09 mmol) in DMSO (6179 µl) was heated at 45° C. for 4 hrs and stirred at rt overnight. The reaction mixture was diluted with EtOAc and washed with water. The combined organic phase was washed with brine, dried over MgSO$_4$, filtered, concentrated and purified by flash chromatography to yield 74A as white solid product (140 mg, 20%). $^1$H NMR (400 MHz, DMSO-d$_6$) δ ppm: 9.95 (s, 1H), 9.02 (s, 1H), 7.96-7.88 (m, 2H), 7.80 (d, J=8.4 Hz, 1H), 2.37 (s, 3H).

Example 74 was prepared by following the procedures described in Example 45 by using 74A as intermediate. $^1$H NMR (400 MHz, METHANOL-d$_4$) δ 8.79 (d, J=5.9 Hz, 1H), 8.62 (s, 1H), 8.07 (d, J=1.3 Hz, 1H), 7.89 (dd, J=5.9, 1.8 Hz, 1H), 7.69 (dd, J=7.5, 1.5 Hz, 1H), 7.62-7.47 (m, 5H), 7.32 (dd, J=7.7, 1.1 Hz, 1H), 5.81 (s, 1H), 5.30 (dd, J=12.4, 4.7 Hz, 1H), 3.65-3.47 (m, 2H), 2.59 (m, 1H), 2.46-2.33 (m, 1H), 2.37 (s, 3H), 2.32-2.19 (m, 2H), 2.05-1.92 (m, 1H), 1.90-1.78 (m, 1H), 1.62-1.49 (m, 1H), 1.33-1.19 (m, 1H), 1.01 (d, J=7.0 Hz, 3H), 0.93 (d, J=6.8 Hz, 1H). MS (ESI) m/z: 567.2 (M+H)$^+$. Analytical HPLC (method A): RT=5.7 min, purity=100%.

Example 75

N-[(10R,14S)-14-[4-(3-Chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2(7),3,5,15,17-hexaen-5-yl]acetamide, TFA Salt

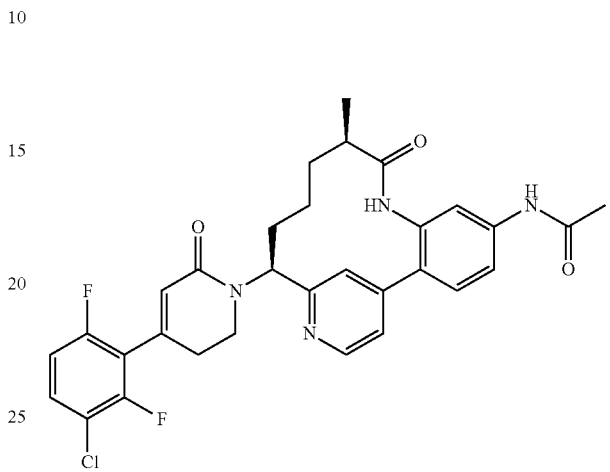

To a cooled (0° C.), clear, pale yellow solution of Example 12 (0.025 g, 0.047 mmol) and pyridine (0.019 ml, 0.233 mmol) in dichloromethane (0.466 ml) was added dropwise a solution of 1.0 M acetyl chloride in dichloromethane (0.047 ml, 0.047 mmol). The resulting bright yellow solution was stirred at 0° C. After 30 minutes, additional 1.0 M acetyl chloride in dichloromethane (0.030 ml, 0.030 mmol) was added. Overtime a white precipitate formed. After an additional 1 h, the reaction was stopped, partitioned between EtOAc and sat. NaHCO$_3$ and the layers were separated. The aqueous layer was extracted with EtOAc (2×). The organic layers were combined and washed with brine, dried over sodium sulfate, filtered and concentrated to give a white solid. Purification by reverse phase chromatography gave the title compound (0.0203 g, 62% yield) as a yellow, granular solid. $^1$H NMR (500 MHz, CD$_3$OD) δ 8.73 (d, J=5.8 Hz, 1H), 7.98 (s, 1H), 7.76 (d, J=5.0 Hz, 1H), 7.71 (br. s, 1H), 7.66-7.63 (m, 2H), 7.53 (td, J=8.7, 5.5 Hz, 1H), 7.09 (td, J=9.2, 1.7 Hz, 1H), 6.10 (s, 1H), 5.45 (dd, J=12.4, 4.4 Hz, 1H), 3.85-3.78 (m, 1H), 3.76-3.69 (m, 1H), 2.87-2.77 (m, 1H), 2.76-2.67 (m, 1H), 2.67-2.59 (m, 1H), 2.31-2.22 (m, 1H), 2.16 (s, 3H), 2.07-1.98 (m, 1H), 1.96-1.87 (m, 1H), 1.65-1.55 (m, 1H), 1.37-1.28 (m, 1H), 1.04 (d, J=6.9 Hz, 3H), 1.01-0.89 (m, 1H). MS (ESI) m/z: 579.1 (M+H)$^+$ and 581.1 (M+2+H)$^+$. Analytical HPLC (method A): RT=6.0 min, purity=98%.

Example 76

N-[(10R,14S)-14-[4-(3-Chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2(7),3,5,15,17-hexaen-5-yl]methanesulfonamide, TFA Salt

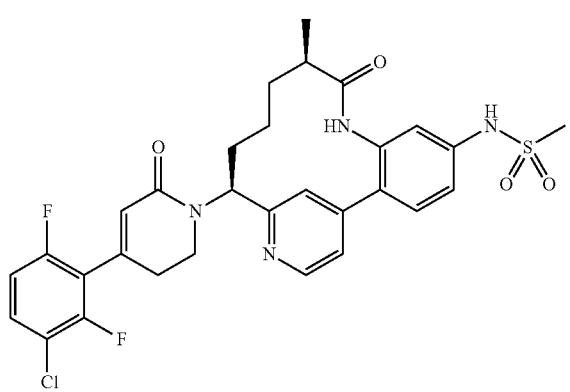 [SMILES: C[C@@H]1CCC[C@H](N2CCC(c3c(F)ccc(Cl)c3F)=CC2=O)c2cc(ccn2)-c2ccc(NS(C)(=O)=O)cc2NC1=O]

To a cooled (0° C.), clear, pale yellow solution of Example 12 (0.020 g, 0.037 mmol) and pyridine (0.015 ml, 0.186 mmol) in dichloromethane (0.74 ml) was added dropwise a solution of 1.0 M methanesulfonyl chloride in dichloromethane (0.037 ml, 0.037 mmol). The resulting orange solution was stirred at 0° C. After 30 minutes, the reaction was allowed to warm to rt. After an additional 2.5 h, the reaction was stopped, partitioned between EtOAc and sat. NaHCO$_3$ and the layers were separated. The aqueous layer was extracted with EtOAc (2×). The organic layers were combined and washed with brine, dried over sodium sulfate, filtered and concentrated to give an orange solid. Purification by reverse phase chromatography gave example 76 (0.0171 g, 62% yield) as a white solid. $^1$H NMR (500 MHz, CD$_3$OD) δ 8.76-8.69 (m, 1H), 7.90 (br. s., 1H), 7.73-7.67 (m, 1H), 7.65 (d, J=8.5 Hz, 1H), 7.53 (td, J=8.7, 5.5 Hz, 1H), 7.35 (dd, J=8.5, 2.2 Hz, 1H), 7.22 (d, J=2.2 Hz, 1H), 7.09 (td, J=9.2, 1.7 Hz, 1H), 6.10 (s, 1H), 5.53-5.45 (m, 1H), 3.91-3.82 (m, 1H), 3.78-3.70 (m, 1H), 3.06 (s, 3H), 2.85-2.76 (m, 1H), 2.76-2.67 (m, 1H), 2.67-2.58 (m, 1H), 2.30-2.19 (m, 1H), 2.05-1.88 (m, 2H), 1.64-1.54 (m, 1H), 1.39-1.27 (m, 1H), 1.04 (d, J=6.9 Hz, 3H), 0.98-0.87 (m, 1H). MS (ESI) m/z: 615.1 (M+H)$^+$ and 617.1 (M+2+H)$^+$. Analytical HPLC (method A): RT=6.4 min, purity=99%.

Example 77

Methyl N-[(10R,11E,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2(7),3,5,11,15,17-heptaen-5-yl]carbamate, TFA Salt

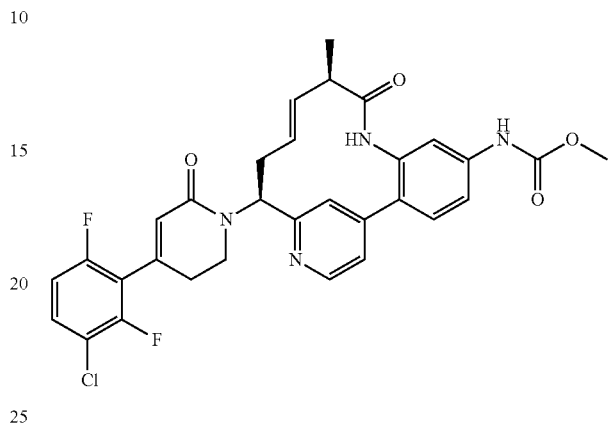

Example 77 (0.044g, yellow solid) was prepared by following the procedures described in Example 1, by replacing 1I with 1H in step 1J and by replacing Intermediate 3 with Intermediate 1 in step 1K. $^1$H NMR (500 MHz, CD$_3$OD) δ 9.62 (s, 1H), 8.66 (d, J=5.8 Hz, 1H), 7.70-7.65 (m, 2H), 7.61-7.49 (m, 3H), 7.42 (d, J=1.4 Hz, 1H), 7.14 (td, J=9.2, 1.7 Hz, 1H), 6.13 (d, J=0.6 Hz, 1H), 5.78 (ddd, J=15.1, 10.6, 4.3 Hz, 1H), 5.30 (dd, J=12.5, 4.0 Hz, 1H), 4.69 (dd, J=15.5, 9.8 Hz, 1H), 4.17 (dt, J=12.1, 6.1 Hz, 1H), 3.90-3.82 (m, 1H), 3.79 (s, 3H), 3.22 (dq, J=9.7, 6.6 Hz, 1H), 3.18-3.09 (m, 1H), 2.97-2.90 (m, 1H), 2.80 (dt, J=17.6, 5.4 Hz, 1H), 2.67-2.58 (m, 1H), 1.12 (d, J=6.6 Hz, 3H). MS (ESI) m/z: 593.2 (M+H)$^+$ and 595.1 (M+2+H)$^+$. Analytical HPLC (method A): RT=6.8 min, purity=99%.

Example 78

Methyl N-[(10R,14S)-14-[4-(6-bromo-3-chloro-2-fluorophenyl)-6-oxo-1,6-dihydropyridazin-1-yl]-10-methyl-9-oxo-8,16-diazatricyclo[13.3.1.0$^{2,7}$]nonadeca-1(19),2(7),3,5,15,17-hexaen-5-yl]carbamate, TFA Salt

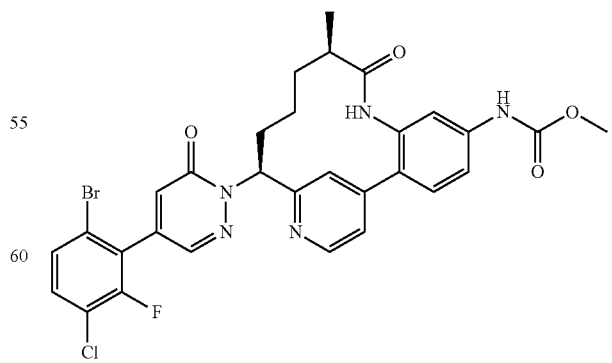

Example 78 was prepared according to the procedures described in Example 11, by replacing Intermediate 11 with Intermediate 15. ¹H NMR (500 MHz, CD₃OD) δ 8.72 (d, J=5.8 Hz, 1H), 8.23 (d, J=1.4 Hz, 1H), 8.08 (d, J=1.9 Hz, 1H), 7.87 (dd, J=5.8, 1.7 Hz, 1H), 7.66-7.51 (m, 5H), 7.12 (d, J=2.2 Hz, 1H), 6.29 (dd, J=12.0, 5.1 Hz, 1H), 3.77 (s, 3H), 2.77-2.69 (m, 1H), 2.59-2.49 (m, 1H), 2.28-2.17 (m, 1H), 2.01-1.93 (m, 1H), 1.74-1.64 (m, 1H), 1.57-1.47 (m, 1H), 1.01 (d, J=6.9 Hz, 3H), 0.82-0.69 (m, 1H). MS (ESI) m/z: 654.1 (M+H)⁺. Analytical HPLC (method A): RT=6.8 min, purity=97%.

Example 79

Methyl N-[(10R,14S)-14-[4-(3-chloro-6-cyano-2-fluorophenyl)-6-oxo-1,6-dihydropyridazin-1-yl]-10-methyl-9-oxo-8,16-diazatricyclo[13.3.1.0²,⁷]nonadeca-1(19),2(7),3,5,15,17-hexaen-5-yl]carbamate, TFA Salt

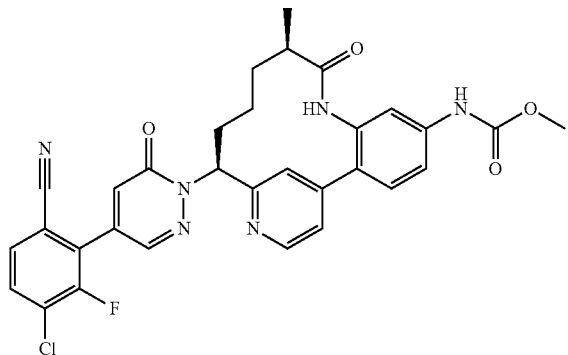 [SMILES: COC(=O)Nc1ccc2c(c1)NC(=O)[C@H](C)CCC[C@H](n1ncc(-c3c(C#N)ccc(Cl)c3F)cc1=O)c1cc-2ccn1]

A vial containing a mixture of the free base of Example 78 (0.018 g, 0.023 mmol), zinc (0.459 mg, 7.02 μmol) and zinc cyanide (5.50 mg, 0.047 mmol) in DMF (1.170 ml) was vacuumed and back filled with argon three times. Then bis(tri-t-butylphosphine)palladium(0) (1.196 mg, 2.341 μmol) was added and the vial was sealed. The reaction was heated at 90° C. for 24 h and then it was cooled to rt. Purification by reverse phase HPLC afforded Example 79 (0.004 g, 24% yield) as a yellow solid. MS (ESI) m/z: 601.1 (M+H)⁺. ¹H NMR (500 MHz, CD₃OD) δ 8.71 (d, J=5.8 Hz, 1H), 8.24-8.20 (m, 2H), 7.88-7.82 (m, 2H), 7.77 (dd, J=8.4, 1.2 Hz, 1H), 7.63 (d, J=8.5 Hz, 1H), 7.58 (d, J=1.9 Hz, 1H), 7.55-7.51 (m, 1H), 7.30 (d, J=2.2 Hz, 1H), 6.28 (dd, J=12.0, 5.1 Hz, 1H), 3.77 (s, 3H), 2.77-2.68 (m, 1H), 2.59-2.50 (m, 1H), 2.29-2.20 (m, 1H), 2.01-1.93 (m, 1H), 1.73-1.63 (m, 1H), 1.57-1.47 (m, 1H), 1.02 (d, J=6.9 Hz, 3H), 0.85-0.73 (m, 1H). Analytical HPLC (method A): RT=6.2 min, purity=100%.

Example 80

(10R,14S)-14-[4-(3-Chloro-2,6-difluorophenyl)-6-oxo-1,2,3,6-tetrahydropyridin-1-yl]-3-fluoro-10-methyl-8,16-diazatricyclo[13.3.1.0²,⁷]nonadeca-1(19),2(7),3,5,15,17-hexaen-9-one, TFA Salt

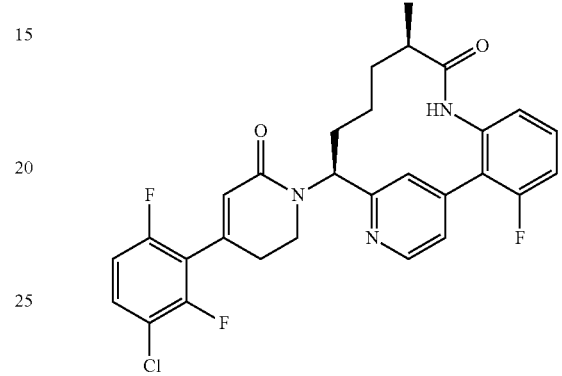

80A. tert-Butyl N-[(1S)-1-[4-(2-amino-6-fluorophenyl)pyridin-2-yl]but-3-en-1-yl]carbamate A sealed tube was charged with 24A (0.05 g, 0.171 mmol), 2-bromo-3-fluoroaniline (0.036 g, 0.188 mmol), (DtBPF)PdCl₂ (5.58 mg, 8.56 μmol), 3M potassium phosphate (0.171 ml, 0.513 mmol), and THF (1.712 ml). The reaction vessel was vacuumed and back-filled with argon three times, then tube was sealed, and the reaction was heated at 90° C. After 20 h, the reaction was cooled to rt. The reaction was diluted with EtOAc, washed with brine, dried over Na₂SO₄, filtered, and concentrated. Purification by normal phase chromatography afforded 80A (0.032 g, 52.3% yield) as a yellow solid. MS (ESI) m/z: 358.0 (M+H)⁺.

Example 80 was prepared according to the procedures described in Example 1, by replacing 1F in step 1G with 80A and by replacing Intermediate 3 with Intermediate 1 in step 1K. MS (ESI) m/z: 540.0 (M+H)⁺. ¹H NMR (400 MHz, CD₃OD) δ 8.78 (d, J=5.7 Hz, 1H), 7.93 (s, 1H), 7.87-7.82 (m, 1H), 7.62-7.50 (m, 2H), 7.30 (ddd, J=9.8, 8.6, 1.0 Hz, 1H), 7.18 (d, J=7.9 Hz, 1H), 7.09 (td, J=9.2, 1.8 Hz, 1H), 6.11 (s, 1H), 5.44 (dd, J=12.3, 4.8 Hz, 1H), 3.93-3.72 (m, 2H), 2.90-2.68 (m, 2H), 2.62-2.52 (m, 1H), 2.33-2.22 (m, 1H), 2.10-1.98 (m, 1H), 1.86-1.75 (m, 1H), 1.56-1.44 (m, 1H), 1.34-1.21 (m, 1H), 1.05-0.83 (m, 4H). Analytical HPLC (method A): RT=8.2 min, purity=100%.

Example 81

(14R,18S)-18-[4-(3-Chloro-2,6-difluorophenyl)-6-oxo-1,2,3,6-tetrahydropyridin-1-yl]-14-methyl-8,12,20-triazatetracyclo[17.3.1.0$^{2,11}$.0$^{4,9}$]tricosa-1(23),2,4(9),5,10,19,21-heptaene-7,13-dione, TFA Salt

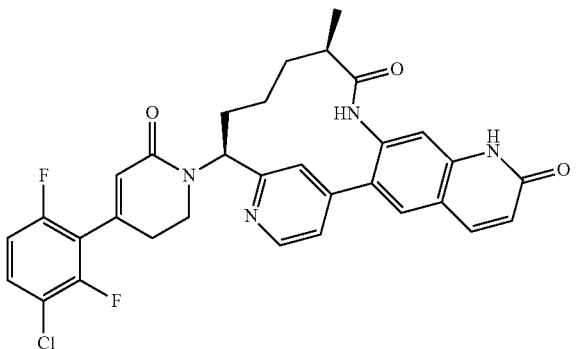 [SMILES: C[C@@H]1CCC[C@H](N2CCC(c3c(F)ccc(Cl)c3F)=CC2=O)c2cc(ccn2)-c2cc3ccc(=O)[nH]c3cc2NC1=O]

Example 82

(2Z)-3-[(10R,14S)-5-Amino-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-4-yl]prop-2-enoic acid, 2 TFA Salt

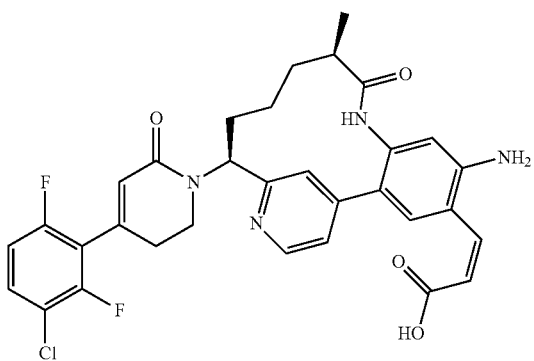 [SMILES: C[C@@H]1CCC[C@H](N2CCC(c3c(F)ccc(Cl)c3F)=CC2=O)c2cc(ccn2)-c2cc(/C=C\C(=O)O)c(N)cc2NC1=O]

81A Methyl (2E)-3-[(10R,14S)-5-amino-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-4-yl]prop-2-enoate, 2 TFA Salt To the solution of Example 61 (0.038 g, 0.057 mmol) in DMF (0.573 ml) was added methyl acrylate (9.87 mg, 0.115 mmol), Pd(OAc)$_2$ (0.515 mg, 2.293 µmol), and tributylamine (0.014 ml, 0.057 mmol). The reaction was microwaved at 150° C. for 10 min, and then the reaction was cooled to rt. Purification by reverse phase HPLC afforded 81A (0.034 g, 69.9% yield) as a yellow solid. MS (ESI) m/z: 621.2 (M+H)$^+$.

Example 81 and 82

The solution of 81A (0.034 g, 0.040 mmol) in 6N HCl (1 mL, 6.00 mmol) was microwaved at 100° C. for 30 min, and then the reaction was cooled to rt. The resulting yellow suspension was concentrated and purified by reverse phase HPLC to afford Example 81 (0.011 g, 38.3% yield) as a yellow solid and Example 82 (0.002 g, 5.9% yield) as a yellow solid. Example 81: MS (ESI) m/z: 589.1 (M+H)$^+$. $^1$H NMR (500 MHz, CD$_3$OD) δ 8.75 (d, J=5.5 Hz, 1H), 8.04 (d, J=9.6 Hz, 1H), 7.98 (s, 1H), 7.89 (s, 1H), 7.73 (dd, J=5.5, 1.4 Hz, 1H), 7.54 (td, J=8.7, 5.5 Hz, 1H), 7.27 (s, 1H), 7.10 (td, J=9.2, 1.7 Hz, 1H), 6.66 (d, J=9.4 Hz, 1H), 6.10 (s, 1H), 5.53 (dd, J=12.4, 4.7 Hz, 1H), 3.99-3.90 (m, J=5.8 Hz, 1H), 3.81-3.72 (m, 1H), 2.86-2.62 (m, 3H), 2.29-2.20 (m, 1H), 2.03-1.89 (m, 2H), 1.64-1.54 (m, 1H), 1.43-1.30 (m, 1H), 1.08-0.78 (m, 4H). Analytical HPLC (method A): RT=6.1 min, purity=99%. Example 82: $^1$H NMR (500 MHz, CD$_3$OD) δ 8.63 (d, J=5.2 Hz, 1H), 7.81 (d, J=9.4 Hz, 1H), 7.66 (s, 1H), 7.59-7.49 (m, 2H), 7.45 (s, 1H), 7.09 (td, J=9.2, 1.7 Hz, 1H), 6.68 (s, 1H), 6.29 (d, J=9.4 Hz, 1H), 6.14 (s, 1H), 5.79 (dd, J=9.4, 6.3 Hz, 1H), 3.72-3.55 (m, 2H), 2.77-2.64 (m, 2H), 2.53-2.44 (m, 1H), 2.26-2.12 (m, 2H), 1.85-1.75 (m, 1H), 1.61-1.43 (m, 3H), 1.16 (d, J=7.2 Hz, 3H). MS (ESI) m/z: 607.0 (M+H)$^+$. Analytical HPLC (method A): RT=6.4 min, purity=99%.

Example 83

(13R,17S)-17-[4-(3-Chloro-2,6-difluorophenyl)-6-oxo-1,2,3,6-tetrahydropyridin-1-yl]-6,13-dimethyl-12-oxo-7,11,19-triazatetracyclo[16.3.1.0$^{2,10}$.0$^{4,8}$]docosa-1(22),2,4(8), 5,9,18,20-heptaene-5-carboxylic acid, TFA Salt

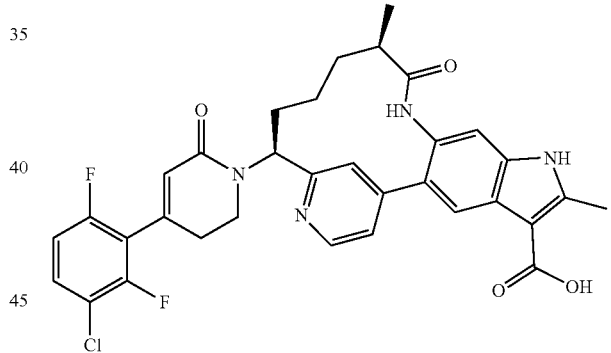

83A. tert-Butyl (13R,17S)-17-[4-(3-chloro-2,6-difluorophenyl)-6-oxo-1,2,3,6-tetrahydropyridin-1-yl]-6,13-dimethyl-12-oxo-7,11,19-triazatetracyclo[16.3.1.0$^{2,10}$.0$^{4,8}$]docosa-1 (22),2,4(8),5,9,18,20-heptaene-5-carboxylate, TFA Salt This compound was prepared according to a modified procedure described by Chen (*Organic Letters*, 2008, 10(4), 625-628.) A sealed tube was charged with Example 61 (0.034 g, 0.051 mmol), L-proline (1.181 mg, 10.26 µmol), cuprous iodide (0.977 mg, 5.13 µmol), DMSO (2 mL), tert-butyl 3-oxobutanoate (0.016 g, 0.103 mmol) and Cs$_2$CO$_3$ (0.067 g, 0.205 mmol). The reaction vessel was vacuumed and back-filled with argon three times and then the tube was sealed. The reaction was heated at 90° C. After 20 h, the reaction was cooled to rt. Purification by reverse phase HPLC afforded 83A (0.016 g, 34.5% yield) as a yellow solid. MS (ESI) m/z: 675.2 (M+H)$^+$.

Example 83

A solution of 83A (0.018 g, 0.020 mmol) in TFA (0.5 mL, 6.49 mmol)/DCM (1 mL) was stirred at rt. After 1h, the reaction was concentrated. Purification by reverse phase HPLC afforded Example 83 (0.012 g, 81% yield) as a yellow solid. MS (ESI) m/z: 619.1 (M+H)$^+$. $^1$H NMR (500 MHz, CD$_3$OD) δ 8.78 (d, J=5.8 Hz, 1H), 8.37 (s, 1H), 8.15 (d, J=1.4 Hz, 1H), 8.01 (dd, J=5.9, 1.8 Hz, 1H), 7.53 (td, J=8.7, 5.6 Hz, 1H), 7.33 (s, 1H), 7.08 (td, J=9.2, 1.7 Hz, 1H), 6.11 (s, 1H), 5.45 (dd, J=12.4, 4.1 Hz, 1H), 3.73-3.59 (m, 2H), 2.85-2.68 (m, 5H), 2.64-2.55 (m, 1H), 2.37-2.27 (m, 1H), 2.17-2.05 (m, 1H), 1.95-1.86 (m, 1H), 1.68-1.57 (m, 1H), 1.24 (br. s., 2H), 1.12 (d, J=6.9 Hz, 3H). Analytical HPLC (method A): RT=5.9 min, purity=99%.

Example 84

(13R,17S)-17-[4-(3-Chloro-2,6-difluorophenyl)-6-oxo-1,2,3,6-tetrahydropyridin-1-yl]-13-methyl-7,11,19-triazatetracyclo[16.3.1.0$^{2,10}$.0$^{4,8}$]docosa-1 (22),2,4(8),9,18,20-hexaene-6,12-dione, TFA Salt

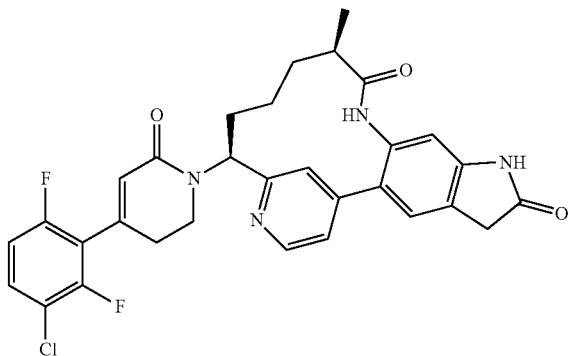 [SMILES: C[C@@H]1CCC[C@H](N2CCC(c3c(F)ccc(Cl)c3F)=CC2=O)c2cc(ccn2)-c2cc3c(cc2NC1=O)NC(=O)C3]

84A. Methyl (13R,17S)-17-[4-(3-chloro-2,6-difluorophenyl)-6-oxo-1,2,3,6-tetrahydropyridin-1-yl]-13-methyl-6,12-dioxo-7,11,19-triazatetracyclo[16.3.1.0$^{2,10}$.0$^{4,8}$]docosa-1 (22),2,4(8),9,18,20-hexaene-5-carboxylate, TFA Salt Compound 84A was prepared according to the procedure described in 73A, by replacing tert-butyl 3-oxobutanoate with dimethyl malonate. MS (ESI) m/z: 635.0 (M+H)$^+$.

Example 84

To a solution of 84A (0.014 g, 0.019 mmol) in MeOH (0.5 mL) was added 6N HCl (0.5 mL, 3.00 mmol). The reaction was microwaved at 90° C. for 30 min. and then the reaction was cooled to rt. Purification by reverse phase HPLC afforded Example 84 (0.007 g, 52.8% yield) as a yellow solid. $^1$H NMR (400 MHz, CD$_3$OD) δ 8.75 (d, J=5.9 Hz, 1H), 8.03 (d, J=1.5 Hz, 1H), 7.82 (dd, J=5.7, 1.8 Hz, 1H), 7.62-7.49 (m, 2H), 7.09 (td, J=9.2, 1.8 Hz, 1H), 6.85 (s, 1H), 6.11 (s, 1H), 5.43 (dd, J=12.4, 4.5 Hz, 1H), 3.81-3.60 (m, 4H), 2.88-2.55 (m, 3H), 2.34-2.22 (m, 1H), 2.12-2.01 (m, 1H), 1.96-1.85 (m, 1H), 1.67-1.55 (m, 1H), 1.36-0.99 (m, 5H). MS (ESI) m/z: 577.3 (M+H)$^+$. Analytical HPLC (method A): RT=5.9 min, purity=98%.

Example 85

(13R,17S)-17-[4-(3-Chloro-2,6-difluorophenyl)-6-oxo-1,2,3,6-tetrahydropyridin-1-yl]-6,13-dimethyl-7,11,19-triazatetracyclo[16.3.1.0$^{2,10}$.0$^{4,8}$]docosa-1(22),2,4(8), 5,9,18,20-heptaen-12-one, TFA Salt

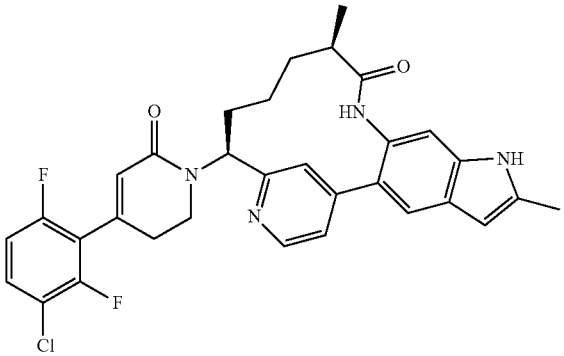 [SMILES: Cc1cc2cc3c(cc2[nH]1)NC(=O)[C@H](C)CCC[C@H](N1CCC(c2c(F)ccc(Cl)c2F)=CC1=O)c1cc-3ccn1]

Example 85 was prepared following the procedure described in Example 84, by replacing 84A with Example 83. MS (ESI) m/z: 575.3 (M+H)$^+$. $^1$H NMR (400 MHz, CD$_3$OD) δ 8.73 (d, J=5.9 Hz, 1H), 8.13 (d, J=1.5 Hz, 1H), 7.99 (dd, J=6.1, 1.7 Hz, 1H), 7.82 (s, 1H), 7.54 (td, J=8.7, 5.5 Hz, 1H), 7.26 (s, 1H), 7.09 (td, J=9.2, 1.8 Hz, 1H), 6.31 (s, 1H), 6.12 (s, 1H), 5.47 (dd, J=12.5, 4.0 Hz, 1H), 3.72-3.54 (m, 2H), 2.84-2.53 (m, 3H), 2.46 (s, 3H), 2.37-2.25 (m, 1H), 2.15-2.04 (m, 1H), 1.96-1.85 (m, 1H), 1.70-1.58 (m, 1H), 1.38-1.10 (m, 5H). Analytical HPLC (method A): RT=6.7 min, purity=95%.

Example 86

(14R,18S)-18-[4-(3-Chloro-2,6-difluorophenyl)-6-oxo-1,2,3,6-tetrahydropyridin-1-yl]-14-methyl-8,12,20-triazatetracyclo[17.3.1.0$^{2,11}$.0$^{4,9}$]tricosa-1(23),2(11),3,9,19,21-hexaene-7,13-dione, TFA Salt

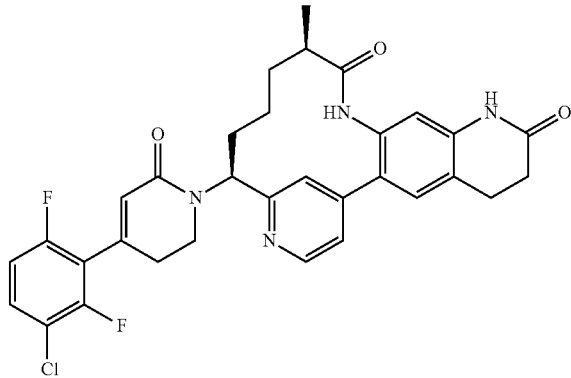 [SMILES: C[C@@H]1CCC[C@H](N2CCC(c3c(F)ccc(Cl)c3F)=CC2=O)c2cc(ccn2)-c2cc3c(cc2NC1=O)NC(=O)CC3]

86A. tert-Butyl N-[(10R,14S)-5-amino-10-methyl-9-oxo-8,16-diazatricyclo[13.3.1.0$^{2,7}$]nonadeca-1(19),2(7),3,5,15,17-hexaen-14-yl]carbamate To the suspension of 1I (1 g, 2.134 mmol) in MeOH (32.8 ml) was added 1N NaOH (12.81 ml, 12.81 mmol). The reaction was stirred in a sealed flask at 75° C. After 18 h, the reaction was cooled to rt and then it was concentrated. The residue was partitioned between EtOAc and water and the layers were separated. The aqueous layer was extracted with EtOAc. The organic layers were combined, washed with brine, dried over Na$_2$SO$_4$, filtered, and concentrated to afford 86A (0.9 g, 103% yield) as a white solid. MS (ESI) m/z: 411.1 (M+H)$^+$. The material was carried onto the next step without further purification.

86B. tert-Butyl N-[(10R,14S)-5-amino-4-iodo-10-methyl-9-oxo-8,16-diazatricyclo[13.3.1.0$^{2,7}$]nonadeca-1(19),2(7),3,5,15,17-hexaen-14-yl]carbamate To cooled (0° C.) solution of 86A (0.87 g, 2.119 mmol) in MeOH (21.19 ml) was added a solution of iodine monochloride (0.516 g, 3.18 mmol) in DCM (5.0 mL). The reaction was stirred at rt for 1 h and then it was concentrated. The residue was redissolved in EtOAc, washed with sat. NaHCO$_3$, brine, dried over Na$_2$SO$_4$, filtered, and concentrated. Purification by normal phase chromatography afforded 86B (0.9 g, 79% yield) as a brown solid. MS (ESI) m/z: 537.1 (M+H)$^+$.

86C. Methyl (2E)-3-[(10R,14S)-5-amino-14-{[(tert-butoxy)carbonyl]amino}-10-methyl-9-oxo-8,16-diazatricyclo[13.3.1.0$^{2,7}$]nonadeca-1(19),2(7),3,5,15,17-hexaen-4-yl]prop-2-enoate To a solution of 86B (0.15 g, 0.280 mmol) in DMF (2.80 ml) was added methyl acrylate (0.048 g, 0.559 mmol), Pd(OAc)$_2$ (2.51 mg, 0.011 mmol), and tributylamine (0.067 ml, 0.280 mmol). The reaction was microwaved at 150° C. for 10 min. and the reaction was cooled to rt. The reaction mixture was diluted with water and extracted with ethyl acetate (3×). The combined organic layers were washed with water, brine, dried over Na$_2$SO$_4$, filtered and concentrated. Purification by normal phase chromatography afforded 86C (0.124 g, 90% yield) as a yellow solid. MS (ESI) m/z: 495.2 (M+H)$^+$.

86D. Methyl 3-[(10R,14S)-5-amino-14-{[(tert-butoxy)carbonyl]amino}-10-methyl-9-oxo-8,16-diazatricyclo[13.3.1.0$^{2,7}$]nonadeca-1(19),2(7),3,5,15,17-hexaen-4-yl]propanoate To a solution of 86C (0.095 g, 0.192 mmol) in EtOH (5 mL) was added 10% palladium on carbon (0.020 g, 0.019 mmol). The reaction was stirred under a H$_2$-balloon. After 18 h, the reaction was stopped and it was filtered through a pad of Celite, rinsing with MeOH. The filtrate was concentrated to afford 86D (0.09 g, 94% yield) as a yellow solid. MS (ESI) m/z: 497.2 (M+H)$^+$. The material was carried onto the next step without further purification.

86E. tert-Butyl N-[(14R,18S)-14-methyl-7,13-dioxo-8,12,20-triazatetracyclo[17.3.1.0$^{2,11}$.0$^{4,9}$]tricosa-1(23),2(11),3,9,19,21-hexaen-18-yl]carbamate, TFA Salt A solution of 86D (0.09 g, 0.181 mmol) in MeOH (5 mL) was heated at 80° C. After 30 h, then p-toluenesulfonic acid monohydrate (3.45 mg, 0.018 mmol) was added and the reaction was heated to reflux. After 3h, the reaction was cooled to rt. Purification by reverse phase HPLC afforded 86E (0.068 g, 64.8% yield) as a yellow solid. MS (ESI) m/z: 465.1 (M+H)$^+$.

Example 86 was prepared following the procedures described in Example 1, by replacing 1I in step 1J with 86E and by replacing Intermediate 3 in step 1K with Intermediate 1. $^1$H NMR (500 MHz, CD$_3$OD) δ 8.77 (d, J=6.1 Hz, 1H), 8.10 (d, J=1.7 Hz, 1H), 7.89 (dd, J=5.9, 1.8 Hz, 1H), 7.59-7.51 (m, 2H), 7.10 (td, J=9.3, 1.8 Hz, 1H), 6.83 (s, 1H), 6.11 (s, 1H), 5.41 (dd, J=12.4, 4.4 Hz, 1H), 3.79-3.68 (m, 2H), 3.07 (t, J=7.6 Hz, 2H), 2.89-2.69 (m, 2H), 2.66-2.57 (m, 3H), 2.35-2.26 (m, 1H), 2.13-2.04 (m, 1H), 1.95-1.87 (m, 1H), 1.67-1.58 (m, 1H), 1.34-1.24 (m, 1H), 1.12-1.01 (m, 4H). MS (ESI) m/z: 591.1 (M+H)$^+$. Analytical (method A): RT=6.1 min, purity=99%.

Example 87 tert-Butyl 2-{[(10R,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamoyl}acetate, TFA Salt

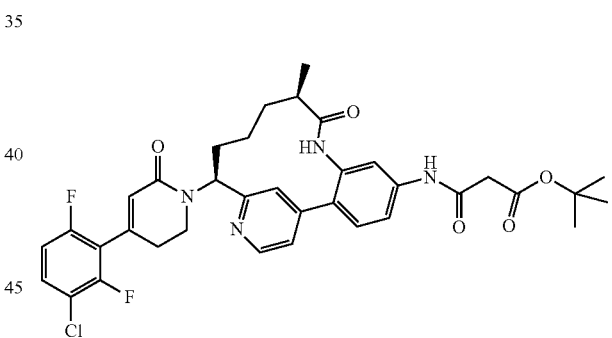

To a solution of Example 12 (0.04 g, 0.074 mmol) in DMF (1 mL) was added 3-(tert-butoxy)-3-oxopropanoic acid (0.024 g, 0.149 mmol), EDC (0.029 g, 0.149 mmol), HOBT (0.023 g, 0.149 mmol), and DIPEA (0.065 mL, 0.372 mmol). The reaction was stirred at rt. After 18 h, additional 3-(tert-butoxy)-3-oxopropanoic acid (0.024 g, 0.149 mmol) was added, and the reaction was warmed to 55° C. After 8 h, the reaction was stopped and it was cooled to rt. Purification by reverse phase HPLC (twice) afforded Example 87 (0.032 g, 53.2% yield) as a white solid. $^1$H NMR (400 MHz, CD$_3$OD) δ 8.79 (d, J=5.9 Hz, 1H), 8.16 (d, J=1.3 Hz, 1H), 7.93 (dd, J=5.9, 1.8 Hz, 1H), 7.77-7.64 (m, 3H), 7.58-7.49 (m, 1H), 7.10 (td, J=9.2, 1.8 Hz, 1H), 6.10 (s, 1H), 5.36 (dd, J=12.3, 4.6 Hz, 1H), 3.85-3.68 (m, 2H), 3.42 (s, 2H), 2.95-2.60 (m, 3H), 2.38-2.25 (m, 1H), 2.16-2.04 (m, 1H), 1.97-1.86 (m, 1H), 1.68-1.56 (m, 1H), 1.49 (s, 9H), 1.40-1.28 (m, 1H), 1.04 (d, J=6.8 Hz, 3H), 1.00-0.86 (m, 1H). MS (ESI) m/z: 679.4 (M+H)$^+$. Analytical HPLC (method A): RT=7.6 min, purity=98%.

Example 88

(10R,14S)-14-[4-(3-Chloro-2,6-difluorophenyl)-6-oxo-1,2,3,6-tetrahydropyridin-1-yl]-10-methyl-5-[(pyridin-2-yl)amino]-8,16-diazatricyclo[13.3.1.0$^{2,7}$]nonadeca-1(19),2(7),3,5,15,17-hexaen-9-one, 2TFA Salt

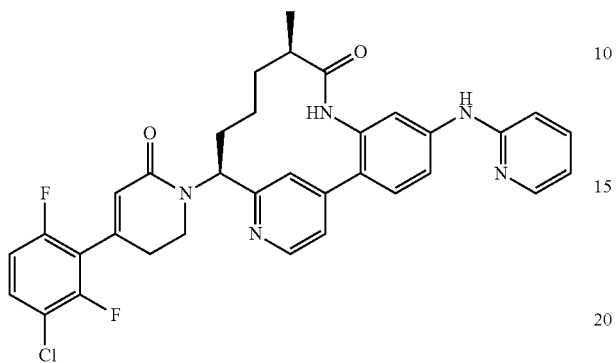

A sealed microwave vial containing Example 12 (0.020 g, 0.026 mmol), 2-fluoropyridine (0.011 ml, 0.131 mmol) in EtOH (0.523 ml) was microwaved at 150° C. for 30 min. Then additional 2-fluoropyridine (0.011 ml, 0.131 mmol) was added and the reaction was microwaved 175° C. for 1.5 h. The reaction was cooled to rt. Purification by reverse phase HPLC (twice) afforded Example 88 (1.11 mg, 5.04% yield) as a yellow solid. $^1$H NMR (400 MHz, CD$_3$OD) δ 8.74 (d, J=5.5 Hz, 1H), 8.05-7.97 (m, 2H), 7.86 (s, 1H), 7.78 (d, J=8.4 Hz, 1H), 7.67 (dd, J=5.5, 1.3 Hz, 1H), 7.60-7.48 (m, 3H), 7.22 (d, J=8.6 Hz, 1H), 7.13-7.04 (m, 2H), 6.10 (s, 1H), 5.51 (dd, J=12.5, 4.6 Hz, 1H), 3.94-3.71 (m, 2H), 2.86-2.57 (m, 3H), 2.23 (d, J=11.7 Hz, 1H), 2.06-1.88 (m, 2H), 1.64-1.52 (m, 1H), 1.40-1.28 (m, 1H), 1.10-0.93 (m, 4H). MS (ESI) m/z: 614.2 (M+H)$^+$. Analytical HPLC (method A): RT=5.5 min, purity=100%.

Example 89

(10R,14S)-14-[4-(3-Chloro-2,6-difluorophenyl)-6-oxo-1,2,3,6-tetrahydropyridin-1-yl]-10-methyl-5-[(pyridin-4-yl)amino]-8,16-diazatricyclo[13.3.1.0$^{2,7}$]nonadeca-1(19),2(7),3,5,15,17-hexaen-9-one, 2 TFA Salt

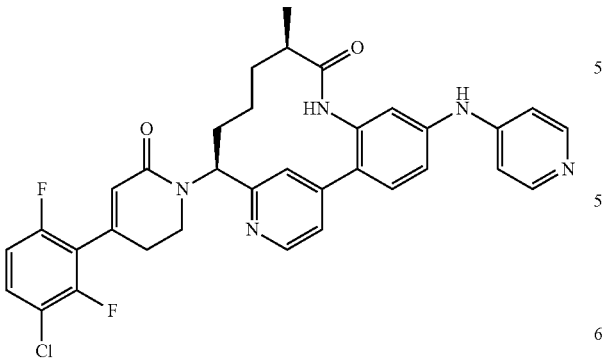

Example 89 was prepared by following the procedures described in Example 88, by replacing 2-fluoropyridine with 4-bromopyridine, 1HCl. $^1$H NMR (400 MHz, CD$_3$OD) δ 8.70 (d, J=5.1 Hz, 1H), 8.24 (d, J=7.5 Hz, 2H), 7.76 (d, J=8.4 Hz, 1H), 7.68 (s, 1H), 7.57-7.43 (m, 3H), 7.29 (d, J=2.2 Hz, 1H), 7.24 (d, J=7.3 Hz, 2H), 7.09 (td, J=9.2, 1.9 Hz, 1H), 6.10 (s, 1H), 5.62 (dd, J=12.7, 4.5 Hz, 1H), 4.02-3.92 (m, 1H), 3.83-3.71 (m, 1H), 2.80-2.55 (m, 3H), 2.26-2.14 (m, 1H), 2.00-1.85 (m, 2H), 1.61-1.49 (m, 1H), 1.40-1.27 (m, 1H), 1.07-0.85 (m, 4H). MS (ESI) m/z: 614.3 (M+H)$^+$. Analytical HPLC (method A): RT=5.2 min, purity=97%.

Example 90

(10R,14S)-14-[4-(3-Chloro-2,6-difluorophenyl)-6-oxo-1,2,3,6-tetrahydropyridin-1-yl]-10-methyl-5-[(pyrimidin-4-yl)amino]-8,16-diazatricyclo[13.3.1.0$^{2,7}$]nonadeca-1(19),2(7),3,5,15,17-hexaen-9-one, 2 TFA Salt

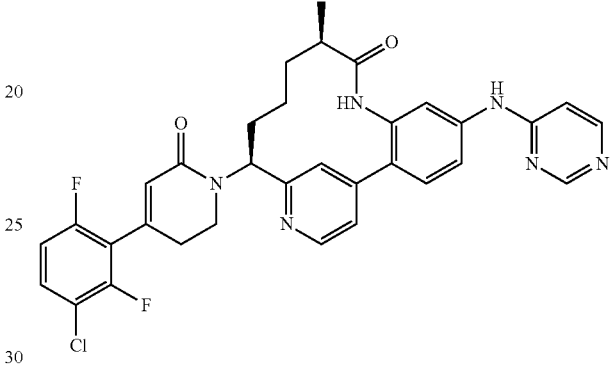

Example 90 was prepared by following the procedures described in Example 88, by replacing 2-fluoropyridine with 4-bromopyrimidine, 1HCl. $^1$H NMR (400 MHz, CD$_3$OD) δ 8.92-8.89 (m, 1H), 8.77 (d, J=5.7 Hz, 1H), 8.35 (dd, J=7.2, 1.4 Hz, 1H), 7.97 (d, J=1.1 Hz, 1H), 7.86-7.74 (m, 4H), 7.58-7.49 (m, 1H), 7.15-7.06 (m, 2H), 6.10 (s, 1H), 5.47 (dd, J=12.4, 4.7 Hz, 1H), 3.95-3.86 (m, 1H), 3.80-3.71 (m, 1H), 2.89-2.60 (m, 3H), 2.34-2.21 (m, 1H), 2.08-1.88 (m, 2H), 1.66-1.54 (m, 1H), 1.42-1.30 (m, 1H), 1.04 (d, J=7.0 Hz, 3H), 0.98-0.82 (m, 1H). MS (ESI) m/z: 615.2 (M+H)$^+$. Analytical HPLC (method A): RT=5.2 min, purity=95%.

Example 91

(10R,14S)-5-Amino-14-[4-(3-chloro-2,6-difluorophenyl)-2-oxo-1,2-dihydropyridin-1-yl]-10-methyl-8,16-diazatricyclo[13.3.1.0$^{2,7}$]nonadeca-1(19),2,4,6,15,17-hexaen-9-one, 2 TFA Salt

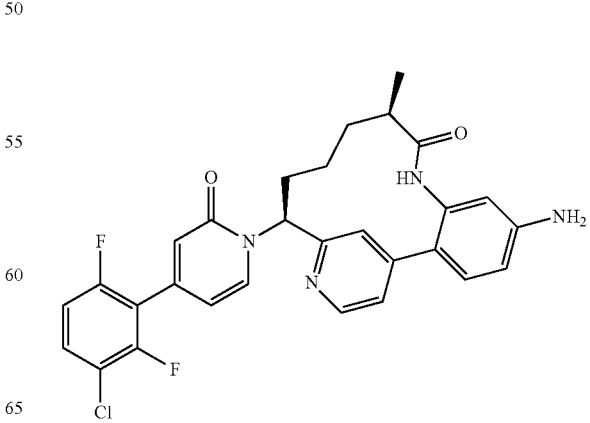

A vial containing Example 12 (0.02 g, 0.026 mmol), L-proline (0.602 mg, 5.23 mol), cuprous iodide (0.498 mg, 2.61 µmol), DMSO (1 mL), 3-iodopyridine (10.72 mg, 0.052 mmol) and Cs$_2$CO$_3$ (0.034 g, 0.105 mmol) was vacuumed and back-filled with argon three times and then the vial was sealed. The reaction was stirred at 80° C. for 20 h and then it was cooled to rt. Purification by reverse phase HPLC afforded Example 91 (0.007 g, 33.6% yield) as a yellow solid. $^1$H NMR (400 MHz, CD$_3$OD) δ 8.64 (d, J=5.7 Hz, 1H), 8.14 (d, J=7.3 Hz, 1H), 8.02 (d, J=1.1 Hz, 1H), 7.69-7.55 (m, 3H), 7.15 (td, J=9.1, 1.8 Hz, 1H), 7.01 (dd, J=8.5, 2.3 Hz, 1H), 6.84 (d, J=2.2 Hz, 1H), 6.68 (s, 1H), 6.57 (dd, J=7.3, 1.3 Hz, 1H), 5.99 (dd, J=12.5, 4.6 Hz, 1H), 2.76-2.64 (m, 1H), 2.48-2.37 (m, 1H), 2.21-1.96 (m, 2H), 1.68-1.46 (m, 2H), 1.02 (d, J=6.8 Hz, 3H), 0.93-0.79 (m, 1H). MS (ESI) m/z: 535.2 (M+H)$^+$. Analytical HPLC (method A): RT=6.2 min, purity=96%.

Example 92

(10R,14S)-14-[4-(3-Chloro-2, 6-difluorophenyl)-2-oxo-1,2-dihydropyridin-1-yl]-10-methyl-5-[(pyrimidin-2-yl)amino]-8,16-diazatricyclo[13.3.1.0$^{2,7}$]nonadeca-1(19),2(7),3,5,15,17-hexaen-9-one, 2 TFA Salt

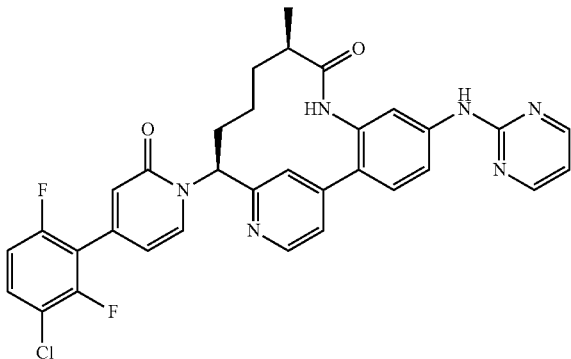 [SMILES: C[C@@H]1CCC[C@H](n2ccc(-c3c(F)ccc(Cl)c3F)cc2=O)c2cc(ccn2)-c2ccc(Nc3ncccn3)cc2NC1=O]

A solution of Example 91 (0.005 g, 6.55 µmol) and 2-chloropyrimidine (2.252 mg, 0.020 mmol) in EtOH (1 mL) was microwaved at 150° C. for 1h and then the reaction was cooled to rt. Next, TFA (1.010 µl, 0.013 mmol) was added and the reaction was microwaved at 150° C. for 1 h and then at 160° C. for 1 h. The reaction was cooled to rt and concentrated. Purification by reverse phase HPLC afforded Example 92 (1.37 mg, 24.8% yield) as a yellow solid. $^1$H NMR (500 MHz, CD$_3$OD) δ 8.69 (d, J=5.5 Hz, 1H), 8.51 (d, J=5.0 Hz, 2H), 8.18 (d, J=7.2 Hz, 1H), 8.11 (s, 1H), 7.93 (d, J=2.2 Hz, 1H), 7.80-7.73 (m, 2H), 7.65-7.58 (m, 2H), 7.16 (td, J=9.3, 1.8 Hz, 1H), 6.89 (t, J=4.8 Hz, 1H), 6.69 (s, 1H), 6.59 (d, J=7.4 Hz, 1H), 6.01 (dd, J=12.2, 4.8 Hz, 1H), 2.79-2.72 (m, 1H), 2.50-2.41 (m, 1H), 2.20-2.01 (m, 2H), 1.70-1.51 (m, 2H), 1.03 (d, J=6.9 Hz, 3H), 0.85-0.73 (m, 1H). MS (ESI) m/z: 613.2 (M+H)$^+$. Analytical HPLC (method A): RT=7.7 min, purity=100%.

Example 93

(10R,14S)-14-[4-(3-Chloro-2,6-difluorophenyl)-6-oxo-1,2,3,6-tetrahydropyridin-1-yl]-10-methyl-5-[(pyrazin-2-yl)amino]-8,16-diazatricyclo[13.3.1.0$^{2,7}$]nonadeca-1(19),2(7),3,5,15,17-hexaen-9-one, 2 TFA Salt

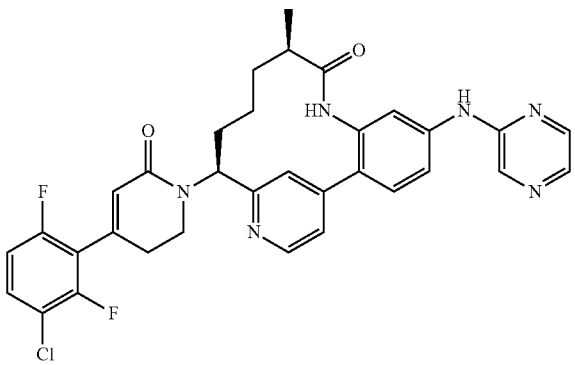

Example 93 was prepared according to a modified procedure described by Lach (*Tetrahedron Lett.*, 2011, 52(16), 1882-1887.) A microwave vial containing Example 12 (0.025 g, 0.047 mmol), cesium carbonate (0.030 g, 0.093 mmol), palladium(II) acetate (1.045 mg, 4.66 µmol), xantphos (5.39 mg, 9.31 µmol), and 2-chloropyrazine (8.00 mg, 0.070 mmol) in 1,4-dioxane (0.931 ml) was degassed with argon for 10 min. The vial was sealed and then it was heated at 85° C. After 4 h, the reaction was cooled to rt and it was concentrated. Purification by reverse phase HPLC afforded Example 93 (0.009 g, 22.8% yield) as a yellow solid. $^1$H NMR (400 MHz, CD$_3$OD) δ 8.76 (d, J=5.9 Hz, 1H), 8.25-8.18 (m, 3H), 7.99-7.92 (m, 3H), 7.82 (dd, J=8.6, 2.2 Hz, 1H), 7.70 (d, J=8.6 Hz, 1H), 7.58-7.51 (m, 1H), 7.10 (td, J=9.3, 1.9 Hz, 1H), 6.11 (s, 1H), 5.35 (dd, J=12.3, 4.6 Hz, 1H), 3.83-3.68 (m, 2H), 2.95-2.64 (m, 3H), 2.39-2.28 (m, 1H), 2.17-2.05 (m, 1H), 2.00-1.89 (m, 1H), 1.71-1.59 (m, 1H), 1.44-1.32 (m, 1H), 1.07 (d, J=7.0 Hz, 3H), 1.03-0.89 (m, 1H). MS (ESI) m/z: 615.2 (M+H)$^+$. Analytical HPLC (method A): RT=6.5 min, purity=99%.

Example 94

Methyl N-[(10R,14S)-14-[4-(6-bromo-3-chloro-2-fluorophenyl)-2-oxo-2,5-dihydro-1H-pyrrol-1-yl]-10-methyl-9-oxo-8,16-diazatricyclo[13.3.1.0$^{2,7}$]nonadeca-1(19),2(7),3,5,15,17-hexaen-5-yl]carbamate, TFA Salt

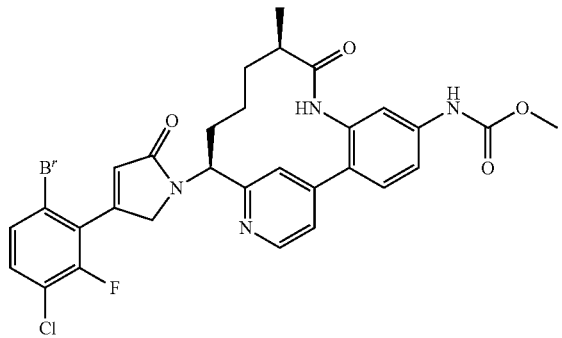 [SMILES: COC(=O)Nc1ccc2c(c1)NC(=O)[C@H](C)CCC[C@H](N1CC(c3c(Br)ccc(Cl)c3F)=CC1=O)c1cc-2ccn1]

To the mixture of Intermediate 15 (0.025 g, 0.081 mmol), and 1J (0.03 g, 0.081 mmol) in CHCl₃ (2 ml) was added sodium cyanoborohydride (7.68 mg, 0.122 mmol) and acetic acid (9.32 μl, 0.163 mmol). The reaction was stirred at rt for 18 h and then it was concentrated. Purification by reverse phase HPLC (twice) afforded Example 94 (4.53 mg, 4.73 μmol, 5.8% yield) as a yellow solid. ¹H NMR (400 MHz, CD₃OD) δ 8.74 (d, J=5.9 Hz, 1H), 8.04 (s, 1H), 7.78 (dd, J=5.7, 1.5 Hz, 1H), 7.64-7.46 (m, 5H), 6.41-6.38 (m, 1H), 5.33 (dd, J=11.8, 5.8 Hz, 1H), 4.93-4.86 (m, 1H), 4.74-4.66 (m, 1H), 3.80-3.75 (m, 3H), 2.79-2.67 (m, 1H), 2.28-2.09 (m, 2H), 2.01-1.91 (m, 1H), 1.68-1.41 (m, 2H), 0.96 (d, J=7.0 Hz, 3H), 0.58-0.44 (m, 1H). MS (ESI) m/z: 641.2 (M+H)⁺, 643.1 (M+2H)⁺. Analytical HPLC (method A): RT=7.0 min, purity=79%.

Example 95

(10S,14S)-14-[4-(3-chloro-2,6-difluorophenyl)-6-oxo-1,2,3,6-tetrahydropyridin-1-yl]-10-(propan-2-yl)-8,16-diazatricyclo[13.3.1.0²,⁷]nonadeca-1(18),2,4,6,15(19),16-hexaen-9-one, TFA Salt

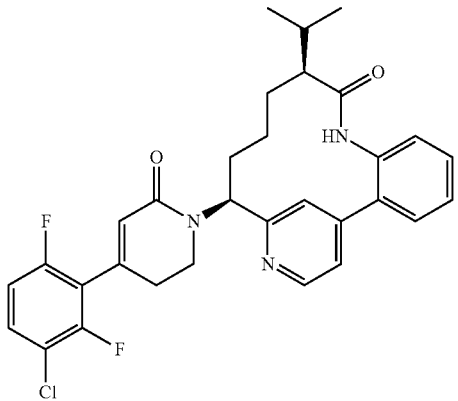 [SMILES: CC(C)[C@@H]1CCC[C@H](N2CCC(c3c(F)ccc(Cl)c3F)=CC2=O)c2cc(ccn2)-c2ccccc2NC1=O]

95A. (S)-tert-Butyl (1-(4-(2-aminophenyl)pyridin-2-yl)but-3-en-1-yl)carbamate

To a 20 ml microwave vial was added 1C (1.0g, 3.54 mmol), (2-aminophenyl)boronic acid (0.533 g, 3.89 mmol), DMSO (17.68 ml) and water (0.319 ml, 17.68 mmol). The suspension was degassed with N₂ for 10 min. Next, PdCl₂(dppf)-CH₂Cl₂ adduct (0.289 g, 0.354 mmol) and potassium phosphate tribasic (3.00 g, 14.15 mmol) were added. The vial was sealed and the dark red suspension was warmed to 90° C. overnight. The reaction was cooled to r.t, partitioned between EtOAc and water, and the layers were separated. The aqueous layer was extracted with EtOAc (3×). The organic layers were combined washed with brine, dried over Na₂SO₄, filtered and concentrated to give a black foam. Purification by normal phase chromatography gave 101A (1.00 g, 83%) as an orange gum. MS (ESI) m/z: 340.3 (M+H)⁺. ¹H NMR (400 MHz, CHLOROFORM-d) δ 8.61 (d, J=4.8 Hz, 1H), 7.37-7.25 (m, 3H), 7.21 (t, J=7.7 Hz, 1H), 7.12 (d, J=7.7 Hz, 1H), 6.85 (t, J=7.5 Hz, 1H), 6.77 (d, J=7.9 Hz, 1H), 5.84-5.56 (m, 2H), 5.09-4.98 (m, 2H), 4.93-4.78 (m, 1H), 3.80 (br. s., 2H), 2.62 (t, J=6.6 Hz, 2H), 1.44 (s, 9H).

95B. tert-Butyl ((1S)-1-(4-(2-(2-isopropylbut-3-enamido)phenyl)pyridin-2-yl)but-3-en-1-yl)carbamate A solution of 95A (0.3 g, 0.88 mmol) and Intermediate 13 (0.13 g, 0.97 mmol) in pyridine (4.42 ml) and acetonitrile (4.42 ml) was cooled in an ice bath. Next, POCl₃ (0.12 ml, 1.33 mmol) was added dropwise. After 10 min the reaction was quenched with aq. NaHCO₃, extracted with EtOAc (3×), then CH₂Cl₂ (2×). The organic layers were combined and then concentrated. Purification by normal phase chromatography gave 95B (0.19 g, 49%) as a yellow glass. MS (ESI) m/z: 450.4 (M+H)⁺. ¹H NMR (400 MHz, CHLOROFORM-d) δ 8.63 (d, J=4.8 Hz, 1H), 8.19 (d, J=8.1 Hz, 1H), 7.51-7.35 (m, 1H), 7.31-7.01 (m, 5H), 5.85-5.51 (m, 3H), 5.24-4.94 (m, 4H), 4.85 (d, J=6.4 Hz, 1H), 2.70-2.43 (m, 3H), 2.17 (ddd, J=13.6, 6.7, 3.4 Hz, 1H), 0.97-0.68 (m, 6H).

95C. tert-butyl N-[(10S,11E,14S)-9-oxo-10-(propan-2-yl)-8,16-diazatricyclo[13.3.1.0²,⁷]nonadeca-1(18), 2,4,6,11,15(19), 16-heptaen-14-yl]carbamate, diastereomer A and 95D. tert-butyl N-[(10R,11E,14S)-9-oxo-10-(propan-2-yl)-8,16-diazatricyclo[13.3.1.0²,⁷]nonadeca-1(18), 2,4,6,11,15(19), 16-heptaen-14-yl]carbamate, Diastereomer B To a 20 mL microwave vial was added 95B (0.217 g, 0.483 mmol) and dichloroethane (12 ml). The solution was degassed with argon for 30 min. Then Grubbs II (0.082 g, 0.097 mmol) was added to the reaction mixture. The vial was sealed and microwaved at 120° C. for 30 min. The reaction was cooled to rt. Additional Grubbs II (0.082 g, 0.097 mmol) was added and the microwave vial was sealed. The reaction was microwaved at 120° C. for 60 min and then cooled to rt. The dark brown solution was concentrated to give a dark brown residue. The residue was purified by normal phase chromatography to give 95C, diastereomer A (0.0181 g, 8.9% yield) as a yellow residue and 95D, diastereomer B (0.0207 g, 10.2% yield) as a reddish-brown residue.

Diastereomer A: MS (ESI) m/z: 422.1 (M+H)⁺. ¹H NMR (500 MHz, METHANOL-d₄) δ 8.55 (d, J=5.2 Hz, 1H), 7.49-7.40 (m, 3H), 7.30-7.24 (m, 2H), 6.87 (s, 1H), 5.66 (ddd, J=15.3, 10.9, 4.3 Hz, 1H), 4.62-4.54 (m, 1H), 4.37 (dd, J=15.3, 9.8 Hz, 1H), 2.79-2.72 (m, 1H), 2.58 (t, J=10.2 Hz, 1H), 2.05-1.96 (m, 1H), 1.84-1.73 (m, 1H), 1.53-1.25 (m, 9H), 0.87 (d, J=6.6 Hz, 3H), 0.79 (d, J=6.6 Hz, 3H).

Diastereomer B: MS (ESI) m/z: 422.1 (M+H)⁺. ¹H NMR (500 MHz, METHANOL-d₄) δ 8.49 (dd, J=5.1, 0.7 Hz, 1H), 7.50-7.40 (m, 3H), 7.30-7.26 (m, 2H), 7.01 (s, 1H), 5.78-5.66 (m, 1H), 4.94-4.86 (m, 1H), 4.53 (dd, J=15.3, 9.8 Hz, 1H), 2.68-2.52 (m, 2H), 2.38-2.24 (m, 1H), 1.96-1.79 (m, 1H), 1.46-1.28 (m, 9H), 0.90 (d, J=6.6 Hz, 3H), 0.81 (d, J=6.6 Hz, 3H).

95E. tert-butyl N-[(10S,14S)-9-oxo-10-(propan-2-yl)-8,16-diazatricyclo[13.3.1.0²,⁷]nonadeca-1(18),2,4,6,15(19),16-hexaen-14-yl]carbamate The TFA salt of compound 95C, diastereomer A (39 mg, 0,073 mmol) was dissolved in MeOH (10 mL). Pearlman catalyst (20% wt) (0.025 g, 0.036 mmol) was added. The reaction was stirred at rt under 55 psi H₂ for 2 days. The reaction mixture was filtered, washed with MeOH, and the filtrate was concentrated to give 95E (30 mg, 97% yield) as a clear glass. MS (ESI) m/z: 424.2 (M+H)⁺.

95F. (10S,14S)-14-amino-10-(propan-2-yl)-8,16-diazatricyclo[13.3.1.0²,⁷]nonadeca-1(18),2,4,6,15(19),16-hexaen-9-one, TFA Salt A solution of 95E (30 mg, 0.071 mmol) in 25% TFA in CH₂Cl₂ (0.5 mL) was stirred at rt. After 1 h, the reaction mixture was concentrated under vacuum to afford 95F (30 mg, 75%), as a beige foam. MS (ESI) m/z: 324.3 (M+H)⁺.

Example 95

Example 95 was prepared according to the procedures described in Example 1, by replacing 1J with 95F and by replacing Intermediate 3 with Intermediate 1 in step 1K. ¹H NMR (400 MHz, METHANOL-d₄) δ 8.78 (br. s., 1H), 8.03 (br. s., 1H), 7.83 (br. s., 1H), 7.71 (d, J=7.5 Hz, 1H), 7.64-7.45 (m, 3H), 7.33 (t, J=3.5 Hz, 2H), 7.10 (t, J=9.2 Hz, 1H), 6.11 (s, 1H), 5.52-5.42 (m, 1H), 3.77-3.66 (m, 2H), 2.85-2.66 (m, 2H), 2.32-2.20 (m, 1H), 2.19-2.12 (m, 2H), 1.99-1.86 (m, 1H), 1.85-1.68 (m, 1H), 1.67-1.55 (m, 1H), 1.26-1.14 (m, 2H), 1.03-0.85 (m, 6H). MS (ESI) m/z: 550.2 (M+H)⁺. Analytical HPLC (method A): RT=7.7 min, purity=96%.

Example 96

(10R,14S)-14-[4-(3-chloro-2,6-difluorophenyl)-6-oxo-1,2,3,6-tetrahydropyridin-1-yl]-10-(propan-2-yl)-8,16-diazatricyclo[13.3.1.0²,⁷]nonadeca-1(18),2,4,6,15(19), 16-hexaen-9-one, TFA Salt

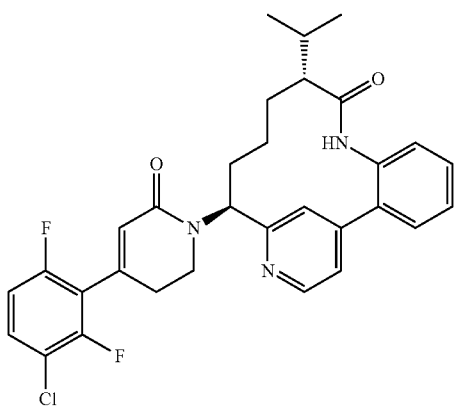 [SMILES: CC(C)[C@H]1CCC[C@H](N2CCC(c3c(F)ccc(Cl)c3F)=CC2=O)c2cc(ccn2)-c2ccccc2NC1=O]

Example 96 was prepared according to the procedures described in Example 95, by replacing 95C, diastereomer A with 95D, diastereomer B. ¹H NMR (400 MHz, METHANOL-d₄) δ 8.76 (br. s., 1H), 8.14 (br. s., 1H), 7.88 (br. s., 1H), 7.78 (dd, J=7.5, 1.5 Hz, 1H), 7.67-7.47 (m, 3H), 7.41-7.26 (m, 1H), 7.10 (td, J=9.3, 1.7 Hz, 1H), 6.09 (s, 1H), 5.44-5.33 (m, 1H), 4.01 (dt, J=12.3, 6.3 Hz, 1H), 3.85 (ddd, J=12.2, 9.5, 5.2 Hz, 1H), 3.00-2.86 (m, 1H), 2.85-2.71 (m, 1H), 2.352.26 (m, 1H), 2.12-1.94 (m, 2H), 1.88-1.76 (m, 1H), 1.74-1.64 (m, 1H), 1.64-1.52 (m, 1H), 1.20-1.09 (m, 2H), 1.02 (dd, J=6.5, 4.3 Hz, 6H). MS (ESI) m/z: 550.2 (M+H)⁺. Analytical HPLC (method A): RT=7.4 min, purity=99%.

Example 97

Methyl N-[(10R,14S)-10-methyl-14-[4-(1-methyl-1H-imidazol-5-yl)-6-oxo-1,2,3,6-tetrahydropyridin-1-yl]-9-oxo-8,16-diazatricyclo[13.3.1.0²,⁷]nonadeca-1(19),2,4,6,15,17-hexaen-5-yl]carbamate, 2 TFA Salt

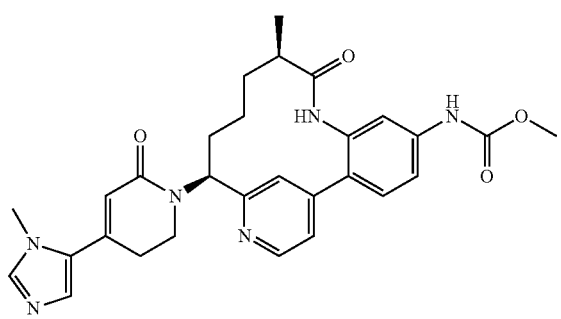 [SMILES: COC(=O)Nc1ccc2c(c1)NC(=O)[C@H](C)CCC[C@H](N1CCC(c3cncn3C)=CC1=O)c1cc-2ccn1]

Example 97 was prepared by following the procedures described in Example 1, by replacing Intermediate 3 with Intermediate 6 in step 1K. ¹H NMR (400 MHz, METHANOL-d₄) δ 9.64 (s, 1H), 8.99 (br. s., 1H), 8.74 (br. s., 1H), 8.03 (br. s., 1H), 7.94-7.73 (m, 2H), 7.66-7.50 (m, 3H), 6.31 (s, 1H), 5.46-5.37 (m, 1H), 4.07-3.92 (m, 3H), 3.87-3.60 (m, 5H), 2.94-2.72 (m, 2H), 2.67-2.58 (m, 1H), 2.362.22 (m, 1H), 2.13-1.96 (m, 1H), 1.95-1.82 (m, 1H), 1.66-1.54 (m, 1H), 1.43-1.22 (m, 2H), 1.06 (d, J=6.8 Hz, 3H), 0.99 (m, 1H). MS (ESI) m/z: 529.3 (M+H)⁺. Analytical HPLC (method A): RT=2.8 min, purity=99%.

Example 98

Methyl N-[(10R,14S)-14-(4-cyclohexyl-6-oxo-1,2,3,6-tetrahydropyridin-1-yl)-10-methyl-9-oxo-8,16-diazatricyclo[13.3.1.0²,⁷]nonadeca-1(19),2,4,6,15,17-hexaen-5-yl]carbamate, TFA Salt

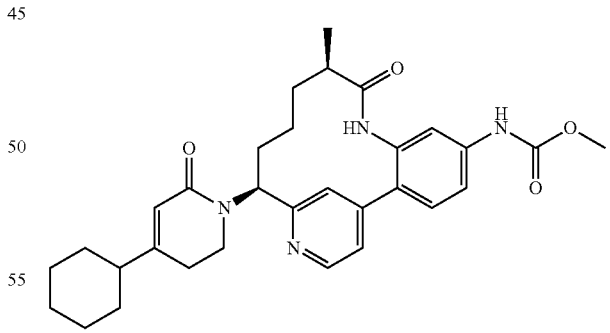

Example 98 was prepared by following the procedures described in Example 1, by replacing Intermediate 3 with Intermediate 4 in step 1K. ¹H NMR (400 MHz, METHANOL-d₄) δ 9.66 (s, 1H), 8.72 (br. s., 1H), 8.07 (br. s., 1H), 7.86 (br. s., 1H), 7.67-7.59 (m, 1H), 7.58-7.49 (m, 2H), 5.64 (s, 1H), 5.36-5.17 (m, 1H), 3.77 (s, 3H), 3.68-3.43 (m, 2H), 2.69-2.56 (m, 1H), 2.53-2.34 (m, 2H), 2.32-2.20 (m, 1H), 2.17-2.07 (m, 1H), 2.051.94 (m, 1H), 1.94-1.75 (m, 5H), 1.75-1.67 (m, 1H), 1.65-1.51 (m, 1H), 1.43-1.13 (m, 6H), 1.03 (d, J=6.8 Hz, 3H), 0.97-0.82 (m, 1H) MS (ESI) m/z: 531.2 (M+H)⁺. Analytical HPLC (method A): RT=6.5 min, purity=97%.

Example 99

Methyl N-[(10R,14S)-14-[4-(5-chloropyridin-3-yl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate, bis TFA Salt

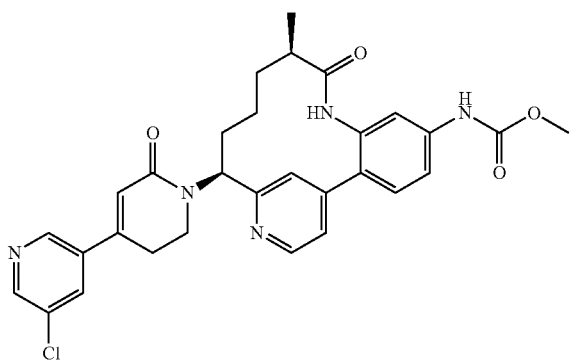 [SMILES: COC(=O)Nc1ccc2c(c1)NC(=O)[C@H](C)CCC[C@H](N1CCC(c3cncc(Cl)c3)=CC1=O)c1cc-2ccn1]

Example 99 was prepared by following the procedures described in Example 1, by replacing Intermediate 3 with Intermediate 5 in step 1K. ¹H NMR (400 MHz, METHANOL-d₄) δ 9.66 (s, 1H), 8.83-8.67 (m, 2H), 8.67-8.52 (m, 1H), 8.19-7.98 (m, 2H), 7.94-7.81 (m, 1H), 7.67-7.59 (m, 1H), 7.59-7.51 (m, 2H), 6.40 (s, 1H), 5.45-5.33 (m, 1H), 3.87-3.64 (m, 5H), 2.95-2.97 (m, 2H), 2.71-2.55 (m, 1H), 2.40-2.20 (m, 1H), 2.13-1.99 (m, 1H), 1.97-1.80 (m, 1H), 1.69-1.51 (m, 1H), 1.42-1.25 (m, 1H), 1.05 (d, J=6.8 Hz, 3H), 1.00-0.84 (m, 1H). MS (ESI) m/z: 560.2 (M+H)⁺. Analytical HPLC (method A): RT=5.0 min, purity=93%.

Example 100

(10S,14S)-14-{4-[3-chloro-2-fluoro-6-(1H-1,2,3,4-tetrazol-1-yl)phenyl]-6-oxo-1,2,3,6-tetrahydropyridin-1-yl}-10-(propan-2-yl)-8,16-diazatricyclo[13.3.1.0$^{2,7}$]nonadeca-1(18),2,4,6,15(19),16-hexaen-9-one, TFA Salt

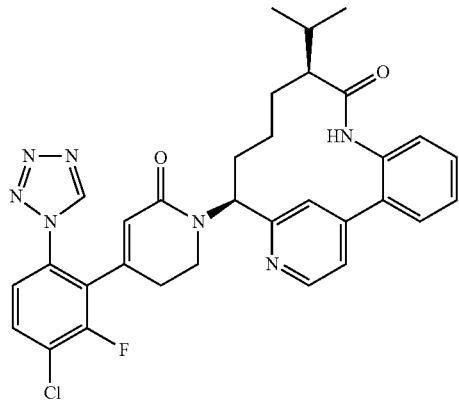 [SMILES: CC(C)[C@@H]1CCC[C@H](N2CCC(c3c(-n4cnnn4)ccc(Cl)c3F)=CC2=O)c2cc(ccn2)-c2ccccc2NC1=O]

Example 100 was prepared by following the procedures described in Example 45, by replacing Intermediate 45H with 95F and by replacing Intermediate 2 with Intermediate 27. ¹H NMR (400 MHz, METHANOL-d₄) δ 9.53 (s, 1H), 8.83-8.62 (m, 1H), 8.04-7.87 (m, 1H), 7.85-7.65 (m, 3H), 7.62-7.47 (m, 3H), 7.30 (dd, J=7.8, 1.2 Hz, 1H), 5.72 (s, 1H), 5.50-5.31 (m, 1H), 3.67-3.53 (m, 2H), 2.65-2.40 (m, 2H), 2.19-2.07 (m, 1H), 2.07-1.84 (m, 3H), 1.81-1.70 (m, 1H), 1.61-1.45 (m, 1H), 1.23-1.07 (m, 2H), 0.96 (t, J=6.2 Hz, 6H). MS (ESI) m/z: 600.1 (M+H)⁺. Analytical HPLC (method A): RT=6.8 min, purity=95%.

Example 101

Methyl N-[(10R,14S)-14-[4-(1-benzyl-1H-imidazol-5-yl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate, bis TFA Salt

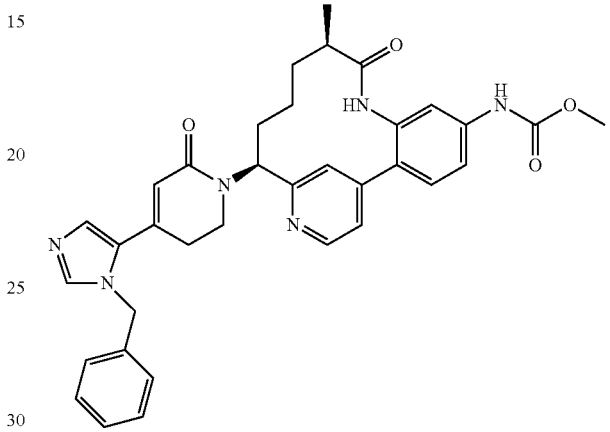

Example 101 was prepared by following the procedures described in Example 1, by replacing Intermediate 3 with Intermediate 7. ¹H NMR (500 MHz, DMSO-d₆) δ 9.89 (s, 1H), 9.70 (s, 1H), 8.57 (d, J=5.0 Hz, 1H), 7.94 (d, J=0.8 Hz, 1H), 7.49 (s, 2H), 7.45-7.39 (m, 2H), 7.38-7.31 (m, 3H), 7.31-7.26 (m, 2H), 6.99 (d, J=7.2 Hz, 2H), 5.74 (s, 1H), 5.52 (dd, J=12.5, 4.5 Hz, 1H), 5.42 (s, 2H), 3.92-3.80 (m, 1H), 3.71 (s, 3H), 3.60-3.50 (m, 1H), 2.71-2.54 (m, 3H), 2.03-1.95 (m, 1H), 1.92-1.83 (m, 1H), 1.60-1.52 (m, 1H), 1.47-1.32 (m, 1H), 1.25-1.11 (m, 1H), 0.86 (d, J=6.9 Hz, 3H), 0.57-0.40 (m, 1H). MS (ESI) m/z: 605.3 (M+H)⁺. Analytical HPLC (method D): RT=1.1 min, purity=100%.

Example 102

Methyl N-[(10R,14S)-14-[4-(3-chloro-6-cyano-2-fluorophenyl)-6-oxo-1,2,3,6-tetrahydropyridin-1-yl]-10-methyl-9-oxo-8,18-diazatricyclo[13.3.1.0$^{2,7}$]nonadeca-1(19),2(7),3,5,15,17-hexaen-5-yl]carbamate, TFA Salt

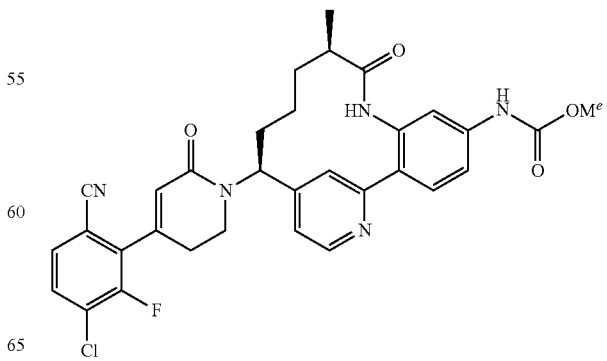

Example 102 was prepared by following the procedures described in Example 1. $^1$H NMR (500 MHz, ACETONITRILE-d3) δ 8.59 (d, J=5.23 Hz, 1H), 8.03 (s, 1H), 7.86 (s, 1H), 7.67 (d, J=8.25 Hz, 2H), 7.49-7.56 (m, 2H), 7.36-7.42 (m, 2H), 7.30 (d, J=4.13 Hz, 1H), 6.01 (s, 1H), 5.45 (dd, J=3.85, 12.38 Hz, 1H), 3.64 (s, 3H), 3.45-3.54 (m, 1H), 3.28 (td, J=6.50, 12.59 Hz, 1H), 2.53 (d, J=9.90 Hz, 3H), 1.98 (td, J=2.48, 4.95 Hz, 2H), 1.71 (td, J=2.48, 4.95 Hz, 2H), 1.38-1.48 (m, 1H), 1.26-1.34 (m, 1H), 1.03-1.12 (m, 1H), 0.98 (d, J=6.88 Hz, 3H). MS (ESI) m/z: 602.3 (M+H)$^+$. Analytical HPLC (method A): RT=6.1 min, purity=100%

Example 103

(10R,14S)-14-[4-(3-Chloro-2,6-difluorophenyl)-6-oxo-1,2,3,6-tetrahydropyridin-1-yl]-5-{[5-(furan-2-yl)-1,3,4-oxadiazol-2-yl]amino}-10-methyl-8,16-diazatricyclo[13.3.1.0$^{2,7}$]nonadeca-1(19),2(7),3,5,15,17-hexaen-9-one, TFA Salt

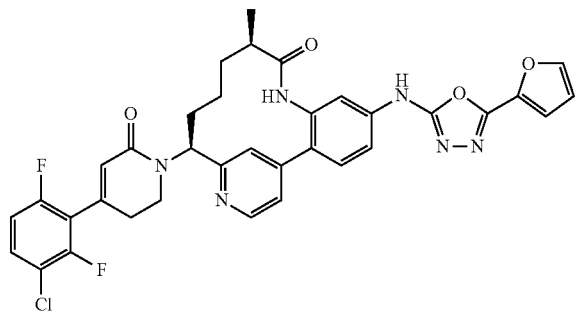 [SMILES: C[C@@H]1CCC[C@H](N2CCC(c3c(F)ccc(Cl)c3F)=CC2=O)c2cc(ccn2)-c2ccc(Nc3nnc(-c4ccco4)o3)cc2NC1=O]

Example 103 was prepared by following the procedures described in Example 1. $^1$H NMR (500 MHz, ACETONITRILE-d3) δ 8.65 (br. s., 1H), 8.56 (d, J=5.23 Hz, 1H), 8.14 (s, 1H), 7.65 (d, J=1.10 Hz, 1H), 7.62 (s, 1H), 7.55 (s, 2H), 7.49 (d, J=0.83 Hz, 2H), 7.40 (dt, J=5.50, 8.67 Hz, 1H), 7.34 (d, J=4.13 Hz, 1H), 6.93-7.00 (m, 2H), 6.58 (dd, J=1.93, 3.58 Hz, 1H), 5.97 (s, 1H), 5.38-5.47 (m, 1H), 3.87-4.00 (m, 1H), 3.61-3.71 (m, 1H), 2.96-3.06 (m, 1H), 1.98 (td, J=2.48, 4.95 Hz, 1H), 1.37-1.47 (m, 1H), 1.23-1.31 (m, 2H), 1.16 (t, J=7.29 Hz, 3H), 0.86 (d, J=6.88 Hz, 3H), 0.54 (br. s., 1H). MS (ESI) m/z: 671.0 (M+H)$^+$. Analytical HPLC (method A): RT=7.1 min, purity=100%

Example 104

Methyl N-[(10R,14S)-14-[4-(6-cyano-2-fluoro-3-methylphenyl)-6-oxo-1,2,3,6-tetrahydropyridin-1-yl]-10-methyl-9-oxo-8,16-diazatricyclo[13.3.1.0$^{2,7}$]nonadeca-1(18),2,4,6,15(19), 16-hexaen-5-yl]carbamate, TFA Salt

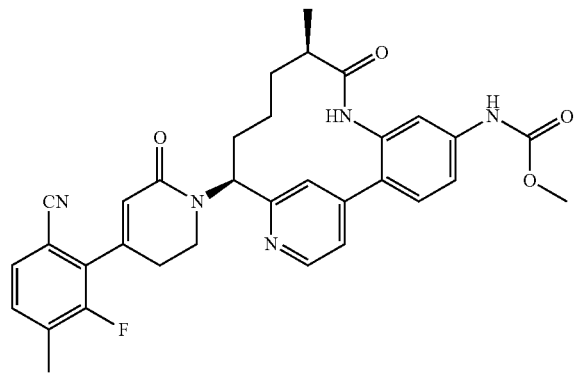 [SMILES: COC(=O)Nc1ccc2c(c1)NC(=O)[C@H](C)CCC[C@H](N1CCC(c3c(C#N)ccc(C)c3F)=CC1=O)c1cc-2ccn1]

Example 104 was prepared by following the procedures described in Example 1. $^1$H NMR (500 MHz, METHANOL-d$_4$) δ 9.66 (s, 1H), 8.76 (d, J=5.8 Hz, 1H), 8.05 (br. s., 1H), 7.83 (d, J=5.8 Hz, 1H), 7.69-7.64 (m, 1H), 7.60-7.55 (m, 3H), 7.51-7.45 (m, 1H), 6.14 (s, 1H), 5.48 (dd, J=12.2, 4.5 Hz, 1H), 3.91-3.81 (m, 1H), 3.80-3.74 (m, 3H), 2.94-2.73 (m, 2H), 2.69-2.60 (m, 1H), 2.39 (d, J=1.9 Hz, 3H), 2.34-2.24 (m, 1H), 2.13-2.02 (m, 2H), 1.95 (dd, J=8.7, 5.4 Hz, 1H), 1.70-1.57 (m, 1H), 1.34 (br. s., 1H), 1.08 (d, J=6.9 Hz, 3H). MS (ESI) m/z: 582.0 (M+H)$^+$. Analytical HPLC (method A): RT=6.3 min, purity=97%.

Example 105

(14S)-14-[4-(3-Chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(18),2,4,6,15(19), 16-hexaene-5-carboxylic acid, TFA Salt

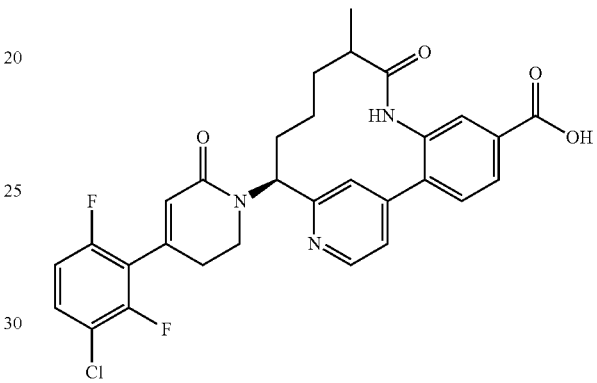

Example 105 was prepared by following the procedures described in Example 1. $^1$H NMR (500 MHz, METHANOL-d$_4$) δ 8.76 (d, J=5.2 Hz, 1H), 8.13 (dd, J=8.1, 1.8 Hz, 1H), 8.00 (s, 1H), 7.96-7.92 (m, 1H), 7.78 (d, J=8.0 Hz, 2H), 7.63-7.52 (m, 2H), 7.11 (td, J=9.2, 1.7 Hz, 1H), 6.12 (s, 1H), 5.63 (dd, J=12.5, 4.5 Hz, 1H), 3.96 (br. s., 1H), 3.84-3.70 (m, 2H), 2.80-2.72 (m, 2H), 2.67-2.60 (m, 1H), 2.28-2.17 (m, 1H), 2.02-1.89 (m, 2H), 1.62-1.52 (m, 1H), 1.10-1.04 (m, 3H). MS (ESI) m/z: 566.1 (M+H)$^+$. Analytical HPLC (method A): RT=7.1 min, purity=99%.

Example 106

(14S)-14-{4-[3-Chloro-2-fluoro-6-(trifluoromethyl)phenyl]-6-oxo-1,2,3,6-tetrahydropyridin-1-yl}-10-methyl-9-oxo-8,16-diazatricyclo[13.3.1.0$^{2,7}$]nonadeca-1(18),2,4,6,15(19), 16-hexaene-5-carboxylic acid, TFA Salt

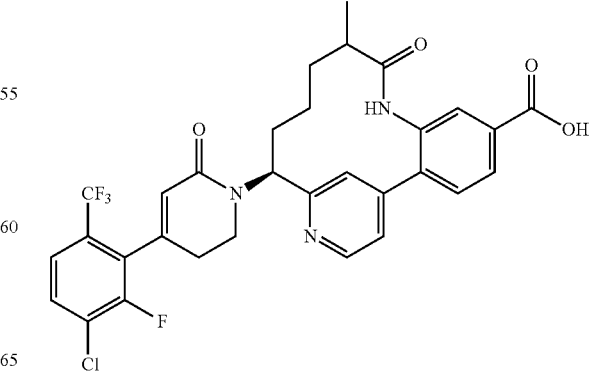

Example 106 was prepared by following the procedures described in Example 1. $^1$H NMR (500 MHz, METHANOL-$d_4$) δ 8.79 (d, J=5.2 Hz, 1H), 8.14 (dd, J=8.1, 1.5 Hz, 1H), 7.95 (d, J=1.7 Hz, 1H), 7.88 (s, 1H), 7.83-7.77 (m, 1H), 7.77-7.67 (m, 2H), 7.66-7.58 (m, 1H), 6.00-5.88 (m, 1H), 5.64-5.54 (m, 1H), 4.03-3.76 (m, 2H), 2.76-2.60 (m, 3H), 2.36-2.20 (m, 1H), 2.06-1.89 (m, 2H), 1.64-1.54 (m, 2H), 1.40-1.32 (m, 1H), 1.11-1.04 (m, 3H). MS (ESI) m/z: 616.2 (M+H)$^+$. Analytical HPLC (method A): RT=7.7 min, purity=99%.

Example 107

(14S)-14-[4-(3-Chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(18),2,4,6,15(19),16-hexaene-5-carboxamide, TFA Salt

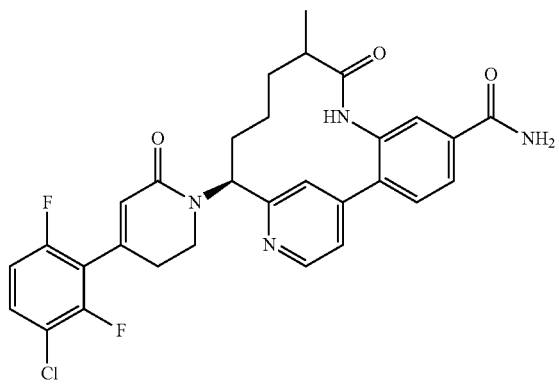 [SMILES: CC1CCC[C@H](N2CCC(c3c(F)ccc(Cl)c3F)=CC2=O)c2cc(ccn2)-c2ccc(C(N)=O)cc2NC1=O]

Example 107 was prepared by following the procedures described in Example 1. $^1$H NMR (500 MHz, METHANOL-$d_4$) δ 8.82 (d, J=5.5 Hz, 1H), 8.08-7.96 (m, 2H), 7.90-7.76 (m, 3H), 7.56 (td, J=8.7, 5.5 Hz, 1H), 7.12 (td, J=9.2, 1.7 Hz, 1H), 6.13 (s, 1H), 5.51 (dd, J=12.4, 4.7 Hz, 1H), 3.93-3.82 (m, 1H), 3.77 (ddd, J=12.4, 9.6, 5.5 Hz, 1H), 2.90-2.71 (m, 2H), 2.70-2.60 (m, 1H), 2.37-2.23 (m, 1H), 2.13-2.01 (m, 1H), 1.93 (dd, J=8.8, 5.8 Hz, 1H), 1.70-1.54 (m, 1H), 1.37-1.29 (m, 1H), 1.08 (d, J=6.9 Hz, 3H), 1.00 (b.r.s, 1H). MS (ESI) m/z: 565.1 (M+H)$^+$. Analytical HPLC (method A): RT=4.2 min, purity=97%.

Example 108

(14S)-14-{4-[3-Chloro-2-fluoro-6-(trifluoromethyl)phenyl]-6-oxo-1,2,3,6-tetrahydropyridin-1-yl}-10-methyl-9-oxo-8,16-diazatricyclo[13.3.1.0$^{2,7}$]nonadeca-1(18),2,4,6,15(19),16-hexaene-5-carboxamide, TFA Salt

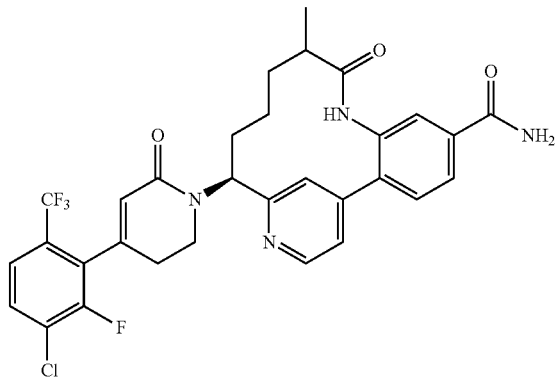

Example 108 was prepared by following the procedures described in Example 1. $^1$H NMR (500 MHz, METHANOL-$d_4$) δ 8.81 (d, J=5.2 Hz, 1H), 8.01 (dd, J=8.0, 1.9 Hz, 1H), 7.95 (s, 1H), 7.85 (d, J=1.7 Hz, 1H), 7.81 (d, J=8.0 Hz, 1H), 7.79-7.71 (m, 2H), 7.64 (d, J=8.5 Hz, 1H), 5.97 (s, 1H), 5.55 (dd, J=12.4, 4.1 Hz, 1H), 3.96-3.74 (m, 2H), 2.65 (br. s., 2H), 2.29 (d, J=7.4 Hz, 1H), 2.09-1.89 (m, 2H), 1.65-1.55 (m, 1H), 1.39-1.32 (m, 2H), 1.08 (d, J=6.9 Hz, 3H), 1.00 (br. s., 1H). MS (ESI) m/z: 615.1 (M+H)$^+$. Analytical HPLC (method A): RT=4.2 min, purity=97%.

Example 109

(14S)-14-[4-(3-Chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(18),2,4,6,15(19),16-hexaene-5-carbonitrile, TFA Salt

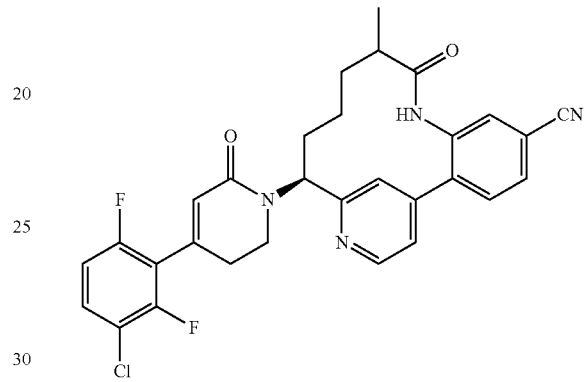

Example 109 was prepared by following the procedures described in Example 1. $^1$H NMR (500 MHz, METHANOL-$d_4$) δ 8.80 (d, J=5.2 Hz, 1H), 7.93-7.77 (m, 3H), 7.73-7.60 (m, 2H), 7.55 (td, J=8.7, 5.5 Hz, 1H), 7.12 (td, J=9.4, 1.7 Hz, 1H), 6.12 (s, 1H), 5.66-5.52 (m, 1H), 4.03 (d, J=6.1 Hz, 1H), 3.87-3.71 (m, 1H), 2.88-2.60 (m, 3H), 2.30-2.15 (m, 1H), 2.03-1.85 (m, 2H), 1.57 (d, J=7.7 Hz, 1H), 1.37 (br. s., 1H), 1.09-0.98 (m, 3H), 0.83 (br. s., 1H). MS (ESI) m/z: 547.1 (M+H)$^+$. Analytical HPLC (method A): RT=8.1 min, purity=98%.

Example 110

Methyl N-[(10R,14S)-14-[4-(5-chloro-2-methylphenyl)-6-oxo-1,2,3,6-tetrahydropyridin-1-yl]-10-methyl-9-oxo-8,16-diazatricyclo[13.3.1.0$^{2,7}$]nonadeca-1(18),2,4,6,15(19),16-hexaen-5-yl]carbamate

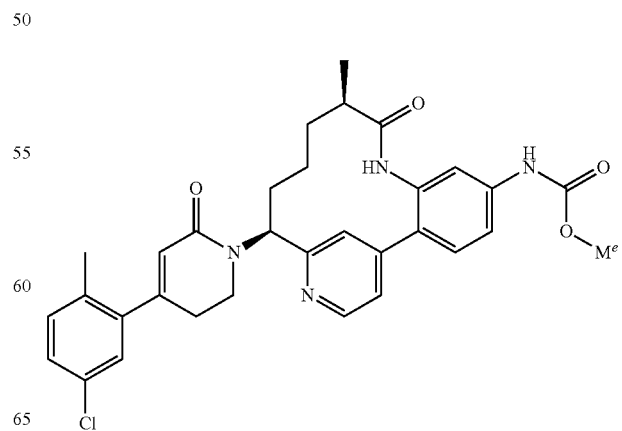

Example 110 was prepared by following the procedures described in Example 1. $^1$H NMR (500 MHz, DMSO-$d_6$) δ 9.91 (s, 1H), 9.73 (s, 1H), 8.60 (d, J=5.0 Hz, 1H), 7.52-7.44 (m, 3H), 7.35 (s, 1H), 7.32-7.25 (m, 4H), 5.76 (s, 1H), 5.62 (dd, J=12.4, 4.1 Hz, 1H), 3.96 (br. s., 1H), 3.74-3.64 (m, 4H), 2.61-2.53 (m, 3H), 2.24 (s, 3H), 2.10-1.98 (m, 1H), 1.91 (br. s., 1H), 1.69-1.56 (m, 1H), 1.43 (dd, J=15.1, 7.4 Hz, 1H), 1.22 (d, J=9.9 Hz, 1H), 0.86 (d, J=6.6 Hz, 3H), 0.50 (br. s., 1H). MS (ESI) m/z: 573.2 (M+H)$^+$. Analytical HPLC (method D): RT=1.6 min, purity=91%.

Example 111

Methyl N-[(10R,14S)-14-[4-(2,6-difluoro-3-methyl-phenyl)-6-oxo-1,2,3,6-tetrahydropyridin-1-yl]-10-methyl-9-oxo-8,16-diazatricyclo[13.3.1.0$^{2,7}$]non-adeca-1(18),2,4,6,15(19), 16-hexaen-5-yl]carbamate

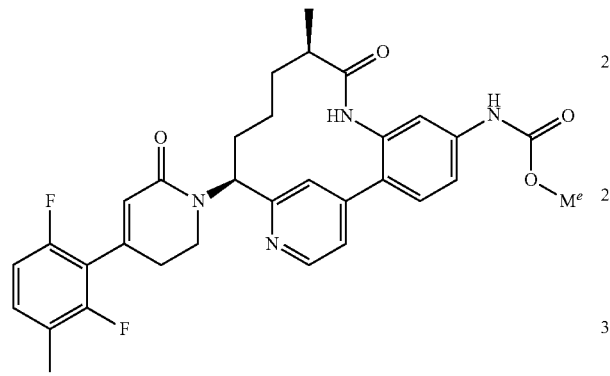

Example 111 was prepared by following the procedures described in Example 1. $^1$H NMR (500 MHz, DMSO-$d_6$) δ 9.88 (s, 1H), 9.70 (s, 1H), 8.60 (d, J=5.0 Hz, 1H), 7.50 (s, 3H), 7.40-7.26 (m, 3H), 7.07 (t, J=8.9 Hz, 1H), 5.95 (s, 1H), 5.60 (dd, J=12.5, 4.5 Hz, 1H), 3.95 (br. s., 1H), 3.75-3.63 (m, 4H), 2.62-2.53 (m, 3H), 2.21 (s, 3H), 2.12-1.98 (m, 1H), 1.91 (br. s., 1H), 1.73-1.60 (m, 1H), 1.49-1.35 (m, 1H), 1.23 (d, J=8.8 Hz, 1H), 0.87 (d, J=6.9 Hz, 3H), 0.54 (br. s., 1H). MS (ESI) m/z: 575.3 (M+H)$^+$. Analytical HPLC (method C): RT=1.8 min, purity=97%.

Example 112

Methyl N-[(10R,14S)-14-[4-(2-fluoro-3-methylphe-nyl)-6-oxo-1,2,3,6-tetrahydropyridin-1-yl]-10-methyl-9-oxo-8,16-diazatricyclo[13.3.1.0$^{2,7}$]non-adeca-1(18),2,4,6,15(19),16-hexaen-5-yl]carbamate, TFA Salt

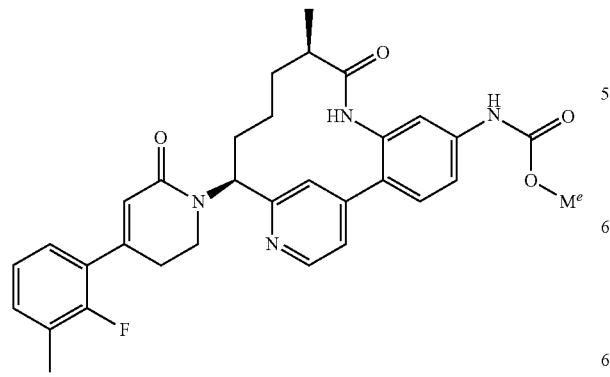

Example 112 was prepared by following the procedures described in Example 1. $^1$H NMR (400 MHz, CHLOROFORM-d) δ 9.42 (br. s., 1H), 8.61 (d, J=5.9 Hz, 1H), 8.45 (s, 1H), 7.84 (dd, J=6.1, 1.7 Hz, 1H), 7.74 (d, J=7.3 Hz, 1H), 7.46 (d, J=8.6 Hz, 1H), 7.22-7.03 (m, 3H), 6.29 (s, 1H), 5.12 (dd, J=12.0, 5.6 Hz, 1H), 4.01-3.85 (m, 2H), 3.82 (s, 3H), 2.93 (t, J=6.8 Hz, 2H), 2.80 (br. s., 1H), 2.77-2.64 (m, 1H), 2.32 (d, J=2.2 Hz, 3H), 2.04-1.90 (m, 5H), 1.68-1.47 (m, 2H), 0.98 (d, J=6.8 Hz, 3H), 0.44 (br. s., 1H). MS (ESI) m/z: 557.2 (M+H)$^+$. Analytical HPLC (method A): RT=7.4 min, purity=98%.

Example 113

Methyl N-[(10R,14S)-14-[4-(2-fluoro-5-methylphe-nyl)-6-oxo-1,2,3,6-tetrahydropyridin-1-yl]-10-methyl-9-oxo-8,16-diazatricyclo[13.3.1.0$^{2,7}$]non-adeca-1(18),2,4,6,15(19), 16-hexaen-5-yl]carbamate

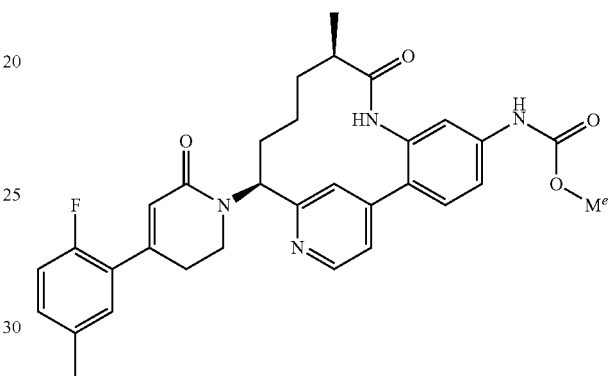

Example 113 was prepared by following the procedures described in Example 1. $^1$H NMR (500 MHz, DMSO-$d_6$) δ 9.90 (s, 1H), 9.71 (s, 1H), 8.61 (d, J=5.0 Hz, 1H), 7.54-7.48 (m, 3H), 7.37 (s, 1H), 7.35-7.29 (m, 2H), 7.27-7.20 (m, 1H), 7.15 (dd, J=11.3, 8.5 Hz, 1H), 6.09 (s, 1H), 5.61 (dd, J=12.5, 4.5 Hz, 1H), 3.95 (br. s., 1H), 3.71 (s, 3H), 3.70-3.64 (m, 1H), 2.73-2.66 (m, 2H), 2.63-2.55 (m, 1H), 2.31 (s, 3H), 2.13-1.99 (m, 1H), 1.92 (br. s., 1H), 1.71-1.59 (m, 1H), 1.50-1.39 (m, 1H), 1.30-1.18 (m, 1H), 0.89 (d, J=6.9 Hz, 3H), 0.55 (br. s., 1H). MS (ESI) m/z: 557.2 (M+H)$^+$. Analytical HPLC (method C): RT=1.6 min, purity=98%.

Example 114

Methyl N-[(10R,14S)-14-[4-(2,3-dimethylphenyl)-6-oxo-1,2,3,6-tetrahydropyridin-1-yl]-10-methyl-9-oxo-8,16-diazatricyclo[13.3.1.0$^{2,7}$]nonadeca-1(18),2,4,6,15(19), 16-hexaen-5-yl]carbamate

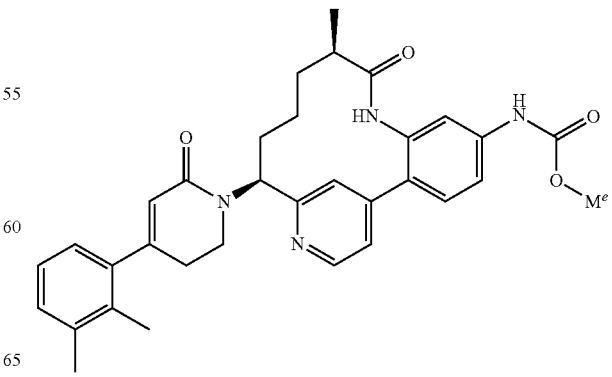

Example 114 was prepared by following the procedures described in Example 1. ¹H NMR (400 MHz, DMSO-d₆) δ 9.90 (s, 1H), 9.72 (s, 1H), 8.63 (d, J=5.3 Hz, 1H), 7.54 (s, 1H), 7.51 (s, 2H), 7.44-7.31 (m, 2H), 7.20-7.05 (m, 2H), 6.98 (d, J=7.5 Hz, 1H), 5.66 (s, 1H), 5.61 (dd, J=13.0, 4.4 Hz, 1H), 3.99-3.92 (m, 2H), 3.77-3.64 (m, 5H), 2.62-2.55 (m, 1H), 2.25 (s, 3H), 2.16 (s, 3H), 2.08 (s, 1H), 1.91 (br. s., 1H), 1.68 (br. s., 1H), 1.46 (d, J=8.8 Hz, 1H), 1.24 (br. s., 1H), 0.88 (d, J=7.0 Hz, 3H), 0.55 (br. s., 1H). MS (ESI) m/z: 553.3 (M+H)⁺. Analytical HPLC (method A): RT=7.4 min, purity=99%.

Example 115

Methyl N-[(10R,14S)-14-[4-(2-fluoro-3-methoxyphenyl)-6-oxo-1,2,3,6-tetrahydropyridin-1-yl]-10-methyl-9-oxo-8,16-diazatricyclo[13.3.1.0$^{2,7}$]nonadeca-1(18),2,4,6,15(19),16-hexaen-5-yl]carbamate, TFA Salt

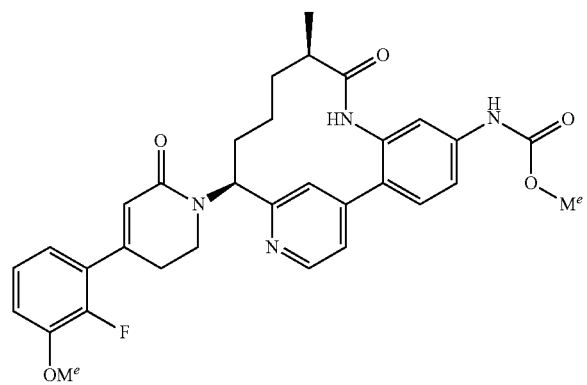 [SMILES: COC(=O)Nc1ccc2c(c1)NC(=O)[C@H](C)CCC[C@H](N1CCC(c3cccc(OC)c3F)=CC1=O)c1cc-2ccn1]

Example 115 was prepared by following the procedures described in Example 1. ¹H NMR (400 MHz, CHLOROFORM-d) δ 8.87 (br. s., 1H), 8.68 (d, J=6.2 Hz, 1H), 8.27 (s, 1H), 7.62 (d, J=5.7 Hz, 2H), 7.55 (d, J=8.4 Hz, 1H), 7.32 (d, J=8.4 Hz, 1H), 7.24 (s, 1H), 7.11 (t, J=8.0 Hz, 1H), 7.01 (t, J=7.9 Hz, 1H), 6.92 (t, J=6.5 Hz, 1H), 6.23 (s, 1H), 5.17 (br. s., 1H), 4.14-4.01 (m, 1H), 3.91 (s, 3H), 3.87-3.76 (m, 1H), 3.70 (s, 3H), 3.05 (d, J=18.9 Hz, 1H), 2.89 (d, J=18.5 Hz, 1H), 2.67 (br. s., 1H), 2.63-2.47 (m, 1H), 1.97 (br. s., 1H), 1.61 (br. s., 1H), 1.54-1.31 (m, 2H), 1.31-1.13 (m, 1H), 1.00 (d, J=6.2 Hz, 3H). MS (ESI) m/z: 573.2 (M+H)⁺. Analytical HPLC (method A): RT=6.8 min, purity=97%.

Example 116

Methyl N-[(10R,14S)-14-[4-(2-methoxyphenyl)-6-oxo-1,2,3,6-tetrahydropyridin-1-yl]-10-methyl-9-oxo-8,16-diazatricyclo[13.3.1.0$^{2,7}$]nonadeca-1(18),2,4,6,15(19),16-hexaen-5-yl]carbamate

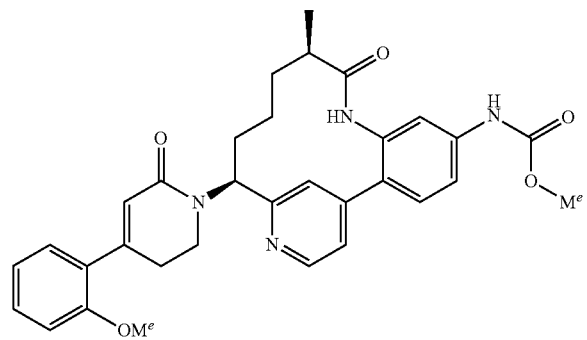 [SMILES: COC(=O)Nc1ccc2c(c1)NC(=O)[C@H](C)CCC[C@H](N1CCC(c3ccccc3OC)=CC1=O)c1cc-2ccn1]

Example 116 was prepared by following the procedures described in Example 1. ¹H NMR (500 MHz, DMSO-d₆) δ 9.90 (s, 1H), 9.72 (s, 1H), 8.62 (d, J=5.0 Hz, 1H), 7.52 (s, 3H), 7.42-7.31 (m, 3H), 7.28 (dd, J=7.6, 1.5 Hz, 1H), 7.13-7.04 (m, 1H), 7.04-6.92 (m, 1H), 5.98 (s, 1H), 5.61 (dd, J=12.4, 4.4 Hz, 1H), 3.90 (br. s., 1H), 3.81 (s, 3H), 3.71 (s, 3H), 3.68-3.59 (m, 1H), 2.66 (t, J=6.6 Hz, 2H), 2.61-2.56 (m, 1H), 2.12-2.01 (m, 1H), 1.92 (br. s., 1H), 1.72-1.60 (m, 1H), 1.44 (dd, J=15.7, 7.4 Hz, 1H), 1.24 (d, J=14.6 Hz, 1H), 0.89 (d, J=6.9 Hz, 3H), 0.57 (br. s., 1H). MS (ESI) m/z: 555.4 (M+H)⁺. Analytical HPLC (method C): RT=1.6 min, purity=96%.

Example 117

Methyl N-[(10R,14S)-14-[4-(4-methoxyphenyl)-6-oxo-1,2,3,6-tetrahydropyridin-1-yl]-10-methyl-9-oxo-8,16-diazatricyclo[13.3.1.0$^{2,7}$]nonadeca-1(18),2,4,6,15(19),16-hexaen-5-yl]carbamate

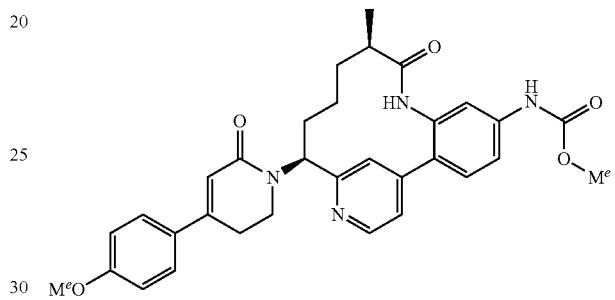

Example 117 was prepared by following the procedures described in Example 1. ¹H NMR (500 MHz, DMSO-d₆) δ 9.93 (s, 1H), 9.74 (s, 1H), 8.61 (d, J=5.2 Hz, 1H), 7.64-7.57 (m, J=8.8 Hz, 2H), 7.53-7.46 (m, 3H), 7.37 (s, 1H), 7.31 (d, J=5.0 Hz, 1H), 7.03-6.95 (m, J=8.8 Hz, 2H), 6.17 (s, 1H), 5.62 (dd, J=12.5, 4.3 Hz, 1H), 3.94 (br. s., 1H), 3.80 (s, 3H), 3.71 (s, 3H), 3.70-3.62 (m, 1H), 2.82-2.72 (m, 1H), 2.70 (br. s., 1H), 2.59 (br. s., 1H), 2.13-2.01 (m, 1H), 1.93 (br. s., 1H), 1.69-1.55 (m, 1H), 1.51-1.39 (m, 1H), 1.28-1.18 (m, 1H), 0.88 (d, J=6.9 Hz, 3H), 0.53 (br. s., 1H). MS (ESI) m/z: 555.4 (M+H)⁺. Analytical HPLC (method C): RT=1.7 min, purity=97%.

Example 118

Methyl N-[(10R,14S)-14-[4-(3-chloro-2-methoxyphenyl)-6-oxo-1,2,3,6-tetrahydropyridin-1-yl]-10-methyl-9-oxo-8,16-diazatricyclo[13.3.1.0$^{2,7}$]nonadeca-1(18),2,4,6,15(19), 16-hexaen-5-yl]carbamate

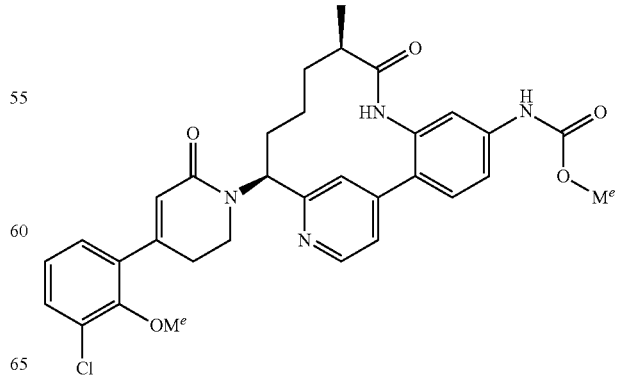

Example 118 was prepared by following the procedures described in Example 1. $^1$H NMR (500 MHz, DMSO-$d_6$) δ 9.93 (br. s., 1H), 9.75 (s, 1H), 8.62 (d, J=5.0 Hz, 1H), 7.57-7.46 (m, 4H), 7.37 (s, 1H), 7.32 (d, J=6.3 Hz, 2H), 7.25-7.13 (m, 1H), 6.04 (s, 1H), 5.63 (dd, J=12.5, 4.3 Hz, 1H), 3.97 (br. s., 1H), 3.78-3.67 (m, 7H), 2.73-2.64 (m, 2H), 2.60 (d, J=4.7 Hz, 1H), 2.13-2.01 (m, 1H), 1.93 (br. s., 1H), 1.73-1.61 (m, 1H), 1.51-1.39 (m, 1H), 1.31-1.18 (m, 1H), 0.88 (d, J=6.6 Hz, 3H), 0.52 (br. s., 1H). MS (ESI) m/z: 589.3 (M+H)$^+$. Analytical HPLC (method C): RT=1.8 min, purity=94%.

Example 119

Methyl N-[(10R,14S)-14-[4-(3-methoxyphenyl)-6-oxo-1,2,3,6-tetrahydropyridin-1-yl]-10-methyl-9-oxo-8,16-diazatricyclo[13.3.1.0$^{2,7}$]nonadeca-1(18),2,4,6,15(19),16-hexaen-5-yl]carbamate, TFA Salt

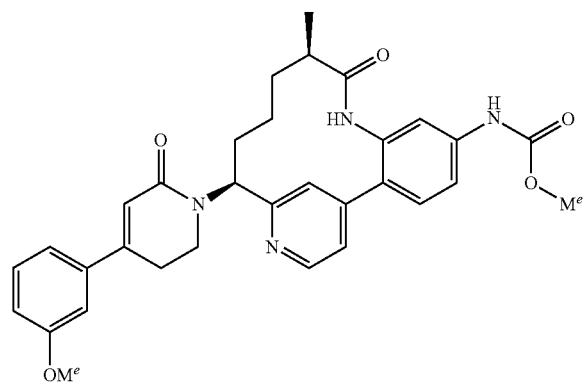 [SMILES: COC(=O)Nc1ccc2c(c1)NC(=O)[C@H](C)CCC[C@H](N1CCC(c3cccc(OC)c3)=CC1=O)c1cc-2ccn1]

Example 119 was prepared by following the procedures described in Example 1. $^1$H NMR (500 MHz, DMSO-$d_6$) δ 9.92 (s, 1H), 9.74 (s, 1H), 8.64 (d, J=5.2 Hz, 1H), 7.60 (s, 1H), 7.57-7.49 (m, 2H), 7.42 (d, J=4.7 Hz, 1H), 7.39-7.37 (m, 1H), 7.36-7.30 (m, 1H), 7.21-7.15 (m, 1H), 7.12 (t, J=1.9 Hz, 1H), 7.04-6.88 (m, 1H), 6.24 (s, 1H), 5.54 (dd, J=12.2, 4.3 Hz, 1H), 3.98-3.86 (m, 1H), 3.84-3.74 (m, 3H), 3.70 (s, 3H), 3.67-3.54 (m, 1H), 2.81-2.69 (m, 2H), 2.62-2.54 (m, 1H), 2.13-2.00 (m, 1H), 1.96-1.81 (m, 1H), 1.79-1.61 (m, 1H), 1.50-1.37 (m, 1H), 1.27-1.17 (m, 1H), 0.88 (d, J=6.9 Hz, 3H), 0.57 (br. s., 1H). MS (ESI) m/z: 555.4 (M+H)$^+$. Analytical HPLC (method C): RT=1.6 min, purity=93%.

Example 120

Methyl N-[(10R,14S)-14-[4-(3-chloro-2-methylphenyl)-6-oxo-1,2,3,6-tetrahydropyridin-1-yl]-10-methyl-9-oxo-8,16-diazatricyclo[13.3.1.0$^{2,7}$]nonadeca-1(18),2,4,6,15(19),16-hexaen-5-yl]carbamate, TFA Salt

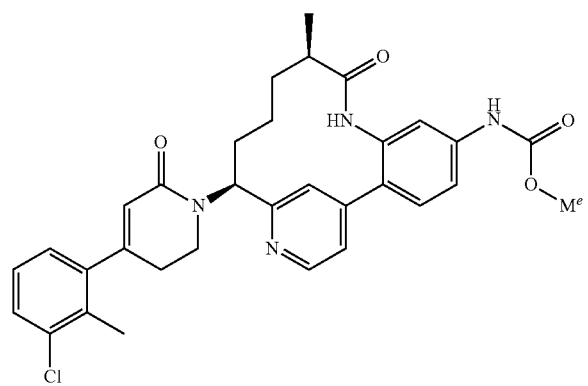 [SMILES: COC(=O)Nc1ccc2c(c1)NC(=O)[C@H](C)CCC[C@H](N1CCC(c3cccc(Cl)c3C)=CC1=O)c1cc-2ccn1]

Example 120 was prepared by following the procedures described in Example 1. $^1$H NMR (500 MHz, DMSO-$d_6$) δ 9.95 (s, 1H), 9.76 (s, 1H), 8.65 (d, J=5.0 Hz, 1H), 7.58 (br. s., 1H), 7.56-7.47 (m, 2H), 7.47-7.34 (m, 3H), 7.24 (t, J=7.8 Hz, 1H), 7.16 (d, J=7.7 Hz, 1H), 5.73 (s, 1H), 5.57 (dd, J=11.8, 3.6 Hz, 1H), 3.73-3.66 (m, 5H), 2.57 (br. s., 3H), 2.29 (s, 3H), 2.07 (t, J=12.7 Hz, 1H), 1.91 (br. s., 1H), 1.69 (br. s., 1H), 1.50-1.36 (m, 1H), 1.31-1.14 (m, 1H), 0.87 (d, J=6.6 Hz, 3H), 0.54 (br. s., 1H). MS (ESI) m/z: 573.3 (M+H)$^+$. Analytical HPLC (method C): RT=1.9 min, purity=94%.

Example 121

Methyl N-[(10R,14S)-14-[4-(5-chloro-2-methoxyphenyl)-6-oxo-1,2,3,6-tetrahydropyridin-1-yl]-10-methyl-9-oxo-8,16-diazatricyclo[13.3.1.0$^{2,7}$]nonadeca-1(18),2,4,6,15(19),16-hexaen-5-yl]carbamate, TFA Salt

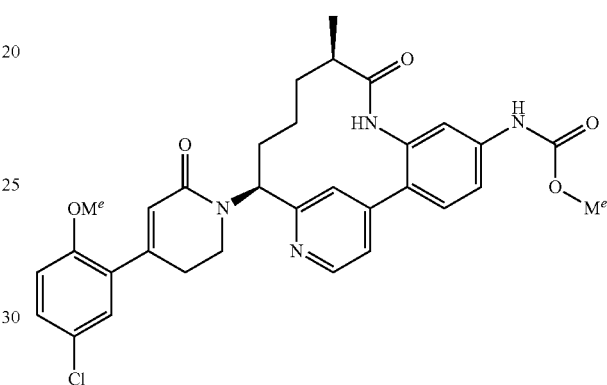

Example 121 was prepared by following the procedures described in Example 1. $^1$H NMR (500 MHz, DMSO-$d_6$) δ 9.94 (s, 1H), 9.76 (s, 1H), 8.64 (d, J=5.0 Hz, 1H), 7.57 (br. s., 1H), 7.55-7.46 (m, 2H), 7.46-7.34 (m, 3H), 7.31 (s, 1H), 7.14-7.04 (m, 1H), 6.01 (s, 1H), 5.54 (d, J=9.4 Hz, 1H), 3.90 (br. s., 2H), 3.79 (s, 3H), 3.69 (s, 3H), 2.65 (br. s., 2H), 2.58 (br. s., 1H), 2.05 (t, J=12.2 Hz, 1H), 1.90 (br. s., 1H), 1.67 (br. s., 1H), 1.51-1.36 (m, 1H), 1.22 (d, J=10.5 Hz, 1H), 0.87 (d, J=6.6 Hz, 3H), 0.55 (br. s., 1H). MS (ESI) m/z: 589.2 (M+H)$^+$. Analytical HPLC (method C): RT=1.8 min, purity=92%.

Example 122

Methyl N-[(10R,14S)-14-[4-(3-chloro-4-methoxyphenyl)-6-oxo-1,2,3,6-tetrahydropyridin-1-yl]-10-methyl-9-oxo-8,16-diazatricyclo[13.3.1.0$^{2,7}$]nonadeca-1(18),2,4,6,15(19),16-hexaen-5-yl]carbamate, TFA Salt

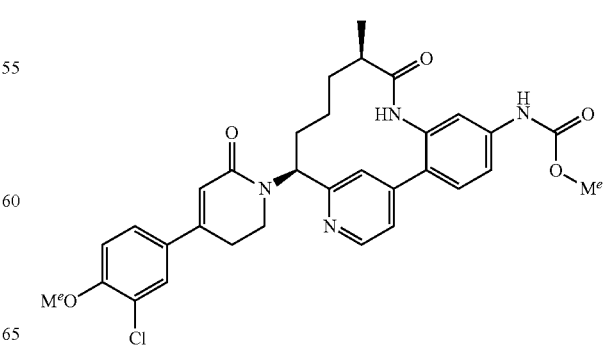

Example 122 was prepared by following the procedures described in Example 1. $^1$H NMR (500 MHz, DMSO-$d_6$) δ 9.92 (s, 1H), 9.73 (s, 1H), 8.60 (d, J=5.0 Hz, 1H), 7.70 (s, 1H), 7.60 (d, J=8.5 Hz, 1H), 7.50 (s, 3H), 7.36 (s, 1H), 7.32 (d, J=4.7 Hz, 1H), 7.17 (d, J=8.5 Hz, 1H), 6.22 (s, 1H), 5.67-5.53 (m, 1H), 3.88 (s, 4H), 3.69 (s, 3H), 3.64 (t, J=12.7 Hz, 1H), 2.72-2.62 (m, 1H), 2.60-2.52 (m, 2H), 2.04 (t, J=12.7 Hz, 1H), 1.91 (br. s., 1H), 1.62 (br. s., 1H), 1.52-1.36 (m, 1H), 1.30-1.16 (m, 1H), 0.86 (d, J=6.6 Hz, 3H), 0.52 (br. s., 1H). MS (ESI) m/z: 589.3 (M+H)$^+$. Analytical HPLC (method C): RT=1.7 min, purity=99%.

Example 123 (Diastereomer 1)

Methyl N-[(14S)-14-[4-(3-chloro-2,6-difluorophenyl)-6-oxo-1,2,3,6-tetrahydropyridin-1-yl]-10-hydroxy-10-methyl-9-oxo-8,16-diazatricyclo [13.3.1.0$^{2,7}$]nonadeca-1(19),2,4,6,15,17-hexaen-5-yl]carbamate, TFA Salt

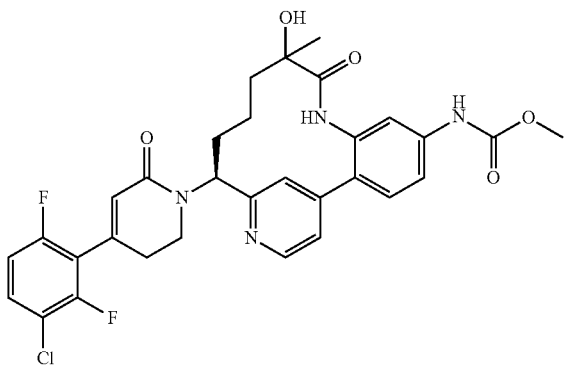 [SMILES: COC(=O)Nc1ccc2c(c1)NC(=O)C(C)(O)CCC[C@H](N1CCC(c3c(F)ccc(Cl)c3F)=CC1=O)c1cc-2ccn1]

And Example 124 (Diastereomer 2)

Methyl N-[(14S)-14-[4-(3-chloro-2,6-difluorophenyl)-6-oxo-1,2,3,6-tetrahydropyridin-1-yl]-10-hydroxy-10-methyl-9-oxo-8,16-diazatricyclo [13.3.1.0$^{2,7}$]nonadeca-1(19),2,4,6,15,17-hexaen-5-yl]carbamate, TFA Salt

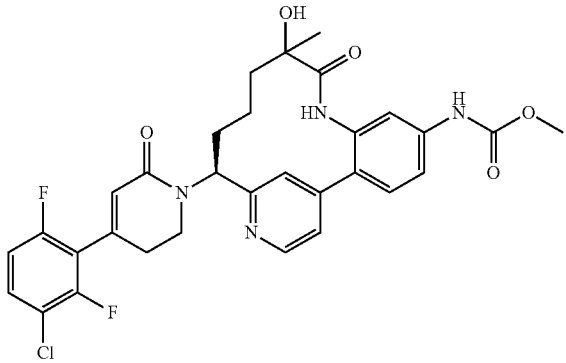 [SMILES: COC(=O)Nc1ccc2c(c1)NC(=O)C(C)(O)CCC[C@H](N1CCC(c3c(F)ccc(Cl)c3F)=CC1=O)c1cc-2ccn1]

123A tert-butyl N-[(11E,14S)-10-(benzyloxy)-5-[(methoxycarbonyl)amino]-9-oxo-8,16-diazatricyclo [13.3.1.0$^{2,7}$]nonadeca-1(19),2,4,6,11,15,17-heptaen-14-yl]carbamate 123A prepared by following the analogous procedures (1A to 1H) described in Example 1 by using intermediate 16 in step 1G instead. MS (ESI) m/z: 559.2 (M+H)$^+$.

123 B tert-butyl N-[(11E,14S)-10-hydroxy-5-[(methoxycarbonyl)amino]-9-oxo-8,16-diazatricyclo [13.3.1.0$^{2,7}$]nonadeca-1(18),2(7),3,5,11,15(19), 16-heptaen-14-yl]carbamate To a solution of 123A (770 mg, 1.378 mmol) in MeOH (125.00 mL) under Ar was added palladium hydroxide on carbon (77 mg, 0.551 mmol) and ammonium formate (3477 mg, 55.1 mmol). The mixture was refluxed at 65° C. overnight. The reaction mixture was filtered through Celite, rinsed with MeOH, and concentrated. The residue was purified by silica gel chromatography to yield 123B (360 mg, 0.765 mmol, 55.5% yield). MS (ESI) m/z: 471.2 (M+H)$^+$.

123C tert-butyl N-[(14S)-5-[(methoxycarbonyl) amino]-9,10-dioxo-8,16-diazatricyclo[13.3.1.0$^{2,7}$] nonadeca-1(19),2,4,6,15,17-hexaen-14-yl]carbamate A solution of 123B (360 mg, 0.765 mmol) in DCM (7.5 mL) was added Dess-MartinPeriodinane (357 mg, 0.842 mmol) and stirred at rt. After 1 hr, the reaction mixture was diluted with a small amount of sat. NaHCO$_3$ and some water was added. The reaction mixture was extracted with DCM (3×). The combined organic extracts were washed with brine, dried (Na$_2$SO$_4$), filtered, and concentrated. This material was used in the next step without purification. MS (ESI) m/z: 487.2 (M+H$_2$O+H)$^+$.

123D methyl N-[(14S)-14-amino-10-hydroxy-10-methyl-9-oxo-8,16-diazatricyclo[13.3.1.0$^{2,7}$]nonadeca-1(19),2,4,6,15,17-hexaen-5-yl]carbamate A solution of 123C (345 mg, 0.736 mmol) in THF (7 mL) was cooled to 0° C. and treated with methylmagnesium bromide (0.245 mL, 0.736 mmol), then stirred at rt for 1 hr. The reaction was cooled to 0° C. again and treated with methylmagnesium bromide (0.491 mL, 1.473 mmol), then stirred at rt for 1 hr. LCMS still showed starting material. The reaction was cooled to 0° C., treated with methylmagnesium bromide (0.491 mL, 1.473 mmol), then stirred at rt overnight. The reaction was quenched with sat. NH$_4$Cl, then diluted with EtOAc and water. The aqueous layer was extracted with EtOAc (3×), and the organic extracts were dried (Na$_2$SO$_4$), filtered, and concentrated. The residue was purified by prep HPLC. The pure material was dissolved in DCM and treated with TFA, then stirred at rt for 2 hrs. The solvent was removed in vacuo and 123D (135 mg, 0.220 mmol, 29.9% yield) was obtained as a yellow solid. The material was used in future steps without purification. MS (ESI) m/z: 385.1 (M+H)$^+$.

Example 123 and Example 124 was prepared by following the procedures described in Example 1 by using 123D in step 1K. Diastereomers were separated, and data for each is given. Example 123: $^1$H NMR (500 MHz, DMSO-d$_6$) δ 9.90 (br. s., 1H), 9.48 (br. s., 1H), 7.69 (d, J=7.7 Hz, 1H), 7.58-7.49 (m, 2H), 7.46 (br. s., 1H), 7.38 (br. s., 1H), 7.34-7.24 (m, 2H), 6.05 (br. s., 1H), 5.54 (d, J=11.8 Hz, 1H), 4.21 (d, J=5.5 Hz, 1H), 3.79-3.74 (m, 1H), 3.70 (br. s., 3H), 2.68 (br. s., 2H), 2.00 (br. s., 1H), 1.93 (t, J=12.2 Hz, 1H), 1.66 (br. s., 1H), 1.45 (d, J=12.9 Hz, 1H), 1.39 (br. s., 4H), 0.53 (d, J=11.6 Hz, 1H). MS (ESI) m/z: 611.3 (M+H)$^+$. Analytical HPLC (method C): RT=1.8 min, purity=85%.

Example 124: $^1$H NMR (500 MHz, DMSO-d$_6$) δ 9.89 (s, 1H), 9.58 (s, 1H), 8.62 (d, J=5.2 Hz, 1H), 7.68 (td, J=8.7, 5.8 Hz, 1H), 7.59 (s, 1H), 7.51 (s, 2H), 7.40-7.31 (m, 2H), 7.31-7.22 (m, 1H), 6.05 (s, 1H), 5.57 (d, J=9.4 Hz, 1H), 3.93-3.82 (m, 1H), 3.70 (s, 4H), 3.66 (br. s., 2H), 2.66-2.54 (m, 2H), 2.11-1.99 (m, 1H), 1.99-1.90 (m, 1H), 1.69 (br. s., 1H), 1.63-1.51 (m, 1H), 1.25-1.13 (m, 4H), 0.53 (br. s., 1H). MS (ESI) m/z: 612.2 (M+H)$^+$. Analytical HPLC (method C): RT=1.8 min, purity=97%.

Example 125

(10R,14S)-14-[4-(3-chloro-2,6-difluorophenyl)-6-oxo-1,2,3,6-tetrahydropyridin-1-yl]-10-methyl-5-{[(3S,4S,5S,6R)-3,4,5-trihydroxy-6-(hydroxymethyl)oxan-2-yl]amino}-8,16-diazatricyclo[13.3.1.0$^{2,7}$]nonadeca-1(19),2,4,6,15,17-hexaen-9-one

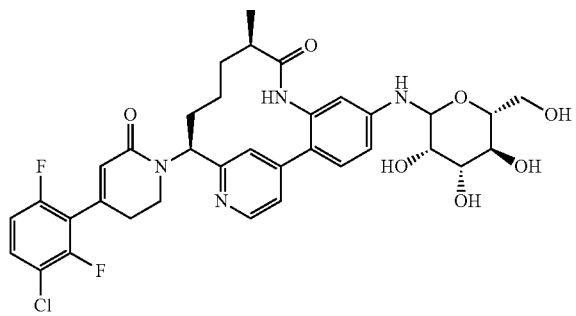 [SMILES: C[C@@H]1CCC[C@H](N2CCC(c3c(F)ccc(Cl)c3F)=CC2=O)c2cc(ccn2)-c2ccc(NC3O[C@H](CO)[C@@H](O)[C@H](O)[C@@H]3O)cc2NC1=O]

Example 125

A mixture of Example 12 (5 mg, 9 μmol) and D-mannose (8.4 mg, 0.05 mmol) in EtOH (1 mL) was stirred at 70° C. under Ar for 2 days. The reaction mixture was concentrated and purified via prepHPLC. $^1$H NMR (500 MHz, DMSO-d$_6$) δ 9.62-9.52 (m, 1H), 8.60-8.50 (m, 1H), 7.95 (s, 1H), 7.68 (d, J=7.4 Hz, 1H), 7.56-7.45 (m, 1H), 7.33 (d, J=8.0 Hz, 1H), 7.31-7.24 (m, 2H), 6.92-6.79 (m, 1H), 6.63 (br. s., 1H), 6.04 (s, 1H), 5.57 (d, J=11.6 Hz, 1H), 4.93-4.82 (m, 1H), 3.90 (s, 1H), 3.77-3.71 (m, 1H), 3.66 (d, J=11.3 Hz, 2H), 3.59-3.48 (m, 3H), 3.17 (br. s., 2H), 2.61-2.53 (m, 2H), 2.04 (br. s., 1H), 1.92 (d, J=14.3 Hz, 1H), 1.66 (br. s., 1H), 1.43 (br. s., 1H), 1.23 (br. s., 1H), 0.87 (d, J=5.8 Hz, 3H), 0.58 (br. s., 1H). MS (ESI) m/z: 699.3 (M+H)$^+$. Analytical HPLC (method C): RT=1.5 min, purity=88%.

The following examples in Table 3 were prepared in a similar manner as Example 125.

TABLE 3

| Example | Structure & Name | Analytical Data |
|---|---|---|
| 126 | (10R,14S)-14-[4-(3-chloro-2,6-difluorophenyl)-6-oxo-1,2,3,6-tetrahydropyridin-1-yl]-10-methyl-5-{[(3R,4S,5S,6R)-3,4,5-trihydroxy-6-(hydroxymethyl)oxan-2-yl]amino}-8,16-diazatricyclo[13.3.1.0$^{2,7}$]nonadeca-1(19),2,4,6,15,17-hexaen-9-one | $^1$H NMR (500 MHz, DMSO-d$_6$) δ 9.59-9.53 (m, 1H), 8.59-8.51 (m, 1H), 7.67 (td, J = 8.7, 5.8 Hz, 1H), 7.51-7.44 (m, 1H), 7.32 (d, J = 8.5 Hz, 1H), 7.30-7.19 (m, 2H), 6.78-6.71 (m, 1H), 6.68 (d, J = 8.0 Hz, 1H), 6.52 (d, J = 1.9 Hz, 1H), 6.04 (s, 1H), 5.58 (dd, J = 12.7, 4.4 Hz, 1H), 5.00 (br. s., 1H), 4.96-4.87 (m, 1H), 4.45 (t, J = 8.3 Hz, 1H), 3.72-3.62 (m, 2H), 3.52-3.44 (m, 1H), 3.25-3.09 (m, 3H), 2.65-2.52 (m, 3H), 2.09-1.99 (m, 1H), 1.94 (br. s., 1H), 1.66 (s, 1H), 1.42 (d, J = 7.4 Hz, 1H), 1.29-1.15 (m, 1H), 0.88 (d, J = 6.9 Hz, 3H), 0.58 (br. s., 1H). MS (ESI) m/z: 699.3 (M + H)$^+$. |

TABLE 3-continued

| Example | Structure & Name | Analytical Data |
|---|---|---|
| 127 | 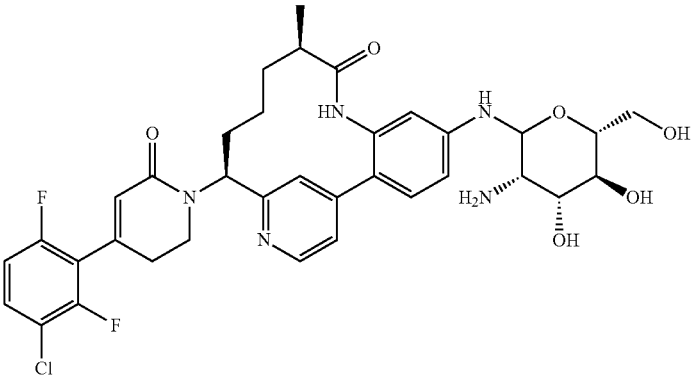<br>(10R,14S)-5-{[(3S,4R,5S,6R)-3-amino-4,5-dihydroxy-6-(hydroxymethyl)oxan-2-yl]amino}-14-[4-(3-chloro-2,6-difluorophenyl)-6-oxo-1,2,3,6-tetrahydropyridin-1-yl]-10-methyl-8,16-diazatricyclo[13.3.1.0$^{2,7}$]nonadeca-1(19),2,4,6,15,17-hexaen-9-one | $^1$H NMR (500 MHz, DMSO-d$_6$) δ 9.59-9.53 (m, 1H), 8.59-8.51 (m, 1H), 7.67 (td, J = 8.7, 5.8 Hz, 1H), 7.51-7.44 (m, 1H), 7.32 (d, J = 8.5 Hz, 1H), 7.30-7.19 (m, 2H), 6.78-6.71 (m, 1H), 6.68 (d, J = 8.0 Hz, 1H), 6.52 (d, J = 1.9 Hz, 1H), 6.04 (s, 1H), 5.58 (dd, J = 12.7, 4.4 Hz, 1H), 5.00 (br. s., 1H), 4.96-4.87 (m, 1H), 4.45 (t, J = 8.3 Hz, 1H), 3.72-3.62 (m, 2H), 3.52-3.44 (m, 1H), 3.25-3.09 (m, 3H), 2.65-2.52 (m, 3H), 2.09-1.99 (m, 1H), 1.94 (br. s., 1H), 1.66 (s, 1H), 1.42 (d, J = 7.4 Hz, 1H), 1.29-1.15 (m, 1H), 0.88 (d, J = 6.9 Hz, 3H), 0.58 (br. s., 1H).<br>MS (ESI) m/z: 698.4 (M + H)$^+$. |
| 128 | 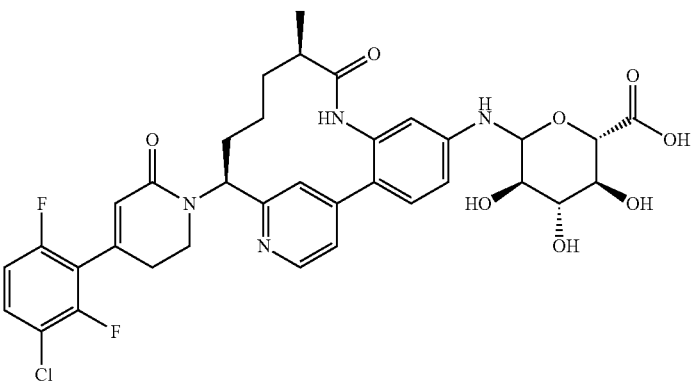<br>(2S,3S,4S,5R)-6-{[(10R,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]amino}-3,4,5-trihydroxyoxane-2-carboxylic acid | $^1$H NMR (500 MHz, DMSO-d$_6$) δ 9.58 (br. s., 1H), 8.55 (d, J = 4.9 Hz, 1H), 7.96 (s, 1H), 7.78-7.61 (m, 1H), 7.49 (br. s., 1H), 7.39-7.14 (m, 3H), 6.75 (d, J = 9.2 Hz, 1H), 6.64 (d, J = 8.5 Hz, 1H), 6.53 (br. s., 1H), 6.05 (s, 1H), 5.59 (d, J = 9.2 Hz, 1H), 5.15-4.98 (m, 1H), 4.60-4.44 (m, 1H), 3.65 (d, J = 12.2 Hz, 1H), 3.08 (br. s., 1H), 2.66-2.52 (m, 2H), 2.14-1.85 (m, 1H), 1.66 (br. s., 1H), 1.44 (br. s., 1H), 1.24 (br. s., 1H), 0.88 (d, J = 6.4 Hz, 3H)<br>MS (ESI) m/z: 713.4 (M + H)$^+$. |
| 129 | 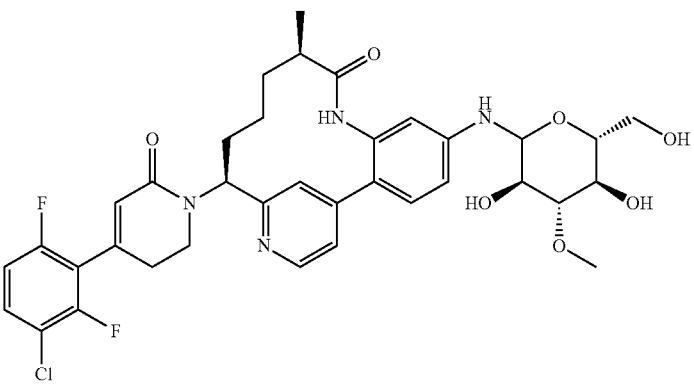<br>(10R,14S)-14-[4-(3-chloro-2,6-difluorophenyl)-6-oxo-1,2,3,6-tetrahydropyridin-1-yl]-5-{[(3R,4S,5R,6R)-3,5-dihydroxy-6-(hydroxymethyl)-4-methoxyoxan-2-yl]amino}-10-methyl-8,16-diazatricyclo[13.3.1.0$^{2,7}$]nonadeca-1(19),2,4,6,15,17-hexaen-9-one | $^1$H NMR (500 MHz, DMSO-d$_6$) δ 9.64-9.45 (m, 1H), 8.64-8.50 (m, 1H), 7.96 (s, 1H), 7.75-7.62 (m, 1H), 7.54-7.43 (m, 1H), 7.37-7.17 (m, 3H), 6.83-6.33 (m, 2H), 6.05 (s, 1H), 5.10 (br. s., 1H), 4.62-4.43 (m, 1H), 3.65 (d, J = 11.6 Hz, 2H), 3.60-3.53 (m, 3H), 2.67-2.53 (m, 3H), 2.06 (d, J = 17.7 Hz, 1H), 1.94 (br. s., 1H), 1.66 (br. s., 1H), 1.44 (br. s., 1H), 1.23 (br. s., 1H), 0.97-0.82 (m, 3H), 0.67-0.45 (m, 1H)<br>MS (ESI) m/z: 713.4 (M + H)$^+$. |

TABLE 3-continued

| Example | Structure & Name | Analytical Data |
|---|---|---|
| 130 | 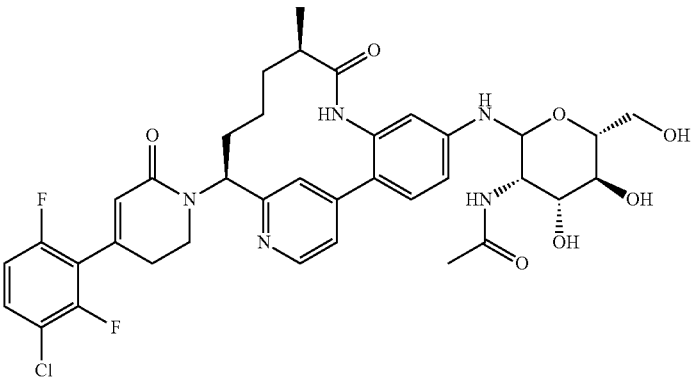  N-[(3S,4R,5S,6R)-2-{[(10R,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]amino}-4,5-dihydroxy-6-(hydroxymethyl)oxan-3-yl]acetamide | $^1$H NMR (500 MHz, DMSO-d$_6$) δ 9.70-9.42 (m, 1H), 8.55 (br. s., 1H), 7.95 (s, 1H), 7.67 (d, J = 5.5 Hz, 1H), 7.54-7.39 (m, 2H), 7.37-7.19 (m, 4H), 6.92-6.73 (m, 1H), 6.64 (s, 1H), 6.21-5.92 (m, 1H), 5.58 (br. s., 1H), 5.00-4.75 (m, 2H), 4.47-4.12 (m, 2H), 3.75-3.53 (m, 4H), 1.99 (s, 3H), 1.66 (br. s., 1H), 1.43 (br. s., 1H), 1.21 (br. s., 1H), 0.88 (d, J = 6.4 Hz, 3H) MS (ESI) m/z: 740.6 (M + H)$^+$. |
| 131 | 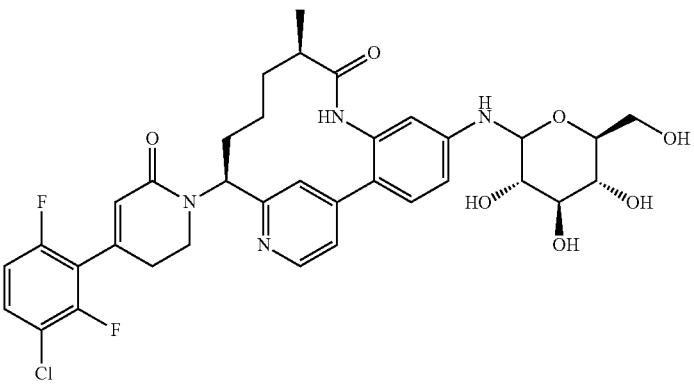  (10R,14S)-14-[4-(3-chloro-2,6-difluorophenyl)-6-oxo-1,2,3,6-tetrahydropyridin-1-yl]-10-methyl-5-{[(3S,4R,5R,6S)-3,4,5-trihydroxy-6-(hydroxymethyl)oxan-2-yl]amino}-8,16-diazatricyclo[13.3.1.0$^{2,7}$]nonadeca-1(19),2,4,6,15,17-hexaen-9-one | $^1$H NMR (500 MHz, DMSO-d$_6$) δ 9.65-9.39 (m, 1H), 8.54 (dd, J = 11.3, 4.9 Hz, 1H), 7.77-7.60 (m, 1H), 7.55-7.42 (m, 1H), 7.38-7.15 (m, 3H), 6.79-6.65 (m, 1H), 6.05 (s, 1H), 5.58 (d, J = 8.5 Hz, 1H), 4.40 (s, 1H), 3.90 (d, J = 10.1 Hz, 1H), 3.71-3.56 (m, 2H), 3.21-3.11 (m, 2H), 2.14-1.86 (m, 2H), 1.66 (br. s., 1H), 1.43 (br. s., 1H), 1.22 (br. s., 1H), 0.89 (d, J = 3.4 Hz, 3H), 0.74-0.52 (m, 1H) MS (ESI) m/z: 699.4 (M + H)$^+$. |
| 132 | 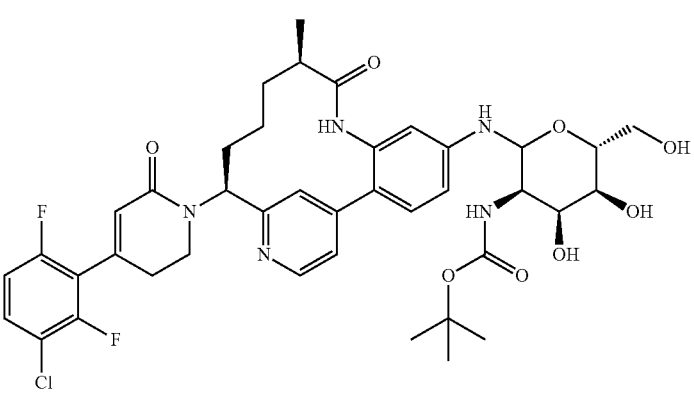  tert-butyl N-[(3R,4S,5S,6R)-2-{[(10R,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]amino}-4,5-dihydroxy-6-(hydroxymethyl)oxan-3-yl]carbamate | $^1$H NMR (500 MHz, DMSO-d$_6$) δ 9.60 (br. s., 1H), 8.54 (d, J = 4.9 Hz, 1H), 7.67 (d, J = 5.8 Hz, 1H), 7.47 (br. s., 1H), 7.38-7.20 (m, 3H), 7.01-6.39 (m, 2H), 6.30-6.17 (m, 1H), 6.04 (s, 1H), 5.58 (d, J = 7.9 Hz, 1H), 5.04 (br. s., 2H), 4.48 (br. s., 2H), 3.90 (br. s., 2H), 2.04 (br. s., 1H), 1.66 (br. s., 1H), 1.48-1.31 (m, 9H), 0.87 (d, J = 6.4 Hz, 3H) MS (ESI) m/z: 798.6 (M + H)$^+$. |

| Example | Structure & Name | Analytical Data |
|---|---|---|
| 133 | 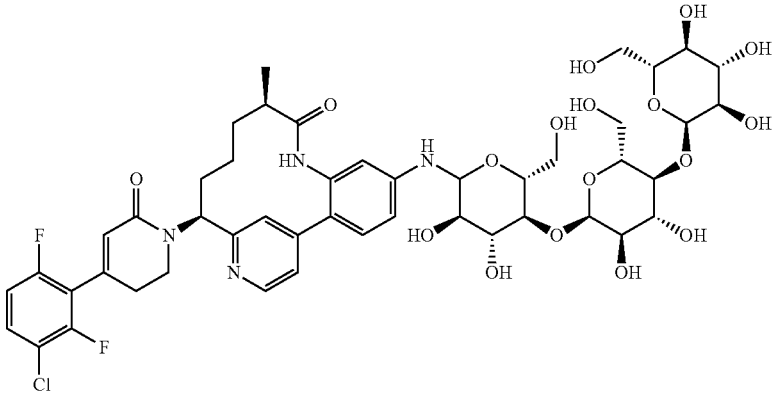<br>(10R,14S)-14-[4-(3-chloro-2,6-difluorophenyl)-6-oxo-1,2,3,6-tetrahydropyridin-1-yl]-5-{[(3R,4R,5S,6R)-5-{[(2R,3R,4R,5S,6R)-3,4-dihydroxy-6-(hydroxymethyl)-5-{[(2R,3R,4S,5S,6R)-3,4,5-trihydroxy-6-(hydroxymethyl)oxan-2-yl]oxy}oxan-2-yl]oxy}-3,4-dihydroxy-6-(hydroxymethyl)oxan-2-yl]amino}-10-methyl-8,16-diazatricyclo[13.3.1.0$^{2,7}$]nonadeca-1(19),2,4,6,15,17-hexaen-9-one | $^1$H NMR (500 MHz, DMSO-d$_6$) δ 9.71-9.38 (m, 1H), 8.54 (br. s., 1H), 7.95 (br. s., 1H), 7.71-7.54 (m, 52H), 7.47 (d, J = 12.2 Hz, 2H), 7.37-7.08 (m, 3H), 6.81-6.33 (m, 4H), 6.04 (br. s., 1H), 5.67-5.31 (m, 2H), 5.12-4.89 (m, 2H), 4.54 (br. s., 2H), 1.43 (br. s., 1H), 1.26-1.09 (m, 1H), 0.88 (br. s., 3H)<br>MS (ESI) m/z: 1023.5 (M + H)$^+$. |
| 134 | 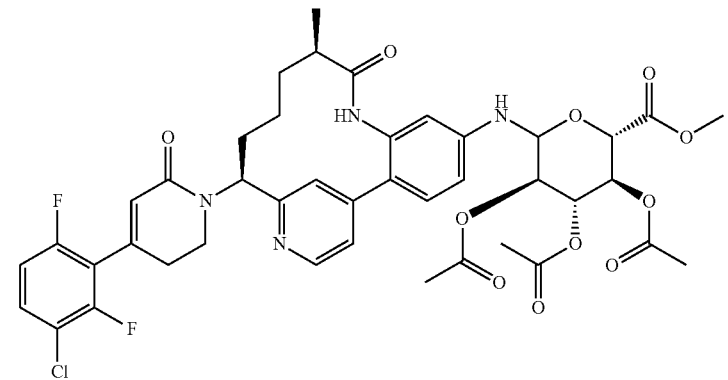<br>methyl (2S,3S,4S,5R)-3,4,5-tris(acetyloxy)-6-{[(10R,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]amino}oxane-2-carboxylate | $^1$H NMR (500 MHz, DMSO-d$_6$) δ 9.63 (d, J = 8.2 Hz, 1H), 8.56 (d, J = 3.7 Hz, 1H), 7.75-7.57 (m, 1H), 7.47 (br. s., 1H), 7.41-7.32 (m, 1H), 7.31-7.14 (m, 2H), 7.07-6.90 (m, 1H), 6.87-6.77 (m, 1H), 6.63 (br. s., 1H), 6.05 (s, 1H), 5.69-5.31 (m, 3H), 5.15-4.84 (m, 2H), 4.67-4.38 (m, 1H), 3.90 (br. s., 1H), 3.72-3.59 (m, 6H), 2.65-2.44 (m, 6H), 1.67 (br. s., 1H), 1.44 (br. s., 1H), 1.21 (br. s., 1H), 0.89 (br. s., 3H)<br>MS (ESI) m/z: 798.6 (M + H)$^+$. |

Example 135

Methyl N-[(10R,14S)-17-chloro-14-[4-(3-chloro-2,6-difluorophenyl)-6-oxo-1,2,3,6-tetrahydropyridin-1-yl]-10-methyl-9-oxo-8,16,18-triazatricyclo[13.2.1.0$^{2,7}$]octadeca-1(17),2,4,6,15(18)-pentaen-5-yl]carbamate, TFA Salt

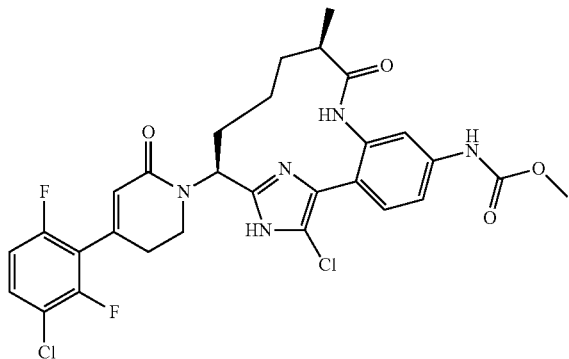 [SMILES: COC(=O)Nc1ccc2c(c1)NC(=O)[C@H](C)CCC[C@H](N1CCC(c3c(F)ccc(Cl)c3F)=CC1=O)c1nc-2c(Cl)[nH]1]

135A. (S)-2-(4-(Methoxycarbonylamino)-2-nitrophenyl)-2-oxoethyl 2-(tert-butoxycarbonylamino)pent-4-enoate To a clear, colorless solution of (S)-2-(tert-butoxycarbonylamino)pent-4-enoic acid (2.91 g, 13.50 mmol) in DMF (33.7 mL) was added potassium hydrogen carbonate (1.622 g, 16.20 mmol). The reaction mixture was stirred for 20 min at rt and then cooled to 0° C. To the above mixture was then added a solution of Intermediate 17 (4.28 g, 13.50 mmol) in DMF (33.7 mL) dropwise and the reaction was allowed to warm to rt and continued to stir at rt for overnight. After 18 h, the reaction was stopped and cooled to 0° C. The reaction mixture was then poured into ice-cold water, then extracted with EtOAc (3×). The combined organic layers were washed with water, brine, dried over Na$_2$SO$_4$, filtered and concentrated. A yellow foam obtained as 135A (6.09 g, 100%). MS (ESI) m/z: 450.5 (M−H)$^+$.

135B. Methyl (4-(2-((1S)-1-((tert-butoxycarbonyl)amino)but-3-en-1-yl)-1H-imidazol-5-yl)-3-nitrophenyl)carbamate To a 1000 mL RBF containing 135A (6.09 g, 13.49 mmol) was added xylene (135 mL). The above mixture was sonicated to obtain a clear yellow solution. To the clear yellow solution was then added ammonium acetate (10.40 g, 135 mmol) and the flask was equipped with a Dean-stark trap and a reflux condenser. The reaction was warmed to 110° C. for 2 h, and then 140° C. for 2 h. After stirring for 4 hours in total, the reaction was allowed to cool to rt. The reaction was diluted with EtOAc and then washed with saturated NaHCO$_3$ solution (2×) followed by brine. The organic layers were then dried over Na$_2$SO$_4$, filtered, and concentrated. The brown gum weighing 5 g was dissolved in DCM and a small amount of MeOH and then purified using silica gel chromatography. A brown foam obtained as 135B (0.91 g, 15.6%). MS (ESI) m/z: 432.5 (M+H)$^+$.

135C. Methyl (4-(2-((1S)-1-((tert-butoxycarbonyl)amino)but-3-en-1-yl)-1-((2-(trimethylsilyl)ethoxy)methyl)-1H-imidazol-4-yl)-3-nitrophenyl)carbamate A flame-dried 25 mL round bottom flask was charged with NaH (0.092 g, 2.295 mmol) and then THF (4.17 mL) was added to give a gray suspension. The suspension was cooled to 0° C. and then a clear, yellow solution of 135B (0.9 g, 2.086 mmol) in THF (4.17 mL) was added dropwise. The reaction mixture was stirred at 0° C. for 30 min and then allowed to warm to rt and stirring was continued at rt for additional 0.5 h. The yellow suspension was again cooled to 0° C. and then SEM-Cl (0.370 mL, 2.086 mmol) was added dropwise. The resulting cloudy reaction mixture was stirred at 0° C. After 1 h, the reaction was stopped and quenched with saturated NH$_4$Cl followed by dilution with EtOAc. The layers were separated and the aqueous layer was extracted with EtOAc. The combined organic layers were washed with saturated NaHCO$_3$, brine, dried over Na$_2$SO$_4$, filtered, and concentrated. The yellow oil weighing 1.6 g was purified by silica gel chromatography. The desired product from the reaction was obtained as yellow foam (0.424 g, 36%). MS (ESI) m/z: 562.0 (M+H)$^+$. 1D NOE confirmed the regioisomeric position of SEM on the imidazole ring.

135D. tert-Butyl N-[(1S)-1-(4-{2-amino-4-[(methoxycarbonyl)amino]phenyl}-1-{[2-(trimethylsilyl)ethoxy]methyl}-1H-imidazol-2-yl)but-3-en-1-yl]carbamate To the solution of 3C (0.424 g, 0.755 mmol) in MeOH (5 mL) was added zinc (0.494 g, 7.55 mmol) and ammonium chloride (0.404 g, 7.55 mmol). The reaction mixture was stirred at 60° C. in a sealed tube. After 4 h, the reaction was cooled to rt. The yellow suspension was diluted with DCM and then washed with water. The aqueous layer extracted with 15% IPA/CHCl$_3$. The combined organic layers were washed with brine, dried over MgSO$_4$, filtered and concentrated. The crude product was purified using silica gel chromatography to give an orange solid as the desired product (0.31 g, 77%). MS (ESI) m/z: 532.4 (M+H)$^+$.

135E. tert-butyl N-[(1S)-1-(4-{4-[(methoxycarbonyl)amino]-2-[(2R)-2-methylbut-3-enamido]phenyl}-1-{[2-(trimethylsilyl)ethoxy]methyl}-1H-imidazol-2-yl)but-3-en-1-yl]carbamate To a cooled (0° C.), clear yellow orange solution of 135D (4.83 g, 9.08 mmol) in ethyl acetate (91 ml) was added Intermediate 10 (1.0 g, 9.99 mmol) and Hunig's base (6.34 ml, 36.3 mmol). Next, 1-propanephosphonic acid cyclic anhydride (T3P) (50% in EtOAc) (13.38 ml, 22.70 mmol) was added dropwise over 20 min. and the reaction was stirred at 0° C. After 3h, the reaction was diluted with EtOAc and washed with sat. NaHCO$_3$. The aqueous layer was extracted with EtOAc (2×). The organic layers were combined and washed with brine, dried over sodium sulfate, filtered and concentrated to give an orange foam. Purification by normal phase chromatography gave 135E (4.53 g, 81% yield) as a white foam. Proton NMR indicated a 3:1 mixture of diastereomers. MS (ESI) m/z: 614.4 (M+H)$^+$.

135F. tert-butyl N-[(10R,11E,14S)-5-[(methoxycarbonyl)amino]-10-methyl-9-oxo-16-{[2-(trimethylsilyl)ethoxy]methyl}-8,16,18-triazatricyclo[13.2.1.0$^{2,7}$]octadeca-1(17),2,4,6,11,15(18)-hexaen-14-yl]carbamate (Diastereomer A) and 135G. tert-butyl N-[(10S,11E,14S)-5-[(methoxycarbonyl)amino]-10-methyl-9-oxo-16-{[2-(trimethylsilyl)ethoxy]methyl}-8,16,18-triazatricyclo[13.2.1.0$^{2,7}$]octadeca-1(17),2,4,6,11,15(18)-hexaen-14-yl]carbamate (Diastereomer B)

To a solution of 135E (4.40 g, 7.17 mmol) in dichloromethane (717 ml) was added pTsOH monohydrate (1.523 g, 7.89 mmol) and the mixture was degassed with argon for 30 min. Next, the flask was equipped with a reflux condensor and the reaction was warmed to 40° C. for 1h. Next, a burgundy solution of Grubbs II (2.440 g, 2.87 mmol) in 20 ml of DCM (degassed with argon) was added dropwise via syringe over 35 to 40 min. After 21.5 h, the reaction was cooled to rt. The reaction mixture was washed with sat. NaHCO$_3$, brine, dried over MgSO$_4$, filtered and concentrated to give a brown foam. Purification by normal phase chromatography gave 135F, Diastereomer A (1.71 g, 40.7% yield) as an off-white solid and a mixture of 135F (Diastereomer A) and 135G (Diastereomer B) (1.4 g). MS (ESI) m/z: 586.3 (M+H)$^+$.

135H. tert-butyl N-[(10R,14S)-5-[(methoxycarbonyl)amino]-10-methyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-14-yl]carbamate A dark brown solution of 135F (1.71 g, 2.92 mmol) in EtOAc (97 ml) was degassed with argon for 30 minutes. Next, platinum(IV) oxide (0.066 g, 0.292 mmol) was added and hydrogen gas from a balloon was bubbled through the reaction mixture for several minutes. The reaction was stirred under a hydrogen atmosphere. After 24 h, an additional amount of platinum(IV) oxide (0.192 g, 0.876 mmol) was added and the reaction was stirred under a hydrogen atmosphere. After 21 h, the reaction was stopped. The vessel was purged with vacuum/argon three times, then Celite was added, and the reaction was filtered rinsing with EtOAc. The resulting clear, yellow brown filtrate was concentrated to give an off-white solid weighing 1.66 g. Recrystallization from methanol (30 mL) gave 135H (0.575 g, 33.5% yield) as a white solid. MS (ESI) m/z: 588.4 (M+H)$^+$.

135I. tert-butyl N-[(10R,14S)-17-chloro-5-[(methoxycarbonyl)amino]-10-methyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-14-yl]carbamate To a solution of 135H (450 mg, 0.766 mmol) in CHCl$_3$ (5.47 mL) and acetonitrile (5.47 mL) in a pressure tube was added NCS (123 mg, 0.919 mmol). The tube was sealed and heated at 55° C. After 3 hrs, the reaction mixture was gradually cooled down to rt and stirred overnight. Reaction had progressed to ~40% desired product by LC/MS. The mixture was reheated to 550 for 4 hrs. The reaction mixture was concentrated and purified by normal phase column chromatography to give 135I (434 mg, 91%) as a solid. MS (ESI) m/z: 588 (M+H)$^+$.

135J. methyl N-[(10R,14S)-14-amino-17-chloro-10-methyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-5-yl]carbamate 135I (0.476 g, 0.765 mmol) was treated with TFA (2.95 mL, 38.2 mmol) in DCM (15 mL). After 1 hour, the reaction mixture was concentrated to dryness. The residue was dissolved in EtOAc and washed with 1.5M potassium phosphate. The organic layer was washed further with brine, dried over sodium sulfate, filtered, and concentrated. This material was carried forward as is. MS (ESI) m/z: 522.3 (M+H)$^+$.

135K. methyl N-[(10R,14S)-17-chloro-14-{N-[3-(3-chloro-2,6-difluorophenyl)-3-oxopropyl]-2-(diethoxyphosphoryl)acetamido}-10-methyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-5-yl]carbamate To a suspension of 135J (0.194 g, 0.372 mmol) in DCM (9.29 ml) was added DIEA (0.649 ml, 3.72 mmol). The mixture was sonicated and stirred at RT for 30 min. Next, Intermediate 1 (0.075 g, 0.372 mmol) in DCM (1.0 mL) was added. After 100 min., the reaction was cooled to 0° C. and then pyridine (0.301 ml, 3.72 mmol) and 2-(diethoxyphosphoryl)acetic acid (0.179 ml, 1.115 mmol) were added, followed by POCl$_3$ (0.104 ml, 1.115 mmol) dropwise. The reaction was allowed to gradually come to rt. After 1 hr, the reaction was diluted with DCM, washed with sat. NaHCO$_3$, brine, dried over MgSO$_4$, filtered and concentrated. The crude material was purified by reverse phase prep. HPLC to give 135K (0.054 g, 0.060 mmol, 16.10% yield) as a brown film. MS (ESI) m/z: 902.4 (M+H)$^+$.

Example 135. methyl N-[(10R,14S)-17-chloro-14-[4-(3-chloro-2,6-difluorophenyl)-6-oxo-1,2,3,6-tetrahydropyridin-1-yl]-10-methyl-9-oxo-8,16,18-triazatricyclo[13.2.1.0$^{2,7}$]octadeca-1(17),2,4,6,15(18)-pentaen-5-yl]carbamate, TFA Salt To 135K (0.054 g, 0.060 mmol) in MeOH (8 mL) was added NaOMe (25 wt % in MeOH) (0.082 mL, 0.359 mmol). After 30 mins, shows nearly a 1:1 ratio of SEM-protected product and des-SEM product. The rxn mixture was neutralized by adding dropwise 1.25 M HCl in MeOH, to make the yellow solution turn into colorless. The resulting solution was filtered, filtrate, and concentrated. The residue was purified by reverse phase prep to give Example 135 (0.008 g, 10.38 µmol, 17.35% yield) is a white solid. $^1$H NMR (400 MHz, DMSO-d6) d 9.77 (s, 1H), 7.63 (td, J=8.7, 5.7 Hz, 1H), 7.37-7.26 (m, 3H), 7.22 (td, J=9.2, 1.8 Hz, 1H), 6.00 (s, 1H), 5.75 (dd, J=11.6, 6.3 Hz, 1H), 4.20-4.10 (m, 2H), 3.77-3.67 (m, 1H), 3.62 (s, 3H), 2.72-2.53 (m, 3H), 1.96-1.80 (m, 2H), 1.54 (br. s., 1H), 1.37-1.15 (m, 2H), 0.79 (d, J=6.8 Hz, 3H). MS (ESI) m/z: 618.2 (M+H)$^+$. Analytical HPLC (method B): RT=7.12 min, purity=>95%.

Example 136

Methyl N-[(10R,14S)-14-[4-(3-chloro-2,6-difluorophenyl)-6-oxo-1,2,3,6-tetrahydropyridin-1-yl]-10-methyl-9,11-dioxo-8,16-diazatricyclo[13.3.1.0$^{2,7}$]nonadeca-1(19),2(7),3,5,15,17-hexaen-5-yl]carbamate

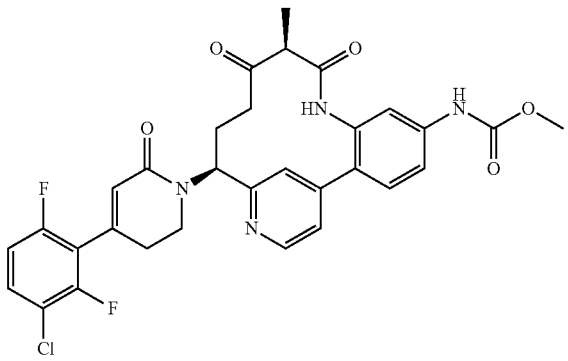 [SMILES: COC(=O)Nc1ccc2c(c1)NC(=O)[C@H](C)C(=O)CC[C@H](N1CCC(c3c(F)ccc(Cl)c3F)=CC1=O)c1cc-2ccn1]

Example 136 was prepared using a procedure analogous to Example 22. ¹H NMR (400 MHz, MeOD) δ 9.63 (s, 1H), 8.81-8.57 (m, 1H), 7.76-7.65 (m, 2H), 7.63-7.42 (m, 4H), 7.19-7.04 (m, 1H), 6.10 (s, 1H), 5.30 (dd, J=12.1, 5.1 Hz, 1H), 4.06 (dt, J=12.4, 6.1 Hz, 1H), 3.87-3.80 (m, 1H), 3.79-3.73 (m, 4H), 3.68 (d, J=6.8 Hz, 1H), 3.04-2.83 (m, 2H), 2.83-2.68 (m, 1H), 2.64-2.43 (m, 2H), 2.34-2.24 (m, 1H), 1.20 (d, J=6.8 Hz, 3H). MS (ESI) m/z: 609.2 (M+H)⁺. Analytical HPLC (method A): RT=6.7 min, purity=99%.

Example 137

(10R,14S)-4-bromo-14-[4-(3-chloro-2,6-difluorophenyl)-6-oxo-1,2,3,6-tetrahydropyridin-1-yl]-10-methyl-8,16-diazatricyclo[13.3.1.0$^{2,7}$]nonadeca-1(19),2(7),3,5,15,17-hexaen-9-one

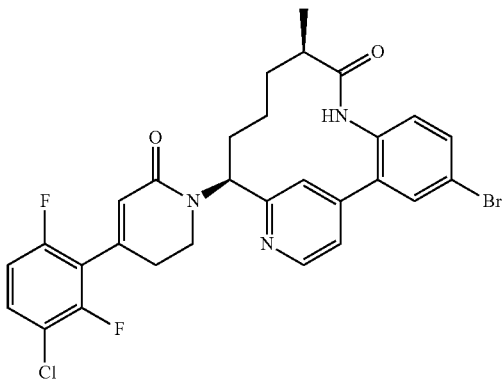 [SMILES: C[C@@H]1CCC[C@H](N2CCC(c3c(F)ccc(Cl)c3F)=CC2=O)c2cc(ccn2)-c2cc(Br)ccc2NC1=O]

137A. tert-butyl N-[(10R,14S)-4-bromo-10-methyl-9-oxo-8,16-diazatricyclo[13.3.1.0$^{2,7}$]nonadeca-1(19),2(7),3,5,15,17-hexaen-14-yl]carbamate To a suspension of 45G (616 mg, 1.558 mmol) in acetonitrile (15.200 ml) in a sealed vial was added NBS (277 mg, 1.558 mmol). The reaction was sealed and heated at 75° C. overnight. Additional NBS (300 mg, 1.686 mmol) was added and heat at 75° C. overnight. The mixture was concentrated and purified by silica gel chromatography to afford 137A as a white solid (664 mg, 90%). MS (ESI) m/z: 476.0 (M+H)⁺.

Example 137 was prepared using a procedure analogous to example 1 by using 137A in step 1J. ¹H NMR (400 MHz, METHANOL-d₄) δ 8.66 (d, J=5.1 Hz, 1H), 7.75 (d, J=2.2 Hz, 1H), 7.66-7.44 (m, 3H), 7.42-7.32 (m, 1H), 7.17 (d, J=8.4 Hz, 1H), 7.07 (td, J=9.1, 1.3 Hz, 1H), 6.09 (s, 1H), 5.66 (dd, J=12.4, 4.3 Hz, 1H), 4.07-3.93 (m, 1H), 3.84-3.69 (m, 1H), 2.77-2.50 (m, 3H), 2.24-2.08 (m, 1H), 1.97-1.76 (m, 2H), 1.57-1.42 (m, 1H), 1.39-1.20 (m, 1H), 0.99 (d, J=6.8 Hz, 3H), 0.93-0.75 (m, 1H). MS (ESI) m/z: 602.0 (M+H)⁺. Analytical HPLC (method A): RT=8.7 min, purity=97%.

Example 138

(10R,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2(7),3,5,15,17-hexaene-4-carbonitrile

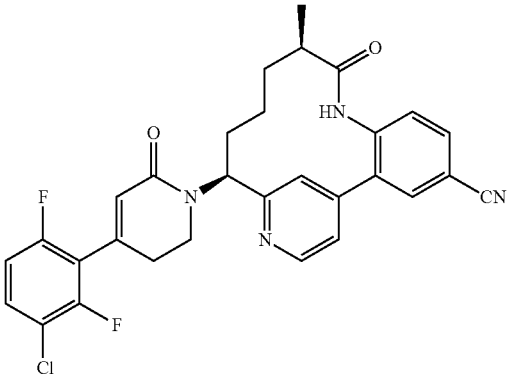 [SMILES: C[C@@H]1CCC[C@H](N2CCC(c3c(F)ccc(Cl)c3F)=CC2=O)c2cc(ccn2)-c2cc(C#N)ccc2NC1=O]

And Example 139

(10R,14S)-14-[4-(3-cyano-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2(7),3,5,15,17-hexaene-4-carbonitrile

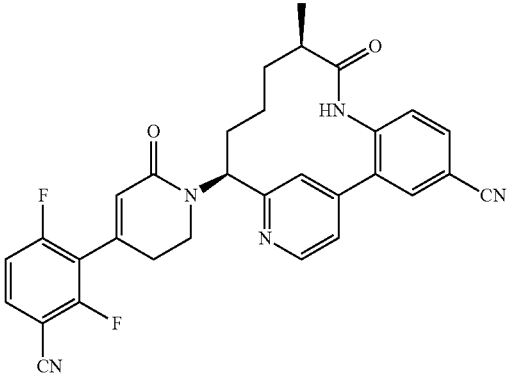 [SMILES: C[C@@H]1CCC[C@H](N2CCC(c3c(F)ccc(C#N)c3F)=CC2=O)c2cc(ccn2)-c2cc(C#N)ccc2NC1=O]

Example 138 and Example 139

Example 137 (40 mg, 0.067 mmol) in a microwave tube was added dicyanozinc (8.60 mg, 0.073 mmol), Zn (1.306 mg, 0.020 mmol) and DMF (1331 µl). Bubbled through Ar for several minutes and bis(tri-t-butylphosphine)palladium (0) (3.40 mg, 6.66 µmol) was added. The reaction was sealed and heated at 80° C. overnight. The reaction mixture was concentrated and purified by prepHPLC to afford Example 138 (32 mg, 72%) and Example 139 (6 mg, 14%).

Example 138: ¹H NMR (400 MHz, METHANOL-d₄) δ 8.82 (d, J=5.5 Hz, 1H), 8.08 (d, J=1.8 Hz, 1H), 7.97 (d, J=1.3 Hz, 1H), 7.91 (dd, J=8.1, 2.0 Hz, 1H), 7.82 (dd, J=5.5, 1.8 Hz, 1H), 7.58-7.50 (m, 1H), 7.47 (d, J=8.1 Hz, 1H), 7.09 (td, J=9.3, 1.9 Hz, 1H), 6.10 (s, 1H), 5.45 (dd, J=12.4, 5.2 Hz, 1H), 4.05-3.99 (m, 1H), 3.79 (ddd, J=12.5, 9.9, 5.3 Hz, 1H), 2.92-2.81 (m, 1H), 2.78-2.62 (m, 2H), 2.28 (tt, J=12.8, 4.4 Hz, 1H), 2.07-1.83 (m, 2H), 1.64-1.33 (m, 2H), 0.99 (d, J=6.8 Hz, 3H), 0.71 (br. s., 1H). MS (ESI) m/z: 547.1 (M+H)$^+$. Analytical HPLC (method A): RT=8.1 min, purity=98%.

Example 139: $^1$H NMR (400 MHz, METHANOL-d$_4$) δ 8.79 (d, J=5.5 Hz, 1H), 8.06 (d, J=1.8 Hz, 1H), 7.91-7.87 (m, 1H), 7.87-7.83 (m, 2H), 7.70 (dd, J=5.5, 1.8 Hz, 1H), 7.46 (d, J=8.1 Hz, 1H), 7.27 (td, J=9.1, 1.3 Hz, 1H), 6.15 (s, 1H), 5.52 (dd, J=12.5, 5.1 Hz, 1H), 4.06 (dt, J=12.7, 6.2 Hz, 1H), 3.80 (ddd, J=12.5, 9.9, 5.3 Hz, 1H), 2.89-2.61 (m, 3H), 2.25 (tt, J=12.7, 4.6 Hz, 1H), 2.01-1.84 (m, 2H), 1.62-1.48 (m, 1H), 1.45-1.32 (m, 1H), 0.98 (d, J=6.8 Hz, 3H), 0.72 (br. s., 1H). MS (ESI) m/z: 538.1 (M+H)$^+$. Analytical HPLC (method A): RT=7.1 min, purity=99%.

Example 140

(10R,14S)-14-[4-(3-chloro-2,6-difluorophenyl)-6-oxo-1,2,3,6-tetrahydropyridin-1-yl]-10-methyl-4-(2H-1,2,3,4-tetrazol-5-yl)-8,16-diazatricyclo[13.3.1.0$^{2,7}$]nonadeca-1(19),2(7),3,5,15,17-hexaen-9-one

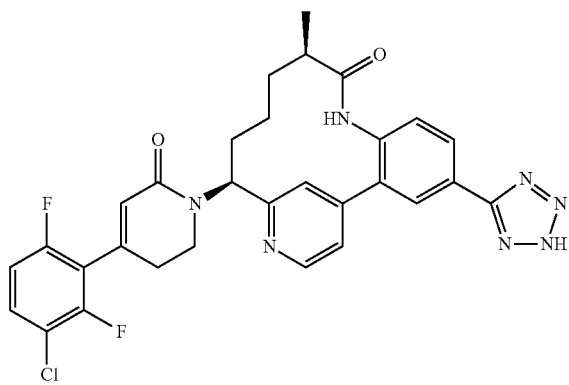 [SMILES: C[C@@H]1CCC[C@H](N2CCC(c3c(F)ccc(Cl)c3F)=CC2=O)c2cc(ccn2)-c2cc(-c3nn[nH]n3)ccc2NC1=O]

Example 140

To a mixture of Example 138 (28 mg, 0.042 mmol), sodium azide (13.77 mg, 0.212 mmol) and ammonium chloride (13.60 mg, 0.254 mmol) in a vial was added DMF (424 μl). The mixture was heated at 90° C. overnight. Then, additional 16 mg of NaN$_3$ and 18 mg of NH$_4$Cl were added. Heated at 90° C. for 16 hrs. The reaction mixture was concentrated and purified by prepHPLC to afford Example 140 (18 mg, 59%) as a off-white solid. $^1$H NMR (400 MHz, METHANOL-d$_4$) δ 8.81 (d, J=5.5 Hz, 1H), 8.34 (d, J=2.0 Hz, 1H), 8.19 (dd, J=8.4, 2.0 Hz, 1H), 7.93 (d, J=1.1 Hz, 1H), 7.78 (dd, J=5.5, 1.8 Hz, 1H), 7.57-7.49 (m, 2H), 7.09 (td, J=9.2, 1.8 Hz, 1H), 6.10 (s, 1H), 5.54 (dd, J=12.3, 4.8 Hz, 1H), 4.00 (dt, J=12.3, 6.2 Hz, 1H), 3.79 (ddd, J=12.5, 9.6, 5.4 Hz, 1H), 2.89-2.62 (m, 3H), 2.27 (tt, J=12.6, 4.8 Hz, 1H), 2.05-1.87 (m, 2H), 1.65-1.52 (m, 1H), 1.37 (td, J=10.1, 5.5 Hz, 1H), 1.02 (d, J=7.0 Hz, 3H), 0.83 (br. s., 1H). MS (ESI) m/z: 590.2 (M+H)$^+$. Analytical HPLC (method A): RT=6.9 min, purity=98%.

Example 141

(10R,14S)-14-[4-(3-chloro-2,6-difluorophenyl)-6-oxo-1,2,3,6-tetrahydropyridin-1-yl]-4,10-dimethyl-8,16-diazatricyclo[13.3.1.0$^{2,7}$]nonadeca-1(19),2(7),3,5,15,17-hexaen-9-one

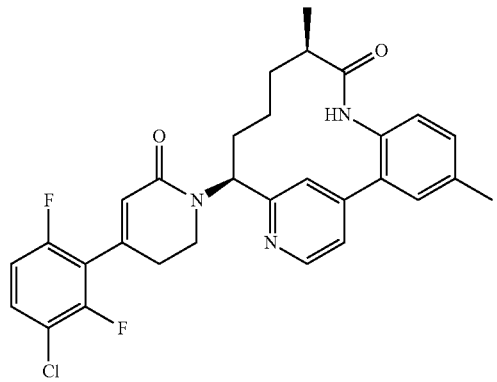 [SMILES: Cc1ccc2c(c1)-c1ccnc(c1)[C@@H](N1CCC(c3c(F)ccc(Cl)c3F)=CC1=O)CCC[C@@H](C)C(=O)N2]

Example 141

To a microwave tube was added Example 137 (14 mg, 0.023 mmol), methylboronic acid (1.534 mg, 0.026 mmol), potassium phosphate (0.023 mL, 0.070 mmol) and THF (0.5 mL). Bubbled through Ar for several minutes and (DtBPF)PdCl2 (0.759 mg, 1.165 μmol) was added. Sealed and heated at 60° C. overnight. The reaction mixture was concentrated and purified by prepHPLC to afford Example 141 (6 mg, 40%). $^1$H NMR (500 MHz, DMSO-d$_6$) δ 9.61 (s, 1H), 8.66 (d, J=5.2 Hz, 1H), 7.70 (td, J=8.6, 5.6 Hz, 1H), 7.54 (s, 1H), 7.43-7.36 (m, 2H), 7.33-7.25 (m, 2H), 7.14-7.07 (m, 1H), 6.07 (s, 1H), 5.61 (dd, J=12.7, 4.4 Hz, 1H), 3.92 (s, 1H), 3.69 (br. s., 1H), 2.67-2.58 (m, 2H), 2.43-2.34 (m, 3H), 2.10-2.01 (m, 1H), 1.95-1.84 (m, 1H), 1.69 (br. s., 1H), 1.41 (d, J=6.1 Hz, 1H), 1.31-1.09 (m, 4H), 0.89 (d, J=6.9 Hz, 3H). MS (ESI) m/z: 536.1 (M+H)$^+$. Analytical HPLC (method D): RT=1.9 min, purity=95%.

Example 142

Methyl N-[(10R,14S)-14-[4-(3-chloro-2,6-difluorophenyl)-2-oxo-1,2,3,4-tetrahydropyridin-1-yl]-10-methyl-9-oxo-8,16-diazatricyclo[13.3.1.0$^{2,7}$]nonadeca-1(19),2(7),3,5,15,17-hexaen-5-yl]carbamate

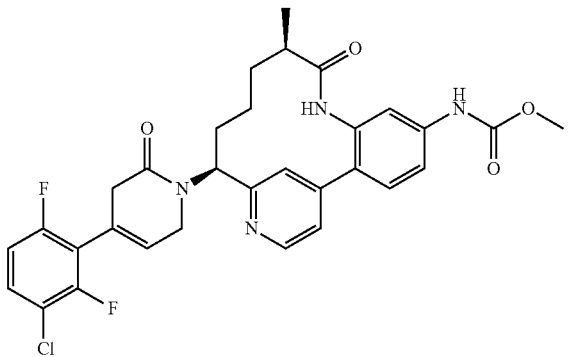 [SMILES: COC(=O)Nc1ccc2c(c1)NC(=O)[C@H](C)CCC[C@H](N1CC=C(c3c(F)ccc(Cl)c3F)CC1=O)c1cc-2ccn1]

Example 142A

Example 12A (106 mg, 0.178 mmol) in BuOH (10 mL) was added sodium hydroxide (1N aq) (8 mL, 8.00 mmol), sealed and stirred vigorously at 90° C. for 4 days. The reaction was cooled down to rt, tBuOH and aqueous layer separated, t-BuOH layer was taken out and biotage removed solvent to give a pale yellow solid. The aqueous layer was extracted with DCM, washed with brine and dried over MgSO4. Combined with residue from tBuOH layers and purification by silica gel chromatography afforded 142A as an offwhite foam (83 mg, 87%). LCMS (ESI) m/z: 537.2 (M+H)$^+$.

Example 142A (83 mg, 0.155 mmol) and PYRIDINE (41.9 μl, 0.518 mmol) in DCM (1546 μl) was cooled down to −78° C. METHYL CHLOROFORMATE (11.97 μl, 0.155 mmol) in small amount of DCM was added. The reaction turned immediately to orange, then pale yellow. Reaction was quenched by sat. NH4Cl, extracted with DCM, combined DCM layers washed with brine, dried over MgSO4, filtered and concentrated. Purification by silica gel chromatography to afford a white solid which was further separated by chiral HPLC to give Example 142 as the minor isomer (11 mg, 12%). $^1$H NMR (500 MHz, CHLOROFORM-d) δ 8.44 (d, J=5.0 Hz, 1H), 7.44 (d, J=8.0 Hz, 1H), 7.30-7.21 (m, 2H), 7.11-6.95 (m, 3H), 6.83 (td, J=8.9, 1.5 Hz, 1H), 5.97 (br. s., 1H), 5.81 (d, J=9.6 Hz, 1H), 5.11 (d, J=17.1 Hz, 1H), 4.37 (dd, J=18.6, 3.4 Hz, 1H), 3.50 (s, 3H), 3.25 (d, J=3.9 Hz, 2H), 2.57 (br. s., 1H), 2.20-2.05 (m, 1H), 1.95 (br. s., 1H), 1.69 (br. s., 1H), 1.40 (br. s., 2H), 0.93 (d, J=6.9 Hz, 3H), 0.55 (br. s., 1H). MS (ESI) m/z: 595.1 (M+H)$^+$.

Example 143

(10R,14S)-5-amino-14-[4-(3-chloro-2,6-difluorophenyl)-6-oxo-1,2,3,6-tetrahydropyridin-1-yl]-4-fluoro-10-methyl-8,16-diazatricyclo[13.3.1.0$^{2,7}$]nonadeca-1(19),2(7),3,5,15,17-hexaen-9-one

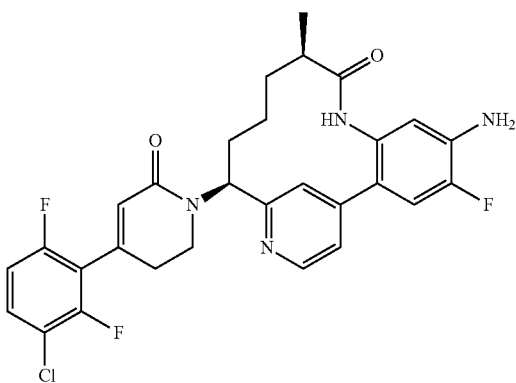 [SMILES: C[C@@H]1CCC[C@H](N2CCC(c3c(F)ccc(Cl)c3F)=CC2=O)c2cc(ccn2)-c2cc(F)c(N)cc2NC1=O]

Example 143

To a solution of Example 12 (23 mg, 0.043 mmol) in MeCN (428 μl) at 0° C. was added Selectfluor (15.17 mg, 0.043 mmol), the reaction turned immediately to brownish. After 30 min, the reaction was quenched by addition of H2O, MeOH, filtered. Purification by prepHPLC to afford Example 143 (4 mg, 12%). $^1$H NMR (400 MHz, METHANOL-d4) δ 8.78-8.56 (m, 1H), 8.22-8.04 (m, 1H), 7.97-7.79 (m, 1H), 7.62-7.50 (m, 1H), 7.49-7.32 (m, 1H), 7.18-6.90 (m, 1H), 6.75 (d, J=8.1 Hz, 1H), 6.12 (s, 1H), 5.57-5.24 (m, 1H), 3.75-3.53 (m, 2H), 2.91-2.52 (m, 3H), 2.41-2.20 (m, 1H), 2.16-2.02 (m, 1H), 1.99-1.81 (m, 1H), 1.71-1.54 (m, 1H), 1.27 (br. s., 2H), 1.16-0.94 (m, 4H). MS (ESI) m/z: 555.1 (M+H)$^+$.

Example 144

Methyl (10R,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2(7),3,5,15,17-hexaene-4-carboxylate

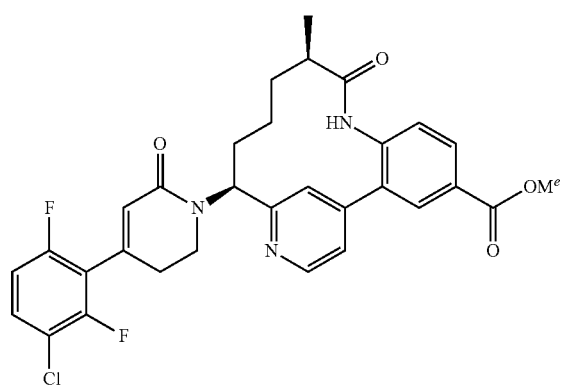 [SMILES: COC(=O)c1ccc2c(c1)-c1ccnc(c1)[C@@H](N1CCC(c3c(F)ccc(Cl)c3F)=CC1=O)CCC[C@@H](C)C(=O)N2]

Example 144 was prepared by following the procedures described in Example 1. $^1$H NMR (400 MHz, METHANOL-d4) δ 8.69 (d, J=4.8 Hz, 1H), 8.28-8.17 (m, 1H), 8.09 (dd, J=8.3, 2.1 Hz, 1H), 7.68-7.30 (m, 4H), 7.08 (td, J=9.2, 1.8 Hz, 1H), 6.09 (s, 1H), 5.68 (dd, J=12.5, 4.6 Hz, 1H), 4.22-4.03 (m, 1H), 3.94 (s, 3H), 3.80 (ddd, J=12.8, 9.1, 5.6 Hz, 1H), 2.84-2.54 (m, 3H), 2.23-2.09 (m, 1H), 2.00-1.69 (m, 2H), 1.66-1.43 (m, 1H), 1.40-1.21 (m, 1H), 1.05-0.92 (m, 3H), 0.78 (br. s., 1H). MS (ESI) m/z: 580.3 (M+H)$^+$. Analytical HPLC (method A): RT=7.7 min. purity=98%.

Example 145

(10R,14S)-14-[4-(3-chloro-2,6-difluorophenyl)-6-oxo-1,2,3,6-tetrahydropyridin-1-yl]-4-fluoro-10-methyl-8,16-diazatricyclo[13.3.1.0$^{2,7}$]nonadeca-1(19),2(7),3,5,15,17-hexaen-9-one

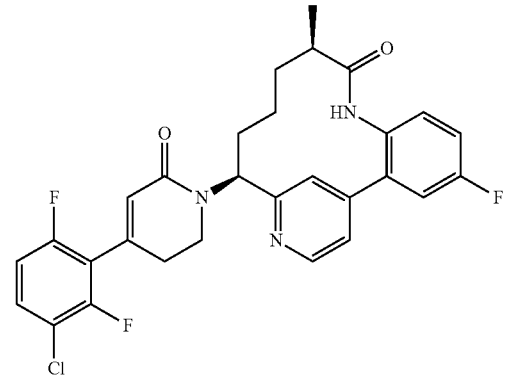 [SMILES: C[C@@H]1CCC[C@H](N2CCC(c3c(F)ccc(Cl)c3F)=CC2=O)c2cc(ccn2)-c2cc(F)ccc2NC1=O]

Example 145 was prepared by following the procedures described in Example 1. $^1$H NMR (400 MHz, METHANOL-$d_4$) δ 8.81 (d, J=5.9 Hz, 1H), 8.06 (d, J=1.5 Hz, 1H), 7.86 (dd, J=5.7, 1.8 Hz, 1H), 7.59-7.49 (m, 2H), 7.40-7.30 (m, 2H), 7.09 (td, J=9.2, 1.8 Hz, 1H), 6.10 (s, 1H), 5.43 (dd, J=12.3, 4.6 Hz, 1H), 3.88-3.66 (m, 2H), 2.90-2.68 (m, 2H), 2.66-2.54 (m, 1H), 2.40-2.19 (m, 1H), 2.14-2.01 (m, 1H), 1.94-1.82 (m, 1H), 1.65-1.50 (m, 1H), 1.27 (br. s., 1H), 1.04 (d, J=6.8 Hz, 3H), 0.99 (br. s., 1H). MS (ESI) m/z: 540.3 (M+H)$^+$. Analytical HPLC (method A): RT=7.7 min, purity=97%.

Example 146

(10R,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2(7),3,5,15,17-hexaene-4-carboxylic acid

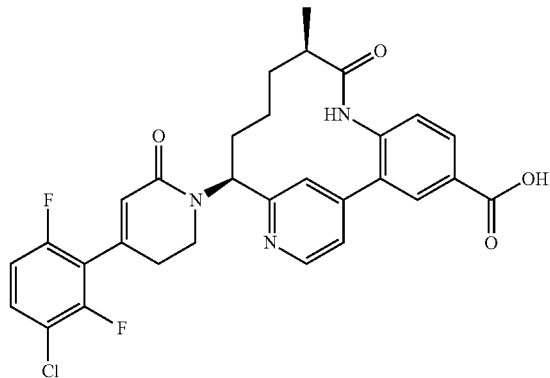 [SMILES: C[C@@H]1CCC[C@H](N2CCC(c3c(F)ccc(Cl)c3F)=CC2=O)c2cc(ccn2)-c2cc(C(=O)O)ccc2NC1=O]

Example 146

Example 144 (25 mg, 0.043 mmol) in MeOH (1 mL) was added lithium hydroxide (0.129 mL, 0.259 mmol). The reaction was stirred at rt overnight. The reaction was concentrated. CH$_3$CN/DMF was added and a drop of TFA was added. Purification by prepHPLC to afford Example 146. $^1$H NMR (400 MHz, ACETONITRILE-$d_3$) δ 8.81 (d, J=5.7 Hz, 1H), 8.61 (s, 1H), 8.21 (d, J=2.0 Hz, 1H), 8.14 (dd, J=8.1, 2.0 Hz, 1H), 8.01 (d, J=1.3 Hz, 1H), 7.82 (dd, J=5.7, 1.5 Hz, 1H), 7.63-7.47 (m, 1H), 7.37 (d, J=8.4 Hz, 1H), 7.10 (td, J=9.2, 1.8 Hz, 1H), 6.14 (s, 1H), 5.20 (dd, J=12.3, 5.5 Hz, 1H), 4.06-3.92 (m, 1H), 3.77 (ddd, J=12.4, 9.1, 5.5 Hz, 1H), 2.99-2.79 (m, 1H), 2.78-2.59 (m, 2H), 2.52-2.36 (m, 1H), 1.91-1.74 (m, 1H), 1.66-1.52 (m, 1H), 1.51-1.37 (m, 1H), 0.94 (d, J=6.8 Hz, 3H), 0.49 (d, J=9.0 Hz, 1H). MS (ESI) m/z: 566.3 (M+H)$^+$. Analytical HPLC (method A): RT=6.6 min, purity=90%.

Example 147

(10R,14S)-14-[4-(6-bromo-3-chloro-2-fluorophenyl)-6-oxo-1,2,3,6-tetrahydropyridin-1-yl]-4-fluoro-10-methyl-8,16-diazatricyclo[13.3.1.0$^{2,7}$]nonadeca-1(19),2(7),3,5,15,17-hexaen-9-one

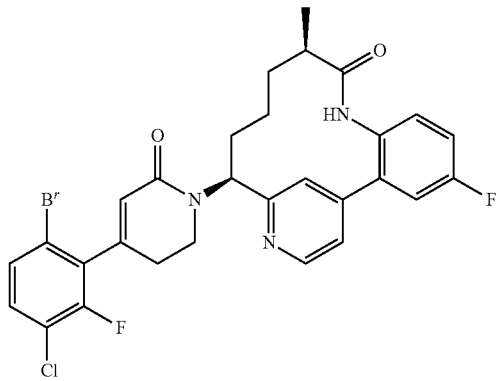 [SMILES: C[C@@H]1CCC[C@H](N2CCC(c3c(Br)ccc(Cl)c3F)=CC2=O)c2cc(ccn2)-c2cc(F)ccc2NC1=O]

Example 147 was prepared by following the procedures described in Example 1. $^1$H NMR (400 MHz, CHLOROFORM-d) δ 8.67-8.32 (m, 2H), 7.40-7.25 (m, 2H), 7.24-7.13 (m, 1H), 7.03 (dd, J=5.1, 1.3 Hz, 1H), 6.97-6.72 (m, 3H), 5.96 (s, 1H), 5.85-5.61 (m, 1H), 4.37-4.16 (m, 1H), 3.78 (ddd, J=12.4, 9.8, 5.1 Hz, 1H), 2.75-2.40 (m, 3H), 2.06 (t, J=12.7 Hz, 1H), 1.97-1.58 (m, 3H), 1.49-1.08 (m, 3H), 0.94-0.84 (m, 3H), 0.41 (br. s., 1H). MS (ESI) m/z: 602.2 (M+H)$^+$. Analytical HPLC (method A): RT=8.4 min, purity=96%.

Example 148

(10R,14S)-14-[4-(3-chloro-2,6-difluorophenyl)-6-oxo-1,2,3,6-tetrahydropyridin-1-yl]-4-(hydroxymethyl)-10-methyl-8,16-diazatricyclo[13.3.1.0$^{2,7}$]nonadeca-1(19),2(7),3,5,15,17-hexaen-9-one

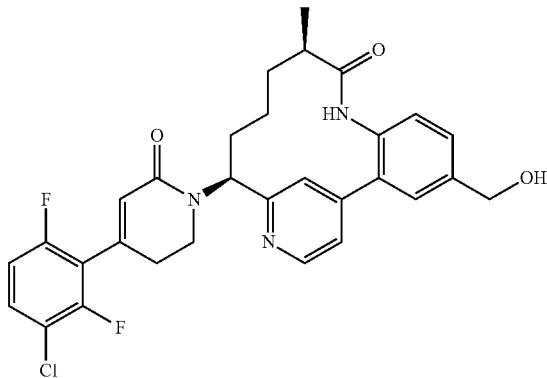 [SMILES: C[C@@H]1CCC[C@H](N2CCC(c3c(F)ccc(Cl)c3F)=CC2=O)c2cc(ccn2)-c2cc(CO)ccc2NC1=O]

Example 148

To a suspension of Example 146 (9.15 mg, 0.013 mmol) and BOP (14.88 mg, 0.034 mmol) in THF (1 mL) was added DIPEA (0.012 mL, 0.067 mmol). The clear colorless solution was stirred at rt for 30 min, NaBH$_4$ (6 mg, 0.159 mmol)

was added. After 1 h, the reaction was concentrated and redissolved in MeOH with a drop of TFA. Purification by prepHPLC to afford Example 148 (5.3 mg, 56%). ¹H NMR (400 MHz, METHANOL-d₄) δ 8.76 (d, J=5.7 Hz, 1H), 7.94 (d, J=1.1 Hz, 1H), 7.74 (dd, J=5.6, 1.7 Hz, 1H), 7.67 (d, J=1.8 Hz, 1H), 7.57-7.49 (m, 2H), 7.30 (d, J=7.9 Hz, 1H), 7.09 (td, J=9.2, 1.8 Hz, 1H), 6.10 (s, 1H), 5.53-5.44 (m, 1H), 4.71 (s, 2H), 3.89-3.67 (m, 2H), 2.85-2.54 (m, 3H), 2.26 (ddt, J=16.0, 12.8, 3.3 Hz, 1H), 2.07-1.84 (m, 2H), 1.65-1.50 (m, 1H), 1.37-1.22 (m, 1H), 1.04 (d, J=6.8 Hz, 3H), 1.01-0.91 (m, 1H). MS (ESI) m/z: 552.3 (M+H)⁺. Analytical HPLC (method A): RT=6.1 min, purity=94%.

Example 149

(10R,14S)-14-[4-(3-chloro-2,6-difluorophenyl)-6-oxo-1,2,3,6-tetrahydropyridin-1-yl]-5-(hydroxymethyl)-10-methyl-8,16-diazatricyclo[13.3.1.0²,⁷]nonadeca-1(19),2(7),3,5,15,17-hexaen-9-one

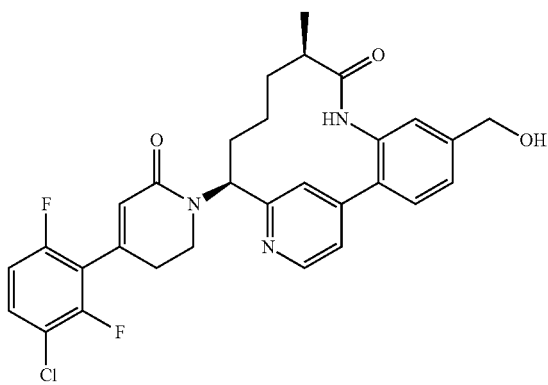 [SMILES: C[C@@H]1CCC[C@H](N2CCC(c3c(F)ccc(Cl)c3F)=CC2=O)c2cc(ccn2)-c2ccc(CO)cc2NC1=O]

Example 149 was prepared by following the procedures described in Example 148 by using Example 105 as starting material instead. ¹H NMR (400 MHz, METHANOL-d₄) δ 8.79 (d, J=5.7 Hz, 1H), 8.06 (d, J=1.1 Hz, 1H), 7.86 (dd, J=5.8, 1.7 Hz, 1H), 7.72 (d, J=7.9 Hz, 1H), 7.61-7.51 (m, 2H), 7.36 (d, J=1.3 Hz, 1H), 7.12 (td, J=9.2, 1.8 Hz, 1H), 6.13 (s, 1H), 5.47 (dd, J=12.5, 4.6 Hz, 1H), 4.73 (s, 2H), 3.85-3.70 (m, 2H), 2.92-2.58 (m, 3H), 2.30 (ddd, J=16.2, 10.0, 3.1 Hz, 1H), 2.16-2.02 (m, 1H), 1.99-1.87 (m, 1H), 1.69-1.56 (m, 1H), 1.32 (d, J=5.5 Hz, 1H), 1.08 (d, J=7.0 Hz, 3H), 1.05-0.94 (m, 1H). MS (ESI) m/z: 551.9 (M+H)⁺. Analytical HPLC (method A): RT=6.2 min, purity=85%.

Example 150

4-chloro-3-fluoro-2-{1-[(10R,14S)-4-fluoro-10-methyl-9-oxo-8,16-diazatricyclo[13.3.1.0²,⁷]nonadeca-1(19),2(7),3,5,15,17-hexaen-14-yl]-6-oxo-1,2,3,6-tetrahydropyridin-4-yl}benzonitrile

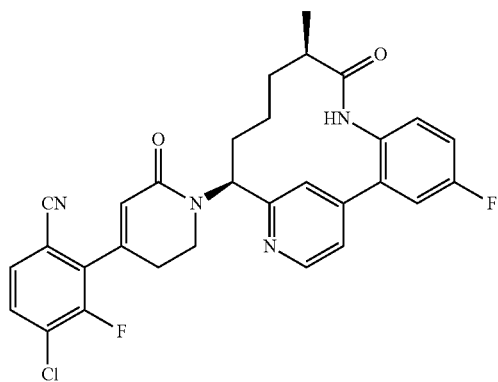 [SMILES: C[C@@H]1CCC[C@H](N2CCC(c3c(C#N)ccc(Cl)c3F)=CC2=O)c2cc(ccn2)-c2cc(F)ccc2NC1=O]

Example 150

Example 147 (24 mg, 0.040 mmol) in a vial was added dicyanozinc (4.69 mg, 0.040 mmol), Zn (0.783 mg, 0.012 mmol), DMF (1997 µl) bubbled through Ar for several minutes. Bis(tri-t-butylphosphine)palladium(0) (2.041 mg, 3.99 µmol) was added. The reaction was sealed and heated at 80° C. for 18 hrs. The reaction was recapped (did not degas) and heated at 80° C. overnight. Purification by prepHPLC to afford Example 150(5.3 mg, 56%). ¹H NMR (400 MHz, METHANOL-d₄) δ 8.82 (d, J=5.7 Hz, 1H), 8.02 (d, J=1.1 Hz, 1H), 7.81 (dd, J=5.6, 1.7 Hz, 1H), 7.77-7.65 (m, 2H), 7.54 (dd, J=8.7, 2.5 Hz, 1H), 7.43-7.31 (m, 2H), 6.20 (s, 1H), 5.59-5.48 (m, 1H), 3.98-3.75 (m, 2H), 2.97-2.73 (m, 2H), 2.69-2.56 (m, 1H), 2.37-2.22 (m, 1H), 2.15-2.01 (m, 1H), 1.99-1.85 (m, 1H), 1.68-1.53 (m, 1H), 1.39-1.23 (m, 1H), 1.07 (d, J=6.8 Hz, 3H), 1.02 (br. s., 1H). MS (ESI) m/z: 547.3 (M+H)⁺. Analytical HPLC (method A): RT=7.3 min, purity=99%

Example 151

Methyl N-[(10R,14S)-14-[4-(3-chloro-2-fluorophenyl)-6-oxo-1,2,3,6-tetrahydropyridin-1-yl]-10,17-dimethyl-9-oxo-8,16,18-triazatricyclo[13.2.1.0²,⁷]octadeca-1(17),2,4,6,15(18)-pentaen-5-yl]carbamate

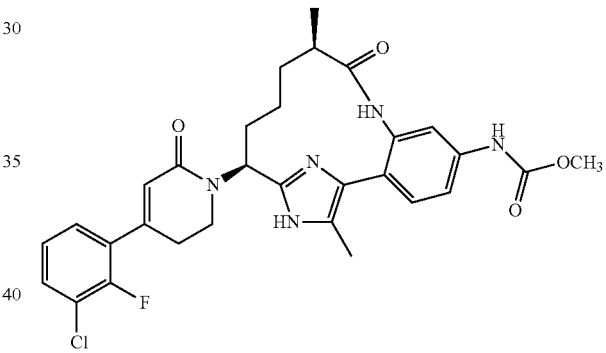

151 A tert-Butyl N-[(10R,14S)-17-bromo-5-[(methoxycarbonyl)amino]-10-methyl-9-oxo-16-{[2-(trimethylsilyl)ethoxy]methyl}-8,16,18-triazatricyclo[13.2.1.0²,⁷]octadeca-1(17),2,4,6,15(18)-pentaen-14-yl]carbamate To a round bottom flask was added 135H (1320 mg, 2.246 mmol) and CHCl₃ (100 mL). The reaction was cooled to 0° C. before NBS (400 mg, 2.246 mmol) was added to the reaction. The reaction was stirred at 0° C. for 20 min. LCMS showed the reaction was completed. The reaction was concentrated and the crude product was purified using ISCO system (0-100% EtOAc/Hex) to give 151A an off-white solid. MS (ESI) m/z: 666.3 (M+H)⁺.

151B tert-Butyl N-[(10R,14S)-5-[(methoxycarbonyl)amino]-10,17-dimethyl-9-oxo-16-{[2-(trimethylsilyl)ethoxy]methyl}-8,16,18-triazatricyclo[13.2.1.0²,⁷]octadeca-1(17),2,4,6,15(18)-pentaen-14-yl]carbamate To a microwave vial was added 151A (300 mg, 0.450 mmol), PdCl₂(dppf)-CH₂Cl₂ adduct (73.5 mg, 0.090 mmol)

methylboronic acid (404 mg, 6.75 mmol) and Dioxane (15 mL). The reaction was purged with argon and then sealed. The reaction was then stirred at 150° C. in a microwave oven for 15 mins. The reaction was cooled and partitioned between EtOAc (15 mL) and water (15 mL). The organic layer was separated, washed with saturated NaCl solution (10 mL), dried over MgSO$_4$, filtered and concentrated. The residue was purified using ISCO system (0-100% EtOAc/Hex) to give 151B (175 mg, 0.291 mmol, 64.6% yield) as an off-white solid. MS (ESI) m/z: 602.5 (M+H)$^+$. $^1$H NMR (400 MHz, METHANOL-d$_4$) δ 7.51 (s, 1H), 7.39 (d, J=0.9 Hz, 2H), 5.58-5.47 (m, 2H), 4.97 (br. s., 1H), 3.74-3.62 (m, 5H), 2.63 (br. s., 1H), 2.35 (s, 3H), 1.99 (br. s., 2H), 1.52 (d, J=11.7 Hz, 2H), 1.43-1.24 (m, 10H), 0.98-0.89 (m, 5H), 0.80-0.57 (m, 1H), 0.03 (m, 9H).

151C: Methyl N-[(10R,14S)-14-amino-10,17-dimethyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-5-yl]carbamate, di-TFA Salt To a round bottom flask was added 151B (140 mg, 0.233 mmol), CH$_2$Cl$_2$ (2 mL) and TFA (0.5 mL). The reaction was stirred at rt for 1 hr. The reaction concentrated to give 151C (178 mg, 0.247 mmol, 100% yield) as a beige solid. MS (ESI) m/z: 502.3 (M+H)$^+$.

151D: Methyl N-[(10R,14S)-14-{N-[3-(3-chloro-2-fluorophenyl)-3-oxopropyl]-2-(diethoxyphosphoryl)acetamido}-10,17-dimethyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-5-yl]carbamate To a round bottom flask was added 151C (50 mg, 0.069 mmol), CH$_2$Cl$_2$ (2 mL) and TEA (0.067 mL, 0.480 mmol). The reaction was stirred for 30 mins before intermediate 1 (12.65 mg, 0.069 mmol) was added into the reaction. The reaction was monitored until SM was all reacted. Then 2-(diethoxyphosphoryl)acetic acid (40.3 mg, 0.206 mmol) and 2,4,6-tripropyl-1,3,5,2,4,6-trioxatriphosphorinane-2,4,6-trioxide (131 mg, 0.206 mmol) was added to the reaction and the reaction was stirred at rt for 30 min. The reaction was then partitioned between EtOAc (30 mL) and water (20 mL). The organic layer was separated, washed with saturated NaCl solution (10 mL), dried over MgSO$_4$, filtered and concentrated. The residue was purified using ISCO system (0-100% EtOAc/Hex) to give 151D (35 mg, 0.040 mmol, 59.1% yield) as an off-white solid. MS (ESI) m/z: 686.4 (M+H)$^+$.

151E: Methyl N-[(10R,14S)-14-[4-(3-chloro-2-fluorophenyl)-6-oxo-1,2,3,6-tetrahydropyridin-1-yl]-10,17-dimethyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-5-yl]carbamate To a round bottom flask was added 151D (35 mg, 0.040 mmol) and MeOH (2 mL). The reaction was cooled to 0° C. and sodium methoxide (26.2 mg, 0.121 mmol) was added to the reaction. The reaction was stirred at 0° C. for 10 min. Then the reaction was quenched by 1N HCl (0.081 mL, 0.081 mmol). The reaction was then partitioned between EtOAc (25 mL) and NaHCO$_3$ (10 mL). The organic layer was separated, washed with saturated NaCl solution (10 mL), dried over MgSO$_4$, filtered and concentrated to give methyl 151E (22 mg, 0.031 mmol, 76% yield) as a white solid. MS (ESI) m/z: 710.3 (M+H)$^+$.

Example 151

To a sealed tube was added 151E (20 mg, 0.028 mmol) and 4N HCl (0.704 mL, 2.82 mmol) in dixoane. The reaction was sealed and stirred at 60° C. for 3 hrs. The reaction was then concentrated and purified using prep-HPLC to give a white solid (10.6 mg, 0.015 mmol, 51.5% yield). MS (ESI) m/z: 580.3 (M+H)$^+$. $^1$H NMR (400 MHz, METHANOL-d$_4$) δ 7.62 (s, 1H), 7.60-7.54 (m, 1H), 7.51-7.43 (m, 3H), 7.28 (td, J=7.9, 0.9 Hz, 1H), 6.24 (s, 1H), 5.54 (dd, J=11.7, 6.2 Hz, 1H), 3.92-3.81 (m, 2H), 3.79 (s, 3H), 3.10-2.88 (m, 2H), 2.73 (d, J=5.5 Hz, 1H), 2.45-2.38 (m, 3H), 2.35-2.23 (m, 1H), 2.19-2.03 (m, 1H), 1.83-1.71 (m, 1H), 1.68-1.47 (m, 2H), 1.12-1.03 (m, 3H), 0.97-0.83 (m, 1H). Analytical HPLC (method A): RT=9.54 min, purity=95%.

Example 152

Methyl N-[(15S)-15-[4-(3-chloro-2,6-difluorophenyl)-6-oxo-1,2,3,6-tetrahydropyridin-1-yl]-8-oxo-9,17-diazatricyclo[14.3.1.0$^{2,7}$]icosa-1(20),2(7),3,5,16,18-hexaen-5-yl]carbamate, TFA Salt

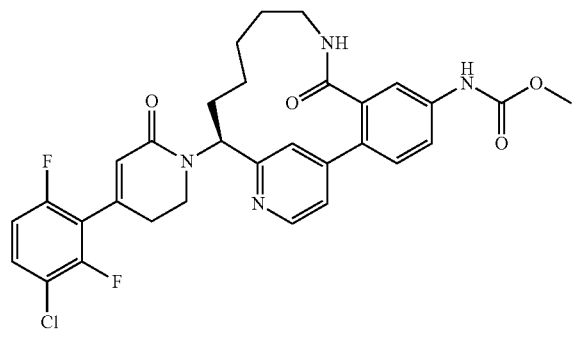 [SMILES: COC(=O)Nc1ccc2c(c1)C(=O)NCCCCC[C@H](N1CCC(c3c(F)ccc(Cl)c3F)=CC1=O)c1cc-2ccn1]

Example 152 was prepared using a procedure analogous to Example 24, by replacing prop-2-en-1-amine with but-3-en-1-amine in step 24E. $^1$H NMR (500 MHz, METHANOL-d$_4$) δ 8.73 (d, J=5.8 Hz, 1H), 7.83 (dd, J=5.8, 1.7 Hz, 1H), 7.78 (d, J=2.2 Hz, 1H), 7.71-7.65 (m, 2H), 7.59 (d, J=8.5 Hz, 1H), 7.56-7.51 (m, 1H), 7.10 (td, J=9.2, 1.7 Hz, 1H), 6.09 (s, 1H), 5.48 (dd, J=11.7, 3.2 Hz, 1H), 3.78 (s, 3H), 3.75-3.60 (m, 3H), 3.35-3.27 (m, 1H), 2.84-2.70 (m, 2H), 2.30-2.20 (m, 1H), 2.10-2.01 (m, 1H), 1.82-1.64 (m, 2H), 1.55-1.22 (m, 4H). MS (ESI) m/z: 595.2 (M+H)$^+$. Analytical HPLC (method A): RT=6.74 min, purity=98.9%.

Example 153 (Isomer 3)

Methyl N-[(10R,14S)-10-methyl-14-[4-(3-methylcyclohexyl)-6-oxo-1,2,3,6-tetrahydropyridin-1-yl]-9-oxo-8,16-diazatricyclo[13.3.1.0$^{2,7}$]nonadeca-1(19),2,4,6,15,17-hexaen-5-yl]carbamate, TFA Salt

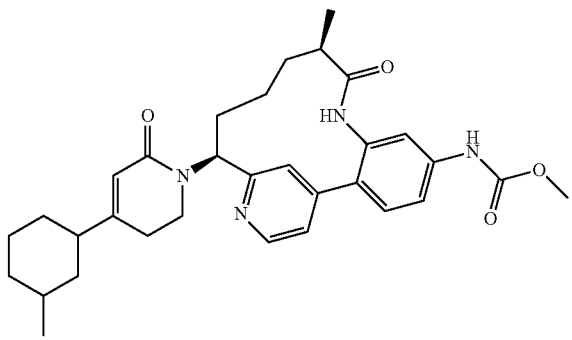 [SMILES: COC(=O)Nc1ccc2c(c1)NC(=O)[C@H](C)CCC[C@H](N1CCC(C3CCCC(C)C3)=CC1=O)c1cc-2ccn1]

Example 153

Example 159 was separated by preparative chiral chromatographic method (Instrument: Burger Multigram II SFC. Column: Chiralpak IB, 30×250 mm, 5 micron. Mobile Phase: 30% MeOH/70% CO$_2$. Flow Conditions: 85 mL/min, 150 Bar, 40° C. Detector Wavelength: 220 nm. Injection Details: 0.75 mL of ~8 mg/mL in MeOH). 4 isomers were obtained.

Example 153 (Isomer 3)

MS (ESI) m/z: 545.35 (M+H)$^+$. Analytical HPLC (method C): RT=2.01 min, purity=79.6%.

Example 154

Methyl N-[(10R,14S)-14-[4-(2-aminopyridin-4-yl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate, 2 TFA Salt

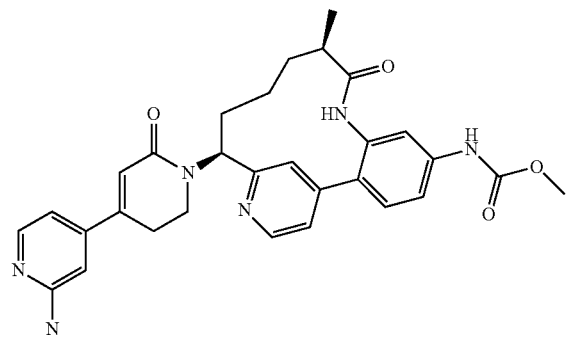 [SMILES: COC(=O)Nc1ccc2c(c1)NC(=O)[C@H](C)CCC[C@H](N1CCC(c3ccnc(N)c3)=CC1=O)c1cc-2ccn1]

154A. Tert-butyl N-(4-{1-[(10R,14S)-5-[(methoxycarbonyl)amino]-10-methyl-9-oxo-8,16-diazatricyclo[13.3.1.0$^{2,7}$]nonadeca-1(19),2,4,6,15,17-hexaen-14-yl]-6-oxo-1,2,3,6-tetrahydropyridin-4-yl}pyridin-2-yl)carbamate The title compound was prepared analogous to the procedures described in Example 1, by replacing Intermediate 3 with Intermediate 19 in step 1K. MS (ESI) m/z: 641.4 (M+H)$^+$.

Example 154

A solution of Example 154A (10 mg, 0.013 mmol) was stirred in 25% TFA in CH$_2$Cl$_2$ (1 ml) for 1 hr at r.t. The reaction was concentrated. Purification by reverse phase HPLC afforded Example 154 (5.9 mg, 56% yield) as a film. MS(ESI) m/z: 541.2 (M+H)$^+$. Analytical HPLC (method A): RT=3.06 min, purity=97%. $^1$H NMR (400 MHz, METHANOL-d$_4$) δ 9.54 (s, 1H), 8.64 (br. s., 1H), 7.83 (d, J=6.8 Hz, 1H), 7.77-7.65 (m, 1H), 7.60-7.42 (m, 4H), 7.15-7.04 (m, 2H), 6.49 (s, 1H), 5.63-5.50 (m, 1H), 3.92-3.79 (m, 1H), 3.76 (s, 3H), 3.74-3.67 (m, 1H), 2.80-2.74 (m, 2H), 2.63-2.55 (m, 1H), 2.25-2.15 (m, 1H), 1.96-1.86 (m, 2H), 1.61-1.51 (m, 1H), 1.32-1.21 (m, 1H), 1.05 (d, J=6.8 Hz, 3H)

Example 155

Methyl N-[(10R,14S)-10-methyl-9-oxo-14-[6-oxo-4-(piperidin-4-yl)-1,2,3,6-tetrahydropyridin-1-yl]-8,16-diazatricyclo[13.3.1.0$^{2,7}$]nonadeca-1(19),2,4,6,15,17-hexaen-5-yl]carbamate, 2 TFA Salt

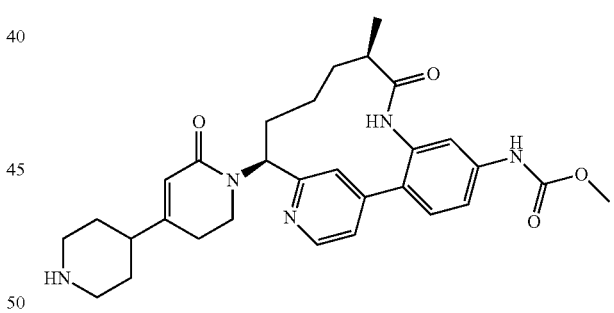

Example 155 was prepared by analogous procedures described in Example 1, by replacing Intermediate 3 with Intermediate 20 in step 1K, followed by the Boc-deprotection with TFA as described in Example 154. $^1$H NMR (500 MHz, DMSO-d$_6$) δ 9.43 (s, 1H), 9.31 (s, 1H), 8.57 (d, J=5.0 Hz, 1H), 8.46-8.34 (m, 1H), 8.14-8.03 (m, 1H), 7.54-7.49 (m, 2H), 7.48-7.43 (m, 1H), 7.38 (s, 1H), 7.27-7.24 (m, 1H), 5.60 (s, 1H), 5.55 (dd, J=12.5, 4.3 Hz, 1H), 3.81-3.75 (m, 1H), 3.73 (s, 3H) 3.59-3.49 (m, 1H), 3.38-3.31 (m, 2H), 3.0-2.91 (m, 2H), 2.46-2.36 (m, 1H), 2.32-1.27 (m, 1H), 2.08-1.99 (m, 1H), 1.96-1.90 (m, 2H), 1.89-1.81 (m, 1H), 1.74-1.54 (m, 3H), 1.44-1.35 (m, 1H), 1.28-1.18 (m, 1H), 0.95 (d, J=6.9 Hz, 3H), 0.88-0.77 (m, 1H). MS(ESI) m/z: 532.3 (M+H)$^+$. Analytical HPLC (method A): RT=2.84 min, purity=97%.

Example 156

Methyl N-[(10R,14S)-14-[4-(2-chloropyridin-4-yl)-6-oxo-1,2,3,6-tetrahydropyridin-1-yl]-10-methyl-9-oxo-8,16-diazatricyclo[13.3.1.0²,⁷]nonadeca-1(19),2,4,6,15,17-hexaen-5-yl]carbamate, 2 TFA Salt

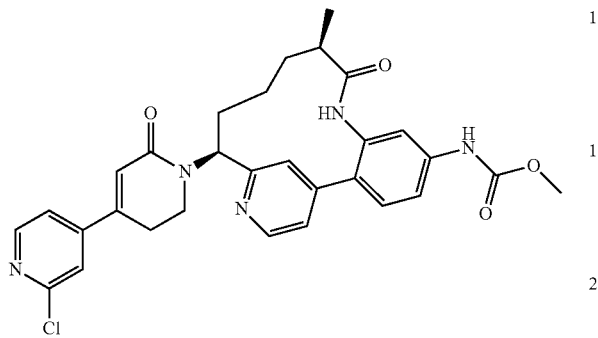

Example 156 was prepared by analogous procedures described in Example 1, by replacing Intermediate 3 with Intermediate 21 in step 1K. ¹H NMR (500 MHz, DMSO-d₆) δ 9.90 (s, 1H), 9.71 (s, 1H), 8.61 (d, J=5.2 Hz, 1H), 8.45 (d, J=5.2 Hz, 1H), 7.74 (d, J=1.1 Hz, 1H), 7.64 (dd, J=5.4, 1.5 Hz, 1H), 7.51 (s, 3H), 7.38 (s, 1H), 7.34-7.27 (m, 1H), 6.53 (s, 1H), 5.60 (dd, J=12.7, 4.4 Hz, 1H), 4.03-3.93 (m, 1H), 3.71 (s, 3H), 3.70-3.65 (m, 1H), 2.80-2.69 (m, 2H), 2.622.56 (m, 1H), 2.12-1.98 (m, 1H), 1.96-1.88 (m, 1H), 1.75-1.58 (m, 1H), 1.49-1.38 (m, 1H), 1.28-1.17 (m, 1H), 0.89 (d, J=6.9 Hz, 3H), 0.65-0.45 (m, 1H). MS (ESI) m/z: 560.3 (M+H)⁺. Analytical HPLC (method C): RT=1.42 min, purity=95%.

Example 157

Methyl N-[(10R,14S)-14-[4-(6-chloropyridin-2-yl)-6-oxo-1,2,3,6-tetrahydropyridin-1-yl]-10-methyl-9-oxo-8,16-diazatricyclo[13.3.1.0²,⁷]nonadeca-1(19),2,4,6,15,17-hexaen-5-yl]carbamate, 2 TFA Salt

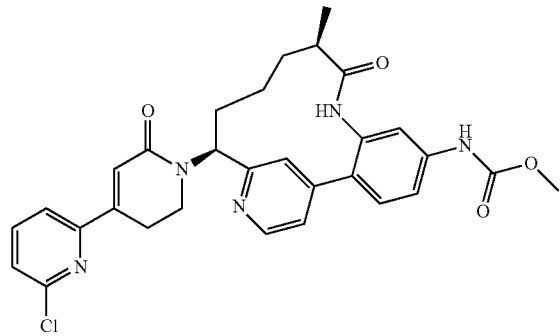 [SMILES: COC(=O)Nc1ccc2c(c1)NC(=O)[C@H](C)CCC[C@H](N1CCC(c3cccc(Cl)n3)=CC1=O)c1cc-2ccn1]

Example 157 was prepared by analogous procedures described in Example 1, by replacing Intermediate 3 with Intermediate 22 in step 1K. ¹H NMR (500 MHz, DMSO-d₆) δ 9.95 (s, 1H), 9.78 (s, 1H), 8.67 (d, J=4.4 Hz, 1H), 8.00-7.90 (m, 1H), 7.90-7.84 (m, 1H), 7.64 (br. s., 1H), 7.59-7.50 (m, 3H), 7.46 (br. s., 1H), 7.41 (s, 1H), 6.65 (s, 1H), 5.62-5.47 (m, 1H), 4.01-3.87 (m, 1H), 3.80-3.62 (m, 4H), 2.96-2.83 (m, 1H), 2.83-2.71 (m, 1H), 2.65-2.55 (m, 1H), 2.15-2.04 (m, 1H), 1.96-1.86 (m, 1H), 1.79-1.65 (m, 1H), 1.511.41 (m, 1H), 1.30-1.19 (m, 1H), 0.90 (d, J=6.6 Hz, 3H), 0.67-0.52 (m, 1H). MS (ESI) m/z: 560.3 (M+H)⁺. Analytical HPLC (method C): RT=1.65 min, purity=99%.

Example 158

Methyl N-[(10R,14S)-10-methyl-14-[4-(1-methylpiperidin-2-yl)-6-oxo-1,2,3,6-tetrahydropyridin-1-yl]-9-oxo-8,16-diazatricyclo[13.3.1.0²,⁷]nonadeca-1(19),2,4,6,15,17-hexaen-5-yl]carbamate, 2 TFA Salt

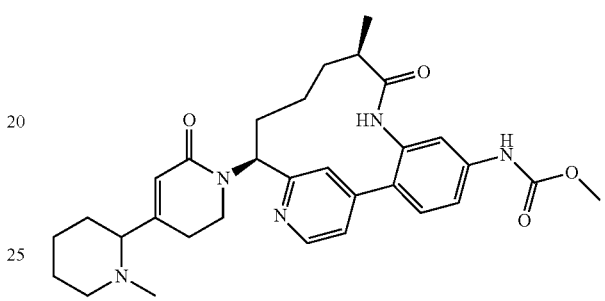

158A. Tert-butyl 2-{1-[(10R,14S)-5-[(methoxycarbonyl)amino]-10-methyl-9-oxo-8,16-diazatricyclo[13.3.1.0²,⁷]nonadeca-1(19),2,4,6,15,17-hexaen-14-yl]-6-oxo-1,2,3,6-tetrahydropyridin-4-yl}piperidine-1-carboxylate The title compound was prepared by analogous procedures described in Example 1, by replacing Intermediate 3 with Intermediate 23 in step 1K. MS (ESI) m/z: 632.3 (M+H)⁺.

158B. Methyl N-[(10R,14S)-10-methyl-9-oxo-14-[6-oxo-4-(piperidin-2-yl)-1,2,3,6-tetrahydropyridin-1-yl]-8,16-diazatricyclo[13.3.1.0²,⁷]nonadeca-1(19),2,4,6,15,17-hexaen-5-yl]carbamate, 2 TFA A solution of 158A (12 mg, 0.016 mmol) was stirred in 50% TFA in CH₂Cl₂ (1 ml). After 1.5h the reaction was concentrated. Purification by reverse phase HPLC afforded Example 158B (11.9 mg, 96% yield) as a white solid. MS(ESI) m/z: 532.3 (M+H)⁺.

Example 158

158B (9 mg, 0.012 mmol) was dissolved in methanol (1.5 mL). Formaldehyde (2 μl, 0.073 mmol) was added and the mixture was stirred for 30 min. Sodium cyanoborohydride (3 mg, 0.048 mmol) was added and the reaction was stirred at rt overnight. The reaction was quenched with water then purified by reverse phase HPLC to afford Example 158 (6.56 mg, 71% yield) as a white amorphous solid. ¹H NMR (400 MHz, METHANOL-d₄) δ 9.55 (s, 1H), 8.86-8.54 (m, 1H), 7.87-7.68 (m, 1H), 7.63-7.43 (m, 4H), 6.08 (s, 1H), 5.58-5.43 (m, 1H), 3.76 (m, 5H), 3.71-3.54 (m, 2H), 3.16-2.99 (m, 1H), (2.80 (s, 1.5H), 2.78 (s, 1.5H)), 2.64-2.31 (m, 3H), 2.22-2.08 (m, 1H), 1.96 (m., 7H), 1.69-1.45 (m, 2H), 1.37-1.15 (m, 2H), 1.05 (m 4H) (~1:1 mixture of diastereomers).

MS (ESI) m/z: 546.3 (M+H)⁺. Analytical HPLC (method A): RT=3.30 min, purity=99%.

Example 159

Methyl N-[(10R,14S)-10-methyl-14-[4-(3-methylcyclohexyl)-6-oxo-1,2,3,6-tetrahydropyridin-1-yl]-9-oxo-8,16-diazatricyclo[13.3.1.0²,⁷]nonadeca-1(19),2,4,6,15,17-hexaen-5-yl]carbamate, TFA Salt (Diastereomeric Isomers)

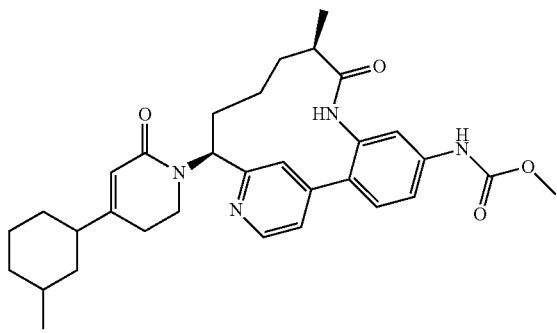 [SMILES: COC(=O)Nc1ccc2c(c1)NC(=O)[C@H](C)CCC[C@H](N1CCC(C3CCCC(C)C3)=CC1=O)c1cc-2ccn1]

Example 159 was prepared by analogous the procedures described in Example 1, by replacing Intermediate 3 with Intermediate 24 in step 1K. ¹H NMR (500 MHz, DMSO-d₆) δ 9.90 (br. s., 1H), 9.71 (br. s., 1H), 8.60 (br. s., 1H), 7.57-7.45 (m, 3H), 7.40-7.27 (m, 2H), 5.61-5.43 (m, 2H), 3.83-3.74 (m, 1H), 3.71 (br. s., 3H), 2.62-2.55 (m, 1H), 2.33-2.19 (m, 2H), 2.13-1.96 (m, 2H), 1.94-1.84 (m, 1H), 1.79-1.53 (m, 5H), 1.47-1.36 (m, 2H), 1.35-1.25 (m, 1H), 1.24-1.14 (m, 1H), 1.11-0.99 (m, 1H), 0.93-0.75 (m, 8H), 0.63-0.42 (m, 1H) as a mixture of 4 diastereomers. MS (ESI) m/z: 545.35 (M+H)⁺. Analytical HPLC (method C): RT=2.06-2.08 min, purity=98%.

Example 160

Methyl N-[(10R,14S)-14-[4-(3-chloro-2,6-difluorophenyl)-6-oxo-1,2,3,6-tetrahydropyridin-1-yl]-10,17-dimethyl-9-oxo-8,16,18-triazatricyclo[13.2.1.0²,⁷]octadeca-1(17),2,4,6,15(18)-pentaen-5-yl]carbamate, TFA Salt

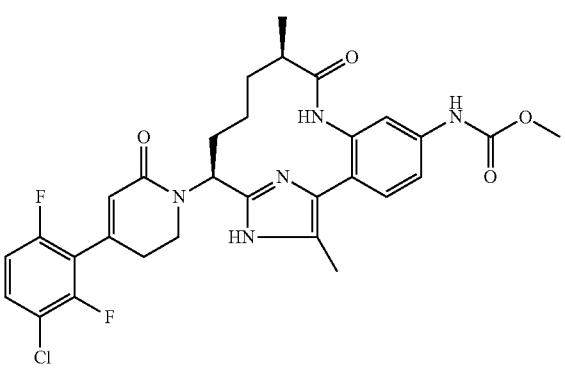 [SMILES: COC(=O)Nc1ccc2c(c1)NC(=O)[C@H](C)CCC[C@H](N1CCC(c3c(F)ccc(Cl)c3F)=CC1=O)c1nc-2c(C)[nH]1]

Example 160 was prepared analogous to the procedures described in Example 151, by replacing 1-(3-Chloro-2-fluorophenyl)prop-2-en-1-one with Intermediate 1 in step 151D. Purification by reverse phase HPLC afforded Example 160 (2.4 mg, 70% yield) as a white solid. MS(ESI) m/z: 559.2 (M+H)⁺. Analytical HPLC (method A): RT=6.27 min, purity=98%. ¹H NMR (400 MHz, METHANOL-d₄) δ 9.58 (s, 1H), 7.65-7.51 (m, 3H), 7.49-7.38 (m, 3H), 7.12 (td, J=9.2, 2.0 Hz, 1H), 6.11 (s, 1H), 5.51 (dd, J=11.6, 6.1 Hz, 1H), 3.93-3.79 (m, 2H), 3.76 (s, 3H), 3.02-2.88 (m, 1H), 2.84 (m, 1H), 2.74-2.62 (m, 1H), 2.38 (s, 3H), 2.30-2.18 (m, 1H), 2.15-2.00 (m, 1H), 1.82-1.64 (m, 1H), 1.63-1.42 (m, 2H), 1.04 (d, J=7.0 Hz, 3H), 0.96-0.74 (m, 1H). ¹⁹F NMR (376 MHz, METHANOL-d₄) δ −113.89 (s, 1F), −114.36 (s, 1F)

Example 161

Methyl N-[(10R,14S)-14-[4-(6-bromo-3-chloro-2-fluorophenyl)-6-oxo-1,2,3,6-tetrahydropyridin-1-yl]-10-methyl-9-oxo-8-azatricyclo[13.3.1.0²,⁷]nonadeca-1(19),2,4,6,15,17-hexaen-5-yl]carbamate

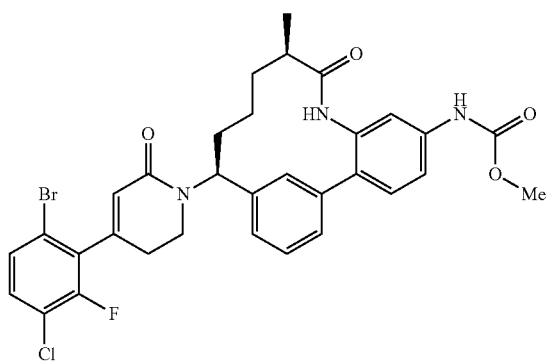 [SMILES: COC(=O)Nc1ccc2c(c1)NC(=O)[C@H](C)CCC[C@H](N1CCC(c3c(Br)ccc(Cl)c3F)=CC1=O)c1cccc-2c1]

161A (R)—N-[(1E)-(3-bromophenyl)methylidene]-2-methylpropane-2-sulfinamide

To a mixture of (R)-2-methylpropane-2-sulfinamide (2.4326 g, 20.07 mmol) and Cs₂CO₃ (9.81 g, 30.1 mmol) in DCM (50 mL) was added dropwise a solution of 3-bromobenzaldehyde (4.08 g, 22.08 mmol) in DCM (50 mL) over 10 min and the mixture stirred at ambient temperature for overnight. The reaction mixture was filtered through celite and the filter pad washed with DCM then with EtOAc. Filtrate was dried over MgSO₄ and concentrated to give an oil which was purified by silica gel chromatography to give 161A (4.7626 g, 16.53 mmol, 82% yield) as an faint yellow colored oil. ¹H NMR (500 MHz, CDCl₃) δ 8.55 (s, 1H), 8.05 (t, J=1.8 Hz, 1H), 7.76 (dt, J=7.7, 1.2 Hz, 1H), 7.68-7.65 (m, 1H), 7.41-7.36 (m, 1H), 1.31-1.29 (m, 9H).

161B (R)—N—((S)-1-(3-Bromophenyl)but-3-en-1-yl)-2-methylpropane-2-sulfinamide To round bottomed flask equipped with a reflux condensor was charged 161A (2.4673 g, 8.56 mmol), allyl bromide (0.889 mL, 10.27 mmol) and THF (40 mL) to which was added indium (1.180 g, 10.27 mmol) and the mixture heated to 60° C. under nitrogen where it was stirred for overnight. The reaction mixture was quenched by addition of water (40 mL) and the mixture stirred for 15 min, diluted with EtOAc (30 mL), and the phases separated. The aqueous phase was extracted with EtOAc (2×) and the combined organics washed with brine, dried (Na₂SO₄), filtered and evaporated to give a faint yellow colored oil which was placed under vacuum for overnight to give 161B (3.18 g, 89%). $^1$H NMR (500 MHz, CDCl₃) δ 7.50 (t, J=1.8 Hz, 1H), 7.45-7.42 (m, 1H), 7.27-7.21 (m, 2H), 5.79-5.69 (m, 1H), 5.24-5.22 (m, 1H), 5.22-5.19 (m, 1H), 4.48 (ddd, J=8.1, 5.5, 2.1 Hz, 1H), 3.69 (s, 1H), 2.64-2.58 (m, 1H), 2.47 (dt, J=14.0, 8.4 Hz, 1H), 1.23 (s, 9H).

Example 161 was prepared by following the procedures described in Example 1 by replacing 1B with 161B in step 1C. $^1$H NMR (500 MHz, DMSO-d₆) δ 9.81 (br. s., 1H), 9.58 (s, 1H), 7.62-7.44 (m, 6H), 7.39-7.33 (m, 2H), 7.26 (d, J=7.4 Hz, 1H), 5.94 (s, 1H), 5.52 (d, J=12.9 Hz, 1H), 3.70 (s, 3H), 3.06 (d, J=6.1 Hz, 1H), 2.56 (s, 1H), 2.48 (d, J=7.7 Hz, 1H), 2.43-2.29 (m, 2H), 2.16-2.04 (m, 1H), 1.81-1.65 (m, 2H), 1.60-1.40 (m, 2H), 1.04 (d, J=6.1 Hz, 3H), 1.01-0.96 (m, 1H). MS (ESI) m/z: 654/656 Br/Cl pattern (M+H)⁺. Analytical HPLC (method C): RT=2.022 min., purity 100%.

Example 162

(10R,14S)-14-[4-(3-chloro-2,6-difluorophenyl)-6-oxo-1,2,3,6-tetrahydropyridin-1-yl]-10-methyl-8-azatricyclo[13.3.1.0$^{2,7}$]nonadeca-1(19),2,4,6,15,17-hexaen-9-one

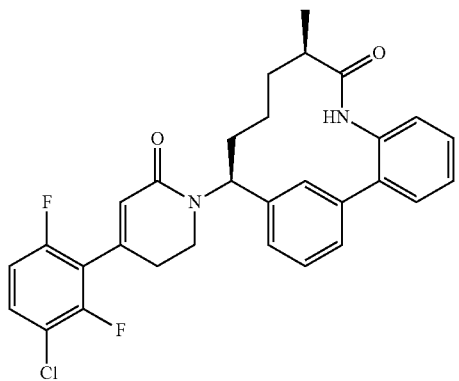 [SMILES: C[C@@H]1CCC[C@H](N2CCC(c3c(F)ccc(Cl)c3F)=CC2=O)c2cccc(c2)-c2ccccc2NC1=O]

Example 162 was prepared by following the procedures described in Example 161. $^1$H NMR (400 MHz, METHANOL-d₄) δ 7.68-7.60 (m, 2H), 7.58-7.43 (m, 5H), 7.38 (d, J=7.5 Hz, 1H), 7.36-7.32 (m, 1H), 7.09 (td, J=9.2, 1.8 Hz, 1H), 6.14 (s, 1H), 5.64 (dd, J=13.0, 3.3 Hz, 1H), 3.51 (ddd, J=12.8, 8.6, 5.4 Hz, 1H), 3.23-3.12 (m, 1H), 2.68-2.56 (m, 1H), 2.53-2.33 (m, 2H), 2.29-2.16 (m, 1H), 1.99-1.66 (m, 3H), 1.65-1.53 (m, 1H), 1.20 (d, J=6.8 Hz, 3H), 1.13-1.02 (m, 1H). MS (ESI) m/z: 521.1 (M+H)⁺. Analytical HPLC (method A): RT=11.03 min., purity >95%.

Example 163

Methyl (10R,14S)-14-[4-(6-bromo-3-chloro-2-fluorophenyl)-6-oxo-1,2,3,6-tetrahydropyridin-1-yl]-10-methyl-9-oxo-8-azatricyclo[13.3.1.0$^{2,7}$]nonadeca-1(19),2,4,6,15,17-hexaene-4-carboxylate

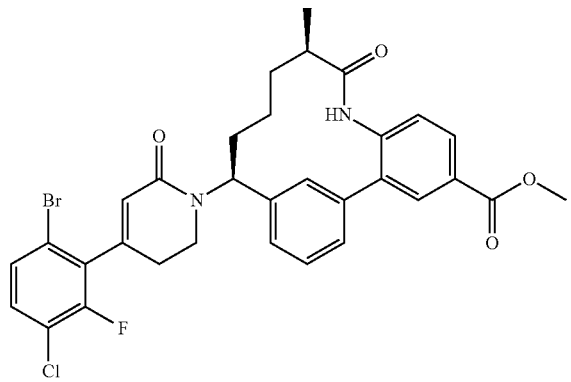 [SMILES: COC(=O)c1ccc2c(c1)-c1cccc(c1)[C@@H](N1CCC(c3c(Br)ccc(Cl)c3F)=CC1=O)CCC[C@@H](C)C(=O)N2]

Example 163 was prepared by following the procedures described in Example 161. $^1$H NMR (500 MHz, CHLOROFORM-d) δ 8.21 (d, J=1.9 Hz, 1H), 8.06 (dd, J=8.3, 1.9 Hz, 1H), 7.57-7.50 (m, 3H), 7.46-7.41 (m, 2H), 7.36-7.33 (m, 1H), 7.27-7.23 (m, 1H), 7.01 (s, 1H), 6.04 (t, J=1.2 Hz, 1H), 5.72 (dd, J=12.9, 3.3 Hz, 1H), 3.94 (s, 3H), 3.47 (ddd, J=12.7, 8.3, 5.5 Hz, 1H), 3.21-3.14 (m, 1H), 2.50-2.35 (m, 2H), 2.24-2.17 (m, 1H), 2.16-2.07 (m, 1H), 2.04-1.95 (m, 1H), 1.90-1.73 (m, 2H), 1.67-1.59 (m, 1H), 1.24 (d, J=6.9 Hz, 3H), 0.96 (t, J=12.4 Hz, 1H). MS (ESI) m/z: 641.1 (M+H)⁺. Analytical HPLC (method A): RT=11.62 min., purity >95%.

Example 164

Methyl (10R,14S)-14-[4-(3-chloro-2,6-difluorophenyl)-6-oxo-1,2,3,6-tetrahydropyridin-1-yl]-10-methyl-9-oxo-8-azatricyclo[13.3.1.0$^{2,7}$]nonadeca-1(19),2,4,6,15,17-hexaene-4-carboxylate

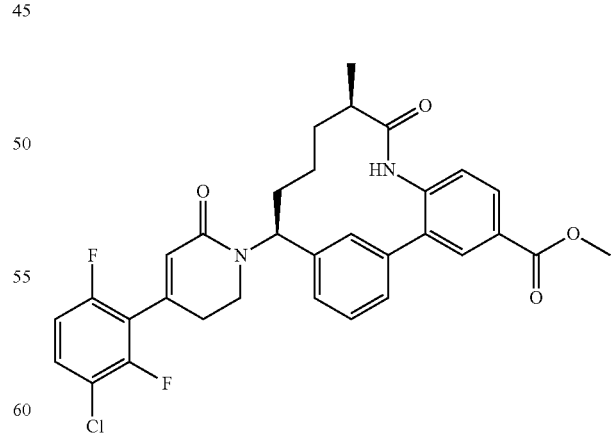

Example 164 was prepared by following the procedures described in Example 161. $^1$H NMR (400 MHz, CHLOROFORM-d) δ 8.20 (d, J=2.0 Hz, 1H), 8.06 (dd, J=8.3, 2.1 Hz, 1H), 7.58-7.49 (m, 3H), 7.45-7.40 (m, 2H), 7.34 (ddd, J=9.0, 8.1, 5.5 Hz, 1H), 6.99 (s, 1H), 6.89 (td, J=9.0, 1.8 Hz, 1H), 6.22 (s, 1H), 5.71 (dd, J=12.9, 3.4 Hz, 1H), 3.94 (s, 3H), 3.41 (ddd, J=12.7, 8.4, 5.7 Hz, 1H), 3.18-3.09 (m, 1H), 2.59-2.40 (m, 2H), 2.25-2.07 (m, 2H), 2.03-1.91 (m, 1H), 1.91-1.71 (m, 2H), 1.68-1.57 (m, 1H), 1.24 (d, J=6.8 Hz, 3H), 1.01-0.91 (m, 1H). MS (ESI) m/z: 579.2 (M+H)+. Analytical HPLC (method A): RT=11.02 min., purity >95%.

Example 165

Methyl (10R,14R)-14-[4-(3-chloro-2,6-difluorophenyl)-6-oxo-1,2,3,6-tetrahydropyridin-1-yl]-10-methyl-9-oxo-8-azatricyclo[13.3.1.0$^{2,7}$]nonadeca-1(19),2,4,6,15,17-hexaene-4-carboxylate

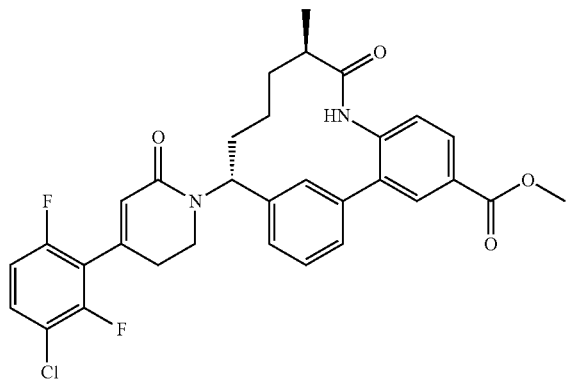 [SMILES: COC(=O)c1ccc2c(c1)-c1cccc(c1)[C@H](N1CCC(c3c(F)ccc(Cl)c3F)=CC1=O)CCC[C@@H](C)C(=O)N2]

Example 165 was isolated as a side product in the synthesis of Example 164. $^1$H NMR (500 MHz, CHLOROFORM-d) δ 8.21 (d, J=1.9 Hz, 1H), 8.07 (dd, J=8.4, 2.1 Hz, 1H), 7.59 (d, J=8.5 Hz, 1H), 7.56-7.52 (m, 1H), 7.51 (s, 1H), 7.44-7.39 (m, 2H), 7.36 (td, J=8.5, 5.5 Hz, 1H), 7.03 (s, 1H), 6.92 (td, J=9.1, 1.9 Hz, 1H), 6.30 (s, 1H), 5.61 (dd, J=11.8, 3.9 Hz, 1H), 3.95 (s, 3H), 3.56 (dt, J=13.0, 7.1 Hz, 1H), 3.39 (dt, J=13.0, 6.6 Hz, 1H), 2.68 (td, J=7.0, 3.0 Hz, 1H), 2.63 (t, J=6.9 Hz, 2H), 2.16-1.99 (m, 2H), 1.86-1.77 (m, 1H), 1.74-1.65 (m, 1H), 1.64-1.53 (m, 1H), 1.32-1.22 (m, 1H), 1.17 (d, J=7.2 Hz, 3H). MS (ESI) m/z: 579.1 (M+H)+. Analytical HPLC (method A): RT=10.64 min., purity >95%.

Example 166

(10R,14S)-14-[4-(3-chloro-2,6-difluorophenyl)-6-oxo-1,2,3,6-tetrahydropyridin-1-yl]-10-methyl-9-oxo-8-azatricyclo[13.3.1.0$^{2,7}$]nonadeca-1(19),2,4,6,15,17-hexaene-4-carboxylic acid

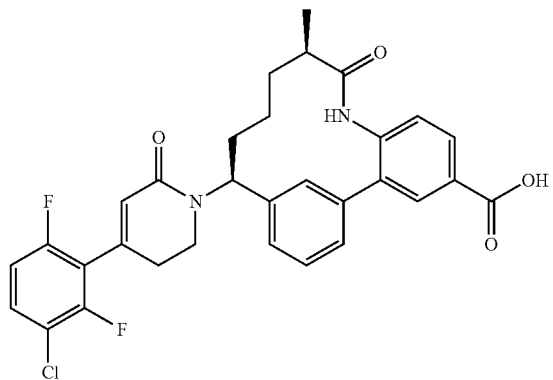 [SMILES: C[C@@H]1CCC[C@H](N2CCC(c3c(F)ccc(Cl)c3F)=CC2=O)c2cccc(c2)-c2cc(C(=O)O)ccc2NC1=O]

Example 166 was prepared from Example 165 by following a procedure analogous to Example 146. $^1$H NMR (500 MHz, DMSO-d$_6$) δ 13.09 (br. s., 1H), 9.73 (s, 1H), 8.07 (d, J=1.9 Hz, 1H), 7.95 (dd, J=8.3, 1.9 Hz, 1H), 7.67 (td, J=8.7, 5.8 Hz, 1H), 7.56-7.44 (m, 3H), 7.38 (d, J=8.3 Hz, 1H), 7.33 (d, J=7.4 Hz, 1H), 7.28-7.23 (m, 1H), 6.07 (s, 1H), 5.51 (dd, J=12.8, 3.2 Hz, 1H), 3.06 (dd, J=13.1, 5.1 Hz, 2H), 2.41 (d, J=6.1 Hz, 1H), 2.12-2.01 (m, 2H), 1.82-1.66 (m, 3H), 1.45 (d, J=13.2 Hz, 2H), 1.05 (d, J=6.9 Hz, 3H). MS (ESI) m/z: 565.2 (M+H)+. Analytical HPLC (method A): RT=9.26 min., purity >95%.

Example 167

(10R,14S)-14-[4-(6-bromo-3-chloro-2-fluorophenyl)-6-oxo-1,2,3,6-tetrahydropyridin-1-yl]-10-methyl-9-oxo-8-azatricyclo[13.3.1.0$^{2,7}$]nonadeca-1(19),2,4,6,15,17-hexaene-4-carboxylic acid

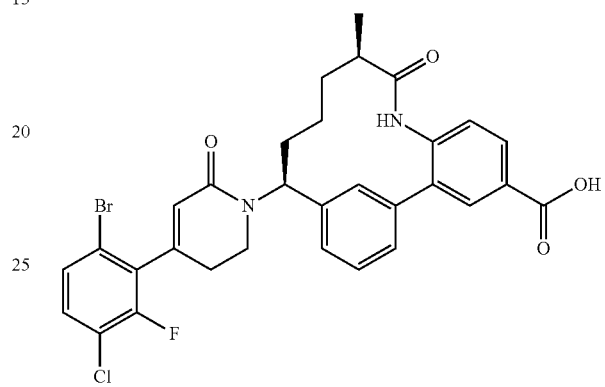

Example 167 was prepared from Example 163 by following a procedure analogous to Example 146. $^1$H NMR (500 MHz, DMSO-d$_6$) δ 13.11-13.04 (m, 1H), 9.72 (s, 1H), 8.07 (d, J=1.9 Hz, 1H), 7.95 (dd, J=8.1, 2.1 Hz, 1H), 7.60-7.51 (m, 4H), 7.49-7.45 (m, 1H), 7.37 (s, 1H), 7.33 (d, J=7.2 Hz, 1H), 5.93 (s, 1H), 5.52 (d, J=12.7 Hz, 1H), 3.10 (d, J=5.0 Hz, 4H), 2.09 (d, J=11.3 Hz, 1H), 1.83-1.66 (m, 2H), 1.47 (br. s., 2H), 1.05 (d, J=6.6 Hz, 3H). MS (ESI) m/z: 627.1 (M+H)+. Analytical HPLC (method A): RT=9.79 min., purity >95%.

Example 168

Methyl (10R,14S)-14-[4-(3,6-dicyano-2-fluorophenyl)-6-oxo-1,2,3,6-tetrahydropyridin-1-yl]-10-methyl-9-oxo-8-azatricyclo[13.3.1.0$^{2,7}$]nonadeca-1(18),2,4,6,15(19),16-hexaene-4-carboxylate

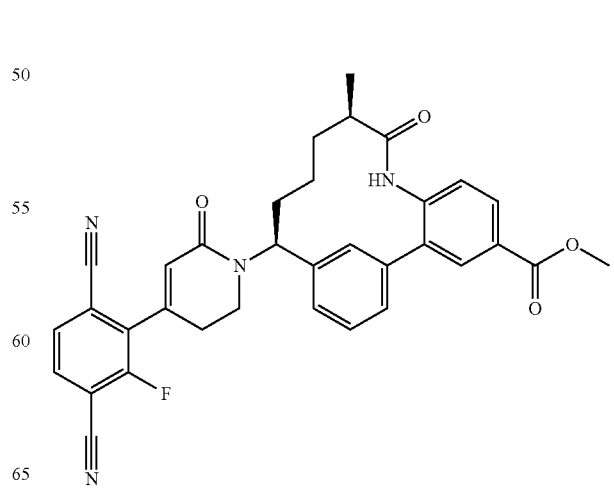

Example 168 was isolated as a side product in the preparation of Example 170. ¹H NMR (500 MHz, METHANOL-d₄) δ 8.20 (d, J=1.9 Hz, 1H), 8.05 (dd, J=8.3, 2.2 Hz, 1H), 7.93 (dd, J=8.1, 6.2 Hz, 1H), 7.80 (dd, J=8.1, 0.7 Hz, 1H), 7.62 (s, 1H), 7.58-7.53 (m, 1H), 7.49-7.45 (m, 1H), 7.42 (d, J=8.3 Hz, 1H), 7.39 (d, J=7.7 Hz, 1H), 6.23 (t, J=1.2 Hz, 1H), 5.65 (dd, J=12.9, 3.3 Hz, 1H), 3.94 (s, 3H), 3.55 (ddd, J=12.9, 8.5, 5.5 Hz, 1H), 3.25-3.18 (m, 1H), 2.69-2.61 (m, 1H), 2.56-2.48 (m, 1H), 2.44-2.36 (m, 1H), 2.24-2.15 (m, 1H), 1.97-1.87 (m, 1H), 1.83-1.68 (m, 2H), 1.63-1.55 (m, 1H), 1.18 (d, J=6.9 Hz, 3H), 1.12-1.03 (m, 1H). MS (ESI) m/z: 577.2 (M+H)⁺. Analytical HPLC (method A): RT=9.39 min., purity >95%.

Example 169

Methyl (1R,14S)-14-[4-(3-chloro-2-fluorophenyl)-6-oxo-1,2,3,6-tetrahydropyridin-1-yl]-10-methyl-9-oxo-8-azatricyclo[13.3.1.0²,⁷]nonadeca-1(18),2,4,6,15(19), 16-hexaene-4-carboxylate

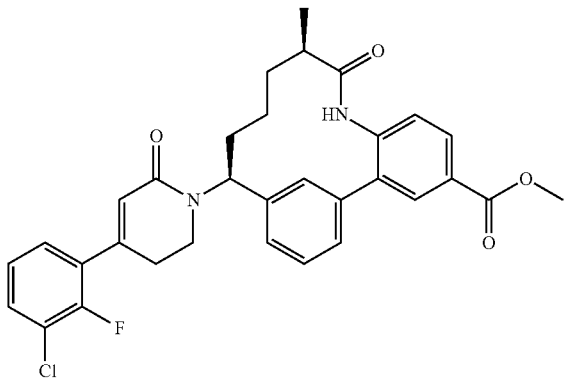 [SMILES: COC(=O)c1ccc2c(c1)-c1cccc(c1)[C@@H](N1CCC(c3cccc(Cl)c3F)=CC1=O)CCC[C@@H](C)C(=O)N2]

Example 169 was isolated as a side product in the preparation of Example 170. ¹H NMR (500 MHz, METHANOL-d₄) δ 8.19 (d, J=1.9 Hz, 1H), 8.05 (dd, J=8.3, 2.2 Hz, 1H), 7.61 (s, 1H), 7.56-7.51 (m, 1H), 7.50-7.44 (m, 2H), 7.42 (d, J=8.3 Hz, 1H), 7.39-7.34 (m, 2H), 7.19 (td, J=8.0, 0.8 Hz, 1H), 6.21 (s, 1H), 5.63 (dd, J=12.9, 3.3 Hz, 1H), 3.94 (s, 3H), 3.48 (ddd, J=12.8, 8.7, 5.5 Hz, 1H), 3.18-3.12 (m, 1H), 2.73-2.64 (m, 1H), 2.59-2.51 (m, 1H), 2.44-2.36 (m, 1H), 2.23-2.13 (m, 1H), 1.94-1.85 (m, 1H), 1.83-1.67 (m, 2H), 1.62-1.54 (m, 1H), 1.18 (d, J=6.9 Hz, 3H), 1.12-1.03 (m, 1H). MS (ESI) m/z: 561.2 (M+H)⁺. Analytical HPLC (method A): RT=11.00 min., purity 92.4%.

Example 170

Methyl (10R,14S)-14-[4-(3-chloro-6-cyano-2-fluorophenyl)-6-oxo-1,2,3,6-tetrahydropyridin-1-yl]-10-methyl-9-oxo-8-azatricyclo[13.3.1.0²,⁷]nonadeca-1(18),2,4,6,15(19), 16-hexaene-4-carboxylate

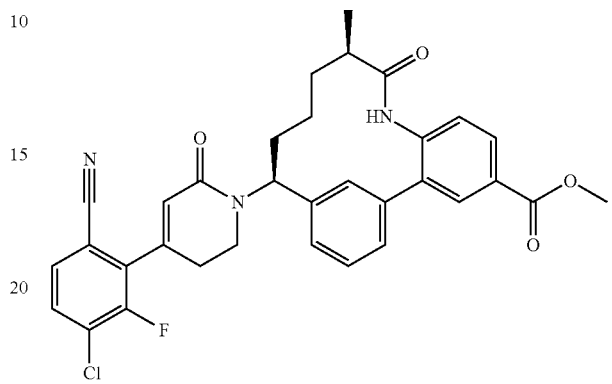

Example 170 was prepared from Example 163 by following the a procedure similar to that described in Example 3. ¹H NMR (500 MHz, METHANOL-d4) δ 8.20 (d, J=1.9 Hz, 1H), 8.05 (dd, J=8.1, 2.1 Hz, 1H), 7.70-7.60 (m, 3H), 7.58-7.53 (m, 1H), 7.47 (d, J=7.4 Hz, 1H), 7.42 (d, J=8.3 Hz, 1H), 7.39 (d, J=7.7 Hz, 1H), 6.18 (s, 1H), 5.65 (dd, J=12.8, 3.2 Hz, 1H), 3.94 (s, 3H), 3.57-3.50 (m, 1H), 3.24-3.17 (m, 1H), 2.69-2.60 (m, 1H), 2.55-2.47 (m, 1H), 2.43-2.36 (m, 1H), 2.24-2.15 (m, 1H), 1.97-1.88 (m, 1H), 1.84-1.67 (m, 2H), 1.63-1.55 (m, 1H), 1.18 (d, J=6.6 Hz, 3H), 1.08 (t, J=12.8 Hz, 1H). MS (ESI) m/z: 586.1 (M+H)⁺. Analytical HPLC (method A): RT=10.31 min., purity >95%.

Example 171

Methyl N-[(10R,14S)-14-[4-(6-acetyl-3-chloro-2-fluorophenyl)-6-oxo-1,2,3,6-tetrahydropyridin-1-yl]-10-methyl-9-oxo-8-azatricyclo[13.3.1.0²,⁷]nonadeca-1(18),2,4,6,15(19), 16-hexaen-5-yl]carbamate

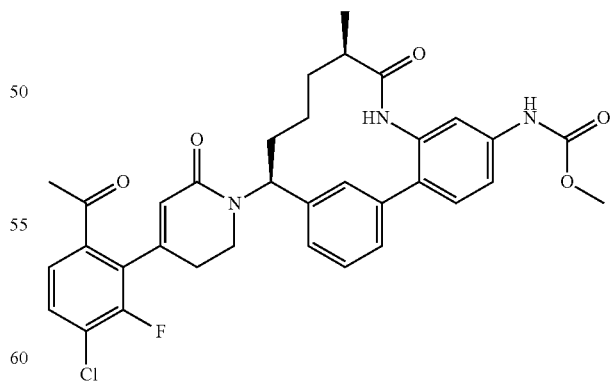

Example 171 was prepared from Example 161 by following the a procedure similar to that described in Example 48. ¹H NMR (500 MHz, DMSO-d₆) δ 9.78 (s, 1H), 9.55 (s, 1H), 7.80-7.73 (m, 2H), 7.55-7.44 (m, 4H), 7.37-7.33 (m, 2H), 7.24 (d, J=7.7 Hz, 1H), 5.71 (s, 1H), 5.50 (dd, J=12.8, 3.2

Hz, 1H), 3.69 (s, 3H), 3.38 (ddd, J=12.5, 7.6, 5.5 Hz, 1H), 3.08-3.02 (m, 1H), 2.54 (s, 3H), 2.48-2.33 (m, 3H), 2.33-2.24 (m, 1H), 2.14-2.04 (m, 1H), 1.79-1.65 (m, 2H), 1.57-1.41 (m, 2H), 1.04 (d, J=6.6 Hz, 3H). MS (ESI) m/z: 618.2 (M+H)⁺. Analytical HPLC (method C): RT=1.858 min., purity 96.6%.

Example 172

Methyl (1R,14S)-14-[4-(6-acetyl-3-chloro-2-fluorophenyl)-6-oxo-1,2,3,6-tetrahydropyridin-1-yl]-10-methyl-9-oxo-8-azatricyclo[13.3.1.0²,⁷]nonadeca-1(18),2,4,6,15(19), 16-hexaene-4-carboxylate

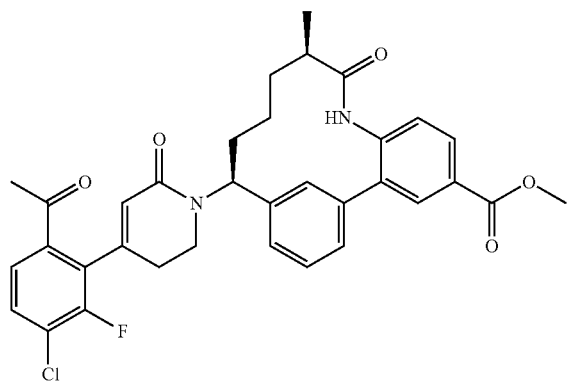 [SMILES: COC(=O)c1ccc2c(c1)-c1cccc(c1)[C@@H](N1CCC(c3c(C(C)=O)ccc(Cl)c3F)=CC1=O)CCC[C@@H](C)C(=O)N2]

Example 172 was prepared from Example 163 by following a procedure similar to that described in Example 48. ¹H NMR (500 MHz, DMSO-d₆) δ 9.76 (s, 1H), 8.10 (d, J=1.9 Hz, 1H), 7.99-7.95 (m, 1H), 7.80-7.73 (m, 2H), 7.56-7.52 (m, 2H), 7.49-7.46 (m, 1H), 7.41 (d, J=8.3 Hz, 1H), 7.33 (d, J=7.7 Hz, 1H), 5.71 (s, 1H), 5.52 (dd, J=12.9, 3.3 Hz, 1H), 3.89 (s, 3H), 3.42 (ddd, J=12.5, 7.6, 5.5 Hz, 1H), 3.14-3.06 (m, 1H), 2.54 (s, 3H), 2.48-2.36 (m, 2H), 2.34-2.26 (m, 1H), 2.13-2.03 (m, 1H), 1.80-1.67 (m, 2H), 1.55-1.40 (m, 2H), 1.05 (d, J=6.6 Hz, 3H), 1.09-1.00 (m, 1H). MS (ESI) m/z: 603.3 (M+H)⁺. Analytical HPLC (method C): RT=1.992 min., purity 100%.

Example 173

Methyl N-[(10R,14S)-14-[4-(3-chloro-6-cyano-2-fluorophenyl)-6-oxo-1,2,3,6-tetrahydropyridin-1-yl]-10-methyl-9-oxo-8-azatricyclo[13.3.1.0²,⁷]nonadeca-1(18),2,4,6,15(19), 16-hexaen-5-yl]carbamate

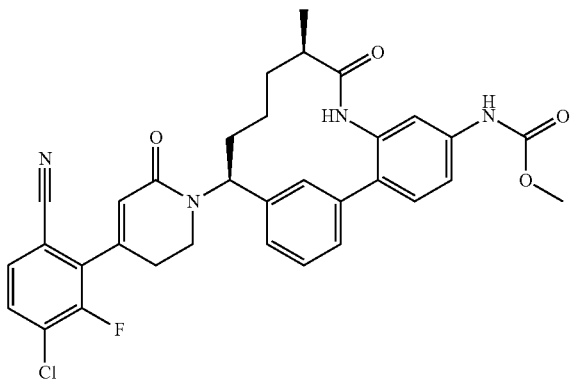 [SMILES: COC(=O)Nc1ccc2c(c1)NC(=O)[C@H](C)CCC[C@H](N1CCC(c3c(C#N)ccc(Cl)c3F)=CC1=O)c1cccc-2c1]

Example 173 was prepared from Example 161 by following a procedure similar to that described in Example 3. ¹H NMR (500 MHz, METHANOL-d₄) δ 7.72-7.68 (m, 1H), 7.67-7.64 (m, 1H), 7.63 (s, 1H), 7.56-7.48 (m, 4H), 7.45 (s, 1H), 7.41 (d, J=7.7 Hz, 1H), 7.34 (d, J=7.7 Hz, 1H), 6.19 (s, 1H), 5.65 (dd, J=12.8, 3.2 Hz, 1H), 3.77 (s, 3H), 3.58-3.51 (m, 1H), 3.23-3.17 (m, 1H), 2.69-2.62 (m, 1H), 2.55-2.48 (m, 1H), 2.40 (d, J=10.5 Hz, 1H), 2.28-2.17 (m, 1H), 1.92 (d, J=11.6 Hz, 1H), 1.83-1.71 (m, 3H), 1.66-1.57 (m, 2H), 1.20 (d, J=6.6 Hz, 3H). MS (ESI) m/z: 601.3 (M+H)⁺. Analytical HPLC (method A): RT=9.46 min., purity 92%.

Example 174

Methyl (10R,14S)-14-[4-(3-chloro-2,6-difluorophenyl)-2-oxo-1,2,3,6-tetrahydropyridin-1-yl]-10-methyl-9-oxo-8-azatricyclo[13.3.1.0²,⁷]nonadeca-1(19),2,4,6,15,17-hexaene-4-carboxylate

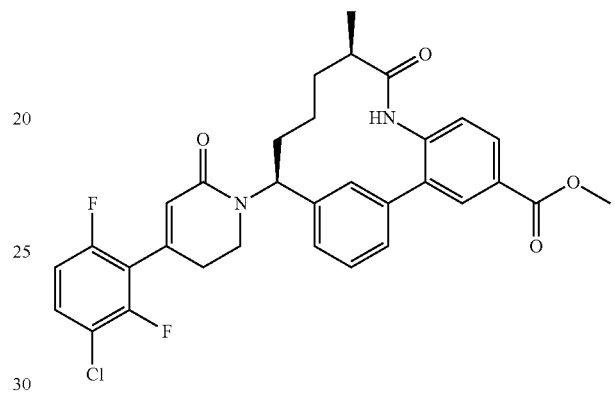

Example 174 was isolated as a side product in the preparation of Example 164. ¹H NMR (500 MHz, CHLOROFORM-d) δ 8.21 (d, J=2.2 Hz, 1H), 8.07 (dd, J=8.3, 1.9 Hz, 1H), 7.58-7.50 (m, 3H), 7.47-7.41 (m, 2H), 7.32-7.27 (m, 1H), 6.88-6.83 (m, 2H), 5.90 (dd, J=12.9, 3.0 Hz, 1H), 5.79 (br. s., 1H), 3.94 (s, 3H), 4.00-3.92 (m, 1H), 3.66-3.59 (m, 1H), 3.32 (q, J=4.9 Hz, 2H), 2.24-1.83 (m, 4H), 1.81-1.72 (m, 1H), 1.69-1.61 (m, 1H), 1.24 (d, J=6.6 Hz, 3H), 0.92 (t, J=12.8 Hz, 1H). MS (ESI) m/z: 579.2 (M+H)⁺. Analytical HPLC (method A): RT=10.86 min., purity >95%.

Example 175

Methyl (10R,14R)-14-[4-(6-bromo-3-chloro-2-fluorophenyl)-6-oxo-1,2,3,6-tetrahydropyridin-1-yl]-10-methyl-9-oxo-8-azatricyclo[13.3.1.0²,⁷]nonadeca-1(19),2,4,6,15,17-hexaene-4-carboxylate

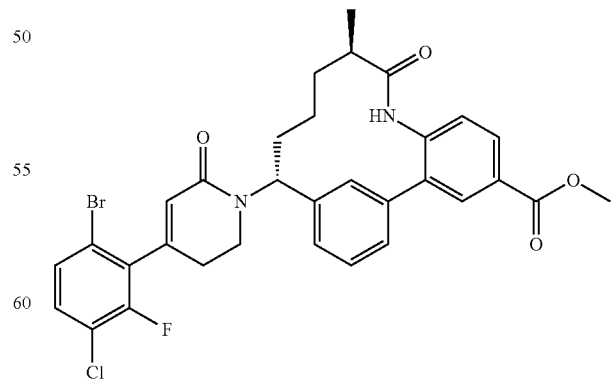

Example 175 was prepared isolated as a side product in the preparation of Example 163. ¹H NMR (500 MHz, CHLOROFORM-d) δ 8.21 (d, J=1.9 Hz, 1H), 8.07 (dd, J=8.3, 1.9 Hz, 1H), 7.59 (d, J=8.3 Hz, 1H), 7.57-7.52 (m, 1H), 7.51 (s, 1H), 7.44-7.40 (m, 2H), 7.36 (dd, J=8.8, 1.4 Hz, 1H), 7.29-7.25 (m, 1H), 7.05 (s, 1H), 6.11 (t, J=1.2 Hz, 1H), 5.62 (dd, J=11.7, 4.0 Hz, 1H), 3.95 (s, 3H), 3.62 (dt, J=12.9, 7.2 Hz, 1H), 3.43 (dt, J=13.0, 6.6 Hz, 1H), 2.68 (td, J=7.0, 3.0 Hz, 1H), 2.55 (t, J=6.6 Hz, 2H), 2.17-2.02 (m, 2H), 1.82 (dq, J=14.3, 7.2 Hz, 1H), 1.74-1.66 (m, 1H), 1.64-1.53 (m, 1H), 1.31-1.22 (m, 1H), 1.17 (d, J=7.2 Hz, 3H). MS (ESI) m/z: 641.1 (M+H)$^+$. Analytical HPLC (method A): RT=11.21 min., purity >95%.

Example 176

Methyl (10R,14S)-14-[4-(6-bromo-3-chloro-2-fluorophenyl)-2-oxo-1,2,3,6-tetrahydropyridin-1-yl]-10-methyl-9-oxo-8-azatricyclo[13.3.1.0$^{2,7}$]nonadeca-1(19),2,4,6,15,17-hexaene-4-carboxylate

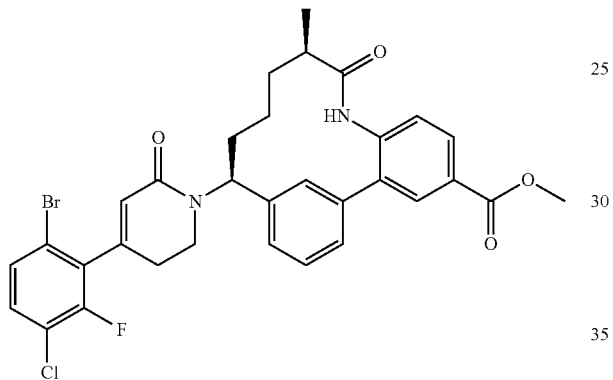

Example 176 was isolated as a side product in the preparation of Example 163. $^1$H NMR (500 MHz, CHLOROFORM-d) δ 8.21 (d, J=2.2 Hz, 1H), 8.07 (dd, J=8.3, 1.9 Hz, 1H), 7.59-7.51 (m, 3H), 7.47-7.41 (m, 2H), 7.31 (dd, J=8.7, 1.5 Hz, 1H), 7.21 (dd, J=8.5, 7.4 Hz, 1H), 6.88 (s, 1H), 5.90 (dd, J=13.1, 3.2 Hz, 1H), 5.64 (dt, J=3.3, 1.7 Hz, 1H), 4.01-3.95 (m, 1H), 3.94 (s, 3H), 3.67-3.59 (m, 1H), 3.25 (dd, J=3.3, 1.4 Hz, 2H), 2.25-2.14 (m, 2H), 2.03-1.94 (m, 1H), 1.92-1.81 (m, 1H), 1.81-1.73 (m, 1H), 1.69-1.61 (m, 1H), 1.24 (d, J=6.6 Hz, 3H), 0.93 (t, J=12.5 Hz, 1H). MS (ESI) m/z: 641.1 (M+H)$^+$. Analytical HPLC (method A): RT=11.45 min., purity >95%.

Example 177

Methyl N-[(10R,14S)-14-[4-(3-chloro-2,6-difluorophenyl)-3-methyl-6-oxo-1,2,3,6-tetrahydropyridin-1-yl]-10-methyl-9-oxo-8,16-diazatricyclo[13.3.1.0$^{2,7}$]nonadeca-1(19),2(7),3,5,15,17-hexaen-5-yl]carbamate (Chirally Pure, Isomer 1)

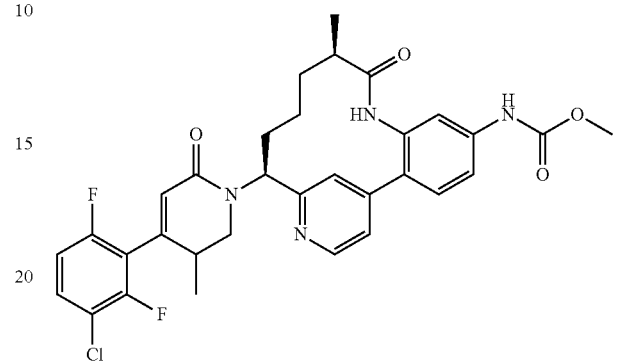

And Example 178

Methyl N-[(10R,14S)-14-[4-(3-chloro-2,6-difluorophenyl)-3-methyl-6-oxo-1,2,3,6-tetrahydropyridin-1-yl]-10-methyl-9-oxo-8,16-diazatricyclo[13.3.1.0$^{2,7}$]nonadeca-1(19),2(7),3,5,15,17-hexaen-5-yl]carbamate (Chirally Pure, Isomer 2)

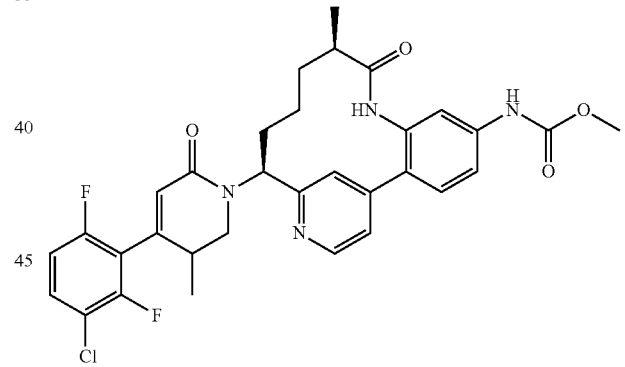

Example 73 (20 mg) was subjected to chiral SFC separation using Regis Whelk-O (R,R) 250×30 mm column, with a mixture of 35% CO$_2$, 65% MeOH and 0.1% DEA with a flow rate of 85 mL/min and 100 bar at 40° C., Peak 1 was designated as Example 177 (isomer 1, 5.2 mg, 99%) and peak 2 was designated as Example 178 (isomer 2, 6.88 mg, 99%). MS (ESI) m/z: 609.2 (M+H)$^+$ for both enantiomers. Analytical HPLC (method A): RT=6.98 min, purity=100% for both enantiomers.

Example 177 $^1$H NMR (400 MHz, METHANOL-d$_4$) δ 8.62 (d, J=4.0 Hz, 1H), 7.61 (s, 1H), 7.57-7.46 (m, 4H), 7.39 (d, J=4.4 Hz, 1H), 7.09 (td, J=9.0, 1.7 Hz, 1H), 5.96 (s, 1H), 5.67 (dd, J=12.8, 3.7 Hz, 1H), 3.87-3.79 (m, 1H), 3.76 (s, 3H), 3.54 (dd, J=12.8, 6.2 Hz, 1H), 2.90-2.80 (m, 1H), 2.62-2.52 (m, 1H), 2.23-2.10 (m, 2H), 1.99-1.79 (m, 2H), 1.63-1.49 (m, 1H), 1.35-1.12 (m, 3H), 1.06 (d, J=6.8 Hz, 3H), 1.04 (d, J=7.0 Hz, 3H)

Example 178 ¹H NMR (400 MHz, METHANOL-d₄) δ 8.62 (d, J=4.4 Hz, 1H), 7.61 (s, 1H), 7.57-7.45 (m, 4H), 7.38 (d, J=4.4 Hz, 1H), 7.08 (td, J=9.0, 1.5 Hz, 1H), 5.96 (s, 1H), 5.69 (dd, J=12.9, 3.9 Hz, 1H), 3.86-3.78 (m, 1H), 3.76 (s, 3H), 3.74-3.66 (m, 1H), 2.86-2.76 (m, 1H), 2.60-2.50 (m, 1H), 2.23-2.11 (m, 1H), 1.98-1.81 (m, 2H), 1.64-1.51 (m, 1H), 1.38-1.09 (m, 3H), 1.06 (d, J=6.8 Hz, 3H), 0.82 (d, J=7.0 Hz, 3H)

Example 179

N-(4-chloro-3-fluoro-2-{1-[(10R,14S)-10-methyl-9-oxo-8,16-diazatricyclo[13.3.1.0²,⁷]nonadeca-1(19),2(7),3,5,15,17-hexaen-14-yl]-6-oxo-1,2,3,6-tetrahydropyridin-4-yl}phenyl)-2,2,2-trifluoroacetamide

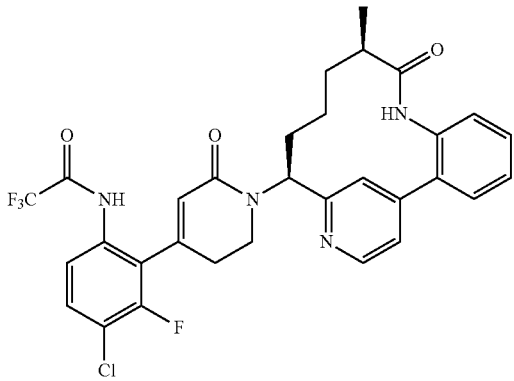 [SMILES: C[C@@H]1CCC[C@H](N2CCC(c3c(NC(=O)C(F)(F)F)ccc(Cl)c3F)=CC2=O)c2cc(ccn2)-c2ccccc2NC1=O]

Example 179 was prepared using a procedure analogous to example 1. ¹H NMR (400 MHz, METHANOL-d4) δ 8.79 (d, J=5.7 Hz, 1H), 8.04 (s, 1H), 7.84 (d, J=4.6 Hz, 1H), 7.71 (dd, J=7.6, 1.4 Hz, 1H), 7.62-7.49 (m, 3H), 7.34 (dd, J=7.8, 1.0 Hz, 1H), 7.20 (dd, J=8.6, 1.3 Hz, 1H), 5.86 (s, 1H), 5.42 (dd, J=12.3, 4.4 Hz, 1H), 3.85-3.64 (m, 2H), 2.89-2.56 (m, 3H), 2.33-2.23 (m, 1H), 2.08-1.95 (m, 1H), 1.94-1.82 (m, 1H), 1.67-1.52 (m, 1H), 1.31 (m, 1H), 1.05 (d, J=6.8 Hz, 3H), 1.00-0.88 (m, 1H). MS (ESI) m/z: 553.2 (M+H)⁺. Analytical HPLC (method A): RT=6.86 min, purity >98%.

Example 180

Methyl N-[(10S,14S)-14-[4-(3-chloro-2,6-difluorophenyl)-6-oxo-1,2,3,6-tetrahydropyridin-1-yl]-11-fluoro-10-methyl-9-oxo-8,16-diazatricyclo[13.3.1.0²,⁷]nonadeca-1(19),2(7),3,5,15,17-hexaen-5-yl]carbamate 180A Methyl N-[(10S,14S)-14-{[(tert-butoxy)carbonyl]amino}-11-fluoro-10-methyl-9-oxo-8,16-diazatricyclo[13.3.1.0²,⁷]nonadeca-1(19),2(7),3,5,15,17-hexaen-5-yl]carbamate In a 500 ml RBF, iron(III) oxalate hexahydrate (818 mg, 1.691 mmol) in water (40 mL) was stirred on a warm water bath, to make it completely dissolved into a clear yellow solution in 3 hrs. In a 100 ml pear shaped RBF, 1H in MeCN (40 mL) stirred vigorously, partially soluable. EtOH (8 mL) was added. Both solution were vacuumed and refilled with Ar 3 times. Selectfluor (599 mg, 1.691 mmol) was added to the iron(III) oxalate hexahydrate (818 mg, 1.691 mmol) aqueous solution, followed by transferring the solution of 1H via cannula under Ar. Then sodium borohydride (171 mg, 4.51 mmol) was added portionwise. After a total of 1 hr, reaction mixture was quenched with 15 ml NH₃H₂O (28%-30% aq) solution extracted with 200 ml 10% MeOH in DCM multiple times, combined organic phase washed with brine, dried over MgSO₄, filtered, concentrated to yield crude product, purified by prep HPLC and SFC to afford 180A (81 mg). ¹H NMR (500 MHz, METHANOL-d₄) δ 8.58 (d, J=5.2 Hz, 1H), 7.54-7.41 (m, 3H), 7.38 (s, 1H), 7.32 (dd, J=5.2, 1.7 Hz, 1H), 5.06-4.89 (m, 1H), 4.82-4.74 (m, 1H), 3.76 (s, 3H), 3.12-3.04 (m, 1H), 2.19-2.07 (m, 1H), 1.75-1.63 (m, 1H), 1.60-1.46 (m, 1H), 1.41-1.20 (m, 9H), 0.93 (d, J=6.9 Hz, 3H), 0.65-0.41 (m, 1H). MS (ESI) m/z: 487.2 (M+H)⁺

Example 180 was prepared using a procedure analogous to example 1 by using 180A in step 1I. MS (ESI) m/z: 613.2 (M+H)⁺. Analytical HPLC (method A): RT=7.59 min, purity >99%. ¹H NMR (500 MHz, METHANOL-d₄) δ 9.62 (s, 1H), 8.73 (d, J=5.8 Hz, 1H), 7.92 (s, 1H), 7.71 (d, J=4.7 Hz, 1H), 7.61-7.51 (m, 3H), 7.47 (dd, J=8.5, 1.9 Hz, 1H), 7.10 (td, J=9.2, 1.4 Hz, 1H), 6.11 (s, 1H), 5.50 (dd, J=12.1, 5.8 Hz, 1H), 5.27-5.12 (m, 1H), 4.25-4.15 (m, 1H), 3.90-3.81 (m, 1H), 3.77 (s, 3H), 3.22-3.11 (m, 1H), 3.01-2.90 (m, 1H), 2.81-2.74 (m, 1H), 2.42-2.31 (m, 1H), 2.29-2.18 (m, 1H), 1.83-1.68 (m, 1H), 0.96 (d, J=6.9 Hz, 3H), 0.73-0.52 (m, 1H).

Example 181

Methyl N-[(10R,14S)-14-[4-(3-chloro-6-ethynyl-2-fluorophenyl)-6-oxo-1,2,3,6-tetrahydropyridin-1-yl]-10-methyl-9-oxo-8,16-diazatricyclo[13.3.1.0²,⁷]nonadeca-1(19),2(7),3,5,15,17-hexaen-5-yl]carbamate

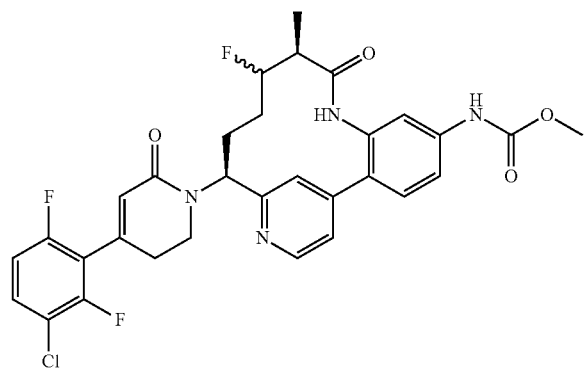 [SMILES: COC(=O)Nc1ccc2c(c1)NC(=O)[C@H](C)C(F)CC[C@H](N1CCC(c3c(F)ccc(Cl)c3F)=CC1=O)c1cc-2ccn1]

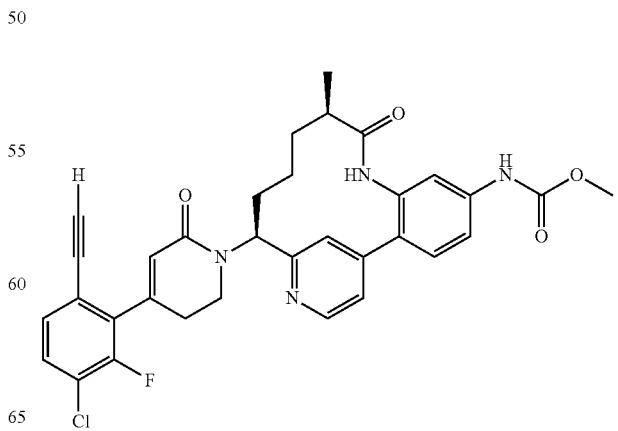

263

Example 181 was prepared using a procedure analogous to Example 1. MS (ESI) m/z: 601.2 (M+H)⁺. Analytical HPLC (method A): RT=7.08 min, purity >98%. ¹H NMR (500 MHz, METHANOL-$d_4$) δ 9.28 (br. s., 1H), 8.64 (d, J=6.1 Hz, 1H), 8.27 (s, 1H), 7.98 (br. s., 1H), 7.65-7.49 (m, 2H), 7.42-7.29 (m, 2H), 7.26-7.12 (m, 2H), 6.07 (s, 1H), 5.16 (br. s., 1H), 4.08 (br. s., 1H), 3.86 (br. s., 1H), 3.64 (s, 3H), 3.34 (s, 1H), 3.01 (m, 1H), 2.83 (m, 1H), 2.73-2.51 (m, 2H), 1.98 (m, 2H), 1.61 (br. s., 1H), 1.50-1.33 (m, 1H), 0.97 (br. s., 3H), 0.57 (br. s., 1H).

Example 182

Methyl N-[(10R,14S)-14-{4-[3-chloro-2-fluoro-6-(1H-1,2,3-triazol-4-yl)phenyl]-6-oxo-1,2,3,6-tetrahydropyridin-1-yl}-10-methyl-9-oxo-8,16-diazatricyclo[13.3.1.0²,⁷]nonadeca-1(19),2(7),3,5,15,17-hexaen-5-yl]carbamate

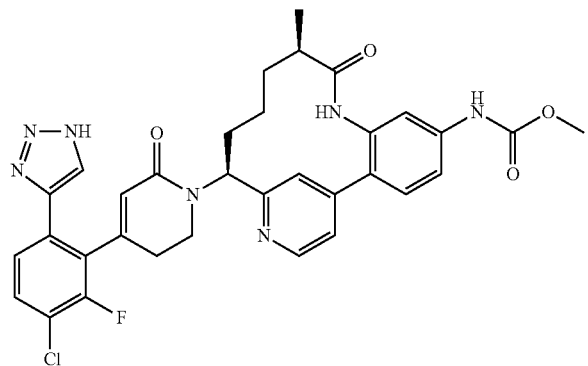 [SMILES: COC(=O)Nc1ccc2c(c1)NC(=O)[C@H](C)CCC[C@H](N1CCC(c3c(-c4c[nH]nn4)ccc(Cl)c3F)=CC1=O)c1cc-2ccn1]

Example 182: In a 1 dram vial, Example 181 (17.6 mg, 0.025 mmol), copper(I) iodide (1.172 mg, 6.15 μmol) was purged with a gentle stream of Ar, DMF (0.5 mL) and MeOH (0.056 mL) was added, vacuumed and refilled with Ar 3 times, azidotrimethylsilane (8.9 mg, 0.077 mmol) was added, pale yellow solution turned into vivid yellow. The reaction mixture was heated at 100° C. for 8 hrs before cooling down to rt. The reaction mixture was purified by prep HPLC to yield Example 182 as 3.42 mg beige solid. TFA salt, 15% yield. MS (ESI) m/z: 644.3 (M+H)⁺. Analytical HPLC (method A): RT=5.99 min, purity 94%. 1H NMR (400 MHz, METHANOL-d4) δ 9.68 (s, 1H), 8.78 (br. s., 1H), 8.07 (br. s., 1H), 7.98-7.78 (m, 1H), 7.70-7.51 (m, 5H), 5.83 (br. s., 1H), 5.57-5.31 (m, 1H), 3.80 (s, 3H), 3.78-3.69 (m, 2H), 2.78-2.51 (m, 3H), 2.38-2.23 (m, 1H), 2.16-1.88 (m, 2H), 1.64 (d, J=7.0 Hz, 1H), 1.42-1.26 (m, 1H), 1.08 (d, J=7.0 Hz, 3H), 1.04-0.94 (m, 1H).

264

Example 183

N-(4-chloro-3-fluoro-2-{1-[(10R,14S)-10-methyl-9-oxo-8,16-diazatricyclo[13.3.1.0²,⁷]nonadeca-1(19),2(7),3,5,15,17-hexaen-14-yl]-6-oxo-1,2,3,6-tetrahydropyridin-4-yl}phenyl)acetamide

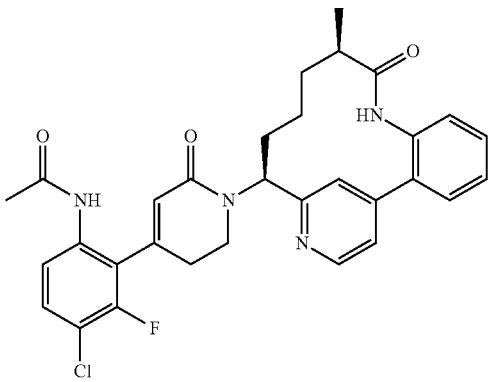 [SMILES: CC(=O)Nc1ccc(Cl)c(F)c1C1=CC(=O)N([C@H]2CCC[C@@H](C)C(=O)Nc3ccccc3-c3ccnc2c3)CC1]

Example 183 was prepared using a procedure analogous to Example 45. MS (ESI) m/z: 561.2 (M+H)⁺. Analytical HPLC (method C): RT=1.67 min, purity 98%. ¹H NMR (500 MHz, DMSO-$d_6$) δ 9.72 (br. s., 1H), 9.58 (br. s., 1H), 8.67 (br. s., 1H), 7.61-7.51 (m, 3H), 7.50-7.37 (m, 3H), 7.33 (d, J=8.5 Hz, 1H), 7.22 (d, J=6.1 Hz, 1H), 5.79 (br. s., 1H), 5.60 (d, J=11.8 Hz, 1H), 3.96 (br. s., 2H), 2.53-2.41 (m, 3H), 2.07 (br. s., 1H), 2.02-1.81 (m, 4H), 1.66 (br. s., 1H), 1.43 (br. s., 1H), 1.22 (d, J=10.2 Hz, 1H), 0.87 (d, J=5.5 Hz, 3H), 0.54 (br. s., 1H)

Example 184

(10R,14S)-14-{4-[3-chloro-2-fluoro-6-(1H-1,2,3,4-tetrazol-1-yl)phenyl]-6-oxo-1,2,3,6-tetrahydropyridin-1-yl}-4-fluoro-10-methyl-8,16-diazatricyclo[13.3.1.0²,⁷]nonadeca-1(19),2(7),3,5,15,17-hexaen-9-one

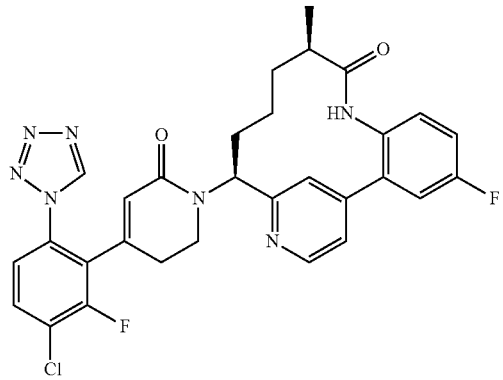 [SMILES: C[C@@H]1CCC[C@H](N2CCC(c3c(-n4cnnn4)ccc(Cl)c3F)=CC2=O)c2cc(ccn2)-c2cc(F)ccc2NC1=O]

Example 184 was prepared using a procedure analogous to Example 68. MS (ESI) m/z: 589.9 (M+H)⁺. Analytical HPLC (method A): RT=6.78 min, purity 100%. ¹H NMR (400 MHz, METHANOL-$d_4$) δ 9.54 (s, 1H), 8.79 (d, J=5.7 Hz, 1H), 7.98 (d, J=1.3 Hz, 1H), 7.85-7.76 (m, 2H), 7.57-7.48 (m, 2H), 7.39-7.29 (m, 2H), 5.72 (s, 1H), 5.38 (dd, J=12.4, 4.7 Hz, 1H), 3.77-3.67 (m, 1H), 3.66-3.56 (m, 1H), 2.71-2.48 (m, 3H), 2.27-2.13 (m, 1H), 2.04-1.92 (m, 1H), 1.91-1.79 (m, 1H), 1.63-1.48 (m, 1H), 1.23 (br. s., 1H), 1.03 (d, J=7.0 Hz, 3H), 0.99-0.81 (m, 1H)

Example 185

(10R,14S)-14-[4-(3-chloro-2,6-difluorophenyl)-2-oxo-1,2-dihydropyridin-1-yl]-10-methyl-5,8,16-triazatricyclo[13.3.1.0²,⁷]nonadeca-1(19),2(7),3,5,15,17-hexaen-9-one

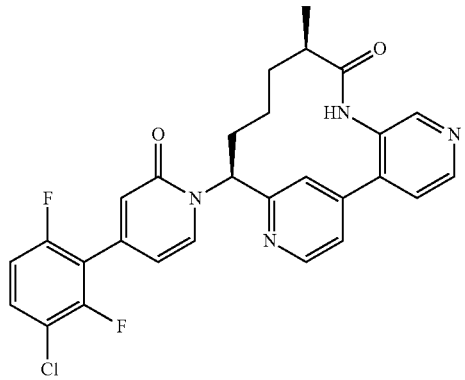 [SMILES: C[C@@H]1CCC[C@H](n2ccc(-c3c(F)ccc(Cl)c3F)cc2=O)c2cc(ccn2)-c2ccncc2NC1=O]

Example 185 was prepared using a procedure analogous to Example 200. MS (ESI) m/z: 521.3 (M+H)⁺. Analytical HPLC (method C): RT=1.699 min, purity 88%. ¹H NMR (500 MHz, DMSO-d₆) δ 9.94 (br. s., 1H), 8.72 (br. s., 1H), 8.62 (br. s., 1H), 8.46 (br. s., 1H), 8.36 (br. s., 1H), 7.75 (br. s., 2H), 7.63 (br. s., 1H), 7.49 (br. s., 1H), 7.33 (br. s., 1H), 6.53 (br. s., 1H), 6.42 (br. s., 1H), 6.09 (d, J=12.9 Hz, 1H), 2.70 (br. s., 1H), 2.20 (br. s., 1H), 2.02 (br. s., 1H), 1.87 (br. s., 1H), 1.56-1.31 (m, 2H), 0.86 (br. s., 3H), 0.35 (br. s., 1H)

Example 186

Methyl (10R,14S)-14-{4-[3-chloro-2-fluoro-6-(trifluoromethyl)phenyl]-6-oxo-1,2,3,6-tetrahydropyridin-1-yl}-10-methyl-9-oxo-8,16-diazatricyclo[13.3.1.0²,⁷]nonadeca-1(19),2(7),3,5,15,17-hexaene-4-carboxylate

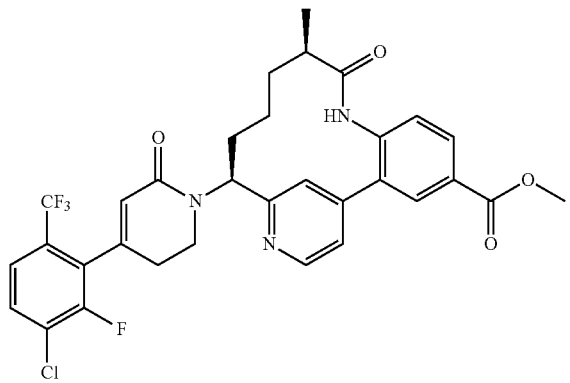 [SMILES: COC(=O)c1ccc2c(c1)-c1ccnc(c1)[C@@H](N1CCC(c3c(C(F)(F)F)ccc(Cl)c3F)=CC1=O)CCC[C@@H](C)C(=O)N2]

Example 186 was prepared using a procedure analogous to Example 1. MS (ESI) m/z: 629.9 (M+H)⁺. Analytical HPLC (method A): RT=8.37 min, purity >99%. 1H NMR (400 MHz, CHLOROFORM-d) δ 9.29 (br. s., 1H), 8.76 (d, J=5.7 Hz, 1H), 8.11 (m, 2H), 8.04 (dd, J=8.4, 2.0 Hz, 1H), 7.66 (dd, J=5.7, 1.3 Hz, 1H), 7.60-7.44 (m, 2H), 7.20 (d, J=8.1 Hz, 1H), 5.97 (s, 1H), 5.36 (dd, J=12.5, 5.3 Hz, 1H), 4.18 (br. s., 1H), 3.98 (s, 3H), 3.81 (br. s., 1H), 3.08-2.39 (m, 4H), 2.02-1.83 (m, 2H), 1.65-1.41 (m, 2H), 0.93 (d, J=6.8 Hz, 3H), 0.41 (br. s., 1H)

Example 187

(10R,14S)-14-{4-[3-chloro-2-fluoro-6-(trifluoromethyl)phenyl]-6-oxo-1,2,3,6-tetrahydropyridin-1-yl}-10-methyl-9-oxo-8,16-diazatricyclo[13.3.1.0²,⁷]nonadeca-1(19),2(7),3,5,15,17-hexaene-4-carboxylic acid

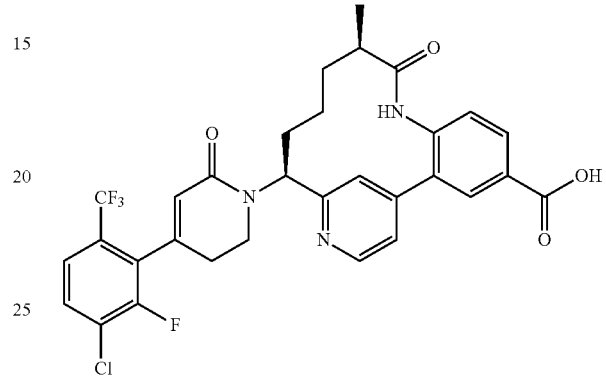

Example 187 was prepared using a procedure analogous to Example 1. MS (ESI) m/z: 616.3 (M+H)⁺. Analytical HPLC (method A): RT=10.88 min, purity >99%. ¹H NMR (400 MHz, METHANOL-d₄) δ 8.82 (d, J=5.5 Hz, 1H), 8.32 (d, J=1.8 Hz, 1H), 8.20 (dd, J=8.1, 2.0 Hz, 1H), 7.93 (s, 1H), 7.81-7.72 (m, 2H), 7.65 (d, J=8.8 Hz, 1H), 7.44 (d, J=8.1 Hz, 1H), 5.98 (s, 1H), 5.56 (dd, J=12.5, 4.8 Hz, 1H), 4.02 (br. s., 1H), 3.84 (br. s., 1H), 2.89-2.55 (m, 3H), 2.35-2.23 (m, 1H), 2.08-1.89 (m, 2H), 1.69-1.54 (m, 1H), 1.47-1.33 (m, 1H), 1.04 (d, J=6.8 Hz, 3H), 0.85 (br. s., 1H)

Example 188

(10R,14S)-14-{4-[5-chloro-2-(1H-1,2,3-triazol-1-yl)phenyl]-6-oxo-1,2,3,6-tetrahydropyridin-1-yl}-4-fluoro-10-methyl-8,16-diazatricyclo[13.3.1.0²,⁷]nonadeca-1(19),2(7),3,5,15,17-hexaen-9-one

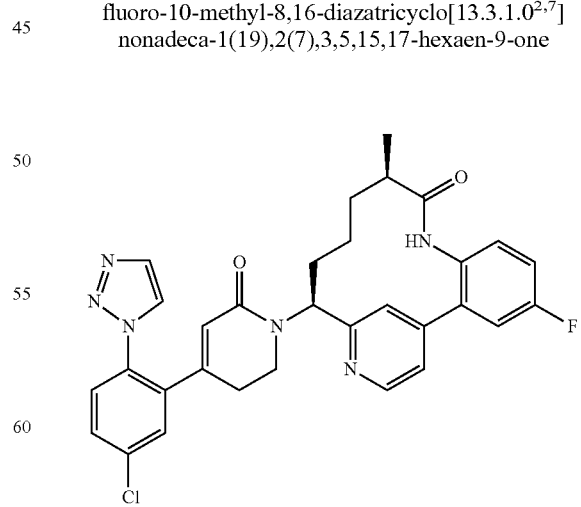

Example 188 was prepared using a procedure analogous to Example 1. MS (ESI) m/z: 571.3 (M+H)⁺. Analytical HPLC (method A): RT=6.34 min, purity >99%. 1H NMR (400 MHz, METHANOL-d4) δ 8.79 (d, J=5.7 Hz, 1H), 8.31 (d, J=1.1 Hz, 1H), 7.99 (d, J=1.1 Hz, 1H), 7.89 (d, J=1.1 Hz, 1H), 7.83 (dd, J=5.7, 1.8 Hz, 1H), 7.66-7.60 (m, 2H), 7.59-7.55 (m, 1H), 7.53-7.48 (m, 1H), 7.36-7.32 (m, 2H), 5.80 (s, 1H), 5.35 (dd, J=12.4, 4.7 Hz, 1H), 3.65-3.46 (m, 2H), 2.58 (m, 1H), 2.36-2.09 (m, 3H), 2.02-1.91 (m, 1H), 1.90-1.76 (m, 1H), 1.62-1.48 (m, 1H), 1.22 (br. s., 1H), 1.03 (d, J=7.0 Hz, 3H), 0.98-0.82 (br. s., 1H)

Example 189

(10R,14S)-14-{4-[5-chloro-2-(1H-1,2,3-triazol-1-yl)phenyl]-6-oxo-1,2,3,6-tetrahydropyridin-1-yl}-10-methyl-8,16-diazatricyclo[13.3.1.0$^{2,7}$]nonadeca-1(19),2(7),3,5,15,17-hexaen-9-one

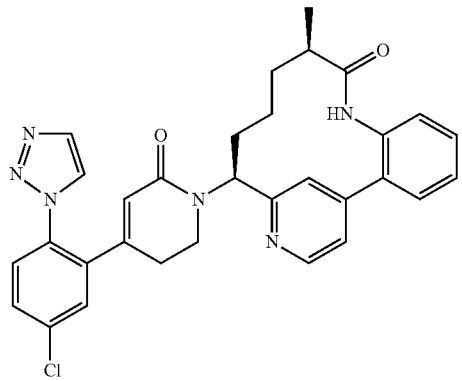

Example 189 was prepared using a procedure analogous to Example 1. MS (ESI) m/z: 553.3 (M+H)$^+$. Analytical HPLC (method D): RT=1.373 min, purity 98%. $^1$H NMR (500 MHz, DMSO-d$_6$) δ 9.68 (s, 1H), 8.63 (d, J=5.0 Hz, 1H), 8.49 (s, 1H), 7.94 (s, 1H), 7.72-7.66 (m, 2H), 7.61 (d, J=8.3 Hz, 1H), 7.57 (d, J=7.4 Hz, 1H), 7.51 (s, 1H), 7.48-7.34 (m, 3H), 7.21 (d, J=7.4 Hz, 1H), 5.68 (s, 1H), 5.49 (dd, J=12.5, 4.3 Hz, 1H), 3.71 (br. s., 2H), 2.54 (br. s., 1H), 2.09-1.92 (m, 3H), 1.86 (br. s., 1H), 1.58 (dt, J=11.3, 5.9 Hz, 1H), 1.46-1.33 (m, 1H), 1.16 (d, J=9.9 Hz, 1H), 0.85 (d, J=6.9 Hz, 3H), 0.50 (br. s., 1H)

Example 190

Methyl N-[(10R,14S)-14-[4-(3-bromo-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate

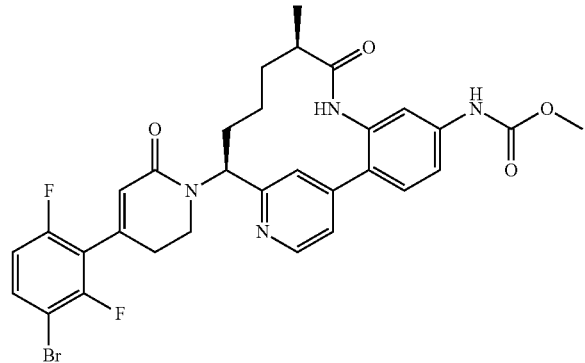 [SMILES: COC(=O)Nc1ccc2c(c1)NC(=O)[C@H](C)CCC[C@H](N1CCC(c3c(F)ccc(Br)c3F)=CC1=O)c1cc-2ccn1]

Example 190 was prepared according to the procedures described in Example 1. $^1$H NMR (400 MHz, METHANOL-d$_4$) δ 9.64-9.57 (m, 1H), 8.78-8.66 (m, 1H), 7.97-7.87 (m, 1H), 7.73-7.67 (m, 2H), 7.65-7.61 (m, 1H), 7.59-7.55 (m, 2H), 7.12-7.04 (m, 1H), 6.15-6.12 (m, 1H), 5.59-5.50 (m, 1H), 3.80 (bs, 6H), 2.85-2.56 (m, 3H), 2.35-2.19 (m, 1H), 2.07-1.90 (m, 2H), 1.65-1.56 (m, 1H), 1.40-1.25 (m, 3H), 1.08 (d, J=6.8 Hz, 3H). MS (ESI) m/z: 639.2 (M+H)$^+$. Analytical HPLC (method B): RT=6.42 min, purity >95%.

Example 191

Methyl N-[(10R,14S)-14-[4-(6-acetyl-3-chloro-2-fluorophenyl)-6-oxo-1,2,3,6-tetrahydropyridin-1-yl]-17-fluoro-10-methyl-9-oxo-8-azatricyclo[13.3.1.0$^{2,7}$]nonadeca-1(19),2,4,6,15,17-hexaen-5-yl]carbamate

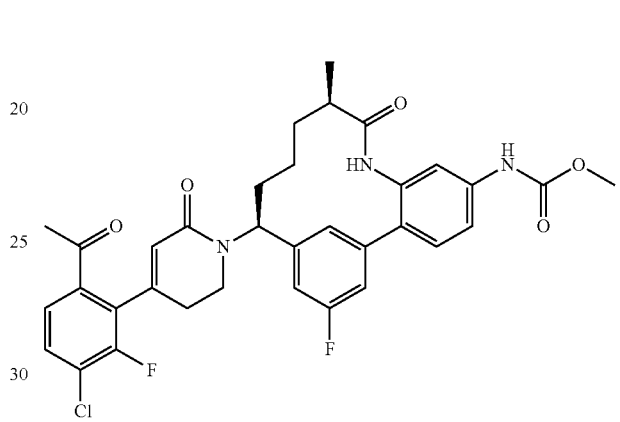

Example 191 was prepared according to the procedures described in Example 161. $^1$H NMR (400 MHz, METHANOL-d$_4$) δ 9.35-9.29 (m, 1H), 7.68-7.61 (m, 2H), 7.56-7.50 (m, 2H), 7.40 (s, 10H), 7.07-7.01 (m, 2H), 6.99-6.93 (m, 2H), 5.64-5.59 (m, 2H), 5.52-5.44 (m, 2H), 3.65 (s, 6H), 3.50-3.42 (m, 2H), 3.19-3.10 (m, 3H), 2.45 (s, 7H), 2.38-2.34 (m, 1H), 2.36-2.24 (m, 6H), 2.16-2.05 (m, 3H), 1.82-1.44 (m, 13H), 1.12-1.04 (m, 9H), 1.02-0.91 (m, 3H) ppm. MS (ESI) m/z: 636.3 (M+H)$^+$. Analytical HPLC (method A): RT=13.56 min., purity >95%.

Example 192

1-[(10R,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]guanidine, 2 TFA Salt

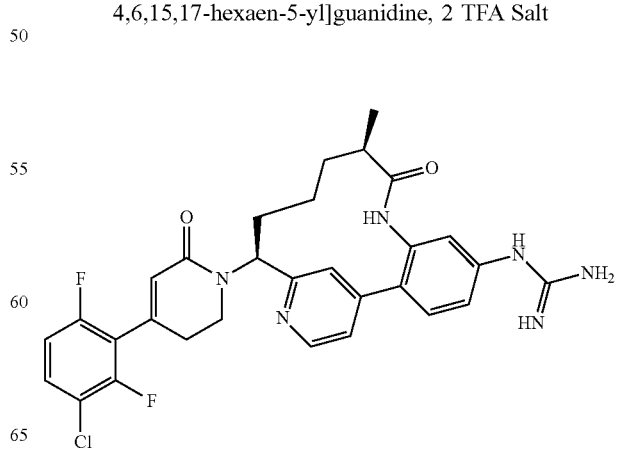

192A: tert-butyl N-[(1Z)-{[(tert-butoxy)carbonyl] imino}({[(10R,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]amino})methyl]carbamate A solution of Example 12 (0.02 g, 0.037 mmol) and (Z)-tert-butyl (((tert-butoxycarbonyl)imino)(1H-pyrazol-1-yl)methyl)carbamate (0.013 g, 0.041 mmol) in DMF (1 mL) and DIEA (0.013 mL, 0.074 mmol) was stirred at RT for 18 h, then warmed to 50° C. for 2 h. The reaction was diluted with MeOH, purified by reverse phase HPLC to afford 192A (0.014 g, 37.3% yield) as a yellow solid. The material was carried onto the next step without further purification.

Example 192

192A (0.014 g, 0.014 mmol) in DCM (1 mL) was added TFA (0.5 mL, 6.49 mmol). The reaction was stirred at rt for 1 h, then concentrated. Purification by reverse phase HPLC afforded Example 192 (1.94 mg, 17.2% yield) as a white solid. $^1$H NMR (400 MHz, METHANOL-d$_4$) δ 8.70 (d, J=5.3 Hz, 1H), 7.73 (d, J=8.1 Hz, 1H), 7.66 (s, 1H), 7.57-7.46 (m, 2H), 7.40 (dd, J=8.3, 2.3 Hz, 1H), 7.23 (d, J=2.2 Hz, 1H), 7.09 (td, J=9.2, 1.8 Hz, 1H), 6.09 (s, 1H), 5.59 (dd, J=12.7, 4.5 Hz, 1H), 4.02-3.92 (m, 1H), 3.81-3.72 (m, 1H), 2.80-2.54 (m, 3H), 2.25-2.14 (m, 1H), 1.98-1.86 (m, 2H), 1.59-1.47 (m, 1H), 1.37-1.25 (m, 1H), 1.07-0.86 (m, 4H). MS (ESI) m/z: 579.2 (M+H)$^+$. Analytical HPLC (method A): RT=5.18 min, purity=99.7%.

Example 193

(10R,14S)-5-amino-4-bromo-14-[4-(3-chloro-2,6-difluorophenyl)-6-oxo-1,2,3,6-tetrahydropyridin-1-yl]-10-methyl-8,16-diazatricyclo[13.3.1.0$^{2,7}$]nonadeca-1(19),2(7),3,5,15,17-hexaen-9-one, 2 TFA Salt

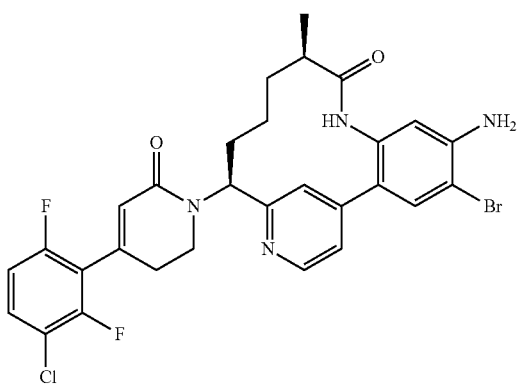 [SMILES: C[C@@H]1CCC[C@H](N2CCC(c3c(F)ccc(Cl)c3F)=CC2=O)c2cc(ccn2)-c2cc(Br)c(N)cc2NC1=O]

Example 193

A solution of Example 12 (0.015 g, 0.028 mmol), 2-chloropyrazine (0.016 g, 0.140 mmol), and 2-bromopyrazine (0.022 g, 0.140 mmol) in DMF (0.8 ml) was microwaved at 150° C. for 60 min. and then the reaction was cooled to rt. Purification by reverse phase HPLC afforded Example 193 (7.4 mg, 31.0% yield) as a yellow solid. $^1$H NMR (400 MHz, METHANOL-d$_4$) δ 8.67 (d, J=6.2 Hz, 1H), 8.04 (d, J=1.8 Hz, 1H), 7.83 (dd, J=6.2, 1.8 Hz, 1H), 7.79 (s, 1H), 7.58-7.50 (m, 1H), 7.10 (td, J=9.2, 1.8 Hz, 1H), 6.74 (s, 1H), 6.11 (s, 1H), 5.39 (dd, J=12.4, 4.5 Hz, 1H), 3.69 (t, J=6.9 Hz, 2H), 2.90-2.55 (m, 3H), 2.34-2.22 (m, 1H), 2.13-2.01 (m, 1H), 1.97-1.86 (m, 1H), 1.69-1.56 (m, 1H), 1.36-1.23 (m, 1H), 1.12-1.00 (m, 4H). MS (ESI) m/z: 615.1 (M+H)$^+$, 617.0 (M+2+H)$^+$. Analytical HPLC (method A): RT=6.80 min, purity=99.2%.

Example 194

Methyl N-[(14S)-14-[4-(3-chloro-2,6-difluorophenyl)-6-oxo-1,2,3,6-tetrahydropyridin-1-yl]-10-methyl-8-oxo-9,16-diazatricyclo[13.3.1.0$^{2,7}$]nonadeca-1(19),2(7),3,5,15,17-hexaen-5-yl]carbamate, diastereomer B, TFA Salt

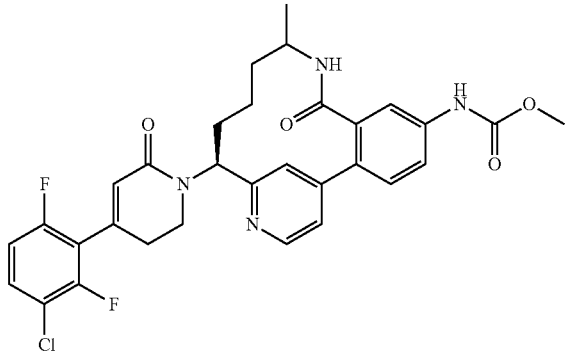 [SMILES: COC(=O)Nc1ccc2c(c1)C(=O)NC(C)CCC[C@H](N1CCC(c3c(F)ccc(Cl)c3F)=CC1=O)c1cc-2ccn1]

Example 194 was prepared using a procedure analogous to Example 24, by replacing prop-2-en-1-amine with but-3-en-2-amine in step 24E. In addition, in step 24F, the diastereomers were separated by normal phase chromatography. The slower eluting diastereomer, designated diastereomer B, was used to prepare the title compound. $^1$H NMR (500 MHz, METHANOL-d$_4$) δ 8.71 (d, J=6.1 Hz, 1H), 8.11 (d, J=1.7 Hz, 1H), 7.96 (dd, J=6.1, 1.7 Hz, 1H), 7.78-7.66 (m, 3H), 7.54 (td, J=8.7, 5.5 Hz, 1H), 7.10 (td, J=9.2, 1.7 Hz, 1H), 6.11 (s, 1H), 5.50 (dd, J=10.6, 4.0 Hz, 1H), 4.23-4.13 (m, 1H), 3.90-3.83 (m, 1H), 3.81-3.74 (m, 4H), 3.01-2.92 (m, 1H), 2.79 (dt, J=17.7, 5.7 Hz, 1H), 2.30-2.21 (m, 1H), 2.03-1.95 (m, 1H), 1.81-1.72 (m, 1H), 1.55-1.46 (m, 1H), 1.43-1.35 (m, 2H), 1.24 (d, J=6.9 Hz, 3H). MS (ESI) m/z: 595.3 (M+H)$^+$. Analytical HPLC (method A): RT=7.00 min, purity=100%.

Example 195

(10R,14S)-14-[4-(3-chloro-2,6-difluorophenyl)-6-oxo-1,2,3,6-tetrahydropyridin-1-yl]-10-methyl-5-[(pyridin-3-yl)amino]-8,16-diazatricyclo[13.3.1.0$^{2,7}$]nonadeca-1(19),2(7),3,5,15,17-hexaen-9-one, 3 TFA Salt

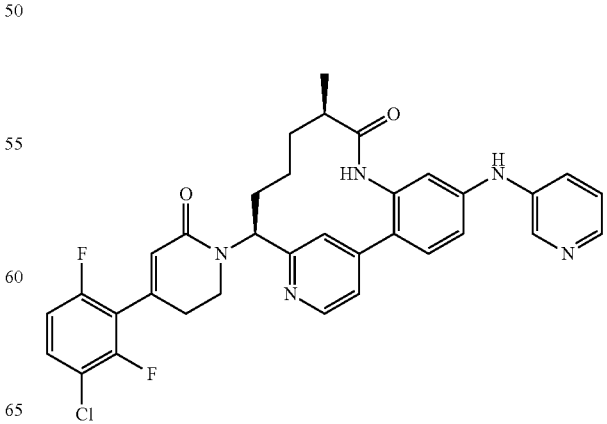

Example 195 was prepared according to the procedure described in Example 93, by replacing 2-chloropyrazine with 3-bromopyridine. A yellow solid. $^1$H NMR (500 MHz, METHANOL-d$_4$) δ 8.74 (d, J=5.5 Hz, 1H), 8.51 (d, J=2.8 Hz, 1H), 8.24 (d, J=5.2 Hz, 1H), 8.20 (ddd, J=8.8, 2.8, 1.1 Hz, 1H), 7.93 (d, J=1.4 Hz, 1H), 7.87 (dd, J=8.5, 5.5 Hz, 1H), 7.75-7.71 (m, 2H), 7.54 (td, J=8.7, 5.5 Hz, 1H), 7.38 (dd, J=8.5, 2.5 Hz, 1H), 7.20 (d, J=2.2 Hz, 1H), 7.10 (td, J=9.3, 1.8 Hz, 1H), 6.10 (s, 1H), 5.48 (dd, J=12.5, 4.5 Hz, 1H), 3.85 (dt, J=12.1, 6.1 Hz, 1H), 3.74 (ddd, J=12.4, 9.7, 5.4 Hz, 1H), 2.86-2.68 (m, 2H), 2.66-2.58 (m, 1H), 2.26 (ddt, J=16.1, 13.0, 3.3 Hz, 1H), 2.07-1.90 (m, 2H), 1.65-1.56 (m, 1H), 1.40-1.28 (m, 1H), 1.10-0.92 (m, 4H). MS (ESI) m/z: 614.2 (M+H)$^+$. Analytical HPLC (method A): RT=5.10 min, purity=98.1%.

Example 196

(10R,14S)-14-[4-(3-chloro-2,6-difluorophenyl)-6-oxo-1,2,3,6-tetrahydropyridin-1-yl]-10-methyl-5-[(pyridazin-3-yl)amino]-8,16-diazatricyclo[13.3.1.0$^{2,7}$]nonadeca-1(19),2(7),3,5,15,17-hexaen-9-one, 2 TFA Salt

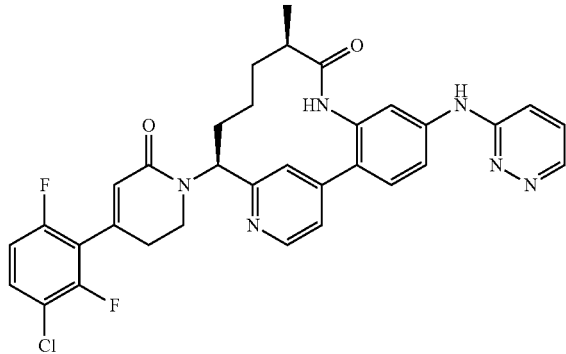

Example 196 was prepared according to the procedure described in Example 93, by replacing 2-chloropyrazine with 3-chloropyridazine. A yellow solid. $^1$H NMR (400 MHz, METHANOL-d$_4$) δ 8.88 (d, J=4.2 Hz, 1H), 8.77 (d, J=5.7 Hz, 1H), 8.05 (d, J=1.1 Hz, 1H), 7.96 (dd, J=9.2, 4.8 Hz, 1H), 7.85-7.71 (m, 5H), 7.54 (td, J=8.7, 5.7 Hz, 1H), 7.10 (td, J=9.2, 1.8 Hz, 1H), 6.10 (s, 1H), 5.43 (dd, J=12.3, 4.6 Hz, 1H), 3.87-3.70 (m, 2H), 2.90-2.60 (m, 3H), 2.34-2.24 (m, 1H), 2.12-2.00 (m, 1H), 1.98-1.89 (m, 1H), 1.67-1.56 (m, 1H), 1.40-1.28 (m, 1H), 1.11-0.93 (m, 4H). MS (ESI) m/z: 615.2 (M+H)$^+$. Analytical HPLC (method A): RT=5.33 min, purity=99.9%.

Example 197

Methyl (10R,14S)-5-amino-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaene-4-carboxylate, 2 TFA Salt

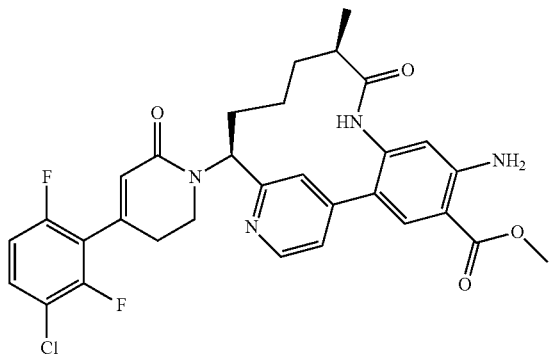 [SMILES: COC(=O)c1cc2c(cc1N)NC(=O)[C@H](C)CCC[C@H](N1CCC(c3c(F)ccc(Cl)c3F)=CC1=O)c1cc-2ccn1]

To a 25 mL round bottomed flask equipped with a stir bar and reflux condenser was added palladium(II) acetate (6.77 mg, 0.030 mmol), DPPF (0.017 g, 0.030 mmol), K$_2$CO$_3$ (0.125 g, 0.905 mmol), TEA (0.042 mL, 0.302 mmol), Example 61 (free of TFA) (0.2 g, 0.302 mmol) and acetonitrile (4 mL)/MeOH (2 mL). The vessel was vacuumed and backfilled with argon three times. Then, carbon monoxide (CO) was bubbled through a needle into the solution for 3 min, and then the mixture was heated under a CO balloon at 70° C. After 3 h, the reaction was cooled to rt, diluted with EtOAc, washed with water, brine, dried over Na$_2$SO$_4$, filtered, and concentrated. Purification by silica gel chromatography afforded a yellow solid (0.153 g). A portion of this solid (32 mg) was purified by reverse phase HPLC to afford Example 197 (0.029 g) as a yellow solid. $^1$H NMR (400 MHz, METHANOL-d$_4$) δ 8.70 (d, J=6.2 Hz, 1H), 8.18 (s, 1H), 8.10 (d, J=1.8 Hz, 1H), 7.92 (dd, J=6.2, 1.8 Hz, 1H), 7.59-7.50 (m, 1H), 7.10 (td, J=9.2, 1.8 Hz, 1H), 6.71 (s, 1H), 6.11 (s, 1H), 5.32 (dd, J=12.3, 4.8 Hz, 1H), 3.90 (s, 3H), 3.82-3.67 (m, 2H), 2.95-2.84 (m, 1H), 2.80-2.61 (m, 2H), 2.37-2.26 (m, 1H), 2.15-1.88 (m, 2H), 1.70-1.59 (m, 1H), 1.44-1.32 (m, 1H), 1.04 (d, J=6.8 Hz, 3H), 0.99-0.85 (m, 1H). MS (ESI) m/z: 595.2 (M+H)$^+$. Analytical HPLC (method A): RT=6.67 min, purity=99.6%.

Example 198

(10R,14S)-5-amino-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaene-4-carboxylic acid, 2 TFA Salt

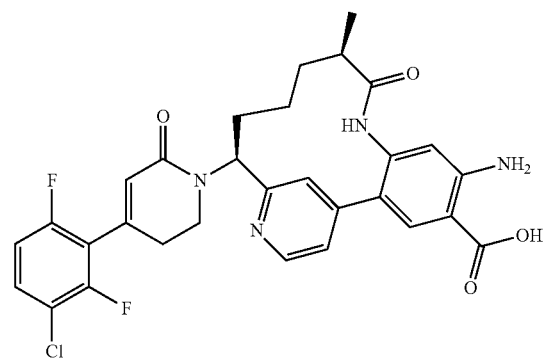 [SMILES: C[C@@H]1CCC[C@H](N2CCC(c3c(F)ccc(Cl)c3F)=CC2=O)c2cc(ccn2)-c2cc(C(=O)O)c(N)cc2NC1=O]

To a solution of Example 197 (0.053 g, 0.089 mmol) in THF (1 mL)/water (1 mL) was added a few drops of MeOH, followed by 1N NaOH (0.356 mL, 0.356 mmol). The reaction was stirred at rt for 18 h and then it was concentrated. Purification by reverse phase HPLC afforded Example 198 (0.036 g, 49.3% yield) as a yellow solid. $^1$H NMR (400 MHz, METHANOL-$d_4$) δ 8.68 (d, J=6.2 Hz, 1H), 8.20 (s, 1H), 8.06 (d, J=1.8 Hz, 1H), 7.88 (dd, J=6.2, 1.8 Hz, 1H), 7.54 (td, J=8.7, 5.7 Hz, 1H), 7.10 (td, J=9.3, 1.9 Hz, 1H), 6.70 (s, 1H), 6.11 (s, 1H), 5.35 (dd, J=12.2, 4.7 Hz, 1H), 3.82-3.66 (m, 2H), 2.93-2.59 (m, 3H), 2.36-2.25 (m, 1H), 2.13-1.89 (m, 2H), 1.70-1.58 (m, 1H), 1.43-1.30 (m, 1H), 1.08-0.86 (m, 4H). MS (ESI) m/z: 581.2 (M+H)$^+$. Analytical HPLC (method A): RT=6.03 min, purity=98.7%.

Example 199

(14R,18S)-18-[4-(3-chloro-2,6-difluorophenyl)-6-oxo-1,2,3,6-tetrahydropyridin-1-yl]-5-hydroxy-14-methyl-8,12,20-triazatetracyclo[17.3.1.0$^{2,11}$.0$^{4,9}$]tricosa-1(23),2,4(9),5,10,19,21-heptaene-7,13-dione, TFA Salt

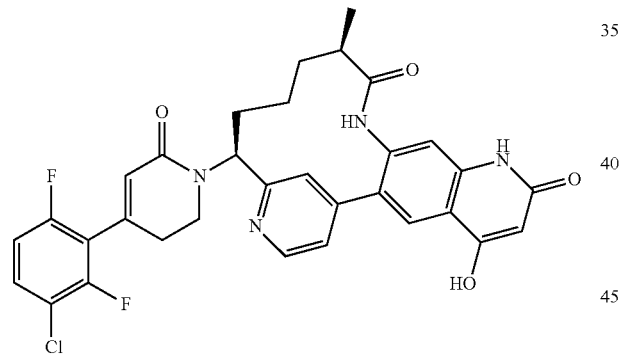

199A: (14R,18S)-18-[4-(3-chloro-2,6-difluorophenyl)-6-oxo-1,2,3,6-tetrahydropyridin-1-yl]-5-methoxy-14-methyl-8,12,20-triazatetracyclo[17.3.1.0$^{2,11}$.0$^{4,9}$]tricosa-1(23),2,4(9),5,10,19,21-heptaene-7,13-dione, TFA Salt A solution of Example 197 (0.02 g, 0.034 mmol) and (triphenylphosphoranylidene)ketene (0.020 g, 0.067 mmol) in THF (0.8 mL) was stirred at rt for 60 min. Then, the reaction was microwaved at 180° C. for 30 min, cooled to rt and concentrated. Purification by reverse phase HPLC afforded 199A (0.009 g, 36.5% yield) as a yellow solid. MS (ESI) m/z: 619.2 (M+H)$^+$.

Example 199

A mixture of 199A (0.009 g, 0.012 mmol) in 6N HCl (1 mL, 6.00 mmol) was microwaved at 100° C. for 30 min, cooled to rt, and concentrated. Purification by reverse phase HPLC (two times) afforded Example 199 (1.5 mg, 16.9% yield) as a white solid. $^1$H NMR (400 MHz, METHANOL-$d_4$) δ 8.75 (d, J=5.5 Hz, 1H), 8.20 (s, 1H), 7.90 (s, 1H), 7.76 (dd, J=5.5, 1.5 Hz, 1H), 7.53 (td, J=8.7, 5.5 Hz, 1H), 7.26 (s, 1H), 7.09 (td, J=9.2, 1.8 Hz, 1H), 6.11 (s, 1H), 5.93 (s, 1H), 5.52 (dd, J=12.3, 4.8 Hz, 1H), 3.97-3.88 (m, 1H), 3.76 (ddd, J=12.4, 9.7, 5.4 Hz, 1H), 2.88-2.61 (m, 3H), 2.31-2.20 (m, 1H), 2.05-1.89 (m, 2H), 1.66-1.54 (m, 1H), 1.44-1.30 (m, 1H), 1.04 (d, J=6.8 Hz, 3H), 0.97-0.82 (m, 1H). MS (ESI) m/z: 605.2 (M+H)$^+$. Analytical HPLC (method A): RT=6.00 min, purity=99.5%.

Example 200

(10R,14S)-14-[4-(3-chloro-2,6-difluorophenyl)-2-oxo-1,2-dihydropyridin-1-yl]-3-fluoro-10-methyl-8,16-diazatricyclo[13.3.1.0$^{2,7}$]nonadeca-1(19),2(7),3,5,15,17-hexaen-9-one, TFA Salt

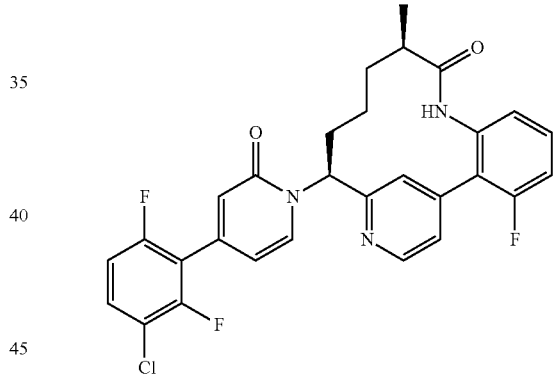

Example 200

To a sealable vial containing Example 80 (0.02 g, 0.031 mmol) and copper(I) iodide (0.582 mg, 3.06 μmol) in DMSO (1 mL) was added 3-iodopyridine (0.013 g, 0.061 mmol) and Cs$_2$CO$_3$ (0.040 g, 0.122 mmol). The vial was vacuumed and back-filled with argon three times, then the vial was sealed and then it was heated at 80° C. After 20 h, the reaction was cooled to rt, diluted with MeOH, filtered and purified by reverse phase HPLC to afford Example 200 (4.24 mg, 20.8% yield) as a white solid. $^1$H NMR (400 MHz, METHANOL-$d_4$) δ 8.68 (d, J=5.1 Hz, 1H), 8.39 (d, J=6.8 Hz, 1H), 7.71 (s, 1H), 7.63-7.46 (m, 3H), 7.25 (ddd, J=9.7, 8.5, 0.9 Hz, 1H), 7.18-7.11 (m, 2H), 6.65 (s, 1H), 6.56 (dd, J=7.3, 1.5 Hz, 1H), 6.11 (dd, J=12.5, 4.8 Hz, 1H), 2.66-2.57 (m, 1H), 2.33-2.23 (m, 1H), 2.13-2.02 (m, 1H), 1.94-1.83 (m, 1H), 1.54-1.34 (m, 2H), 0.97 (d, J=7.0 Hz, 3H), 0.86-0.70 (m, 1H). MS (ESI) m/z: 538.1 (M+H)$^+$. Analytical HPLC (method A): RT=9.35 min, purity=99.5%.

Example 201

(10R,14S)-14-[4-(3-chloro-2,6-difluorophenyl)-6-oxo-1,2,3,6-tetrahydropyridin-1-yl]-3,5-difluoro-10-methyl-8,16-diazatricyclo[13.3.1.0$^{2,7}$]nonadeca-1(19),2(7),3,5,15,17-hexaen-9-one, TFA Salt

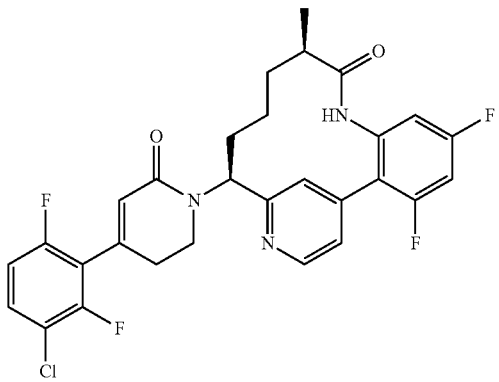 [SMILES: C[C@@H]1CCC[C@H](N2CCC(c3c(F)ccc(Cl)c3F)=CC2=O)c2cc(ccn2)-c2c(F)cc(F)cc2NC1=O]

Example 201 was prepared according to the procedures described in Example 80, by replacing 2-bromo-3-fluoroaniline in step 80A with 2-chloro-3,5-difluoroaniline. $^1$H NMR (400 MHz, METHANOL-d$_4$) δ 8.76 (d, J=5.7 Hz, 1H), 7.82 (s, 1H), 7.77-7.73 (m, 1H), 7.54 (td, J=8.7, 5.5 Hz, 1H), 7.18 (ddd, J=10.5, 8.7, 2.6 Hz, 1H), 7.09 (td, J=9.2, 1.8 Hz, 1H), 7.00 (dt, J=9.1, 2.1 Hz, 1H), 6.11 (s, 1H), 5.47 (dd, J=12.3, 4.8 Hz, 1H), 3.99-3.90 (m, 1H), 3.78 (ddd, J=12.5, 9.5, 5.5 Hz, 1H), 2.89-2.68 (m, 2H), 2.62-2.52 (m, 1H), 2.30-2.19 (m, 1H), 2.06-1.95 (m, 1H), 1.86-1.75 (m, 1H), 1.55-1.42 (m, 1H), 1.37-1.24 (m, 1H), 0.99 (d, J=7.0 Hz, 3H), 0.92-0.76 (m, 1H). MS (ESI) m/z: 558.2 (M+H)$^+$. Analytical HPLC (method A): RT=8.50 min, purity=98.8%.

Example 202

(10R,14S)-14-[4-(6-bromo-3-chloro-2-fluorophenyl)-6-oxo-1,2,3,6-tetrahydropyridin-1-yl]-3,5-difluoro-10-methyl-8,16-diazatricyclo[13.3.1.0$^{2,7}$]nonadeca-1(19),2(7),3,5,15,17-hexaen-9-one

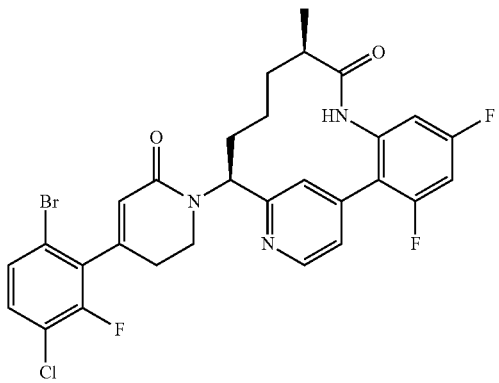 [SMILES: C[C@@H]1CCC[C@H](N2CCC(c3c(Br)ccc(Cl)c3F)=CC2=O)c2cc(ccn2)-c2c(F)cc(F)cc2NC1=O]

Example 202 was prepared according to the procedures described in Example 80, by replacing 2-bromo-3-fluoroaniline in step 80A with 2-chloro-3,5-difluoroaniline and by replacing Intermediate 1 with Intermediate 2. $^1$H NMR (400 MHz, METHANOL-d$_4$) δ 8.65 (d, J=5.1 Hz, 1H), 7.53-7.38 (m, 4H), 7.12 (ddd, J=10.2, 8.9, 2.5 Hz, 1H), 6.95 (dt, J=9.2, 2.0 Hz, 1H), 5.92 (t, J=1.4 Hz, 1H), 5.66 (dd, J=12.7, 4.7 Hz, 1H), 4.17-4.05 (m, 1H), 3.92-3.83 (m, 1H), 2.72-2.48 (m, 3H), 2.22-2.11 (m, 1H), 1.91-1.77 (m, 2H), 1.48-1.19 (m, 2H), 0.99 (d, J=7.0 Hz, 3H), 0.93-0.79 (m, 1H). MS (ESI) m/z: 618.1 (M+H)$^+$. Analytical HPLC (method A): RT=8.95 min, purity=98.8%.

Example 203

(10R,14S)-14-[4-(3-chloro-2,6-difluorophenyl)-6-oxo-1,2,3,6-tetrahydropyridin-1-yl]-3,4-difluoro-10-methyl-8,16-diazatricyclo[13.3.1.0$^{2,7}$]nonadeca-1(19),2(7),3,5,15,17-hexaen-9-one, TFA Salt

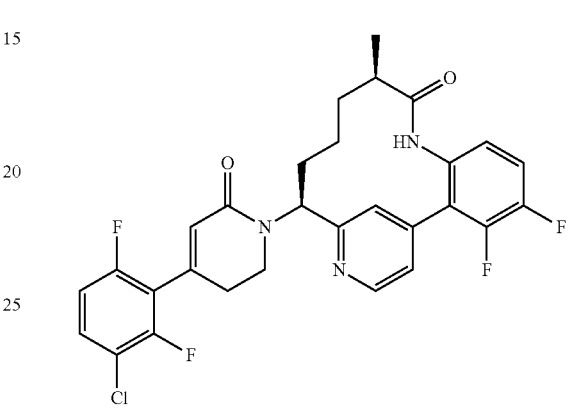

Example 203 was prepared according to the procedures described in Example 80, by replacing 2-bromo-3-fluoroaniline in step 80A with 2-chloro-3,4-difluoroaniline. $^1$H NMR (400 MHz, METHANOL-d$_4$) δ 8.76 (d, J=5.3 Hz, 1H), 7.73 (s, 1H), 7.70-7.66 (m, 1H), 7.57-7.41 (m, 2H), 7.18-7.05 (m, 2H), 6.10 (s, 1H), 5.54 (dd, J=12.5, 4.6 Hz, 1H), 4.00-3.90 (m, 1H), 3.78 (ddd, J=12.4, 9.2, 5.6 Hz, 1H), 2.85-2.66 (m, 2H), 2.58-2.48 (m, 1H), 2.27-2.16 (m, 1H), 2.03-1.91 (m, 1H), 1.86-1.75 (m, 1H), 1.51-1.18 (m, 2H), 1.04-0.83 (m, 4H). MS (ESI) m/z: 558.2 (M+H)$^+$. Analytical HPLC (method A): RT=8.64 min, purity=99.9%.

Example 204

(10R,14S)-14-[4-(6-bromo-3-chloro-2-fluorophenyl)-6-oxo-1,2,3,6-tetrahydropyridin-1-yl]-3,4-difluoro-10-methyl-8,16-diazatricyclo[13.3.1.0$^{2,7}$]nonadeca-1(19),2(7),3,5,15,17-hexaen-9-one, TFA Salt

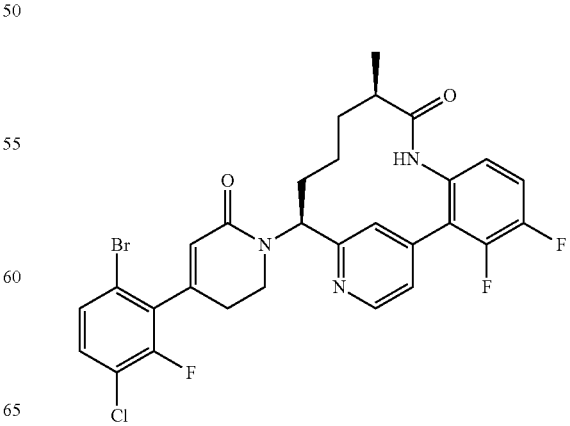

Example 204 was prepared according to the procedures described in Example 80, by replacing 2-bromo-3-fluoroaniline in step 80A with 2-chloro-3,4-difluoroaniline and by replacing Intermediate 1 with Intermediate 2. $^1$H NMR (400 MHz, METHANOL-$d_4$) δ 8.76 (d, J=5.5 Hz, 1H), 7.73 (s, 1H), 7.70-7.66 (m, 1H), 7.53-7.40 (m, 3H), 7.16 (ddd, J=8.9, 4.5, 1.9 Hz, 1H), 5.93 (s, 1H), 5.56 (dd, J=12.3, 4.6 Hz, 1H), 4.06-3.95 (m, 1H), 3.85 (ddd, J=12.4, 9.1, 5.7 Hz, 1H), 2.78-2.48 (m, 3H), 2.28-2.17 (m, 1H), 2.02-1.92 (m, 1H), 1.86-1.75 (m, 1H), 1.51-1.16 (m, 2H), 1.04-0.85 (m, 4H). MS (ESI) m/z: 618.2 (M+H)$^+$. Analytical HPLC (method A): RT=9.27 min, purity=100%.

Example 205

(10R,14S)-14-[4-(3-chloro-2,6-difluorophenyl)-6-oxo-1,2,3,6-tetrahydropyridin-1-yl]-4,5-difluoro-10-methyl-8,16-diazatricyclo[13.3.1.0$^{2,7}$]nonadeca-1(19),2(7),3,5,15,17-hexaen-9-one, TFA Salt

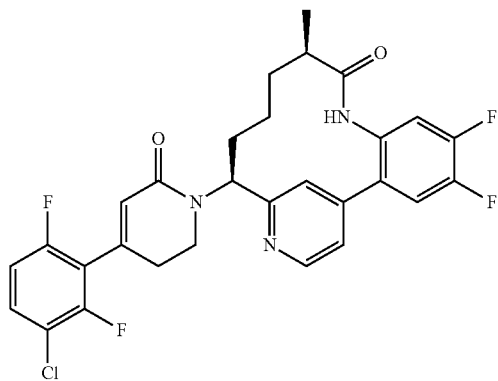 [SMILES: C[C@@H]1CCC[C@H](N2CCC(c3c(F)ccc(Cl)c3F)=CC2=O)c2cc(ccn2)-c2cc(F)c(F)cc2NC1=O]

Example 205 was prepared according to the procedures described in Example 80, by replacing 2-bromo-3-fluoroaniline in step 80A with 2-bromo-4,5-difluoroaniline. $^1$H NMR (400 MHz, METHANOL-$d_4$) δ 8.78 (d, J=5.7 Hz, 1H), 7.93 (d, J=1.3 Hz, 1H), 7.75-7.65 (m, 2H), 7.57-7.49 (m, 1H), 7.31 (dd, J=11.0, 7.5 Hz, 1H), 7.09 (td, J=9.3, 1.9 Hz, 1H), 6.10 (s, 1H), 5.47 (dd, J=12.4, 4.7 Hz, 1H), 3.88 (dt, J=12.3, 6.3 Hz, 1H), 3.75 (ddd, J=12.4, 9.6, 5.5 Hz, 1H), 2.87-2.67 (m, 2H), 2.64-2.54 (m, 1H), 2.30-2.19 (m, 1H), 2.07-1.84 (m, 2H), 1.62-1.50 (m, 1H), 1.37-1.24 (m, 1H), 1.03 (d, J=6.8 Hz, 3H), 0.97-0.84 (m, 1H). MS (ESI) m/z: 558.3 (M+H)+. Analytical HPLC (method A): RT=8.15 min, purity=99.8%.

Example 206

(10R,14S)-14-[4-(6-bromo-3-chloro-2-fluorophenyl)-6-oxo-1,2,3,6-tetrahydropyridin-1-yl]-4,5-difluoro-10-methyl-8,16-diazatricyclo[13.3.1.0$^{2,7}$]nonadeca-1(19),2(7),3,5,15,17-hexaen-9-one, TFA Salt

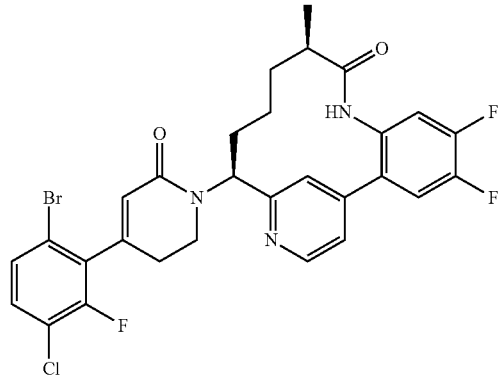 [SMILES: C[C@@H]1CCC[C@H](N2CCC(c3c(Br)ccc(Cl)c3F)=CC2=O)c2cc(ccn2)-c2cc(F)c(F)cc2NC1=O]

Example 206 was prepared according to the procedures described in Example 80, by replacing 2-bromo-3-fluoroaniline in step 80A with 2-bromo-4,5-difluoroaniline and by replacing Intermediate 1 with Intermediate 2. $^1$H NMR (400 MHz, METHANOL-$d_4$) δ 8.78 (d, J=5.5 Hz, 1H), 7.93 (d, J=1.3 Hz, 1H), 7.75-7.66 (m, 2H), 7.54-7.49 (m, 1H), 7.47-7.41 (m, 1H), 7.31 (dd, J=10.9, 7.4 Hz, 1H), 5.94-5.91 (m, 1H), 5.49 (dd, J=12.4, 4.7 Hz, 1H), 3.98-3.89 (m, 1H), 3.81 (ddd, J=12.4, 9.5, 5.4 Hz, 1H), 2.80-2.55 (m, 3H), 2.31-2.20 (m, 1H), 2.07-1.84 (m, 2H), 1.63-1.51 (m, 1H), 1.37-1.24 (m, 1H), 1.03 (d, J=7.0 Hz, 3H), 0.97-0.82 (m, 1H). MS (ESI) m/z: 618.1 (M+H)+. Analytical HPLC (method A): RT=8.73 min, purity=99.7%.

Example 207

4-chloro-2-{1-[(10R,14S)-3,5-difluoro-10-methyl-9-oxo-8,16-diazatricyclo[13.3.1.0$^{2,7}$]nonadeca-1(19),2(7),3,5,15,17-hexaen-14-yl]-6-oxo-1,2,3,6-tetrahydropyridin-4-yl}-3-fluorobenzonitrile, TFA Salt

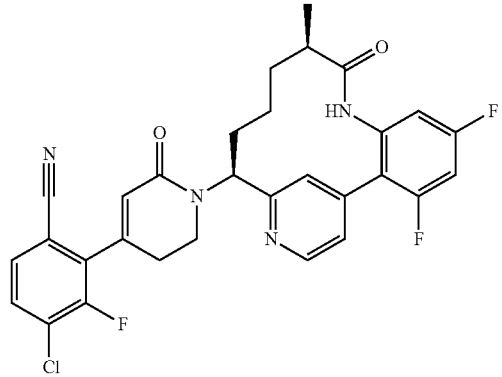 [SMILES: C[C@@H]1CCC[C@H](N2CCC(c3c(C#N)ccc(Cl)c3F)=CC2=O)c2cc(ccn2)-c2c(F)cc(F)cc2NC1=O]

Example 207

The mixture of Example 202 (0.012 g, 0.019 mmol) and zinc cyanide (2.277 mg, 0.019 mmol) in DMF (0.7 ml) was vacuumed and back filled with argon three times, then added bis(tri-t-butylphosphine)palladium(0) (0.991 mg, 1.939 μmol) and zinc (0.380 mg, 5.82 μmol) was added and the vial was sealed. The reaction was microwaved at 150° C. for 0.5 h and then cooled to rt. Purification by reverse phase HPLC afforded Example 207 (3.27 mg, 24.8% yield) as a white solid. $^1$H NMR (400 MHz, METHANOL-$d_4$) δ 8.76 (d, J=5.7 Hz, 1H), 7.78 (s, 1H), 7.75-7.64 (m, 3H), 7.19 (ddd, J=10.3, 8.7, 2.5 Hz, 1H), 7.00 (dd, J=9.1, 1.7 Hz, 1H), 6.18 (s, 1H), 5.52 (dd, J=12.5, 4.8 Hz, 1H), 4.09-3.96 (m, 1H), 3.88-3.79 (m, 1H), 2.93-2.71 (m, 2H), 2.62-2.51 (m, 1H), 2.30-2.17 (m, 1H), 2.05-1.94 (m, 1H), 1.88-1.76 (m, 1H), 1.55-1.41 (m, 1H), 1.37-1.24 (m, 1H), 0.99 (d, J=6.8 Hz, 3H), 0.92-0.71 (m, 1H). MS (ESI) m/z: 565.3 (M+H)$^+$. Analytical HPLC (method A): RT=7.90 min, purity=99.9%.

Example 208

4-chloro-2-{1-[(10R,14S)-3,4-difluoro-10-methyl-9-oxo-8,16-diazatricyclo[13.3.1.0$^{2,7}$]nonadeca-1(19),2(7),3,5,15,17-hexaen-14-yl]-6-oxo-1,2,3,6-tetrahydropyridin-4-yl}-3-fluorobenzonitrile, TFA Salt

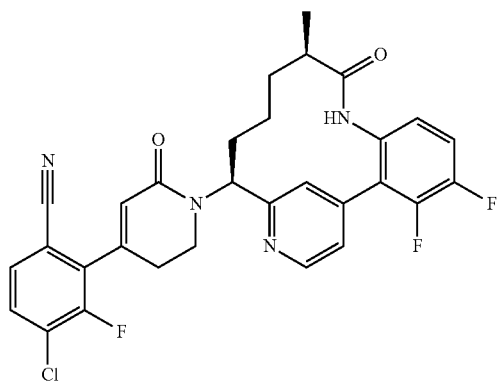 [SMILES: C[C@@H]1CCC[C@H](N2CCC(c3c(C#N)ccc(Cl)c3F)=CC2=O)c2cc(ccn2)-c2c(ccc(F)c2F)NC1=O]

Example 208 was prepared according to the procedure described in Example 207, by replacing Example 202 with Example 204. $^1$H NMR (400 MHz, METHANOL-$d_4$) δ 8.76 (d, J=5.3 Hz, 1H), 7.75-7.63 (m, 4H), 7.50-7.40 (m, 1H), 7.15 (ddd, J=8.8, 4.4, 1.8 Hz, 1H), 6.18 (s, 1H), 5.57 (dd, J=12.5, 4.6 Hz, 1H), 4.08-3.96 (m, 1H), 3.88-3.79 (m, 1H), 2.90-2.70 (m, 2H), 2.59-2.48 (m, 1H), 2.28-2.16 (m, 1H), 2.03-1.92 (m, 1H), 1.87-1.75 (m, 1H), 1.51-1.38 (m, 1H), 1.31-1.18 (m, 1H), 1.05-0.81 (m, 4H). MS (ESI) m/z: 565.2 (M+H)$^+$. Analytical HPLC (method A): RT=8.17 min, purity=99.1%.

Example 209

2-{1-[(10R,14S)-3,4-difluoro-10-methyl-9-oxo-8,16-diazatricyclo[13.3.1.0$^{2,7}$]nonadeca-1(19),2(7),3,5,15,17-hexaen-14-yl]-6-oxo-1,2,3,6-tetrahydropyridin-4-yl}-3-fluorobenzene-1,4-dicarbonitrile, TFA Salt

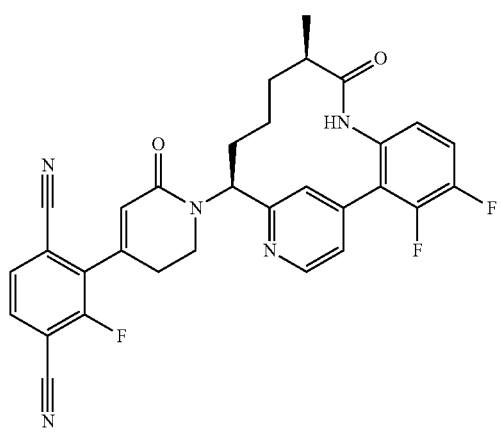 [SMILES: C[C@@H]1CCC[C@H](N2CCC(c3c(C#N)ccc(C#N)c3F)=CC2=O)c2cc(ccn2)-c2c(ccc(F)c2F)NC1=O]

Example 209 was obtained as a by-product in the procedure described for Example 208. $^1$H NMR (400 MHz, METHANOL-$d_4$) d 8.78 (d, J=5.3 Hz, 1H), 7.96 (dd, J=8.1, 6.2 Hz, 1H), 7.86-7.81 (m, 1H), 7.77 (s, 1H), 7.74-7.69 (m, 1H), 7.51-7.41 (m, 1H), 7.16 (ddd, J=8.9, 4.4, 1.7 Hz, 1H), 6.23 (s, 1H), 5.56 (dd, J=12.3, 4.6 Hz, 1H), 4.07-3.96 (m, 1H), 3.89-3.79 (m, 1H), 2.92-2.71 (m, 2H), 2.59-2.49 (m, 1H), 2.28-2.16 (m, 1H), 2.05-1.93 (m, 1H), 1.87-1.75 (m, 1H), 1.52-1.38 (m, 1H), 1.33-1.18 (m, 1H), 1.05-0.81 (m, 4H). MS (ESI) m/z: 556.2 (M+H)$^+$. Analytical HPLC (method A): RT=7.39 min, purity=99.9%.

Example 210

2-{1-[(10R,14S)-4,5-difluoro-10-methyl-9-oxo-8,16-diazatricyclo[13.3.1.0$^{2,7}$]nonadeca-1(19),2(7),3,5,15,17-hexaen-14-yl]-6-oxo-1,2,3,6-tetrahydropyridin-4-yl}-3-fluorobenzene-1,4-dicarbonitrile, TFA Salt

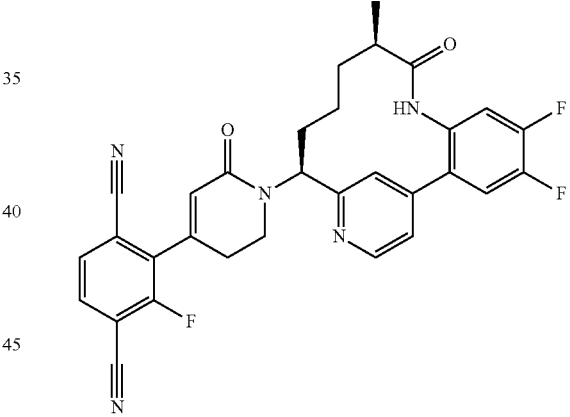

Example 210 was obtained as a by-product following the procedure described in Example 207, by replacing Example 202 with Example 206 and by using 1.5 eq. of zinc cyanide. $^1$H NMR (400 MHz, METHANOL-$d_4$) δ 8.78 (d, J=5.5 Hz, 1H), 7.97 (dd, J=7.9, 6.2 Hz, 1H), 7.91 (d, J=1.3 Hz, 1H), 7.83 (dd, J=8.1, 0.7 Hz, 1H), 7.73-7.66 (m, 2H), 7.31 (dd, J=10.9, 7.4 Hz, 1H), 6.22 (s, 1H), 5.52 (dd, J=12.5, 4.6 Hz, 1H), 3.95 (dt, J=12.2, 6.0 Hz, 1H), 3.81 (ddd, J=12.4, 9.6, 5.5 Hz, 1H), 2.93-2.72 (m, 2H), 2.64-2.55 (m, 1H), 2.30-2.18 (m, 1H), 2.07-1.85 (m, 2H), 1.63-1.50 (m, 1H), 1.37-1.25 (m, 1H), 1.02 (d, J=7.0 Hz, 3H), 0.97-0.81 (m, 1H). MS (ESI) m/z: 556.3 (M+H)$^+$. Analytical HPLC (method A): RT=7.06 min, purity=99.7%.

Example 211

4-chloro-2-{1-[(10R,14S)-4, 5-difluoro-10-methyl-9-oxo-8,16-diazatricyclo[13.3.1.0²,⁷]nonadeca-1(19),2(7),3,5,15,17-hexaen-14-yl]-6-oxo-1,2,3,6-tetrahydropyridin-4-yl}-3-fluorobenzonitrile, TFA Salt

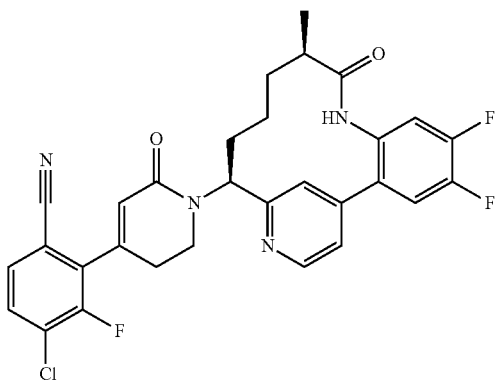 [SMILES: C[C@@H]1CCC[C@H](N2CCC(c3c(C#N)ccc(Cl)c3F)=CC2=O)c2cc(ccn2)-c2cc(F)c(F)cc2NC1=O]

Example 211 was prepared according to the procedure described in Example 207, by replacing Example 202 with Example 206 and by using less zinc cyanide (0.45 eq). ¹H NMR (400 MHz, METHANOL-d₄) δ 8.77 (d, J=5.5 Hz, 1H), 7.90 (d, J=1.1 Hz, 1H), 7.74-7.64 (m, 4H), 7.30 (dd, J=11.0, 7.5 Hz, 1H), 6.17 (s, 1H), 5.52 (dd, J=12.5, 4.8 Hz, 1H), 3.99-3.90 (m, 1H), 3.80 (ddd, J=12.4, 9.5, 5.4 Hz, 1H), 2.90-2.71 (m, 2H), 2.64-2.54 (m, 1H), 2.30-2.18 (m, 1H), 2.07-1.84 (m, 2H), 1.62-1.50 (m, 1H), 1.37-1.25 (m, 1H), 1.03 (d, J=7.0 Hz, 3H), 0.96-0.82 (m, 1H). MS (ESI) m/z: 565.2 (M+H)⁺. Analytical HPLC (method A): RT=7.73 min, purity=99.8%.

Example 212

(10R,14S)-14-[4-(3-chloro-2-fluorophenyl)-2-oxo-1,2-dihydropyridin-1-yl]-3,5-difluoro-10-methyl-8,16-diazatricyclo[13.3.1.0²,⁷]nonadeca-1(19),2(7),3,5,15,17-hexaen-9-one, TFA Salt

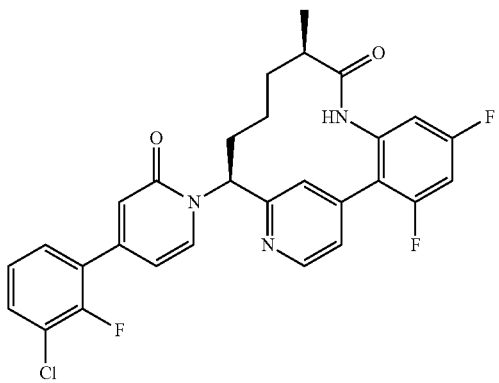 [SMILES: C[C@@H]1CCC[C@H](n2ccc(-c3cccc(Cl)c3F)cc2=O)c2cc(ccn2)-c2c(F)cc(F)cc2NC1=O]

A mixture of Example 202 (0.02 g, 0.032 mmol), 28% aq. ammonium hydroxide (0.058 mL, 0.420 mmol), copper(I) oxide (0.925 mg, 6.46 μmol), and potassium carbonate (0.013 g, 0.097 mmol) in DMF (0.5 mL) was bubbled with Ar for a few minutes and then the vial was sealed. The reaction was heated at 95° C. for 18 h and then the reaction was cooled to rt. The reaction was diluted with MeOH, filtered, and purified by reverse phase HPLC to afford Example 212 (5.84 mg, 26.7% yield) as a yellow solid. ¹H NMR (400 MHz, METHANOL-d₄) δ 8.68 (d, J=5.1 Hz, 1H), 8.37 (d, J=7.0 Hz, 1H), 7.70 (s, 1H), 7.61-7.45 (m, 3H), 7.28 (td, J=8.0, 1.0 Hz, 1H), 7.13 (ddd, J=10.2, 8.9, 2.5 Hz, 1H), 6.96 (dt, J=9.1, 1.9 Hz, 1H), 6.73-6.66 (m, 2H), 6.10 (dd, J=12.5, 5.1 Hz, 1H), 2.67-2.57 (m, 1H), 2.35-2.24 (m, 1H), 2.12-2.01 (m, 1H), 1.94-1.82 (m, 1H), 1.55-1.34 (m, 2H), 0.96 (d, J=6.8 Hz, 3H), 0.83-0.63 (m, 1H). MS (ESI) m/z: 538.2 (M+H)⁺. Analytical HPLC (method A): RT=9.82 min, purity=96.9%.

Example 213

Methyl (10R,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0²,⁷]nonadeca-1(19),2(7),3,5,15,17-hexaene-3-carboxylate, TFA Salt

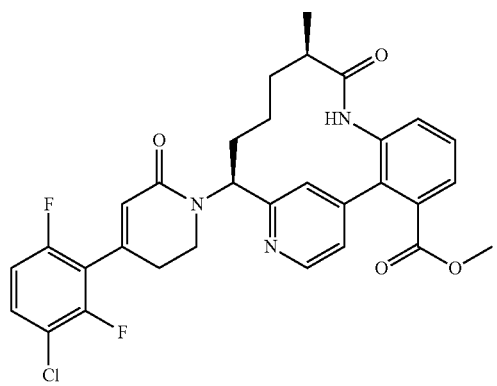 [SMILES: COC(=O)c1cccc2c1-c1ccnc(c1)[C@@H](N1CCC(c3c(F)ccc(Cl)c3F)=CC1=O)CCC[C@@H](C)C(=O)N2]

213A: methyl 2-chloro-3-nitrobenzoate

To the solution of 2-chloro-3-nitrobenzoic acid (1 g, 4.96 mmol), DMF (0.02 ml, 0.258 mmol) in DCM (20 mL) at 0° C. was added dropwise oxalyl chloride (0.478 ml, 5.46 mmol). The reaction was warmed to rt after the addition. After 3 h, methanol (10 mL) was added dropwise to the reaction mixture and the reaction was stirred at rt for 18 h and then the reaction was concentrated. The residue was dissolved in dichloromethane and passed through a plug of silica gel eluting with a 50% ethyl acetate/n-hexanes mixture. The filtrate was concentrated in vacuo to give the title compound as a white solid (1 g, 93% yield). MS (ESI) m/z: 216.0 (M+H)⁺.

213B: methyl 3-amino-2-chlorobenzoate

To the solution of 213A: (1 g, 4.64 mmol) in MeOH (23.19 ml) was added ammonium chloride (2.481 g, 46.4 mmol) and zinc dust (1.516 g, 23.19 mmol). The reaction was stirred at rt for 2 h, then warmed to 60° C. for 1 h. The reaction was filtered through a pad of Celite, rinsing with MeOH. The filtrate was concentrated. The residue was partitioned between EtOAc and water and the layers were separated. The organic layer washed with sat. NaHCO₃, brine, dried over Na₂SO₄, filtered, and concentrated. Purification by silica gel chromatography afforded 213B (0.85 g, 99% yield) as a yellow oil. MS (ESI) m/z: 186.0 (M+H)+.

Example 213 was prepared according to the procedures described in Example 80, by replacing 2-bromo-3-fluoroaniline in step 80A with 213B. $^1$H NMR (500 MHz, DMSO-$d_6$) 90° C., δ 8.57 (d, J=5.0 Hz, 1H), 7.77 (dd, J=7.7, 1.1 Hz, 1H), 7.65-7.54 (m, 2H), 7.44 (dd, J=7.8, 1.2 Hz, 1H), 7.36 (s, 1H), 7.20 (td, J=9.2, 1.7 Hz, 1H), 7.06 (dd, J=5.1, 1.5 Hz, 1H), 6.03 (s, 1H), 5.52 (dd, J=12.2, 4.5 Hz, 1H), 4.06-3.94 (m, 1H), 3.82-3.73 (m, 1H), 3.65 (s, 3H), 2.66 (t, J=6.5 Hz, 2H), 2.40-2.31 (m, 1H), 2.05-1.95 (m, 1H), 1.87-1.77 (m, 1H), 1.61-1.52 (m, 1H), 1.22-0.96 (m, 3H), 0.93 (d, J=6.9 Hz, 3H). MS (ESI) m/z: 580.3 (M+H)+. Analytical HPLC (method A): RT=7.16 min, purity=98.8%.

Example 214

(10R,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0[2,7]]nonadeca-1(19),2(7),3,5,15,17-hexaene-3-carboxylic acid, TFA Salt

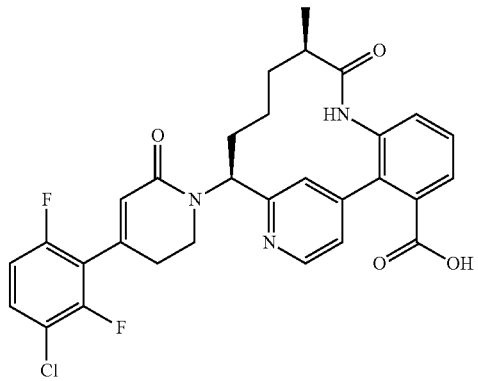 [SMILES: C[C@@H]1CCC[C@H](N2CCC(c3c(F)ccc(Cl)c3F)=CC2=O)c2cc(ccn2)-c2c(cccc2C(=O)O)NC1=O]

Example 214

To the solution of Example 213 (0.007 g, 10.09 μmol) in THF (1 mL) was added a few drops of MeOH, followed by 1N NaOH (0.050 mL, 0.050 mmol). The reaction was stirred at rt for 18 h and then it was quenched with 1N HCl. Purification by reverse phase HPLC afforded Example 214 (0.0055 g, 80% yield) as a white solid. $^1$H NMR (500 MHz, DMSO-$d_6$, with two drops of D$_2$O, 120° C.) δ 8.56 (d, J=4.7 Hz, 1H), 7.75 (dd, J=7.7, 1.4 Hz, 1H), 7.60 (td, J=8.7, 5.8 Hz, 1H), 7.53 (t, J=7.8 Hz, 1H), 7.41 (dd, J=7.7, 1.1 Hz, 1H), 7.35 (s, 1H), 7.19 (td, J=9.2, 1.7 Hz, 1H), 7.13 (dd, J=5.2, 1.7 Hz, 1H), 6.03 (s, 1H), 5.54 (dd, J=12.2, 4.5 Hz, 1H), 4.10-4.01 (m, 1H), 3.83-3.75 (m, 1H), 2.67 (t, J=6.7 Hz, 2H), 2.39-2.30 (m, 1H), 2.06-1.97 (m, 1H), 1.89-1.79 (m, 1H), 1.60-1.51 (m, 1H), 1.24-1.05 (m, 2H), 1.01-0.91 (m, 4H). MS (ESI) m/z: 566.1 (M+H)+. Analytical HPLC (method A): RT=6.27 min, purity=100%.

Example 215

(10R,14S)-14-{4-[3-chloro-2-fluoro-6-(1H-1,2,3,4-tetrazol-1-yl)phenyl]-6-oxo-1,2,3,6-tetrahydropyridin-1-yl}-4,5-difluoro-10-methyl-8,16-diazatricyclo[13.3.1.0[2,7]]nonadeca-1(19),2(7),3,5,15,17-hexaen-9-one, TFA Salt

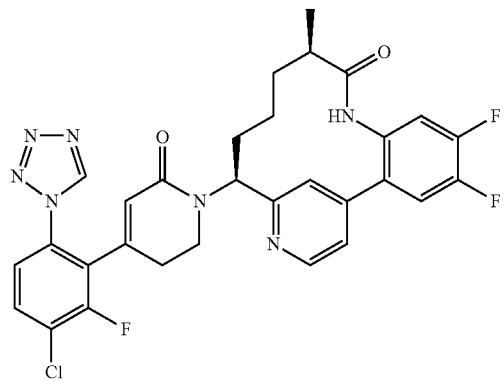 [SMILES: C[C@@H]1CCC[C@H](N2CCC(c3c(-n4cnnn4)ccc(Cl)c3F)=CC2=O)c2cc(ccn2)-c2cc(F)c(F)cc2NC1=O]

Example 215 was prepared according to the procedures described in Example 68. A white solid. $^1$H NMR (500 MHz, METHANOL-$d_4$) δ 9.54 (s, 1H), 8.74 (d, J=5.5 Hz, 1H), 7.87-7.77 (m, 2H), 7.71-7.64 (m, 2H), 7.53 (dd, J=8.7, 1.5 Hz, 1H), 7.29 (dd, J=10.9, 7.3 Hz, 1H), 5.71 (t, J=1.2 Hz, 1H), 5.41 (dd, J=12.4, 4.7 Hz, 1H), 3.83-3.74 (m, 1H), 3.62 (ddd, J=12.5, 9.4, 5.4 Hz, 1H), 2.66-2.48 (m, 3H), 2.21-2.11 (m, 1H), 1.97-1.81 (m, 2H), 1.59-1.48 (m, 1H), 1.33-1.21 (m, 1H), 1.01 (d, J=6.9 Hz, 3H), 0.93-0.78 (m, 1H). MS (ESI) m/z: 608.4 (M+H)+. Analytical HPLC (method A): RT=7.26 min, purity=98.6%.

Example 216

Methyl N-[(12E,15S)-15-[4-(3-chloro-2,6-difluorophenyl)-6-oxo-1,2,3,6-tetrahydropyridin-1-yl]-8-oxo-9,17-diazatricyclo[14.3.1.0[2,7]]icosa-1(20),2(7),3,5,12,16,18-heptaen-5-yl]carbamate, TFA Salt

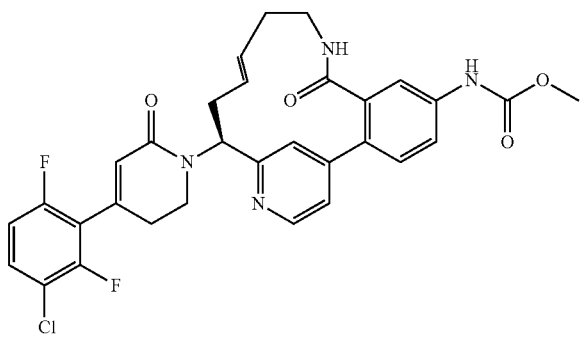 [SMILES: COC(=O)Nc1ccc2c(c1)C(=O)NCC/C=C/C[C@H](N1CCC(c3c(F)ccc(Cl)c3F)=CC1=O)c1cc-2ccn1]

Example 216 was prepared using a procedure analogous to Example 24, by replacing prop-2-en-1-amine with but-3-en-1-amine in step 24E, and by skipping step 24G. $^1$H NMR (500 MHz, METHANOL-$d_4$) δ 8.68-8.64 (m, 1H), 7.77 (d, J=1.9 Hz, 1H), 7.71-7.68 (m, 2H), 7.65 (dd, J=8.3, 2.2 Hz, 1H), 7.55 (td, J=8.7, 5.5 Hz, 1H), 7.47 (d, J=8.3 Hz, 1H), 7.11 (td, J=9.2, 1.9 Hz, 1H), 6.11 (s, 1H), 5.70-5.61 (m, 1H), 5.55 (dd, J=11.4, 3.2 Hz, 1H), 5.51-5.43 (m, 1H), 3.92-3.85 (m, 1H), 3.81-3.73 (m, 4H), 3.56-3.49 (m, 1H), 3.46-3.38 (m, 1H), 3.00-2.72 (m, 4H), 2.46-2.28 (m, 2H). MS (ESI) m/z: 593.2 (M+H)+. Analytical HPLC (method A): RT=6.49 min, purity=99.2%.

Example 217

(10R,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0²,⁷]nonadeca-1(19),2(7),3,5,15,17-hexaene-3-carbonitrile, TFA Salt

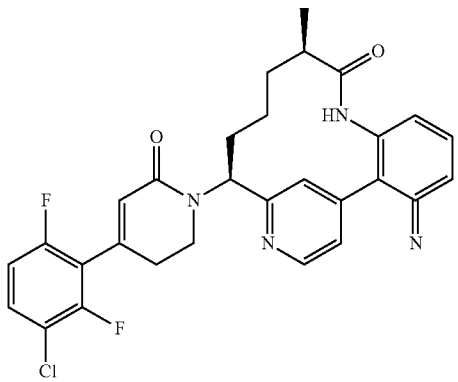

Example 217 was prepared according to the procedures described in Example 80, by replacing 2-bromo-3-fluoroaniline in step 80A with 3-amino-2-chlorobenzonitrile. ¹H NMR (500 MHz, METHANOL-d₄) 60° C., δ 8.79 (d, J=5.2 Hz, 1H), 7.87 (dd, J=7.7, 1.4 Hz, 1H), 7.70-7.59 (m, 4H), 7.53-7.47 (m, 1H), 7.06 (td, J=9.3, 1.8 Hz, 1H), 6.10 (s, 1H), 5.57 (dd, J=12.4, 4.7 Hz, 1H), 4.09-3.97 (m, 1H), 3.86-3.78 (m, 1H), 2.83-2.66 (m, 2H), 2.52-2.44 (m, 1H), 2.18 (tt, J=12.8, 5.0 Hz, 1H), 2.01-1.92 (m, 1H), 1.77-1.68 (m, 1H), 1.36-0.97 (m, 6H). MS (ESI) m/z: 547.3 (M+H)+. Analytical HPLC (method A): RT=8.48 min, purity=100%.

Example 218 (Isomer 4)

Methyl N-[(10R,14S)-10-methyl-14-[4-(3-methylcyclohexyl)-6-oxo-1,2,3,6-tetrahydropyridin-1-yl]-9-oxo-8,16-diazatricyclo[13.3.1.0²,⁷]nonadeca-1(19),2,4,6,15,17-hexaen-5-yl]carbamate, TFA Salt

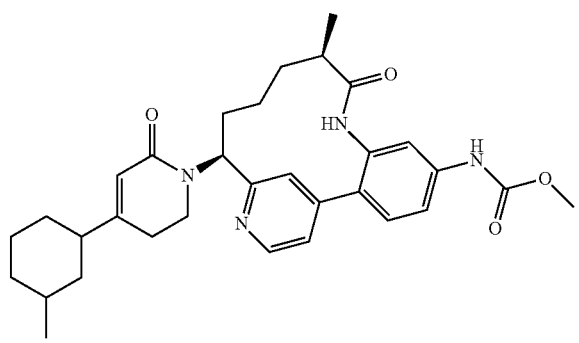 [SMILES: COC(=O)Nc1ccc2c(c1)NC(=O)[C@H](C)CCC[C@H](N1CCC(C3CCCC(C)C3)=CC1=O)c1cc-2ccn1]

Example 128

Example 159 was separated by preparative chiral chromatographic method (Instrument: Burger Multigram II SFC. Column: Chiralpak IB, 30×250 mm, 5 micron. Mobile Phase: 30% MeOH/70% CO₂. Flow Conditions: 85 mL/min, 150 Bar, 40° C. Detector Wavelength: 220 nm. Injection Details: 0.75 mL of ~8 mg/mL in MeOH). 4 isomers were obtained.

Example 218 (Isomer 4)

¹H NMR (500 MHz, METHANOL-d4) δ 8.51 (m, 1H), 7.51 (m, 1H), 7.41 (s, 2H), 7.37 (s, 1H), 7.29 (m, 1H), 5.57-5.52 (m, 1H), 5.49 (m, 1H), 3.66 (s, 3H), 3.54 (m, 1H), 3.42 (m, 1H), 2.45 (m, 1H), 2.21 (m, 2H), 2.07-1.97 (m, 2H), 1.80 (m, 1H), 1.76-1.57 (m, 5H), 1.47-1.31 (m, 6H), 1.30-1.17 (m, 2H), 1.12 (m, 1H), 1.03 (m, 1H), 0.94 (d, J=6.6 Hz, 3H), 0.82 (d, J=6.3 Hz, 3H), 0.77 (m, 1H). MS (ESI) m/z: 545.35 (M+H)+. Analytical HPLC (method C): RT=2.05 min, purity=97.4%.

Example 219

Methyl N-[(15S)-15-[4-(3-chloro-2,6-difluorophenyl)-6-oxo-1,2,3,6-tetrahydropyridin-1-yl]-9-oxo-8,17-diazatricyclo[14.3.1.0²,⁷]icosa-1 (20),2(7),3,5,16,18-hexaen-5-yl]carbamate, TFA Salt

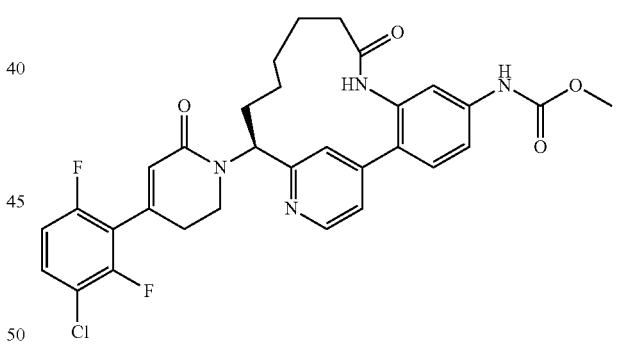

Example 219 was prepared according to the procedures described in Example 1, by replacing Intermediate 10 with pent-4-enoic acid in step 1G and by replacing Intermediate 3 with Intermediate 1 in step 1K. ¹H NMR (500 MHz, DMSO-d₆) δ 9.79 (s, 1H), 9.37 (s, 1H), 8.59 (d, J=5.0 Hz, 1H), 7.61 (td, J=8.8, 5.8 Hz, 1H), 7.50 (d, J=1.9 Hz, 1H), 7.41 (dd, J=8.4, 2.1 Hz, 1H), 7.31 (d, J=8.5 Hz, 1H), 7.25-7.14 (m, 3H), 5.95 (s, 1H), 5.42 (dd, J=12.7, 3.3 Hz, 1H), 3.83-3.76 (m, 1H), 3.64-3.54 (m, 4H), 2.60-2.48 (m, 2H), 2.28-2.13 (m, 2H), 2.07-1.97 (m, 1H), 1.78-1.69 (m, 1H), 1.63-1.46 (m, 2H), 1.42-1.16 (m, 3H), 0.95-0.86 (m, 1H). MS (ESI) m/z: 595.3 (M+H)+. Analytical HPLC (method A): RT=6.72 min, purity=99.2%.

Example 220

(10R,14S)-14-[4-(3-chloro-2,6-difluorophenyl)-6-oxo-1,2,3,6-tetrahydropyridin-1-yl]-10,17-dimethyl-8,16,18-triazatricyclo[13.2.1.0$^{2,7}$]octadeca-1(17),2,4,6,15(18)-pentaen-9-one, TFA Salt

Example 221

13-[4-(3-chloro-2,6-difluorophenyl)-6-oxo-1,2,3,6-tetrahydropyridin-1-yl]-9-methyl-4,5,7,15-tetraazatricyclo[12.3.1.0$^{2,6}$]octadeca-1(18),2(6),3,14,16-pentaen-8-one, 2TFA Salt

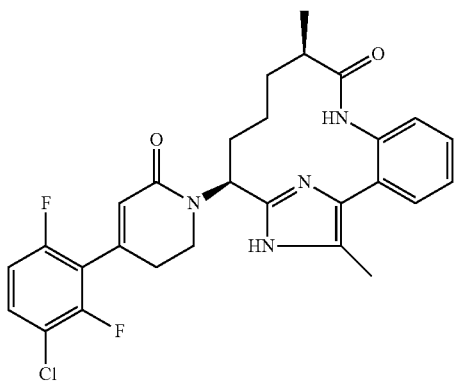 [SMILES: Cc1[nH]c2nc1-c1ccccc1NC(=O)[C@H](C)CCC[C@@H]2N1CCC(c2c(F)ccc(Cl)c2F)=CC1=O]

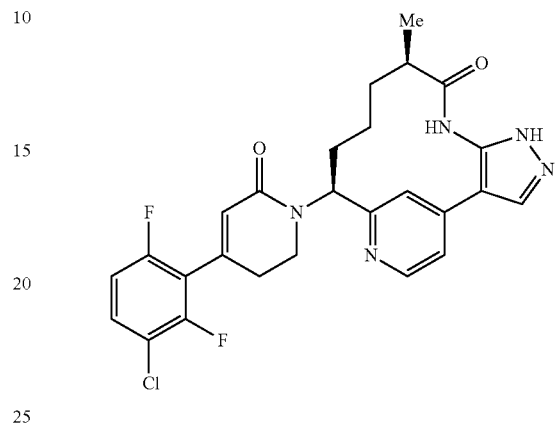

220A: (10R,14S)-5-amino-14-[4-(3-chloro-2,6-difluorophenyl)-6-oxo-1,2,3,6-tetrahydropyridin-1-yl]-10,17-dimethyl-8,16,18-triazatricyclo[13.2.1.0$^{2,7}$]octadeca-1(17),2,4,6,15(18)-pentaen-9-one To the suspension of Example 160 (0.038 g, 0.064 mmol) in DCM (2.5 ml) was added iodotrimethylsilane (0.090 ml, 0.635 mmol), and the reaction was sealed and heated at 50° C. for 24 h. The reaction mixture was diluted with DCM and washed with sat. sodium sulfite. The cloudy aqueous layer was extracted with DCM until clear (3×). The organic layers were combined and washed with 10% KH$_2$PO$_4$, brine, dried over MgSO$_4$, filtered, and concentrated. Purification by normal phase chromatography afforded 220A (0.015 g, 43.7% yield) as a yellow solid. MS (ESI) m/z: 540.3 (M+H)$^+$.

Example 220

To a solution of 220A (15 mg, 0.028 mmol) in DMF (1 mL) was added isoamyl nitrite (0.011 mL, 0.083 mmol). The reaction was heated at 65° C. in a sealed tube for 1 h and then the reaction was cooled to rt. Additional isoamyl nitrite (0.011 mL, 0.083 mmol) was added and the reaction was heated in a sealed tube at 65° C. for 1.5 h. The reaction was cooled to rt. Purification by reverse phase HPLC afforded Example 220 (2.39 mg, 13% yield) as a yellow solid. $^1$H NMR (500 MHz, METHANOL-d$_4$) δ 7.59-7.53 (m, 3H), 7.49-7.45 (m, 1H), 7.31 (dd, J=8.0, 0.8 Hz, 1H), 7.12 (td, J=9.2, 1.9 Hz, 1H), 6.11 (s, 1H), 5.51 (dd, J=11.6, 6.3 Hz, 1H), 3.90-3.77 (m, 2H), 3.00-2.90 (m, 1H), 2.87-2.78 (m, 1H), 2.74-2.66 (m, 1H), 2.40 (s, 3H), 2.31-2.22 (m, 1H), 2.15-2.07 (m, 1H), 1.78-1.70 (m, 1H), 1.64-1.46 (m, 2H), 1.04 (d, J=6.9 Hz, 3H), 0.97-0.83 (m, 1H). MS (ESI) m/z: 525.3 (M+H)$^+$. Analytical HPLC (method A): RT=9.41 min, purity=97.1%.

221A. 4-bromo-1-((2-(trimethylsilyl)ethoxy)methyl)-1H-pyrazol-5-amine

To a solution of 4-bromo-1H-pyrazol-5-amine (1 g, 6.17 mmol) in THF (20 mL) at 0° C. was added NaH (0.494 g, 12.35 mmol) and stirred at the same temperature for 30 mins. To this mixture was then added SEM-Cl (1.095 mL, 6.17 mmol) and slowly allowed to raise to rt and stirred at rt for 1 h. The rxn mix was then quenched with Satd. NH$_4$Cl and then extracted with EtOAc, dried over Na$_2$SO$_4$, filtered, and concentrated. Purification by normal phase chromatography afforded 221A (1.45 g, 80% yield) as a pale yellow oil. MS (ESI) m/z: 292.0 (M+H)$^+$.

221B. (S)-tert-butyl (1-(4-(5-amino-1-((2-(trimethylsilyl)ethoxy)methyl)-1H-pyrazol-4-yl)pyridin-2-yl)but-3-en-1-yl)carbamate A sealed tube was charged with 24A (0.05 g, 0.171 mmol), 221A (0.500 g, 1.712 mmol), (DtBPF)PdCl2 (0.056 g, 0.086 mmol), 3M Potassium phosphate (1.712 mL, 5.13 mmol), and THF (15 mL). The reaction vessel was vacuumed and back-filled with argon three times, then tube was sealed, and the reaction was heated at 130° C. in a microwave for 30 mins. After 30 mins, the reaction was cooled to rt. The reaction was diluted with EtOAc, washed with brine, dried over Na$_2$SO$_4$, filtered, and concentrated. Purification by normal phase chromatography afforded 221B (0.238 g, 29% yield) as a yellow oil. MS (ESI) m/z: 460.3 (M+H)$^+$.

Example 221 was prepared according to the procedures described in Example 1, by replacing 1F in step 1G with 221B. Additionally macrocyclization protocol in step 1H was done as shown in step 95C. MS (ESI) m/z: 512.2 (M+H)$^+$. $^1$H NMR (400 MHz, CD$_3$OD) δ 8.62 (d, J=6.1 Hz, 1H), 8.38 (s, 1H), 8.01 (s, 1H), 7.78 (d, J=6.1 Hz, 1H), 7.57 (td, J=8.7, 5.5 Hz, 1H), 7.13 (td, J=9.2, 1.7 Hz, 1H), 6.16 (s, 1H), 5.57 (dd, J=11.6, 3.3 Hz, 1H), 3.72-3.58 (m, 2H), 2.88-2.67 (m, 3H), 2.33-2.23 (m, 1H), 2.20-2.07 (m, 2H), 1.84-1.72 (m, 1H), 1.58-1.32 (m, 3H) 1.24-1.22 (d, J=6.9 Hz, 3H). Analytical HPLC (method A): RT=5.9 min, purity=>95%.

Example 222

(9R,13S)-13-[4-(3-chloro-2,6-difluorophenyl)-6-oxo-1,2,3,6-tetrahydropyridin-1-yl]-9-methyl-8-oxo-2,3,7,15-tetraazatricyclo[12.3.1.0²,⁶]octadeca-1(18),3,5,14,16-pentaene-4-carboxylic acid

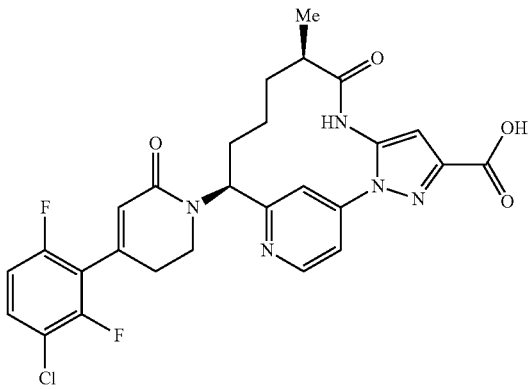 [SMILES: C[C@@H]1CCC[C@H](N2CCC(c3c(F)ccc(Cl)c3F)=CC2=O)c2cc(ccn2)-n2nc(C(=O)O)cc2NC1=O]

222A (S)-tert-butyl (1-(4-hydrazinylpyridin-2-yl)but-3-en-1-yl)carbamate

A vial with a Teflon septum cap was charged with a solution of 1C (2 g, 7.0 mmol) and hydrazine (35% in water) (10 mL, 111 mmol, 15.75 equiv) in ethanol (10 mL). The solution was heated by an aluminum block set to 115° C. for 18 hours. The reaction was concentrated to give a pink oil. Purification by normal phase silica gel chromatography yielded 222A (1.67 g, 85%) as a yellow, foaming solid. ¹H NMR (400 MHz, CHLOROFORM-d) δ 8.22 (d, J=5.7 Hz, 1H), 6.60 (s, 1H), 6.57 (dd, J=5.5, 2.4 Hz, 1H), 5.79-5.54 (m, 3H), 5.14-4.99 (m, 2H), 4.74-4.62 (m, 1H), 2.59 (t, J=6.7 Hz, 2H), 1.52-1.40 (m, 9H). MS (ESI) m/z: 279.2 (M+H)⁺.

222B sodium (Z)-1-cyano-3-ethoxy-3-oxoprop-1-en-2-olate (0.29 g, 1.8 mmol) was suspended in a solution of 222A (0.50 g, 1.8 mmol) in ethanol (15 ml). TFA (0.4 ml, 5.39 mmol, 3 equiv) was added dropwise and the solid slowly dissolved upon heating to 80° C. Stirring was continued at 80° C. for two hours, then the reaction was cooled to room temperature. The reaction was then concentrated to an oil and the residue dissolved in ethyl acetate. The organic was washed with pH=7 phosphate buffer, separated and concentrated to yield an oil. Purification by normal phase silica gel chromatography yielded 222B (0.7 g, 97% yield) as a clear, colorless, thick oil. ¹H NMR (400 MHz, CHLOROFORM-d) δ 8.71-8.67 (m, 1H), 7.64 (d, J=2.0 Hz, 1H), 7.60 (dd, J=5.4, 2.1 Hz, 1H), 6.20 (s, 1H), 5.79-5.66 (m, 1H), 5.56-5.42 (m, 1H), 5.15-5.06 (m, 3H), 4.93-4.82 (m, 1H), 4.44 (q, J=7.1 Hz, 2H), 4.03 (br. s., 2H), 2.66 (m, 2H), 1.46 (s, 9H), 1.45-1.41 (t, J=7.1 Hz, 3H). MS (ESI) m/z: 402.2 (M+H)⁺.

Example 222

Example 222 was prepared according to the procedures described in Example 1, by replacing 1F in step 1G with 222B. Additional hydrolysis of ethyl ester to acid was done as shown in Example 146. ¹H NMR (500 MHz, DMSO-d₆) δ 9.95 (s, 1H), 8.54 (d, J=5.0 Hz, 1H), 7.50 (br. s., 2H), 7.32 (d, J=4.7 Hz, 1H), 7.10 (t, J=9.1 Hz, 1H), 6.63 (s, 1H), 5.88 (s, 1H), 5.52 (d, J=10.2 Hz, 1H), 3.99 (br. s., 2H), 2.55 (d, J=7.2 Hz, 1H), 2.49 (br. s., 2H), 2.01-1.91 (m, 1H), 1.88 (br. s., 1H), 1.50 (br. s., 1H), 1.34 (br. s., 1H), 1.15 (br. s., 1H), 0.68 (d, J=6.3 Hz, 3H). MS (ESI) m/z: 556.1 (M+H). Analytical HPLC (method D): RT=1.45 min, purity=95%.

Example 223

(9R,13S)-13-[4-(3-chloro-2,6-difluorophenyl)-6-oxo-1,2,3,6-tetrahydropyridin-1-yl]-4-cyclopropyl-9-methyl-2,3,7,15-tetraazatricyclo[12.3.1.0²,⁶]octadeca-1(18),3,5,14,16-pentaen-8-one

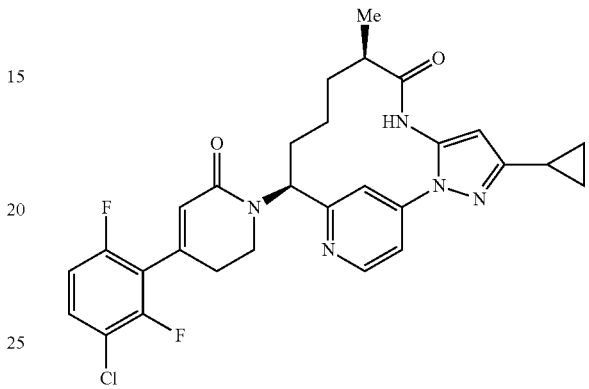

Example 223

Example 223 was prepared according to the procedures described in Example 222. ¹H NMR (400 MHz, METHANOL-d₄) δ 8.72 (d, J=5.9 Hz, 1H), 7.92 (d, J=2.0 Hz, 1H), 7.88 (dd, J=6.2, 2.2 Hz, 1H), 7.63-7.51 (m, 1H), 7.12 (d, J=1.8 Hz, 1H), 6.24 (s, 1H), 6.14 (s, 1H), 5.62-5.51 (m, 1H), 3.97-3.84 (m, 1H), 3.83-3.69 (m, 1H), 2.97-2.83 (m, 1H), 2.83-2.67 (m, 2H), 2.31-2.18 (m, 1H), 2.03 (s, 3H), 1.81-1.65 (m, 1H), 1.51-1.36 (m, 1H), 1.11 (d, J=6.8 Hz, 3H), 1.08-1.01 (m, 3H), 0.92-0.85 (m, 2H). MS (ESI) m/z: 552.1 (M+H)⁺. Analytical HPLC (method A): RT=8.5 min, purity=99%.

Example 224

Methyl N-[(9R,13S)-13-[4-(3-chloro-2,6-difluorophenyl)-6-oxo-1,2,3,6-tetrahydropyridin-1-yl]-9-methyl-8-oxo-2,3,7,15-tetraazatricyclo[12.3.1.0²,⁶]octadeca-1(18),3,5,14,16-pentaen-4-yl]carbamate

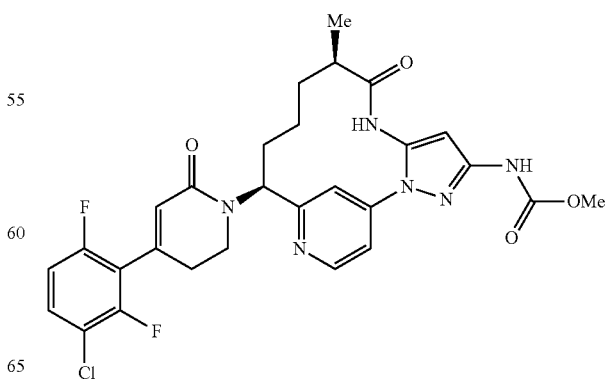

Example 224

To a well-stirred solution of Example 222 (0.02 g, 0.036 mmol) in toluene (0.7 ml) was added triethylamine (0.013 ml, 0.090 mmol) and diphenylphosphoryl azide (0.025 g, 0.090 mmol). The reaction stirred at 100° C. for 1 hour, at which point methanol (0.01 mL, 0.180 mmol) was added and stirring was continued for 10 minutes. The reaction was concentrated to a clear, colorless oil and the residue was purified by reverse phase prep HPLC. $^1$H NMR (500 MHz, DMSO-$d_6$) δ 10.50-10.33 (m, 1H), 10.10-10.00 (m, 1H), 8.69-8.61 (m, 1H), 7.76-7.68 (m, 1H), 7.67-7.61 (m, 1H), 7.41-7.36 (m, 1H), 7.35-7.27 (m, 1H), 6.54-6.46 (m, 1H), 6.14-6.04 (m, 1H), 5.75-5.62 (m, 1H), 4.23-4.09 (m, 1H), 3.82-3.72 (m, 1H), 3.69 (br. s., 3H), 2.80-2.72 (m, 2H), 2.71-2.61 (m, 2H), 2.25-2.12 (m, 1H), 2.12-1.99 (m, 1H), 1.79-1.64 (m, 1H), 1.62-1.48 (m, 1H), 1.43-1.29 (m, 1H), 0.91 (d, J=5.8 Hz, 3H). MS (ESI) m/z: 585.1 (M+H). Analytical HPLC (method D): RT=1.50 min, purity=90%.

Example 225 (Isomer 1) and Example 226 (Isomer 2)

Methyl N-[(10R,14S)-10-methyl-14-[4-(3-methylcyclohexyl)-6-oxo-1,2,3,6-tetrahydropyridin-1-yl]-9-oxo-8,16-diazatricyclo[13.3.1.0$^{2,7}$]nonadeca-1(19),2,4,6,15,17-hexaen-5-yl]carbamate, TFA Salt

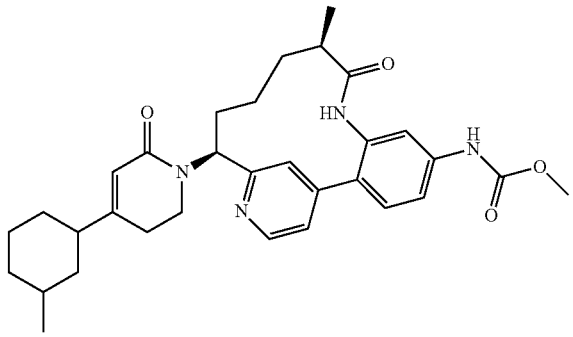 [SMILES: COC(=O)Nc1ccc2c(c1)NC(=O)[C@H](C)CCC[C@H](N1CCC(C3CCCC(C)C3)=CC1=O)c1cc-2ccn1]

Example 225 to Example 226: Example 159 was separated by preparative chiral chromatographic method (Instrument: Burger Multigram II SFC. Column: Chiralpak IB, 30×250 mm, 5 micron. Mobile Phase: 30% MeOH/70% CO$_2$. Flow Conditions: 85 mL/min, 150 Bar, 40° C. Detector Wavelength: 220 nm. Injection Details: 0.75 mL of ~8 mg/mL in MeOH). 4 isomers were obtained.

Example 225 (Isomer 1)

$^1$H NMR (500 MHz, METHANOL-$d_4$) ⌀ 580.61 (d, Hz, 1H), 7.60 (s, 1H), 7.54 (s, 2H), 7.50 (s, 1H), 7.39 (d, J=5.0 Hz, 1H), 5.67 (s, 1H), 5.60 (dd, J=12.4, 3.9 Hz, 1H), 4.58 (s, 2H), 3.79 (s, 3H), 3.72-3.62 (m, 1H), 3.57-3.48 (m, 1H), 2.58 (m, 1H), 2.34 (m, 2H), 2.21-2.09 (m, 2H), 1.92 (m, 1H), 1.88-1.69 (m, 5H), 1.61-1.45 (m, 2H), 1.45-1.31 (m, 2H), 1.24 (m, 1H), 1.20-1.10 (m, 1H), 1.07 (d, J=6.9 Hz, 3H), 0.95 (d, J=6.3 Hz, 3H), 0.93-0.85 (m, 2H). MS (ESI) m/z: 545.35 (M+H)$^+$. Analytical HPLC (method C): RT=2.05 min, purity=97.0%.

Example 226 (Isomer 2)

MS (ESI) m/z: 545.35 (M+H)$^+$. Analytical HPLC (method C): RT=2.01 min, purity=54.0%.

Example 227

Methyl N-[(10R,14S)-14-[4-(3-chloro-2,6-difluorophenyl)-6-oxo-1,2,3,6-tetrahydropyridin-1-yl]-10-methyl-9-oxo-17-(pyrimidin-5-yl)-8,16,18-triazatricyclo-[13.2.1.0$^{2,7}$]octadeca-1(17),2,4,6,15(18)-pentaen-5-yl]carbamate

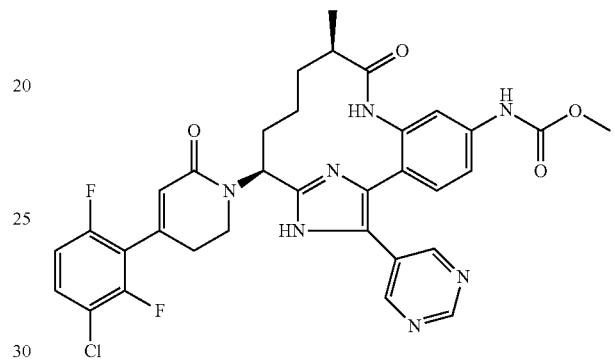

227A. Methyl N-[(10R,14S)-14-amino-17-bromo-10-methyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-5-yl]carbamate, 2TFA Salt 151A (0.99 g, 1.49 mmol) was treated with TFA (4.0 mL) and DCM (20 mL). After 1 hour, the reaction mixture was concentrated on a rotovap followed by azeotropic removal of TFA with toluene. The residue was place under high vacuum overnight and carried forward to subsequent reaction as is without further purification. MS (ESI) m/z: 566/568 (M+H)$^+$, bromine isotope.

227B. Methyl N-[(10R,14S)-17-bromo-14-{N-[3-(3-chloro-2,6-difluorophenyl)-3-oxopropyl]-2-(diethoxyphosphoryl)acetamido}-10-methyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-5-yl]carbamate To a round bottom flask was 227A (1.18 g, 1.49 mmol), DCM (47.9 mL) and TEA (1.45 mL, 10.40 mmol). The reaction was stirred for 30 minutes before adding Intermediate 1 (0.301 g, 1.49 mmol). After 4 hours, 2-(diethoxyphosphoryl)acetic acid (0.874 g, 4.46 mmol) and T$_3$P (2.83 g, 4.46 mmol) were added. After 1 hour, the reaction was then partitioned between EtOAc (150 ml) and water (100 ml). The organic layer was separated, washed with brine (100 ml), dried over MgSO4, filtered and concentrated. The residue was purified by normal phase chromatography to give 227B (1.34 g, 95%). MS (ESI) m/z: 946/948 (M+H)$^+$, bromine isotope.

227C. Methyl N-[(10R,14S)-17-bromo-14-[4-(3-chloro-2,6-difluorophenyl)-6-oxo-1,2,3,6-tetrahydropyridin-1-yl]-10-methyl-9-oxo-16-{[2-(trimethylsilyl)ethoxy]-methyl}-8,16,18-triazatricyclo[13.2.1.0$^{2,7}$]octadeca-1(17),2,4,6,15(18)-pentaen-5-yl]carbamate To the solution of 227B (1.35 g, 1.27 mmol) in MeOH (36.3 ml) at 0° C. was added sodium methoxide (25% wt in MeOH) (1.454 ml, 6.36 mmol). The reaction was warmed to RT. After 1 h, the reaction mixture was concentrated. The residue dissolved in EtOAc, washed twice with 1.5 dipotassium phosphate solution (aq.), brine, dried over Na$_2$SO$_4$, filtered, and concentrated. The crude residue was purified by normal phase column chromatography to give 227C (765 mg, 76%) as a tan solid. MS (ESI) m/z: 792/794 (M+H)$^+$, bromine isotope.

Example 227

227C (0.025 g, 0.032 mmol), pyrimidine-5-boronic acid (0.016 g, 0.126 mmol), and Na$_2$CO$_3$ (2.0M aq. solution) (0.079 ml, 0.158 mmol) were added to dioxane (0.267 ml) and degassed with a stream of argon for 15 minutes. Afterwards, tetrakis(triphenylphosphine)palladium(0) (5.46 mg, 4.73 µmol) was added and the mixture irradiated at 120° C. for 20 minutes. The reaction mixture was partitioned between EtOAc and water. The organics were washed with brine, dried over sodium sulfate, filtered, and concentrated. The SEM group was removed by treatment with 50% TFA/DCM overnight. The reaction mixture was concentrated and purified by reverse phase prep. HPLC to give the desired product (7.2 mg, 29%). 1H NMR (400 MHz, METHANOL-d4) δ 9.58 (s, 1H), 9.14-9.09 (m, 1H), 9.03-8.98 (m, 2H), 8.00 (s, 1H), 7.66 (d, J=1.5 Hz, 1H), 7.58 (td, J=8.7, 5.5 Hz, 1H), 7.54-7.47 (m, 1H), 7.35-7.25 (m, 2H), 7.18-7.10 (m, 1H), 6.19-6.12 (m, 1H), 5.74 (dd, J=11.7, 5.9 Hz, 1H), 4.14 (dt, J=12.0, 6.1 Hz, 1H), 3.92 (ddd, J=12.4, 9.3, 5.4 Hz, 1H), 3.79 (s, 3H), 3.00-2.91 (m, 1H), 2.87-2.79 (m, 1H), 2.72 (br. s., 1H), 2.30-2.21 (m, 1H), 2.11-2.00 (m, 1H), 1.81 (d, J=13.2 Hz, 1H), 1.64-1.43 (m, 3H), 1.06 (d, J=6.8 Hz, 3H) ppm. MS (ESI) m/z: (M+H)$^+$. Analytical HPLC (method D): RT=1.43 min, purity=95.7%.

What is claimed is:
1. A compound having Formula (XI):

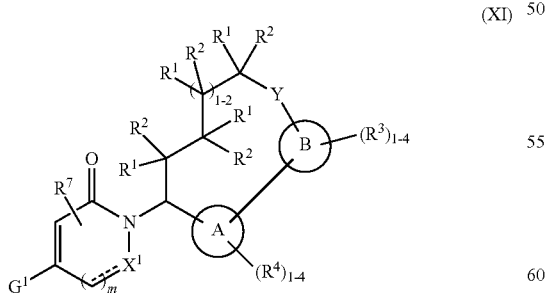

or a stereoisomer, a tautomer, a pharmaceutically acceptable salt thereof, wherein:
ring A is independently selected from a 6-membered aryl and a 5- to 6-membered heterocycle containing carbon atoms and 1, 2, 3 or 4 heteroatoms independently selected from the group consisting of N, O, and S, wherein said aryl and heterocycle are substituted with 1-4 R$^4$;

ring B is pyridyl substituted with 1-4 R$^3$;

G$^1$ is independently selected from a C$_{3-10}$ carbocycle and a 5- to 10-membered heterocycle containing carbon atoms and 1, 2, 3 or 4 heteroatoms independently selected from the group consisting of N, O, and S, wherein said carbocycle and heterocycle are substituted with 1-4 R$^8$;

X$^1$ is CR$^7$;

- - - is an optional bond;

Y is —C(O)—NH—;

R$^1$ and R$^2$ are independently selected from H, halogen, haloalkyl, C$_{1-4}$ alkyl (optionally substituted with R$^6$), hydroxyl, and alkoxy (optionally substituted with R$^6$), and C$_{3-5}$ cycloalkyl optionally substituted with R$^6$;

R$^3$ is independently selected from H, =O, halogen, haloalkyl, C$_{1-4}$alkyl (optionally substituted with R$^6$), C$_{2-4}$alkenyl (optionally substituted with R$^6$), C$_{2-4}$alkynyl (optionally substituted with R$^6$), CN, NO$_2$, —(CH$_2$)$_n$—OR$^5$, —(CH$_2$)$_n$—NR$^5$R$^5$, —(CH$_2$)$_n$—C(O)OR$^5$, —(CH$_2$)$_n$—NR$^9$C(O)OR$^5$, —(CH$_2$)$_n$—NR$^9$C(O)R$^5$, —(CH$_2$)$_n$—NR$^9$C(N=CN)NHR$^5$, —(CH$_2$)$_n$—NR$^9$C(NH)NHR$^5$, —(CH$_2$)$_n$—N=CR$^9$NR$^5$R$^5$, —(CH$_2$)$_n$—NR$^9$C(O)NR$^5$R$^5$, —(CH$_2$)$_n$—C(O)NR$^5$R$^5$, —(CH$_2$)$_n$—NR$^9$C(S)NR$^9$C(O)R$^5$, —(CH$_2$)$_n$—S(O)$_p$R$^{12}$, —(CH$_2$)$_n$—S(O)$_p$NR$^5$R$^5$, —(CH$_2$)$_n$—NR$^9$S(O)$_p$NR$^5$R$^5$, —(CH$_2$)$_n$—NR$^9$S(O)$_p$R$^{12}$, —(CH$_2$)$_n$—C$_{3-10}$ carbocycle and —(CH$_2$)$_n$-4- to 10-membered heterocycle containing carbon atoms and 1, 2, 3 or 4 heteroatoms independently selected from the group consisting of N, O, and S, wherein said carbocycle and heterocycle are optionally substituted with R$^6$; optionally, two adjacent R$^3$ groups on the carbocycle and heterocycle may form a ring optionally substituted with R$^6$, R$^4$ is independently selected from H, OH, halogen, CN, C$_{1-4}$ alkyl, C$_{1-4}$ haloalkyl, C$_{1-4}$ alkoxy, —C(O)NH$_2$, —C(O)NH(C$_{1-4}$ alkyl), —C(O)N(C$_{1-4}$ alkyl)$_2$, C$_{3-6}$ cycloalkyl, aryl, and 5- to 6-membered heterocycle containing carbon atoms and 1, 2, 3 or 4 heteroatoms independently selected from the group consisting of N, O, and S, wherein said cycloalkyl, aryl and heterocycle are optionally substituted with R$^6$;

R$^5$ is independently selected from H, C$_{1-4}$ alkyl (optionally substituted with halogen, hydroxyl, alkoxy, carboxy, alkoxycarbonyl, amino, substituted amino), C$_{3-10}$ carbocycle and 4- to 10-membered heterocycle containing carbon atoms and 1, 2, 3 or 4 heteroatoms independently selected from the group consisting of N, O, and S, wherein said carbocycle and heterocycle are optionally substituted with R$^6$; alternatively, R$^5$ and R$^5$ together with the nitrogen atom to which they are both attached form a heterocyclic ring optionally substituted with R$^6$;

R$^6$ is independently selected from OH, =O, —(CH$_2$)$_n$NH$_2$, —(CH$_2$)$_n$CN, halogen, C$_{1-6}$ alkyl, —(CH$_2$)$_n$—C(=O)OH, —(CH$_2$)$_n$—C(=O)OC$_{1-4}$ alkyl, —(CH$_2$)$_n$—OC$_{1-4}$ alkyl, —(CH$_2$)$_n$—C$_{3-10}$ carbocycle, —(CH$_2$)$_n$-4- to 10-membered heterocycle containing carbon atoms and 1, 2, 3 or 4 heteroatoms independently selected from the group consisting of N, O, and S, and —(CH$_2$)$_n$-4- to 10-membered heterocycle containing carbon atoms and 1, 2, 3 or 4 heteroatoms independently selected from the group consisting of N, O, and S, wherein said carbocycle and heterocycle are optionally substituted with $R^{10}$;

$R^7$ is independently selected from H, hydroxyl, alkoxy, halogen, methyl, ethyl, and isopropyl;

$R^8$ is independently selected from H, halogen, CN, $NH_2$, $C_{1-6}$ alkyl, haloalkyl, alkylcarbonyl, alkoxy, haloalkoxy, —$(CH_2)_n$-aryl, —$(CH_2)_n$—$C_{3-6}$ cycloalkyl, and —$(CH_2)_n$-4-6 membered heterocycle containing carbon atoms and 1, 2, 3 or 4 heteroatoms independently selected from the group consisting of N, O, and S; optionally, two adjacent $R^8$ groups on the carbocycle and heterocycle may form a ring optionally substituted with $R^{10}$;

$R^9$ is H or $C_{1-6}$ alkyl;

$R^{10}$ is independently selected from $C_{1-6}$ alkyl (optionally substituted with $R^{11}$), $C_{2-6}$ alkenyl, $C_{2-6}$ alkynyl, —$(CH_2)_n$—$C_{3-6}$ cycloalkyl, —O-4- to 10-membered heterocycle containing carbon atoms and 1, 2, 3 or 4 heteroatoms independently selected from the group consisting of N, O, and S (optionally substituted with $R^{11}$), F, Cl, Br, CN, $NO_2$, =O, $CO_2H$, —$(CH_2)_n$—$OC_{1-5}$ alkyl, —$(CH_2)_n$—$OR^{11}$, and —$(CH_2)_n$—$NR^{11}R^{11}$;

$R^{11}$, at each occurrence, is independently selected from H, $C_{1-5}$ alkyl, —$(CH_2)_n$—OH, $C_{3-6}$ cycloalkyl, and phenyl, or $R^{11}$ and $R^{11}$ together with the nitrogen atom to which they are both attached form a heterocyclic ring optionally substituted with $C_{1-4}$alkyl;

$R^{12}$ is $C_{1-6}$ alkyl optionally substituted with $R^{11}$;

m is an integer of 1;

n, at each occurrence, is an integer independently selected from 0, 1, 2, 3, and 4;

p, at each occurrence, is an integer independently selected from 0, 1, and 2.

2. The compound of claim 1, or a stereoisomer, a tautomer, a pharmaceutically acceptable salt thereof, wherein:

ring A is independently selected from

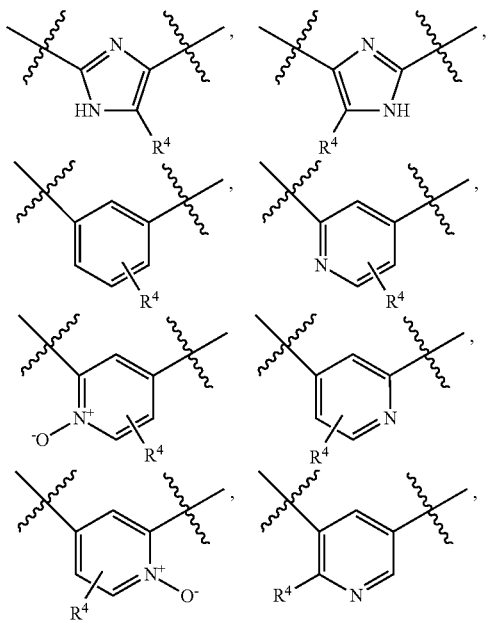

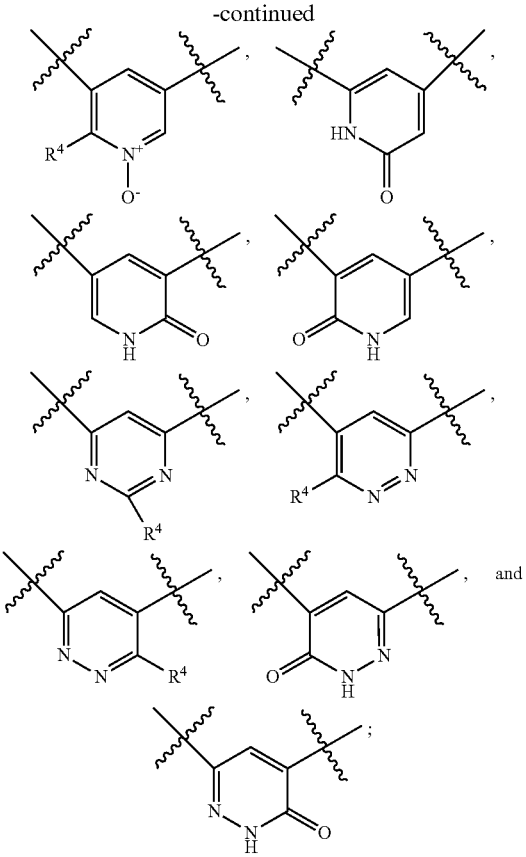

ring B is pyridyl substituted with 1-4 $R^3$;

$G^1$ is independently selected from

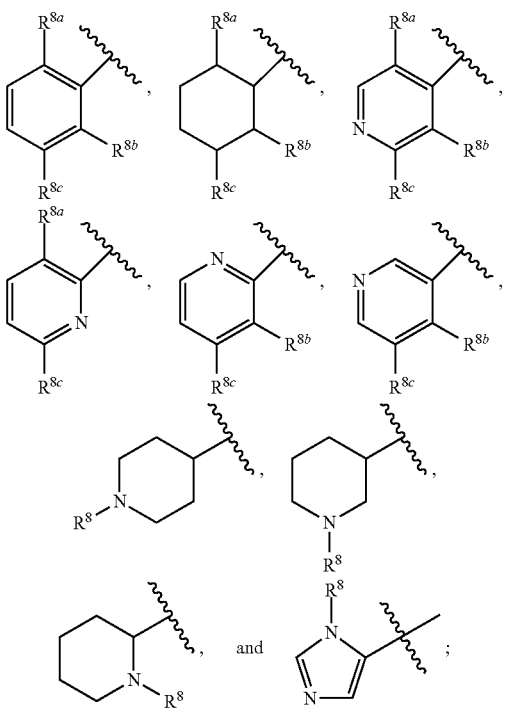

R¹ and R² are independently selected from H, F, methyl, ethyl, isopropyl, and hydroxyl;

R³ is independently selected from H, =O, halogen, haloalkyl, $C_{1-4}$alkyl optionally substituted with $R^6$, $C_{2-4}$alkenyl optionally substituted with $R^6$, $C_{2-4}$alkynyl optionally substituted with $R^6$, CN, NO$_2$, —(CH$_2$)$_n$—OR$^5$, —(CH$_2$)$_n$—NR$^5$R$^5$, —(CH$_2$)$_n$—C(O)OR$^5$, —(CH$_2$)$_n$—NR$^9$C(O)OR$^5$, —(CH$_2$)$_n$—NR$^9$C(O)R$^5$, —(CH$_2$)$_n$—NR$^9$C(N—CN)NHR$^5$, —(CH$_2$)$_n$—NR$^9$C(NH)NHR$^5$, —(CH$_2$)$_n$—N=CR$^9$NR$^5$R$^5$, —(CH$_2$)$_n$—NR$^9$C(O)NR$^5$R$^5$, —(CH$_2$)$_n$—C(O)NR$^5$R$^5$, —(CH$_2$)$_n$—NR$^9$C(S)NR$^9$C(O)R$^5$, —(CH$_2$)$_n$—S(O)$_p$R$^{12}$, —(CH$_2$)$_n$—S(O)$_p$NR$^5$R$^5$, —(CH$_2$)$_n$—NR$^9$S(O)$_p$NR$^5$R$^5$, —(CH$_2$)$_n$—NR$^9$S(O)$_p$R$^{12}$, —(CH$_2$)$_n$—C$_{3-10}$ carbocycle and —(CH$_2$)$_n$-4- to 10-membered heterocycle containing carbon atoms and 1, 2, 3 or 4 heteroatoms independently selected from the group consisting of N, O, and S, wherein said carbocycle and heterocycle are optionally substituted with $R^6$; optionally, two adjacent $R^3$ groups on the carbocycle and heterocycle may form a ring optionally substituted with $R^6$;

R⁴ is independently selected from H, OH, halogen, CN, $C_{1-4}$ alkyl, $C_{1-4}$ haloalkyl, $C_{1-4}$ alkoxy, —C(O)NH$_2$, —C(O)NH($C_{1-4}$ alkyl), —C(O)N($C_{1-4}$ alkyl)$_2$, $C_{3-6}$ cycloalkyl, aryl, and 5- to 6-membered heterocycle containing carbon atoms and 1, 2, 3 or 4 heteroatoms independently selected from the group consisting of N, O, and S, wherein said cycloalkyl, aryl and heterocycle are optionally substituted with $R^6$;

R⁵ is independently selected from H, $C_{1-4}$ alkyl (optionally substituted with halogen, hydroxyl, alkoxy, carboxy, alkoxycarbonyl, amino, substituted amino), $C_{3-10}$ carbocycle and 4- to 10-membered heterocycle containing carbon atoms and 1, 2, 3 or 4 heteroatoms independently selected from the group consisting of N, O, and S, wherein said carbocycle and heterocycle are optionally substituted with $R^6$; alternatively, $R^5$ and $R^5$ together with the nitrogen atom to which they are both attached form a heterocyclic ring optionally substituted with $R^6$;

R⁶ is independently selected from OH, =O, —(CH$_2$)$_n$NH$_2$, —(CH$_2$)$_n$CN, halogen, $C_{1-6}$ alkyl, —(CH$_2$)$_n$—C(=O)OH, —(CH$_2$)$_n$—C(=O)OC$_{1-4}$ alkyl, —(CH$_2$)$_n$—OC$_{1-4}$ alkyl, —(CH$_2$)$_n$—C$_{3-10}$ carbocycle and —(CH$_2$)$_n$-4- to 10-membered heterocycle containing carbon atoms and 1, 2, 3 or 4 heteroatoms independently selected from the group consisting of N, O, and S, —O-4- to 10-membered heterocycle containing carbon atoms and 1, 2, 3 or 4 heteroatoms independently selected from the group consisting of N, O, and S, wherein said carbocycle and heterocycle are optionally substituted with $R^{10}$;

R⁷ is independently selected from H, F, methyl, and ethyl;

R⁸ is independently selected from H, $C_{1-6}$ alkyl, alkylcarbonyl, haloalkyl, aryl, $C_{3-6}$ cycloalkyl, and 4-6 membered heterocycle containing carbon atoms and 1, 2, 3 or 4 heteroatoms independently selected from the group consisting of N, O, and S;

R$^{8a}$ is independently selected from H, halogen, CN, $C_{1-3}$ alkyl, C(O)C$_{1-4}$ alkyl, OC$_{1-3}$alkyl, CF$_3$, OCHF$_2$, NHC(O)C$_{1-4}$ alkyl, aryl, $C_{3-6}$ cycloalkyl, and 4-6 membered heterocycle containing carbon atoms and 1, 2, 3 or 4 heteroatoms independently selected from the group consisting of N, O, and S;

R$^{8b}$ is independently selected from H and halogen; and

R$^{8c}$ is independently selected from H, halogen, CN, $C_{1-4}$ alkyl, alkoxy, NH$_2$ and haloalkoxy;

R$^{10}$ is independently selected from $C_{1-6}$ alkyl optionally substituted with $R^{11}$, $C_{2-6}$ alkenyl, $C_{2-6}$ alkynyl, —(CH$_2$)$_n$—C$_{3-6}$ cycloalkyl, —O-4- to 10-membered heterocycle (optionally substituted with $R^{11}$), F, Cl, Br, CN, NO$_2$, =O, CO$_2$H, —(CH$_2$)$_n$—OC$_{1-5}$ alkyl, —(CH$_2$)$_n$—OR$^{11}$, and —(CH$_2$)$_n$—NR$^{11}$R$^{11}$;

R$^{11}$, at each occurrence, is independently selected from H, $C_{1-5}$ alkyl, $C_{3-6}$ cycloalkyl, and phenyl, or $R^{11}$ and $R^{11}$ together with the nitrogen atom to which they are both attached form a heterocyclic ring optionally substituted with $C_{1-4}$alkyl;

R$^{12}$ is $C_{1-6}$ alkyl optionally substituted with $R^{11}$;

m is an integer of 1;

n, at each occurrence, is an integer independently selected from 0, 1, 2, 3, and 4;

p, at each occurrence, is an integer independently selected from 0, 1, and 2.

3. The compound of claim 2, or a stereoisomer, a tautomer, a pharmaceutically acceptable salt thereof, wherein:

ring B is

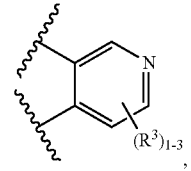

R³ is independently selected from H, =O, halogen, $C_{1-4}$alkyl optionally substituted with $R^6$, —OR$^5$, —NR$^5$R$^5$, —C(O)OR$^5$, —NR$^9$C(O)OR$^5$, —(CH$_2$)$_n$—NR$^9$C(O)R$^5$, —(CH$_2$)$_n$—C(O)NR$^5$R$^5$, —S(O)$_p$NR$^5$R$^5$, and $C_{3-10}$ carbocycle; and R⁵ is independently selected from H and $C_{1-4}$ alkyl.

4. A pharmaceutical composition comprising one or more compounds according to claim 1 and a pharmaceutically acceptable carrier or diluent.

5. A method for the treatment and/or prophylaxis of a thromboembolic disorder, comprising: administering to a patient in need thereof a therapeutically effective amount of a compound of to claim 1, or a stereoisomer, a tautomer, or a pharmaceutically acceptable salt thereof, wherein the thromboembolic disorder is selected from arterial cardiovascular thromboembolic disorders, venous cardiovascular thromboembolic disorders, and thromboembolic disorders in the chambers of the heart or in the peripheral circulation.

6. A method according to claim 5, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

7. A compound of claim 1, selected from:
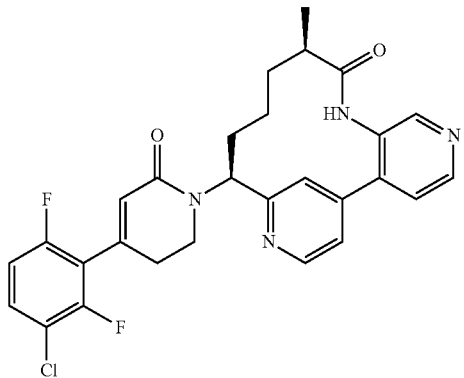
and
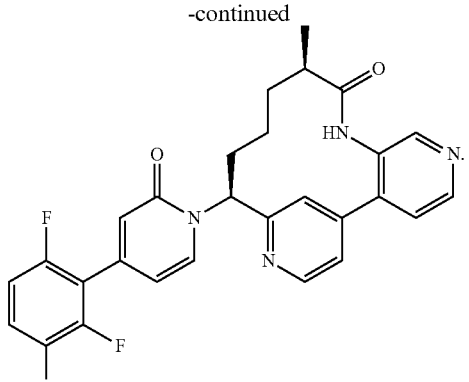
* * * * *